(12) United States Patent
Priepke et al.

(10) Patent No.: US 8,674,113 B2
(45) Date of Patent: Mar. 18, 2014

(54) COMPOUNDS

(75) Inventors: Henning Priepke, Warthausen (DE); Henri Doods, Warthausen (DE); Alexander Heim-Riether, Biberach an der Riss (DE); Raimund Kuelzer, Mittelbiberach (DE); Roland Pfau, Biberach an der Riss (DE); Klaus Rudolf, Warthausen (DE); Dirk Stenkamp, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 13/314,561

(22) Filed: Dec. 8, 2011

(65) Prior Publication Data
US 2012/0149676 A1    Jun. 14, 2012

(30) Foreign Application Priority Data

Dec. 10, 2010  (EP) .................................. 10194458

(51) Int. Cl.
| | |
|---|---|
| A61K 31/4184 | (2006.01) |
| A61K 31/5377 | (2006.01) |
| A61K 31/4545 | (2006.01) |
| A61K 31/4995 | (2006.01) |
| C07D 235/30 | (2006.01) |
| C07D 401/12 | (2006.01) |
| C07D 403/12 | (2006.01) |
| C07D 513/04 | (2006.01) |
| C07D 413/12 | (2006.01) |
| C07D 417/12 | (2006.01) |

(52) U.S. Cl.
USPC .................. 548/307.4; 548/300.7; 548/266.4; 548/248; 548/153; 546/144; 546/273.4; 546/194; 546/199; 546/187; 546/16; 544/62; 544/105; 544/236; 544/250; 544/370; 544/139; 514/228.2; 514/230.5; 514/234.5; 514/248; 514/249; 514/254.06; 514/278; 514/307; 514/299; 514/316; 514/318; 514/322; 514/338; 514/367; 514/383; 514/378; 514/388

(58) Field of Classification Search
USPC ...................................................... 548/307.4
See application file for complete search history.

(56) References Cited

U.S. PATENT DOCUMENTS

| | | |
|---|---|---|
| 6,608,084 B1 | 8/2003 | Bourzat et al. |
| 2004/0198768 A1 | 10/2004 | Park Choo et al. |
| 2006/0287344 A1 | 12/2006 | Albers et al. |
| 2007/0060598 A1 | 3/2007 | Albers et al. |
| 2010/0004301 A1 | 1/2010 | Pelcman et al. |
| 2010/0256188 A1 | 10/2010 | Pfau et al. |
| 2011/0275656 A1 | 11/2011 | Pfau et al. |
| 2011/0312935 A1 | 12/2011 | Pfau et al. |
| 2012/0115902 A1 | 5/2012 | Pfau et al. |
| 2012/0122930 A1 | 5/2012 | Pfau et al. |
| 2012/0149676 A1 | 6/2012 | Priepke et al. |
| 2012/0196897 A1 | 8/2012 | Pfau et al. |
| 2012/0208839 A1 | 8/2012 | Priepke et al. |
| 2012/0214786 A1 | 8/2012 | Priepke et al. |
| 2012/0309738 A1 | 12/2012 | Priepke et al. |
| 2012/0309755 A1 | 12/2012 | Priepke et al. |

FOREIGN PATENT DOCUMENTS

| | | |
|---|---|---|
| EP | 0034743 A1 | 9/1981 |
| EP | 0295656 A1 | 12/1988 |
| EP | 0419210 A1 | 3/1991 |
| EP | 1069124 A1 | 1/2001 |
| FR | 2851563 A1 | 8/2004 |
| FR | 2852957 A1 | 10/2004 |
| WO | 0015612 A1 | 3/2000 |
| WO | 0049005 A1 | 8/2000 |
| WO | 0061580 A1 | 10/2000 |
| WO | 0068213 A1 | 11/2000 |
| WO | 0125238 A2 | 4/2001 |
| WO | 03053939 A1 | 7/2003 |
| WO | 03074515 A1 | 9/2003 |
| WO | 03082272 A1 | 10/2003 |
| WO | 2004005323 A2 | 1/2004 |
| WO | 2004035740 A2 | 4/2004 |
| WO | 2004072068 A1 | 8/2004 |
| WO | 2004085425 A1 | 10/2004 |
| WO | 2004089951 A1 | 10/2004 |

(Continued)

OTHER PUBLICATIONS

Lala et al., Cancer and Metastasis reviews (1998), 17 (1), 91-106.

(Continued)

*Primary Examiner* — Laura L. Stockton
(74) *Attorney, Agent, or Firm* — Michael P. Morris; Philip I. Datlow

(57) ABSTRACT

This invention relates to compounds of formula I

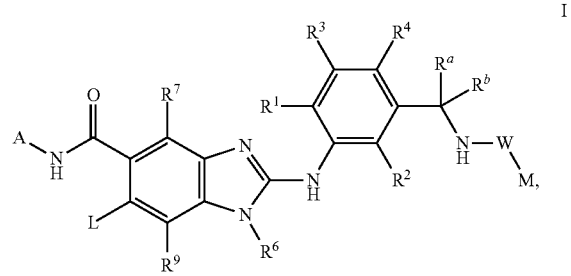

their use as inhibitors of the microsomal prostaglandin $E_2$ synthase-1 (mPGES-1), pharmaceutical compositions containing them, and their use as medicaments for the treatment and/or prevention of inflammatory diseases and associated conditions. A, L, M, W, $R^1$, $R^2$, $R^3$, $R^4$, $R^6$, $R^7$, $R^9$, $R^a$, $R^b$ have meanings given in the description.

13 Claims, No Drawings

(56) References Cited

FOREIGN PATENT DOCUMENTS

| WO | 2005044793 | A2 | 5/2005 |
| WO | 2005070906 | A1 | 8/2005 |
| WO | 2005070920 | A1 | 8/2005 |
| WO | 2005123674 | A1 | 12/2005 |
| WO | 2006077366 | A1 | 7/2006 |
| WO | 2006090167 | A2 | 8/2006 |
| WO | 2007095124 | A2 | 8/2007 |
| WO | 2007127382 | A1 | 11/2007 |
| WO | 2008009924 | A2 | 1/2008 |
| WO | 2008035956 | A1 | 3/2008 |
| WO | 2008071944 | A1 | 6/2008 |
| WO | 2008129276 | A1 | 10/2008 |
| WO | 2010034796 | A1 | 4/2010 |
| WO | 2010034797 | A1 | 4/2010 |
| WO | 2010034798 | A1 | 4/2010 |
| WO | 2010034799 | A1 | 4/2010 |
| WO | 2010100249 | A1 | 9/2010 |

OTHER PUBLICATIONS

Golub et al., Science (1999), vol. 286, 531-537.
Cancer [online], [retrieved on Jul. 6, 2007]. Retrieved from the internet, URL http://www.nlm.nih.gov/medlineplus/cancer.html>.
Cancer [online], [retrieved on Jul. 6, 2007]. Retrieved from the internet, URL http://en.wikipedia.org|wiki|Cancer.
R.D. Carpenter et al., Carbodiimide-based benzinidazole library method, Journal of Combinatorial Chemistry, Oct. 27, 2006, pp. 907-914, vol. 8, No. 6.
International Search Report Form PCT/ISA/210 and Written Opinion Form PCT/ISA/237 for corresponding PCT/EP2011/072257; date of mailing: Jan. 12, 2012.
D.J. Gale et al., The Amidomethylation of Some N,N-Dialkylanilines; Aust.J. Chem.; pp. 2447-2458; vol. 28; 1975.

US 8,674,113 B2

COMPOUNDS

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and cyclooxygenase (COX)-2 inhibitors are efficacious, but show a prevalence for gastrointestinal and cardiovascular side effects. There is a high need for new treatment options showing equivalent efficacy with an improved side effect profile.

mPGES inhibitors may show such an improved side effect profile because they block the generation of $PGE_2$ in a more specific manner as described below.

NSAIDs and COX-2 inhibitors reduce inflammation and pain through inhibition of one or both isoforms of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$. However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably inhibits the transformation of $PGH_2$ to the pro-inflammatory mediator $PGE_2$ selectively might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described. mPGES-1 is proposed to be closely linked to COX-2 and both enzyme's are upregulated during e.g. inflammation. Thus agents that are capable of inhibiting the action of mPGES-1 and thereby reducing the formation of $PGE_2$ are likely to be of benefit for the treatment of inflammation and more general acute and chronic pain conditions Benzimidazole and imidazopyridine derivatives with mPGES-1 inhibitory activity are disclosed in WO 2010/034796, WO 2010/034797, WO 2010/034798, WO 2010/034799.

WO 2010/100249 describes a broad class of different 2-arylamino benzimidazoles in which the aryl group bears a particular side chain.

Compounds of the present invention are distinguished over compounds of WO 2010/100249 by enhanced biological activity in a cell-based assay.

Compounds with a similar affinity for the mPGES-1 enzyme as measured in the enzyme assay may have different potencies in the cell-based assay.

Data from a cell based pharmacological assay when compared with data from an enzyme assay are considered to allow for a better predictability and estimation of therapeutic effective concentrations/doses. Compounds of the present invention show high potency in both assays. Consequently, they are likely to be more suitable for the in-vivo use.

DETAILED DESCRIPTION OF THE INVENTION

The present invention provides a compound of formula I,

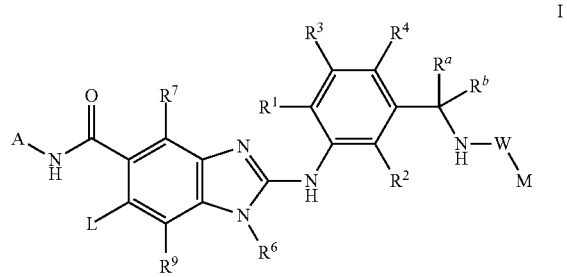

in which $R^1$ represents halo, OH, —CN, $C_{1-3}$ alkyl, $C_{2-6}$ alkynyl, $OC_{1-3}$ alkyl which latter three groups are optionally substituted by one or more substituents selected from fluoro, —CN, =O, OH, —OCH$_3$, —OCF$_3$;

$R^2$ represents halo, —CN, $C_{1-3}$ alkyl, $OC_{1-3}$ alkyl which latter two groups are optionally substituted by one or more substituents selected from fluoro, —CN, =O, OH, —OCH$_3$, —OCF$_3$;

$R^3$ and $R^4$ independently represent hydrogen, halo, —CN, $C_{1-3}$ alkyl, $OC_{1-3}$ alkyl which latter two groups are optionally substituted by one or more substituents selected from fluoro, —CN, =O, OH, —OCH$_3$, —OCF$_3$;

$R^a$, $R^b$ independently represent hydrogen, $C_{1-3}$ alkyl optionally substituted by one or more fluoro atoms,
or both together with the carbon atom which they are bound to, form a $C_{3-7}$ cycloalkylene ring, or a 4-6 membered heterocycloalkylene ring which latter two rings are optionally substituted by one or more fluorine atoms;

W represents —C(O)—, —S(O)—, —S(O)$_2$—, —C(O)O—, —C(O)NR$^d$— which groups are bound to the nitrogen of the —NH-moiety via carbon or sulfur atom;

R$^d$ represents hydrogen, C$_{1-3}$ alkyl;

M represents C$_{1-8}$ alkyl, C$_{2-8}$ alkynyl, C$_{3-8}$ cycloalkyl-C$_{0-4}$ alkyl,
  4-10 membered heterocycloalkyl-C$_{0-4}$ alkyl- which latter four groups are optionally substituted by one or more groups selected from
    fluoro, —OH, =O, —CN, —NH$_2$, C$_{1-3}$ alkyl, —NH(C$_{1-3}$ alkyl), —N(C$_{1-3}$ alkyl)$_2$, azetidinyl, pyrrolidinyl, piperidinyl, —OC$_{1-3}$ alkyl [which latter seven alkyl groups can be substituted by one or more substituents selected from fluoro, OH, —CN, OC$_{1-2}$ alkyl (which latter alkyl group is optionally substituted by one or more fluorine atoms)],
    aryl, heteroaryl [which latter two groups are optionally substituted by one or more substituents selected from halo, OH, —CN, C$_{1-3}$ alkyl, OC$_{1-3}$ alkyl (which latter two alkyl groups are optionally substituted by one or more fluorine atoms)],
    or
  aryl, heteroaryl which latter two groups are optionally substituted by one or more substituents selected from
    halo, —OH, —CN, —NH$_2$, aryl, heteroaryl [which latter two groups are optionally substituted by one or more substituents selected from halo, OH, —CN, C$_{1-3}$ alkyl, —OC$_{1-3}$ alkyl (which latter two alkyl groups are optionally substituted by one or more fluorine atoms)],
    C$_{1-7}$alkyl, C$_{2-7}$ alkynyl, C$_{3-7}$ cycloalkyl, 4-7 membered heterocycloalkyl, —NH(C$_{1-3}$ alkyl), —N(C$_{1-3}$ alkyl)$_2$, —OC$_{1-3}$ alkyl, —O—C$_{0-2}$alkyl-aryl, —SC$_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH(C$_{1-3}$ alkyl), —N(C$_{1-3}$ alkyl)$_2$, —OH, —OC$_{1-3}$alkyl)];

R$^6$ represents hydrogen, C$_{1-3}$ alkyl, C$_{3-6}$ alkynyl, 4-7 membered hetero-cycloalkyl-C$_{0-2}$ alkyl or C$_{3-7}$cycloalkyl-C$_{0-2}$ alkyl [which latter four groups are optionally substituted by one or more substituents selected from fluoro, —CN, =O, —C(O)—NH$_2$, —C(O)—NH(C$_{1-3}$ alkyl), —C(O)—N(C$_{1-3}$ alkyl)$_2$, C$_{1-3}$ alkyl optionally substituted by OH or fluoro, —OH, —NH$_2$, —OC$_{1-3}$ alkyl, —NH(C$_{1-3}$ alkyl), —N(C$_{1-3}$ alkyl)$_2$];

R$^7$ and R$^9$ independently represent hydrogen, halo, —CN, C$_{1-5}$ alkyl, C$_{3-5}$ cycloalkyl-C$_{0-2}$ alkyl-, C$_{1-5}$ alkyl-O—, C$_{3-5}$cycloalkyl-C$_{0-2}$ alkyl-O— (in which latter four groups the alkyl and cycloalkyl fragments are optionally substituted by one or more substituents selected from fluoro, —CN, =O, OH, —OC$_{1-3}$ alkyl or by one or more C$_{1-3}$ alkyl groups which are optionally substituted by one or more fluorine atoms);

L represents —NH$_2$. —NHR$^{10}$, —NR$^{10}$R$^{11}$, or a
  4-10-membered heterocycloalkyl group which is bound to the benzimidazole through a nitrogen atom and which can optionally be annulated to a phenyl or a 5- or 6-membered heteroaryl ring and which is optionally substituted by one or more substituents R$^{12}$;

R$^{10}$ and R$^{11}$ independently represent C$_{1-7}$alkyl, C$_{3-6}$ alkynyl, C$_{3-7}$ cycloalkyl-C$_{0-4}$ alkyl- or C$_{4-7}$ heterocycloalkyl-C$_{0-4}$ alkyl- [which latter four groups are optionally substituted by one or more groups selected from fluoro, —OH, NH$_2$, —C(O)NH$_2$, —CN, =O, C$_{1-3}$ alkyl, —NH(C$_{1-3}$ alkyl), —N(C$_{1-3}$ alkyl)$_2$, —OC$_{1-5}$ alkyl, —OC$_{3-6}$ cycloalkyl, —OC$_{4-6}$ heterocycloalkyl, —SC$_{1-3}$ alkyl, —S(O)C$_{1-3}$ alkyl, —S(O)$_2$C$_{1-3}$ alkyl (which latter nine groups are optionally substituted by one or more substituents selected from fluoro, —CF$_3$, —CHF$_2$, —CH$_2$F, —CH$_3$)],
  or
  aryl-C$_{0-4}$ alkyl-, heteroaryl-C$_{0-4}$ alkyl- [which latter two groups are optionally substituted by one or more substituents selected from halo, —OH, —NH$_2$, —CN, C$_{1-3}$ alkyl, C$_{3-5}$ cycloalkyl, C$_{1-3}$ alkyl-O—, C$_{3-5}$ cycloalkyl-O— (which latter four groups are optionally substituted by one or more fluorine atoms)];

each R$^{12}$ independently represents halo, —OH, —NH$_2$, =O, —CN, —C(=O)—NH$_2$, C$_{1-4}$ alkyl, C$_{3-5}$ cycloalkyl-C$_{0-2}$ alkyl-, C$_{4-5}$ heterocycloalkyl-C$_{0-2}$ alkyl-, C$_{1-4}$ alkyl-O—, C$_{1-3}$ alkyl-C(=O)—, —C(=O)—NH(C$_{1-3}$ alkyl), —C(=O)—N(C$_{1-3}$ alkyl)$_2$ [which latter seven groups are optionally substituted by one or more groups selected from: fluoro, —OH, oxo, —NH$_2$, —CN, C$_{1-3}$ alkyl, —NH(C$_{1-3}$ alkyl), —N(C$_{1-3}$ alkyl)$_2$, —OC$_{1-3}$ alkyl, —OC$_{3-5}$ cycloalkyl [which latter five groups are optionally substituted by one or more substituents selected from fluoro, —CF$_3$, —CHF$_2$, —CH$_2$F],
  or
  aryl-C$_{0-4}$ alkyl-, heteroaryl-C$_{0-4}$ alkyl- [which latter two groups are optionally substituted by one or more substituents selected from halo, —OH, —CN, C$_{1-3}$ alkyl, C$_{3-5}$ cycloalkyl, C$_{1-3}$ alkyl-O—, C$_{3-5}$ cycloalkyl-O- (which latter four groups are optionally substituted by one or more fluorine atoms)];

A represents C$_{1-8}$ alkyl, C$_{3-8}$ alkynyl, aryl-C$_{0-3}$alkyl-, C$_{3-8}$cycloalkyl-C$_{0-3}$alkyl-, 4-7 membered heterocycloalkyl-C$_{0-3}$ alkyl-, heteroaryl-C$_{0-3}$alkyl- in which latter six groups the alkyl-, alkynyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each R$^{14}$ independently represents fluoro, —OH, —CN, =O, —NH$_2$, —NH(C$_{1-3}$ alkyl), —N(C$_{1-3}$ alkyl)$_2$, —OC$_{1-6}$ alkyl, C$_{1-6}$alkyl [in which latter four groups the alkyl fragments are optionally substituted by one or more substituents selected from fluoro, —CN, =O, —NH$_2$, —NH(C$_{1-3}$ alkyl), N(C$_{1-3}$ alkyl)$_2$, —OH, —OC$_{1-3}$ alkyl] or aryl, heteroaryl [which latter two groups are optionally substituted by one or more substituents selected from halo, OH, —CN, C$_{1-3}$ alkyl, OC$_{1-3}$ alkyl (which latter two alkyl groups are optionally substituted by one or more fluorine atoms)];

each R$^{15}$ independently represents halo, —OH, —CN, —NH$_2$, —NH(C$_{1-3}$ alkyl), —N(C$_{1-3}$ alkyl)$_2$, —OC$_{1-3}$ alkyl [in which latter three groups the alkyl fragments are optionally substituted by one or more substituents selected from fluoro, —CN, =O, —NH$_2$, —NH(C$_{1-3}$ alkyl), N(C$_{1-3}$ alkyl)$_2$, —OH, —OC$_{1-3}$ alkyl] or aryl, heteroaryl [which latter two groups are optionally substituted by one or more substituents selected from halo, OH, —CN, C$_{1-3}$ alkyl, OC$_{1-3}$ alkyl (which latter two alkyl groups are optionally substituted by one or more fluorine atoms)] or C$_{1-7}$alkyl, C$_{2-7}$ alkynyl, C$_{3-7}$ cycloalkyl, 4-7 membered heterocycloalkyl [which latter alkyl, alkynyl, heterocycloalkyl or cycloalkyl groups are optionally substituted by one or more substituents selected from fluoro, —CN, =O, —NH$_2$, —NH(C$_{1-3}$ alkyl), N(C$_{1-3}$ alkyl)$_2$, —OH, OC$_{1-3}$alkyl];

or a salt thereof, particularly a physiologically acceptable salt thereof.

Alternatively, the present invention provides a compound of formula I, in which $R^1$ represents halo, OH, —CN, $C_{1-3}$ alkyl, $C_{2-6}$ alkynyl, $OC_{1-3}$ alkyl which latter three groups are optionally substituted by one or more substituents selected from fluoro, —CN, =O, OH, —OCH$_3$, —OCF$_3$;

$R^2$ represents halo, —CN, $C_{1-3}$ alkyl, $OC_{1-3}$ alkyl which latter two groups are optionally substituted by one or more substituents selected from fluoro, —CN, =O, OH, —OCH$_3$, —OCF$_3$;

$R^3$ and $R^4$ independently represent hydrogen, halo, —CN, $C_{1-3}$ alkyl, $OC_{1-3}$ alkyl which latter two groups are optionally substituted by one or more substituents selected from fluoro, —CN, =O, OH, —OCH$_3$, —OCF$_3$;

$R^a$, $R^b$ independently represent hydrogen, $C_{1-3}$ alkyl optionally substituted by one or more fluoro atoms,
  or both together with the carbon atom which they are bound to, form a $C_{3-7}$ cycloalkylene ring, or a 4-6 membered heterocycloalkylene ring which latter two rings are optionally substituted by one or more fluorine atoms;

W represents —C(O)—, —S(O)—, —S(O)$_2$—, —C(O)O—, —C(O)NR$^d$— which groups are bound to the nitrogen of the —NH-moiety via carbon or sulfur atom;

$R^d$ represents hydrogen, $C_{1-3}$ alkyl;

M represents $C_{1-8}$ alkyl, $C_{2-8}$ alkynyl, $C_{3-8}$ cycloalkyl-$C_{0-4}$ alkyl,
  4-10 membered heterocycloalkyl-$C_{0-4}$alkyl- which latter four groups are optionally substituted by one or more groups selected from
    fluoro, —OH, =O, —CN, —NH$_2$, $C_{1-3}$ alkyl, —NH($C_{1-3}$ alkyl), —N($C_{1-3}$ alkyl)$_2$, azetidinyl, pyrrolidinyl, piperidinyl, —OC$_{1-3}$ alkyl [which latter seven alkyl groups can be substituted by one or more substituents selected from fluoro, OH, —CN, $OC_{1-2}$ alkyl (which latter alkyl group is optionally substituted by one or more fluorine atoms)],
    aryl, heteroaryl [which latter two groups are optionally substituted by one or more substituents selected from halo, OH, —CN, $C_{1-3}$ alkyl, $OC_{1-3}$ alkyl (which latter two alkyl groups are optionally substituted by one or more fluorine atoms)],
    or
  aryl, heteroaryl which latter two groups are optionally substituted by one or more substituents selected from
    halo, —OH, —CN, —NH$_2$, aryl, heteroaryl [which latter two groups are optionally substituted by one or more substituents selected from halo, OH, —CN, $C_{1-3}$ alkyl, —OC$_{1-3}$ alkyl (which latter two alkyl groups are optionally substituted by one or more fluorine atoms)],
    $C_{1-7}$alkyl, $C_{2-7}$ alkynyl, $C_{3-7}$ cycloalkyl, 4-7 membered heterocycloalkyl, —NH$_2$, —NH($C_{1-3}$ alkyl), —N($C_{1-3}$ alkyl)$_2$, —OC$_{1-3}$ alkyl, —O—C$_{0-2}$alkyl-aryl, —SC$_{1-3}$ alkyl, (which latter alkyl, alkynyl, heterocycloalkyl, aryl or cycloalkyl groups are optionally substituted by one or more substituents selected from fluoro, —CN, =O, —NH$_2$, —NH($C_{1-3}$ alkyl), —N($C_{1-3}$ alkyl)$_2$, —OH, —OC$_{1-3}$alkyl)];

$R^6$ represents hydrogen, $C_{1-5}$ alkyl, $C_{3-6}$ alkynyl, 4-7 membered hetero-cycloalkyl-$C_{0-2}$ alkyl or $C_{3-7}$cycloalkyl-$C_{0-2}$ alkyl (which latter four groups are optionally substituted by one or more substituents selected from fluoro, —CN, =O, $C_{1-3}$ alkyl, —OH, —NH$_2$, —OC$_{1-3}$ alkyl, —NH($C_{1-3}$ alkyl), —N($C_{1-3}$ alkyl)$_2$);

$R^7$ and $R^9$ independently represent hydrogen, halo, —CN, $C_{1-5}$ alkyl, $C_{3-5}$ cycloalkyl-$C_{0-2}$ alkyl-, $C_{1-5}$ alkyl-O—, $C_{3-5}$cycloalkyl-$C_{0-2}$ alkyl-O— (in which latter four groups the alkyl and cycloalkyl fragments are optionally substituted by one or more substituents selected from fluoro, —CN, =O, OH, —OC$_{1-3}$ alkyl or by one or more $C_{1-3}$ alkyl groups which are optionally substituted by one or more fluorine atoms);

L represents —NH$_2$, —NHR$^{10}$, —NR$^{10}$R$^{11}$, or a 4-10-membered heterocycloalkyl group which is bound to the benzimidazole through a nitrogen atom, and which is optionally substituted by one or more substituents $R^{12}$;

$R^{10}$ and $R^{11}$ independently represent $C_{1-7}$alkyl, $C_{3-7}$ cycloalkyl-$C_{0-4}$ alkyl- or $C_{4-7}$ heterocycloalkyl-$C_{0-4}$ alkyl- [which latter three groups are optionally substituted by one or more groups selected from fluoro, —OH, NH$_2$, —CN, $C_{1-3}$ alkyl, —NH($C_{1-3}$ alkyl), —N($C_{1-3}$ alkyl)$_2$, —OC$_{1-5}$ alkyl, —OC$_{3-6}$ cycloalkyl, —OC$_{4-6}$ heterocycloalkyl (which latter six groups are optionally substituted by one or more substituents selected from fluoro, —CF$_3$, —CHF$_2$, —CH$_2$F, —CH$_3$)],
  or
  aryl-$C_{0-4}$ alkyl-, heteroaryl-$C_{0-4}$ alkyl- [which latter two groups are optionally substituted by one or more substituents selected from halo, —OH, —CN, $C_{1-3}$ alkyl, $C_{3-5}$ cycloalkyl, $C_{1-3}$ alkyl-O—, $C_{3-5}$ cycloalkyl-O- (which latter four groups are optionally substituted by one or more fluorine atoms)];

each $R^{12}$ independently represents halo, —OH, —NH$_2$, =O, —CN, $C_{1-4}$ alkyl, $C_{3-5}$ cycloalkyl-$C_{0-2}$ alkyl-, $C_{4-5}$ heterocycloalkyl-$C_{0-2}$ alkyl-, $C_{1-4}$ alkyl-O—, $C_{1-3}$ alkyl-C(=O)—, —C(=O)—NH($C_{1-3}$ alkyl), —C(=O)—N($C_{1-3}$ alkyl)$_2$ [which latter six groups are optionally substituted by one or more groups selected from: fluoro, —OH, oxo, —NH$_2$, —CN, $C_{1-3}$ alkyl, —NH($C_{1-3}$ alkyl), —N($C_{1-3}$ alkyl)$_2$, —OC$_{1-3}$ alkyl, —OC$_{3-5}$ cycloalkyl [which latter five groups are optionally substituted by one or more substituents selected from fluoro, —CF$_3$, —CHF$_2$, —CH$_2$F],
  or
  aryl-$C_{0-4}$ alkyl-, heteroaryl-$C_{0-4}$ alkyl- [which latter two groups are optionally substituted by one or more substituents selected from halo, —OH, —CN, $C_{1-3}$ alkyl, $C_{3-5}$ cycloalkyl, $C_{1-3}$ alkyl-O—, $C_{3-5}$ cycloalkyl-O- (which latter four groups are optionally substituted by one or more fluorine atoms)];

A represents $C_{1-8}$ alkyl, $C_{3-8}$ alkynyl, aryl-$C_{0-3}$alkyl-, $C_{3-8}$ cycloalkyl-$C_{0-3}$ alkyl-, 4-7 membered heterocycloalkyl-$C_{0-3}$ alkyl-, heteroaryl-$C_{0-3}$alkyl- in which latter six groups the alkyl-, alkynyl-, cycloalkyl- and heterocycloalkyl-fragments are optionally substituted by one or more substituents selected from $R^{14}$ and the aryl and heteroaryl fragments are optionally substituted by one or more substituents selected from $R^{15}$;

each $R^{14}$ independently represents fluoro, —OH, —CN, =O, —NH$_2$, —NH($C_{1-3}$ alkyl), —N($C_{1-3}$ alkyl)$_2$, —OC$_{1-6}$ alkyl, $C_{1-6}$alkyl (in which latter four groups the alkyl fragments are optionally substituted by one or more substituents selected from fluoro, —CN, =O, —NH$_2$, —NH($C_{1-3}$ alkyl), N($C_{1-3}$ alkyl)$_2$, —OH, —OC$_{1-3}$ alkyl) or aryl, heteroaryl [which latter two groups are optionally substituted by one or more substituents selected from halo, OH, —CN, $C_{1-3}$ alkyl, $OC_{1-3}$ alkyl (which latter two alkyl groups are optionally substituted by one or more fluorine atoms)];

each $R^{15}$ independently represents halo, —OH, —CN, —NH$_2$, —NH($C_{1-3}$ alkyl), —N($C_{1-3}$ alkyl)$_2$, —OC$_{1-3}$ alkyl, aryl, heteroaryl [which latter two groups are optionally substituted by one or more substituents selected from halo, OH, —CN, $C_{1-3}$ alkyl, $OC_{1-3}$ alkyl (which latter two alkyl groups are optionally substituted by one or more fluorine atoms)], $C_{1-7}$alkyl, $C_{2-7}$ alkynyl, $C_{3-7}$ cycloalkyl, 4-7 membered heterocycloalkyl (which latter alkyl, alkynyl, heterocycloalkyl or cycloalkyl groups are optionally substituted by one or more substituents selected from fluoro, —CN, =O, —NH$_2$, —NH(C$_{1-3}$ alkyl), N(C$_{1-3}$ alkyl)$_2$, —OH, OC$_{1-3}$alkyl);

or a salt thereof, particularly a physiologically acceptable salt thereof.

In a second embodiment, in the general formula I, A, L, M, W, R$^2$, R$^3$, R$^4$, R$^6$, R$^7$, R$^9$, R$^a$, R$^b$ have the same meaning as defined in any of the preceding embodiments, and R$^1$ represents halo, C$_{1-3}$ alkyl, —OC$_{1-3}$ alkyl which latter two groups are optionally substituted by one or more fluorine atoms.

In another embodiment, in the general formula I, A, L, M, W, R$^1$, R$^3$, R$^4$, R$^6$, R$^7$, R$^9$, R$^a$, R$^b$ have the same meaning as defined in any of the preceding embodiments, and R$^2$ represents halo, C$_{1-3}$ alkyl optionally substituted by one or more fluorine atoms.

In another embodiment, in the general formula I, A, L, M, W, R$^1$, R$^2$, R$^6$, R$^a$, R$^b$ have the same meaning as defined in any of the preceding embodiments, and R$^3$, R$^4$, R$^7$ and R$^9$ independently represent hydrogen, fluoro, chloro, methyl.

In another embodiment, in the general formula I, A, L, M, W, R$^1$, R$^2$, R$^3$, R$^4$, R$^6$, R$^7$, R$^9$ have the same meaning as defined in any of the preceding embodiments, and R$^a$ and R$^b$ represent hydrogen.

In another embodiment, in the general formula I, A, L, M, R$^1$, R$^2$, R$^3$, R$^4$, R$^6$, R$^7$, R$^9$, R$^a$, R$^b$ have the same meaning as defined in any of the preceding embodiments, and W represents —C(O)—, —S(O)$_2$—, —C(O)O— which groups are bound to the nitrogen of the —NH— moiety via carbon or sulfur atom.

In another embodiment, in the general formula I, A, L, W, R$^1$, R$^2$, R$^3$, R$^4$, R$^6$, R$^7$, R$^9$, R$^a$, R$^b$ have the same meaning as defined in any of the preceding embodiments, and M represents C$_{1-6}$ alkyl, C$_{3-8}$ cycloalkyl-C$_{0-1}$ alkyl- [which latter two groups are optionally substituted by one or more groups selected from fluoro, —OH, C$_{1-3}$ alkyl optionally substituted by —OH or one or more fluorine atoms];

or phenyl, pyrazolyl, imidazolyl, 1,2,3-triazolyl, 1,2,4-triazolyl, oxazolyl, isoxazolyl, thiazolyl, pyridinyl, pyridazinyl, pyrazinyl or

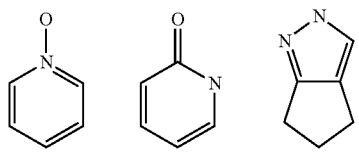

all of which groups are optionally substituted by one or more substituents selected from halo, —OH, —CN, —NH$_2$, C$_{1-3}$ alkyl, —NH(C$_{1-3}$alkyl), —N(C$_{1-3}$alkyl)$_2$, —OC$_{1-3}$ alkyl (which latter alkyl groups are optionally substituted by one or more substituents selected from fluoro or —OH).

In another embodiment, in the general formula I, A, L, W, R$^1$, R$^2$, R$^3$, R$^4$, R$^6$, R$^7$, R$^9$, R$^a$, R$^b$ have the same meaning as defined in any of the preceding embodiments, and M represents C$_{1-6}$ alkyl, C$_{3-8}$ cycloalkyl-C$_{0-1}$ alkyl- [which latter two groups are optionally substituted by one or more groups selected from fluoro, C$_{1-3}$ alkyl optionally substituted by one or more fluorine atoms].

In another embodiment, in the general formula I, A, L, M, W, R$^1$, R$^2$, R$^3$, R$^4$, R$^7$, R$^9$, R$^a$, R$^b$ have the same meaning as defined in any of the preceding embodiments, and R$^6$ represents hydrogen, C$_{1-5}$ alkyl or C$_{3-7}$cycloalkyl-C$_{0-2}$ alkyl [which latter two groups are optionally substituted by one or more substituents selected from fluoro, —OH, C$_{1-3}$ alkyl optionally substituted by OH, —OC$_{1-3}$ alkyl or —C(O)—NH$_2$].

In another embodiment, in the general formula I, A, L, M, W, R$^1$, R$^2$, R$^3$, R$^4$, R$^7$, R$^9$, R$^a$, R$^b$ have the same meaning as defined in any of the preceding embodiments, and R$^6$ represents hydrogen, C$_{1-5}$ alkyl or C$_{3-7}$cycloalkyl-C$_{0-2}$ alkyl [which latter two groups are optionally substituted by one or more substituents selected from fluoro, C$_{1-3}$ alkyl, —OC$_{1-3}$ alkyl].

In another embodiment, in the general formula I, L, M, W, R$^1$, R$^2$, R$^3$, R$^4$, R$^6$, R$^7$, R$^9$, R$^a$, R$^b$ have the same meaning as defined in any of the preceding embodiments, and A represents C$_{1-6}$ alkyl, aryl-C$_{0-3}$alkyl-, C$_{3-8}$cycloalkyl-C$_{0-3}$alkyl-,
4-7 membered heterocycloalkyl-C$_{0-3}$ alkyl-, heteroaryl-C$_{0-3}$alkyl- in which latter groups the alkyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each R$^{14}$ independently represents fluoro, C$_{1-3}$alkyl optionally substituted by one or more fluorine atoms, phenyl optionally substituted by one or more halogen atoms;

each R$^{15}$ represents independently halo, —OC$_{1-3}$ alkyl, C$_{1-5}$ alkyl [which latter two groups are optionally substituted by one or more —OH or one or more fluorine atoms].

In another embodiment, in the general formula I, L, M, W, R$^1$, R$^2$, R$^3$, R$^4$, R$^6$, R$^7$, R$^9$, R$^a$, R$^b$ have the same meaning as defined in any of the preceding embodiments, and A represents C$_{1-6}$ alkyl, aryl-C$_{0-3}$alkyl-, C$_{3-8}$cycloalkyl-C$_{0-3}$alkyl- in which groups the alkyl- or cycloalkyl-fragments are optionally substituted by one or more substituents selected from R$^{14}$ and the aryl fragments are optionally substituted by one or more substituents selected from R$^{15}$;

each R$^{14}$ independently represents fluoro, C$_{1-3}$alkyl optionally substituted by one or more fluorine atoms;

each R$^{15}$ represents independently halo, —OC$_{1-3}$ alkyl, C$_{1-3}$ alkyl [which latter two groups are optionally substituted by one or more fluorine atoms].

In another embodiment, in the general formula I, A, M, W, R$^1$, R$^2$, R$^3$, R$^4$, R$^6$, R$^7$, R$^9$, R$^a$, R$^b$ have the same meaning as defined in any of the preceding embodiments, and L represents —NH$_2$, —NHR$^{10}$, —NR$^{10}$R$^{11}$, or
azetidinyl-, pyrrolidinyl-, thiazolidinyl-, piperidinyl-, morpholinyl-, thiomorpholinyl-, piperazinyl- or

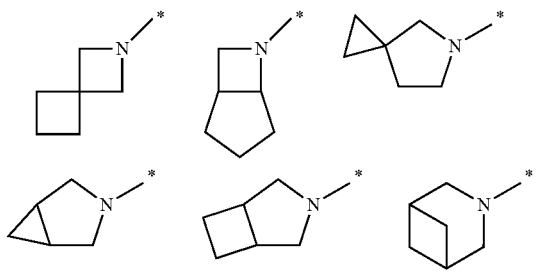

-continued

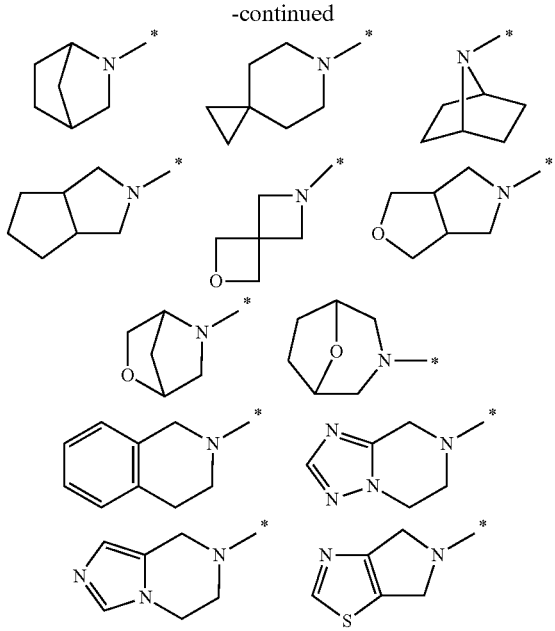

all of which heterocyclic groups are optionally substituted by one or more substituents $R^{12}$, while the above mentioned groups are bonded to the benzimidazole core through a nitrogen atom;

$R^{10}$ and $R^{11}$ independently represent $C_{1-5}$ alkyl, $C_{3-5}$ alkynyl, $C_{3-6}$ cycloalkyl-$C_{0-1}$ alkyl- or $C_{4-6}$ heterocycloalkyl-$C_{0-1}$ alkyl- [which latter four groups are optionally substituted by one or more groups selected from fluoro, —OH, —CN, =O, $C_{1-3}$ alkyl, —O$C_{1-3}$ alkyl, —C(O)—NH$_2$, —S$C_{1-3}$ alkyl, —S(O)$C_{1-3}$ alkyl, —S(O)$_2$$C_{1-3}$ alkyl (which latter five groups are optionally substituted by one or more fluorine atoms)], or phenyl-$C_{0-1}$ alkyl-, imidazolyl-$C_{0-1}$ alkyl-, triazolyl-$C_{0-1}$ alkyl- [which latter three groups are optionally substituted by one or more substituents selected from fluoro, chloro, CH$_3$, CH$_2$F, CHF$_2$, CF$_3$, —OCH$_3$, —OCH$_2$F, —OCHF$_2$, —OCF$_3$];

each $R^{12}$ independently represents fluoro, —OH, =O, —C(=O)NH$_2$, $C_{1-4}$ alkyl, $C_{3-5}$ cycloalkyl, $C_{1-4}$ alkyl-O— [which latter three groups are optionally substituted by one or more groups selected from fluoro or —OH], or phenyl optionally substituted by one or more substituents selected from halo, $C_{1-3}$ alkyl which is optionally substituted by one or more fluorine atoms.

In another embodiment, in the general formula I, A, M, W, $R^1$, $R^2$, $R^3$, $R^4$, $R^6$, $R^7$, $R^9$, $R^a$, $R^b$ have the same meaning as defined in any of the preceding embodiments, and L represents —NH$_2$, —NHR$^{10}$, —NR$^{10}$R$^{11}$, or
azetidinyl-, pyrrolidinyl-, piperidinyl-, morpholinyl-, piperazinyl- or

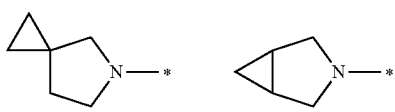

all of which heterocyclic groups are optionally substituted by one or more substituents $R^{12}$ and optionally annulated to a phenyl or a 5- or 6-membered heteroaryl ring, while the above mentioned groups are bonded to the benzimidazole core through a nitrogen atom;

$R^{10}$ and $R^{11}$ independently represent $C_{1-5}$ alkyl, $C_{3-6}$ cycloalkyl-$C_{0-1}$ alkyl- [which latter two groups are optionally substituted by one or more groups selected from fluoro, —OH, $C_{1-3}$ alkyl optionally substituted by one or more fluorine atoms], or aryl-$C_{0-1}$ alkyl- optionally substituted by one or more substituents selected from halo, —OH, —CN, $C_{1-3}$ alkyl, $C_{1-3}$ alkyl-O— [which latter two groups are optionally substituted by one or more fluorine atoms];

each $R^{12}$ independently represents fluoro, =O, $C_{1-4}$ alkyl optionally substituted by one or more fluorine atoms, or phenyl optionally substituted by one or more substituents selected from halo, $C_{1-3}$ alkyl which is optionally substituted by one or more fluorine atoms.

A further embodiment of the present invention comprises compounds of formula Ia

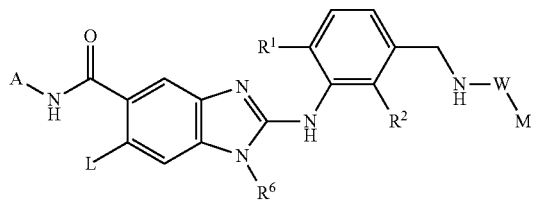

Ia in which $R^1$ represents halo, $C_{1-3}$ alkyl, —O$C_{1-3}$ alkyl which latter two groups are optionally substituted by one or more fluorine atoms;

$R^2$ represents halo, $C_{1-3}$ alkyl optionally substituted by one or more fluorine atoms;

$R^6$ represents hydrogen, $C_{1-5}$ alkyl or $C_{3-7}$cycloalkyl-$C_{0-2}$alkyl [which latter two groups are optionally substituted by one or more substituents selected from fluoro, —OH, $C_{1-3}$ alkyl optionally substituted by OH, —O$C_{1-3}$ alkyl or —C(O)—NH$_2$];

W represents —C(O)—, —S(O)$_2$—, —C(O)O— which groups are bound to the nitrogen of the —NH— moiety via carbon or sulfur atom;

M represents $C_{1-6}$ alkyl, $C_{3-8}$ cycloalkyl-$C_{0-1}$ alkyl- [which latter two groups are optionally substituted by one or more groups selected from fluoro, —OH, $C_{1-3}$ alkyl optionally substituted by —OH or one or more fluorine atoms];

or phenyl, pyrazolyl, imidazolyl, 1,2,3-triazolyl, 1,2,4-triazolyl, oxazolyl, isoxazolyl, thiazolyl, pyridinyl, pyridazinyl, pyrazinyl or

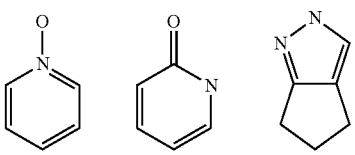

all of which groups are optionally substituted by one or more substituents selected from halo, —OH, —CN, —NH$_2$, $C_{1-3}$ alkyl, —NH($C_{1-3}$alkyl), —N($C_{1-3}$alkyl)$_2$, —OC$_{1-3}$ alkyl (which latter alkyl groups are optionally substituted by one or more substituents selected from fluoro or —OH);

A represents C$_{1-6}$ alkyl, aryl-C$_{0-3}$alkyl-, C$_{3-8}$cycloalkyl-C$_{0-3}$alkyl-, 4-7 membered heterocycloalkyl-C$_{0-3}$ alkyl-, heteroaryl-C$_{0-3}$alkyl- in which latter groups the alkyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each R$^{14}$ independently represents fluoro, C$_{1-3}$alkyl optionally substituted by one or more fluorine atoms, phenyl optionally substituted by one or more halogen atoms;

each R$^{15}$ represents independently halo, —OC$_{1-3}$ alkyl, C$_{1-6}$ alkyl [which latter two groups are optionally substituted by one or more —OH or one or more fluorine atoms];

L represents —NH$_2$, —NHR$^{10}$, —NR$^{10}$R$^{11}$, or azetidinyl-, pyrrolidinyl-, thiazolidinyl-, piperidinyl-, morpholinyl-, thiomorpholinyl-, piperazinyl- or

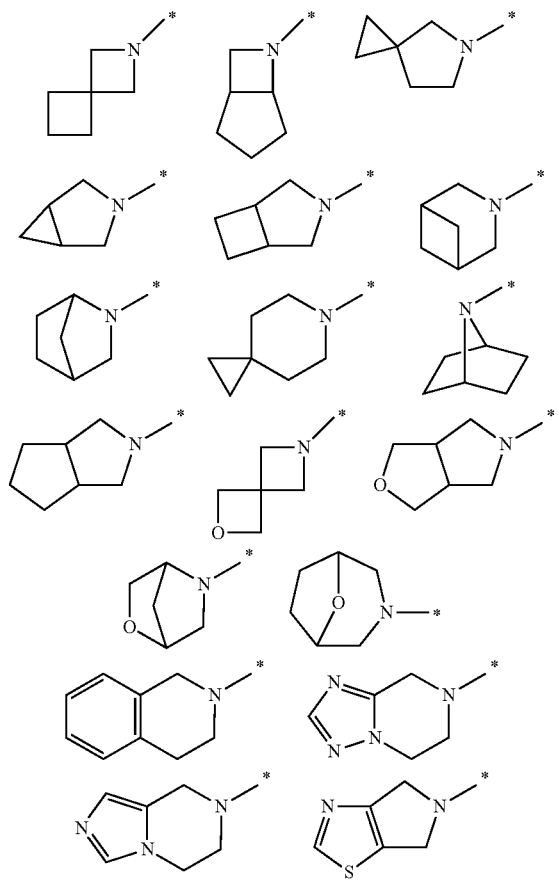

all of which heterocyclic groups are optionally substituted by one or more substituents R$^{12}$, while the above mentioned groups are bonded to the benzimidazole core through a nitrogen atom;

R$^{10}$ and R$^{11}$ independently represent C$_{1-5}$ alkyl, C$_{3-5}$ alkynyl, C$_{3-6}$ cycloalkyl-C$_{0-1}$ alkyl- or C$_{4-6}$ heterocycloalkyl-C$_{0-1}$ alkyl- [which latter four groups are optionally substituted by one or more groups selected from fluoro, —OH, —CN, =O, C$_{1-3}$ alkyl, —OC$_{1-3}$ alkyl, —C(O)—NH$_2$, —SC$_{1-3}$ alkyl, —S(O)C$_{1-3}$ alkyl, —S(O)$_2$C$_{1-3}$ alkyl (which latter five groups are optionally substituted by one or more fluorine atoms)], or phenyl-C$_{0-1}$ alkyl-, imidazolyl-C$_{0-1}$ alkyl-, triazolyl-C$_{0-1}$ alkyl- [which latter three groups are optionally substituted by one or more substituents selected from fluoro, chloro, CH$_3$, CH$_2$F, CHF$_2$, CF$_3$, —OCH$_3$, —OCH$_2$F, —OCHF$_2$, —OCF$_3$];

each R$^{12}$ independently represents fluoro, —OH, =O, —C(=O)NH$_2$, C$_{1-4}$ alkyl, C$_{3-5}$cycloalkyl, C$_{1-4}$ alkyl-O— [which latter three groups are optionally substituted by one or more groups selected from fluoro or —OH], or phenyl optionally substituted by one or more substituents selected from halo, C$_{1-3}$ alkyl which is optionally substituted by one or more fluorine atoms.

A further embodiment of the present invention comprises compounds of formula Ia in which R$^1$ represents halo, C$_{1-3}$ alkyl, —OC$_{1-3}$ alkyl which latter two groups are optionally substituted by one or more fluorine atoms;

R$^2$ represents hydrogen, halo, C$_{1-3}$ alkyl optionally substituted by one or more fluorine atoms;

R$^6$ represents hydrogen, C$_{1-5}$ alkyl, C$_{3-7}$cycloalkyl-C$_{0-2}$alkyl [which latter two groups are optionally substituted by one or more substituents selected from fluoro, C$_{1-3}$ alkyl, —OC$_{1-3}$ alkyl];

W represents —C(O)—, —S(O)$_2$—, —C(O)O— which groups are bound to the nitrogen of the —NH— moiety via carbon or sulfur atom;

M represents C$_{1-6}$ alkyl, C$_{3-8}$ cycloalkyl-C$_{0-1}$ alkyl- [which latter two groups are optionally substituted by one or more groups selected from fluoro, C$_{1-3}$ alkyl optionally substituted by one or more fluorine atoms];

A represents C$_{1-6}$ alkyl, aryl-C$_{0-3}$alkyl-, C$_{3-8}$cycloalkyl-C$_{0-3}$alkyl- in which latter three groups the alkyl- or cycloalkyl-fragments are optionally substituted by one or more substituents selected from R$^{14}$ and the aryl fragments are optionally substituted by one or more substituents selected from R$^{15}$;

each R$^{14}$ independently represents fluoro, C$_{1-3}$alkyl optionally substituted by one or more fluorine atoms;

each R$^{15}$ independently represents halo, —OC$_{1-3}$ alkyl, C$_{1-3}$ alkyl [which latter two groups are optionally substituted by one or more fluorine atoms];

L represents —NH$_2$, —NHR$^{10}$, —NR$^{10}$R$^{11}$, or azetidinyl-, pyrrolidinyl-, piperidinyl-, morpholinyl-, piperazinyl- or

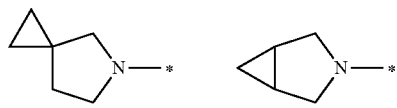

all of which heterocyclic groups can optionally be substituted by one or more substituents R$^{12}$ and optionally annulated to a phenyl or a 5- or 6-membered heteroaryl ring, while the above mentioned groups are bonded to the benzimidazole core through a nitrogen atom;

R$^{10}$ and R$^{11}$ independently represent C$_{1-5}$ alkyl, C$_{3-6}$ cycloalkyl-C$_{0-1}$ alkyl- [which latter two groups are optionally substituted by one or more groups selected from fluoro, —OH, C$_{1-3}$ alkyl optionally substituted by one or more fluorine atoms], or
  aryl-$C_{0-1}$ alkyl- optionally substituted by one or more substituents selected from halo, —OH, —CN, $C_{1-3}$ alkyl, $C_{1-3}$ alkyl-O— [which latter two groups are optionally substituted by one or more fluorine atoms];
each $R^{12}$ independently represents fluoro, =O, $C_{1-4}$ alkyl optionally substituted by one or more fluorine atoms,
or
  phenyl optionally substituted by one or more substituents selected from halo, $C_{1-3}$ alkyl which is optionally substituted by one or more fluorine atoms.

In another embodiment, in the general formula I or Ia, L, M, W, $R^1$, $R^2$, $R^3$, $R^4$, $R^6$, $R^7$, $R^9$, $R^a$, $R^b$ have the same meaning as defined in any of the preceding embodiments, and A represents phenyl-$C_{0-2}$ alkyl-, pyridyl-$C_{0-1}$ alkyl-, pyrimidinyl-$C_{0-1}$ alkyl-, thienyl-$C_{0-1}$ alkyl-, thiazolyl-$C_{0-1}$ alkyl-, thiadiazolyl-$C_{0-1}$ alkyl-, isoxazolyl-$C_{0-1}$ alkyl-, $C_{1-6}$ alkyl,
  $C_{3-6}$cycloalkyl-$C_{0-1}$ alkyl-, piperidin-4-yl [in which groups the alkyl- or cycloalkyl- and piperidin-4-yl fragments are optionally substituted by one or more substituents selected from $R^{14}$ and the phenyl or heteroaryl fragments are optionally substituted by one or more substituents selected from $R^{15}$;
each $R^{14}$ independently represents fluoro, $CH_3$, $CH_2F$, $CHF_2$, $CF_3$, ethyl optionally substituted by one or more fluorine atoms, phenyl optionally substituted by one or more fluorine or chlorine atoms;
each $R^{15}$ represents independently fluoro, chloro, $CH_3$, $CH_2F$, $CHF_2$, $CF_3$, $C_{2-4}$ alkyl optionally substituted by —OH or one or more fluorine atoms, —$OCH_3$, —$OCH_2F$, —$OCHF_2$, —$OCF_3$.

In another embodiment, in the general formula I, A, L, M, W, $R^1$, $R^2$, $R^3$, $R^4$, $R^7$, $R^9$, $R^a$, $R^b$ have the same meaning as defined in any of the preceding embodiments, and $R^6$ represents hydrogen, $CH_3$, —$CH_2CH_2F$, —$CH_2CHF_2$, —$CH_2CF_3$, tert.-butyl,

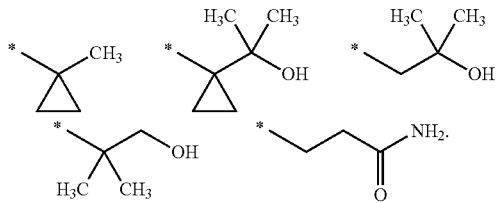

In another embodiment, in the general formula I, A, L, W, $R^1$, $R^2$, $R^3$, $R^4$, $R^6$, $R^7$, $R^9$, $R^a$, $R^b$ have the same meaning as defined in any of the preceding embodiments, and M represents a group selected from

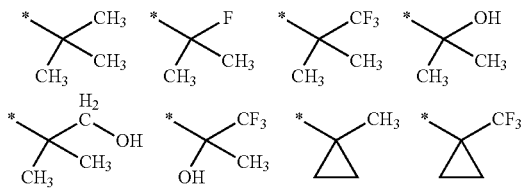

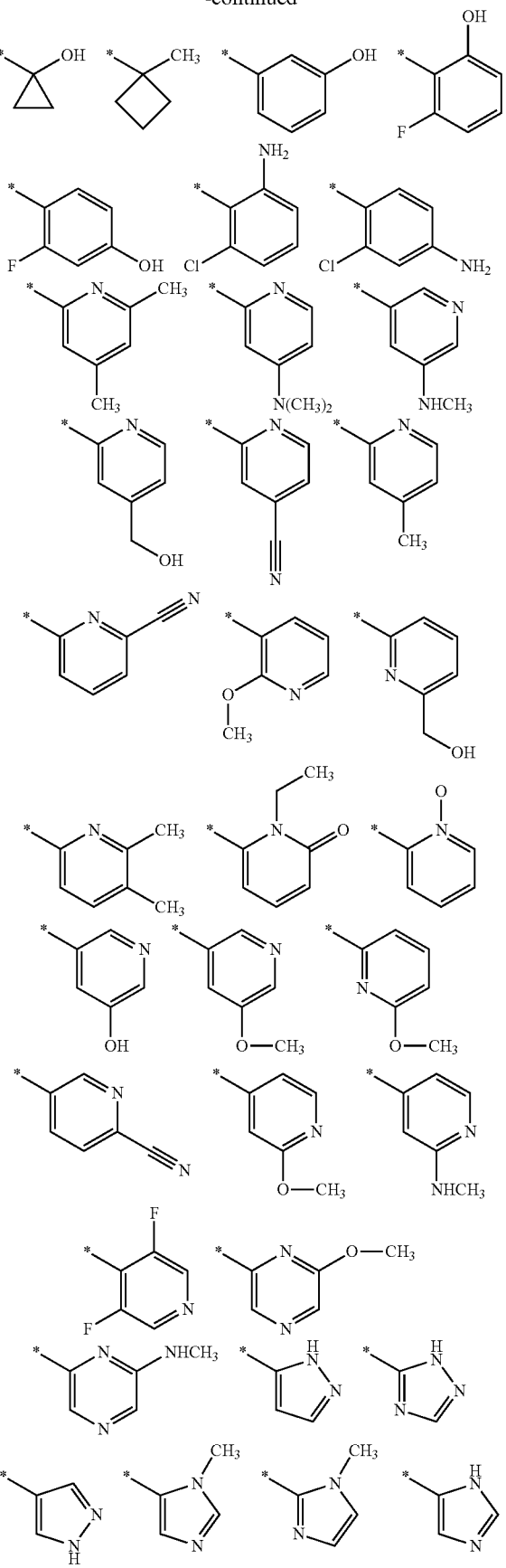

-continued

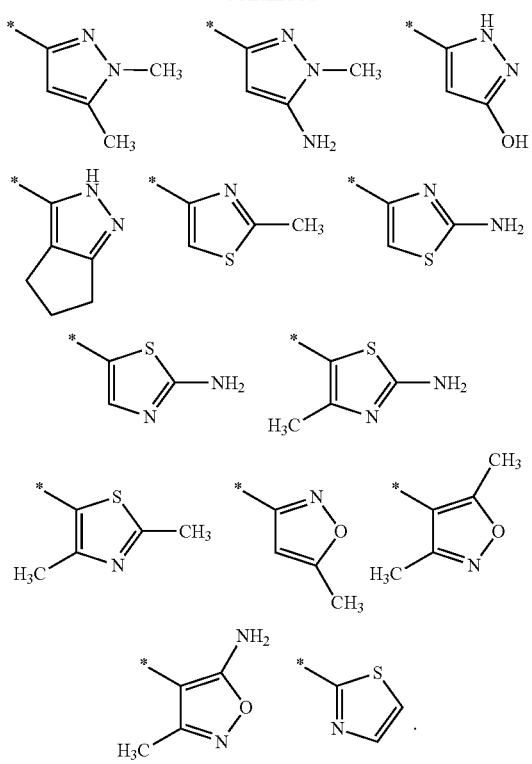

In another embodiment, in the general formula I, L, M, W, $R^1$, $R^2$, $R^3$, $R^4$, $R^6$, $R^7$, $R^9$, $R^a$, $R^b$ have the same meaning as defined in any of the preceding embodiments, and A represents a group selected from

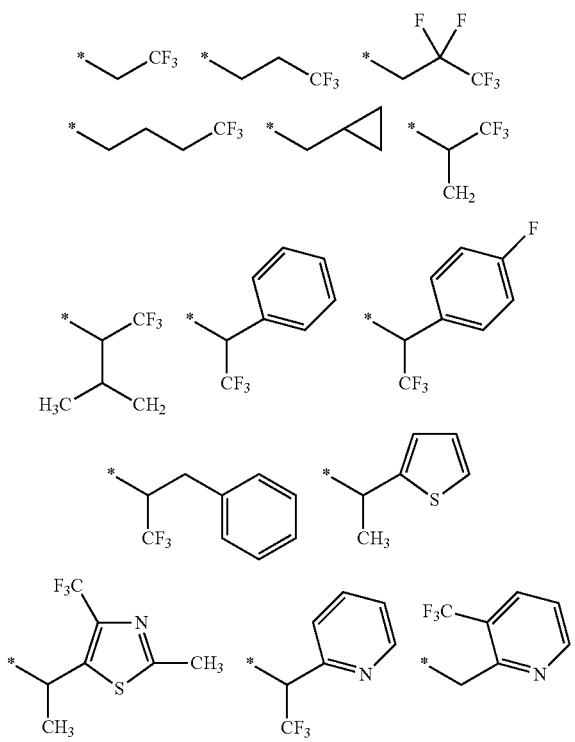

-continued

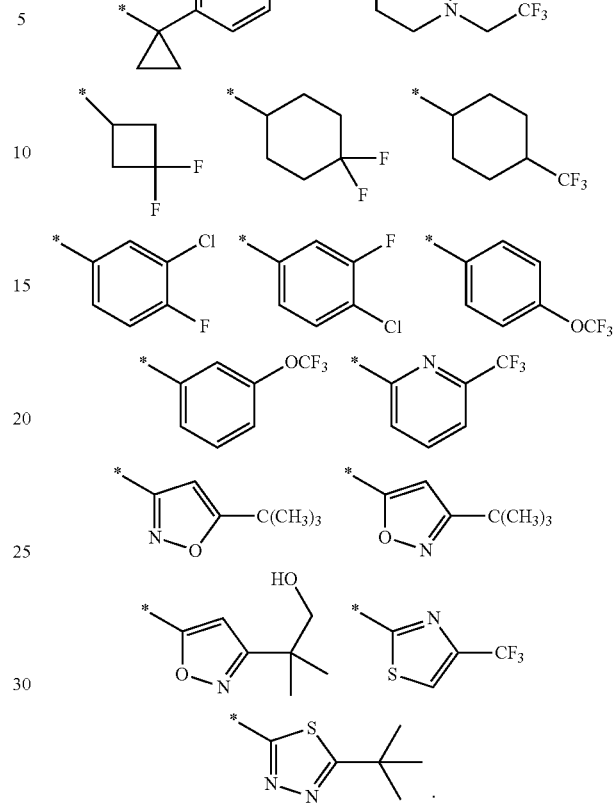

In another embodiment, in the general formula I, A, M, W, $R^1$, $R^2$, $R^3$, $R^4$, $R^6$, $R^7$, $R^9$, $R^a$, $R^b$ have the same meaning as defined in any of the preceding embodiments, and L represents a group selected from

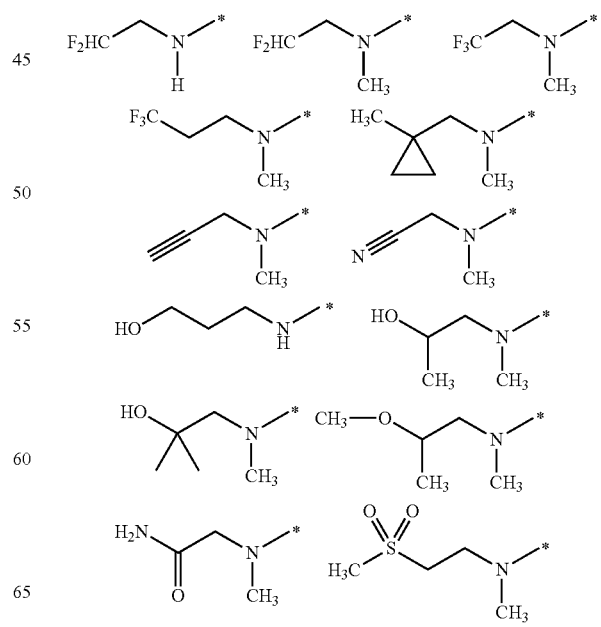

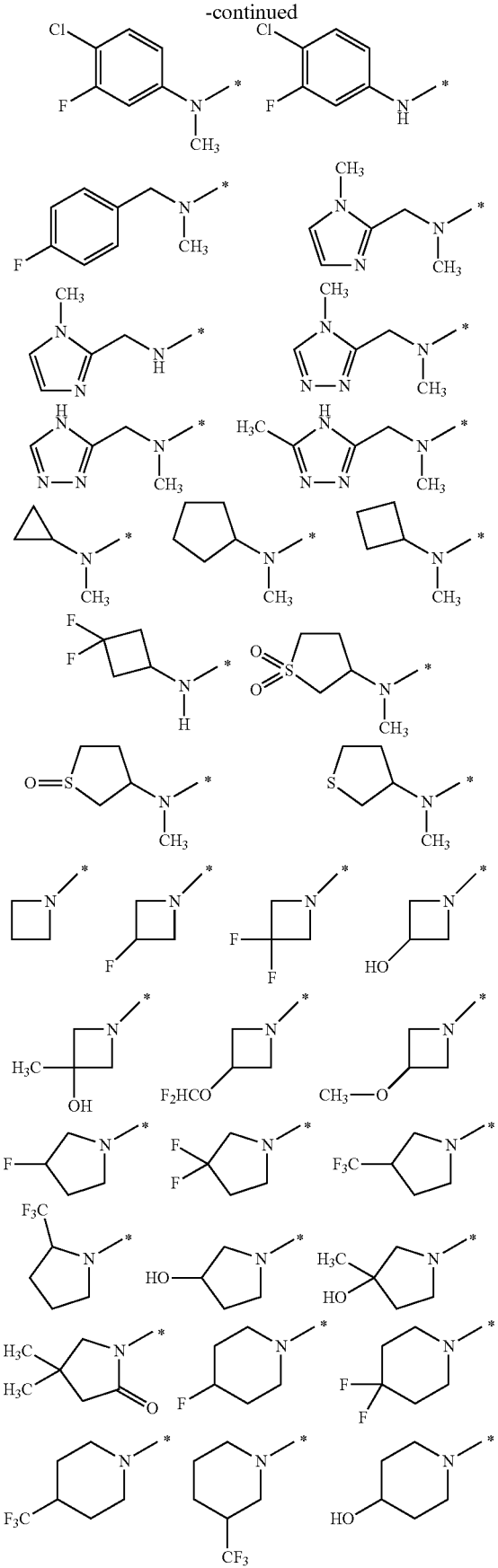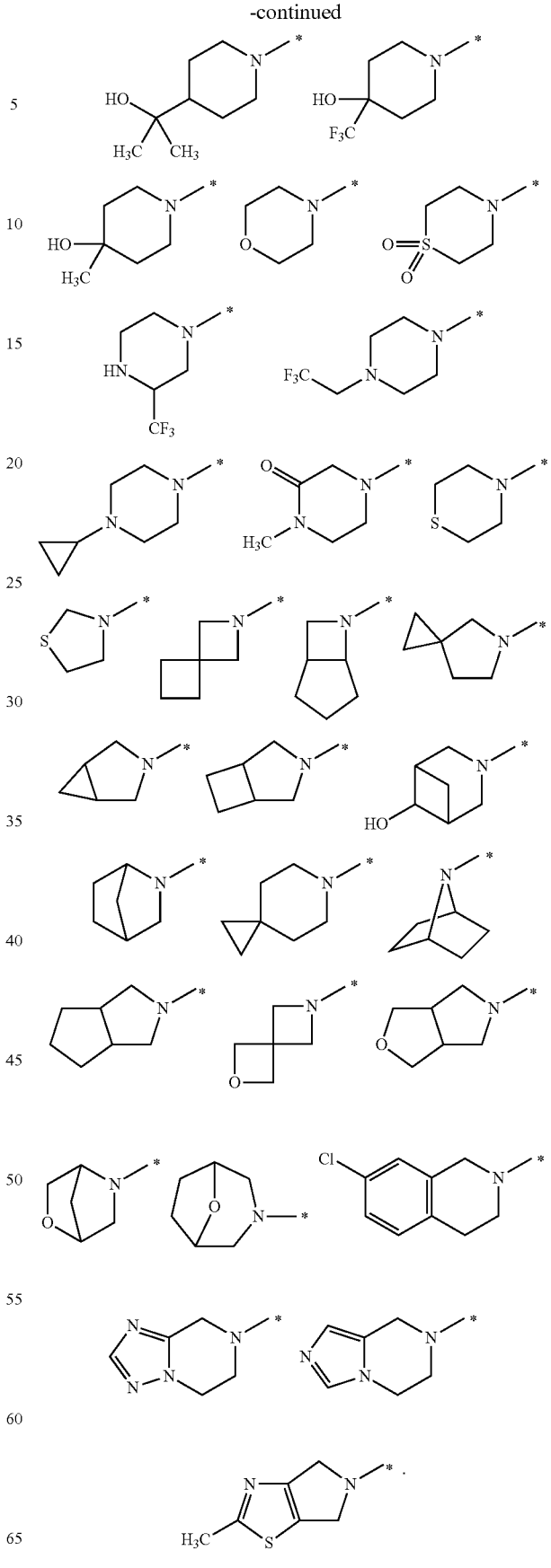

A further embodiment of the present invention comprises compounds of formula Ib
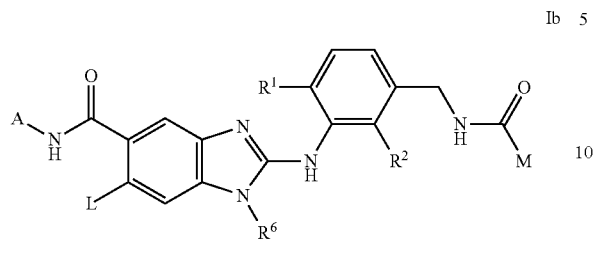
in which
R¹ represents fluoro, chloro;
R² represents fluoro, chloro;
R⁶ represents hydrogen, CH₃, —CH₂CH₂F, —CH₂CHF₂, —CH₂CF₃, tert.-butyl,
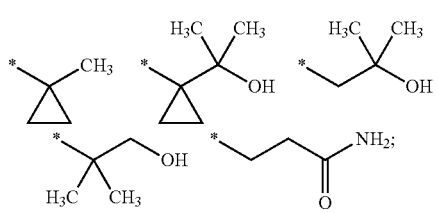
M represents a group selected from
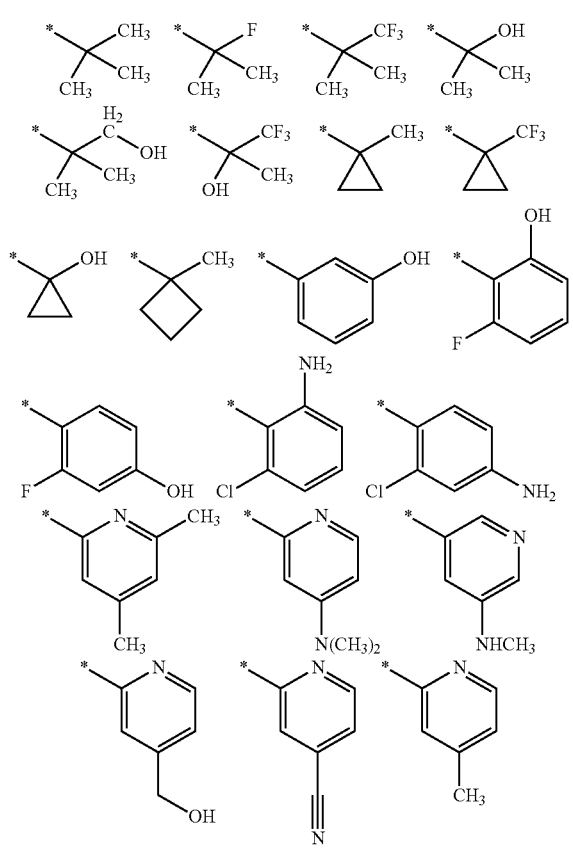
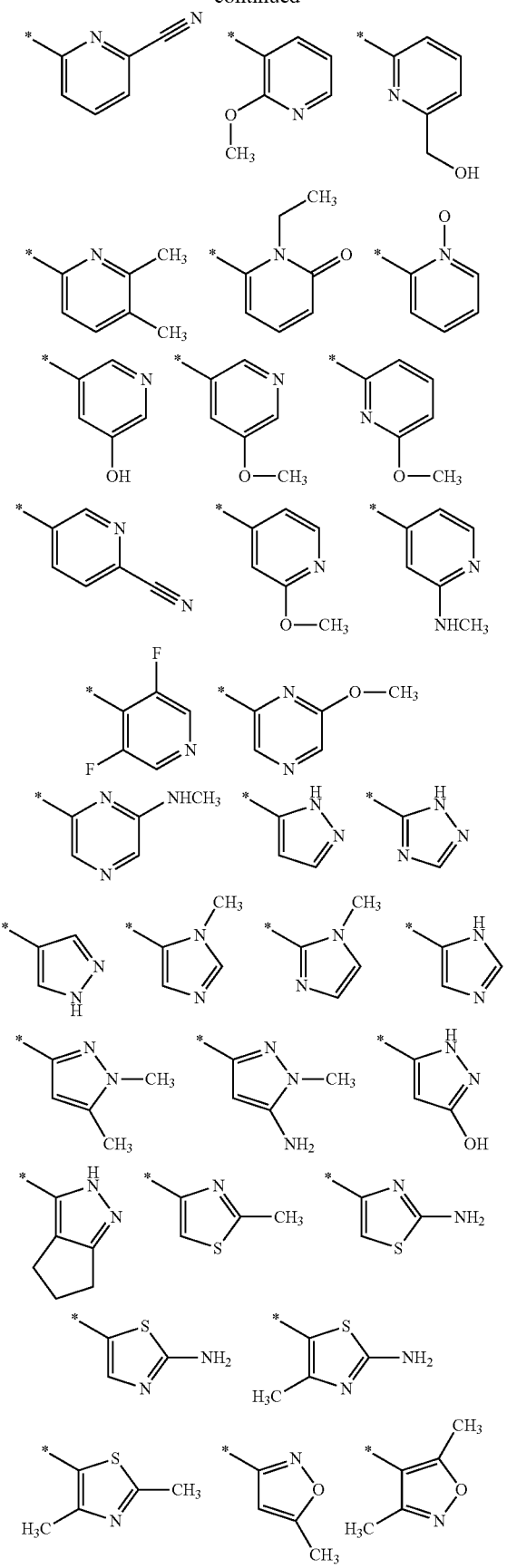

-continued
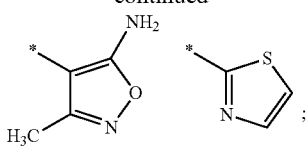
A represents a group selected from
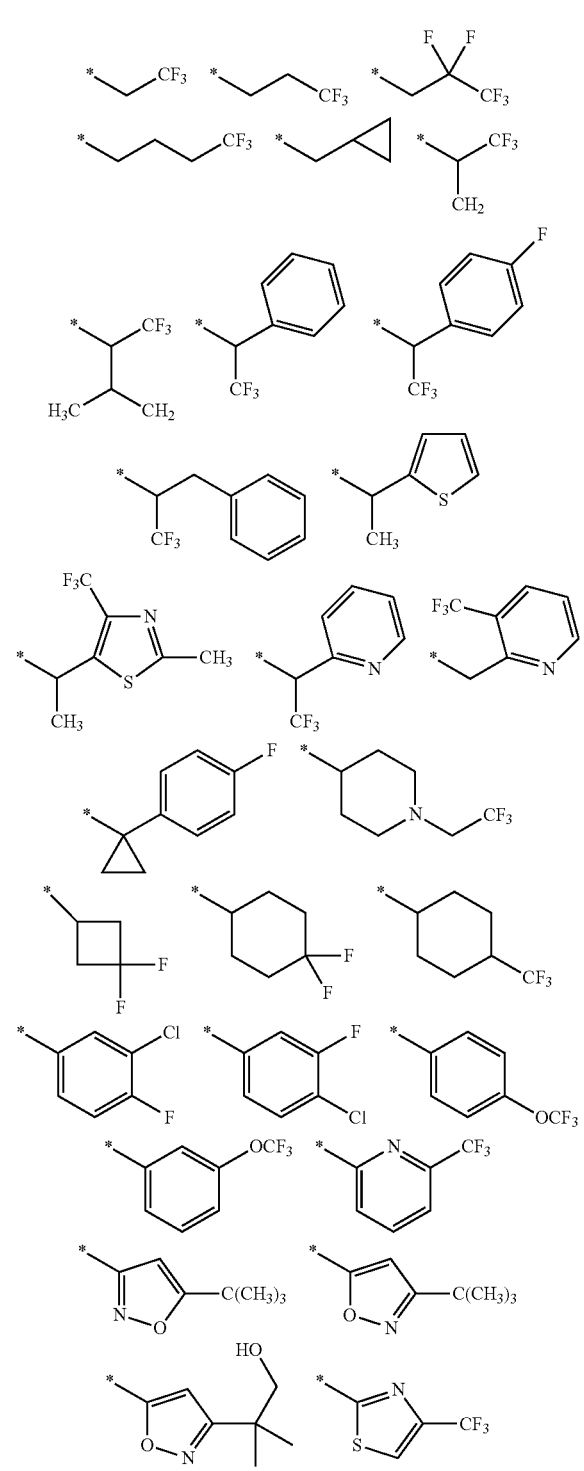
-continued
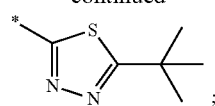
L represents a group selected from
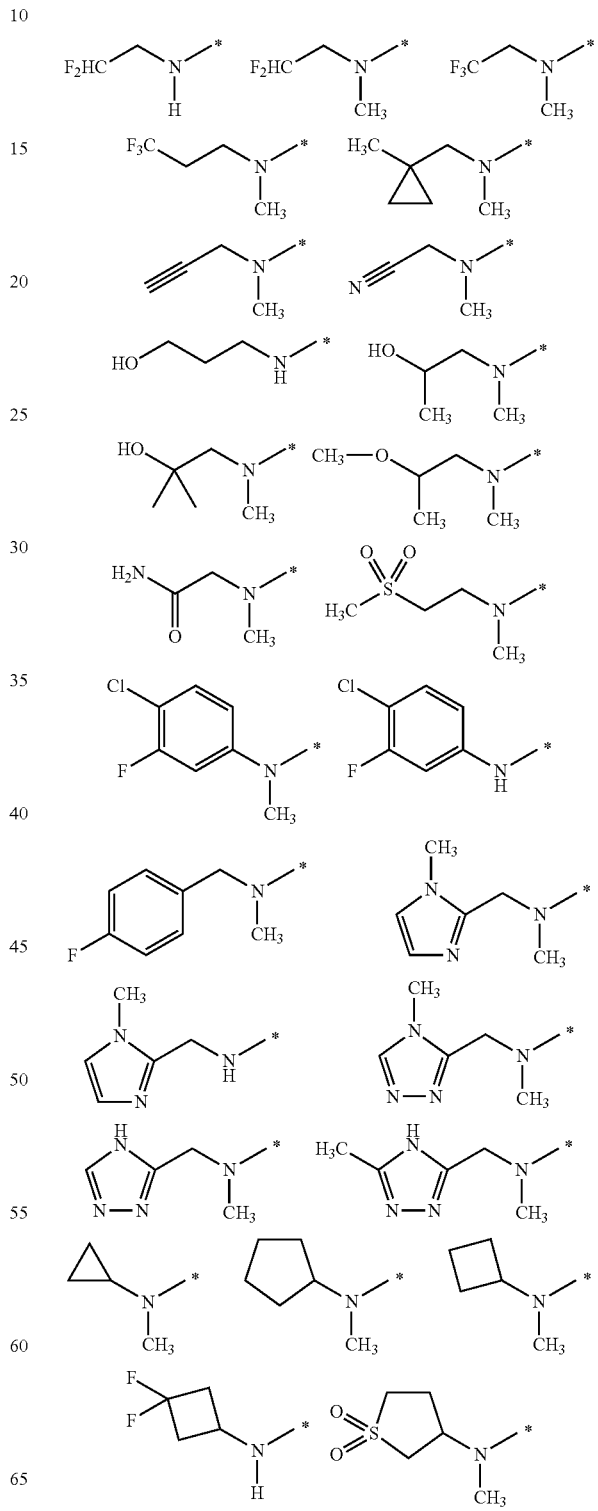

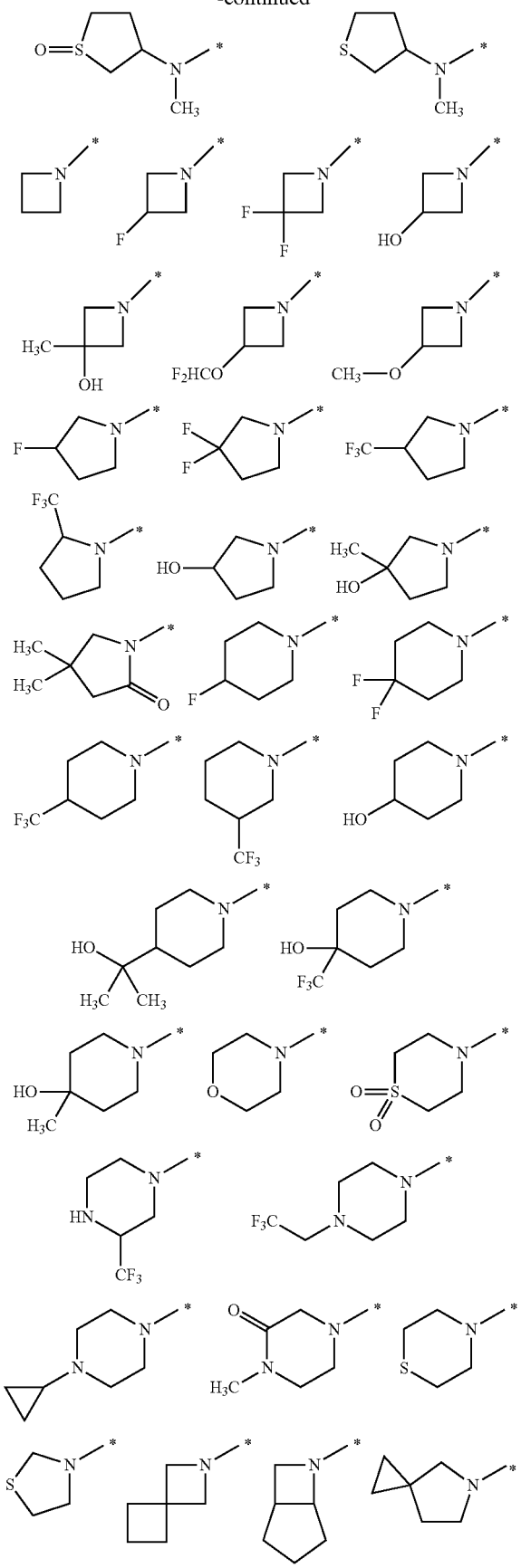
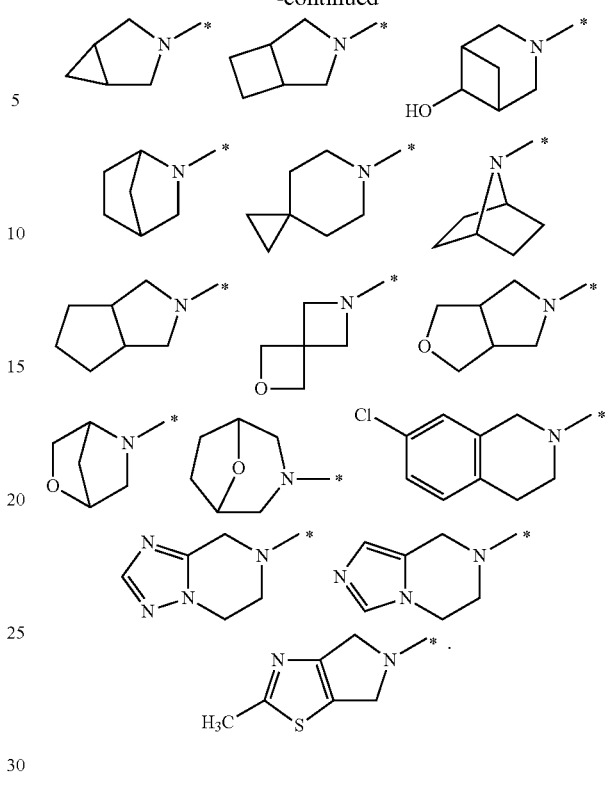
A further embodiment of the present invention comprises compounds of formula Ib in which
$R^1$ represents fluoro, chloro;
$R^2$ represents hydrogen, fluoro, chloro;
$R^6$ represents hydrogen, $CH_3$;
M represents a group selected from
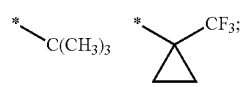
A represents a group selected from
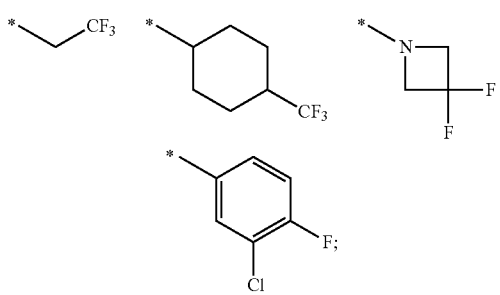
L represents a group selected from
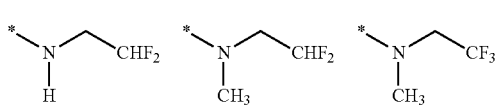

-continued

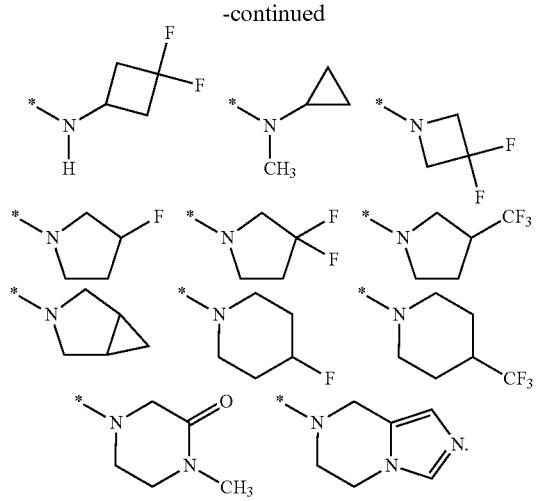

TERMS AND DEFINITIONS USED

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined, for example a cyclopropylmethyl-group would be represented by the following drawing:

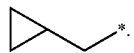

Tautomers/Stereochemistry/Solvates/Hydrates:

Unless specifically indicated, throughout the specification and the appended claims, a given chemical formula or name shall encompass tautomers (e.g. 1H-benzimidazole may be considered to be identical to a corresponding compound containing a 3H-benzimidazole) and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanol-amine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

Alkynyl:

The term "$C_{2-n}$-alkynyl", wherein n is an integer from 3 to n, is used for a group as defined in the definition for "$C_{1-n}$-alkyl" with at least two carbon atoms, if at least two of those carbon atoms of said group are bonded to each other by a triple bond.

Cycloalkyl:

The term "$C_{3-n}$-cycloalkyl", wherein n is an integer >3, either alone or in combination with another radical denotes a mono-, bi-, tri- or tetracyclic, saturated, hydrocarbon radical with 3 to n C atoms. For example the term $C_{3-7}$-cycloalkyl includes cyclopropyl, cyclobutyl, cyclopentyl, cyclohexyl and cycloheptyl.

The term "cycloalkyl" encompasses fused, bridged and spirocyclic systems. The cycloalkyl radical may further be fused to a phenyl ring or to a 5-6-membered heteroaryl ring, e.g a thienyl-, pyrrolyl-, thiazolyl-, oxazolyl-, isoxazolyl-, imidazolyl-, pyrazolyl-, triazolyl-, tetrazolyl-, pyridinyl-, pyrimidinyl-pyrazinyl- or pyridazinyl-ring.

Furthermore, the term "cycloalkyl" includes the following exemplary structures, which are not depicted as radicals as they may be attached through a covalent bond to any atom of the cycloalkyl ring fragment but not to an atom of the aryl or heteroaryl fragment:

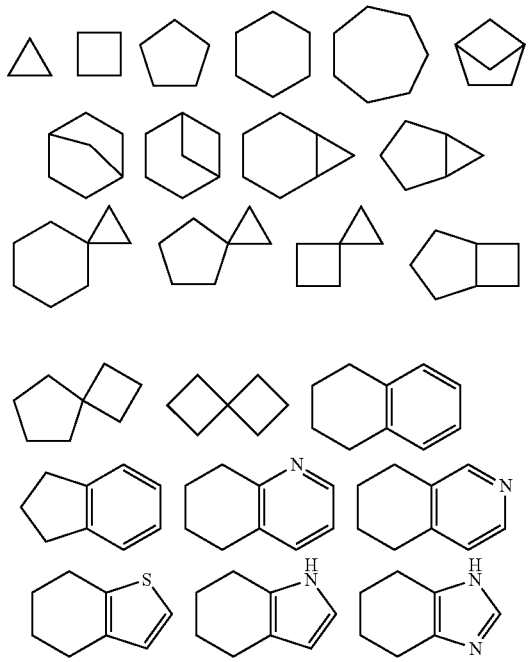

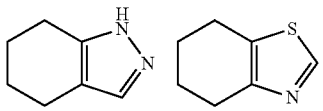

Heterocycloalkyl:

The term "4-n-membered heterocycloalkyl", wherein n is an integer >4, means a saturated or partially unsaturated mono- or polycyclic ring system containing one or more heteroatoms selected from N, O or S(O)$_r$, wherein r=0, 1 or 2, consisting of 4 to n ring atoms. The heterocycloalkyl ring system may further be fused to a phenyl- or 5-6-membered heteroaryl ring such as a thienyl-, pyrrolyl-, thiazolyl-, oxazolyl-, isoxazolyl-, imidazolyl-, pyrazolyl-, triazolyl-, tetrazolyl-, pyridinyl-, pyrimidinyl-pyrazinyl- or pyridazinyl-ring. The term "heterocycloalkyl" is intended to include all the possible isomeric forms.

The term "heterocycloalkyl" includes the following exemplary structures, which are not depicted as radicals as they may be attached through a covalent bond to any atom of the heterocycloalkyl or cycloalkyl ring fragment but not to an atom of the aryl or heteroaryl fragment:

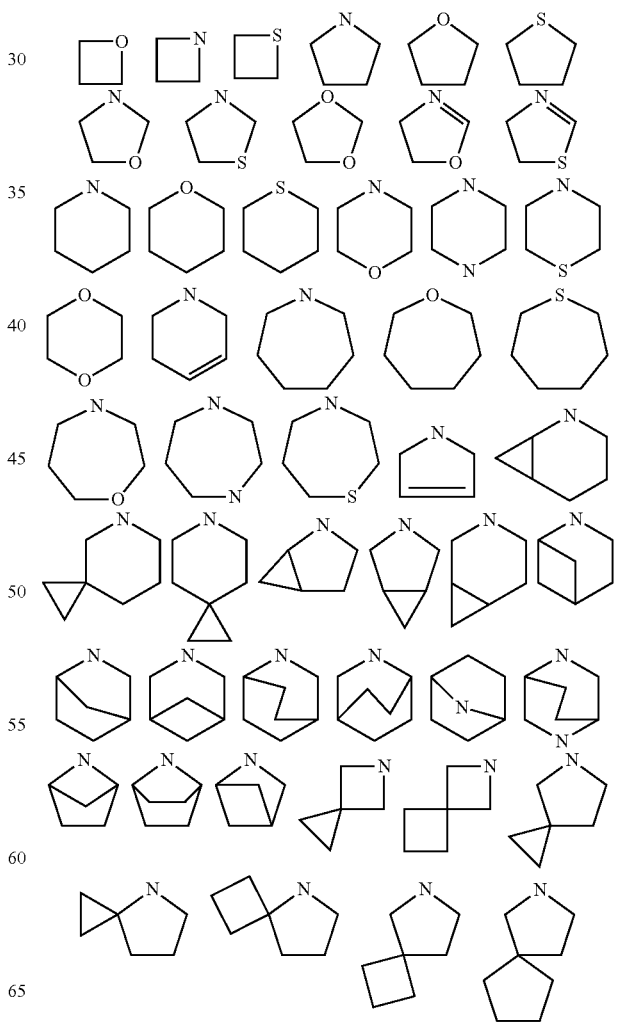

-continued

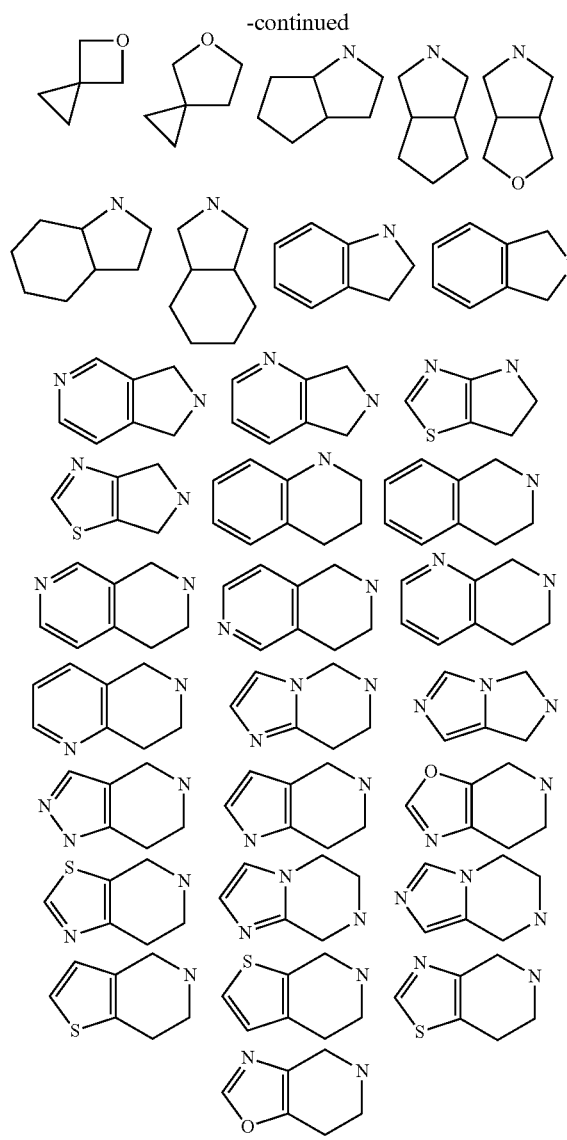

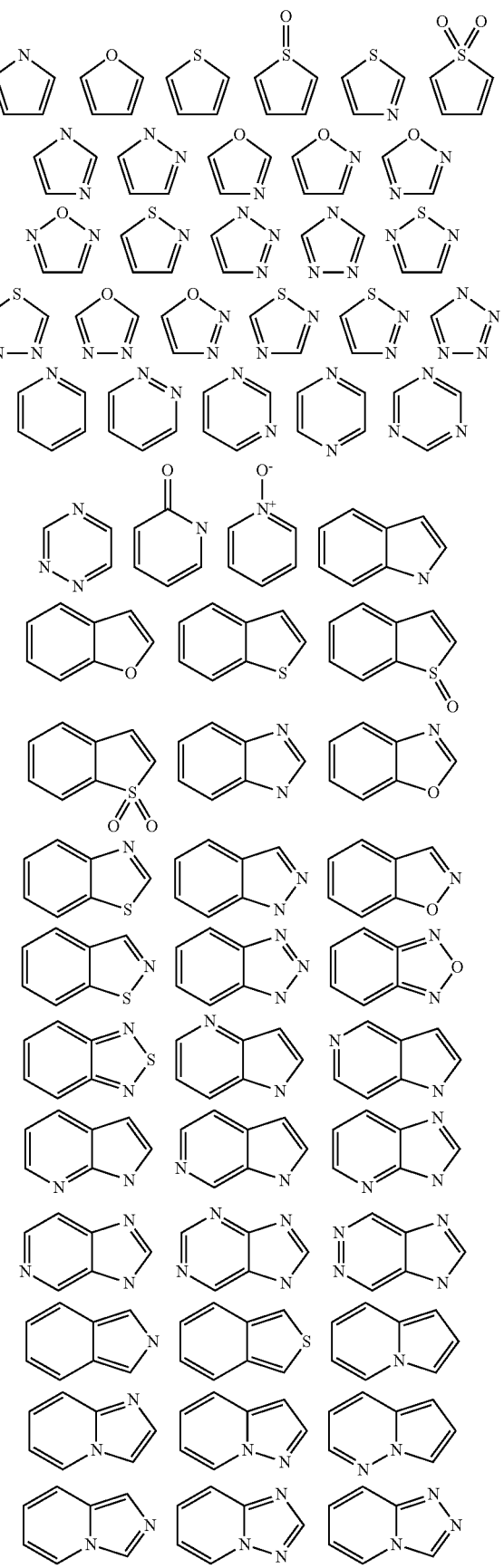

Aryl:

The term "aryl" as used herein, either alone or in combination with another radical, denotes a carbocyclic aromatic monocyclic group containing 6 carbon atoms which may further be fused to a second 5- or 6-membered aromatic, saturated or unsaturated carbocyclic group. The term "aryl" includes phenyl, indanyl, indenyl, naphthyl, anthracenyl, phenanthrenyl, tetrahydronaphthyl and dihydronaphthyl which may be attached through a covalent bond to any atom of the aromatic fragment.

Heteroaryl:

The term "heteroaryl" means a mono- or polycyclic ring system containing one or more heteroatoms selected from N, O or S(O)$_r$, wherein r=0, 1 or 2, consisting of 5 to 14 ring atoms wherein at least one of the heteroatoms is part of the aromatic ring which may further be fused to a second 5- or 7-membered aromatic, saturated or unsaturated cycloalkyl or heterocycloalkyl group. The term "heteroaryl" is intended to include all the possible isomeric forms.

The term "heteroaryl" includes the following exemplary structures, which are not depicted as radicals as they may be attached through a covalent bond to any atom of the heteroaryl ring but not to an atom of the cycloalkyl or heterocycloalkyl fragment:

31

-continued

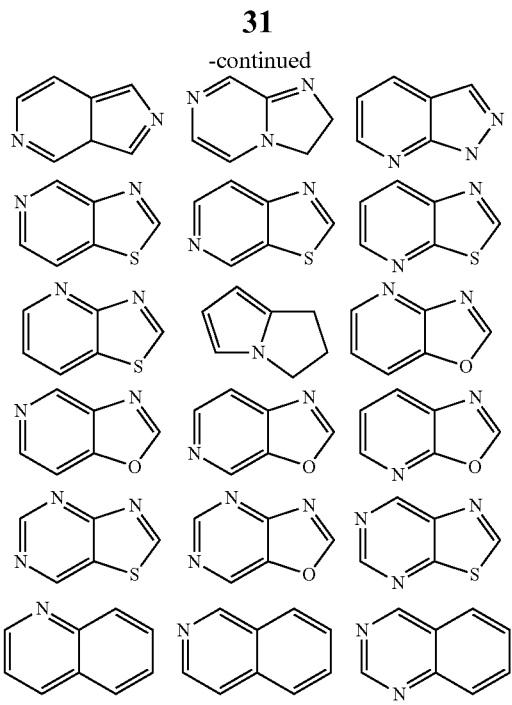

32

-continued

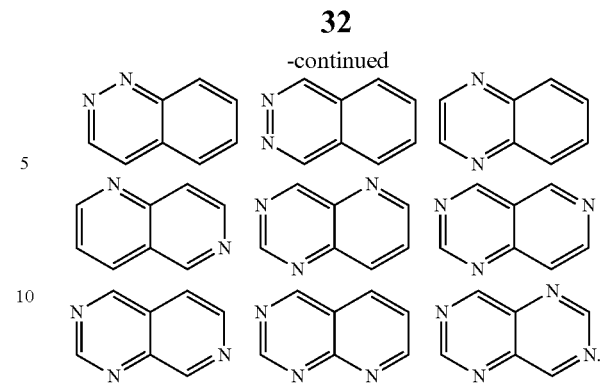

Methods of Preparation

Compounds of the present invention can be prepared in accordance with techniques that are well known to those skilled in the art, for example as described hereinafter and in the experimental section or in analogy to methods described in WO2010/034796, WO2010/034797 and WO2010/100249. According to a further aspect of the invention there is provided a process for the preparation of a compound of formula I, which process can be performed for example according to the following schemes A-C.

Scheme A (all variable groups are as defined in claim 1):

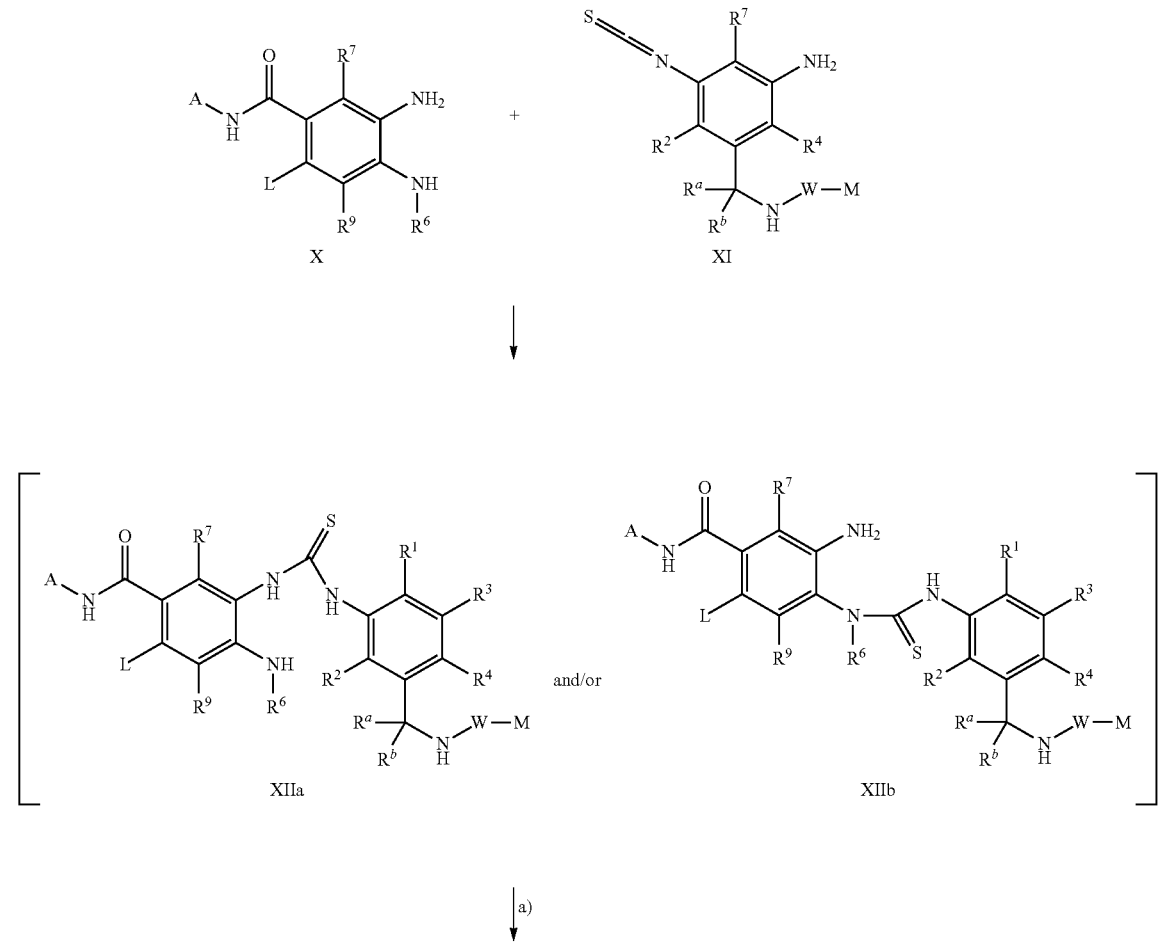

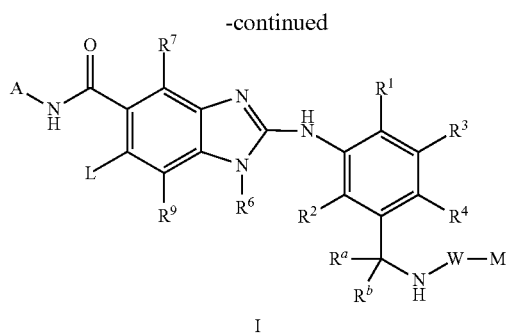

I

The reaction between phenylenediamine X and the thioisocyanate XI (Step a) can be performed under standard conditions known to those skilled in the art—for example in analogy to the process described in WO2010/034796 or WO2010/100249—in presence of a suitable solvent such as diethyl ether ($Et_2O$), dimethylformamide (DMF), dichloromethane (DCM), acetonitrile (MeCN) and/or tetrahydrofuran (THF). The reaction is preferably performed in the presence of a suitable reagent which enhances the cyclisation step as for instance $CH_3$—I or a carbodiimide based compound such as N,N'-dicyclohexylcarbodiimide (DCC), 1-ethyl-3-(3-dimethylaminopropyl)carbodiimide (EDCI, or its salt, e.g. hydrochloride) or N,N'-diisopropylcarbodiimide (DIC) or in presence of an amine base e.g. triethylamine (TEA) or diisopropyl ethyl amine (DIPEA). The reaction may proceed at any suitable temperature between 0° C. to 200° C., preferably between room temperature and 100° C. Step a can be performed in a step-wise reaction under isolation of the thiourea intermediates XIIa and/or XIIb or in a one-pot procedure.

Alternatively the compounds of formula I can be synthesized according to scheme B.

Scheme B (all variable groups are as defined in claim 1 and $PG^{acid}$ is a protecting group of a carboxylic acid function):

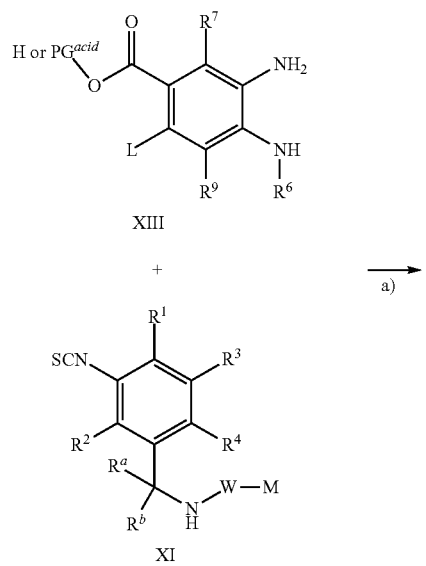

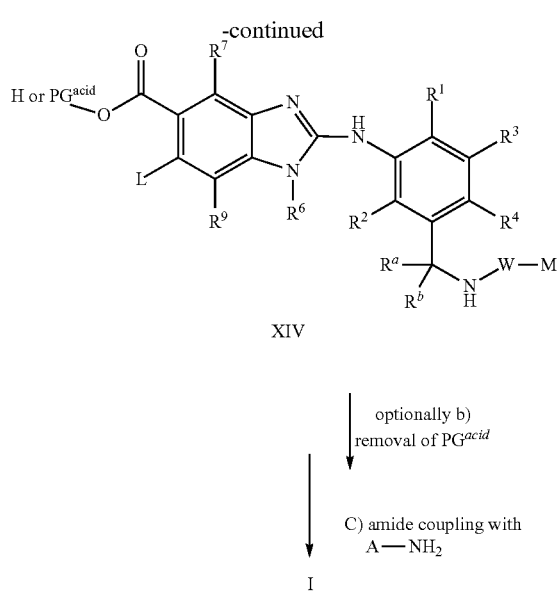

The protecting group $PG^{acid}$ is a literature known protecting group of a carboxylic acid, well known to those skilled in the art as for example described in "*Protective Groups in Organic Synthesis*", 3$^{rd}$ edition, T. W. Greene & P. G. M. Wutz, Wiley-Interscience (1999), for example a $C_{1-3}$-alkyl-, allyl- or a benzyl-group.

Step a) can be performed as described in scheme A, but may also be performed in the presence of an additive (such as 2,2,2-trifluoro-N,O-bis-(trimethylsilyl)-acetamide) when an unprotected carboxylic acid moiety is present in XIII.

Step b) can be performed under known saponification conditions, for example with aqueous LiOH, NaOH or KOH in ethanol (EtOH), methanol (MeOH), DMF, MeCN, THF or dioxane or with Pd/C in MeOH.

The amide formation in step c) can be performed with an additional in-situ activating agent like 1-propylphosphonic acid cyclic anhydride (PPA), O-(benzotriazol-1-yl)-N,N,N',N'-tetra-methyl-uronium tetrafluoroborate (TBTU), O-(benzotriazol-1-yl)-N,N,N',N'-tetramethyl-uronium hexafluorophosphate (HBTU), O-(7-azabenzotriazol-1-yl)-N,N,N',N'-tetramethyluronium-hexafluorophosphate (HATU), DCC, EDCI, carbonyldiimidazole (CDI), carbonylditriazole (CDT), 1-chloro-2-methyl-propenyl-dimethylamine, oxalyl chloride or other activating agents of the state of the art.

The coupling reaction is preferably performed in the presence of a base such as NaOH, KOH, $NaHCO_3$, triethylamine (TEA), N-ethyldiisopropylamine (DIPEA), pyridine, N,N,-dimethylaminopyridine (DMAP) or other appropriate bases of the state of the art and for example described in Houben-Weyl, "Methods in Organic Synthesis", Vol. E22a, p 425ff. The coupling reactions are performed in an appropriate solvent for example DCM, dioxane, THF, MeCN, DMF, dimethylacetamide (DMA), N-methylpyrrolidone (NMP) or in mixtures of the above mentioned solvents at any suitable temperature between 0° C. to 100° C.

When $PG^{acid}$ is a methyl or ethyl group the conversion of XIV to I can also be carried out in a one-pot procedure for example with trimethylaluminium or triethylaluminium in hexane, dioxane, THF at 20-80° C.

Alternatively, the compounds of formula I can be synthesized according to scheme C.

Scheme C (all variable groups are as defined in claim 1 and $PG^{amino}$ is protecting group of the benzylic amino group):

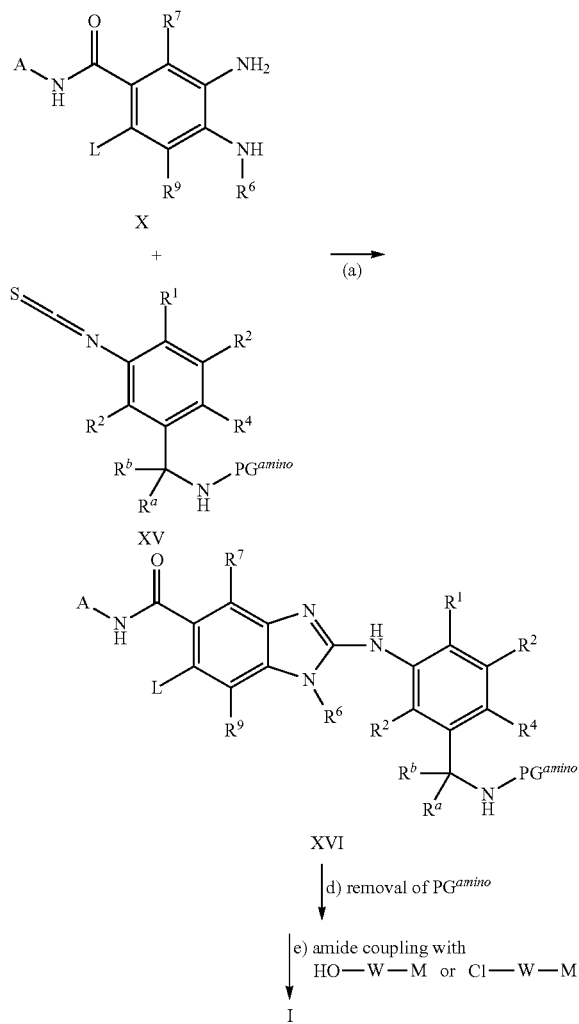

HCl or $H_2SO_4$ solutions, KOH; $Ba(OH)_2$, Pd on carbon (Pd/C), trimethylsilyl iodide or other conditions as described in "Protective Groups in Organic Synthesis", $3^{rd}$ edition, T. W. Greene & P. G. M. Wutz, Wiley-Interscience (1999). Appropriate co-solvent for this step is for example DCM, THF, MeCN, DMF, DMA, NMP or mixtures of the above mentioned solvents at any suitable temperature between 0° C. to 100° C. The amide formation in step e) can be performed with the acids HO—W-M and an additional in-situ activating agent like PPA, TBTU, HBTU, HATU, DCC, EDCI, CD, CTI, 1-chloro-2-methyl-propenyl-dimethylamine, oxalyl chloride or other activating agents of the state of the art in analogy to Scheme B, step c; or directly with the corresponding acid chloride Cl—W-M under analogous conditions without an additional in situ activating agent.

The coupling reaction is preferably performed in the presence of a base such as NaOH, KOH, $NaHCO_3$, TEA, DIPEA, pyridine, DMAP or other appropriate bases of the state of the art and for example described in described in Houben-Weyl, "Methods in Organic Synthesis", Vol. E22a, p 425ff. The coupling reactions are performed in an appropriate solvent for example DCM, dioxane, THF, MeCN, DMF, DMA, NMP or in mixtures of the above mentioned solvents.

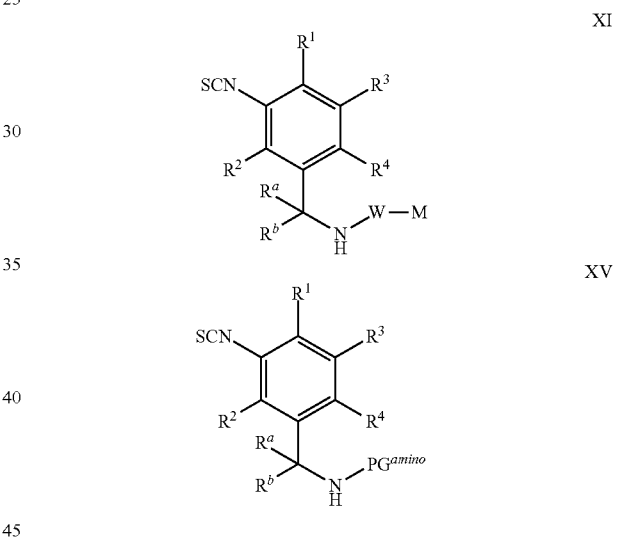

The synthesis of the building blocks XI and XV—wherein all variable groups are as defined in claim 1 and $PG^{amino}$ is a protecting group of the benzylic amino group—is employing standard reaction conditions according to scheme D known to those skilled in the art which are exemplified in the experimental part in detail or in WO2010/100249.

The protecting group $PG^{amino}$ in XV is a literature known protecting group of an amino group well known to those skilled in the art as for example described in "Protective Groups in Organic Synthesis", $3^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step a) can be performed as described in Scheme 1.

Step d) $PG^{amino}$ in XVI can be removed in accordance with techniques that are well known to those skilled in the art and which are exemplified hereinafter. For example XVI can be deprotected using an appropriate agent (depending on the protecting group) such as for example trifluoro acetic acid, Scheme D (all variable groups are as defined in claim 1 and $PG^{amino}$ is a protecting group of the benzylic amino group):

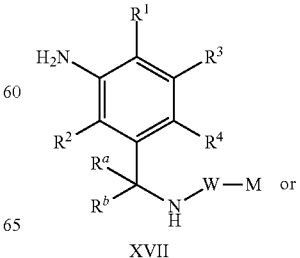

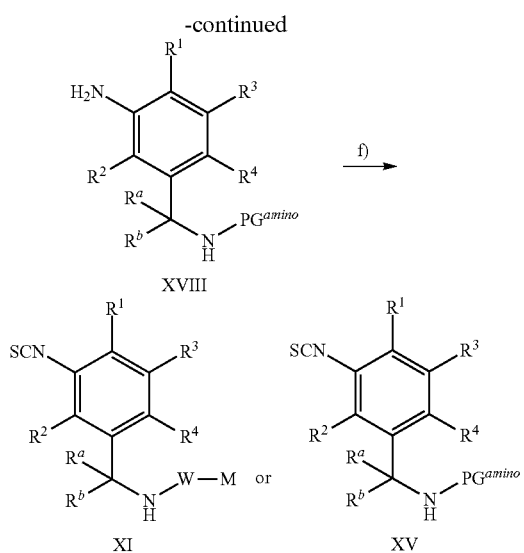

Step f) can be performed according to standard literature procedures for example with reagents such as 1,1'-thiocarbonyldi-2-pyridone, O,O'-di-2-pyridylthiocarbonate, 1,1'-thiocarbonyldiimidazole or with thiophosgene in a solvent as for example DCM, dioxane or DMF at temperatures between 0-150° C. and optionally under addition of a base like DMAP or TEA.

The building blocks XVII and XVIII can be prepared according to scheme E:

The amide formation in step g) can be performed in analogy to step c) or step e) to synthesize compound XVII or by using common reagents for amino group protection for example di-tert-butyl-dicarbonate, methyl-, ethyl-, benzyl or allyl-chloroformate under standard reaction conditions as described in "Protective Groups in Organic Synthesis", 3$^{rd}$ edition, T. W. Greene & P. G. M. Wutz, Wiley-Interscience (1999) to synthesize compounds XVIII.

The nitro group in precursor XVIIa or XVIIIa can be reduced to the amino group in step h) under literature known reduction conditions for example via hydrogenation (preferably at 1-5 bar) in presence of Pd/C, Pt/C or RaNi in MeOH, EtOH or THF optionally under acidic conditions in presence of HCl, or by using $SnCl_2$/HCl, $Na_2S_2O_4$, Zn/HCl, Fe/HCl, Fe-powder/aqueous $NH_4Cl$ solution or according to procedures described in the literature for example R. Larock, *Comprehensive Organic Transformations*, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

Scheme E (all variable groups are as defined in claim 1 and PG$^{amino}$ is a protecting group of the benzylic amino group):

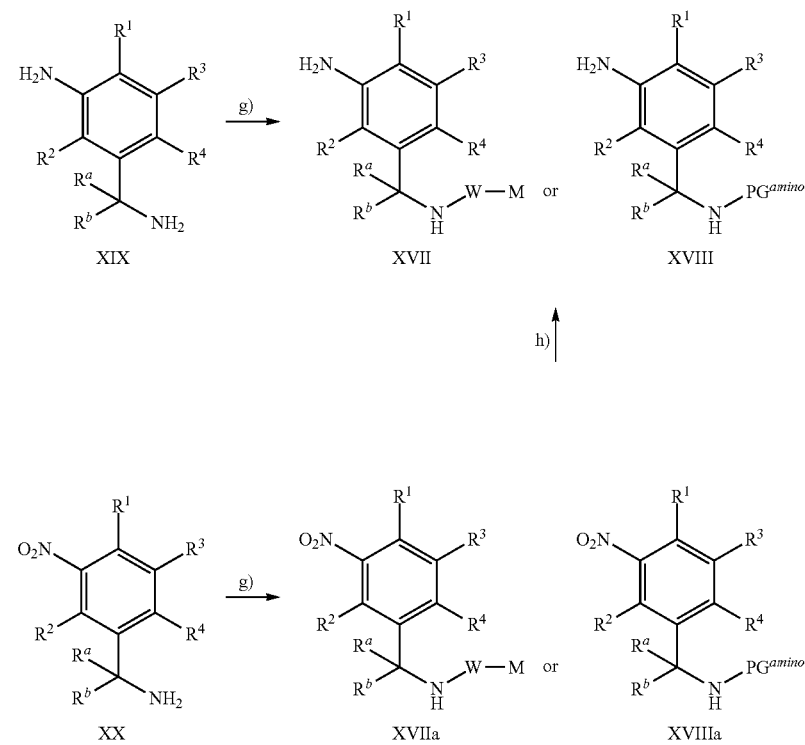

The building blocks XIX and XX can be prepared according to scheme F—H:

Scheme F ($R^a$ and $R^b$ are hydrogen atoms, all other variable groups are as defined as in claim 1):

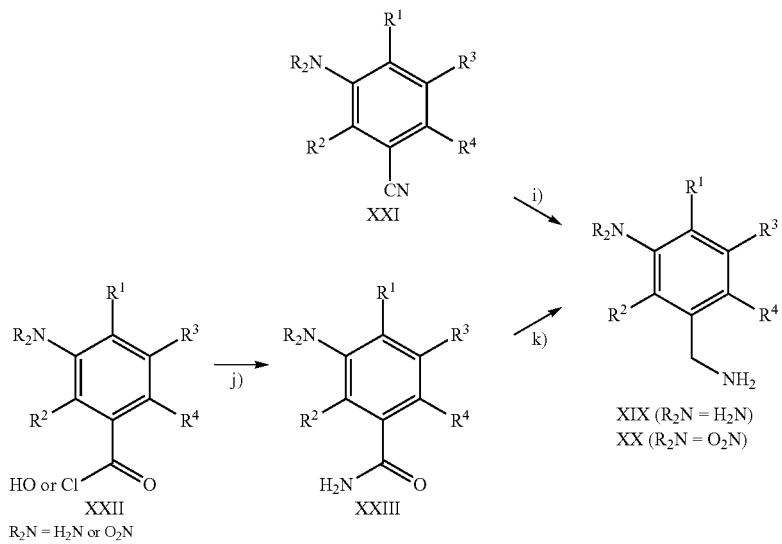

Step i) can be performed via hydrogenation (1-5 bar) with a catalyst like Pd/C, PtC, or RaNi in a suitable solvent like MeOH or EtOH optionally using HCl or $NH_3$ as additive at temperatures between 0-60° C. or via reduction with $LiAlH_4$ or $BH_3$-containing reagents in a suitable solvent like THF, MeOH or EtOH under literature-known conditions.

Step j) can be performed under the amide coupling conditions described for step e) and using $NH_3$ as coupling partner, for example 1-chloro-2-methyl-propenyl-dimethylamine in THF can be used as activating agent.

Step k) can be performed using $LiAlH_4$ or $BH_3$-containing reagents under literature known conditions as for example compiled in R. C. Larock, Comprehensive Organic Transformations, VCH, 1989, p. 432-433, preferably with $LiAlH_4$ in THF at 0-80° C.

Alternatively, compounds XIX and XX can be prepared as described in WO2010/100249 or according to scheme G Scheme G (all variable groups are as defined in claim 1):

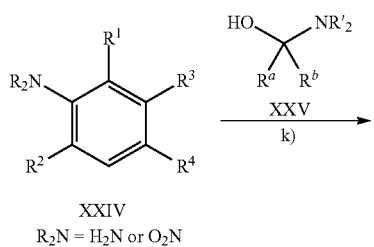

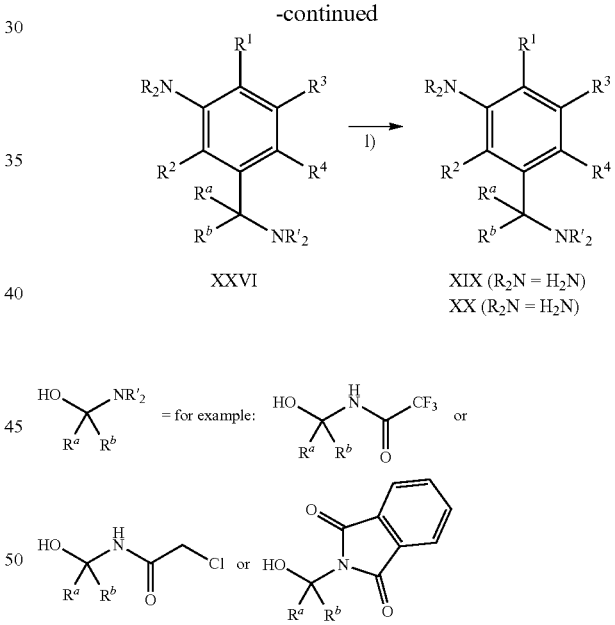

Step k) can be performed mixing XXIV with reagent XXV in concentrated $H_2SO_4$ or $F_3C$—$SO_3H$ at temperatures between 0-150° C., preferably between 20-80° C.

Step l) can be performed using literature known deprotection procedures for the corresponding nitrogen protecting groups for example treatment of the phthalimide with hydrazine or cleavage of the amide bond using bases like NaOH in MeOH or EtOH at temperatures between 20-80° C. or under acidic conditions using aqueous HCl solution or HCl in dioxane at temperatures between 20-80° C.

Alternatively, compounds XIX and XX can be prepared according to scheme H.

Scheme H ($R^b$ = H, all variable groups are as defined in claim 1):

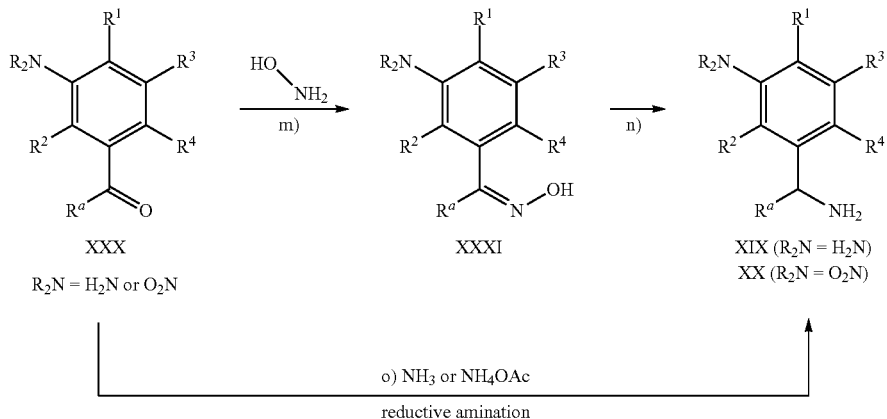

Step m) can be performed mixing XXX with HO—NH$_2$ in an appropriate solvent for example MeCN, DCM, THF, optionally using HCl as additive at temperatures between 0-60° C.
Step n) can be performed applying literature known reduction conditions for example via hydrogenation preferably at 1-5 bar H$_2$ pressure in presence of Pd/C or Ra—Ni in MeOH, EtOH or THF optionally using HCl or HOAc as catalyst, or by using SnCl$_2$/HCl, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989).
Step o) can be performed applying literature known reduction conditions e.g. using ammonia or ammonium salts (e.g. ammonium acetate) and Borane reagents, for example NaBH$_3$CN, BH$_3$-THF-complex or BH$_3$—SMe$_2$-complex in water, MeOH, EtOH, THF or mixtures thereof, under buffered conditions preferably at a pH between 5-9 or employing hydrogenations using Pd/C or Ra—Ni as catalysts in MeOH, EtOH or THF optionally using HCl or HOAc as co-catalyst or according to procedures described in the literature for example in WO2010/100249 or R. Larock, *Comprehensive Organic Transformations*, VCH Verlagsgemeinschaft, Weinheim (1989).

The synthesis of building blocks X and XIII can be performed as described in the experimental part or in scheme I, wherein A, L, $R^6$, $R^7$ and $R^9$ have the meaning as defined in claim 1 and PG$^{acid}$ is a literature known carboxylic acid protecting group as described above and LG is a leaving group on the aromatic ring (for example a fluoro, chloro, bromo, iodo or trifluormethylsulfonyl group). The individual steps can also be performed in analogy to standard literature procedures which are well known to those skilled in the art, as for example in analogy to methods described in WO2010/034796, WO2010/034797 or WO2010/100249.

Scheme I [all variable groups are as defined in claim 1 nad LG is a leaving group as for example Fluror, Chloro, Bromo, Iodo, or CF$_2$(SO$_3$)]

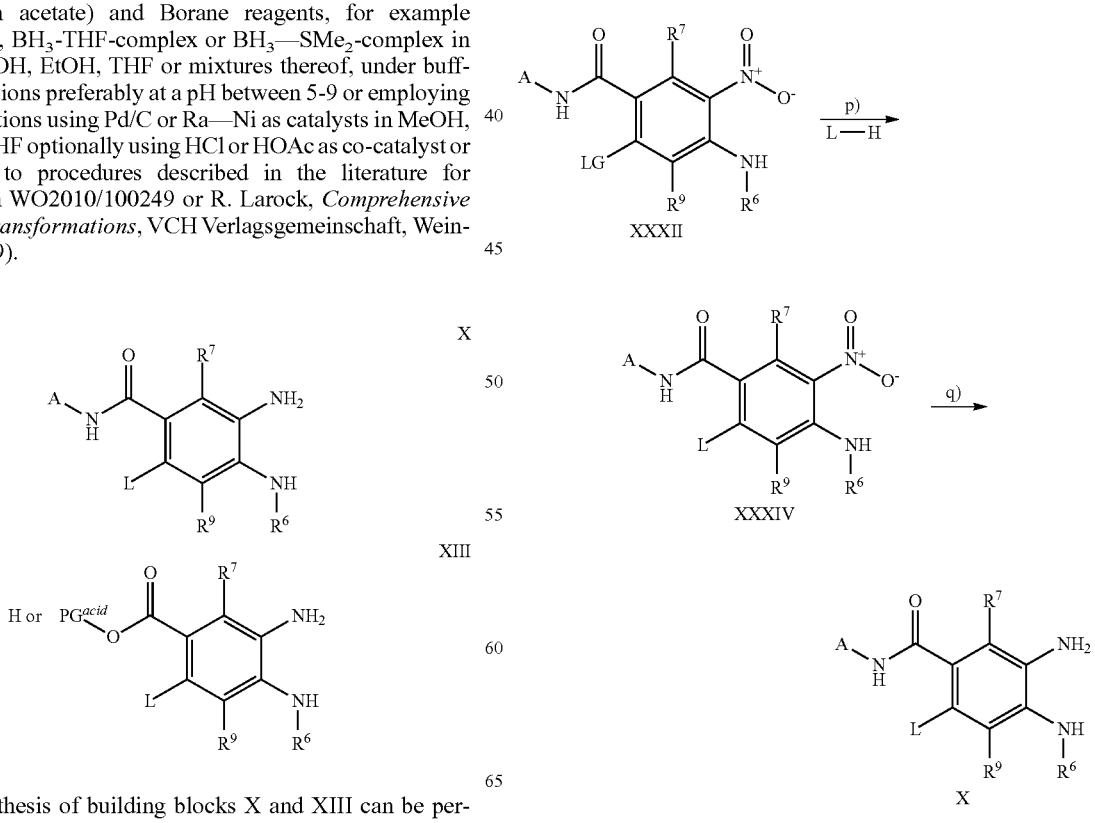

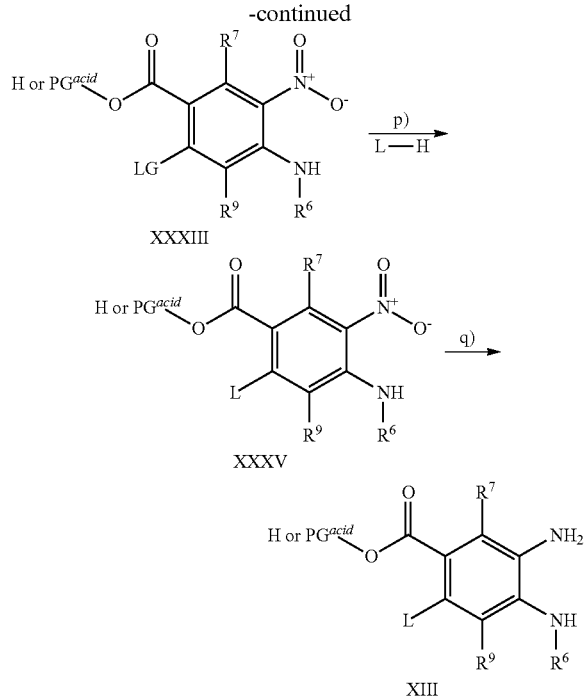

Step p can be performed by an aromatic substitution reaction of the building blocks XXXII or XXXIII with the amine L-H or an appropriate salt thereof and using literature known reaction conditions. For example the reaction can be performed employing a building blocks XXXII or XXXIII wherein LG is preferably a fluoro or chloro substituent in presence of a suitable base like $K_2CO_3$, $Na_2CO_3$, $Cs_2CO_3$, TEA, DIPEA in an appropriate solvent for example DMF, DMSO, DMA, NMP or mixtures of the above mentioned solvents at any suitable temperature between 0° C. to 180° C. The reaction may also be performed in a microwave oven preferably at temperatures between 80-170° C.

Alternatively the reaction can also be performed in presence of a Pd-catalyst, in this case the preferred groups LG are bromo, iodo or trifluormethylsulfonyl in XXXII or XXXIII. For example $Pd(PPh_3)_4$ can be used in presence of a suitable base for example $K_2CO_3$, $Na_2CO_3$, $Cs_2CO_3$, TEA, DIPEA in an appropriate solvent for example THF, MeCN, DMF or mixtures of the mentioned solvents preferably at a temperature between 0° C. to 120° C.

The nitro group in XXXIV or XXXV can be reduced to the amino group in step q) under literature known reduction conditions for example via hydrogenation (preferably at 1-5 bar) in presence of Pt/C, Pd/C or Raney-Nickel (Ra/Ni) in MeOH, EtOH or THF or mixtures thereof, optionally under acidic conditions in presence of HCl, or by using $SnCl_2$/HCl, $Na_2S_2O_4$, Zn/HCl, Fe/HCl, Fe-powder/aqueous $NH_4Cl$ solution or according to procedures described in the literature for example R. Larock, *Comprehensive Organic Transformations*, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

Biological Assays mPGES Protein Production

Microsomes from Rosetta *E. coli* bacteria expressing recombinant human mPGES-1 can be derived as described below:

Inoculate 5 ml LB with Ampicilin (50 μg/ml) and Chloramphenicol (34 μg/ml) with bacteria from freeze culture. Incubate 8 h at 37° C. with 200 rpm. Thereafter, inoculate 500-1000 ml LB containing Amp and Chloro with the 5 ml on culture and grow to OD640 of 0.8-1.0. Chill the culture to +4° C. before induction. Induce the culture with IPTG at a final concentration of 400 μM. Express the protein at room temp 18-23° C. with 200 rpm shaking over night.

The following steps can be performed on the following day:
1. Spin down the cells in 250 ml centrifuge flasks for 15 min at 7000 rpm (Beckmann Coulte Avanti J-E centrifuge)
2. Dissolve the pellet from 250 ml culture in 12.5 ml homogenization buffer
3. (15 mM Tris-HCL pH8, 1 mM EDTA pH8, 0.25 mM Sucrose, 2.5 mM GSH, 1 Tablet Protease inhibitor per 50 ml buffer)
4. Disintegrate the cells by sonication, 5×10 seconds at 48% amplitude of a 750 W sonifier
5. Add 2.5 ml $MgCl_2$ (100 mM) and DNase 12.5 μl (0.8 mg/ml) and incubate on ice for 30 min
6. Spin down the bacteria debris and save the supernatant, 7000 rpm for 15 min
7. Isolate the protein containing membranes in the supernatant by ultracentrifugation 120000×g for 2 hour at 4° C. (Sorvall T880 rotor).
8. Discard the supernatant and dissolve the pellet in 20 mM Potassium phosphate buffer pH7.4 ($KH_2PO_4$ and $K_2HPO_4$) buffer by sonication (5×10 s, 30% of a 50 W sonifier) and aliquot the enzyme and store aliquots at −80° C.

Before each experiment is performed an aliquot of the enzyme is thawed and it can then be dissolved in 0.1 M Potassium phosphate buffer pH7.4 ($KH_2PO_4$ and $K_2HPO_4$) buffer containing 2.5 mM GSH.

mPGES-1 Enzyme Assay

The aim of this assay is to determine the affinity of a test compound for the mPGES-1 enzyme.

47 μl of recombinant human mPGES-1 (~0.5 μg protein/well) containing microsomal suspension in a buffer containing GSH, (2.5 mmol/L L-Glutathione reduced, dissolved in 0.1 mol/L Phosphat Buffer pH 7.4) is dispensed in a 384-well plate and thereafter 1 μl of the test compound(s) is/are added and incubated for 25 minutes at room temperature. The enzyme reaction is started by the addition of 2 ul PGH2 (final conc 2 μM) dissolved in water-free Diglyme. After 60 seconds the reaction is terminated by addition of a stop solution containing $FeCl_2$ (10 μL 0.074 mol/l $FeCl_2$). The samples are diluted between 1:25 in PBS (Phosphate Buffered Saline). 10 μl of the diluted samples are transferred to 384-well low volume plate. In order to quantify the amount of $PGE_2$ that has been formed, a homogenous time resolved fluorescent (HTRF) detecting of $PGE_2$ has been performed using a commercially available kit from Cisbio according to the manufactures recommendation. This HTRF-based assay has been described in detail (see: Goedken et al., J Biomol Screen, 2008, 13(7), 619-625). Briefly, the diluted samples are mixed with 5 μl $PGE_2$-d2 conjugate and 5 μl anti-$PGE_2$ cryptate conjugate. After an incubation period of the plates over night, the fluorescence is measured by the use of an appropriate microplate reader.

The fluorescence of Europium cryptate (maxex=307 nm, maxem=620 nm) and d2-PGE$_2$ (maxex=620 nm, maxem=665 nm) are measured.

The extent of the specific HTRF is measured as a ratio of the emission intensity at 665 nm vs. that at 620 nm at an excitation puts of 320 nm. The quantification plate contains also wells with different concentrations of PGE$_2$ as calibration curve for the calculation of the PGE$_2$ concentrations from the HTRF ratio values.

From all mPGES enzyme assay the background is subtracted and the IC$_{50}$ is calculated over a nonlinear regression with conventional software.

TABLE A mPGES-1 inhibitory effect (IC$_{50}$ values in nM) of compounds in the enzyme assay

| example | IC50 [nM] | example | IC50 [nM] | example | IC50 [nM] |
|---|---|---|---|---|---|
| 1 | 2 | 92 | 2 | 182 | 2 |
| 2 | 2 | 93 | 3 | 183 | |
| 3 | | 94 | 4 | 184 | |
| 4 | 5 | 95 | 2 | 185 | |
| 5 | 2 | 96 | 16 | 186 | |
| 6 | 4 | 97 | 3 | 187 | |
| 7 | | 98 | 5 | 188 | |
| 8 | | 99 | 1 | 189 | |
| 9 | | 100 | 3 | 190 | |
| 10 | 2 | 101 | 2 | 191 | |
| 11 | 3 | 102 | 2 | 192 | |
| 12 | 3 | 103 | 1 | 193 | |
| 14 | 1 | 104 | 2 | 194 | |
| 15 | 4 | 105 | 2 | 195 | |
| 16 | | 106 | 2 | 196 | |
| 17 | 3 | 107 | 1 | 197 | |
| 18 | 3 | 108 | 1 | 198 | |
| 19 | 3 | 109 | 2 | 199 | |
| 20 | 3 | 110 | 2 | 200 | |
| 21 | 4 | 111 | 2 | 201 | |
| 22 | 5 | 112 | 3 | 202 | |
| 23 | 4 | 113 | 8 | 203 | |
| 24 | 5 | 114 | | 204 | |
| 25 | 4 | 115 | | 205 | |
| 26 | 3 | 116 | | 206 | |
| 27 | 2 | 117 | 2 | 207 | |
| 28 | 2 | 118 | 3 | 208 | |
| 29 | 2 | 119 | 2 | 209 | |
| 30 | 5 | 120 | 3 | 210 | |
| 31 | 4 | 121 | 3 | 211 | |
| 32 | 2 | 122 | 3 | 212 | |
| 33 | 3 | 123 | | 213 | |
| 34 | 3 | 124 | | 214 | |
| 35 | 2 | 125 | | 215 | |
| 36 | 5 | 126 | 2 | 216 | |
| 37 | 5 | 127 | 2 | 217 | |
| 38 | 4 | 128 | 2 | 218 | |
| 39 | 1 | 129 | 3 | 219 | |
| 40 | 2 | 130 | 2 | 220 | |
| 41 | 2 | 131 | 2 | 221 | |
| 42 | 2 | 132 | 5 | 222 | |
| 43 | 3 | 133 | 3 | 223 | |
| 44 | 4 | 134 | 2 | 224 | |
| 45 | 5 | 135 | 3 | 225 | |
| 46 | 3 | 136 | 3 | 226 | |
| 47 | 2 | 137 | 3 | 227 | |
| 48 | 2 | 138 | 2 | 228 | |
| 49 | 4 | 139 | 3 | 229 | |
| 50 | 3 | 140 | 2 | 230 | |
| 51 | 3 | 141 | 2 | 231 | 2.0 |
| 52 | 3 | 142 | | 232 | 1.7 |
| 53 | 2 | 143 | | 233 | 3.9 |
| 54 | 2 | 144 | 5 | 234 | 3.1 |
| 55 | 2 | 145 | 3 | 235 | 3.9 |
| 56 | 1 | 146 | | 236 | 3.3 |
| 57 | 1 | 147 | | 237 | 1.8 |
| 58 | 3 | 148 | 3 | 238 | 2.2 |
| 59 | 4 | 149 | 3 | 239 | 3.5 |

TABLE A-continued mPGES-1 inhibitory effect (IC$_{50}$ values in nM) of compounds in the enzyme assay

| example | IC50 [nM] | example | IC50 [nM] | example | IC50 [nM] |
|---|---|---|---|---|---|
| 60 | 1 | 150 | 2 | 240 | 4.9 |
| 61 | 2 | 151 | | 241 | 3.5 |
| 62 | 2 | 152 | | 242 | 1.7 |
| 63 | 3 | 153 | | 243 | 2.9 |
| 64 | 3 | 154 | 2 | 244 | 4.2 |
| 65 | 1 | 155 | 3 | 245 | 3.8 |
| 66 | 3 | 156 | 2 | 246 | 2.9 |
| 67 | 4 | 157 | 4 | 247 | 3.0 |
| 68 | 4 | 158 | 4 | 248 | 6.7 |
| 69 | 2 | 159 | 3 | 249 | 4.2 |
| 70 | 2 | 160 | 4 | 250 | 1.7 |
| 71 | 1 | 161 | 3 | 251 | 3.9 |
| 72 | 4 | 162 | 3 | 252 | 2.9 |
| 73 | 2 | 163 | | 253 | 5.7 |
| 74 | 3 | 164 | 4 | 254 | 3.1 |
| 75 | 1 | 165 | 2 | 255 | 4.3 |
| 76 | 1 | 166 | 2 | 256 | 3.9 |
| 77 | 3 | 167 | | 257 | 1.9 |
| 78 | 2 | 168 | 3 | 258 | 2.2 |
| 79 | 3 | 169 | | 259 | 4.1 |
| 80 | 2 | 170 | | 260 | 4.0 |
| 81 | 4 | 171 | | 261 | 2.9 |
| 82 | 3 | 172 | | 262 | |
| 83 | 2 | 173 | 2 | 263 | |
| 84 | 3 | 174 | | 264 | |
| 85 | 15 | 175 | 4 | 265 | |
| 86 | 4 | 176 | 4 | 266 | |
| 87 | 2 | 177 | 2 | 267 | |
| 88 | 2 | 178 | 5 | 268 | |
| 89 | 2 | 179 | 2 | 269 | |
| 90 | 3 | 180 | | | |
| 91 | 4 | 181 | | | |

A549 Cell-Based Assay

Although the enzymatic assay is a high throughput assay the disadvantage is that it uses a recombinant protein which is not in its natural environment. Accordingly a cellular assay was established in which a cell line of human origin (A549) expressing the mPGES-1 protein was used. In addition in order to mimic the situation in humans in which compounds can be bound to plasma proteins 50% human serum is added in the assay. By having the combination of testing mPGES-1 in a cellular environment and the presence of 50% human serum this assay has a higher relevance to judge the therapeutic potential of a mPGES-inhibitor than the pure enzyme assay.

A549 cells (ATCC: CCL-185) are grown to about 90% confluence in F-12K Nutrient Mixture (Kaighn's Mod. Gibco) containing 10% FBS in a humified incubator at 37° C. and 5% CO$_2$. Cells were detached using Trypsin-EDTA. A549 cells were seeded in a 384-well collagene plate at a density of 7000 cells/well (50 μl) in F-12 medium containing 1% Penicillin-Streptomycin and 50% human serum. The cells were allowed to attach for 3-4 h. After that the cells were incubated for 20-24 h in F-12k medium supplemented with 50% human serum, 1% Penicillin-Streptomycin and containing IL-1β at a final concentration of 5 ng/ml as well as 10 nM arachidonic acid in the presence of a vehicle or a test compound. The total volume is 100 μl.

Concentrations of PGE$_2$ in the cell free medium (10 μl) were measured using a commercially available HTRF kit from Cisbio (as described above). The PGE$_2$ formation in the absence of test compound was taken as 100%.

IC$_{50}$ values were derived from at 6-8 point titrations using conventional software.

The compounds listed in table B are in general efficacious to block the generation of PGE$_2$. Compounds of formula I may therefore be expected to have therapeutic potential to treat inflammatory diseases and associated conditions such as inflammatory/nociceptive pain.

TABLE B mPGES-1 inhibitory effect (IC$_{50}$ values in nM) of compounds in the cell assay

| example | IC50 [nM] | example | IC50 [nM] | example | IC50 [nM] |
|---|---|---|---|---|---|
| 1 | 1 | 92 | 1.4 | 182 | 7 |
| 2 | <1 | 93 | 17 | 183 | >100 |
| 3 | | 94 | 6 | 184 | >100 |
| 4 | 20 | 95 | 7 | 185 | |
| 5 | 39 | 96 | 21 | 186 | 2 |
| 6 | 4 | 97 | 3 | 187 | 1 |
| 7 | | 98 | 5 | 188 | 1 |
| 8 | | 99 | 5 | 189 | 3 |
| 9 | | 100 | 1 | 190 | 9 |
| 10 | 1 | 101 | 1.5 | 191 | 2 |
| 11 | 3 | 102 | 1.5 | 192 | 1 |
| 12 | 3 | 103 | <1 | 193 | 2.5 |
| 14 | <1 | 104 | 1 | 194 | 2.1 |
| 15 | 23 | 105 | 10 | 195 | 51 |
| 16 | 197 | 106 | <1 | 196 | 9 |
| 17 | 6 | 107 | <1 | 197 | |
| 18 | 4 | 108 | <1 | 198 | >100 |
| 19 | 1 | 109 | 1 | 199 | 8 |
| 20 | 1 | 110 | 1.6 | 200 | >100 |
| 21 | 2.5 | 111 | 22 | 201 | 6 |
| 22 | 1.5 | 112 | 1 | 202 | 57 |
| 23 | 1 | 113 | 62 | 203 | 46 |
| 24 | 44 | 114 | 3.5 | 204 | 49 |
| 25 | 12 | 115 | 2 | 205 | >100 |
| 26 | 3.6 | 116 | 80 | 206 | 42 |
| 27 | 2 | 117 | 2 | 207 | 170 |
| 28 | 1.5 | 118 | 10 | 208 | 21 |
| 29 | 3 | 119 | 1 | 209 | 6.5 |
| 30 | 144 | 120 | 1 | 210 | 8 |
| 31 | 33 | 121 | 2.0 | 211 | 106 |
| 32 | 6 | 122 | 1 | 212 | 1.7 |
| 33 | 8 | 123 | 1 | 213 | 41 |
| 34 | 1 | 124 | 2 | 214 | 113 |
| 35 | 1 | 125 | 1.4 | 215 | >100 |
| 36 | 6.5 | 126 | 1 | 216 | 27 |
| 37 | 3 | 127 | 6, 5 | 217 | >100 |
| 38 | 6 | 128 | 1 | 218 | 98 |
| 39 | 2 | 129 | 5 | 219 | >100 |
| 40 | <1 | 130 | 7 | 220 | 119 |
| 41 | 7 | 131 | 1 | 221 | 53 |
| 42 | 2 | 132 | 1.5 | 222 | 100 |
| 43 | 5 | 133 | 10 | 223 | 12 |
| 44 | 6 | 134 | <1 | 224 | 67 |
| 45 | 7 | 135 | 5 | 225 | 71 |
| 46 | 7 | 136 | 1 | 226 | 98 |
| 47 | 1 | 137 | <1 | 227 | 43 |
| 48 | 8 | 138 | 3 | 228 | >100 |
| 49 | 4 | 139 | <1 | 229 | 4.6 |
| 50 | 2 | 140 | 5 | 230 | 40 |
| 51 | <1 | 141 | 1 | 231 | 1.1 |
| 52 | <1 | 142 | 2 | 232 | 1.4 |
| 53 | 1 | 143 | 2.6 | 233 | 1 |
| 54 | 1.4 | 144 | 1 | 234 | 8 |
| 55 | 5 | 145 | 2.5 | 235 | 4.4 |
| 56 | <1 | 146 | <1 | 236 | 2 |
| 57 | 1 | 147 | 2 | 237 | <1 |
| 58 | 1 | 148 | 20 | 238 | 2 |
| 59 | <1 | 149 | 3 | 239 | 5 |
| 60 | 1 | 150 | 2 | 240 | 2 |
| 61 | <1 | 151 | 1.4 | 241 | <1 |
| 62 | <1 | 152 | 17 | 242 | 5 |
| 63 | 6 | 153 | 4.6 | 243 | 4.5 |
| 64 | 2.6 | 154 | <1 | 244 | 27 |
| 65 | 1 | 155 | 6 | 245 | 2.4 |
| 66 | 1.6 | 156 | 2 | 246 | 1.5 |
| 67 | 2 | 157 | 1 | 247 | 3 |
| 68 | 1 | 158 | 4 | 248 | 6 |
| 69 | 1 | 159 | 4 | 249 | 6 |
| 70 | 2 | 160 | 3 | 250 | 1 |
| 71 | <1 | 161 | 3 | 251 | 1 |
| 72 | 4 | 162 | 2 | 252 | 1.4 |
| 73 | <1 | 163 | 2 | 253 | 2.4 |
| 74 | 4 | 164 | 7 | 254 | 1 |
| 75 | 2 | 165 | 3 | 255 | 4 |
| 76 | 1 | 166 | 12 | 256 | 1 |
| 77 | 2 | 167 | 2.4 | 257 | 3.5 |
| 78 | <1 | 168 | | 258 | 4 |
| 79 | 1 | 169 | 5 | 259 | 2 |
| 80 | 1 | 170 | 110 | 260 | 2 |
| 81 | <1 | 171 | 6 | 261 | 1.6 |
| 82 | 1 | 172 | | 262 | |
| 83 | 1.4 | 173 | 2 | 263 | |
| 84 | 16 | 174 | >100 | 264 | |
| 85 | 86 | 175 | 7 | 265 | |
| 86 | 5 | 176 | 34 | 266 | 23 |
| 87 | 8 | 177 | 3 | 267 | 1.7 |
| 88 | 1.5 | 178 | 28 | 268 | 6.5 |
| 89 | 1 | 179 | >100 | 269 | 55 |
| 90 | 2 | 180 | >100 | | |
| 91 | <1 | 181 | >100 | | |

TABLE C

Comparison of enzym and cell IC50 (nM) of selected benzimidazoles

| Structure | Enzym IC50 | Cell IC50 |
|---|---|---|
| Example 17 | 3 | 6 |

TABLE C-continued
Comparison of enzym and cell IC50 (nM) of selected benzimidazoles
| Structure | Enzym IC50 | Cell IC50 |
|---|---|---|
| 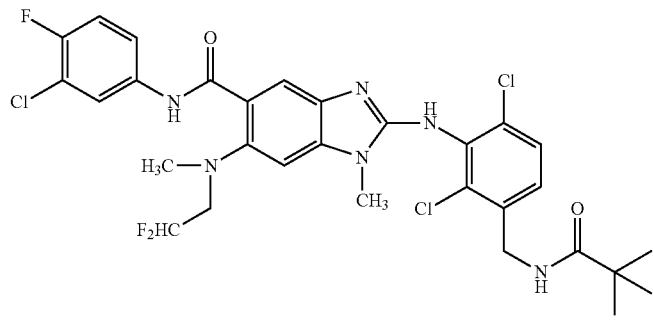 [SMILES: CN(CC(F)F)c1cc2c(cc1C(=O)Nc1ccc(F)c(Cl)c1)nc(Nc1c(Cl)ccc(CNC(=O)C(C)(C)C)c1Cl)n2C]<br>Example 2 | 2 | <1 |
| 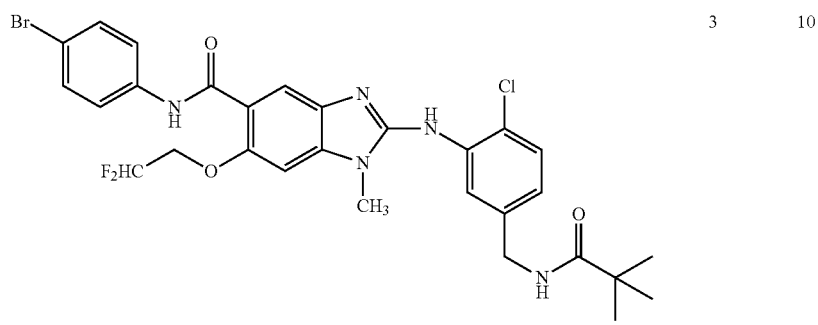<br>of WO 2010/100249 | 3 | 10 |
| 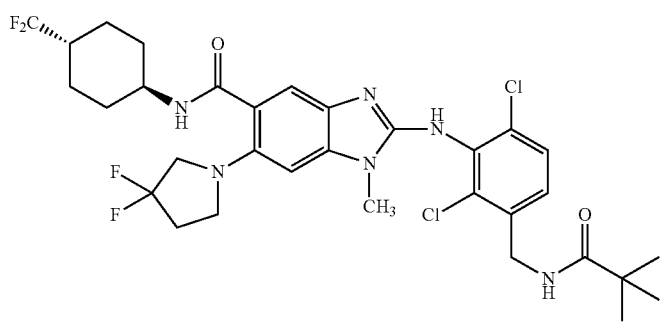<br>Example 20 | 3 | 1 |
| 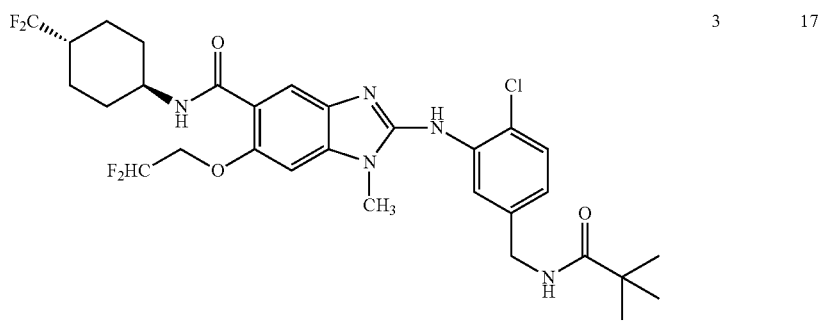<br>of WO 2010/100249 | 3 | 17 |

TABLE C-continued

Comparison of enzym and cell IC50 (nM) of selected benzimidazoles

| Structure | Enzym IC50 | Cell IC50 |
|---|---|---|
| Example 45 | 5 | 7 |
| of WO 2010/100249 | 2 | >200 |

Tables A, B and C demonstrate that compounds with a similar affinity for the mPGES-1 enzyme as measured in the enzyme assay may have different potencies in the cell based assay.

Data from a cell based pharmacological assay when compared with data from an enzyme assay are considered to allow for a better predictability and estimation of therapeutic effective concentrations/doses. Compounds of the present invention show high potency in both assays. Consequently, they are likely to be more suitable for the in-vivo use.

Method of Treatment

The present invention relates to compounds of formula I which are useful in the prevention and/or treatment of a disease and/or condition in which the inhibition of prostaglandin E synthases, in particular that of the microsomal prostaglandin $E_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament.

Another aspect of the present invention is the use of compounds of formula I for the treatment and/or prevention of a disease and/or condition in which the inhibition of the mPGES-1 is of therapeutic benefit.

A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:

1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;

2. Headaches such as migraines with and without aura, tension-type headaches, cluster headaches and headaches with different origins;
3. Sympathetically maintained pain like complex regional pain syndrome Type I and II;
4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;
5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases;
6. Visceral disorders such as chronic pelvic pain, pancreatitis, peptic ulcer, interstitial cystitis, cystitis, renal colic, angina, dysmenorrhoea, menstruation, gynaecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;
7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;
8. Neurological diseases such as cerebral oedema and angioedema, cerebral dementia like e.g. Parkinson's and Alzheimers disease, senile dementia; multiple sclerosis, epilepsy, drug resistant epilepsy, stroke, myasthenia gravis, brain and meningeal infections like encephalomyelitis, meningitis, including HIV as well as schizophrenia, delusional disorders, autism, affective disorders and tic disorders;
9. Work-related diseases like pneumoconiosis, including aluminosis, anthracosis, asbestosis, chalicosis, ptilosis, siderosis, silicosis, tabacosis and byssinosis;
10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;
11. Skin diseases such as psoriasis and eczema, dermatitis, sunburn, burns as well as aprains and strains and tissue trauma;
12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;
13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);
14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.
15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Dosage

The dose range of the compounds of formula I applicable per day is usually from 0.01 to 5000 mg, preferably from 1 to 2000 mg, more preferably from 5 to 500 mg, most preferably 10 to 250 mg. Each dosage unit may conveniently contain from 2 to 500 mg, preferably 5 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Formulations

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
- non-steroidal antiinflammatory drugs (NSAIDs) including COX-2 inhibitors;
- opiate receptor agonists;
- Cannabionoid agonists or inhibitors of the endocannabinoid pathway
- Sodium channel blockers;
- N-type calcium channel blockers;
- serotonergic and noradrenergic modulators;
- corticosteroids;
- histamine H1 receptor antagonists;
- histamine H2 receptor antagonists;
- proton pump inhibitors;
- leukotriene antagonists and 5-lipoxygenase inhibitors;
- local anesthetics;
- VR1 agonists and antagonists;
- Nicotinic acetylcholine receptor agonists;
- P2X3 receptor antagonists;
- NGF agonists and antagonists or anti-NGF antibodies;
- NK1 and NK2 antagonists;
- Bradykinin B1 antagonists
- CCR2 antagonists
- iNOS or nNOS or eNOS inhibitors
- NMDA antagonist;
- potassium channel modulators;
- GABA modulators;
- serotonergic and noradrenergic modulators;
- anti-migraine drugs;
- neuropathic pain drugs such as pregabaline or duloxetine.

Said list is not considered to have a limiting character.

In the Following Representative Examples of Such Treatment Options Shall be Given.
- Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;
- Antiviral drugs like acyclovir, tenovir, pleconaril, peramivir, pocosanol and the like.
- Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;
- Opiate receptor agonists: morphine, propoxyphene (Darvon), tramadol, buprenorphin and the like.
- Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs including but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;
- anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;
- IL-1 receptor antagonists such as but not limited to Kineret;
- Sodium channel blockers: carbamazepine, mexiletine, lamotrigine, tectin, lacosamide and the like.
- N-type calcium channel blockers: Ziconotide and the like.
- Serotonergic and noradrenergic modulators: paroxetine, duloxetine, clonidine, amitriptyline, citalopram;
- Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;
- Histamine H2 receptor antagonists: cimetidine, famotidine and ranitidine and the like;
- Proton pump inhibitors: omeprazole, pantoprazole and esomeprazole and the like;
- Leukotriene antagonists and 5-lipoxygenase inhibitors: zafirlukast, montelukast, pranlukast and zileuton and the like;
- Local anesthetics such as ambroxol, lidocaine and the like;
- Potassium channel modulators: like retigabine;
- GABA modulators: lacosamide, pregabalin, gabapentin and the like;
- Anti-migraine drugs: sumatriptan, zolmitriptan, naratriptan, eletriptan, telcegepant and the like;
- NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS

AcOH acetic acid
aq aqueous
Boc tert-butoxycarbonyl
$Boc_2O$ di-tert-butyl-dicarbonate
CE chromatography equipment
conc concentrated
DCM dichloromethane
DIC N,N-diisopropylcarbodiimide
DIPEA N-ethyldiisopropylamine
DMSO dimethylsulphoxide
DMF N,N-dimethylformamide
EDC 1-(3-dimethylaminopropyl)-3-ethylcarbodiimide hydrochloride
EtOAc ethyl acetate
$Et_2O$ diethyl ether
EtOH ethanol
HATU O-(7-azabenzotriazol-1-yl)N.N.N.N',N'-tetramethyluroniumhexafluoro-phosphate
HPLC high performance liquid chromatography
i-PrOH isopropanol
mCPBA meta-chloroperbenzoic acid ~75%
MeCN acetonitrile
MeOH methanol
MS mass spectrometry
NMP N-methyl-2-pyrrolidon
PE petrol ether
PPA 1-propylphosphonic-acid cyclic anhydride
Pd/C 10% Palladium on carbon
Ra—Ni Raney-Nickel
RP reversed phase
rt room temperature
$R_f$ retention factor
$R_t$ retention time
sat saturated
TBTU O-(benzotriazol-1-yl)-N,N,N',N'-tetramethyluronium tetrafluoroborate
TCDI thiocarbonyl diimidazole
TEA triethylamine
THF tetrahydrofuran
TFA trifluoroacetic acid
TLC thin layer chromatography Analytical Methods All compounds specified in the examples below gave the correct mass spectra matching the theoretical isotope pattern. For practical reasons, only one of the major isotope peaks is given as representative data for the mass spectrum.

The TLC data is obtained by using the following tlc plates
a) Silica gel plates 60 F254 Merck No 1.05714.0001 abbreviated in the experimental part as "silica gel"
b) Reversed phase plates: RP-8 F 254s Merck No: 1.15684.0001 abbreviated in the experimental part as "RP-8".
c) Aluminiumoxide plates 60 F254 Merck 1.05713.0001 abbreviated in the experimental part as "Alox"

The $R_f$ values given are determined without chamber saturation.

Microwave irradiations are performed using a Biotage Initiator microwave oven and Biotage microwave reaction kits.

Flash chromatography purifications are performed using silica gel from Millipore (MATREX™, 35 bis 70 μm) or Alox (E. Merck, Darmstadt, Aluminiumoxid 90 standardisiert, 63 bis 200 μm, Artikel-Nr: 1.01097.9050).

The HPLC/MS data, where specified, are obtained under the following conditions:

CE1:

Agilent HP 1200 with binary pump, Agilent MS 6140, HiPALS1367C

The diode array detection is measured in a wavelength range of 190-400 nm.

Range of mass-spectrometric detection: m/z 100 to m/z 1000.

CE 2:

Agilent HP 1100, Agilent MS G6140

The diode array detection is measured in a wavelength range of 210-400 nm.

CE3

Waters Acquity with DA and MS detector.

CE4

Agilent 1200 with DA and MS-detector.

CE5

Agilent1100 with DA and Waters MS detector.

The following methods are used (if not stated otherwise the column temperature is 25° C.):

Method A (CE 2):

Stationary phase (column temperature: constant at 60° C.): XBridge C18, 4.6×30 mm, 3.5 μm Mobile phase: E1: water with 0.1% TFA, E2: MeOH with 0.1% TFA Eluent Gradient:

| time in min | % E1 | % E2 | flow rate in mL/min |
|---|---|---|---|
| 0.0 | 95 | 5 | 4 |
| 0.15 | 95 | 5 | 4 |
| 1.7 | 0 | 100 | 4 |
| 2.25 | 0 | 100 | 4 |

Method B (CE1):
Stationary phase: Zorbax Stable Bond C18, 1.8 μm, 3.0×30 mm
Mobile phase: E1: water with 0.15% HCOOH, E2: MeCN
Eluent Gradient:

| time in min | % E1 | % E2 | flow rate in mL/min |
|---|---|---|---|
| 0.00 | 95 | 5 | 1.6 |
| 1.00 | 10 | 90 | 1.6 |
| 2.50 | 10 | 90 | 1.6 |
| 2.75 | 95 | 5 | 1.6 |

Method C(CE1):
Stationary phase: As described in method B.
Mobile phase: E1: water with 0.15% HCOOH, E2: MeCN
Eluent Gradient:

| time in min | % E1 | % E2 | flow rate in mL/min |
|---|---|---|---|
| 0.00 | 95 | 5 | 1.6 |
| 2.25 | 10 | 90 | 1.6 |
| 2.50 | 10 | 90 | 1.6 |
| 2.75 | 95 | 5 | 1.6 |

Method E (CE1):
Stationary phase (column temperature: constant at 40° C.): Waters XBridge C18, 2.5 μm, 3.0×30 mm
Mobile phase and eluent gradient as described in method C.

Method F (CE3)
Stationary phase (column temperature: constant at 60° C.): Ascentis Express C18_2.1×50 mm, 2.7 μm.
Mobile phase: E1: water with 0.1% TFA, E2: MeCN with 0.08% TFA
Eluent Gradient:

| time in min | % E1 | % E2 | flow rate in mL/min |
|---|---|---|---|
| 0.00 | 95 | 5 | 1.5 |
| 0.7 | 1 | 99 | 1.5 |
| 0.8 | 1 | 99 | 1.5 |
| 0.81 | 95 | 5 | 1.5 |

Method G (CE5)
Stationary phase (column temperature: constant at 60° C.): Sunfire C18_4.6×50 mm, 3.5 μm.
Mobile phase: E1: water with 0.1% TFA, E2: MeOH
Eluent Gradient:

| time in min | % E1 | % E2 | flow rate in mL/min |
|---|---|---|---|
| 0.00 | 80 | 20 | 2.0 |
| 1.7 | 0 | 100 | 2.0 |
| 2.5 | 0 | 100 | 2.0 |
| 2.6 | 80 | 20 | 2.0 |

Method H (CE2)
Stationary phase (column temperature: constant at 60° C.): Sunfire C18_4.6×30 mm, 3.5 μm.
Mobile phase: E1: water with 0.1% TFA, E2: MeOH
Eluent Gradient:

| time in min | % E1 | % E2 | flow rate in mL/min |
|---|---|---|---|
| 0.00 | 95 | 5 | 4.0 |
| 0.15 | 95 | 5 | 4.0 |
| 1.7 | 0 | 100 | 4.0 |
| 2.25 | 0 | 100 | 4.0 |

Method I (CE2)
Stationary phase (column temperature: constant at 60° C.): XBridgeC18_4.6×30 mm, 3.5 μm.
Mobile phase: E1: water with 0.1% NH$_4$OH, E2: MeOH
Eluent Gradient:

| time in min | % E1 | % E2 | flow rate in mL/min |
|---|---|---|---|
| 0.00 | 95 | 5 | 4.0 |
| 0.15 | 95 | 5 | 4.0 |
| 1.7 | 0 | 100 | 4.0 |
| 2.1 | 0 | 100 | 4.0 |

Method J (CE1)
Stationary phase (column temperature: constant at 60° C.): SunfireC18_3×30 mm, 2.5 μm.
Mobile phase: E1: water with 0.1% HCOOH, E2: MeOH
Eluent Gradient:

| time in min | % E1 | % E2 | flow rate in mL/min |
|---|---|---|---|
| 0.00 | 95 | 5 | 2.2 |
| 0.05 | 95 | 5 | 2.2 |
| 1.4 | 0 | 100 | 2.2 |
| 1.8 | 0 | 100 | 2.2 |

Method K (CE2)
Stationary phase (column temperature: constant at 60° C.): XBridgeC18_4.6×30 mm, 3.5 μm.
Mobile phase: E1: water with 0.1% NH$_4$OH, E2: MeOH
Eluent Gradient:

| time in min | % E1 | % E2 | flow rate in mL/min |
|---|---|---|---|
| 0.00 | 50 | 50 | 4.0 |
| 0.15 | 50 | 50 | 4.0 |
| 1.7 | 0 | 100 | 4.0 |
| 2.1 | 0 | 100 | 4.0 |

Method L (CE4)
Stationary phase (column temperature: constant at 60° C.): HaloC18_2.1×30 mm, 2.7 μm.
Mobile phase: E1: water with 0.1% TFA, E2: MeCN
Eluent Gradient:

| time in min | % E1 | % E2 | flow rate in mL/min |
|---|---|---|---|
| 0.00 | 93 | 7 | 3.0 |
| 0.1 | 93 | 7 | 3.0 |
| 0.11 | 60 | 40 | 3.0 |
| 0.5 | 0 | 100 | 3.0 |

Synthesis of building blocks of the 2,3,4-trisubstituted benzylamine-type

Building Block A

N-(2,4-Dichloro-3-isothiocyanato-benzyl)-2,2-dimethyl-propionamide

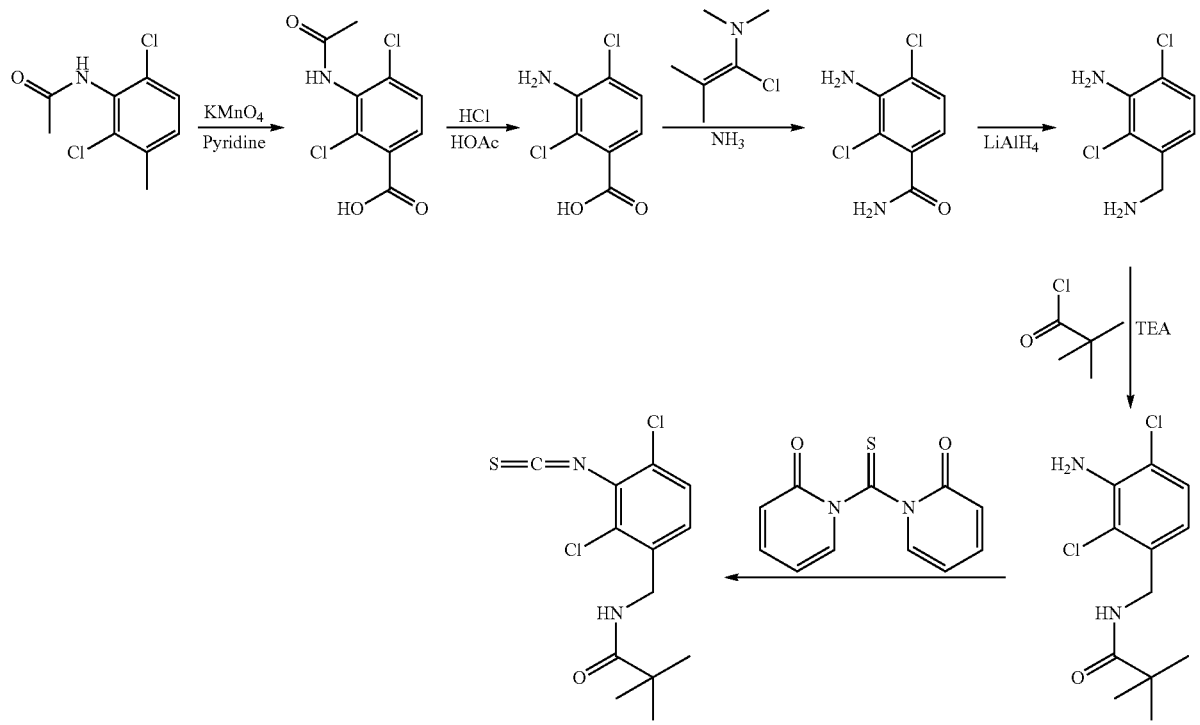

(a) 3-Acetylamino-2,4-dichloro-benzoic acid

Water (110 mL) is added to N-(2,6-dichloro-3-methyl-phenyl)-acetamide (13 g, 59 mmol) in pyridine (30 mL). The mixture is heated to 70° C. and KMnO$_4$ (47 g, 298 mmol) is cautiously added portionwise. After 6 h at reflux the reaction mixture is filtered through a pad of celite and washed with hot water. The filtrate is cooled to rt, concentrated and slowly acidified with 6 M aq HCl solution. The mixture is cooled in an ice bath, filtered and the filtercake is washed with cold water and dried to give the sub-title compound.

Yield: 11.6 g (78%). R$_f$=0.1 (silica gel, DCM:EtOH 9:1). MS m/z: 248 [M+H]$^+$.

(b) 3-Amino-2,4-dichloro-benzoic acid

3-Acetylamino-2,4-dichloro-benzoic acid (21.0 g, 84.6 mmol) is stirred in 6 M aq HCl-solution (120 mL) and acetic acid (250 mL) at reflux for 24 h. The reaction mixture is cooled, concentrated, diluted with water and concentrated again. The residue is diluted with water, stirred under cooling and filtered. The filtercake is washed and dried to give the sub-title compound.

Yield: 16.8 g (96%). MS m/z: 204 [M−H]$^-$. HPLC-method C: R$_t$=1.46 min.

(c) 3-Amino-2,4-dichloro-benzamide (1-Chloro-2-methyl-propenyl)-dimethyl-amine (16.1 mL, 116 mmol) is added to 3-amino-2,4-dichloro-benzoic acid (20.0 g, 97.1 mmol) in THF (320 mL). After 4 h at rt the mixture is added dropwise to conc NH$_3$ (320 mL) and stirred at rt overnight. The reaction mixture is concentrated, cooled and filtered. The filtercake is dried to give the sub-title compound.

Yield: 17.4 g (87%). MS m/z: 205 [M+H]$^+$. HPLC-method C: R$_t$=1.19 min.

(d) 3-Amino-2,4-dichloro-benzylamine

3-Amino-2,4-dichloro-benzamide (2.00 g, 9.8 mmol) in THF (45 mL) is added dropwise to LiAlH$_4$ (1 M in THF, 24.4 mL) in THF (45 mL). The reaction mixture is stirred for 1 h at rt and 10 h at reflux. Excess LiAlH$_4$ is destroyed under cooling as described by L. F. Fieser & M. Fieser Vol 1, p 584 Wiley 1967. After 30 min the mixture is filtered and the filtrate is concentrated to give the sub-title compound.

Yield: 1.85 g (99%). R$_f$=0.12 (silica gel, DCM:EtOH 95:5). MS m/z: 191 [M+H]$^+$.

(e) N-(3-Amino-2,4-dichloro-benzyl)-2,2-dimethyl-propionamide

3-Amino-2,4-dichloro-benzylamine (2.28 g, 11.9 mmol) is added to a mixture of 2,2-dimethyl-propionic acid chloride (1.47 mL, 11.9 mmol) and TEA (4.14 mL, 29.8 mmol) in THF (90 mL) and it is stirred for 3 h. The reaction mixture is concentrated, diluted with EtOAc, washed with 5% aq NaHCO$_3$ solution and water, dried with Na$_2$SO$_4$, filtered and concentrated to give the sub-title compound.

Yield: 3.1 g (94%). R$_f$=0.61 (silica gel, DCM:EtOH 95:5).

(f) N-(2,4-Dichloro-3-isothiocyanato-benzyl)-2,2-dimethyl-propionamide 1,1'-Thiocarbonyldi-2-pyridone (4.87 g, 21 mmol) is added to a mixture of N-(3-amino-2,4-dichloro-benzyl)-2,2- dimethyl-propionamide (5.50 g, 20 mmol) and dioxane (200 mL) and stirred at rt for 2 h and at reflux for 8 h. The mixture is concentrated, diluted with DCM and filtered over silica gel. The filtrate is concentrated to give the sub-title compound.

Yield: 6.00 g (95%). HPLC-method B: $R_t$=1.58 min. MS m/z: 318 [M+H]$^+$.

Alternatively, building block A can also be prepared according to the following scheme:

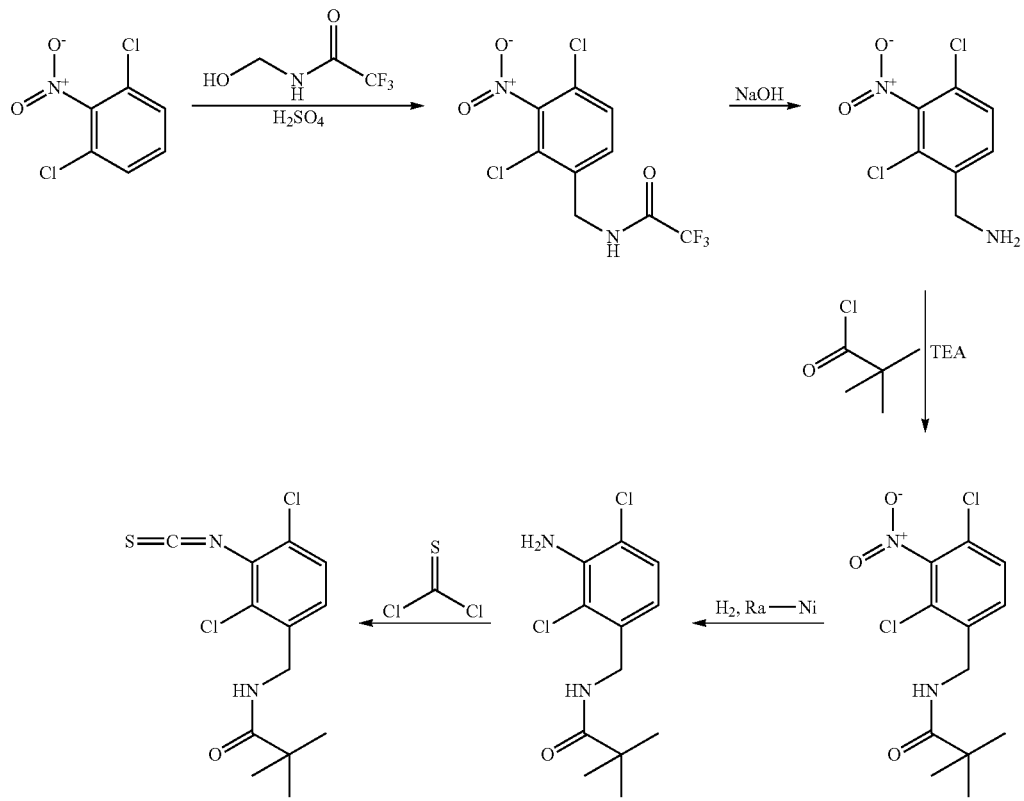

(g) N-(3-Nitro-2,4-dichloro-benzyl)-2,2,2-trifluoro-acetamide

N-(Hydroxymethyl)trifluoroacetamide (6.6 mmol; 0.946 g) is added to a mixture of 2,6-dichloro-nitrobenzene (0.899 mL; 6.6 mmol) and conc $H_2SO_4$ (15 mL) at 75° C. The mixture is stirred at 75° C. overnight, poured into ice water and stirred for 1 h. The precipitate is collected by filtration and dried. Yield 0.32 g (15%). MS [M−H]$^-$=315, HPLC-method B: $R_t$=1.43 min.

(h) 3-Nitro-2,4-dichloro-benzylamine

A mixture of N-(3-nitro-2,4-dichloro-benzyl)-2,2,2-trifluoroacetamide (0.66 g, impure, content ~50%), 4M NaOH-solution (1.3 mL, 5.2 mmol) and MeOH (15 mL) is refluxed for 4 h. Then the mixture is concentrated, diluted with water, acidified with 4M HCl, filtered, 4M NaOH-solution is added and it is extracted with EtOAc. The organic phase is dried with $Na_2SO_4$, filtered and concentrated. Yield 0.17 g MS m/z: 221 [M+H]$^+$. HPLC-method B: $R_t$=1.02 min.

(i) N-(3-Nitro-2,4-dichloro-benzyl)-2,2-dimethyl-propionamide 2,2-Dimethyl-propionic acid chloride (0.124 mL, 1.01 mmol) is added to a mixture of 3-nitro-2,4-dichloro-benzylamine (0.28 g, 1.01 mmol) and TEA (0.35 mL, 2.52 mmol) in THF (10 mL) and it is stirred overnight. The reaction mixture is concentrated, diluted with EtOAc, washed successively with 5% aq $NaHCO_3$ solution and brine, dried with $Na_2SO_4$ filtered and concentrated.

Yield: 0.29 g. MS m/z: 306 [M+H]$^+$. HPLC-method B: $R_t$=1.42 min.

(g) N-(3-Amino-2,4-dichloro-benzyl)-2,2-dimethyl-propionamide

A mixture of 3-nitro-2,4-dichloro-benzylamine (290 mg, 0.95 mmol), Ra—Ni (50 mg) and THF (15 mL) is stirred for 7 h under a hydrogen atmosphere (50 psi). The catalyst is removed by filtration and the filtrate is concentrated.

Yield: 0.26 g. MS m/z: 276 [M+H]$^+$. HPLC-method B: $R_t$=1.32 min.

(h) N-(2,4-Dichloro-3-isothiocyanato-benzyl)-2,2-dimethyl-propionamide

A mixture of N-(3-amino-2,4-dichloro-benzyl)-2,2-dimethyl-propionamide (0.95 g, 3.4 mmol) in 4.0 mL dioxane is added to thiophosgene (0.45 mL, 5.8 mmol) in 2.5 mL water. The mixture is stirred overnight, extracted with DCM and the organic phase is washed with 5% aq $NaHCO_3$ solution and water and dried with $Na_2SO_4$. After filtration and concentration, the crude product is diluted with DCM, filtered through a pad of silica gel and concentrated.

65
Building Block B (2,4-Dichloro-3-isothiocyanato-benzyl)-carbamic acid tert-butyl ester

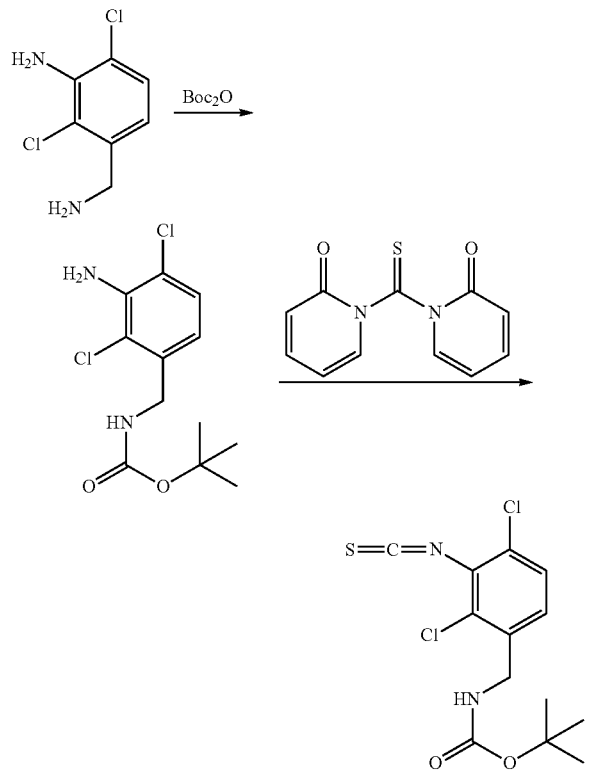

(a) (3-Amino-2,4-dichloro-benzyl)-carbamic acid tert-butyl ester

Boc$_2$O (1.48 g, 6.68 mmol) in 3.3 mL DCM is added at 0° C. to a mixture of 3-amino-2,4-dichloro-benzylamine (1.16 g, 6.07 mmol), 6.7 mL DCM and 12.1 mL 1 N NaOH-solution. The mixture is stirred vigorously for 2 d and diluted with 5% aq NH$_3$-solution. The organic phase is separated and the aq phase is washed 2× with DCM. The combined organic phase is washed with brine, dried with Na$_2$SO$_4$, filtered and concentrated to give the sub-title compound.

Yield: 1.71 g (97%). R$_f$=0.65 (silica gel, DCM:EtOH 95:5). MS m/z: 291 [M+H]$^+$.

(b) (2,4-Dichloro-3-isothiocyanato-benzyl)-carbamic acid tert-butyl ester 1,1'-Thiocarbonyldi-2-pyridone (0.42 g, 1.8 mmol) is added to a mixture of (3-amino-2,4-dichloro-benzyl)-carbamic acid tert-butyl ester (0.50 g, 1.7 mmol) and dioxane (25 mL) and stirred at rt for 2 h and at reflux for 2 d. The mixture is concentrated, diluted with DCM and filtered over silica gel. The filtrate is concentrated to give the title compound.

Yield: 0.49 g (86%). R$_f$=0.83 (silica gel, DCM:EtOH 95:5).

66
Building Block C

N-(2,4-Difluoro-3-isothiocyanato-benzyl)-2,2-dimethyl-propionamide

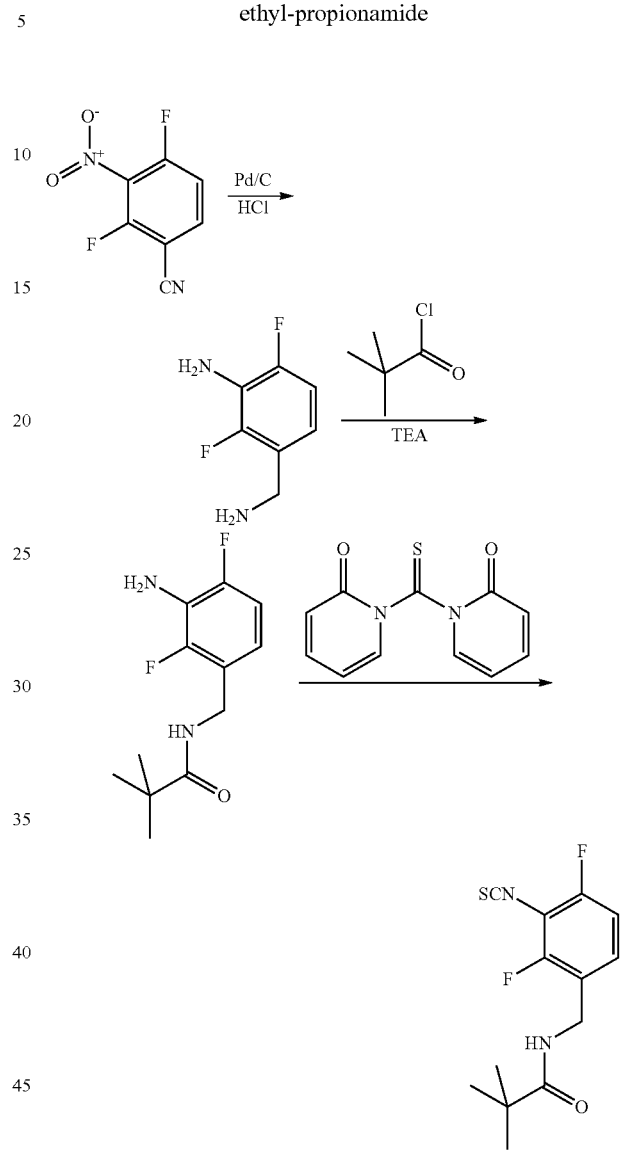

(a) 3-Amino-2,4-difluoro-benzylamine

A mixture of 3-nitro-2,4-difluoro-benzonitrile (500 mg, 2.72 mmol), Pd/C (200 mg), conc HCl (1.50 mL) and MeOH (25 mL) is stirred at rt overnight under a hydrogen atmosphere (3 bar). The catalyst is removed by filtration, the filtrate is concentrated and evaporated twice from EtOH to give the sub-title compound as HCl salt.

Yield: 580 mg. MS m/z: 159 [M+H]$^+$.

(b) N-(3-Amino-2,4-difluoro-benzyl)-2,2-dimethyl-propionamide

TEA (400 µL, 2.86 mmol) followed by pivaloyl chloride (60 µL, 0.52 mmol) are added to 3-amino-2,4-difluoro-benzylamine (120 mg as HCl salt) in THF (10 mL) and the mixture is stirred at rt overnight. The reaction mixture is diluted with EtOAc and sat NaHCO$_3$-solution, the organic layer is washed with water and brine, dried and concentrated to give the sub-title compound.

Yield: 110 mg. HPLC-method B: R$_t$=1.19 min. MS m/z: 243 [M+H]$^+$. R$_1$=0.45 (silica gel, DCM:EtOH 95:5).

(c) N-(2,4-Difluoro-3-isothiocyanato-benzyl)-2,2-dimethyl-propionamide

A mixture of N-(3-amino-2,4-difluoro-benzyl)-2,2-dimethyl-propionamide (570 mg, 2.35 mmol), 1,1'-thiocarbonyldi-2(1H)-pyridone (550 mg, 2.35 mmol) and dioxane (20 mL) is stirred at reflux overnight. The reaction mixture is concentrated, diluted with DCM, filtered through a pad of silica gel and the filtrate is concentrated to give the title compound.

Yield: 440 mg (65%). R$_f$=0.80 (silica gel, DCM:EtOH 95:5).

Building Block D

N-(4-Chloro-fluoro-3-isothiocyanato-benzyl)-2,2-dimethyl-propionamide

(b) 3-Acetylamino-4-chloro-2-fluoro-benzoic acid

The sub-title compound is prepared from N-(6-chloro-2-fluoro-3-methyl-phenyl)-acetamide and KMnO$_4$ in pyridine in analogy to step Aa.

Yield: 49%. R$_f$=0.2 (silica gel, DCM/EtOH 4:1). HPLC R$_t$=0.93 min (method B). MS m/z: 232 [M+H]$^+$.

(c) 3-Amino-4-chloro-2-fluoro-benzoic acid

The sub-title compound is prepared from 3-acetylamino-4-chloro-2-fluoro-benzoic acid and 6 M HCl-solution in analogy to step Ab.

Yield: 96%. HPLC R$_t$=1.10 min (method B). MS m/z: 190 [M+H]$^+$.

(d) 3-Amino-4-chloro-2-fluoro-benzamide

The sub-title compound is prepared from 3-amino-4-chloro-2-fluoro-benzoic acid, (1-chloro-2-methyl-propenyl)-dimethyl-amine and conc NH$_3$ in analogy to step Ac.

Yield: 69%. R$_f$=0.3 (silica gel, PE:EtOAc 4:6). HPLC-method B: R$_t$=0.97 min. MS m/z: 189 [M+H]$^+$.

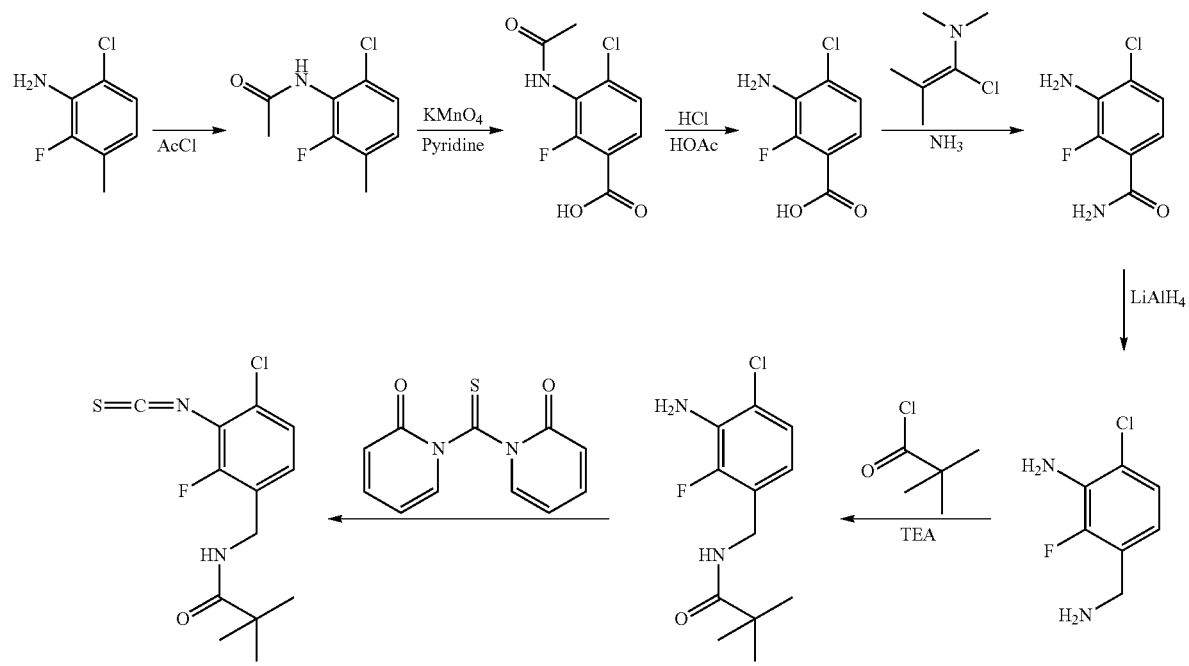

(a) N-(6-Chloro-2-fluoro-3-methyl-phenyl)-acetamide

Acetylchloride (2.56 mL, 36.0 mmol) is added to a mixture of 6-chloro-2-fluoro-3-methyl-aniline (5.00 g, 31.3 mmol) and toluene (200 mL), additional toluene (50 mL) is added and the mixture is heated to reflux for 3 h. Then it is cooled with an ice bath and the formed precipitate is filtered off, washed with cold toluene and dried.

Yield: 4.75 g (75%). HPLC-method B: R$_t$=1.12 min. MS m/z: 202 [M+H]$^+$.

(e) 3-Amino-4-chloro-2-fluoro-benzylamine

The crude sub-title compound is prepared from 3-amino-4-chloro-2-fluoro-benzamide and LiAlH$_4$ in analogy to step Ad. HPLC-method B: R$_t$=0.37 min. MS m/z: 175 [M+H]$^+$.

(f) N-(3-Amino-4-chloro-2-fluoro-benzyl)-2,2-dimethyl-propionamide

The sub-title compound is prepared from crude 3-amino-4-chloro-2-fluoro-benzylamine, 2,2-dimethyl-propionic acid chloride and TEA in analogy to example Ae.

Yield: 36% (side product in 29%: N-(3-Amino-4-chloro-benzyl)-2,2-dimethyl-propionamide). $R_f$=0.6 (silica gel, PE:EtOAc 6:4). HPLC-method B: $R_t$=1.27 min. MS m/z: 259 [M+H]$^+$.

(g) N-(4-Chloro-2-fluoro-3-isothiocyanato-benzyl)-2,2-dimethyl-propionamide

The title compound is prepared from N-(3-amino-4-chloro-2-fluoro-benzyl)-2,2-dimethyl-propionamide, 1,1'-thiocarbonyldi-2-pyridone in analogy to step Af.
Yield: 65%. $R_1$=0.9 (silica gel, DCM:EtOH 95:5).

Building Block E

N-(2,4-Dichloro-3-isothiocyanato-benzyl)-2-methyl-2-fluoro-propionamide

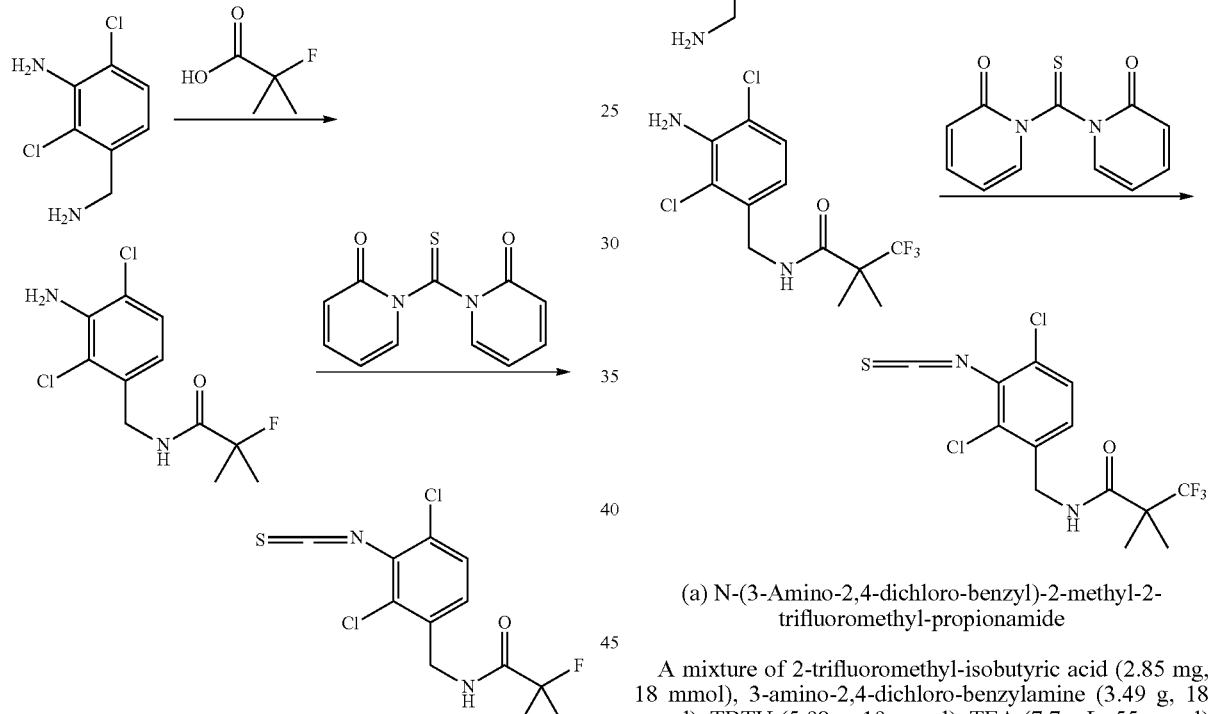

(a) N-(3-Amino-2,4-dichloro-benzyl)-2-methyl-2-fluoro-propionamide

A mixture of 2-fluoroisobutyric acid (555 mg, 5.2 mmol), 3-amino-2,4-dichloro-benzylamine (1.00 g, 5.2 mmol), TBTU (1.85 g, 5.8 mmol), TEA (1.82 mL, 13 mmol) and THF is stirred at rt overnight. The mixture is concentrated, stirred with sat. aq NaHCO$_3$-solution and the resulting precipitate is collected by filtration, washed with water and dried.
Yield: 1.32 g (90%). HPLC $R_t$=1.23 min (method A). MS m/z: 281 [M+H]$^+$.

(b) N-(2,4-Dichloro-3-isothiocyanato-benzyl)-2-methyl-2-fluoro-propionamide 1,1'-Thiocarbonyldi-2-pyridone (1.21 g, 5.2 mmol) is added to a mixture of N-(3-amino-2,4-dichloro-benzyl)-2-methyl-2-fluoro-propionamide (1.32 g, 4.7 mmol) and dioxane (25 mL) and it is stirred at reflux for 2 d. The mixture is diluted with water, most of the dioxane is removed under reduced pressure and the resulting precipitate is collected by filtration, washed with water and dried.
Yield: 1.46 g (96%). HPLC $R_t$=1.60 min (method A). MS m/z: 321 [M+H]$^+$.

Building Block F

N-(2,4-Dichloro-3-isothiocyanato-benzyl)-2-methyl-2-trifluoromethyl-propionamide (a) N-(3-Amino-2,4-dichloro-benzyl)-2-methyl-2-trifluoromethyl-propionamide A mixture of 2-trifluoromethyl-isobutyric acid (2.85 mg, 18 mmol), 3-amino-2,4-dichloro-benzylamine (3.49 g, 18 mmol), TBTU (5.98 g, 19 mmol), TEA (7.7 mL, 55 mmol) and 65 mLTHF is stirred at 45° C. overnight. The mixture is washed with sat aq NaHCO$_3$-solution and water and the organic phase is dried with Na$_2$SO$_4$, filtered, concentrated and purified by chromatography (silicagel, Cyclohexane:EtOAc 11:1→7:3).
Yield: 3.9 g (65%). HPLC $R_t$=1.42 min (method I). MS m/z: 329 [M+H]$^+$.

(b) N-(2,4-Dichloro-3-isothiocyanato-benzyl)-2-methyl-2-trifluoromethyl-propionamide 1,1'-Thiocarbonyldi-2-pyridone (3.12 g, 13 mmol) is added to a mixture of N-(3-amino-2,4-dichloro-benzyl)-2-methyl-2-trifluoromethyl-propionamide (3.90 g, 11.8 mmol) and dioxane (135 mL) and stirred at reflux overnight. The mixture is diluted with water, most of the dioxane is removed under reduced pressure and the resulting precipitate is filtered, washed with water and dried.
Yield: 4.26 g (92%). HPLC $R_t$=1.71 min (method I). MS m/z: 371 [M+H]$^+$.

Example 1
N-(4-Fluoro-3-chloro-phenyl)-2-{2,6-dichloro-3-[(2,2-dimethyl-propionylamino)-methyl]-phenylamino}-6-(4-fluoro-piperidinyl)-1-methyl-1H-benzimidazole-5-carboxylic acid amide
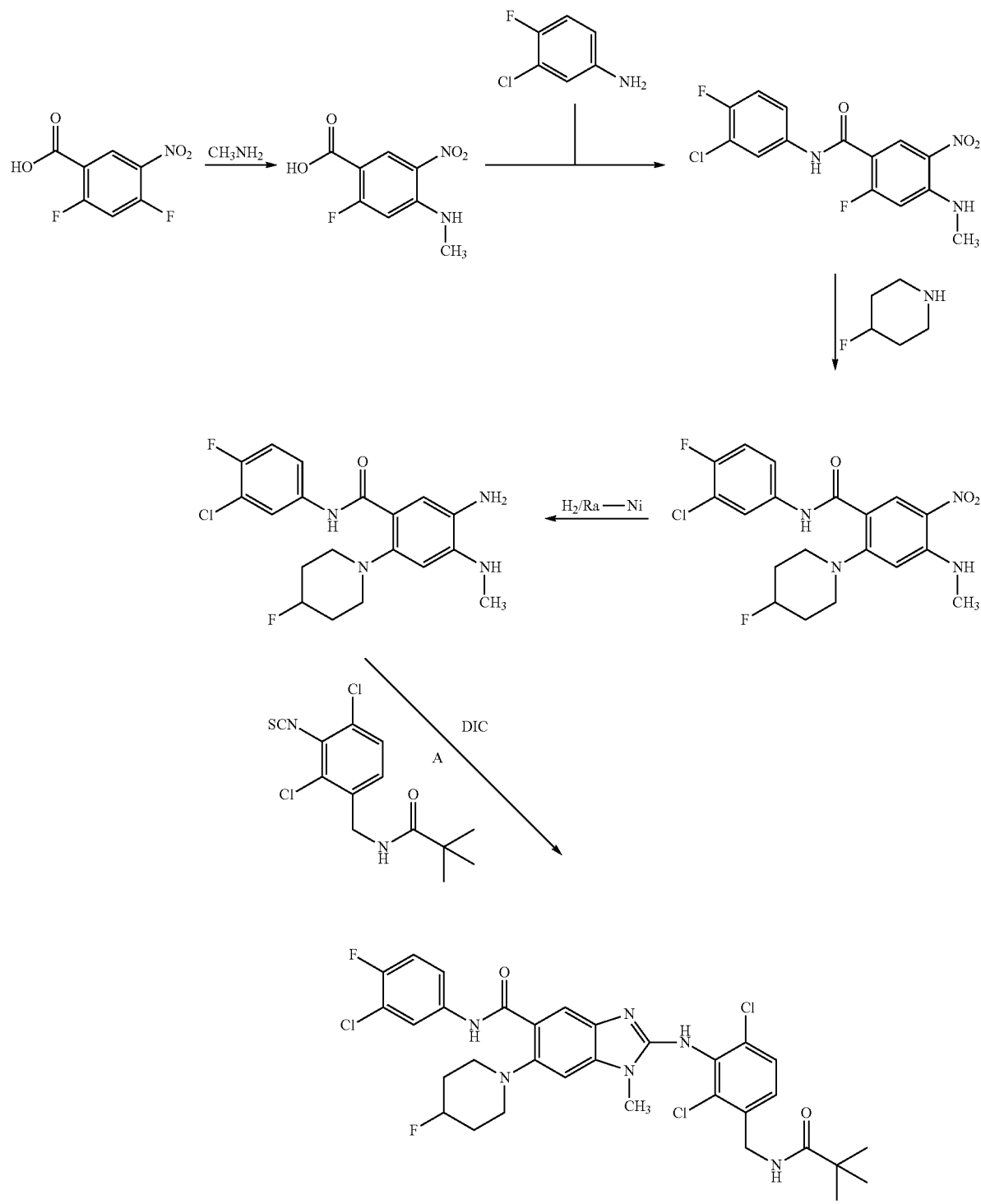

(a) 2-Fluoro-4-methylamino-5-nitro-benzoic acid

Methylamine (13.5 mL, 40% in water) is added to an ice-cooled mixture of 2,4-difluoro-5-nitro-benzoic acid (10.0 g, 49 mmol) in water (100 mL) and it is stirred for 30 min at rt. The mixture is acidified with 6N aq HCl-solution and the precipitate is filtered, washed with water and dried at 60° C. The crude material is recrystallized from MeOH. The final product is slightly contaminated by its regioisomer 4-fluoro-2-methylamino-5-nitro-benzoic acid.

(b) N-(4-Fluoro-3-chloro-phenyl)-2-fluoro-4-methylamino-5-nitro-benzoic acid amide A mixture of 2-fluoro-4-methylamino-5-nitro-benzoic acid (0.500 g, 2.34 mmol), (1-chloro-2-methyl-propenyl)-dimethylamine (0.371 mL, 2.80 mmol) and DCM (50 mL) is stirred for 30 min, then 4-fluoro-3-chloro-aniline (0.340 g, 2.34 mmol) and DIPEA (0.549 mL, 3.15 mmol) are added and it is stirred for 2 h. The mixture is concentrated, water is added and the precipitate is filtered, washed with water and dried to give the subtitle compound.

Yield: 0.510 g (64%). HPLC $R_t$=1.47 min (method B). MS m/z: 342 [M+H]$^+$.

(c) N-(4-Fluoro-3-chloro-phenyl)-2-(4-fluoro-piperidinyl)-4-methylamino-5-nitro-benzoic acid amide A mixture of 4-fluoropiperidine×HCl (67 mg, 0.48 mmol), DIPEA (0.64 ml, 3.73 mmol), N-(4-fluoro-3-chloro-phenyl)-2-fluoro-4-methylamino-5-nitro-benzoic acid amide (150 mg, 0.44 mmol) and MeCN (5 mL) is stirred for 6 h at reflux. Then the mixture is concentrated, diluted with EtOAc, washed with water and concentrated.

Yield: 180 mg. HPLC $R_t$=1.56 min (method B). MS m/z: 425 [M+H]$^+$.

(d) N-(4-Fluoro-3-chloro-phenyl)-2-(4-fluoro-piperidinyl)-4-methylamino-5-amino-benzoic acid amide A mixture of N-(4-fluoro-3-chloro-phenyl)-2-(4-fluoro-piperidinyl)-4-methylamino-5-nitro-benzoic acid amide (90 mg, 0.21 mmol), Ra—Ni (30 mg) and THF (10 mL) is stirred under 50 psi H$_2$-atmosphere for 4 h. The mixture is filtered, and the filtrate is concentrated.

HPLC $R_t$=1.31 min (method B). MS m/z: 395 [M+H]$^+$.

(e) N-(4-Fluoro-3-chloro-phenyl)-2-{2,6-dichloro-3-[(2,2-dimethyl-propionylamino)-methyl]-phenylamino}-6-(4-fluoro-piperidinyl)-1-methyl-1H-benzimidazole-5-carboxylic acid amide A mixture of N-(4-fluoro-3-chloro-phenyl)-2-(4-fluoro-piperidinyl)-4-methylamino-5-amino-benzoic acid amide (90 mg, 0.21 mmol), N-(2,4-dichloro-3-isothiocyanato-benzyl)-2,2-dimethyl-propionamide (67 mg, 0.21 mmol) and DMF (5.0 mL) is stirred for 4 h. Then EtOAc is added and the organic phase is washed with water, dried with Na$_2$SO$_4$, filtered and concentrated. DMF (5.0 ml) and DIC (38 μl, 0.24 mmol) is added to the residue and it is stirred for 3 h at 80° C. The crude mixture is concentrated, diluted with EtOAc, washed with water, dried with Na$_2$SO$_4$, filtered and purified by flash chromatography (silica gel; DCM→DCM/EtOH 97:3).

Yield: 70 mg (49%). $R_t$=0.38 (DCM/EtOH 95:5). MS m/z: 677 [M+H]$^+$.

Example 2

N-(4-Fluoro-3-chloro-phenyl)-2-{2,6-dichloro-3-[(2,2-dimethyl-propionylamino)-methyl]-phenylamino}-6-[N-methyl-N-(2,2-difluoroethyl)-amino]-1-methyl-1H-benzimidazole-5-carboxylic acid amide

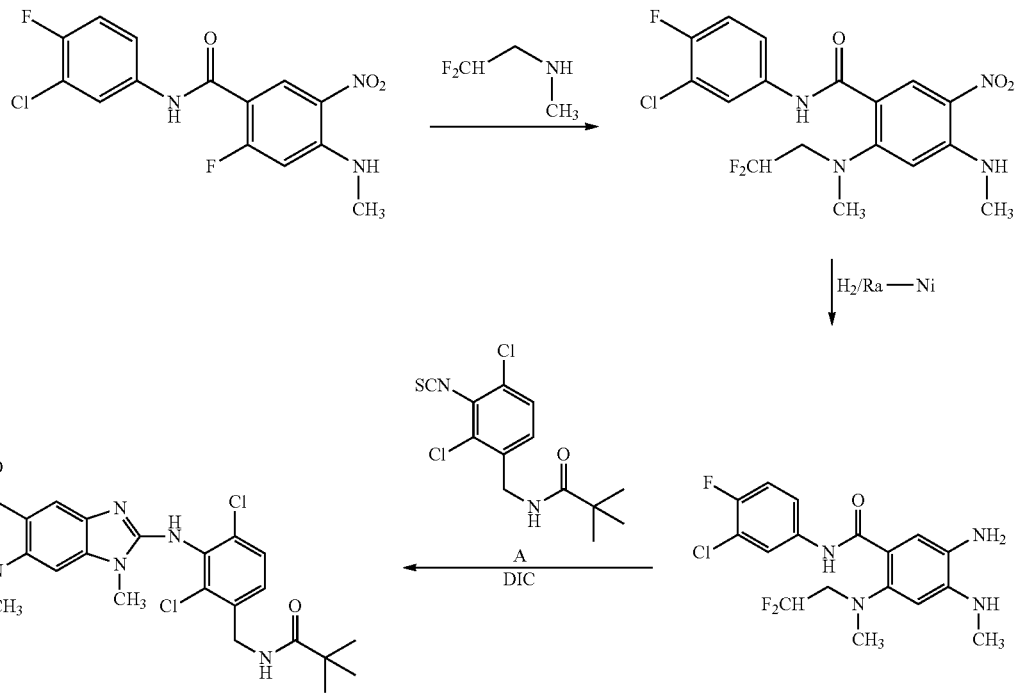

(a) N-(4-Fluoro-3-chloro-phenyl)-2-[N-methyl-N-(2,2-difluoroethyl)-amino]-4-methylamino-5-nitro-benzoic acid amide A mixture of N-(2,2-difluoroethyl)-N-methyl-amine×HCl (64 mg, 0.48 mmol), DIPEA (0.64 ml, 3.73 mmol), N-(4-fluoro-3-chloro-phenyl)-2-fluoro-4-methylamino-5-nitro-benzoic acid amide (150 mg, 0.44 mmol) and MeCN (5 mL) is stirred for two weeks at reflux. Then the mixture is concentrated, diluted with EtOAc, washed with water, dried with $Na_2SO_4$ and concentrated and directly used in the next step.

(b) N-(4-Fluoro-3-chloro-phenyl)-2-[N-methyl-N-(2,2-difluoroethyl)-amino]-4-methylamino-5-amino-benzoic acid amide A mixture of N-(4-fluoro-3-chloro-phenyl)-2-(4-fluoro-piperidinyl)-4-methylamino-5-nitro-benzoic acid amide (crude material from the reaction above), Ra—Ni (100 mg) and THF (10 mL) is stirred under 50 psi $H_2$-atmosphere for 4 h. The mixture is filtered, and the filtrate is concentrated.

HPLC $R_t$=1.40 min (method B). MS m/z: 387 [M+H]$^+$.

(c) N-(4-Fluoro-3-chloro-phenyl)-2-{2,6-dichloro-3-[(2,2-dimethyl-propionylamino)-methyl]-phenylamino}-6-[N-methyl-N-(2,2-difluoroethyl)-amino]-1-methyl-1H-benzimidazole-5-carboxylic acid amide The crude mixture from the reaction above, N-(2,4-dichloro-3-isothiocyanato-benzyl)-2,2-dimethyl-propionamide (139 mg, 0.44 mmol) and DMF (5.0 mL) is stirred overnight. Then EtOAc is added and the organic phase is washed with water, dried with $Na_2SO_4$, filtered and concentrated. DMF (20 ml) and DIC (69 µl, 0.44 mmol) is added to the residue and it is stirred for 4 h at 80° C. The mixture is concentrated, diluted with EtOAc, washed with water, dried with $Na_2SO_4$, filtered and purified by flash chromatography (silica gel; DCM→DCM/EtOH 97:3).

Yield: 84 mg. $R_f$=0.29 (DCM/EtOH 95:5). MS m/z: 669 [M+H]$^+$.

Example 4

N-(trans-4-Trifluoromethyl-cyclohexyl)-2-{2,6-dichloro-3-[(2,2-dimethyl-propionylamino)-methyl]-phenylamino}-6-[3,3-difluoro-cyclobutylamino]-1-methyl-1H-benzimidazole-5-carboxylic acid amide

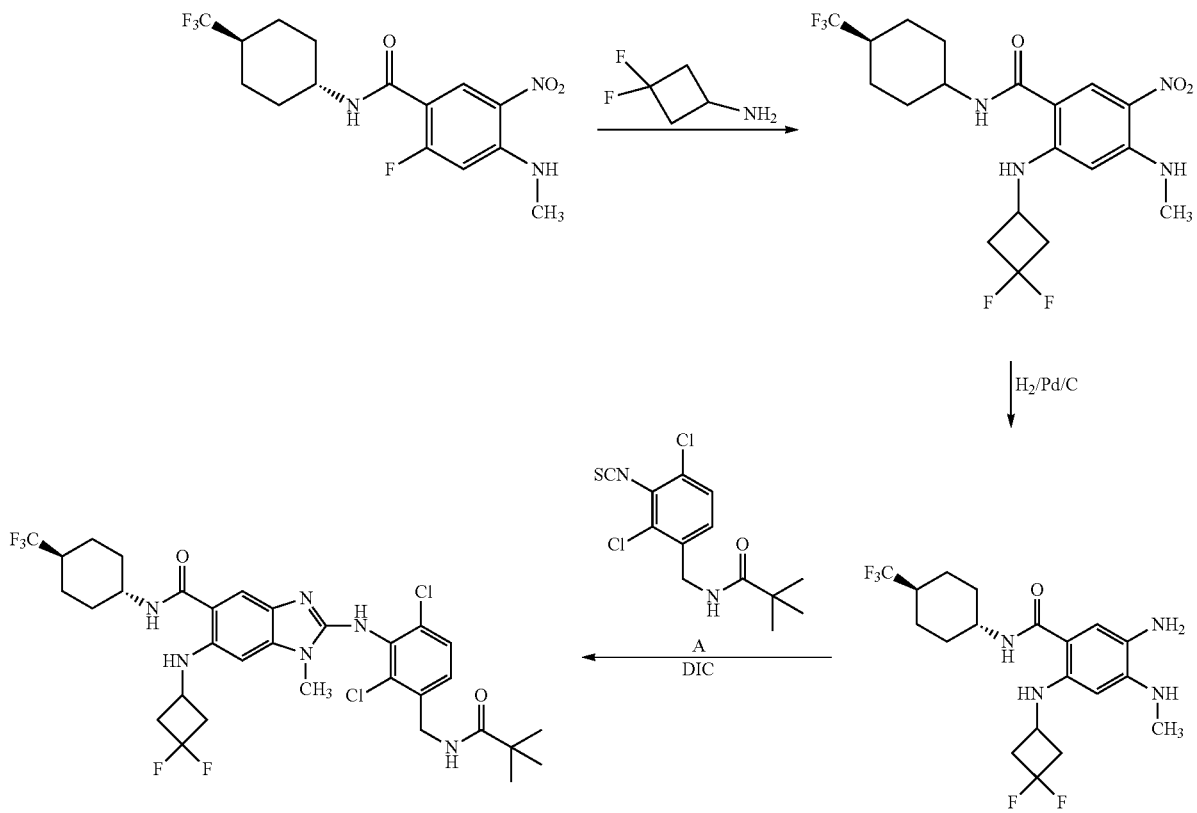

(a) N-(trans-4-Trifluoromethyl-cyclohexyl)-2-[3,3-difluoro-cyclobutylamino]-4-methylamino-5-nitro-benzoic acid amide A mixture of 3,3-difluoro-cyclobutylamine×HCl (49 mg, 0.34 mmol), DIPEA (0.26 ml, 1.5 mmol), N-(trans-4-trifluoromethyl-cyclohexyl)-2-fluoro-4-methylamino-5-nitro-benzoic acid amide (125 mg, 0.34 mmol, prepared according to WO2010/100249) and MeCN (5 mL) is stirred for 16 h at reflux. Then the mixture is concentrated, diluted with EtOAc, washed with water, concentrated, dried and directly used in the next step.

HPLC $R_t$=1.62 min (method A). MS m/z: 451 [M+H]$^+$.

(b) N-(trans-4-Trifluoromethyl-cyclohexyl)-2-[3,3-difluoro-cyclobutylamino]-4-methylamino-5-amino-benzoic acid amide A mixture of N-(trans-4-trifluoromethyl-cyclohexyl)-2-[3,3-difluoro-cyclobutylamino]-4-methylamino-5-nitro-benzoic acid amide (crude product from the reaction above), Pd/C (50 mg) and MeOH (10 ml) is stirred under 3 bar $H_2$-atmosphere for 6 h. The mixture is filtered, and the filtrate is concentrated and directly used in the next step.

(c) N-(trans-4-Trifluoromethyl-cyclohexyl)-2-{2,6-dichloro-3-[(2,2-dimethyl-propionylamino)-methyl]-phenylamino}-6-[3,3-difluoro-cyclobutylamino]-1-methyl-1H-benzimidazole-5-carboxylic acid amide The title compound is prepared in analogy to 2c from crude material of the reaction above (100 mg), and N-(2,4-dichloro-3-isothiocyanato-benzyl)-2,2-dimethyl-propionamide (75 mg, 0.24 mmol), DIC (43 µL) and DMF (5.0 mL).

Yield: 112 mg. $R_f$=0.28 (DCM/EtOH 95:5). MS m/z: 703 $[M+H]^+$.

Example 5

N-(trans-4-Trifluoromethyl-cyclohexyl)-2-{2,6-difluoro-3[(2,2-dimethyl-propionylamino)-methyl]-phenylamino}-6-[4-fluoro-piperidinyl]-1H-benzimidazole-5-carboxylic acid amide

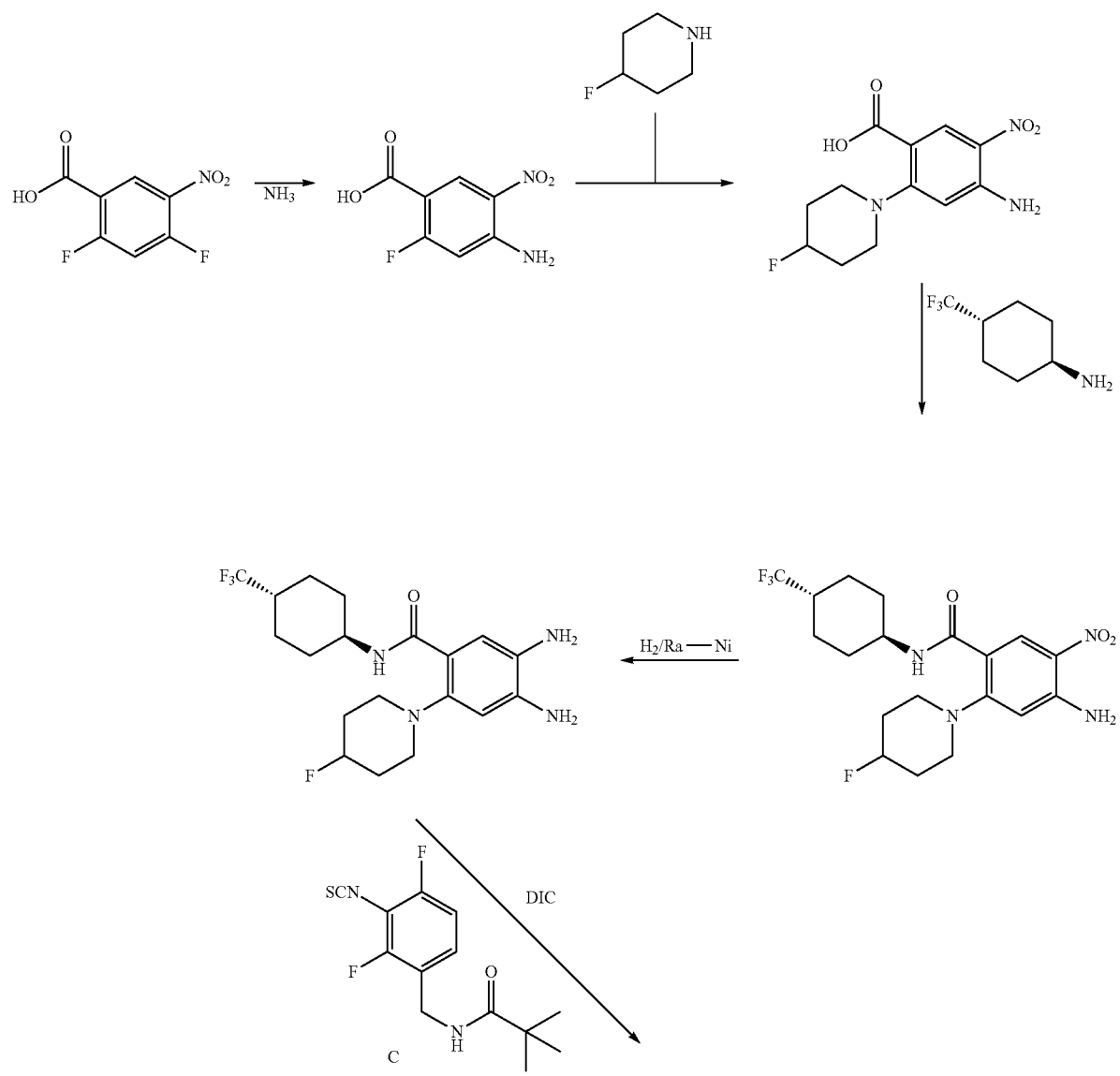

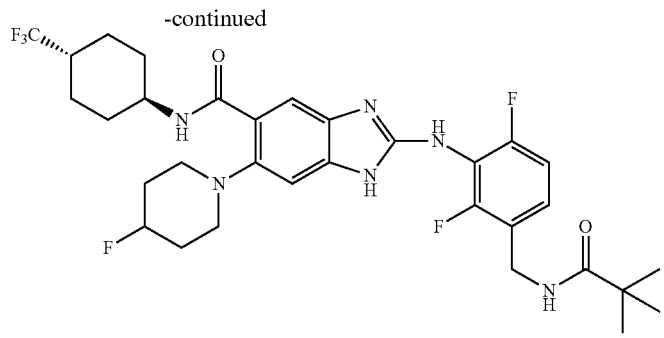

(a) 2-Fluoro-4-amino-5-nitro-benzoic acid

Aq ammonia (6.0 mL, 32% in water) is added to a mixture of 2,4-difluoro-5-nitro-benzoic acid (6.0 g, 30 mmol) in THF (80 mL) and it is stirred over the weekend at rt. The mixture is acidified with 6N aq HCl-solution and the precipitate is filtered, washed with water and dried at 55° C. and directly used in the next step.

(b) 2-(4-Fluoro-piperidinyl)-4-amino-5-nitro-benzoic acid

A mixture of 4-fluoropiperidine×HCl (691 mg, 4.9 mmol), TEA (2.2 ml, 16 mmol), 2-fluoro-4-amino-5-nitro-benzoic acid (900 mg, 4.5 mmol) and DMF (15 mL) is stirred for 4.5 h at 50° C. Then the mixture is concentrated, diluted with water and the precipitate is filtered and dried.
Yield: 1.2 g. HPLC $R_t$=1.26 min (method E).

(c) N-(trans-4-Trifluoromethyl-cyclohexyl)-2-(4-fluoro-piperidinyl)-4-amino-5-nitro-benzoic acid amide A mixture of 2-(4-fluoro-piperidinyl)-4-amino-5-nitro-benzoic acid (0.100 g, 0.35 mmol), TBTU (119 mg, 0.37 mmol), TEA (0.15 mL, 1.1 mmol) and THF (5 mL) is stirred for 5 min, then 4-trans-trifluoromethyl-cyclohexylamine× HCl (72 mg, 0.35 mmol) is added and it is stirred for 2.5 h. The mixture is diluted with EtOAc, washed with sat aq NaHCO₃ solution, water and brine, and the organic phase is dried with Na₂SO₄ and concentrated.
Yield: 0.150 g (98%). HPLC $R_t$=1.42 min (method B). MS m/z: 433 [M+H]⁺.

(d) N-(trans-4-Trifluoromethyl-cyclohexyl)-2-(4-fluoro-piperidinyl)-4,5-diamino-benzoic acid amide A mixture of N-(trans-4-trifluoromethyl-cyclohexyl)-2-(4-fluoro-piperidinyl)-4-amino-5-nitro-benzoic acid amide (150 mg, 0.35 mmol), Ra—Ni (15 mg), MeOH (2 mL) and THF (10 mL) is stirred under 50 psi H₂-atmosphere for 1 h. The mixture is filtered and concentrated.
HPLC $R_t$=1.21 min (method B). MS m/z: 403 [M+H]⁺.

(e) N-(trans-4-Trifluoromethyl-cyclohexyl)-2-{2,6-difluoro-3-[(2,2-dimethyl-propionylamino)-methyl]-phenylamino}-6-[4-fluoro-piperidinyl]-1H-benzimidazole-5-carboxylic acid amide The title compound is prepared in analogy to 2c from N-(trans-4-trifluoromethyl-cyclohexyl)-2-(4-fluoro-piperidinyl)-4,5-diamino-benzoic acid amide (50 mg, 0.12 mmol), and N-(2,4-difluoro-3-isothiocyanato-benzyl)-2,2-dimethyl-propionamide (70 mg, 0.24 mmol), DIC (30 μL) and DMF (2.0 mL).
Yield: 50 mg. $R_f$=0.2 (DCM/EtOH 95:5). HPLC $R_t$=1.42 min (method B). MS m/z: 653 [M+H]⁺.

Example 6

N-(trans-4-Trifluoromethyl-cyclohexyl)-2-{(6-chloro-2-fluoro-3-[(2,2-dimethyl-propionylamino)-methyl]-phenylamino}-6-[3-trifluoromethyl-pyrrolidinyl]-1-methyl-1H-benzimidazole-5-carboxylic acid amide

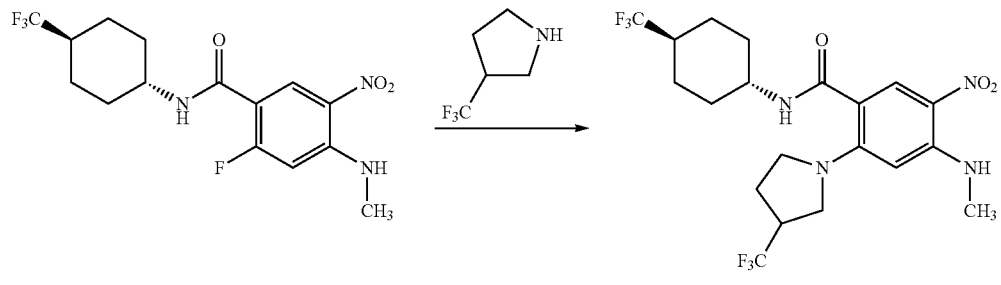

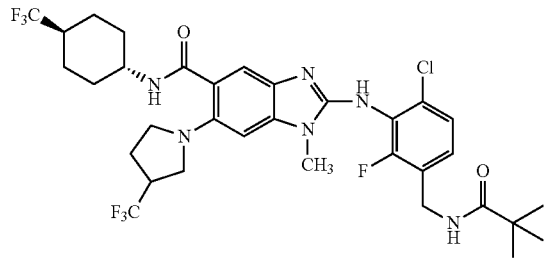
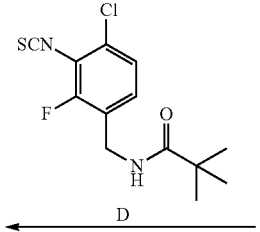
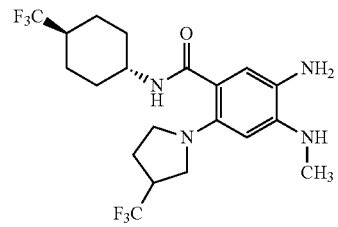

(a) N-(trans-4-Trifluoromethyl-cyclohexyl)-2-[3-trifluoromethyl-pyrrolidinyl]-4-methylamino-5-nitro-benzoic acid amide A mixture of 3-trifluoromethyl-pyrrolidine×HCl (53 mg, 0.30 mmol), DIPEA (0.40 ml, 2.4 mmol), N-(trans-4-trifluoromethyl-cyclohexyl)-2-fluoro-4-methylamino-5-nitro-benzoic acid amide (100 mg, 0.28 mmol) and MeCN (2 mL) is stirred for 4.5 h at reflux. Then the mixture is diluted with water and the formed precipitate is filtered, washed with water and dried Yield: 110 mg (82%); $R_t$=1.52 min (method B). MS m/z: 483 [M+H]$^+$.

(b) N-(trans-4-Trifluoromethyl-cyclohexyl)-2-[3-trifluoromethyl-pyrrolidinyl]-4-methylamino-5-amino-benzoic acid amide A mixture of N-(trans-4-trifluoromethyl-cyclohexyl)-2-[3-trifluoromethyl-pyrrolidinyl]-4-methylamino-5-nitro-benzoic acid amide (110 mg, 0.23 mmol), Pd/C (10 mg), THF (5 mL) and MeOH (10 mL) is stirred under 3 bar H$_2$-atmosphere for 2 d. The mixture is filtered, and the filtrate is concentrated and directly used in the next step.

(c) N-(trans-4-Trifluoromethyl-cyclohexyl)-2-{6-chloro-2-fluoro-3-[(2,2-dimethyl-propionylamino)-methyl]-phenylamino}-6-[3-trifluoromethyl-pyrrolidinyl]-1-methyl-1H-benzimidazole-5-carboxylic acid amide A mixture of N-(trans-4-trifluoromethyl-cyclohexyl)-2-[3-trifluoromethyl-pyrrolidinyl]-4-methylamino-5-amino-benzoic acid amide (80 mg, 0.18 mmol), N-(4-chloro-2-fluoro-3-isothiocyanato-benzyl)-2,2-dimethyl-propionamide (53 mg, 0.18 mmol) and DMF (2.0 mL) is stirred for 3.5 h. Then DIC (28 µL, 0.18 mmol) is added and it is stirred at 80° C. overnight.

The crude mixture is purified by flash chromatography (silica gel, DCM:EtOH 99:1→98:2)

Yield: 52 mg. $R_f$=0.4 (DCM/EtOH 95:5). $R_t$=1.54 min (method A). MS m/z: 719 [M+H]$^+$.

Example 20

N-(trans-4-Trifluoromethyl-cyclohexyl)-2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid amide

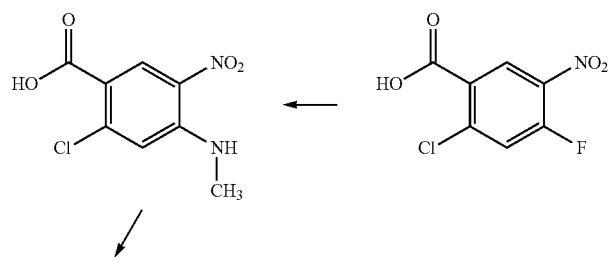

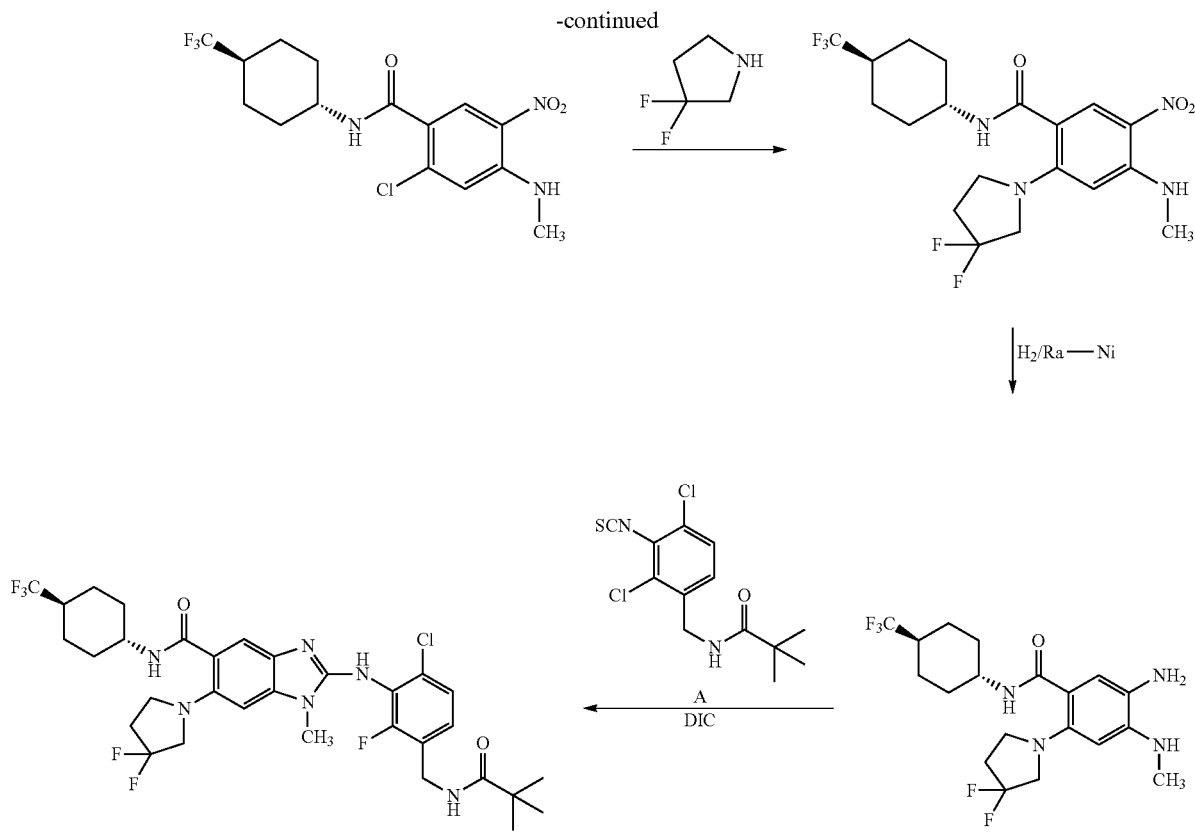

(a) 2-Chloro-4-methylamino-5-nitro-benzoic acid

Methylamine (40% aq solution, 8.25 mL) is added to an ice-cooled mixture of 2-chloro-4-fluoro-5-nitro-benzoic acid (7.00 g, 31 mmol) and 70 mL water. After 2 h additional 0.5 mL methylamine solution is added and it is stirred for additional 3 h. Then 200 mL of water and 47 mL 1N aq HCl are added and the resulting precipitate is filtered off, washed with water and dried.

Yield: 6.4 g (88%); $R_t$=1.20 min (method B). MS m/z: 231 [M+H]$^+$.

(b) N-(trans-4-Trifluoromethyl-cyclohexyl)-2-chloro-4-methylamino-5-nitro-benzoic acid amide The sub-title compound is prepared in analogy to procedure 5c from 2-chloro-4-methylamino-5-nitro-benzoic acid (2.00 g, 8.6 mmol), 4-trans-trifluoromethyl-cyclohexylamine×HCl (1.76 g, 8.6 mmol), TBTU (3.06 g, 9.5 mmol), DIPEA (4.4 mL, 20 mmol) and THF (30 mL).

Yield: 3.3 g. HPLC $R_t$=2.08 min (method E). MS m/z: 380 [M+H]$^+$.

(c) N-(trans-4-Trifluoromethyl-cyclohexyl)-2-[3,3-difluoro-pyrrolidinyl]-4-methylamino-5-nitro-benzoic acid amide The sub-title compound is prepared in analogy to procedure 6a from N-(trans-4-trifluoromethyl-cyclohexyl)-2-chloro-4-methylamino-5-nitro-benzoic acid amide (190 mg, 0.50 mmol), 3,3-difluoro-pyrrolidine×HCl (143 mg, 1.00 mmol), DIPEA (0.34 mL, 2.0 mmol) and dioxane (10 mL).

Yield: 160 mg. MS m/z: 451 [M+H]$^+$.

(d) N-(trans-4-Trifluoromethyl-cyclohexyl)-2-[3,3-difluoro-pyrrolidinyl]-4-methylamino-5-amino-benzoic acid amide A mixture of N-(trans-4-trifluoromethyl-cyclohexyl)-2-[3,3-difluoro-pyrrolidinyl]-4-methylamino-5-amino-benzoic acid amide (160 mg, 0.35 mmol), Ra—Ni (80 mg), THF (5 mL) is stirred under 3 bar H$_2$-atmosphere overnight. The mixture is filtered, and the filtrate is concentrated.

Yield: 140 mg. HPLC $R_t$=1.41 min (method A). MS m/z: 421 [M+H]$^+$.

(e) N-(trans-4-Trifluoromethyl-cyclohexyl)-2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid amide The title compound is prepared in analogy to 6c from N-(trans-4-trifluoromethyl-cyclohexyl)-2-[3,3-difluoro-pyrrolidinyl]-4-methylamino-5-amino-benzoic acid amide (140 mg, 0.33 mmol), and N-(2,4-dichloro-3-isothiocyanato-benzyl)-2,2-dimethyl-propionamide (93 mg, 0.29 mmol), DIC (63 µL) and MeCN (3.0 mL).

Yield: 75 mg. HPLC $R_t$=1.51 min (method A). MS m/z: 704 [M+H]$^+$.

Example 26

N-(2,2,2-Trifluoroethyl)-2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid amide

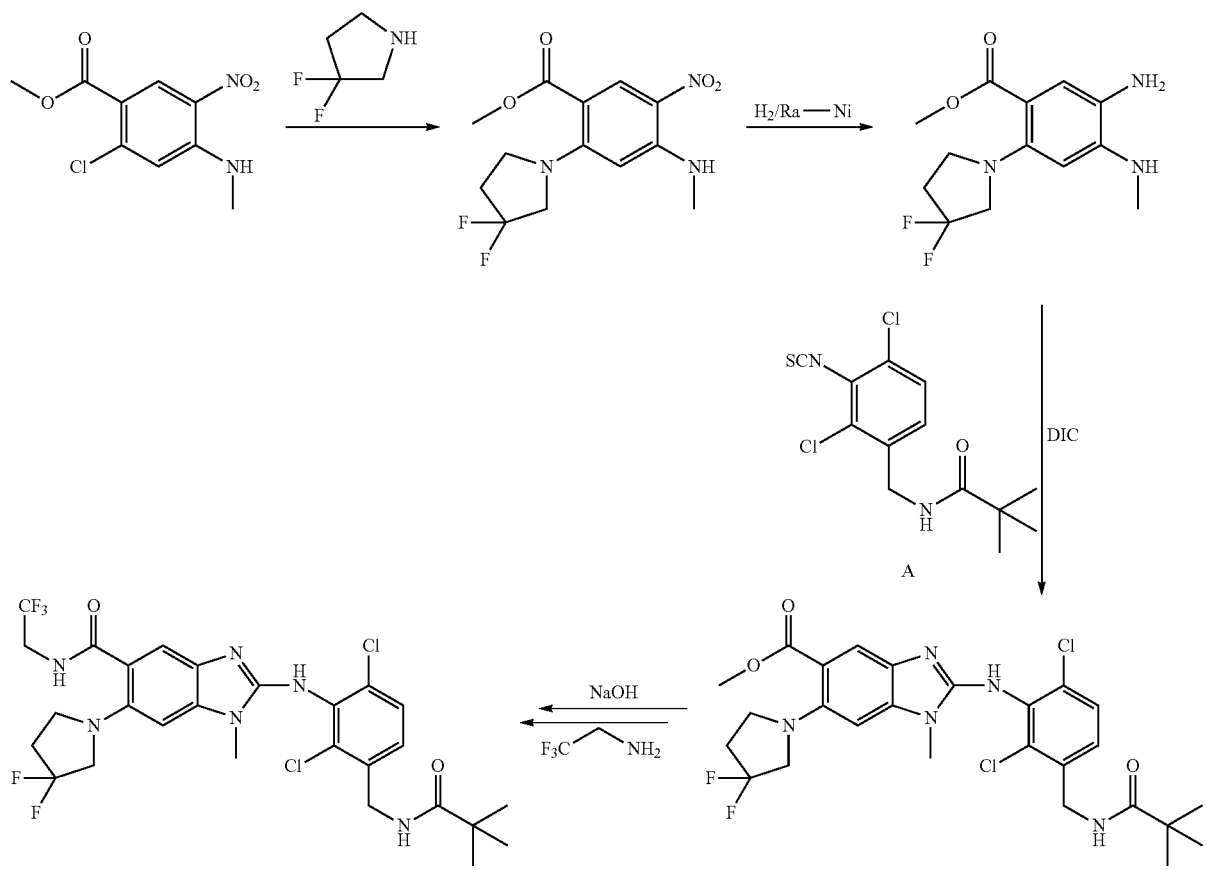

(a) Methyl-2-[3,3-difluoro-pyrrolidinyl]-4-methylamino-5-nitro-benzoate

The sub-title compound is prepared in analogy to procedure 6a from methyl-2-chloro-4-methylamino-5-nitro-benzoate (1.00 g, 4.09 mmol), 3,3-difluoro-pyrrolidine×HCl (880 mg, 6.13 mmol), DIPEA (2.8 mL, 16 mmol) and dioxane (10 mL).

Yield: 1.32 g. HPLC $R_t$=1.37 min (method A). MS m/z: 316 [M+H]$^+$.

(b) Methyl-2-[3,3-difluoro-pyrrolidinyl]-4-methylamino-5-amino-benzoate

A mixture of methyl-2-[3,3-difluoro-pyrrolidinyl]-4-methylamino-5-nitro-benzoate (1.32 g, 4.19 mmol), Pd/C (100 mg) and MeOH (25 mL) is stirred for 5 h under 3 bar H$_2$-atmosphere. The mixture is filtered, and the filtrate is concentrated.

Yield: 1.19 g. HPLC $R_t$=1.01 min (method A). MS m/z: 286 [M+H]$^+$.

(c) 2-{2,6-Dichloro-3-[(2,2-dimethyl-propionylamino)-methyl]-phenylamino}-6-[3,3-difluoro-pyrrolidinyl]-1-methyl-1H-benzimidazole-5-carboxylic acid methyl ester The title compound is prepared in analogy to 6c from methyl-2-[3,3-difluoro-pyrrolidinyl]-4-methylamino-5-amino-benzoate (1.19 g, 4.17 mmol), and N-(2,4-dichloro-3-isothiocyanato-benzyl)-2,2-dimethyl-propionamide (1.32 g, 4.17 mmol), DIC (0.65 mL, 4.2 mmol) and DMF (20 mL).

Yield: 2.37 g. HPLC $R_t$=1.38 min (method A). MS m/z: 568 [M+H]$^+$.

(d) 2-{2,6-Dichloro-3-[(2,2-dimethyl-propionylamino)-methyl]-phenylamino}-6-[3,3-difluoro-pyrrolidinyl]-1-methyl-1H-benzimidazole-5-carboxylic acid A mixture of 2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid methyl ester (2.37 g, 4.17 mmol), 2 N NaOH-solution (9.8 ml) and EtOH (20 ml) is stirred for 1 h at rt and for 2 h at 50° C. and concentrated. Water is added and it is filtered. The filtrate is acidified with 4N HCl (pH 5) and the precipitate is filtered, washed with water and dried.

Yield: 1.98 g. HPLC $R_t$=1.26 min (method A). MS m/z: 554 [M+H]$^+$.

(e) N-(2,2,2-Trifluoroethyl)-2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid amide A mixture of 2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid (50 mg, 0.090 mmol), TBTU (30 mg, 0.095 mmol), TEA (54 µL, 0.39 mmol) and THF (3 mL) is stirred for 10 min, then 2,2,2-trifluoroethylamine (8.5 µL, 0.11 mmol) is added and it is stirred for 2 h. The mixture is diluted with water and 2N NaOH-solution (2 mL) and the resulting precipitate is filtered, diluted with dioxane and lyophilized.

Yield: 30 mg. $R_f$=0.4 (DCM/EtOH 95:5). HPLC $R_t$=1.37 min (method B). MS m/z: 635 [M+H]$^+$.

Example 29

N-(2,2,2-Trifluoroethyl)-2-{2,6-dichloro-3-[(2,2-dimethyl-propionylamino)-methyl]-phenylamino}-6-[4-(1-hydroxy-1-methyl-ethyl)-piperidinyl]-1-methyl-1H-benzimidazole-5-carboxylic acid amide (a) N-(2,2,2-Trifluoroethyl)-2-[4-(1-hydroxy-1-methyl-ethyl)-piperidinyl]-4-methylamino-5-nitro-benzoic acid amide A mixture of 4-(1-hydroxy-1-methyl-ethyl)-piperidine (24 mg, 0.17 mmol), NaH-suspension (50% in mineral oil, 8 mg, ~0.17 mmol) and THF (1 mL) is stirred for 10 min. Then, N-(2,2,2-trifluoro-ethyl)-2-fluoro-4-methylamino-5-nitro-benzoic acid amide is added and it is stirred for 1.5 h. The mixture is diluted with EtOAc, washed with water, concentrated, dried and directly used in the next step.

HPLC $R_t$=1.34 min (method A). MS m/z: 419 [M+H]$^+$.

(b) N-(2,2,2-Trifluoroethyl)-2-[4-(1-hydroxy-1-methyl-ethyl)-piperidinyl]-4-methylamino-5-amino-benzoic acid amide A mixture of N-(2,2,2-trifluoroethyl)-2-[4-(1-hydroxy-1-methyl-ethyl)-piperidinyl]-4-methylamino-5-nitro-benzoic acid amide (crude product from the reaction above), Pd/C (10 mg), THF (5 ml) and MeOH (5 ml) is stirred under 3 bar $H_2$-atmosphere for 7 h. The mixture is filtered and the filtrate is concentrated and directly used in the next step.

(c) N-(2,2,2-Trifluoroethyl)-2-{2,6-dichloro-3-[(2,2-dimethyl-propionylamino)-methyl]-phenylamino}-6-[4-(1-hydroxy-1-methyl-ethyl)-piperidinyl]-1-methyl-1H-benzimidazole-5-carboxylic acid amide The title compound is prepared in analogy to 6c from crude material of the reaction above (65 mg), and N-(2,4-dichloro-3-isothiocyanato-benzyl)-2,2-dimethyl-propionamide (53 mg, 0.17 mmol), DIC (26 µL) and DMF (2.0 mL).

Yield: 60 mg. $R_f$=0.25 (DCM/EtOH 95:5). HPLC $R_t$=1.39 min (method A). MS m/z: 671 [M+H]$^+$.

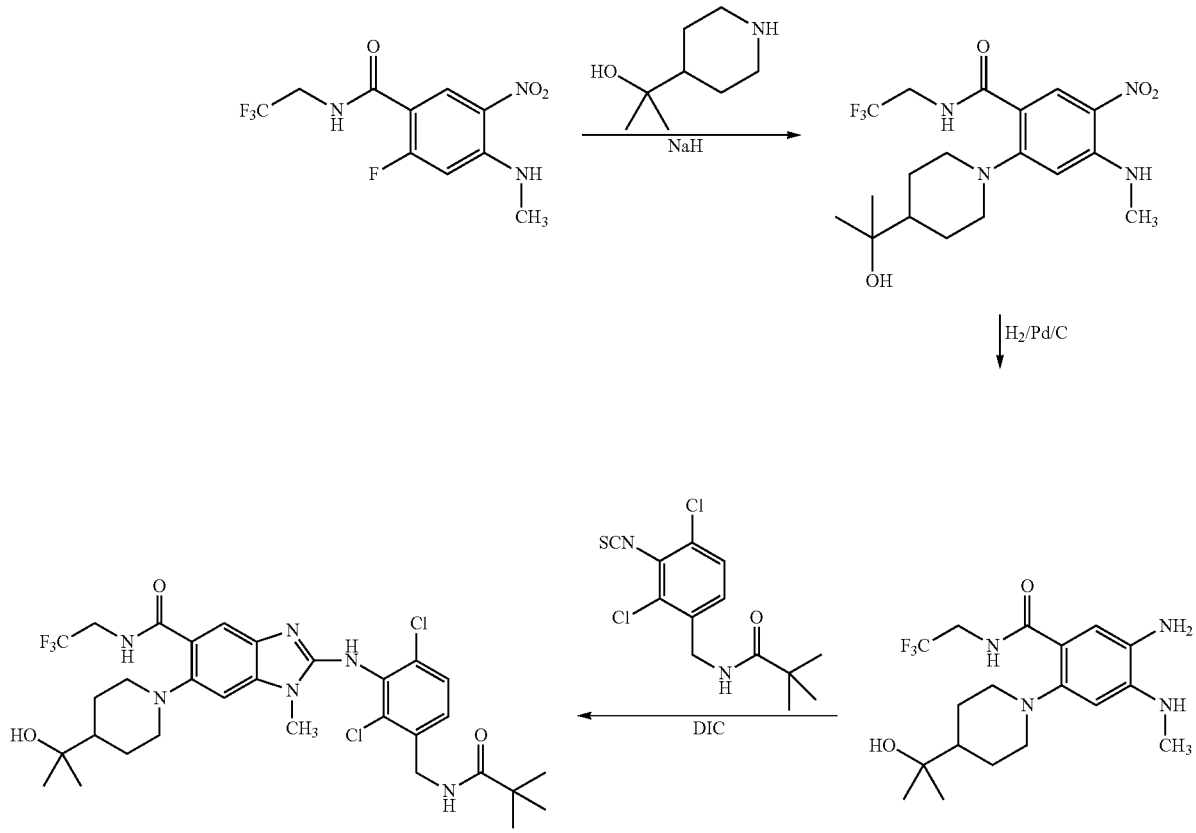

Example 35

N-(4-Trifluoromethoxy-phenyl)-2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid amide

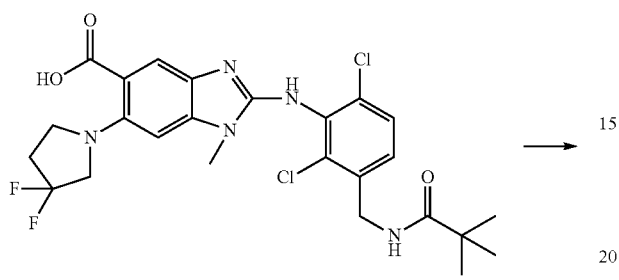

A mixture of 2-{2,6-dichloro-3-[(2,2-dimethyl-propionylamino)-methyl]-phenylamino}-6-[3,3-difluoro-pyrrolidinyl]-1-methyl-1H-benzimidazole-5-carboxylic acid (50 mg, 0.090 mmol), (1-chloro-2-methyl-propenyl)-dimethylamine (0.026 mL, 0.20 mmol) and DCM (2 mL) is stirred for 30 min. This mixture is added to 4-trifluoromethoxyaniline (0.100 mmol) and pyridine (25 μL, 0.32 mmol) in MeCN (1 mL) and it is stirred for 2 h at 40° C. and overnight at 60° C. The mixture is concentrated and the residue diluted with DMF/water 19/1 (2 mL) and purified via reverse phase HPLC.

Yield: 32 mg. HPLC $R_t$=0.61 min (method F). MS m/z: 713 [M+H]$^+$.

Example 52

N-(trans-4-Trifluoromethyl-cyclohexyl)-2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid amide

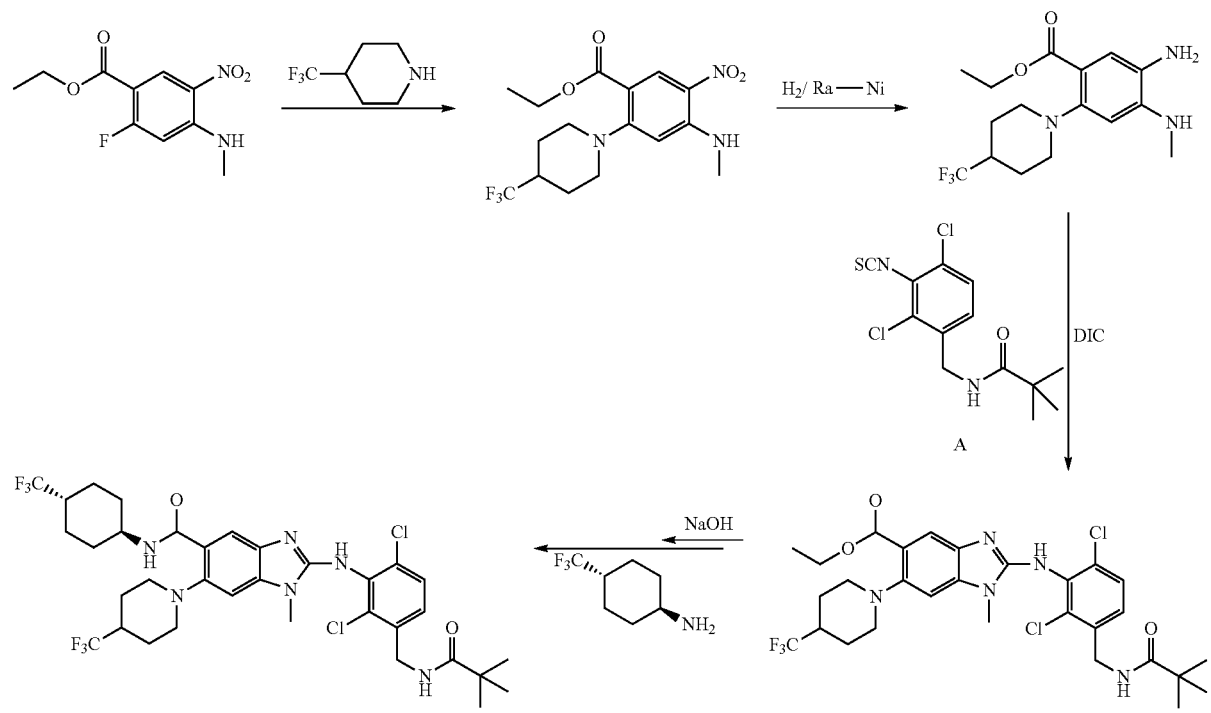

-continued

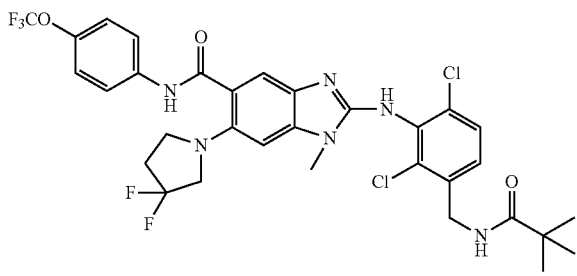

(a) Ethyl-2-[4-trifluoromethyl-piperidinyl]-4-methylamino-5-nitro-benzoate

A mixture of ethyl-2-fluoro-4-methylamino-5-nitro-benzoate (1.00 g, 4.13 mmol), 4-trifluoro-piperidine×HCl (940 mg, 4.96 mmol), TEA (1.6 mL, 12 mmol), Cs$_2$CO$_3$ (3.2 g, 10 mmol) and DMF (25 mL) is heated for 16 h at 80° C. The mixture is poured into water, extracted with EtOAc, washed with brine, dried with Na$_2$SO$_4$, concentrated and purified by flash chromatography (silica gel; PE→PE/EtOAc 4:1)

Yield: 400 mg.

(b) Ethyl-2-[4-trifluoromethyl-piperidinyl]-4-methy-lamino-5-amino-benzoate

A mixture of ethyl-2-[4-trifluoromethyl-piperidinyl]-4-methylamino-5-nitro-benzoate (380 mg, 1.01 mmol), Ra—Ni (500 mg) and THF (20 mL) is stirred overnight under 10 bar $H_2$-atmosphere. The mixture is filtered, and the filtrate is concentrated.
Yield: quantitative.

(c) 2-{2,6-Dichloro-3-[(2,2-dimethyl-propionylamino)-methyl]-phenylamino}-6-[4-trifluoromethyl-piperidinyl]-1-methyl-1H-benzimidazole-5-carboxylic acid ethyl ester The title compound is prepared in analogy to 6c from methyl-2-[4-trifluoromethyl-piperidinyl]-4-methylamino-5-amino-benzoate (349 mg, 1.01 mmol), and N-(2,4-dichloro-3-isothiocyanato-benzyl)-2,2-dimethyl-propionamide (336 mg, 1.06 mmol), DIC (0.19 mL, 1.2 mmol) and THF (20 mL).
Yield: 550 mg.

(d) 2-{2,6-Dichloro-3-[(2,2-dimethyl-propionylamino)-methyl]-phenylamino}-6-[4-trifluoromethyl-piperidinyl]-1-methyl-1H-benzimidazole-5-carboxylic acid A mixture of 2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid ethyl ester (550 mg, 0.86 mmol), 1 N NaOH-solution (10 ml) and dioxane (20 ml) is stirred for 24 h at 100° C. and acidified with 1 N HCl (to pH ~5). The mixture is extracted with EtOAc and the organic layer is washed with brine, dried with $Na_2SO_4$, filtered and concentrated.
Yield: 470 mg.

(e) N-(trans-4-Trifluoromethyl-cyclohexyl)-2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid amide A mixture of 2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid (230 mg, 0.38 mmol), TBTU (134 mg, 0.42 mmol), TEA (174 µL, 1.25 mmol) and DMF (5 mL) is stirred for 4 h, then trans-4-trifluoromethyl-cyclohexylamine×HCl (78 mg, 0.38 mmol) is added and it is stirred overnight. The mixture is diluted with water and extracted with EtOAc. The organic layer is washed with brine, dried with $Na_2SO_4$, filtered, concentrated and purified via flash chromatography (silica gel; PE/EtOAc 1:1)

Yield: 125 mg. $R_f$=0.35 (PE/EtOAc 1:1). MS m/z: 749 $[M+H]^+$.

Example 54

N-(3-Chloro-4-fluoro-phenyl)-2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid amide

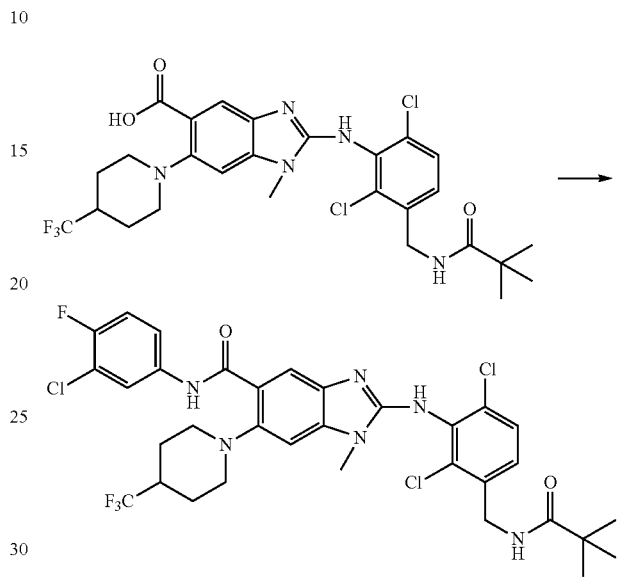

A mixture of 2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid (72 mg, 0.120 mmol), (1-chloro-2-methyl-propenyl)-dimethylamine (33 mg, 0.25 mmol) and MeCN (2 mL) is stirred for 20 min. This mixture is added to 3-chloro-4-fluoro-aniline (36 mg, 0.25 mmol) and DIPEA (129 µL, 0.75 mmol) in MeCN (3 mL) and it is stirred overnight. The mixture is concentrated and the residue is taken up in DMF (2 mL) and purified by reverse phase HPLC.
Yield: 40 mg. HPLC $R_t$=1.82 min (method G). MS m/z: 727 $[M+H]^+$.

Example 71

N-(trans-4-Trifluoromethyl-cyclohexyl)-2-{2,6-dichloro-3-[(2,2-dimethyl-propionylamino)-methyl]-phenylamino}-6-[morpholin-1-yl]-(2,2-difluoroethyl)-benzimidazole-5-carboxylic acid amide

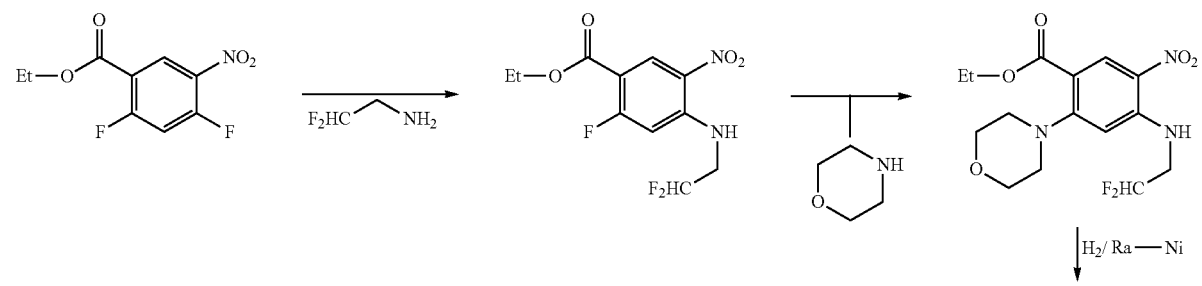

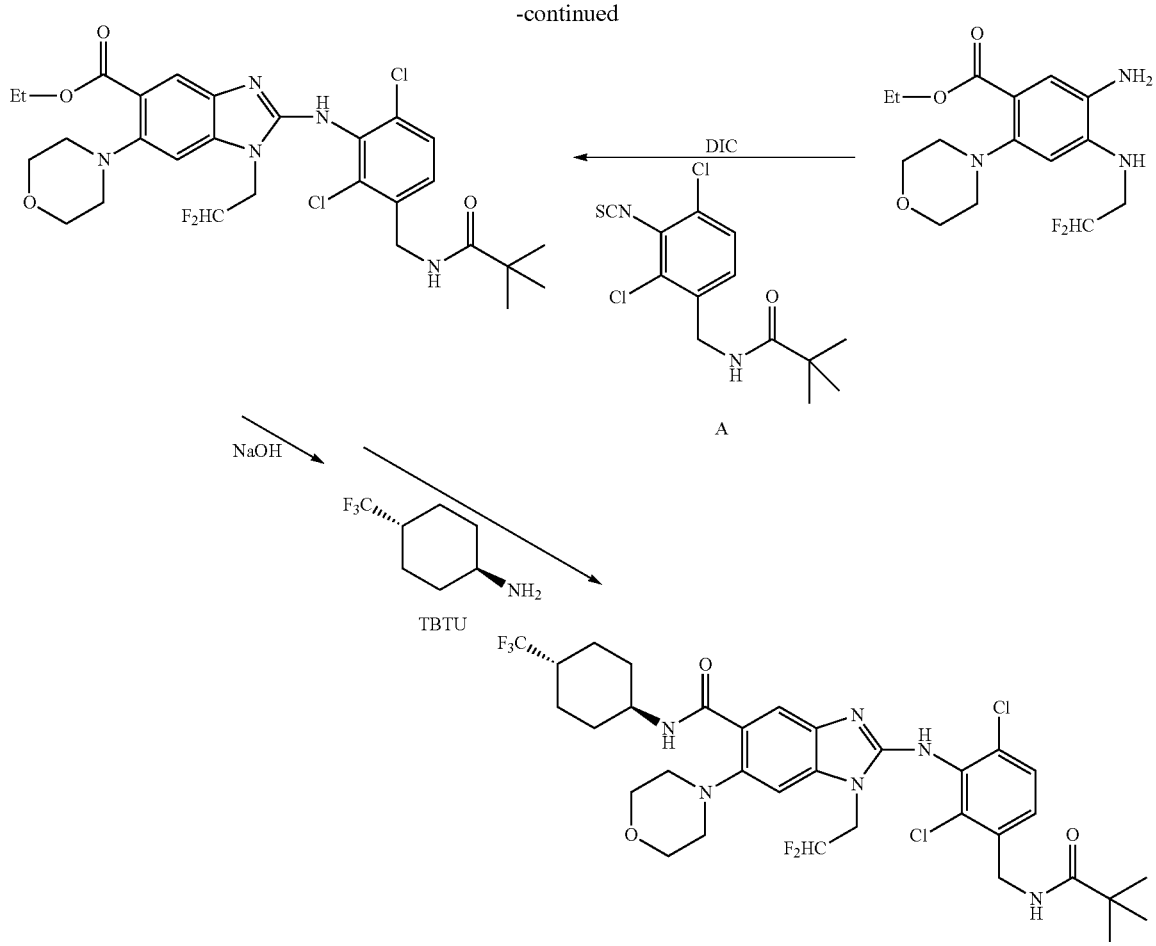

(a) Ethyl-2-fluoro-4-(2,2-difluoro-ethylamino)-5-nitro-benzoate 2,2-Difluoro-ethylamine (2.4 g, 29.8 mmol) in THF is added at 0° C. to ethyl-2,4-difluoro-5-nitro-benzoate (4.6 g, 20 mmol) and it is stirred overnight at rt. Water is added to the mixture and the mixture is concentrated. The precipitate is filtered, washed with water and dried with $P_2O_5$ in vacuo. Yield: 3.8 g (66%).

(b) Ethyl-2-(morpholin-1-yl)-4-(2,2-difluoro-ethylamino)-5-nitro-benzoate

A mixture of morpholine (5 ml), ethyl-2-fluoro-4-(2,2-difluoro-ethylamino)-5-nitro-benzoate (1.0 g, 3.4 mmol) and dioxane (15 mL) is stirred for 16 h at 80° C. Then the mixture is poured into water, extracted with EtOAc and the combined organic extracts are washed with brine, dried with $Na_2SO_4$, filtered and concentrated. Yield: 620 mg (52%).

(c) Ethyl-2-(morpholin-1-yl)-4-(2,2-difluoro-ethylamino)-5-amino-benzoate

A mixture of ethyl-2-(morpholin-1-yl)-4-(2,2-difluoro-ethylamino)-5-nitro-benzoate (600 mg, 1.67 mmol), Ra—Ni (600 mg) and THF (30 mL) is stirred under 10 atm $H_2$-atmosphere for 16 h. The mixture is filtered and concentrated and directly used in the next step.

(d) Ethyl-2-{2,6-dichloro-3-[(2,2-dimethyl-propionylamino)-methyl]-phenylamino}-6-[morpholin-1-yl]-1-(2,2-difluoro-ethyl)-benzimidazole-5-carboxylate The title compound is prepared in analogy to 2c from ethyl-2-(morpholin-1-yl)-4-(2,2-difluoro-ethylamino)-5-amino-benzoate (550 mg, 1.67 mmol), and N-(2,4-dichloro-3-isothiocyanato-benzyl)-2,2-dimethyl-propionamide (556 mg, 1.75 mmol), DIC (308 μL) and THF.

Yield: 1.0 g. $R_f$=0.11 (EtOAc/PE 4:10).

(e) 2-{2,6-Dichloro-3-[(2,2-dimethyl-propionylamino)-methyl]-phenylamino}-6-[morpholin-1-yl]-1-(2,2-difluoro-ethyl)-benzimidazole-5-carboxylic acid A mixture of ethyl-2-{2,6-dichloro-3-[(2,2-dimethyl-propionylamino)-methyl]-phenylamino}-6-[morpholin-1-yl]-1-(2,2-difluoro-ethyl)-benzimidazole-5-carboxylate (1.0 g, 1.63 mmol), 2 N NaOH-solution (3 ml) and dioxane (10 ml) is stirred for 24 h at 100° C. and acidified with 1 N HCl (to pH ~5). The mixture is extracted with EtOAc and the organic layer is washed with brine, dried with $Na_2SO_4$, filtered and concentrated.

Yield: 880 mg.

(f) N-(trans-4-Trifluoromethyl-cyclohexyl)-2-{2,6-dichloro-3-[(2,2-dimethyl-propionylamino)-methyl]-phenylamino}-6-[morpholin-1-yl]-1-(2,2-difluoroethyl)-benzimidazole-5-carboxylic acid amide A mixture of 2-{2,6-dichloro-3-[(2,2-dimethyl-propionylamino)-methyl]-phenylamino}-6-[morpholin-1-yl]-1-(2,2-difluoro-ethyl)-benzimidazole-5-carboxylic acid (0.300 g, 0.51 mmol), TBTU (180 mg, 0.56 mmol), TEA (0.23 mL, 1.7 mmol) and DMF (5 mL) is stirred for 4 h, then 4-trans-trifluoromethyl-cyclohexylamine×HCl (104 mg, 0.51 mmol) is added and it is stirred overnight. The mixture is diluted with water and extracted with EtOAc. The combined organic phases are washed with brine, dried with $Na_2SO_4$ and concentrated. The title compound is purified by flash chromatography (silicagel, EtOAc/PE 1:1)

Yield: 0.180 g (48%). $R_f$=0.15 (EtOAc/PE 1:1). MS m/z: 734 [M+H]$^+$.

Example 77

(R)—N-(4-Trifluoromethoxy-phenyl)-2-{2,6-dichloro-3-[(2,2-dimethyl-propionylamino)-methyl]-phenylamino}-6-[3-fluoro-pyrrolidinyl]-1-(2,2-difluorethyl)-1H-benzimidazole-5-carboxylic acid amide (a) 2-Chloro-4-(2,2-difluoro-ethylamino)-5-nitro-benzoic acid A mixture of 2,2-difluoroethylamine (1.65 mL, 23 mmol) and THF (50 mL) is added to a mixture of 2-chloro-4-fluoro-5-nitro-benzoic acid (5.00 g, 22 mmol), TEA (6.33 mL, 45 mmol) and 50 mL THF. The mixture is stirred overnight at rt and 30 h at 60° C., concentrated and diluted with water. The resulting precipitate is collected by filtration, washed with water and dried. Yield: 3.3 g (61%); HPLC $R_t$=1.14 min (method A). MS m/z: 281 [M+H]$^+$.

(b) N-(4-Trifluoromethoxy-phenyl)-2-chloro-4-(2,2-difluoro-ethylamino)-5-nitro-benzoic acid amide The sub-title compound is prepared in analogy to 1b from 2-chloro-4-(2,2-difluoro-ethylamino)-5-nitro-benzoic acid (2.00 g, 7.1 mmol), 4-trifluoromethoxyaniline (0.96 mL, 7.1 mmol), (1-chloro-2-methyl-propenyl)-dimethylamine (1.13 mL, 8.5 mmol), DIPEA (2.85 mL, 16 mmol) and DCM (40 mL).

Yield: 3.1 g (98%). HPLC $R_t$=1.53 min (method A). MS m/z: 440 [M+H]$^+$.

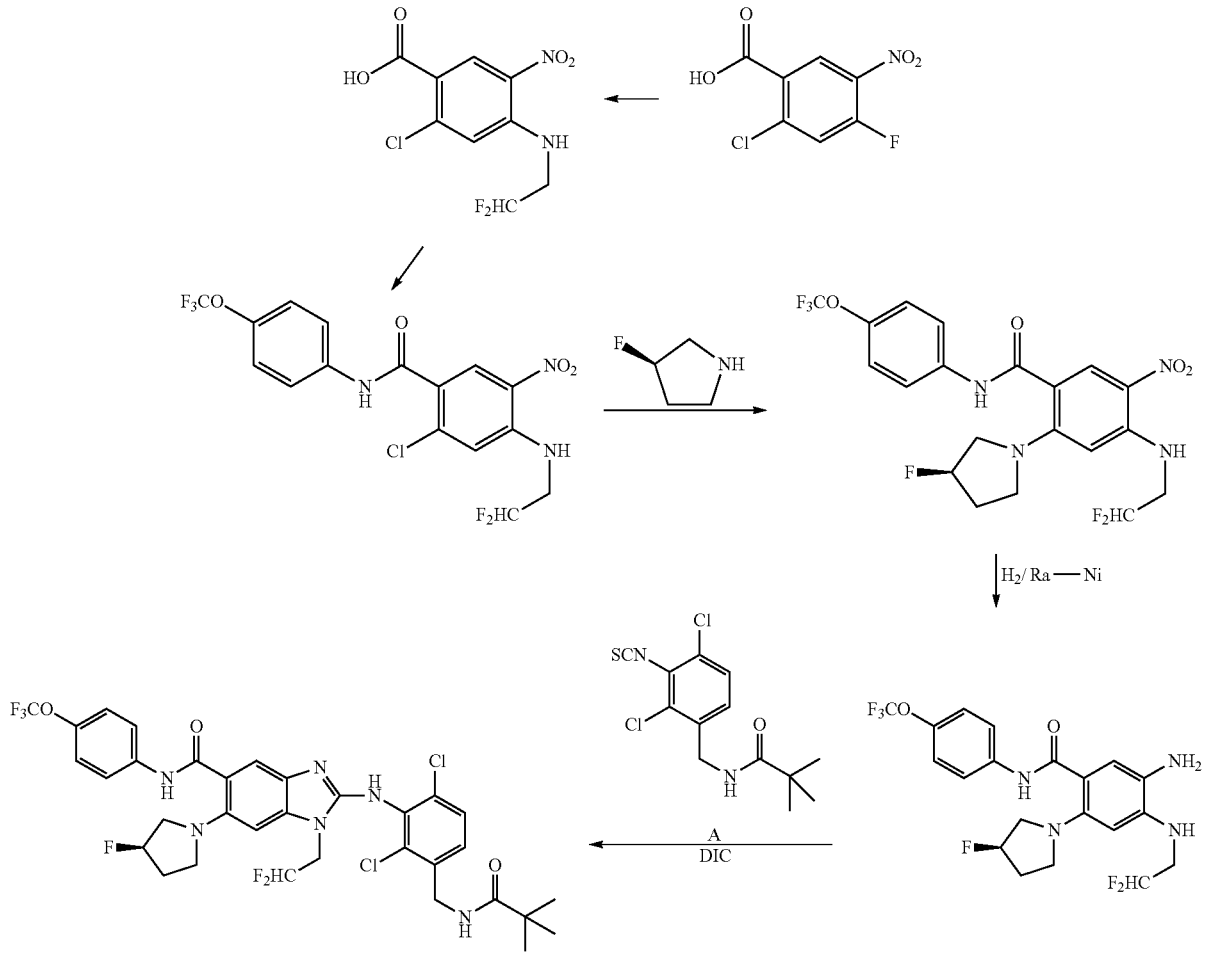

(c) (R)—N-(4-Trifluoromethoxyphenyl)-2-[3-fluoro-pyrrolidinyl]-4-(2,2-difluoro-ethylamino)-5-nitro-benzoic acid amide The sub-title compound is prepared in analogy to 6a from N-(4-trifluoromethoxy-phenyl)-2-chloro-4-(2,2-difluoro-ethylamino)-5-nitro-benzoic acid amide (177 mg, 0.40 mmol), (R)-3-fluoro-pyrrolidine×HCl (56 mg, 0.44 mmol), DIPEA (0.55 mL, 3.2 mmol) and MeCN (5 mL).
Yield: 198 mg. HPLC R$_t$=1.51 min (method A). MS m/z: 493 [M+H]$^+$.

(d) (R)—N-(4-Trifluoromethoxyphenyl)-2-[3-fluoro-pyrrolidinyl]-4-(2,2-difluoro-ethylamino)-5-amino-benzoic acid amide A mixture of (R)—N-(4-trifluoromethoxyphenyl)-2-[3-fluoro-pyrrolidinyl]-4-(2,2-difluoro-ethylamino)-5-nitro-benzoic acid amide (100 mg, 0.20 mmol), Ra—Ni (40 mg) and THF (10 mL) is stirred under 3 bar H$_2$-atmosphere overnight. The mixture is filtered, and the filtrate is concentrated. Yield: 94 mg. HPLC R$_t$=1.41 min (method A). MS m/z: 463 [M+H]$^+$.

(e) (R)—N-(4-Trifluoromethoxy-phenyl)-2-{2,6-dichloro-3-[(2,2-dimethyl-propionylamino)-methyl]-phenylamino}-6-[3-fluoro-pyrrolidinyl]-1-(2,2-difluoroethyl)-1H-benzimidazole-5-carboxylic acid amide The title compound is prepared in analogy to 6c from (R)—N-(4-trifluoromethoxyphenyl)-2-[3-fluoro-pyrrolidinyl]-4-(2,2-difluoro-ethylamino)-5-amino-benzoic acid amide (94 mg, 0.20 mmol), and N-(2,4-dichloro-3-isothiocyanato-benzyl)-2,2-dimethyl-propionamide (64 mg, 0.20 mmol), DIC (62 μL, 0.40 mmol) and THF (10 mL).
Yield: 110 mg. HPLC R$_t$=1.59 min (method A). MS m/z: 746 [M+H]$^+$.

Example 81

N-(3,3,3-Trifluoropropyl)-2-{2,6-dichloro-3-[(2,2-dimethyl-propionylamino)-methyl]-phenylamino}-6-[3-trifluoromethyl-piperidinyl]-1-methyl-1H-benzimidazole-5-carboxylic acid amide

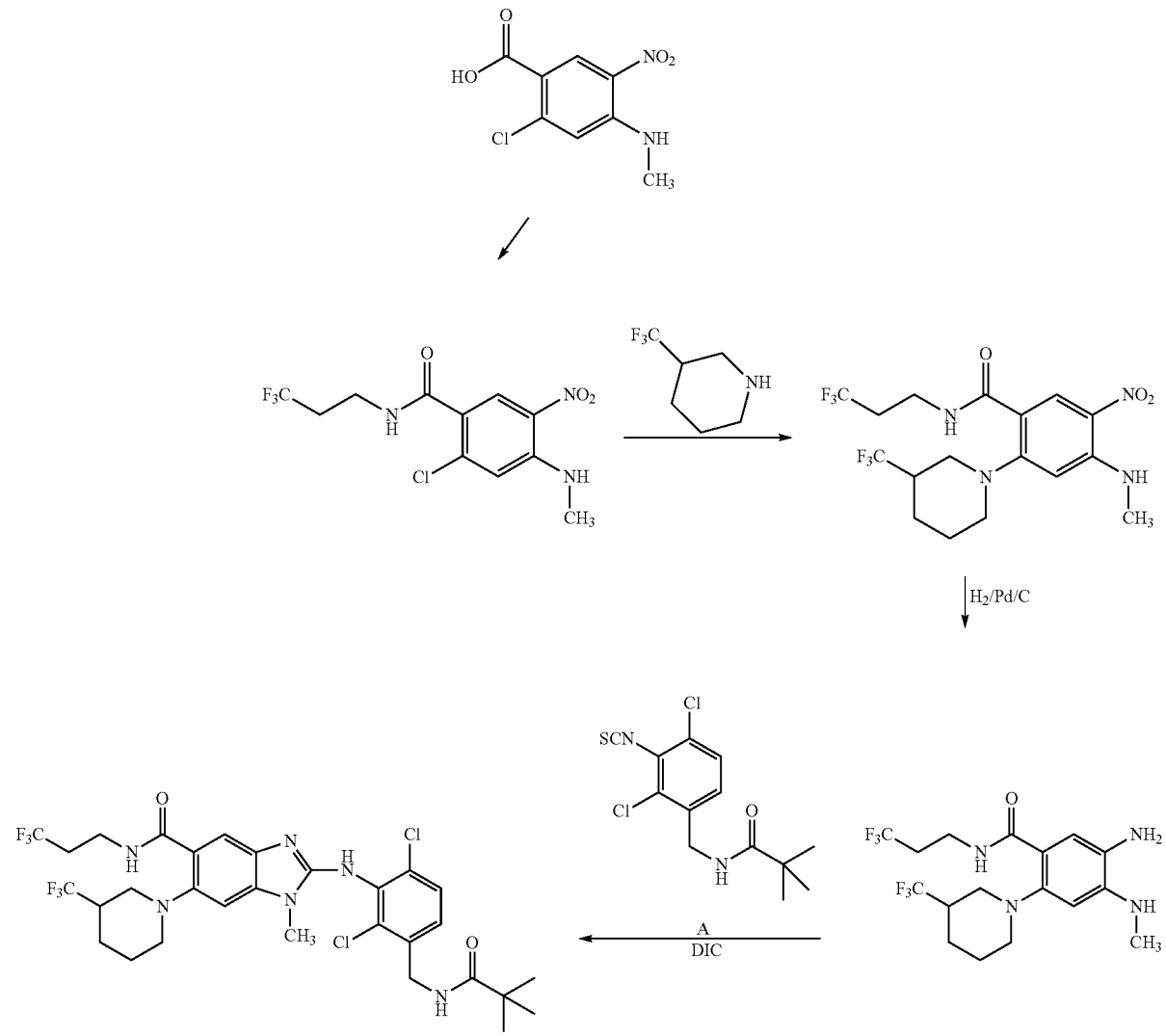

(a) N-(3,3,3-Trifluoro-propyl)-2-chloro-4-methylamino-5-nitro-benzoic acid amide The sub-title compound is prepared in analogy to 5c from 2-chloro-4-methylamino-5-nitro-benzoic acid (900 mg, 3.9 mmol), 3,3,3-trifluoro-propylamine (0.58 g, 3.9 mmol), TBTU (1.38 g, 4.2 mmol), DIPEA (2.0 mL, 11.7 mmol) and THF (20 mL).

Yield: 1.26 g. HPLC $R_f$=1.20 min (method A). MS m/z: 326 [M+H]$^+$.

(b) N-(3,3,3-Trifluoro-propyl)-2-[3-trifluoromethyl-piperidinyl]-4-methylamino-5-nitro-benzoic acid amide The sub-title compound is prepared in analogy to 6a from N-(3,3,3-trifluoro-propyl)-2-chloro-4-methylamino-5-nitro-benzoic acid amide (80 mg, 0.246 mmol), 3-trifluormethyl-piperidine (150 mg, 0.98 mmol), DIPEA (0.34 mL, 2.0 mmol) and dioxane (5 mL).

Yield: 100 mg. HPLC $R_f$=1.49 min (method A). MS m/z: 443 [M+H]$^+$.

(c) N-(3,3,3-Trifluoro-propyl)-2-[3-trifluoromethyl-piperidinyl]-4-methylamino-5-amino-benzoic acid amide A mixture of N-(3,3,3-trifluoro-propyl)-2-[3-trifluoromethyl-piperidinyl]-4-methylamino-5-nitro-benzoic acid amide (100 mg, 0.22 mmol), Pd/C (10 mg), THF (5 mL) and MeOH (15 mL) is stirred under 3 bar $H_2$-atmosphere overnight. The mixture is filtered, and the filtrate is concentrated.

Yield: 93 mg. HPLC $R_f$=1.30 min (method A). MS m/z: 413 [M+H]$^+$.

(d) N-(3,3,3-Trifluoropropyl)-2-{2,6-dichloro-3-[(2,2-dimethyl-propionylamino)-methyl]-phenylamino}-6-[3-trifluoromethyl-piperidinyl]-1-methyl-1H-benzimidazole-5-carboxylic acid amide The title compound is prepared in analogy to 6c from N-(3,3,3-trifluoro-propyl)-2-[3-trifluoromethyl-piperidinyl]-4-methylamino-5-amino-benzoic acid amide (93 mg, 0.22 mmol), and N-(2,4-dichloro-3-isothiocyanato-benzyl)-2,2-dimethyl-propionamide (71 mg, 0.22 mmol), DIC (35 μL) and MeCN (2.0 mL).

Yield: 80 mg. HPLC $R_f$=1.50 min (method A). MS m/z: 695 [M+H]$^+$.

Example 103

N-(trans-4-Trifluoromethyl-cyclohexyl)-2-{2,6-dichloro-3-[(2,2-dimethyl-propionylamino)-methyl]-phenylamino}-6-[N-methyl-N-propargylamino]-1-methyl-1H-benzimidazole-5-carboxylic acid amide

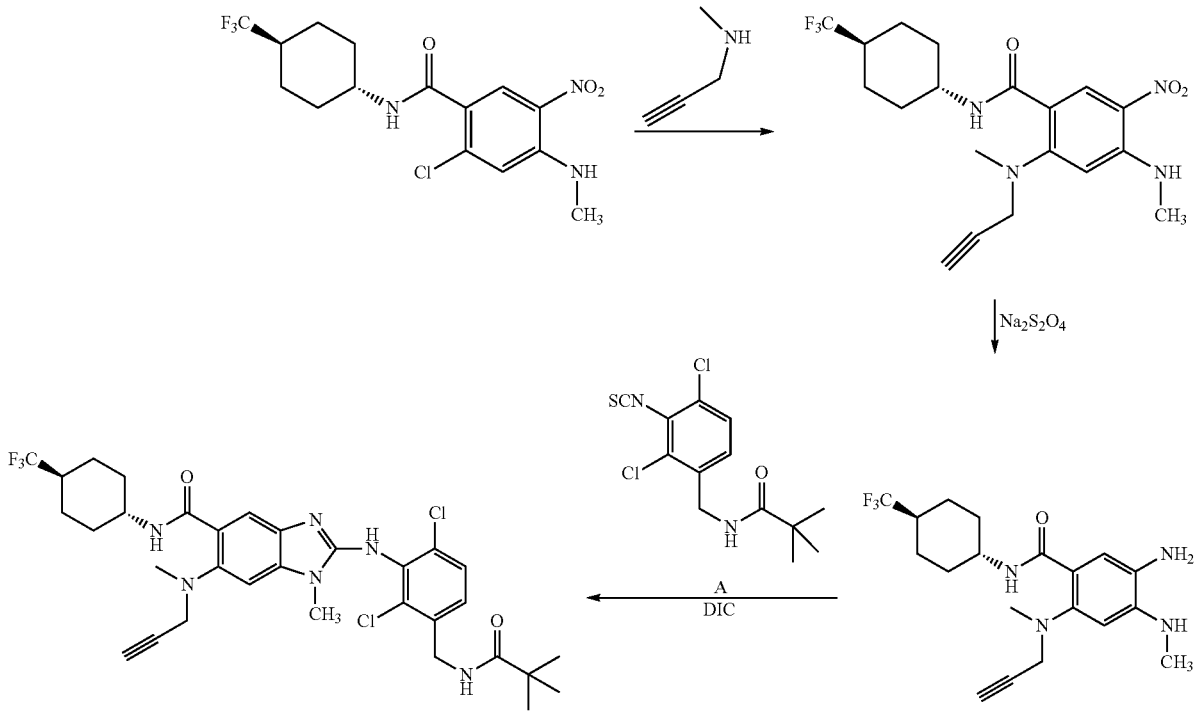

(a) N-(trans-4-Trifluoromethyl-cyclohexyl)-2-[N-methyl-N-propargylamino]-4-methylamino-5-nitro-benzoic acid amide A mixture of N-(trans-4-trifluoromethyl-cyclohexyl)-2-chloro-4-methylamino-5-nitro-benzoic acid amide (60 mg, 0.158 mmol), N-methyl-propargylamine (79 μL, 0.95 mmol) and MeCN (10 mL) is irradiated in a microwave oven for 45 min at 160° C., and after cooling diluted with water. The mixture is extracted with EtOAc, the combined organic phases are dried with $Na_2SO_4$, filtered and concentrated.

Yield: 60 mg. HPLC $R_f$=1.44 min (method A). MS m/z: 413 [M+H]$^+$.

(b) N-(trans-4-Trifluoromethyl-cyclohexyl)-2-[N-methyl-N-propargylamino]-4-methylamino-5-amino-benzoic acid amide A mixture of N-(trans-4-trifluoromethyl-cyclohexyl)-2-[N-methyl-N-propargylamino]-4-methylamino-5-nitro-benzoic acid amide (60 mg, 0.145 mmol), $Na_2S_2O_4$ (127 mg and a second 150 mg portion is added after 8 h), 1 mL water and 5 mL EtOH is stirred at 55° C. for 24 h. The mixture is diluted with sat aq $NaHCO_3$ and extracted with EtOAc. The combined organic phases are dried with $Na_2SO_4$, filtered and concentrated.
Yield: 50 mg. HPLC $R_t$=1.27 min (method A). MS m/z: 383 $[M+H]^+$.

(c) N-(trans-4-Trifluoromethyl-cyclohexyl)-2-{2,6-dichloro-3-[(2,2-dimethyl-propionylamino)-methyl]-phenylamino}-6-[N-methyl-N-propargyl-amino]-1-methyl-1H-benzimidazole-5-carboxylic acid amide The title compound is prepared in analogy to 6c from N-(trans-4-trifluoromethyl-cyclohexyl)-2-[N-methyl-N-propargylamino]-4-methylamino-5-amino-benzoic acid amide (50 mg, 0.13 mmol), and N-(2,4-dichloro-3-isothiocyanato-benzyl)-2,2-dimethyl-propionamide (41 mg, 0.13 mmol), DIC (20 μL) and DMF (2.0 mL).
Yield: 20 mg. HPLC $R_t$=1.66 min (method I). MS m/z: 665 $[M+H]^+$.

Example 110

N-(trans-4-Trifluoromethyl-cyclohexyl)-2-{2,6-dichloro-3-[(2,2-dimethyl-propionylamino)-methyl]-phenylamino}-6-[N-methyl-N-(4-fluorobenzyl)amino]-1-methyl-1H-benzimidazole-5-carboxylic acid amide (a) N-(trans-4-Trifluoromethyl-cyclohexyl)-2-[N-methyl-N-(4-fluorobenzyl)amino]-4-methylamino-5-nitro-benzoic acid amide A mixture of N-(trans-4-trifluoromethyl-cyclohexyl)-2-chloro-4-methylamino-5-nitro-benzoic acid amide (60 mg, 0.158 mmol), N-methyl-N-(4-fluorobenzyl)amine (24 μL, 0.18 mmol) and MeCN (1 mL) is irradiated in a microwave oven for 45 min at 160° C., and after cooling diluted with water. The mixture is extracted with EtOAc, the combined organic phases are dried with $Na_2SO_4$, filtered and concentrated and directly used in the next step. Yield: 80 mg.

(b) N-(trans-4-Trifluoromethyl-cyclohexyl)-2-[N-methyl-N-(4-fluorobenzyl)amino]-4-methylamino-5-amino-benzoic acid amide A mixture of N-(trans-4-trifluoromethyl-cyclohexyl)-2-[N-methyl-N-(4-fluorobenzyl)amino]-4-methylamino-5-nitro-benzoic acid amide (80 mg, 0.166 mmol), $SnCl_2$ (183 mg 0.81 mmol) and 5 mL EtOAc is stirred at reflux for 1 h. The mixture is filtered through a pad of celite and the celite pad is washed with EtOAc. The combined organic phases are dried with $Na_2SO_4$, filtered and concentrated. Yield: 68 mg. HPLC $R_t$=1.35 min (method A). MS m/z: 453 $[M+H]^+$.

(c) N-(trans-4-Trifluoromethyl-cyclohexyl)-2-{2,6-dichloro-3-[(2,2-dimethyl-propionylamino)-methyl]-phenylamino}-6-[N-methyl-N-(4-fluorobenzyl)amino]-1-methyl-1H-benzimidazole-5-carboxylic acid amide The title compound is prepared in analogy to 1e from N-(trans-4-trifluoromethyl-cyclohexyl)-2-[N-methyl-N-(4-fluorobenzyl)amino]-4-methylamino-5-amino-benzoic acid amide (68 mg, 0.15 mmol), and N-(2,4-dichloro-3-isothiocyanato-benzyl)-2,2-dimethyl-propionamide (48 mg, 0.15 mmol), DIC (23 μL) and DMF (2.0 mL).
Yield: 75 mg. HPLC $R_t$=1.53 min (method A). MS m/z: 735 $[M+H]^+$.

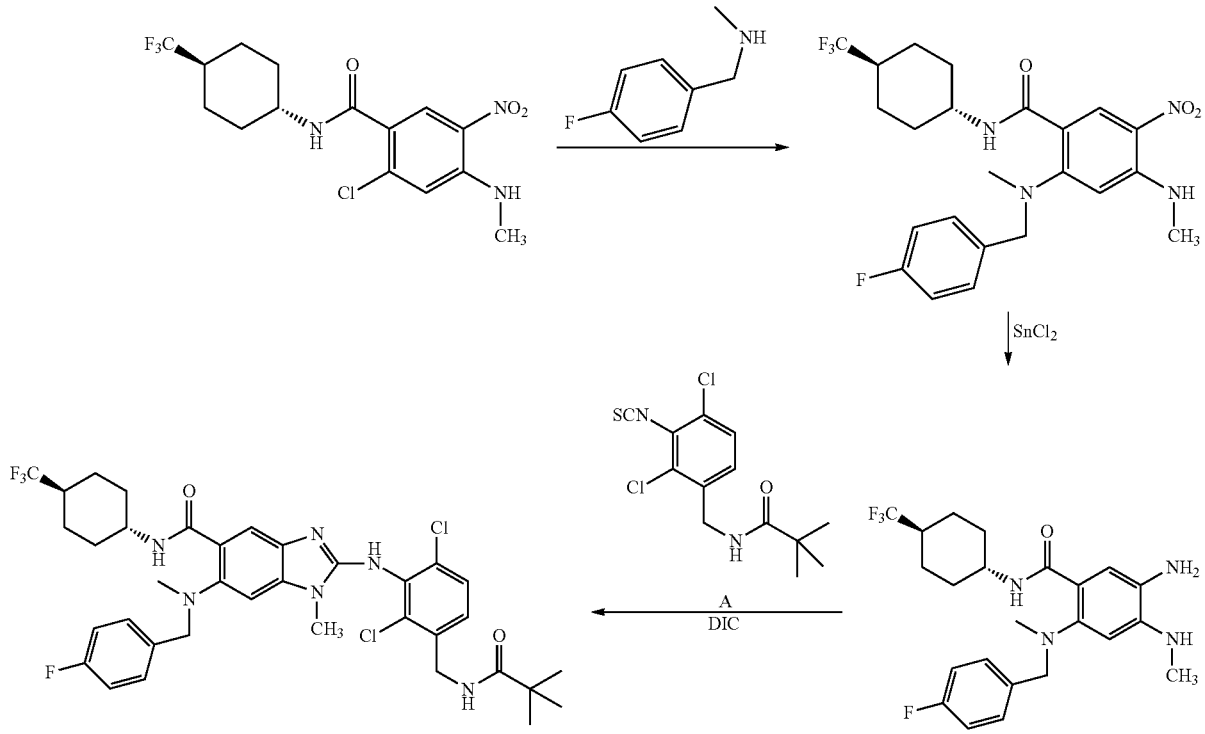

Example 112

N-(trans-4-Trifluoromethyl-cyclohexyl)-2-{2,6-dichloro-3-[(2,2-dimethyl-propionylamino)-methyl]-phenylamino}-6-[N-methyl-N-cyanomethyl-amino]-1-methyl-1H-benzimidazole-5-carboxylic acid amide

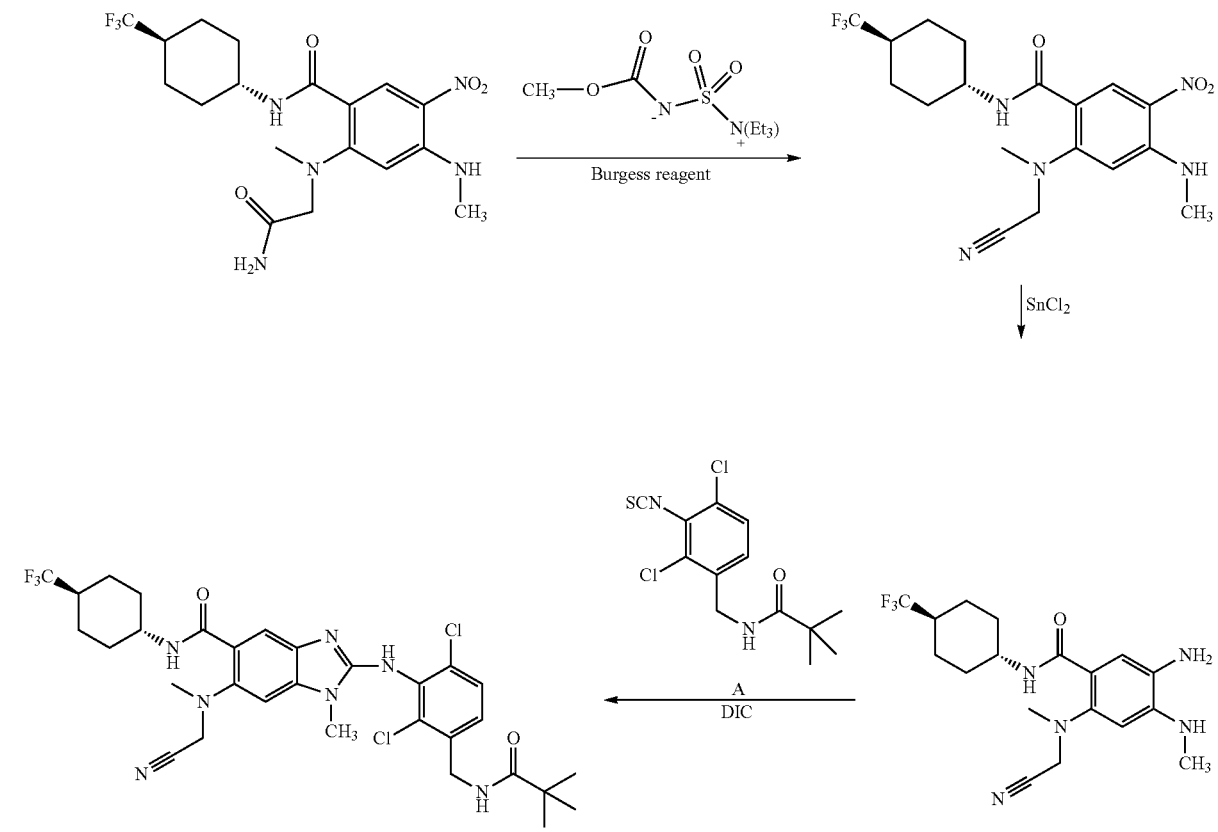

(a) N-(trans-4-Trifluoromethyl-cyclohexyl)-2-[N-methyl-N-cyanomethyl-amino]-4-methylamino-5-nitro-benzoic acid amide A mixture of N-(trans-4-trifluoromethyl-cyclohexyl)-2-[N-methyl-N-aminocarbonylmethyl-amino]-4-methylamino-5-nitro-benzoic acid amide (compound IIIa, 45 mg, 0.104 mmol), Burgess reagent (27 mg, 0.11 mmol, +20 mg after 0.5 h, +15 mg after 2.5 h, +20 mg after 16 h), DCM (2 mL) and THF (2 mL) is stirred for 2.5 h at rt, then for 13.5 h at 40° C. and then for 2 h at reflux. The mixture is diluted with sat aq NaHCO$_3$, extracted with EtOAc and the combined organic phases are dried with Na$_2$SO$_4$, filtered and concentrated and directly used in the next step. Yield: 80 mg. HPLC R$_t$=1.36 min (method A). MS m/z: 414 [M+H]$^+$.

(b) N-(trans-4-Trifluoromethyl-cyclohexyl)-2-[N-methyl-N-cyanomethyl-amino]-4-methylamino-5-amino-benzoic acid amide A mixture of N-(trans-4-trifluoromethyl-cyclohexyl)-2-[N-methyl-N-cyanomethyl-amino]-4-methylamino-5-nitro-benzoic acid amide (50 mg, 0.12 mmol), SnCl$_2$ (134 mg 0.59 mmol and 5 mL EtOAc is stirred at reflux for 4 h. The mixture is diluted with EtOAc, washed with sat aq NaHCO$_3$, filtered through a pad of celite and the celite pad is washed with EtOAc. The combined organic phases are dried with Na$_2$SO$_4$, filtered and concentrated.

Yield: 48 mg. HPLC R$_t$=1.22 min (method A). MS m/z: 384 [M+H]$^+$.

(c) N-(trans-4-Trifluoromethyl-cyclohexyl)-2-{2,6-dichloro-3-[(2,2-dimethyl-propionylamino)-methyl]-phenylamino}-6-[N-methyl-N-cyanomethyl-amino]-1-methyl-1H-benzimidazole-5-carboxylic acid amide The title compound is prepared in analogy to 1e from N-(trans-4-trifluoromethyl-cyclohexyl)-2-[N-methyl-N-cyanomethyl-amino]-4-methylamino-5-amino-benzoic acid amide (48 mg, 0.125 mmol), and N-(2,4-dichloro-3-isothiocyanato-benzyl)-2,2-dimethyl-propionamide (40 mg, 0.125 mmol), DIC (19 μL) and DMF (2.0 mL).

Yield: 30 mg. HPLC R$_t$=1.60 min (method A). MS m/z: 666 [M+H]$^+$.

Example 118

N-(trans-4-Trifluoromethyl-cyclohexyl)-2-{2,6-dichloro-3-[(2,2-dimethyl-propionylamino)-methyl]-phenylamino}-6-[N-methyl-N-(1-oxo-tetrahydro-thiophen-3-yl)-amino]-1-methyl-1H-benzimidazole-5-carboxylic acid amide

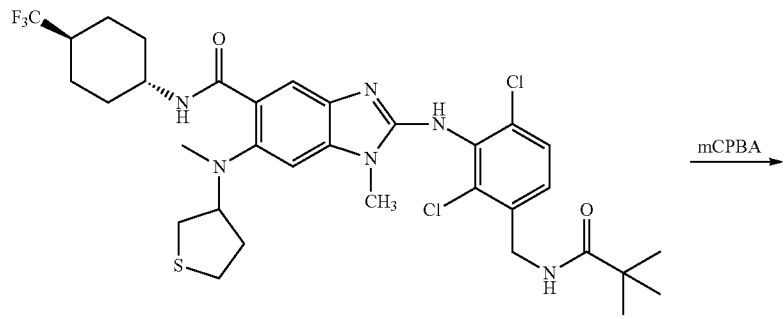

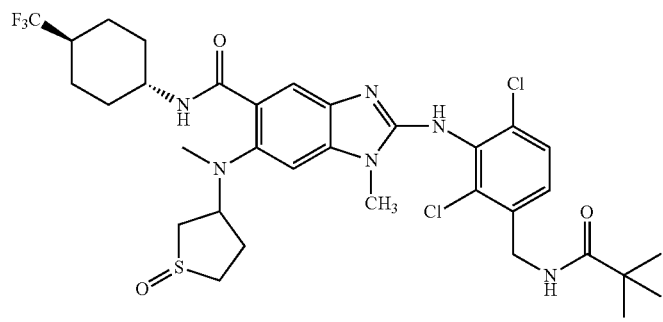

A mixture of N-(trans-4-trifluoromethyl-cyclohexyl)-2-{2,6-dichloro-3-[(2,2-dimethyl-propionylamino)-methyl]-phenylamino}-6-[N-methyl-N-(tetrahydro-thiophen-3-yl)-amino]-1-methyl-1H-benzimidazole-5-carboxylic acid amide (compound 117, 70 mg, 0.098 mmol), mCPBA (23 mg, ~0.10 mmol), DCM (5 mL) and glacial acetic acid (0.5 mL) is stirred for 2.5 h at rt. The mixture is diluted with sat aq NaHCO$_3$, extracted with EtOAc, the combined organic phases are dried with Na$_2$SO$_4$, filtered and concentrated.

Yield: 70 mg. HPLC R$_t$=1.41 min (method A). MS m/z: 729 [M+H]$^+$.

Example 119

N-(trans-4-Trifluoromethyl-cyclohexyl)-2-{2,6-dichloro-3-[(2,2-dimethyl-propionylamino)-methyl]-phenylamino}-6-[N-methyl-N-(1,1-dioxo-tetrahydro-thiophen-3-yl)-amino]-1-methyl-1H-benzimidazole-5-carboxylic acid amide

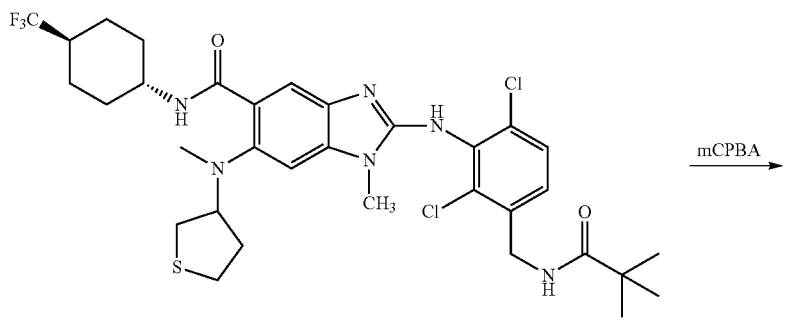

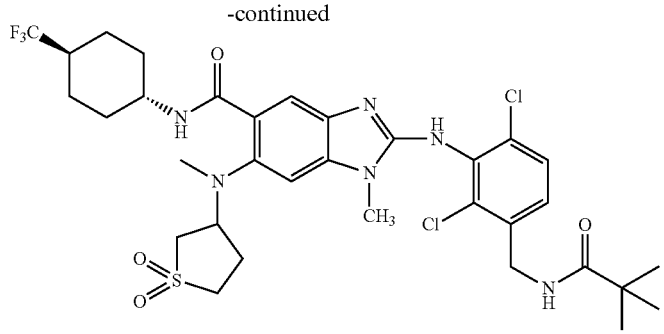

A mixture of N-(trans-4-trifluoromethyl-cyclohexyl)-2-{2,6-dichloro-3-[(2,2-dimethyl-propionylamino)-methyl]-phenylamino}-6-[N-methyl-N-(tetrahydro-thiophen-3-yl)-amino]-1-methyl-1H-benzimidazole-5-carboxylic acid amide (compound 117, 70 mg, 0.098 mmol), mCPBA (112 mg, ~0.55 mmol, added in four portions), DCM (5 mL) and glacial acetic acid (0.5 mL) is stirred for 7.5 h at rt. The mixture is diluted with sat aq NaHCO₃, extracted with EtOAc, the combined organic phases are dried with Na₂SO₄, filtered, concentrated and purified via prep. HPLC. Yield: 10 mg. HPLC $R_t$=1.59 min (method I). MS m/z: 745 [M+H]⁺.

Example 144

N-(trans-4-Trifluoromethyl-cyclohexyl)-2-{2,6-dichloro-3-[(2,2-dimethyl-propionylamino)-methyl]-phenylamino}-6-[3-aza-bicyclo[3.1.0]hex-3-yl]-1,7-dimethyl-1H-benzimidazole-5-carboxylic acid amide

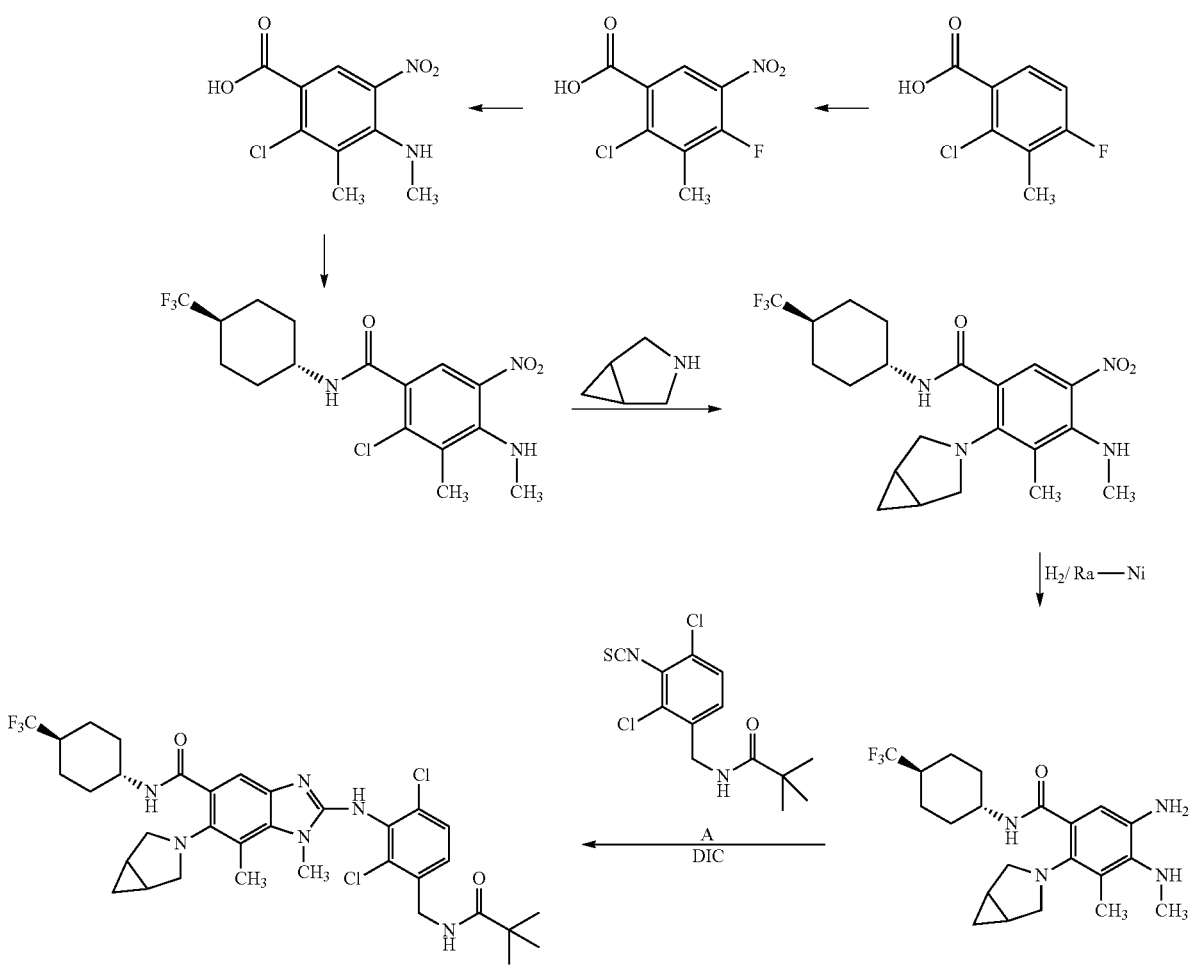

(a) 2-Chloro-3-methyl-4-fluoro-5-nitro-benzoic acid

Aq HNO₃ (65%, 0.39 mL) is added at 0° C. to a mixture of 2-chloro-3-methyl-4-fluoro-benzoic acid (880 mg, 4.7 mmol) and 8 mL conc H$_2$SO$_4$ and it is stirred for 2 h without further cooling. The mixture is poured into ice water and the precipitate is collected by filtration and dried.

Yield: 1.1 g (100%); MS m/z: 232 [M−H]$^−$.

(b)
2-Chloro-3-methyl-4-methylamino-5-nitro-benzoic acid

A mixture of methylamine (2M THF solution, 8.56 mL, 17 mmol), 2-chloro-3-methyl-4-fluoro-5-nitro-benzoic acid (1.00 g, 4.2 mmol) and 20 mL THF is stirred over the weekend at rt. Then the mixture is acidified with 4M aq HCl and concentrated and the residue is washed with water and dried.

Yield: 1.0 g (96%); MS m/z: 245 [M+H]$^+$.

(c) N-(trans-4-Trifluoromethyl-cyclohexyl)-2-chloro-3-methyl-4-methylamino-5-nitro-benzoic acid amide The sub-title compound is prepared in analogy to 5c from 2-chloro-3-methyl-4-methylamino-5-nitro-benzoic acid (1.00 g, 4.1 mmol), 4-trans-trifluoromethyl-cyclohexylamine×HCl (0.92 g, 4.4 mmol), TBTU (1.6 g, 4.9 mmol), TEA (1.44 mL, 10 mmol) and THF (30 mL). Yield: 1.5 g. MS m/z: 394 [M+H]$^+$.

(d) N-(trans-4-Trifluoromethyl-cyclohexyl)-2-[3-aza-bicyclo[3.1.0]hex-3-yl]-3-methyl-4-methylamino-5-nitro-benzoic acid amide The sub-title compound is prepared in analogy to 6a from N-(trans-4-trifluoromethyl-cyclohexyl)-2-chloro-3-methyl-4-methylamino-5-nitro-benzoic acid amide (250 mg, 0.64 mmol), 3-aza-bicyclo[3.1.0]hexane (151 mg, 1.27 mmol), DIPEA (0.44 mL, 2.5 mmol) and dioxane (8 mL). Yield: 130 mg. HPLC R$_t$=1.62 min (method H). MS m/z: 441 [M+H]$^+$.

(e) N-(trans-4-Trifluoromethyl-cyclohexyl)-2-[3-aza-bicyclo[3.1.0]hex-3-yl]-3-methyl-4-methylamino-5-amino-benzoic acid amide The sub-title compound is prepared in analogy to 6b from N-(trans-4-trifluoromethyl-cyclohexyl)-2-[3-aza-bicyclo[3.1.0]hex-3-yl]-3-methyl-4-methylamino-5-nitro-benzoic acid amide (130 mg, 0.295 mmol), Pd/C (50 mg), MeOH (40 mL) and 3 bar H$_2$-atmosphere. Yield: 85 mg. HPLC R$_t$=1.31 min (method A). MS m/z: 411 [M+H]$^+$.

(f) N-(trans-4-Trifluoromethyl-cyclohexyl)-2-{2,6-dichloro-3-[(2,2-dimethyl-propionylamino)-methyl]-phenylamino}-6-[3-aza-bicyclo[3.1.0]hex-3-yl]-1,7-dimethyl-1H-benzimidazole-5-carboxylic acid amide The title compound is prepared in analogy to 6c from N-(trans-4-trifluoromethyl-cyclohexyl)-2-[3-aza-bicyclo[3.1.0]hex-3-yl]-3-methyl-4-methylamino-5-amino-benzoic acid amide (80 mg, 0.195 mmol), and N-(2,4-dichloro-3-isothiocyanato-benzyl)-2,2-dimethyl-propionamide (62 mg, 0.19 mmol), DIC (36 µL) and dioxane (5.0 mL).

Yield: 14 mg. HPLC R$_t$=1.51 min (method A). MS m/z: 693 [M+H]$^+$.

Example 145

(R)—N-(trans-4-Trifluoromethyl-cyclohexyl)-2-{2,6-dichloro-3-[(2,2-dimethyl-propionylamino)-methyl]-phenylamino}-6-[3-fluoro-pyrrolidinyl]-1-methyl-7-fluoro-1H-benzimidazole-5-carboxylic acid amide

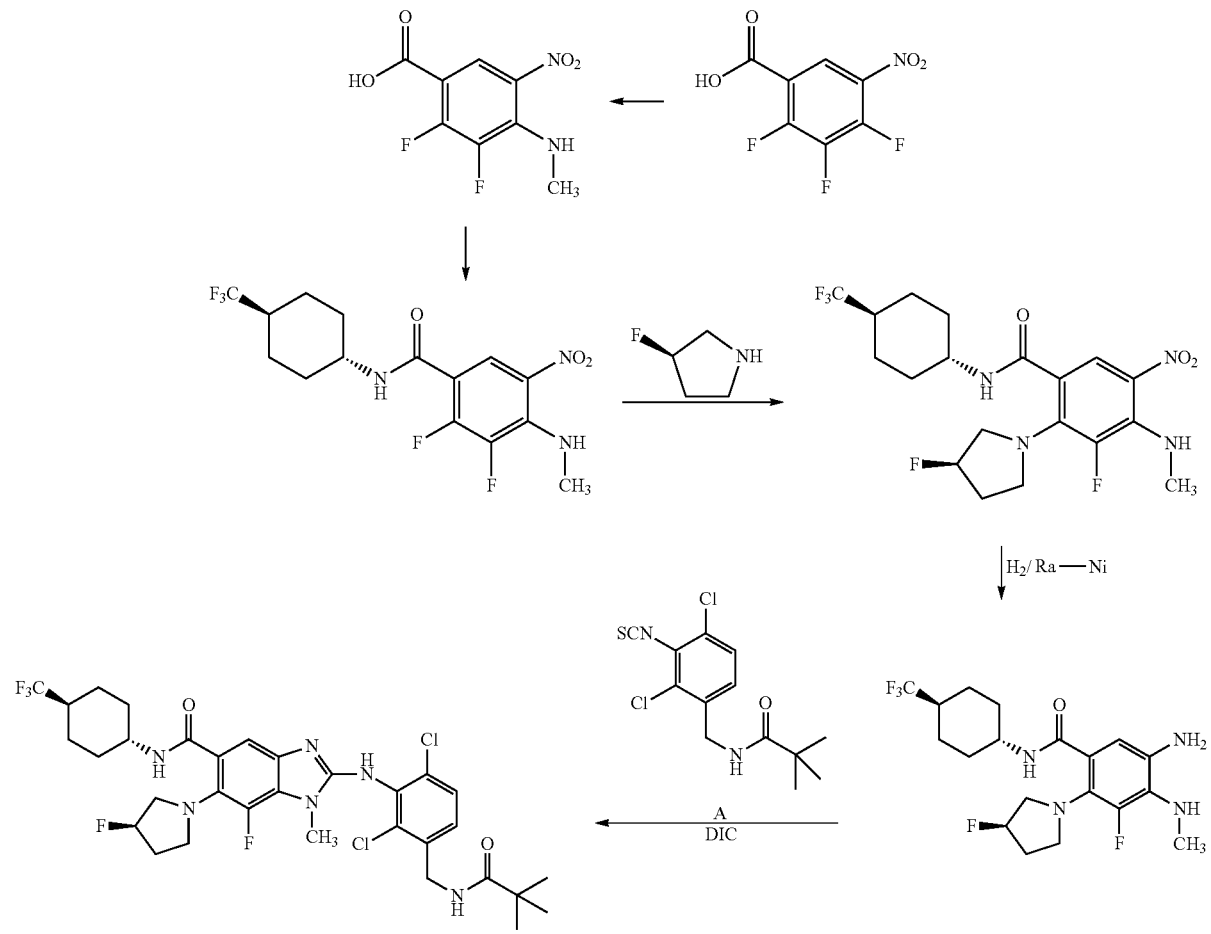

(a) 2,3-Difluoro-4-methylamino-5-nitro-benzoic acid

A mixture of methylamine (40% aq solution, 0.68 mL, 6.7 mmol), 2,3,4-trifluoro-5-nitro-benzoic acid (0.50 g, 2.3 mmol) and 5 mL water is stirred for 3 h in an ice bath. Then the mixture is acidified with 6M aq HCl and the resulting precipitate is collected by filtration washed with water and dried.

Yield: 0.45 g (86%); HPLC $R_t$=1.13 min (method A). MS m/z: 233 [M+H]$^+$.

(b) N-(trans-4-Trifluoromethyl-cyclohexyl)-2,3-difluoro-4-methylamino-5-nitro-benzoic acid amide The sub-title compound is prepared in analogy to 5c from 2,3-difluoro-4-methylamino-5-nitro-benzoic acid (0.45 g, 1.9 mmol), 4-trans-trifluoromethyl-cyclohexylamine×HCl (0.39 g, 1.9 mmol), TBTU (0.68 g, 2.1 mmol), DIPEA (0.99 mL, 5.8 mmol) and THF (15 mL). Yield: 0.75 g. HPLC $R_t$=1.55 min (method A). MS m/z: 382 [M+H]$^+$.

(c) (R)—N-(trans-4-Trifluoromethyl-cyclohexyl)-2-[3-fluoro-pyrrolidinyl]-3-fluoro-4-methylamino-5-nitro-benzoic acid amide The sub-title compound is prepared in analogy to procedure 6a from N-(trans-4-trifluoromethyl-cyclohexyl)-2,3-difluoro-4-methylamino-5-nitro-benzoic acid amide (200 mg, 0.52 mmol), (R)-3-fluoropyrrolidine×HCl (72 mg, 0.57 mmol), DIPEA (0.76 mL, 4.4 mmol) and MeCN (5 mL). Yield: 230 mg. HPLC $R_t$=1.52 min (method A). MS m/z: 451 [M+H]$^+$.

(d) (R)—N-(trans-4-Trifluoromethyl-cyclohexyl)-2-[3-fluoro-pyrrolidinyl]-3-fluoro-4-methylamino-5-amino-benzoic acid amide The sub-title compound is prepared in analogy to procedure 6b from (R)—N-(trans-4-trifluoromethyl-cyclohexyl)-2-[3-fluoro-pyrrolidinyl]-3-fluoro-4-methylamino-5-nitro-benzoic acid amide (230 mg, 0.51 mmol), Pd/C (20 mg), MeOH (15 mL), THF (5 mL) and 3 bar H$_2$-atmosphere. Yield: 215 mg.

(e) (R)—N-(trans-4-Trifluoromethyl-cyclohexyl)-2-{2,6-dichloro-3-[(2,2-dimethyl-propionylamino)-methyl]-phenylamino}-6-[3-fluoro-pyrrolidinyl]-1-methyl-7-fluoro-1H-benzimidazole-5-carboxylic acid amide The title compound is prepared in analogy to 1e from (R)—N-(trans-4-trifluoromethyl-cyclohexyl)-2-[3-fluoro-pyrrolidinyl]-3-fluoro-4-methylamino-5-amino-benzoic acid amide (215 mg, 0.51 mmol), and N-(2,4-dichloro-3-isothiocyanato-benzyl)-2,2-dimethyl-propionamide (162 mg, 0.51 mmol), DIC (80 μL) and DMF (4.0 mL).

Yield: 210 mg. HPLC $R_t$=1.58 min (method A). MS m/z: 703 [M+H]$^+$.

Example 157

N-(3-tert.-Butyl-isoxazol-5-O-2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid amide

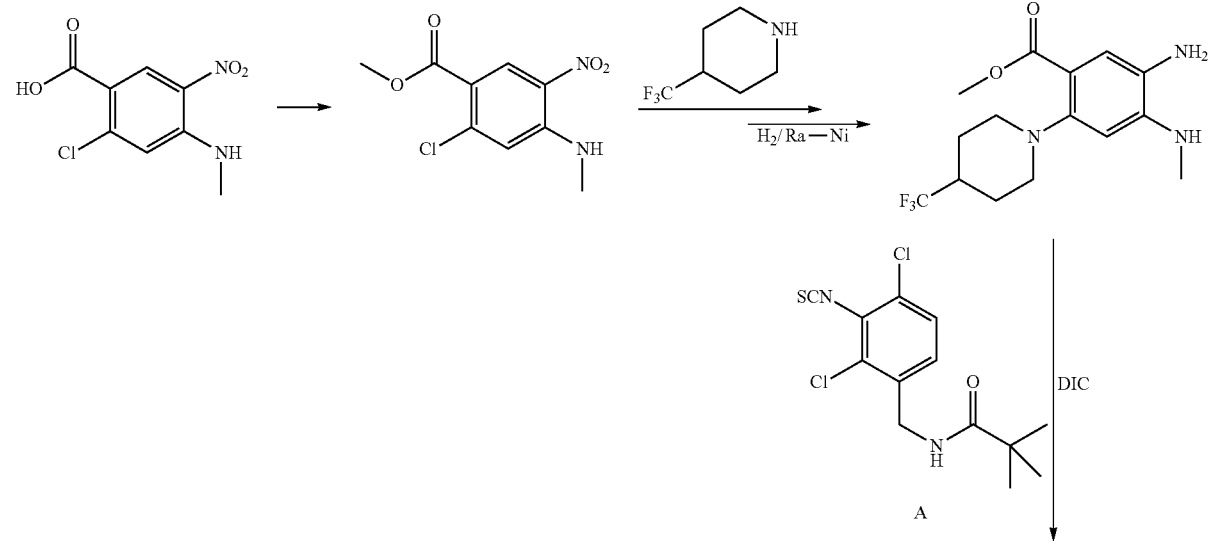

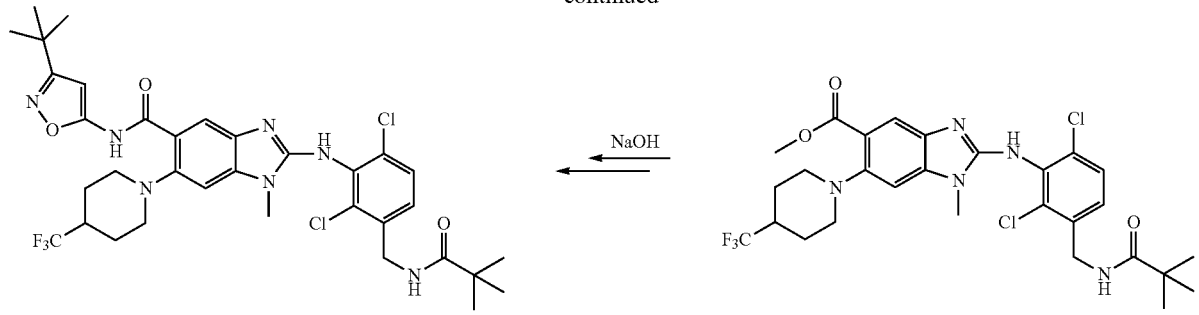

(a) Methyl-2-chloro-4-methylamino-5-nitro-benzoate

Thionylchloride (3.87 g, 32 mmol) is added dropwise at rt to a mixture of 2-chloro-4-methylamino-5-nitro-benzoic acid (5.00 g, 22 mmol) and 45 mL MeOH and it is stirred at reflux overnight. The mixture is cooled to rt and the precipitate is collected by filtration and dried. Yield: 5.01 g. MS m/z: 245 [M+H]⁺.

(b) Methyl-2-[4-trifluoromethyl-piperidinyl]-4-methylamino-5-nitro-benzoate

The sub-title compound is prepared in analogy to 26a from methyl-2-chloro-4-methylamino-5-nitro-benzoate (1.37 g, 5.6 mmol), 4-trifluoromethylpiperidine×HCl (1.27 g, 6.7 mmol), DIPEA (3.8 mL, 22 mmol) and dioxane (50 mL).
Yield: 1.80 g. HPLC $R_t$=1.51 min (method A). MS m/z: 362 [M+H]⁺.

(c) Methyl-2-[4-trifluoromethyl-piperidinyl]-4-methylamino-5-amino-benzoate

A mixture of methyl-2-[4-trifluoromethyl-piperidinyl]-4-methylamino-5-nitro-benzoate (1.80 g, 4.19 mmol), Ra—Ni (200 mg) and MeOH (100 mL) is stirred for 5 h under 3 bar H₂-atmosphere. The mixture is filtered, and the filtrate is concentrated.
Yield: 1.65 g. HPLC $R_t$=0.96 min (method A). MS m/z: 332 [M+H]⁺.

(d) 2-{2,6-Dichloro-3-[(2,2-dimethyl-propionylamino)-methyl]-phenylamino}-6-[4-trifluoromethyl-piperidinyl]-1-methyl-1H-benzimidazole-5-carboxylic acid methyl ester The sub-title compound is prepared in analogy to 6c from methyl-2-[4-trifluoromethyl-piperidinyl]-4-methylamino-5-amino-benzoate (1.60 g, 4.82 mmol), and N-(2,4-dichloro-3-isothiocyanato-benzyl)-2,2-dimethyl-propionamide (1.53 g, 4.82 mmol), DIC (0.82 mL, 5.3 mmol) and DMF (20 mL). Yield: 2.54 g. HPLC $R_t$=1.42 min (method A). MS m/z: 614 [M+H]⁺.

(e) 2-{2,6-Dichloro-3-[(2,2-dimethyl-propionylamino)-methyl]-phenylamino}-6-[4-trifluoromethyl-piperidinyl]-1-methyl-1H-benzimidazole-5-carboxylic acid A mixture of 2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid methyl ester (2.54 g, 4.17 mmol), 50% aq NaOH-solution (10.3 ml) and MeOH (41 ml) is stirred for 2.5 h at rt and concentrated. The concentrate is acidified with 4N HCl (to pH ~6) and the precipitate is filtered, washed with water and dried.
Yield: 2.47 g. HPLC $R_t$=1.24 min (method A). MS m/z: 600 [M+H]⁺.

(f) N-(3-tert.-Butyl-isoxazol-5-yl)-2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid amide The title compound is prepared in analogy to 1b from 2-{2,6-dichloro-3-[(2,2-dimethyl-propionylamino)-methyl]-phenylamino}-6-[4-trifluoromethyl-piperidinyl]-1-methyl-1H-benzimidazole-5-carboxylic acid (100 mg, 0.16 mmol), 5-amino-3-tert.-butyl-isoxazole (23 mg, 0.16 mmol), (1-chloro-2-methyl-propenyl)-dimethylamine (0.026 mL, 0.20 mmol) TEA (0.114 mL, 0.81 mmol) and THF.
Yield: 197 mg. HPLC $R_t$=1.59 min (method A). MS m/z: 722 [M+H]⁺.

Example 166

N-(4-Trifluoromethoxy-phenyl)-2-{2,6-dichloro-3-[(2,2-dimethyl-propionylamino)-methyl]-phenylamino}-6-[morpholinyl]-1-(2-hydroxy-2-methyl-propyl)-1H-benzimidazole-5-carboxylic acid amide

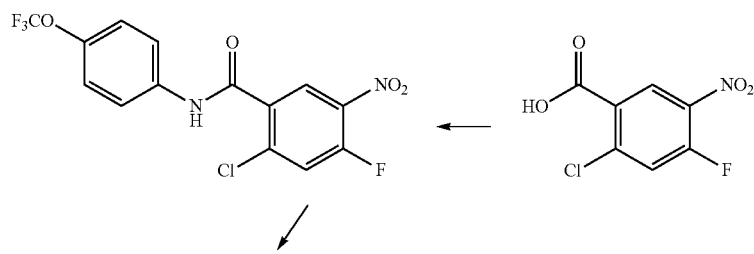

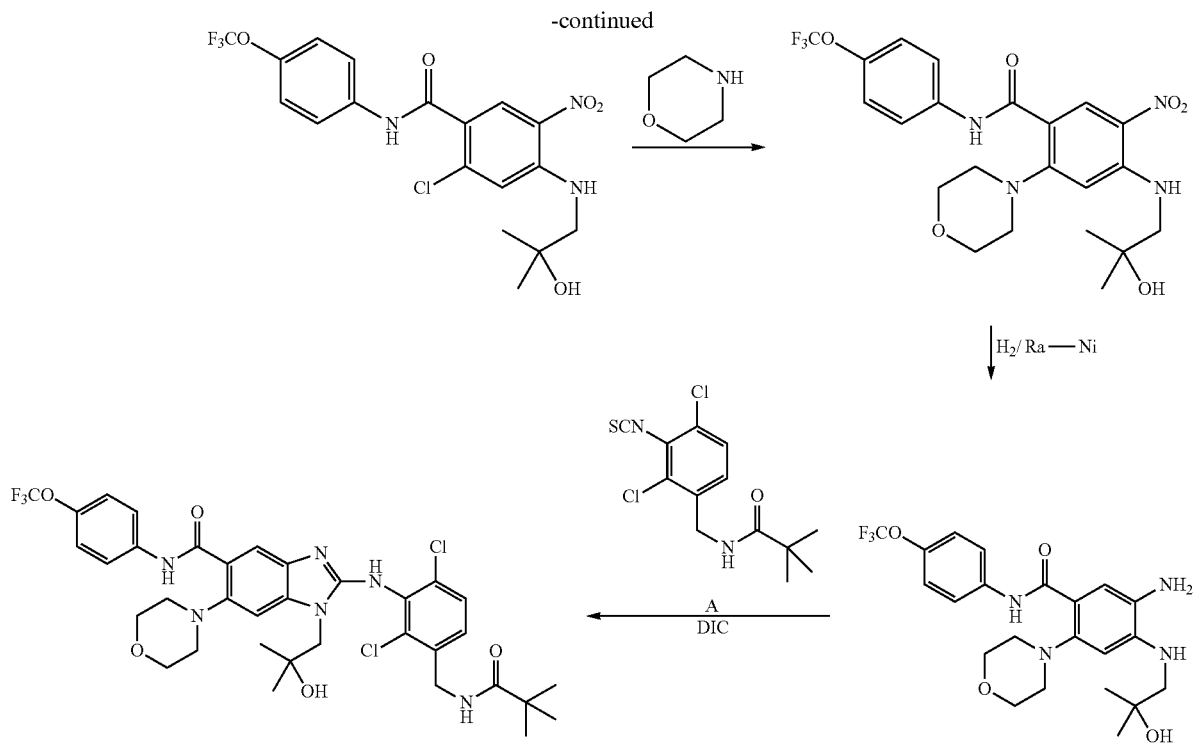

(a) N-(4-Trifluoromethoxy-phenyl)-2-chloro-4-fluoro-5-nitro-benzoic acid amide A mixture of 3-chloro-4-fluoro-5-nitrobenzoic acid (2.5 g, 11 mmol), 4.3 mL thionyl chloride (59 mmol), 50 mL DCM and three drops of DMF is stirred at reflux. After 2 h 1 mL thionyl chloride is added and it is stirred for another 1 h. The mixture is concentrated and directly used in the next step.

A mixture of 4-trifluoromethoxy-aniline (0.82 mL, 5.9 mmol), TEA (2.07 mL, 15 mmol) and THF (20 mL) is slowly dropped to the crude 2-chloro-4-fluoro-5-nitro-benzoic acid chloride (1.40 g, 5.9 mmoll) in 30 mL THF. The mixture is stirred for 1 h, poured into ice water and acidified to pH3 with $KHSO_4$. The mixture is concentrated and the resulting precipitate is collected by filtration, washed with water and dried.

Yield: 2.1 g (92%); HPLC $R_t$=1.59 min (method H). MS m/z: 379 [M+H]$^+$.

(b) N-(4-Trifluoromethoxy-phenyl)-2-chloro-4-(2-hydroxy-2-methyl-propylamino)-5-nitro-benzoic acid amide A mixture of 1-amino-2-methyl-propan-2-ol (184 mg, 2.06 mmol), N-(4-trifluoromethoxy-phenyl)-2-chloro-4-fluoro-5-nitro-benzoic acid amide (650 mg, 1.7 mmol), $Cs_2CO_3$ (839 mg, 2.6 mmol) and 10 mL DMF is stirred for 1 h at 50° C., poured into ice water, concentrated and the resulting precipitate is collected by filtration, washed with water and dried.

Yield: 742 mg (97%); MS m/z: 448 [M+H]$^+$.

(c) N-(4-Trifluoromethoxyphenyl)-2-(morpholinyl)-4-(2-hydroxy-2-methyl-propylamino)-5-nitro-benzoic acid amide The sub-title compound is prepared in analogy to 103a from N-(4-trifluoromethoxy-phenyl)-2-chloro-4-(2-hydroxy-2-methyl-propylamino)-5-nitro-benzoic acid amide (300 mg, 0.67 mmol), morpholine (233 µL, 2.7 mmol), DIPEA (1.1 mL, 6.7 mmol) and MeCN (3 mL) in a microwave oven at 150° C. (45 min). Yield: 324 mg. HPLC $R_t$=1.58 min (method H). MS m/z: 499 [M+H]$^+$.

(d) N-(4-Trifluoromethoxyphenyl)-2-(morpholinyl)-4-(2-hydroxy-2-methyl-propylamino)-5-amino-benzoic acid amide A mixture of N-(4-trifluoromethoxyphenyl)-2-(morpholinyl)-4-(2-hydroxy-2-methyl-propylamino)-5-nitro-benzoic acid amide (100 mg, 0.20 mmol), Pd/C (50 mg), MeOH (3.5 mL) and THF (10 mL) is stirred under 4 bar $H_2$-atmosphere overnight. The mixture is filtered, and the filtrate is concentrated. Yield: 94 mg. HPLC $R_t$=1.36 min (method H). MS m/z: 468 [M+H]$^+$.

(e) N-(4-Trifluoromethoxy-phenyl)-2-{2,6-dichloro-3-[(2,2-dimethyl-propionylamino)-methyl]-phenylamino}-6-[morpholinyl]-1-(2-hydroxy-2-methyl-propyl)-1H-benzimidazole-5-carboxylic acid amide The title compound is prepared in analogy to 6c from N-(4-trifluoromethoxyphenyl)-2-(morpholinyl)-4-(2-hydroxy-2-methyl-propylamino)-5-amino-benzoic acid amide (94 mg, 0.20 mmol), and N-(2,4-dichloro-3-isothiocyanato-benzyl)-2,2-dimethyl-propionamide (64 mg, 0.20 mmol), DIC (31 µL, 0.20 mmol) and MeCN (5 mL).

Yield: 104 mg. HPLC $R_t$=1.50 min (method H). MS m/z: 751 [M+H]$^+$.

Example 172

N-(3,3,3-Trifluoropropyl)-2-{2,6-dichloro-3-[(tert.-butoxycarbonylamino)-methyl]-phenylamino}-6-[4-trifluoromethyl-piperidinyl]-1-methyl-1H-benzimidazole-5-carboxylic acid amide

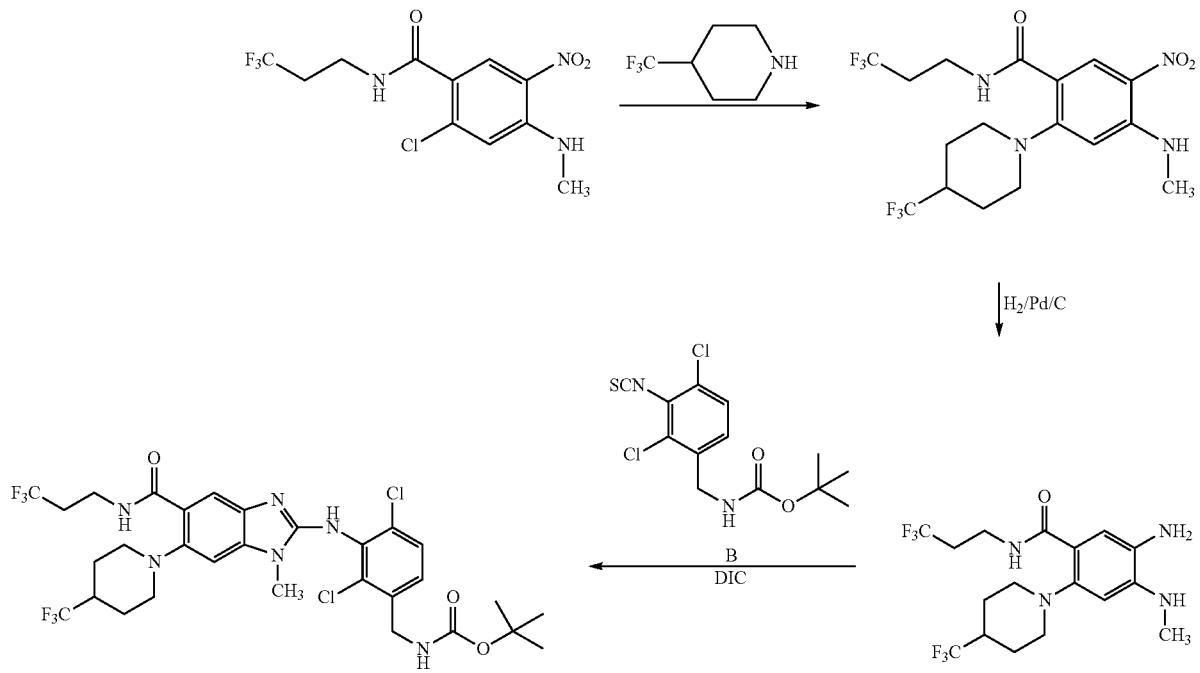

(a) N-(3,3,3-Trifluoro-propyl)-2-[4-trifluoromethyl-piperidinyl]-4-methylamino-5-nitro-benzoic acid amide The sub-title compound is prepared in analogy to 6a from N-(3,3,3-trifluoro-propyl)-2-chloro-4-methylamino-5-nitro-benzoic acid amide (compound 81a; 2.0 g, 6.5 mmol), 4-trifluormethyl-piperidine×HCl (2.45 g, 13 mmol), DIPEA (4.9 mL, 29 mmol) and MeCN (25 mL) in a pressure flask at 80° C.

Yield: 2.78 g. HPLC $R_t$=1.47 min (method A). MS m/z: 443 [M+H]$^+$.

(b) N-(3,3,3-Trifluoro-propyl)-2-[4-trifluoromethyl-piperidinyl]-4-methylamino-5-amino-benzoic acid amide A mixture of N-(3,3,3-trifluoro-propyl)-2-[4-trifluoromethyl-piperidinyl]-4-methylamino-5-nitro-benzoic acid amide (2.5 g, 5.7 mmol), Pd/C (200 mg), THF (10 mL) and MeOH (100 mL) is stirred for 2 h under 3 bar H$_2$-atmosphere. The mixture is filtered, and the filtrate is concentrated. Yield: 2.3 g. HPLC $R_t$=1.25 min (method A). MS m/z: 413 [M+H]$^+$.

(c) N-(3,3,3-Trifluoropropyl)-2-{2,6-dichloro-3-[(tert.-butoxycarbonylamino)-methyl]-phenylamino}-6-[4-trifluoromethyl-piperidinyl]-1-methyl-1H-benzimidazole-5-carboxylic acid amide The title compound is prepared in analogy to 1e from N-(3,3,3-trifluoro-propyl)-2-[4-trifluoromethyl-piperidinyl]-4-methylamino-5-amino-benzoic acid amide (2.3 g, 5.6 mmol), (2,4-dichloro-3-isothiocyanato-benzyl)-carbamic acid tert.-butyl ester (compound B; 1.85 g, 5.6 mmol), DIC (1.0 mL) and DMF (10 mL).

Yield: 3.2 g. $R_f$=0.26 (DCM/EtOAc 95:5). MS m/z: 712 [M+H]$^+$.

Example 173

N-(3,3,3-Trifluoropropyl)-2-{2,6-dichloro-3-[(2-fluoro-4-hydroxy-phenyl)-carbonylamino)-methyl]-phenylamino}-6-[4-trifluoromethyl-piperidinyl]-1-methyl-1H-benzimidazole-5-carboxylic acid amide

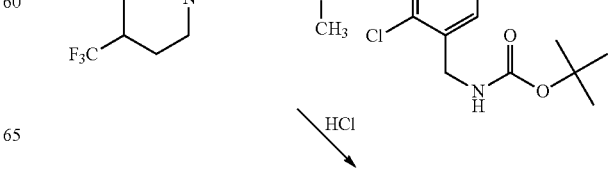

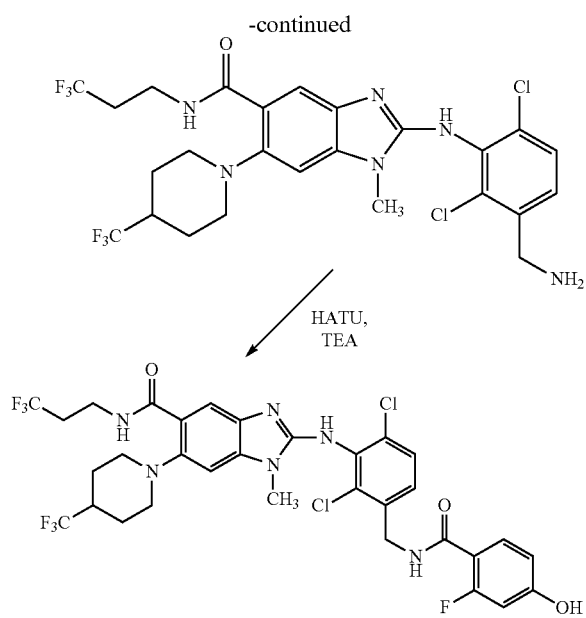

(a) N-(3,3,3-Trifluoropropyl)-2-{2,6-dichloro-3-[aminomethyl]-phenylamino}-6-[4-trifluoromethyl-piperidinyl]-1-methyl-1H-benzimidazole-5-carboxylic acid amide A mixture of N-(3,3,3-trifluoropropyl)-2-{2,6-dichloro-3-[(tert.-butoxycarbonylamino)-methyl]-phenylamino}-6-[4-trifluoromethyl-piperidinyl]-1-methyl-1H-benzimidazole-5-carboxylic acid amide (2.73 g, 3.8 mmol), 15 mL 6M aq HCl and 15 mL THF is stirred for 2 h, concentrated and the sub title compound is purified by chromatography (silica gel, DCM→DCM/10% EtOH+few drops of $NH_4OH$). Yield: 2.3 g. $R_f$=0.27 (DCM/EtOH/$NH_4OH$ 90:10:1). MS m/z: 712 $[M+H]^+$.

(b) N-(3,3,3-Trifluoropropyl)-2-{2,6-dichloro-3-[(2-fluoro-4-hydroxy-phenyl)-carbonylamino)-methyl]-phenylamino}-6-[4-trifluoromethyl-piperidinyl]-1-methyl-1H-benzimidazole-5-carboxylic acid amide A mixture of 2-fluoro-4-hydroxy benzoic acid (26 mg, 0.16 mmol), HATU (68 mg, 0.18 mmol), TEA (68 μL, 0.49 mmol) and THF is stirred for 10 min, then N-(3,3,3-trifluoropropyl)-2-{2,6-dichloro-3-[aminomethyl]-phenylamino}-6-[4-trifluoromethyl-piperidinyl]-1-methyl-1H-benzimidazole-5-carboxylic acid amide (100 mg, 0.16 mmol) is added and it is stirred overnight. The mixture is concentrated and the title compound is purified by chromatography (silica gel, DCM→DCM/EtOH 96:4), Yield: 84 mg. $R_f$=0.25 (DCM/EtOH 95:5). MS m/z: 749 $[M+H]^+$.

Example 174

N-(3,3,3-Trifluoropropyl)-2-{2,6-dichloro-3-[(N-oxo-pyridin-2-yl)carbonylamino)-methyl]-phenylamino}-6-[4-trifluoromethyl-piperidinyl]-1-methyl-1H-benzimidazole-5-carboxylic acid amide

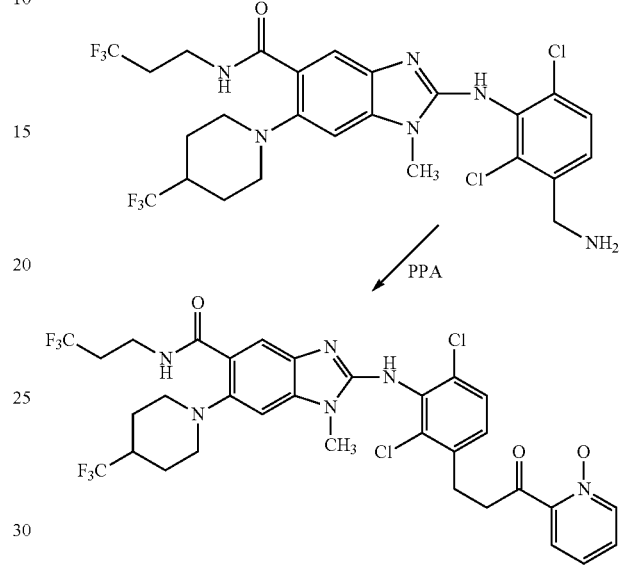

A mixture of picolinic acid-N-oxide (16 mg, 0.11 mmol), N-(3,3,3-trifluoropropyl)-2-{2,6-dichloro-3-[aminomethyl]-phenylamino}-6-[4-trifluoromethyl-piperidinyl]-1-methyl-1H-benzimidazole-5-carboxylic acid amide (70 mg, 0.11 mmol), N-methylmorpholine (0.13 mL, 1.14 mmol), PPA (0.20 mL, 0.34 mmol) and DCM is stirred for 1 h at rt. The mixture is diluted with sat aq $NaHCO_3$, extracted with EtOAc and the combined organic layers are dried with $Na_2SO_4$, concentrated and purified by prep HPLC.

Yield: 50 mg. HPLC $R_t$=1.40 min (method A). MS m/z: 732 $[M+H]^+$.

Example 185

N-(trans-4-Trifluoromethyl-cyclohexyl)-2-{2,6-dichloro-3-[(tert.-butoxycarbonylamino)-methyl]-phenylamino}-6-[3-aza-bicyclo[3.1.0]hex-1-yl]-methyl-1H-benzimidazole-5-carboxylic acid amide

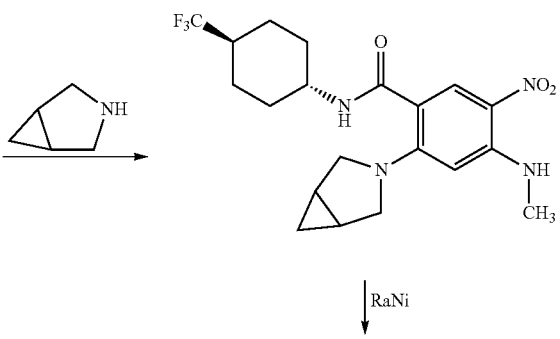

-continued

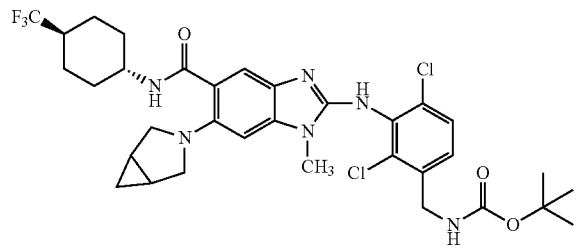 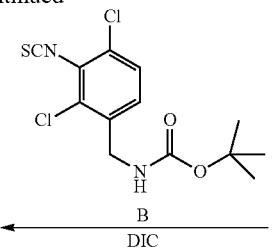 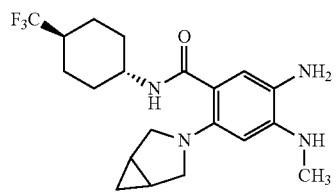

(a) N-(trans-4-Trifluoromethyl-cyclohexyl)-6-[3-aza-bicyclo[3.1.0]hex-1-yl]-4-methylamino-5-nitro-benzoic acid amide The sub-title compound is prepared in analogy to procedure 6a from N-(trans-4-trifluoromethyl-cyclohexyl)-2-chloro-4-methylamino-5-nitro-benzoic acid amide (compound 20b; 1.6 g, 4.2 mmol), 3-aza-bicyclo[3.1.0]hexane (1.00 g, 5.3 mmol), DIPEA (3.0 mL, 17 mmol) and dioxane (40 mL) at reflux (overnight).

Yield: 1.80 g. HPLC $R_t$=1.46 min (method A). MS m/z: 427 [M+H]$^+$.

(b) N-(trans-4-Trifluoromethyl-cyclohexyl)-6-[3-aza-bicyclo[3.1.0]hex-1-yl]-4-methylamino-5-amino-benzoic acid amide A mixture of N-(trans-4-trifluoromethyl-cyclohexyl)-6-[3-aza-bicyclo[3.1.0]hex-1-yl]-4-methylamino-5-amino-benzoic acid amide (1.8 g, 4.2 mmol), Ra—Ni (500 mg) and THF (50 mL) is stirred for 24 h under 3 bar H$_2$-atmosphere. The mixture is filtered, and the filtrate is concentrated.

Yield: 1.7 g. HPLC $R_t$=1.31 min (method A). MS m/z: 397 [M+H]$^+$.

(c) N-(trans-4-Trifluoromethyl-cyclohexyl)-2-{2,6-dichloro-3-[(tert.-butoxycarbonylamino)-methyl]-phenylamino}-6-[3-aza-bicyclo[3.1.0]hex-1-yl]-1-methyl-1H-benzimidazole-5-carboxylic acid amide The title compound is prepared in analogy to 1e from N-(trans-4-trifluoromethyl-cyclohexyl)-6-[3-aza-bicyclo[3.1.0]hex-1-yl]-4-methylamino-5-amino-benzoic acid amide (3.2 g, 8.0 mmol), (2,4-dichloro-3-isothiocyanato-benzyl)-carbamic acid tert.-butyl ester (compound B; 2.69 g, 8.0 mmol), DIC (1.25 mL) and MeCN (30 mL).

Yield: 3.3 g. HPLC $R_t$=1.47 min (method H). MS m/z: 695 [M+H]$^+$.

Example 186

N-(trans-4-Trifluoromethyl-cyclohexyl)-2-{2,6-dichloro-3-[(1-methyl-cyclobutyl)-carbonylamino)-methyl]-phenylamino}-6-[3-aza-bicyclo[3.1.0]hex-1-yl]-1-methyl-1H-benzimidazole-5-carboxylic acid amide

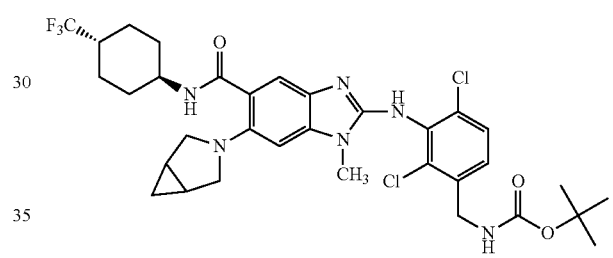

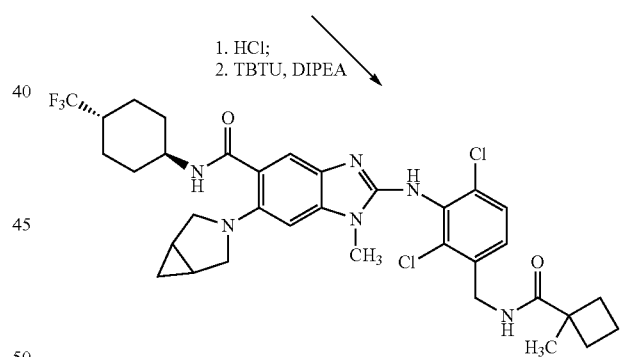

(a) N-(trans-4-Trifluoromethyl-cyclohexyl)-2-{2,6-dichloro-3-[aminomethyl]-phenylamino}-6-[3-aza-bicyclo[3.1.0]hex-1-yl]-1-methyl-1H-benzimidazole-5-carboxylic acid amide A mixture of N-(trans-4-trifluoromethyl-cyclohexyl)-2-{2,6-dichloro-3-[(tert.-butoxycarbonylamino)-methyl]-phenylamino}-6-[3-aza-bicyclo[3.1.0]hex-1-yl]-1-methyl-1H-benzimidazole-5-carboxylic acid amide (compound 185, 3.3 g, 4.7 mmol), 6 mL 4M HCl in dioxane, 10 mL dioxane and 5 mL 2-propanol is stirred overnight. The resulting precipitate is collected by filtration, diluted with EtOAc and washed with 1N aq NaOH. The organic phase is dried with Na$_2$SO$_4$, filtered and concentrated.

Yield: 2.4 g. HPLC $R_t$=1.22 min (method H). MS m/z: 595 [M+H]$^+$.

(b) N-(trans-4-Trifluoromethyl-cyclohexyl)-2-{2,6-dichloro-3-[(1-methyl-cyclobutyl)-carbonylamino)-methyl]-phenylamino}-6-[3-aza-bicyclo[3.1.0]hex-1-yl]-1-methyl-1H-benzimidazole-5-carboxylic acid amide A mixture of 1-methyl-cyclobutylcarboxylic acid (7.5 mg, 0.066 mmol), TBTU (20 mg, 0.063 mmol), DIPEA (40 µL, 0.23 mmol), N-(trans-4-trifluoromethyl-cyclohexyl)-2-{2,6-dichloro-3-[aminomethyl]-phenylamino}-6-[3-aza-bicyclo[3.1.0]hex-1-yl]-1-methyl-1H-benzimidazole-5-carboxylic acid amide (36 mg, 0.060 mmol) and 2 mL DMF is stirred overnight and directly purified by chromatography (silica gel, DCM→DCM/EtOH 96:4).
Yield: 27 mg. HPLC R$_t$=0.275 min (method L). MS m/z: 691 [M+H]$^+$.

Example 231

N-(3-Chloro-4-fluoro-phenyl)-2-{2,6-dichloro-3-[(2-fluoro-2-methyl-propionylamino)-methyl]-phenylamino}-6-[4-trifluoromethyl-piperidinyl]-1-methyl-1H-benzimidazole-5-carboxylic acid amide (a) 2-{2,6-Dichloro-3-[(tert.-butoxycarbonylamino)-methyl]-phenylamino}-6-[4-trifluoromethyl-piperidinyl]-1-methyl-1H-benzimidazole-5-carboxylic acid ethyl ester The title compound is prepared in analogy to 1e from ethyl-2-[4-trifluoromethyl-piperidinyl]-4-methylamino-5-amino-benzoate (compound 52b, 4.31 g, 12.5 mmol), (2,4-dichloro-3-isothiocyanato-benzyl)-carbamic acid tert-butyl ester (compound B; 4.16 g, 12.5 mmol), DIC (2.17 mL, 15.4 mmol) and DMF (50 mL). Yield: 6.9 g. HPLC R$_t$=1.49 min (method A). MS m/z: 644 [M+H]$^+$.

(b) 2-{2,6-Dichloro-3-[aminomethyl]-phenylamino}-6-[4-trifluoromethyl-piperidinyl]-1-methyl-1H-benzimidazole-5-carboxylic acid ethyl ester A mixture of 2-{2,6-dichloro-3-[(tert.-butoxycarbonylamino)-methyl]-phenylamino}-6-[4-trifluoromethyl-piperidinyl]-1-methyl-1H-benzimidazole-5-carboxylic acid ethyl ester (6.95 g, 11 mmol) and 26 mL 4M HCl in dioxane is stirred overnight. Then the organic phase is concentrated and the crude sub-title compound is directly used in the next step.

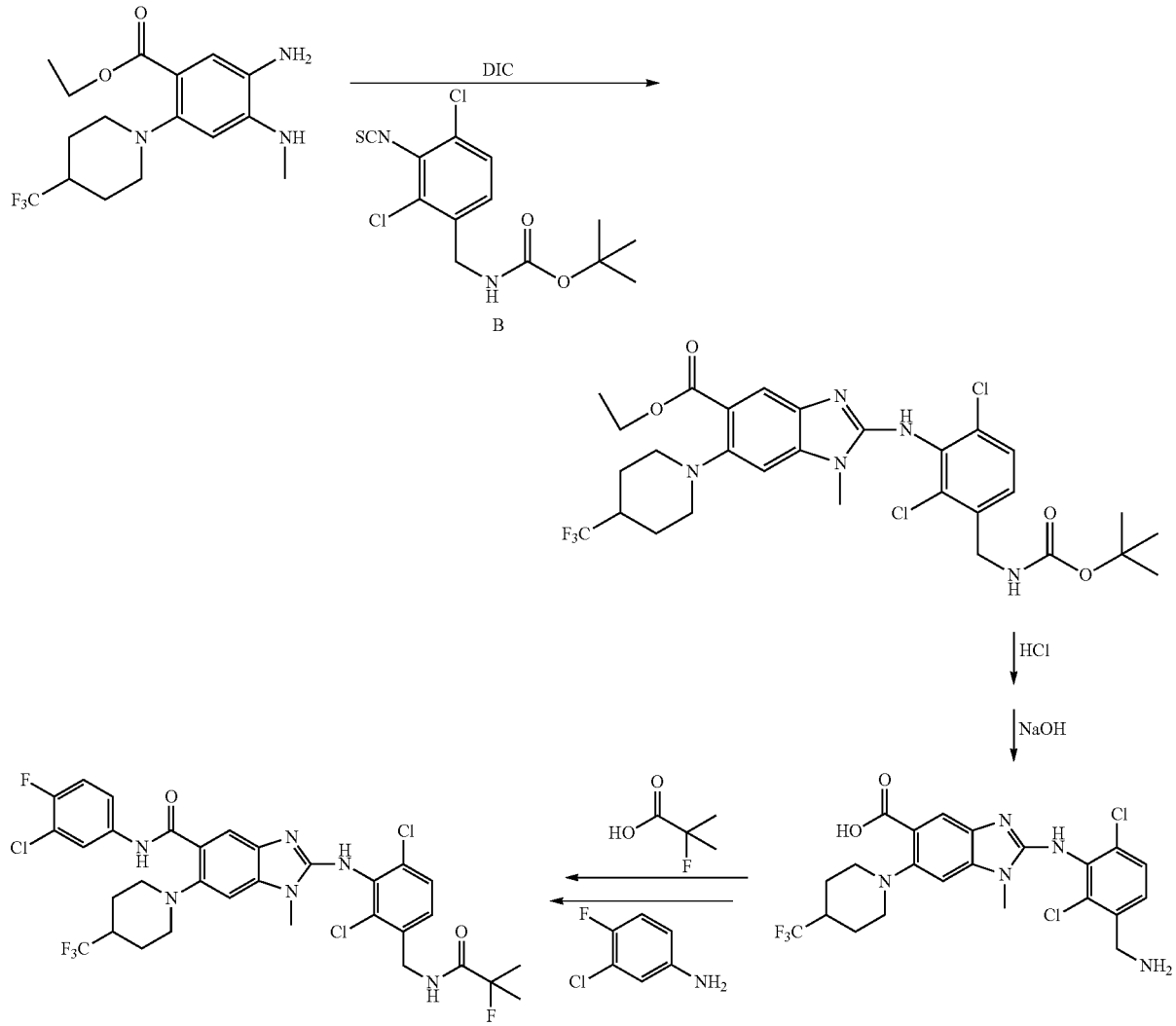

Yield: 6.4 g. HPLC $R_t$=1.17 min (method A). MS m/z: 544 [M+H]+.

(c) 2-{2,6-Dichloro-3-[aminomethyl]-phenylamino}-6-[4-trifluoromethyl-piperidinyl]-1-methyl-1H-benzimidazole-5-carboxylic acid A mixture of 2-{2,6-dichloro-3-[aminomethyl]-phenylamino}-6-[4-trifluoromethyl-piperidinyl]-1-methyl-1H-benzimidazole-5-carboxylic acid ethyl ester (5.83 g, 10 mmol), 50% aq NaOH-solution (25 ml) and MeOH (100 ml) is stirred for 2.5 h at rt. The mixture is concentrated and slowly added to ice-cooled 12 M aq HCl (39.5 mL). Then aq NaHCO$_3$ solution is added (to pH 8) and the resulting precipitate is collected by filtration and dried.

Yield: 4.08 g. HPLC $R_t$=0.995 min (method A). MS m/z: 516 [M+H]+.

(d) 2-{2,6-Dichloro-3-[(2-fluoro-2-methyl-propionylamino)-methyl]-phenylamino}-6-[4-trifluoromethyl-piperidinyl]-1-methyl-1H-benzimidazole-5-carboxylic acid A mixture of 2-fluoroisobutyric acid (191 mg, 1.80 mmol), TBTU (578 mg, 1.80 mmol), DIPEA (1.00 mL, 5.7 mmol) and 10 mL DMF is stirred for 10 min and then the mixture is added to 2-{2,6-dichloro-3-[aminomethyl]-phenylamino}-6-[4-trifluoromethyl-piperidinyl]-1-methyl-1H-benzimidazole-5-carboxylic acid (929 mg, 1.80 mmol) in 10 mL DMF and it is stirred overnight. Then the mixture is concentrated and purified via prep HPLC.

Yield: 945 mg. MS m/z: 604 [M+H]+.

(e) N-(3-Chloro-4-fluoro-phenyl)-2-{2,6-dichloro-3-[(2-fluoro-2-methyl-propionylamino)-methyl]-phenylamino}-6-[4-trifluoromethyl-piperidinyl]-1-methyl-1H-benzimidazole-5-carboxylic acid amide A mixture of 2-{2,6-dichloro-3-[(2-fluoro-2-methyl-propionylamino)-methyl]-phenylamino}-6-[4-trifluoromethyl-piperidinyl]-1-methyl-1H-benzimidazole-5-carboxylic acid (60 mg, 0.100 mmol), (1-chloro-2-methyl-propenyl)-dimethylamine (33 mg, 0.25 mmol), DIPEA (86 µL, 0.50 mmol) and MeCN (2 mL) is stirred for 20 min. This mixture is added to 3-chloro-4-fluoro-aniline (0.200 mmol) and it is stirred overnight at rt. The mixture is directly purified via reverse phase HPLC. Yield: 39 mg. HPLC $R_t$=0.607 min (method F). MS m/z: 731 [M+H]+.

The following intermediates in Table I are precursors for the corresponding examples in Table II (e.g. compound 10c is the precursor of example 10). The intermediates are prepared in a reaction sequence in analogy to the procedures described above (e.g. compound 10c is prepared from 10b which in turn is prepared from 10a following the procedures described in 1b, 1c and 6b).

TABLE I

Intermediates (prepared in analogy to the indicated procedure)

| Ex. | Structure | remarks | MS* m/z [M + H]+ | $R_f$(TLC, silica gel) or $R_t$ [min] (HPLC-method) | Prepared in analogy to example |
|---|---|---|---|---|---|
| 21a | 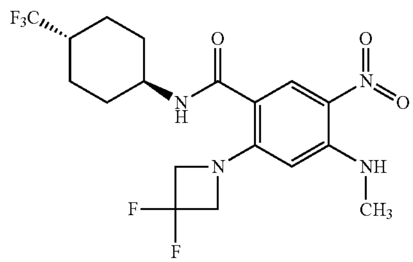 [SMILES: CNc1cc(N2CC(F)(F)C2)c(C(=O)N[C@H]2CC[C@H](C(F)(F)F)CC2)cc1[N+](=O)[O-]] | | 437 | $R_t$: 1.46 min Method B | 6a |
| 21b | 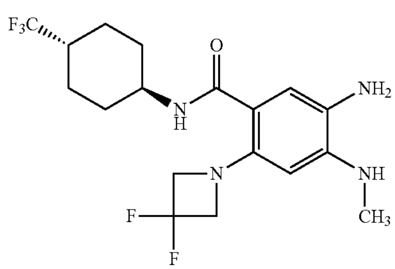 [SMILES: CNc1cc(N2CC(F)(F)C2)c(C(=O)N[C@H]2CC[C@H](C(F)(F)F)CC2)cc1N] | | 407 | $R_t$: 1.25 min Method B | 6b |
| 10a | 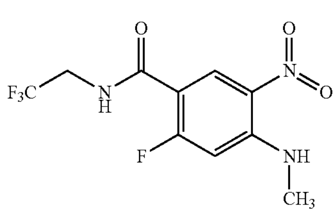 [SMILES: CNc1cc(F)c(C(=O)NCC(F)(F)F)cc1[N+](=O)[O-]] | | 296 | $R_t$: 1.28 min Method B | 1b |

TABLE I-continued

Intermediates (prepared in analogy to the indicated procedure)

| Ex. | Structure | remarks | MS* m/z [M + H]+ | R_f (TLC, silica gel) or R_t [min] (HPLC-(method) | Prepared in analogy to example |
|---|---|---|---|---|---|
| 10b | 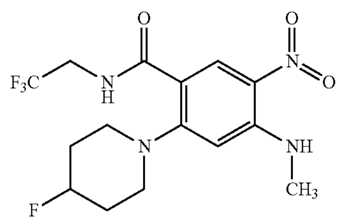 [SMILES: CNc1cc(N2CCC(F)CC2)c(C(=O)NCC(F)(F)F)cc1[N+](=O)[O-]] | | 379 | R_t: 1.38 min Method B | 1c |
| 10c | 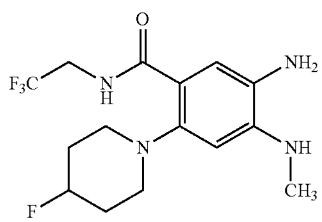 [SMILES: CNc1cc(N2CCC(F)CC2)c(C(=O)NCC(F)(F)F)cc1N] | | 349 | R_t: 1.11 min Method B | 6b |
| 11a | 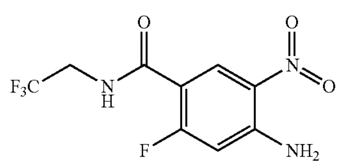 [SMILES: Nc1cc(F)c(C(=O)NCC(F)(F)F)cc1[N+](=O)[O-]] | | 282 | R_t: 1.21 min Method B | 1b |
| 11b | 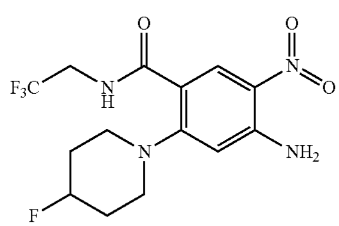 [SMILES: Nc1cc(N2CCC(F)CC2)c(C(=O)NCC(F)(F)F)cc1[N+](=O)[O-]] | | 365 | R_t: 1.32 min Method B | 1c |
| 11c | 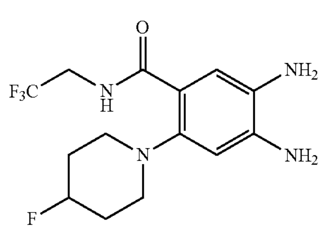 [SMILES: Nc1cc(C(=O)NCC(F)(F)F)c(N2CCC(F)CC2)cc1N] | | 334 | R_t: 1.04 min Method B | 6b |
| 12a | 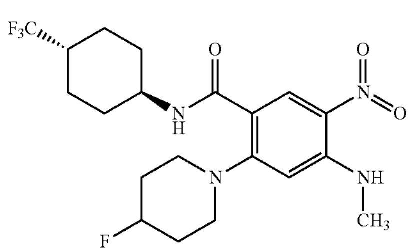 [SMILES: CNc1cc(N2CCC(F)CC2)c(C(=O)N[C@H]2CC[C@H](C(F)(F)F)CC2)cc1[N+](=O)[O-]] | | 447 | R_t: 1.49 min Method B | 2a |

TABLE I-continued

Intermediates (prepared in analogy to the indicated procedure)

| Ex. | Structure | remarks | MS* m/z [M + H]+ | $R_f$ (TLC, silica gel) or $R_t$ [min] (HPLC-(method) | Prepared in analogy to example |
|---|---|---|---|---|---|
| 12b | 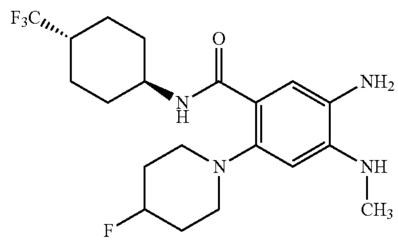 [SMILES: CNc1cc(N2CCC(F)CC2)c(C(=O)N[C@H]2CC[C@H](C(F)(F)F)CC2)cc1N] | | 417 | $R_t$: 1.26 min Method B | 6b |
| 14a | 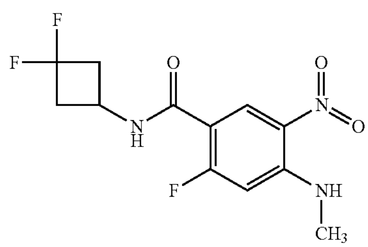 [SMILES: CNc1cc(F)c(C(=O)NC2CC(F)(F)C2)cc1[N+](=O)[O-]] | | 304 | $R_t$: 1.29 min Method B | 1b |
| 14b | 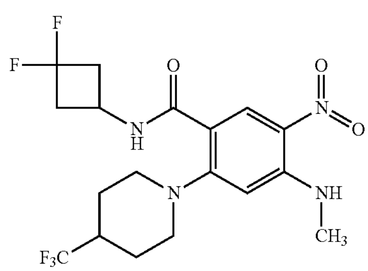 [SMILES: CNc1cc(N2CCC(C(F)(F)F)CC2)c(C(=O)NC2CC(F)(F)C2)cc1[N+](=O)[O-]] | | 437 | $R_t$: 1.47 min Method B | 1c |
| 14c | 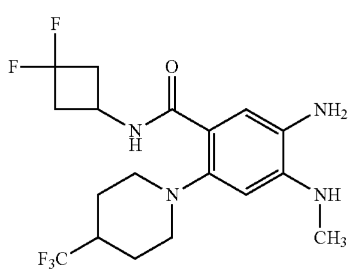 [SMILES: CNc1cc(N2CCC(C(F)(F)F)CC2)c(C(=O)NC2CC(F)(F)C2)cc1N] | | 407 | $R_t$: 1.21 min Method B | 6b |
| 15a | 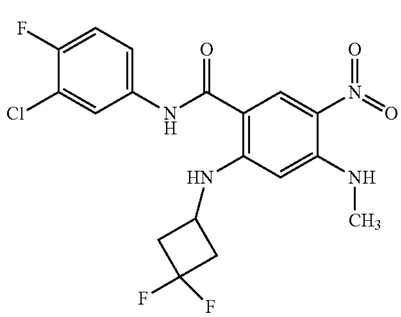 [SMILES: CNc1cc(NC2CC(F)(F)C2)c(C(=O)Nc2ccc(F)c(Cl)c2)cc1[N+](=O)[O-]] | | 429 | $R_t$: 1.66 min Method A | 1c |

TABLE I-continued

Intermediates (prepared in analogy to the indicated procedure)

| Ex. | Structure | remarks | MS* m/z [M + H]+ | R_f (TLC, silica gel) or R_t [min] (HPLC-(method) | Prepared in analogy to example |
|---|---|---|---|---|---|
| 15b | 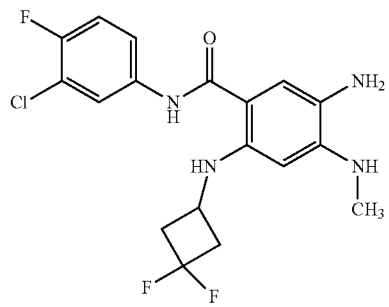 [SMILES: CNc1cc(NC2CC(F)(F)C2)c(C(=O)Nc2ccc(F)c(Cl)c2)cc1N] | | 399 | R_t: 1.44 min Method A | 1d |
| 16a | 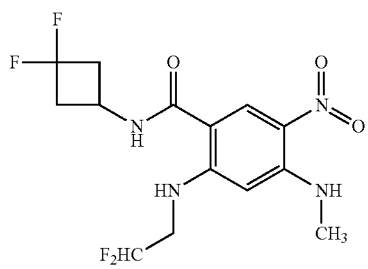 [SMILES: CNc1cc(NCC(F)F)c(C(=O)NC2CC(F)(F)C2)cc1[N+](=O)[O-]] | | 365 | R_t: 1.37 min Method A | 1c |
| 16b | 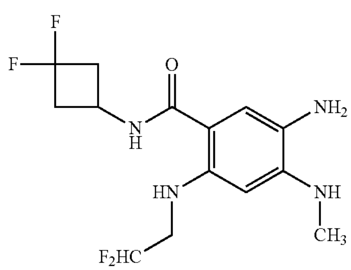 [SMILES: CNc1cc(NCC(F)F)c(C(=O)NC2CC(F)(F)C2)cc1N] | | 335 | R_t: 1.06 min Method A | 4b |
| 17a | 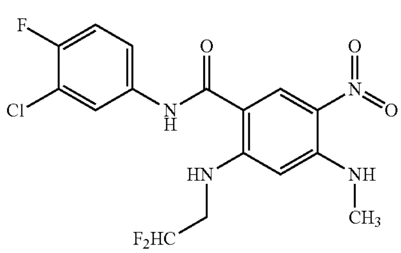 [SMILES: CNc1cc(NCC(F)F)c(C(=O)Nc2ccc(F)c(Cl)c2)cc1[N+](=O)[O-]] | | 403 | R_t: 1.57 min Method A | 1c |
| 17b | 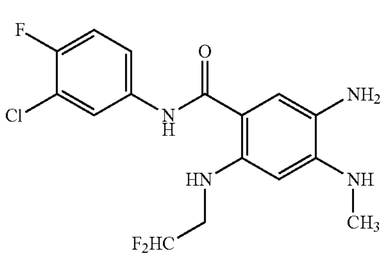 [SMILES: CNc1cc(NCC(F)F)c(C(=O)Nc2ccc(F)c(Cl)c2)cc1N] | Pt/C was used as catalyst | 373 | R_t: 1.32 min Method A | 4b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC- (method) | Prepared in analogy to example |
|---|---|---|---|---|---|
| 18a | 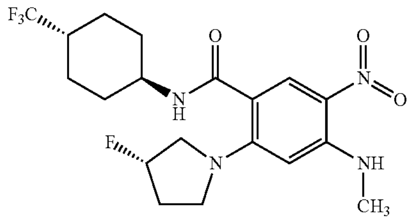 [SMILES: CNc1cc(N2CC[C@H](F)C2)c(C(=O)N[C@H]2CC[C@H](C(F)(F)F)CC2)cc1[N+](=O)[O-]] | | 433 | R$_t$: 1.40 min Method A | 6a |
| 18b | 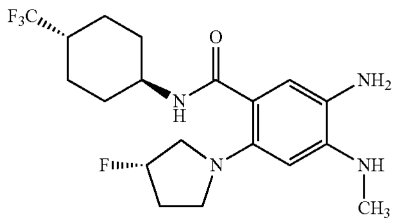 [SMILES: CNc1cc(N2CC[C@H](F)C2)c(C(=O)N[C@H]2CC[C@H](C(F)(F)F)CC2)cc1N] | | | | 6b |
| 22a | 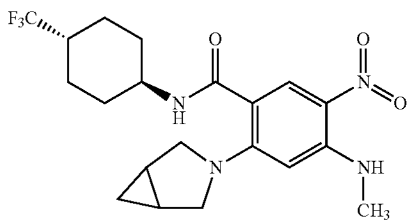 [SMILES: CNc1cc(N2CC3CC3C2)c(C(=O)N[C@H]2CC[C@H](C(F)(F)F)CC2)cc1[N+](=O)[O-]] | | 427 | R$_t$: 1.48 min Method A | 20c |
| 22b | 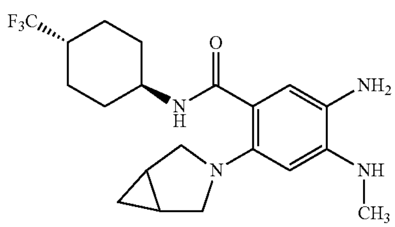 [SMILES: CNc1cc(N2CC3CC3C2)c(C(=O)N[C@H]2CC[C@H](C(F)(F)F)CC2)cc1N] | | 397 | R$_t$: 1.33 min Method A | 20d |
| 23a | 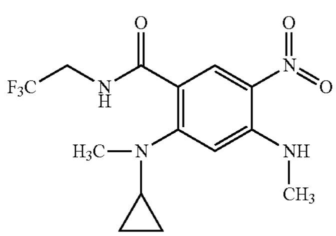 [SMILES: CNc1cc(N(C)C2CC2)c(C(=O)NCC(F)(F)F)cc1[N+](=O)[O-]] | | 347 | R$_t$: 1.31 min Method A | 4a |
| 23b | 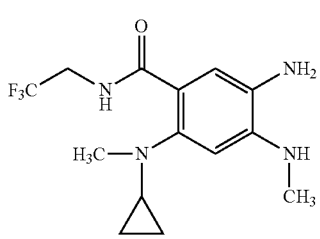 [SMILES: CNc1cc(N(C)C2CC2)c(C(=O)NCC(F)(F)F)cc1N] | | 317 | R$_t$: 1.09 min Method A | 4b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 24a | 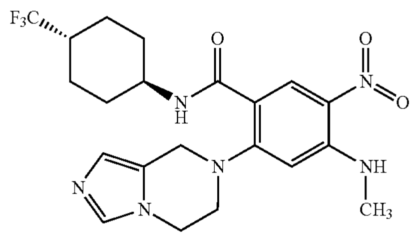 [SMILES: CNc1cc(N2CCn3cncc3C2)c(C(=O)N[C@H]2CC[C@H](C(F)(F)F)CC2)cc1[N+](=O)[O-]] | | 467 | R$_t$: 1.23 min Method A | 20c |
| 24b | 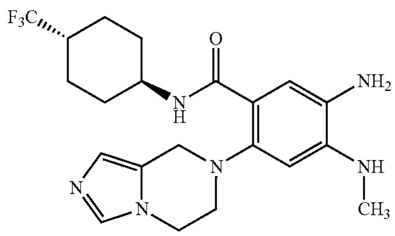 [SMILES: CNc1cc(N2CCn3cncc3C2)c(C(=O)N[C@H]2CC[C@H](C(F)(F)F)CC2)cc1N] | | 437 | R$_t$: 0.95 min Method A | 20d |
| 25a | 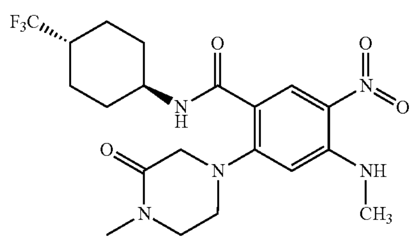 [SMILES: CNc1cc(N2CCN(C)C(=O)C2)c(C(=O)N[C@H]2CC[C@H](C(F)(F)F)CC2)cc1[N+](=O)[O-]] | | 458 | R$_t$: 1.33 min Method A | 20c |
| 25b | 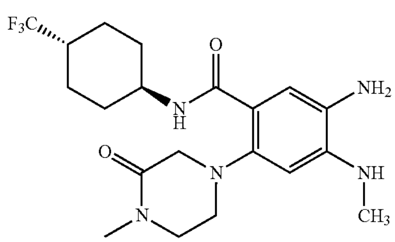 [SMILES: CNc1cc(N2CCN(C)C(=O)C2)c(C(=O)N[C@H]2CC[C@H](C(F)(F)F)CC2)cc1N] | | 428 | R$_t$: 1.15 min Method A | 20d |
| 27a | 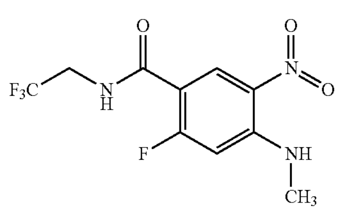 [SMILES: CNc1cc(F)c(C(=O)NCC(F)(F)F)cc1[N+](=O)[O-]] | | 296 | R$_t$: 1.3 min Method B | 1b |
| 27b | 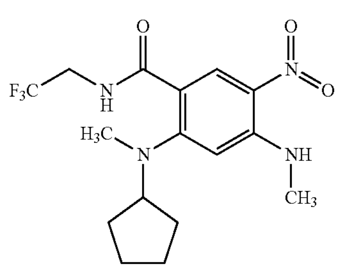 [SMILES: CNc1cc(N(C)C2CCCC2)c(C(=O)NCC(F)(F)F)cc1[N+](=O)[O-]] | | 375 | R$_t$: 1.43 min Method A | 1c |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC- (method) | Prepared in analogy to example |
|---|---|---|---|---|---|
| 27c | 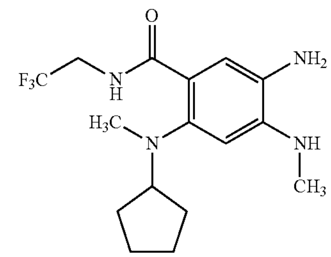 [SMILES: CNc1cc(N(C)C2CCCC2)c(C(=O)NCC(F)(F)F)cc1N] | | 345 | R$_t$: 1.12 min Method A | 6b |
| 28a | 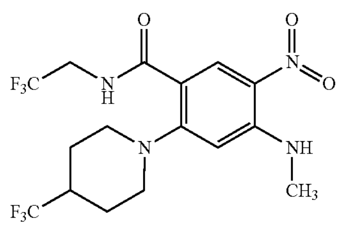 [SMILES: CNc1cc(N2CCC(C(F)(F)F)CC2)c(C(=O)NCC(F)(F)F)cc1[N+](=O)[O-]] | Microwave irradiation (10 min at 180° C.) | 429 | R$_t$: 1.46 min Method A | 1c |
| 28b | 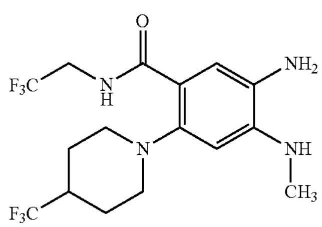 [SMILES: CNc1cc(N2CCC(C(F)(F)F)CC2)c(C(=O)NCC(F)(F)F)cc1N] | | 399 | R$_t$: 1.26 min Method A | 1c |
| 30a | 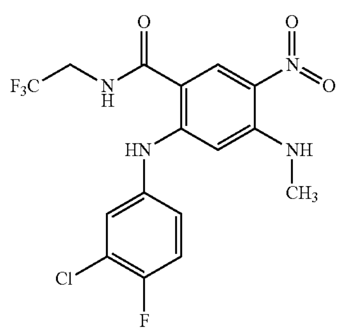 [SMILES: CNc1cc(Nc2ccc(F)c(Cl)c2)c(C(=O)NCC(F)(F)F)cc1[N+](=O)[O-]] | | 421 | R$_t$: 1.64 min Method A | 29a |
| 30b | 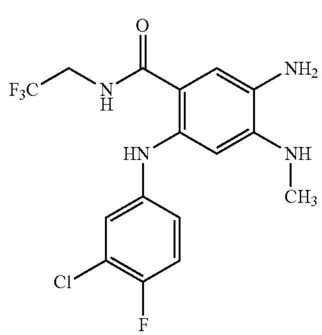 [SMILES: CNc1cc(Nc2ccc(F)c(Cl)c2)c(C(=O)NCC(F)(F)F)cc1N] | | 391 | R$_t$: 1.40 min Method A | 1d |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 31a | 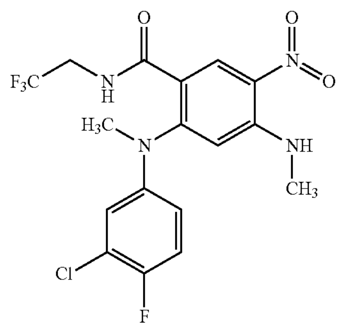 [SMILES: CNc1cc(N(C)c2ccc(F)c(Cl)c2)c(C(=O)NCC(F)(F)F)cc1[N+](=O)[O-]] | | 435 | R$_t$: 1.43 min Method A | 29a |
| 31b | 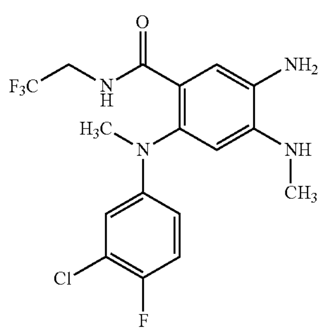 [SMILES: CNc1cc(N(C)c2ccc(F)c(Cl)c2)c(C(=O)NCC(F)(F)F)cc1N] | | 405 | R$_t$: 1.31 min Method A | 1d |
| 32a | 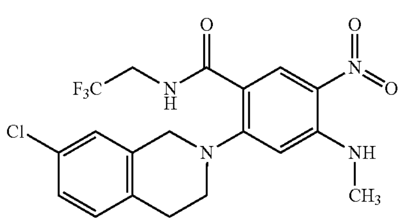 [SMILES: CNc1cc(N2CCc3ccc(Cl)cc3C2)c(C(=O)NCC(F)(F)F)cc1[N+](=O)[O-]] | Microwave irradiation (8 h at 180° C.) K$_2$CO$_3$ as base | 443 | R$_t$: 1.54 min Method A | 1c |
| 32b | 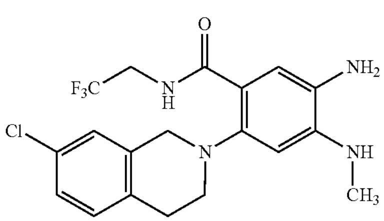 [SMILES: CNc1cc(N2CCc3ccc(Cl)cc3C2)c(C(=O)NCC(F)(F)F)cc1N] | | 413 | R$_t$: 1.39 min Method A | 1d |
| 33a | 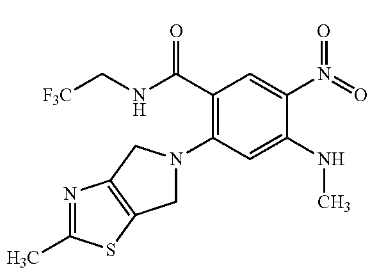 [SMILES: CNc1cc(N2Cc3nc(C)sc3C2)c(C(=O)NCC(F)(F)F)cc1[N+](=O)[O-]] | NMP as solvent (2 h at 100° C.) DIPEA as base | 416 | R$_t$: 1.26 min Method A | 1c |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 33b | 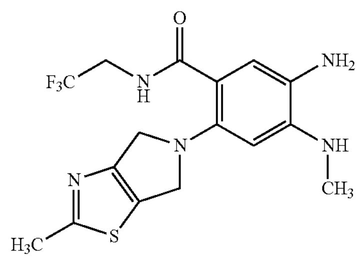 | | 386 | R_t: 1.09 min Method A | 6b |
| 34a | 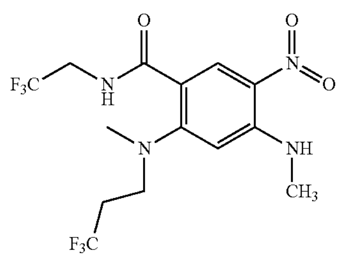 [SMILES: CNc1cc(N(C)CCC(F)(F)F)c(C(=O)NCC(F)(F)F)cc1[N+](=O)[O-]] | Microwave irradiation (2 h at 180° C.) K_2CO_3 as base | 403 | R_t: 1.34 min Method A | 1c |
| 34b | 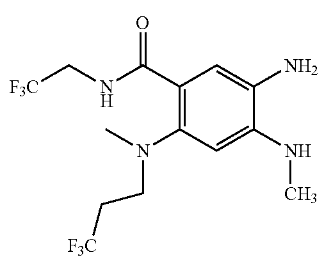 [SMILES: CNc1cc(N(C)CCC(F)(F)F)c(C(=O)NCC(F)(F)F)cc1N] | | 373 | R_t: 1.13 min Method A | 6b |
| 51a | 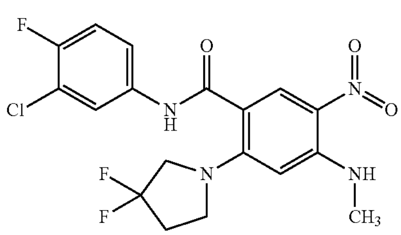 [SMILES: CNc1cc(N2CCC(F)(F)C2)c(C(=O)Nc2ccc(F)c(Cl)c2)cc1[N+](=O)[O-]] | | 429 | R_t: 2.27 min Method E | 1c |
| 51b | 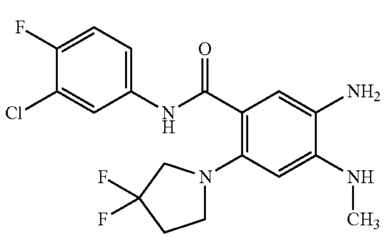 [SMILES: CNc1cc(N2CCC(F)(F)C2)c(C(=O)Nc2ccc(F)c(Cl)c2)cc1N] | | 399 | R_t: 1.43 min Method A | 1d |
| 63a | 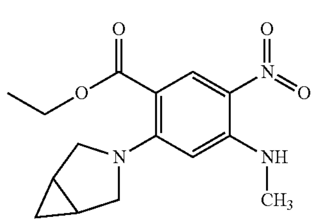 [SMILES: CCOC(=O)c1cc([N+](=O)[O-])c(NC)cc1N1CC2CC2C1] | MeCN as solvent | 306 | | 52a |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 63b | 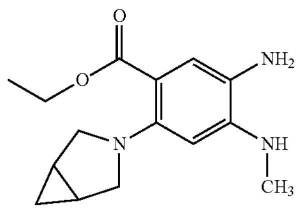 [SMILES: CCOC(=O)c1cc(N)c(NC)cc1N1CC2CC2C1] | | 276 | | 52b |
| 63c | 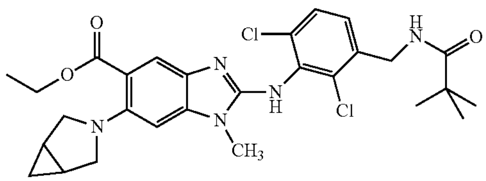 [SMILES: CCOC(=O)c1cc2nc(Nc3c(Cl)ccc(CNC(=O)C(C)(C)C)c3Cl)n(C)c2cc1N1CC2CC2C1] | MeCN as solvent | 558 | | 52c |
| 63d | 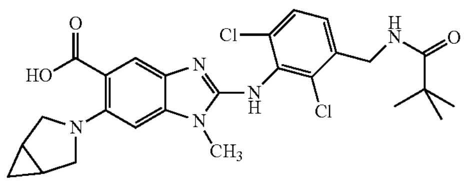 [SMILES: Cn1c(Nc2c(Cl)ccc(CNC(=O)C(C)(C)C)c2Cl)nc2cc(C(=O)O)c(N3CC4CC4C3)cc21] | EtOH as solvent | 530 | | 52d |
| 67a | 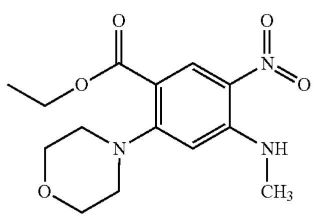 [SMILES: CCOC(=O)c1cc([N+](=O)[O-])c(NC)cc1N1CCOCC1] | morpholine as solvent | | R$_f$: = 0.5 PE/EtOAc 1:1 | 52a |
| 67b | 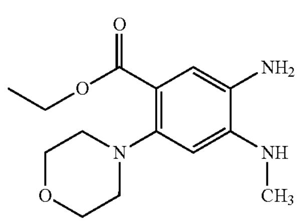 [SMILES: CCOC(=O)c1cc(N)c(NC)cc1N1CCOCC1] | | | R$_f$: = 0.25 PE/EtOAc 1:1 | 52b |
| 67c | 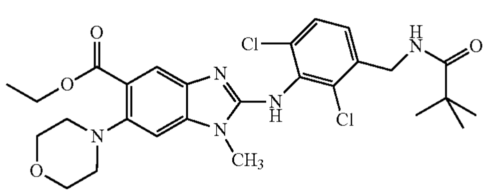 [SMILES: CCOC(=O)c1cc2nc(Nc3c(Cl)ccc(CNC(=O)C(C)(C)C)c3Cl)n(C)c2cc1N1CCOCC1] | | | R$_f$: = 0.22 PE/EtOAc 1:1 | 52c |
| 67d | 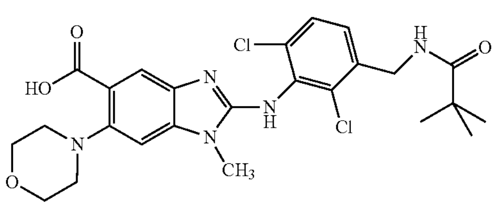 [SMILES: Cn1c(Nc2c(Cl)ccc(CNC(=O)C(C)(C)C)c2Cl)nc2cc(C(=O)O)c(N3CCOCC3)cc21] | The compound is directly used in the next step | | | 52d |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC- (method) | Prepared in analogy to example |
|---|---|---|---|---|---|
| 69a | 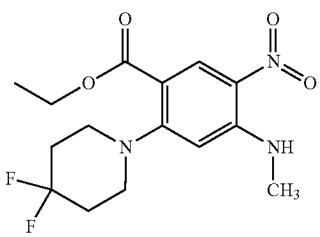 [SMILES: CCOC(=O)c1cc([N+](=O)[O-])c(NC)cc1N1CCC(F)(F)CC1] | | | R$_f$: = 0.7 PE/EtOAc 10:4 | 52a |
| 69b | 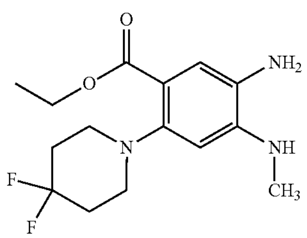 [SMILES: CCOC(=O)c1cc(N)c(NC)cc1N1CCC(F)(F)CC1] | | | R$_f$: = 0.2 PE/EtOAc 10:4 | 52b |
| 69c | 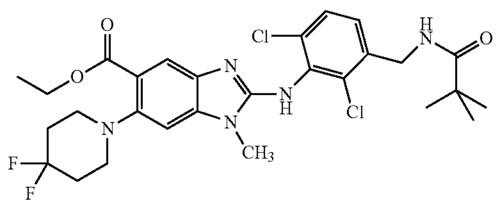 [SMILES: CCOC(=O)c1cc2nc(Nc3c(Cl)ccc(CNC(=O)C(C)(C)C)c3Cl)n(C)c2cc1N1CCC(F)(F)CC1] | | | R$_f$: = 0.41 PE/EtOAc 10:4 | 52c |
| 69d | 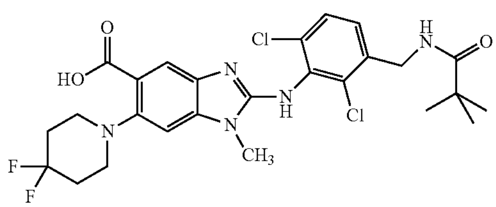 [SMILES: Cn1c(Nc2c(Cl)ccc(CNC(=O)C(C)(C)C)c2Cl)nc2cc(C(=O)O)c(N3CCC(F)(F)CC3)cc21] | The compound is directly used in the next step | | | 52d |
| 73a | 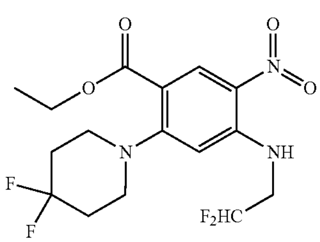 [SMILES: CCOC(=O)c1cc([N+](=O)[O-])c(NCC(F)F)cc1N1CCC(F)(F)CC1] | | | | 71b |
| 73b | 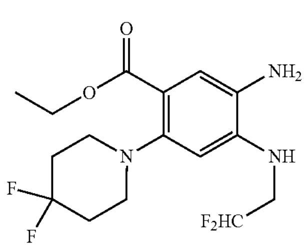 [SMILES: CCOC(=O)c1cc(N)c(NCC(F)F)cc1N1CCC(F)(F)CC1] | | | | 71c |

TABLE I-continued

Intermediates (prepared in analogy to the indicated procedure)

| Ex. | Structure | remarks | MS* m/z [M + H]+ | R<sub>f</sub>(TLC, silica gel) or R<sub>t</sub> [min] (HPLC- method) | Prepared in analogy to example |
|---|---|---|---|---|---|
| 73c | 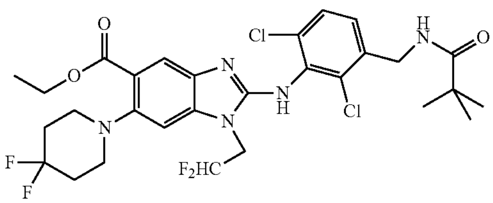 [SMILES: CCOC(=O)c1cc2nc(Nc3c(Cl)ccc(CNC(=O)C(C)(C)C)c3Cl)n(CC(F)F)c2cc1N1CCC(F)(F)CC1] | | | R<sub>f</sub>: = 0.21 PE/EtOAc 10:4 | 71d |
| 73d | 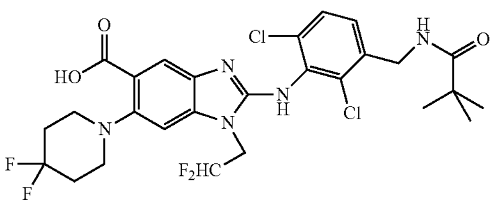 [SMILES: CC(C)(C)C(=O)NCc1ccc(Cl)c(Nc2nc3cc(C(=O)O)c(N4CCC(F)(F)CC4)cc3n2CC(F)F)c1Cl] | The compound is directly used in the next step | | | 71e |
| 75a | 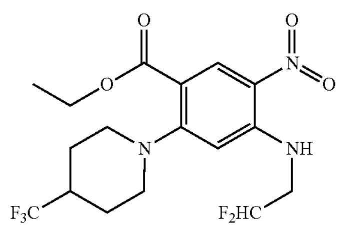 [SMILES: CCOC(=O)c1cc([N+](=O)[O-])c(NCC(F)F)cc1N1CCC(C(F)(F)F)CC1] | | | | 71b |
| 75b | 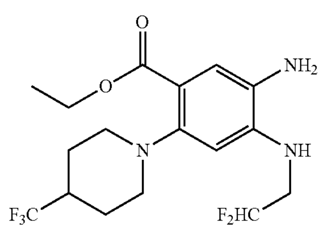 [SMILES: CCOC(=O)c1cc(N)c(NCC(F)F)cc1N1CCC(C(F)(F)F)CC1] | | | R<sub>f</sub>: = 0.45 PE/EtOAc 1:1 | 71c |
| 75c | 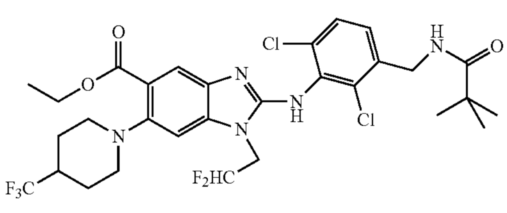 [SMILES: CCOC(=O)c1cc2nc(Nc3c(Cl)ccc(CNC(=O)C(C)(C)C)c3Cl)n(CC(F)F)c2cc1N1CCC(C(F)(F)F)CC1] | | | R<sub>f</sub>: = 0.25 PE/EtOAc 10:4 | 71d |
| 75d | 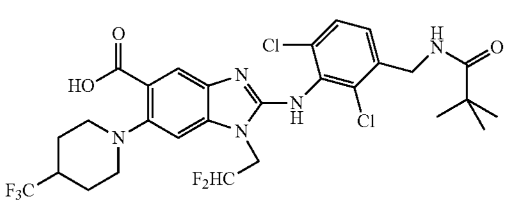 [SMILES: CC(C)(C)C(=O)NCc1ccc(Cl)c(Nc2nc3cc(C(=O)O)c(N4CCC(C(F)(F)F)CC4)cc3n2CC(F)F)c1Cl] | The compound is directly used in the next step | | | 71e |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-(method) | Prepared in analogy to example |
|---|---|---|---|---|---|
| 78a | 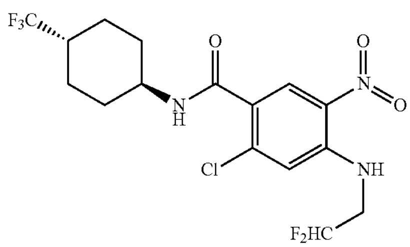 [SMILES: O=C(N[C@H]1CC[C@H](C(F)(F)F)CC1)c1cc([N+](=O)[O-])c(NCC(F)F)cc1Cl] | TBTU is used as coupling agent | 430 | R$_t$: 1.44 min Method A | 77b |
| 78b | 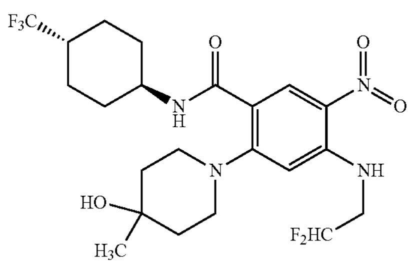 | | 509 | R$_t$: 1.53 min Method H | 77c |
| 78c | 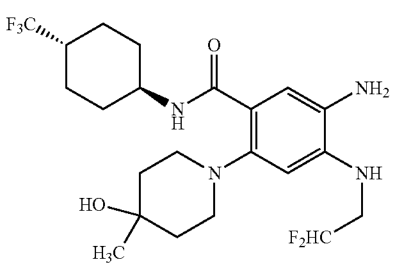 | Pd/C is used as catalyst | | | 77d |
| 79a | 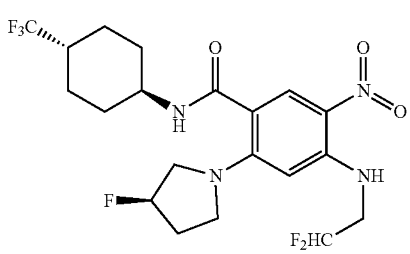 [SMILES: O=C(N[C@H]1CC[C@H](C(F)(F)F)CC1)c1cc([N+](=O)[O-])c(NCC(F)F)cc1N1CC[C@@H](F)C1] | Educt 78a | 483 | R$_t$: 1.43 min Method A | 77c |
| 79b | 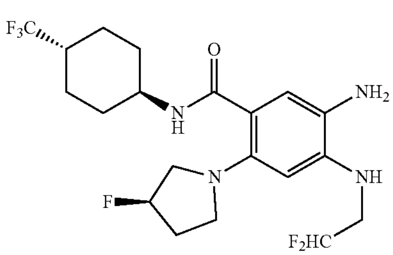 [SMILES: Nc1cc(C(=O)N[C@H]2CC[C@H](C(F)(F)F)CC2)c(N2CC[C@@H](F)C2)cc1NCC(F)F] | | 453 | R$_t$: 1.43 min Method A | 77d |

TABLE I-continued

Intermediates (prepared in analogy to the indicated procedure)

| Ex. | Structure | remarks | MS* m/z [M + H]+ | $R_f$(TLC, silica gel) or $R_t$ [min] (HPLC-method) | Prepared in analogy to example |
|---|---|---|---|---|---|
| 80a | 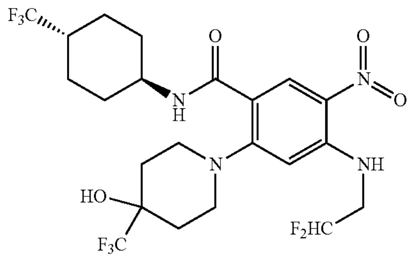 [SMILES: O=C(N[C@H]1CC[C@H](C(F)(F)F)CC1)c1cc([N+](=O)[O-])c(NCC(F)F)cc1N1CCC(O)(C(F)(F)F)CC1] | Educt 78a | 563 | $R_t$: 1.59 min Method H | 77c |
| 80b | 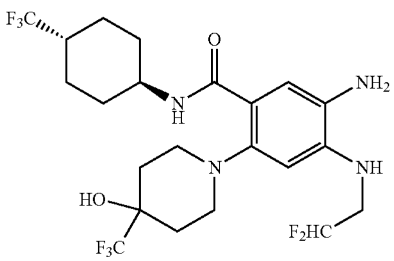 [SMILES: Nc1cc(C(=O)N[C@H]2CC[C@H](C(F)(F)F)CC2)c(N2CCC(O)(C(F)(F)F)CC2)cc1NCC(F)F] | The compound is directly used in the next step | | | 77d |
| 82a | 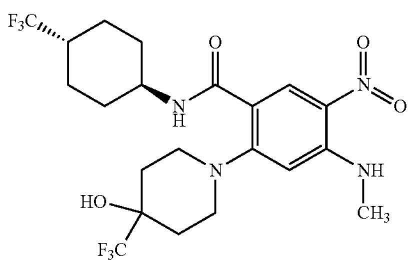 [SMILES: CNc1cc(N2CCC(O)(C(F)(F)F)CC2)c(C(=O)N[C@H]2CC[C@H](C(F)(F)F)CC2)cc1[N+](=O)[O-]] | Educt: WO2010/100249 See example 4a | 513 | $R_t$: 1.53 min Method A | 6a |
| 82b | 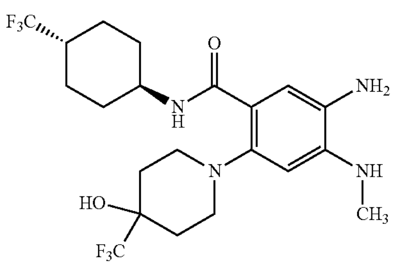 [SMILES: CNc1cc(N2CCC(O)(C(F)(F)F)CC2)c(C(=O)N[C@H]2CC[C@H](C(F)(F)F)CC2)cc1N] | | 483 | $R_t$: 1.40 min Method A | 6b |
| 83a | 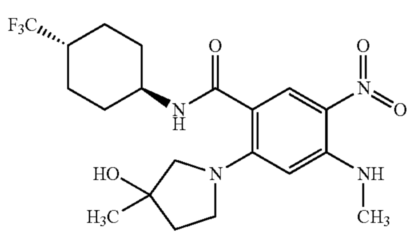 [SMILES: CNc1cc(N2CCC(C)(O)C2)c(C(=O)N[C@H]2CC[C@H](C(F)(F)F)CC2)cc1[N+](=O)[O-]] | Educt: WO2010/100249 See example 4a | 445 | $R_t$: 1.37 min Method A | 6a |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 83b | 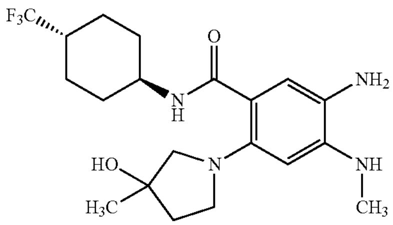 [SMILES: CNc1cc(N2CCC(C)(O)C2)c(C(=O)N[C@H]2CC[C@H](C(F)(F)F)CC2)cc1N] | | 415 | R_t: 1.20 min Method A | 6b |
| 84a | 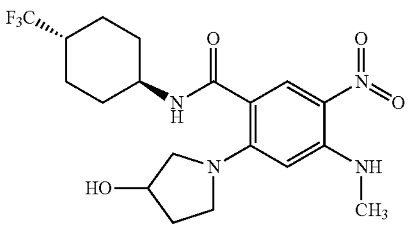 [SMILES: CNc1cc(N2CCC(O)C2)c(C(=O)N[C@H]2CC[C@H](C(F)(F)F)CC2)cc1[N+](=O)[O-]] | Educt: 20b | 431 | R_t: 1.30 min Method A | 6a |
| 84b | 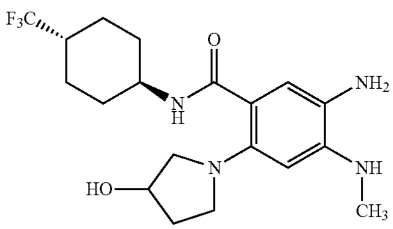 [SMILES: CNc1cc(N2CCC(O)C2)c(C(=O)N[C@H]2CC[C@H](C(F)(F)F)CC2)cc1N] | | 401 | R_t: 1.16 min Method A | 6b |
| 85a | 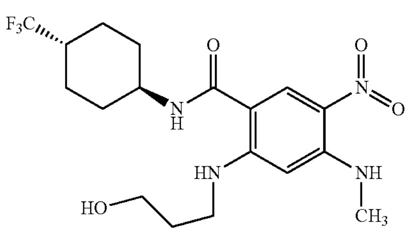 [SMILES: CNc1cc(NCCCO)c(C(=O)N[C@H]2CC[C@H](C(F)(F)F)CC2)cc1[N+](=O)[O-]] | Educt: 20b | 419 | R_t: 1.44 min Method A | 6a |
| 85b | 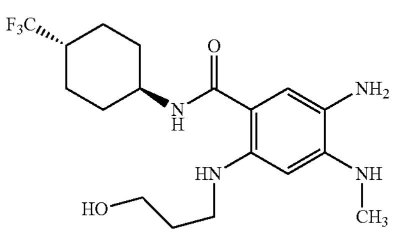 [SMILES: CNc1cc(NCCCO)c(C(=O)N[C@H]2CC[C@H](C(F)(F)F)CC2)cc1N] | | 389 | R_t: 1.14 min Method A | 6b |
| 86a | 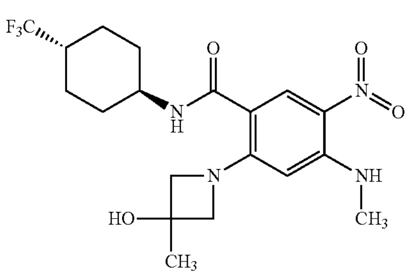 [SMILES: CNc1cc(N2CC(C)(O)C2)c(C(=O)N[C@H]2CC[C@H](C(F)(F)F)CC2)cc1[N+](=O)[O-]] | Educt: 20b | 431 | R_t: 1.34 min Method A | 6a |

TABLE I-continued

Intermediates (prepared in analogy to the indicated procedure)

| Ex. | Structure | remarks | MS* m/z [M + H]+ | R_f (TLC, silica gel) or R_t [min] (HPLC-(method) | Prepared in analogy to example |
|---|---|---|---|---|---|
| 86b | 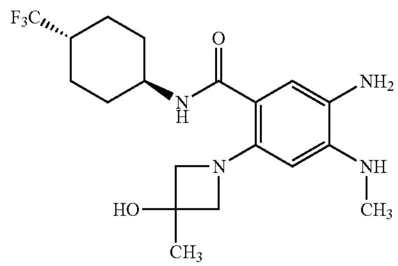 [SMILES: CNc1cc(N2CC(C)(O)C2)c(C(=O)N[C@H]2CC[C@H](C(F)(F)F)CC2)cc1N] | | 401 | R_t: 1.40 min Method I | 6b |
| 87a | 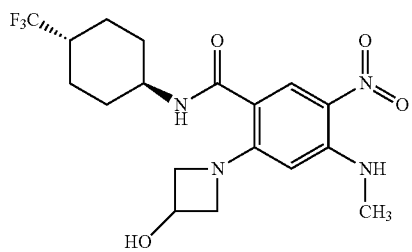 [SMILES: CNc1cc(N2CC(O)C2)c(C(=O)N[C@H]2CC[C@H](C(F)(F)F)CC2)cc1[N+](=O)[O-]] | Educt:20b | 417 | R_t: 1.29 min Method A | 6a |
| 87b | 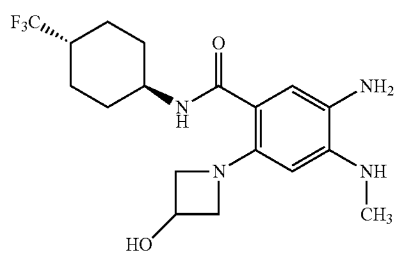 [SMILES: CNc1cc(N2CC(O)C2)c(C(=O)N[C@H]2CC[C@H](C(F)(F)F)CC2)cc1N] | | 387 | R_t: 1.10 min Method A | 6b |
| 88a | 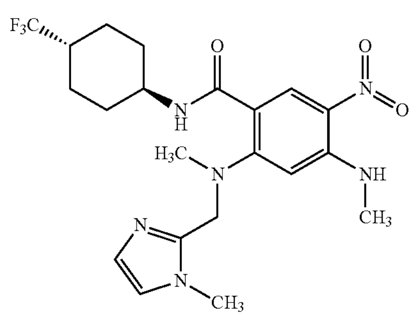 [SMILES: CNc1cc(N(C)Cc2nccn2C)c(C(=O)N[C@H]2CC[C@H](C(F)(F)F)CC2)cc1[N+](=O)[O-]] | Educt: WO2010/100249 See example 4a | 469 | R_t: 1.23 min Method A | 4a |
| 88b | 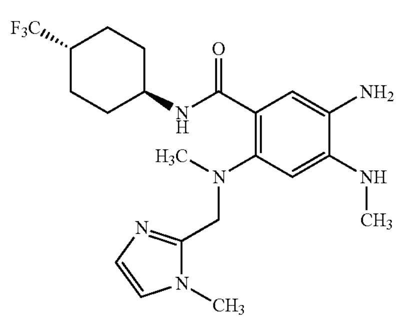 [SMILES: CNc1cc(N(C)Cc2nccn2C)c(C(=O)N[C@H]2CC[C@H](C(F)(F)F)CC2)cc1N] | | 439 | R_t: 1.03 min Method A | 4b |

TABLE I-continued

Intermediates (prepared in analogy to the indicated procedure)

| Ex. | Structure | remarks | MS* m/z [M + H]+ | R_f (TLC, silica gel) or R_t [min] (HPLC-method) | Prepared in analogy to example |
|---|---|---|---|---|---|
| 89a | 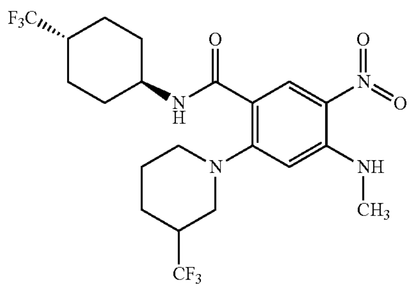 [SMILES: CNc1cc(N2CCCC(C(F)(F)F)C2)c(C(=O)N[C@H]2CC[C@H](C(F)(F)F)CC2)cc1[N+](=O)[O-]] | Educt: 20b Dioxane as solvent | 497 | R_t: 1.60 min Method A | 6a |
| 89b | 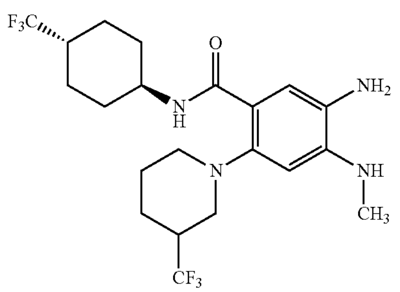 [SMILES: CNc1cc(N2CCCC(C(F)(F)F)C2)c(C(=O)N[C@H]2CC[C@H](C(F)(F)F)CC2)cc1N] | | 467 | R_t: 1.46 min Method A | 6b |
| 90a | 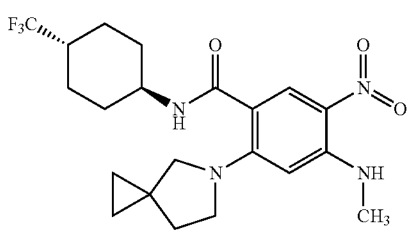 [SMILES: CNc1cc(N2CCC3(CC3)C2)c(C(=O)N[C@H]2CC[C@H](C(F)(F)F)CC2)cc1[N+](=O)[O-]] | Educt: 20b Dioxane as solvent | 441 | R_t: 1.51 min Method A | 6a |
| 90b | 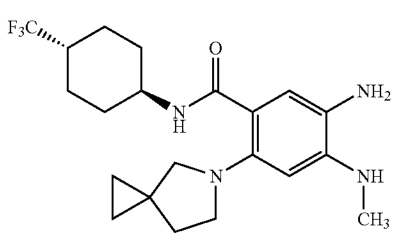 [SMILES: CNc1cc(N2CCC3(CC3)C2)c(C(=O)N[C@H]2CC[C@H](C(F)(F)F)CC2)cc1N] | | 411 | R_t: 1.34 min Method A | 6b |
| 91a | 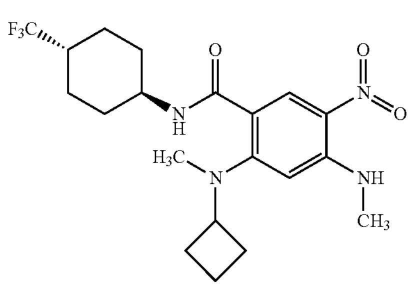 [SMILES: CNc1cc(N(C)C2CCC2)c(C(=O)N[C@H]2CC[C@H](C(F)(F)F)CC2)cc1[N+](=O)[O-]] | Educt: 20b Dioxane as solvent | 429 | R_t: 1.55 min Method A | 6a |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 91b | 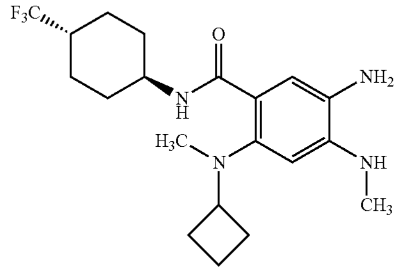 [SMILES: CNc1cc(N(C)C2CCC2)c(C(=O)N[C@H]2CC[C@H](C(F)(F)F)CC2)cc1N] | | 399 | R$_t$: 1.32 min Method A | 6b |
| 92a | 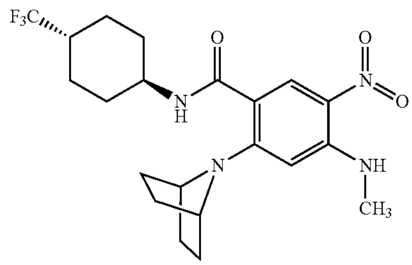 [SMILES: CNc1cc(N2C3CCC2CC3)c(C(=O)N[C@H]2CC[C@H](C(F)(F)F)CC2)cc1[N+](=O)[O-]] | Educt: 20b and 7-azabicyclo[2.2.1]heptane Dioxane as solvent | 441 | R$_t$: 1.54 min Method A | 6a |
| 92b | 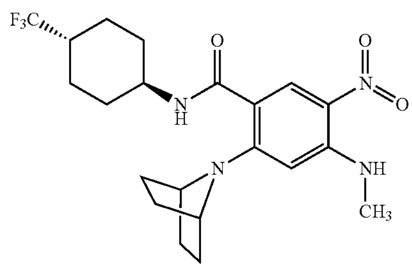 [SMILES: CNc1cc(N2C3CCC2CC3)c(C(=O)N[C@H]2CC[C@H](C(F)(F)F)CC2)cc1[N+](=O)[O-]] | | 411 | R$_t$: 1.64 min Method I | 6b |
| 93a | 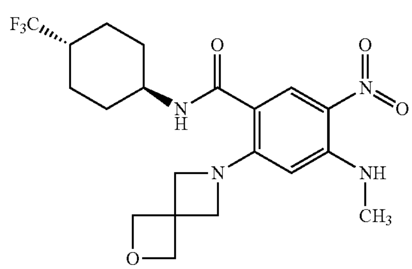 [SMILES: CNc1cc(N2CC3(COC3)C2)c(C(=O)N[C@H]2CC[C@H](C(F)(F)F)CC2)cc1[N+](=O)[O-]] | Educt: 20b | 443 | R$_t$: 1.34 min Method A | 6a |
| 93b | 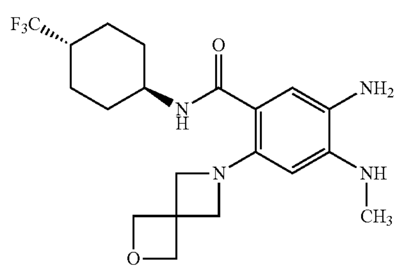 [SMILES: CNc1cc(N2CC3(COC3)C2)c(C(=O)N[C@H]2CC[C@H](C(F)(F)F)CC2)cc1N] | | 413 | R$_t$: 1.13 min Method A | 6b |

TABLE I-continued

Intermediates (prepared in analogy to the indicated procedure)

| Ex. | Structure | remarks | MS* m/z [M + H]+ | R*f* (TLC, silica gel) or R*t* [min] (HPLC-(method) | Prepared in analogy to example |
|---|---|---|---|---|---|
| 94a | 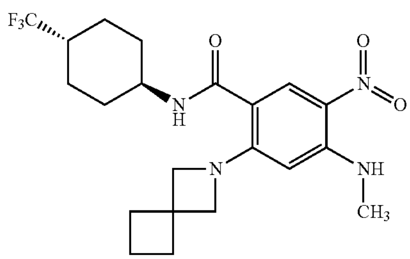 [SMILES: CNc1cc(N2CC3(CCC3)C2)c(C(=O)N[C@H]2CC[C@H](C(F)(F)F)CC2)cc1[N+](=O)[O-]] | Educt: 20b | 441 | R*t*: 1.55 min Method A | 6a |
| 94b | 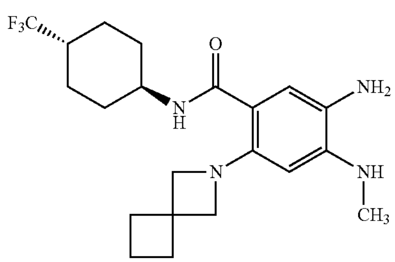 [SMILES: CNc1cc(N2CC3(CCC3)C2)c(C(=O)N[C@H]2CC[C@H](C(F)(F)F)CC2)cc1N] | | 411 | R*t*: 1.37 min Method A | 6b |
| 95a | 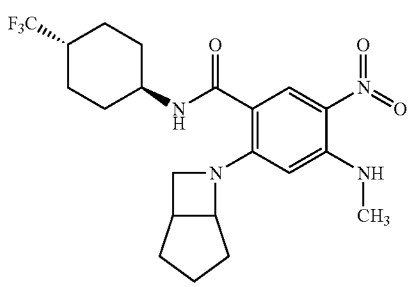 [SMILES: CNc1cc(N2CC3CCCC32)c(C(=O)N[C@H]2CC[C@H](C(F)(F)F)CC2)cc1[N+](=O)[O-]] | Educt: 20b reaction at 160° C. (microwave irradiation) | 441 | R*t*: 1.52 min Method A | 6a |
| 95b | 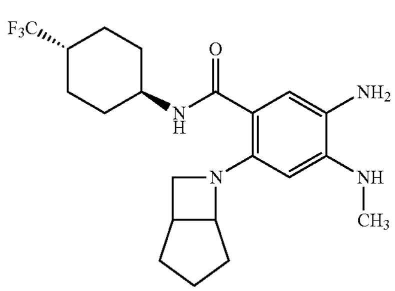 [SMILES: CNc1cc(N2CC3CCCC32)c(C(=O)N[C@H]2CC[C@H](C(F)(F)F)CC2)cc1N] | | 411 | R*t*: 1.35 min Method A | 6b |
| 96a | 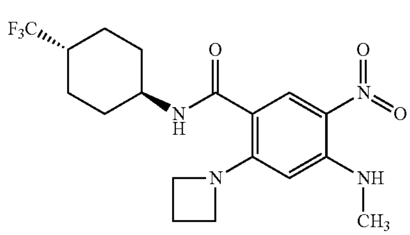 [SMILES: CNc1cc(N2CCC2)c(C(=O)N[C@H]2CC[C@H](C(F)(F)F)CC2)cc1[N+](=O)[O-]] | Educt: 20b reaction at 160° C. (microwave irradiation) | 401 | R*t*: 1.47 min Method I | 6a |

TABLE I-continued

Intermediates (prepared in analogy to the indicated procedure)

| Ex. | Structure | remarks | MS* m/z [M + H]⁺ | $R_f$ (TLC, silica gel) or $R_t$ [min] (HPLC-method) | Prepared in analogy to example |
|---|---|---|---|---|---|
| 96b | 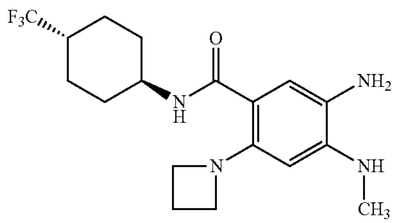 [SMILES: CNc1cc(N2CCC2)c(C(=O)N[C@H]2CC[C@H](C(F)(F)F)CC2)cc1N] | | 371 | $R_t$: 1.51 min Method I | 6b |
| 97a | 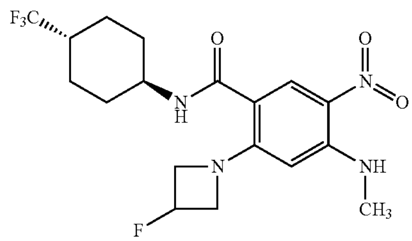 [SMILES: CNc1cc(N2CC(F)C2)c(C(=O)N[C@H]2CC[C@H](C(F)(F)F)CC2)cc1[N+](=O)[O-]] | Educt: 20b | 419 | $R_t$: 1.39 min Method A | 6a |
| 97b | 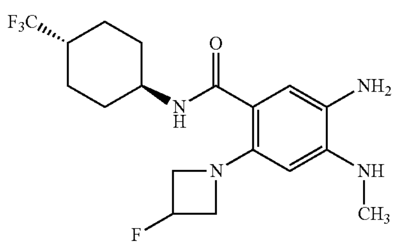 [SMILES: CNc1cc(N2CC(F)C2)c(C(=O)N[C@H]2CC[C@H](C(F)(F)F)CC2)cc1N] | | 389 | $R_t$: 1.47 min Method I | 6b |
| 98a | 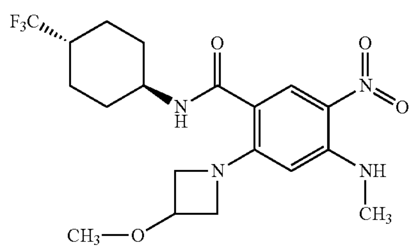 [SMILES: CNc1cc(N2CC(OC)C2)c(C(=O)N[C@H]2CC[C@H](C(F)(F)F)CC2)cc1[N+](=O)[O-]] | Educt: 20b | 431 | $R_t$: 1.39 min Method A | 6a |
| 98b | 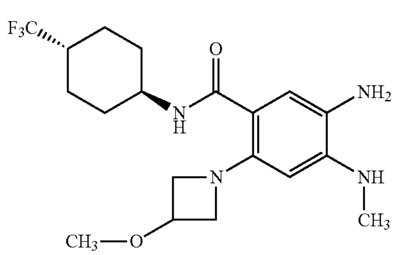 [SMILES: CNc1cc(N2CC(OC)C2)c(C(=O)N[C@H]2CC[C@H](C(F)(F)F)CC2)cc1N] | | 401 | $R_t$: 1.46 min Method I | 6b |
| 99a | 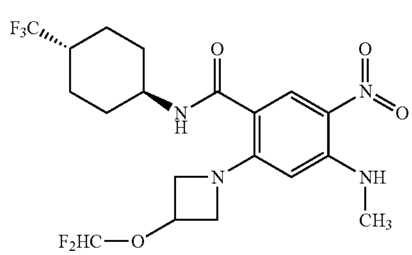 | Educt: 20b reaction at 165° C. (microwave irradiation) | 467 | $R_t$: 1.51 min Method H | 6a |

TABLE I-continued

Intermediates (prepared in analogy to the indicated procedure)

| Ex. | Structure | remarks | MS* m/z [M + H]+ | R_f (TLC, silica gel) or R_t [min] (HPLC- (method) | Prepared in analogy to example |
|---|---|---|---|---|---|
| 99b | (structure) | | 437 | R_t: 1.26 min Method H | 6b |
| 100a | (structure) | Educt: WO2010/100249 See example 4a; 45 min at 190° C. (microwave irradiation) K_2CO_3 as base | 483 | R_t: 1.55 min Method A | 6a |
| 100b | (structure) | The compound is directly used in the next step | | | 6b |
| 101a | (structure) | Educt: 20b | 455 | R_t: 1.61 min Method I | 6a |
| 101b | (structure) | The compound is directly used in the next step | | | 6b |
| 102a | (structure) | MeCN as solvent | 336 | R_t: 1.38 min Method H | 26a |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC- (method) | Prepared in analogy to example |
|---|---|---|---|---|---|
| 102b | 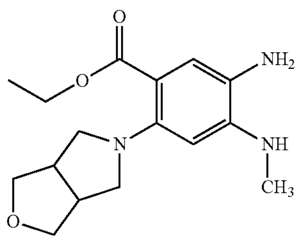 [SMILES: CCOC(=O)c1cc(N)c(NC)cc1N1CC2COCC2C1] | | 306 | R$_t$: 0.76 min Method H | 6b |
| 102c | 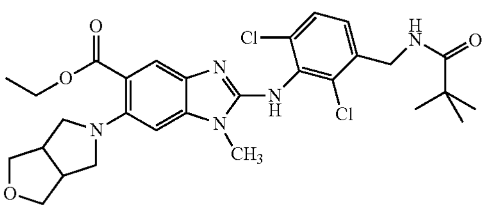 [SMILES: CCOC(=O)c1cc2nc(Nc3c(Cl)ccc(CNC(=O)C(C)(C)C)c3Cl)n(C)c2cc1N1CC2COCC2C1] | MeCN as solvent | 588 | R$_t$: 1.22 min Method H | 6c |
| 102d | 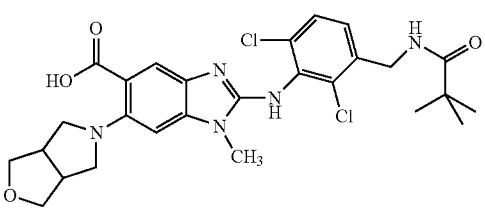 [SMILES: Cn1c(Nc2c(Cl)ccc(CNC(=O)C(C)(C)C)c2Cl)nc2cc(C(=O)O)c(N3CC4COCC4C3)cc21] | | 560 | R$_t$: 1.05 min Method H | 26d |
| 104a | 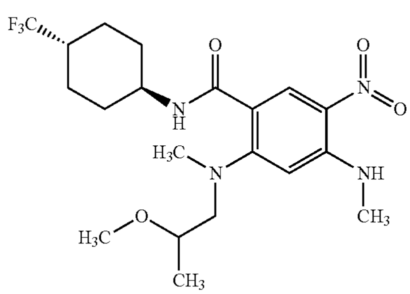 [SMILES: CNc1cc(N(C)CC(C)OC)c(C(=O)N[C@H]2CC[C@H](C(F)(F)F)CC2)cc1[N+](=O)[O-]] | Educt: WO2010/100249 See example 4a; N-methyl-2-methoxy-propylamine as base | 447 | R$_t$: 1.47 min Method A | 6a |
| 104b | 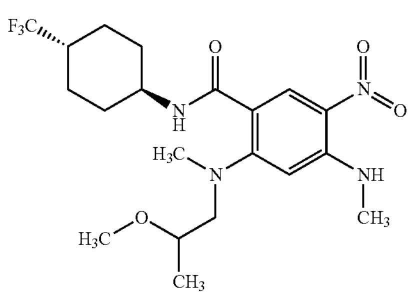 [SMILES: CNc1cc(N(C)CC(C)OC)c(C(=O)N[C@H]2CC[C@H](C(F)(F)F)CC2)cc1[N+](=O)[O-]] | | 417 | R$_t$: 1.26 min Method A | 6b |

TABLE I-continued

Intermediates (prepared in analogy to the indicated procedure)

| Ex. | Structure | remarks | MS* m/z [M + H]+ | $R_f$ (TLC, silica gel) or $R_t$ [min] (HPLC-method) | Prepared in analogy to example |
|---|---|---|---|---|---|
| 105a | 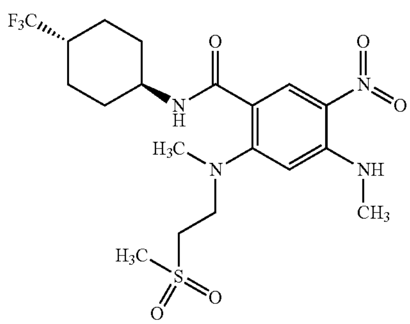 [SMILES: CNc1cc(N(C)CCS(C)(=O)=O)c(C(=O)N[C@H]2CC[C@H](C(F)(F)F)CC2)cc1[N+](=O)[O-]] | Educt: 20b 2(methylamino)-1-methylsulfonyle-ethane as base | 481 | $R_t$: 1.33 min Method A | 6a |
| 105b | 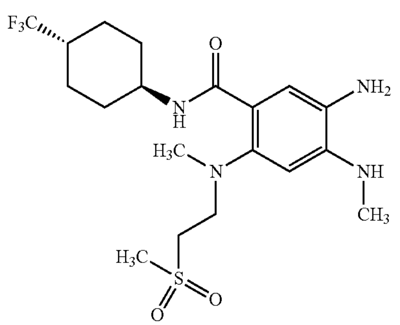 [SMILES: CNc1cc(N(C)CCS(C)(=O)=O)c(C(=O)N[C@H]2CC[C@H](C(F)(F)F)CC2)cc1N] | | 451 | $R_t$: 1.39 min Method I | 6b |
| 106a | 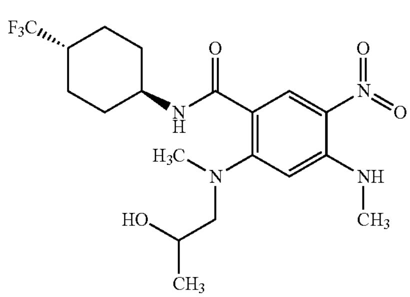 [SMILES: CNc1cc(N(C)CC(C)O)c(C(=O)N[C@H]2CC[C@H](C(F)(F)F)CC2)cc1[N+](=O)[O-]] | Educt: 45 min at 190° C. (microwave irradiation); N-methyl-2-hydroxy-propylamine as base | 433 | $R_t$: 1.45 min Method I | 6a |
| 106b | 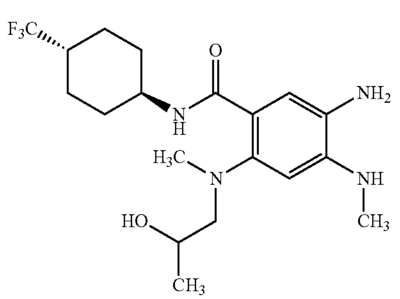 [SMILES: CNc1cc(N(C)CC(C)O)c(C(=O)N[C@H]2CC[C@H](C(F)(F)F)CC2)cc1N] | | 403 | $R_t$: 1.14 min Method A | 6b |

TABLE I-continued

Intermediates (prepared in analogy to the indicated procedure)

| Ex. | Structure | remarks | MS* m/z [M + H]⁺ | $R_f$(TLC, silica gel) or $R_t$ [min] (HPLC-method) | Prepared in analogy to example |
|---|---|---|---|---|---|
| 107a | 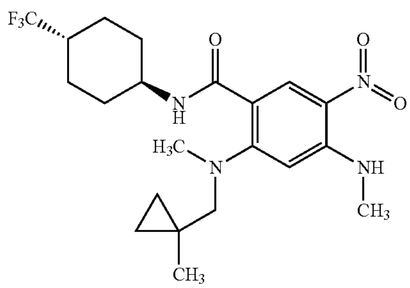 [SMILES: CNc1cc(N(C)CC2(C)CC2)c(C(=O)N[C@H]2CC[C@H](C(F)(F)F)CC2)cc1[N+](=O)[O-]] | Educt: 20b | 443 | $R_t$: 1.55 min Method A | 6a |
| 107b | 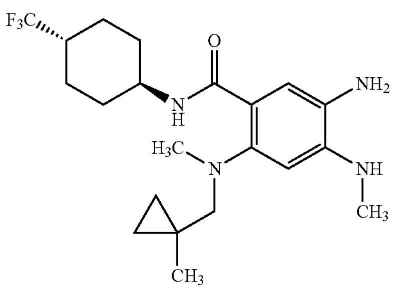 [SMILES: CNc1cc(N(C)CC2(C)CC2)c(C(=O)N[C@H]2CC[C@H](C(F)(F)F)CC2)cc1N] | | 413 | $R_t$: 1.36 min Method A | 6b |
| 108a | 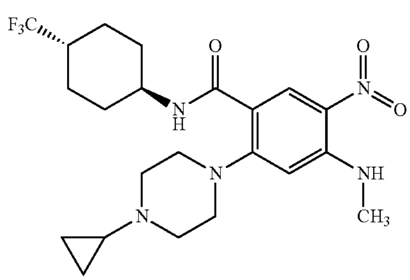 [SMILES: CNc1cc(N2CCN(C3CC3)CC2)c(C(=O)N[C@H]2CC[C@H](C(F)(F)F)CC2)cc1[N+](=O)[O-]] | Educt: 20b | 470 | $R_t$: 1.23 min Method A | 6a |
| 108b | 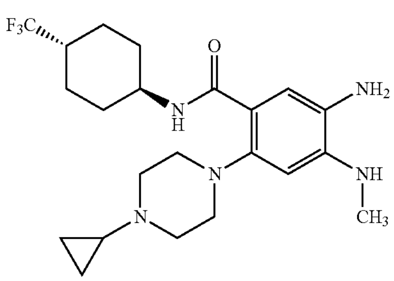 [SMILES: CNc1cc(N2CCN(C3CC3)CC2)c(C(=O)N[C@H]2CC[C@H](C(F)(F)F)CC2)cc1N] | The compound is directly used in the next step | | | 6b |
| 109a | 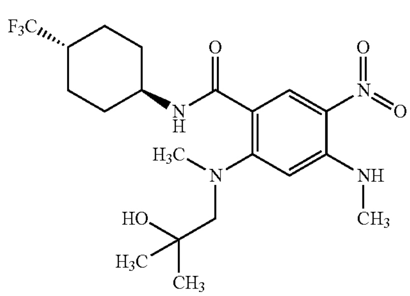 [SMILES: CNc1cc(N(C)CC(C)(C)O)c(C(=O)N[C@H]2CC[C@H](C(F)(F)F)CC2)cc1[N+](=O)[O-]] | Educt: 45 min at 65° C. (microwave irradiation); | 447 | $R_t$: 1.47 min Method H | 6a |

TABLE I-continued

Intermediates (prepared in analogy to the indicated procedure)

| Ex. | Structure | remarks | MS* m/z [M + H]+ | $R_f$ (TLC, silica gel) or $R_t$ [min] (HPLC-(method) | Prepared in analogy to example |
|---|---|---|---|---|---|
| 109b | 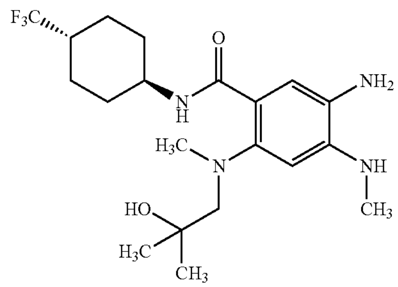 [SMILES: CNc1cc(N(C)CC(C)(C)O)c(C(=O)N[C@H]2CC[C@H](C(F)(F)F)CC2)cc1N] | | 417 | $R_t$: 1.15 min Method H | 6b |
| 110a | 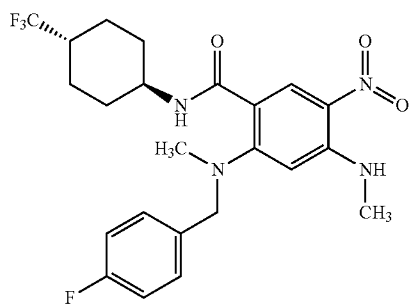 [SMILES: CNc1cc(N(C)Cc2ccc(F)cc2)c(C(=O)N[C@H]2CC[C@H](C(F)(F)F)CC2)cc1[N+](=O)[O-]] | Educt: WO2010/100249 See example 4a The compound is directly used in the next step. | | | 6a |
| 110b | 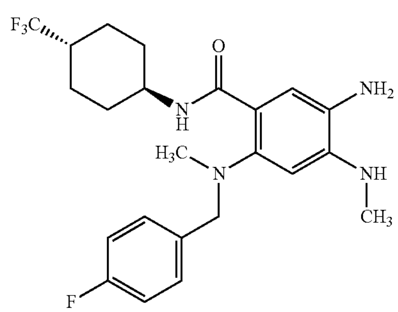 [SMILES: CNc1cc(N(C)Cc2ccc(F)cc2)c(C(=O)N[C@H]2CC[C@H](C(F)(F)F)CC2)cc1N] | | 417 | $R_t$: 1.15 min Method H | 6b |
| 111a | 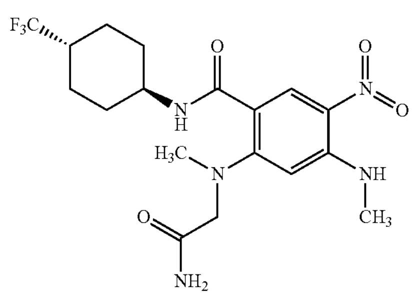 [SMILES: CNc1cc(N(C)CC(N)=O)c(C(=O)N[C@H]2CC[C@H](C(F)(F)F)CC2)cc1[N+](=O)[O-]] | Educt: 20b; | 432 | $R_t$: 1.38 min Method H | 6a |
| 111b | 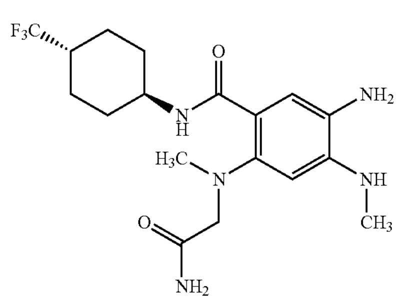 [SMILES: CNc1cc(N(C)CC(N)=O)c(C(=O)N[C@H]2CC[C@H](C(F)(F)F)CC2)cc1N] | The compound is directly used in the next step. | | | 6b |

TABLE I-continued

Intermediates (prepared in analogy to the indicated procedure)

| Ex. | Structure | remarks | MS* m/z [M + H]+ | R*f*(TLC, silica gel) or R*t* [min] (HPLC-method) | Prepared in analogy to example |
|---|---|---|---|---|---|
| 113a | 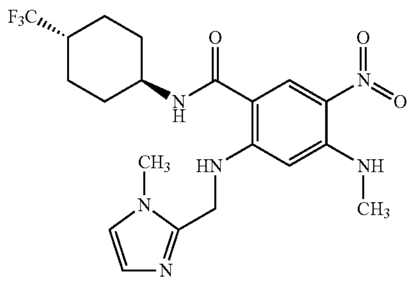 [SMILES: CNc1cc(NCc2nccn2C)c(C(=O)N[C@H]2CC[C@H](C(F)(F)F)CC2)cc1[N+](=O)[O-]] | Educt: 20b | 455 | R*t*: 1.21 min Method H | 6a |
| 113b | 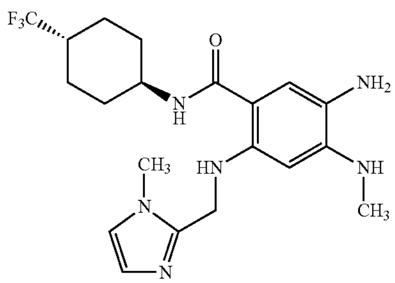 [SMILES: CNc1cc(NCc2nccn2C)c(C(=O)N[C@H]2CC[C@H](C(F)(F)F)CC2)cc1N] | | 425 | R*t*: 0.93 min Method H | 6b |
| 114a | 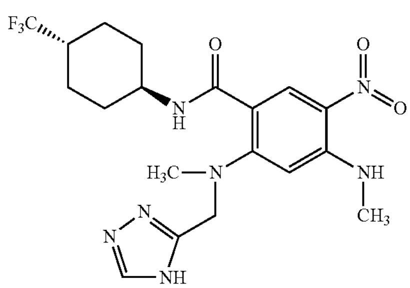 [SMILES: CNc1cc(N(C)Cc2nnc[nH]2)c(C(=O)N[C@H]2CC[C@H](C(F)(F)F)CC2)cc1[N+](=O)[O-]] | Educt: 20b | 456 | | 6a |
| 114b | 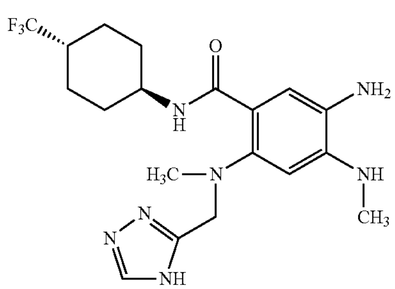 [SMILES: CNc1cc(N(C)Cc2nnc[nH]2)c(C(=O)N[C@H]2CC[C@H](C(F)(F)F)CC2)cc1N] | | 426 | R*t*: 1.11 min Method H | 6b |
| 115a | 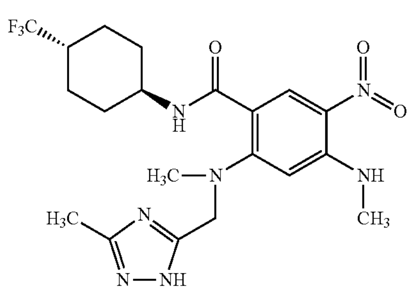 [SMILES: CNc1cc(N(C)Cc2nc(C)n[nH]2)c(C(=O)N[C@H]2CC[C@H](C(F)(F)F)CC2)cc1[N+](=O)[O-]] | Educt: 45 min at 150° C. (microwave irradiation) | 470 | R*t*: 1.45 min Method H | 6a |

TABLE I-continued

Intermediates (prepared in analogy to the indicated procedure)

| Ex. | Structure | remarks | MS* m/z [M + H]⁺ | R_f (TLC, silica gel) or R_t [min] (HPLC-method) | Prepared in analogy to example |
|---|---|---|---|---|---|
| 115b | (structure) | | 440 | R_t: 1.14 min Method H | 6b |
| 116a | (structure) | Educt: 120 min at 165° C. (microwave irradiation) | 470 | R_t: 1.37 min Method H | 6a |
| 116b | (structure) | | 440 | R_t: 1.08 min Method H | 6b |
| 117a | (structure) | Educt: WO2010/100249 See example 4a | 461 | R_t: 1.55 min Method A | 6a |

TABLE I-continued

Intermediates (prepared in analogy to the indicated procedure)

| Ex. | Structure | remarks | MS* m/z [M + H]+ | R_f (TLC, silica gel) or R_t [min] (HPLC-(method) | Prepared in analogy to example |
|---|---|---|---|---|---|
| 117b | 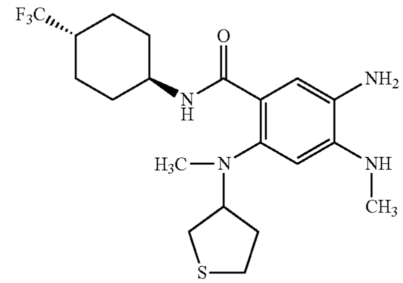 [SMILES: CNc1cc(N(C)C2CCSC2)c(C(=O)N[C@H]2CC[C@H](C(F)(F)F)CC2)cc1N] | | 431 | R_t: 1.33 min Method A | 112b |
| 120a | 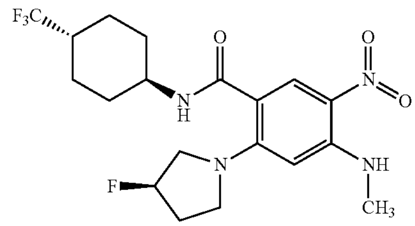 [SMILES: CNc1cc(N2CC[C@@H](F)C2)c(C(=O)N[C@H]2CC[C@H](C(F)(F)F)CC2)cc1[N+](=O)[O-]] | Educt: 20b | 433 | R_t: 1.40 min Method A | 6a |
| 120b | 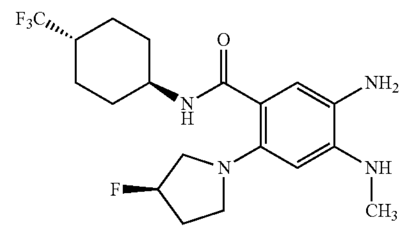 [SMILES: CNc1cc(N2CC[C@@H](F)C2)c(C(=O)N[C@H]2CC[C@H](C(F)(F)F)CC2)cc1N] | | 403 | R_t: 0.92 min Method J | 6b |
| 121a | 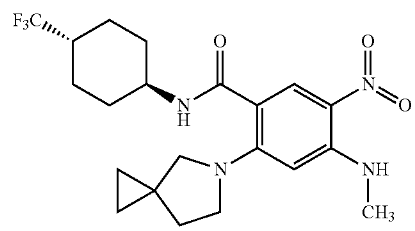 [SMILES: CNc1cc(N2CCC3(CC3)C2)c(C(=O)N[C@H]2CC[C@H](C(F)(F)F)CC2)cc1[N+](=O)[O-]] | Educt: 20b; 5-aza-spiro-[2,4]-heptane as base | 441 | R_t: 1.51 min Method A | 6a |
| 121b | 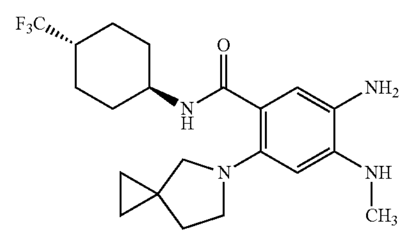 [SMILES: CNc1cc(N2CCC3(CC3)C2)c(C(=O)N[C@H]2CC[C@H](C(F)(F)F)CC2)cc1N] | | 411 | R_t: 1.34 min Method A | 6b |
| 122a | 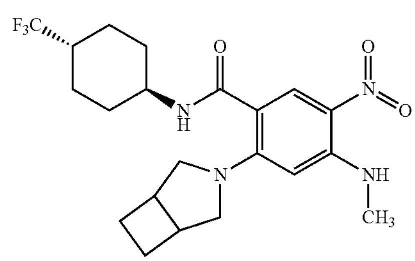 [SMILES: CNc1cc(N2CC3CCC3C2)c(C(=O)N[C@H]2CC[C@H](C(F)(F)F)CC2)cc1[N+](=O)[O-]] | Educt: 20b | 441 | R_t: 1.53 min Method A | 6a |

TABLE I-continued

Intermediates (prepared in analogy to the indicated procedure)

| Ex. | Structure | remarks | MS* m/z [M + H]+ | R_f (TLC, silica gel) or R_t [min] (HPLC- (method) | Prepared in analogy to example |
|---|---|---|---|---|---|
| 122b | 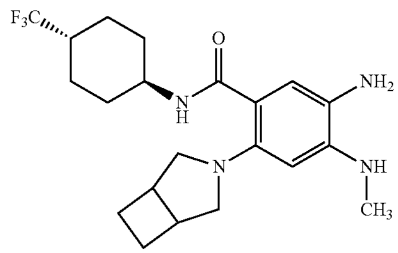 [SMILES: CNc1cc(N2CC3CCC3C2)c(C(=O)N[C@H]2CC[C@H](C(F)(F)F)CC2)cc1N] | | 411 | R_t: 1.36 min Method A | 6b |
| 123a | 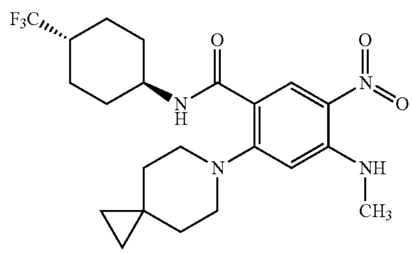 [SMILES: CNc1cc(N2CCC3(CC2)CC3)c(C(=O)N[C@H]2CC[C@H](C(F)(F)F)CC2)cc1[N+](=O)[O-]] | Educt: 20b | 455 | R_t: 1.61 min Method A | 6a |
| 123b | 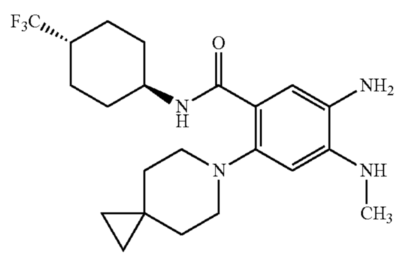 [SMILES: CNc1cc(N2CCC3(CC2)CC3)c(C(=O)N[C@H]2CC[C@H](C(F)(F)F)CC2)cc1N] | | 425 | R_t: 1.40 min Method A | 6b |
| 124a | 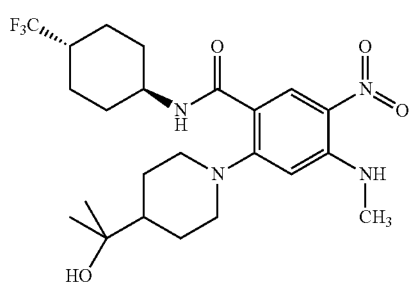 [SMILES: CNc1cc(N2CCC(C(C)(C)O)CC2)c(C(=O)N[C@H]2CC[C@H](C(F)(F)F)CC2)cc1[N+](=O)[O-]] | Educt: 20b | 487 | R_t: 1.50 min Method A | 6a |
| 124b | 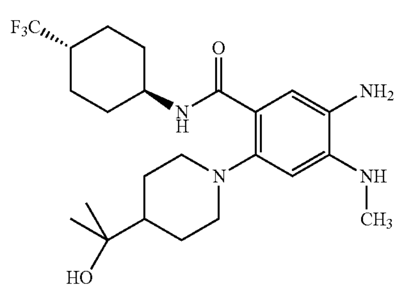 [SMILES: CNc1cc(N2CCC(C(C)(C)O)CC2)c(C(=O)N[C@H]2CC[C@H](C(F)(F)F)CC2)cc1N] | | 457 | R_t: 1.30 min Method A | 6b |

TABLE I-continued

Intermediates (prepared in analogy to the indicated procedure)

| Ex. | Structure | remarks | MS* m/z [M + H]+ | R_f (TLC, silica gel) or R_t [min] (HPLC-(method) | Prepared in analogy to example |
|---|---|---|---|---|---|
| 125a | 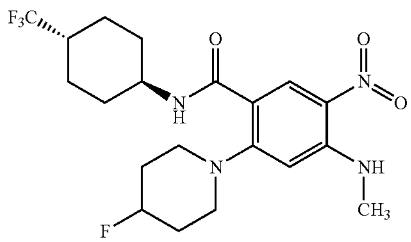 [SMILES: CNc1cc(N2CCC(F)CC2)c(C(=O)N[C@H]2CC[C@H](C(F)(F)F)CC2)cc1[N+](=O)[O-]] | Educt: 20b | 447 | R_t: 1.59 min Method H | 6a |
| 125b | 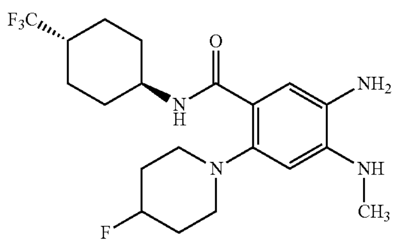 [SMILES: CNc1cc(N2CCC(F)CC2)c(C(=O)N[C@H]2CC[C@H](C(F)(F)F)CC2)cc1N] | | 417 | R_t: 1.22 min Method H | 6b |
| 126a | 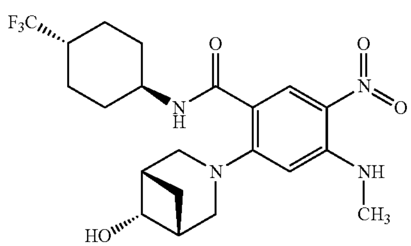 [SMILES: CNc1cc(N2C[C@H]3C[C@@H](C2)[C@H]3O)c(C(=O)N[C@H]2CC[C@H](C(F)(F)F)CC2)cc1[N+](=O)[O-]] | Educt: 20b 45 min at 170° C. (microwave irradiation) | | | 6a |
| 126b | 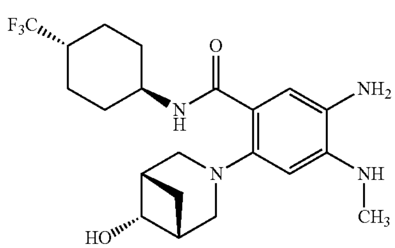 [SMILES: CNc1cc(N2C[C@H]3C[C@@H](C2)[C@H]3O)c(C(=O)N[C@H]2CC[C@H](C(F)(F)F)CC2)cc1N] | | | | 6b |
| 127a | 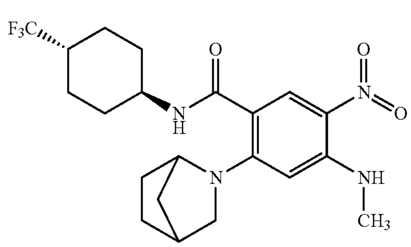 [SMILES: CNc1cc(N2CC3CCC2C3)c(C(=O)N[C@H]2CC[C@H](C(F)(F)F)CC2)cc1[N+](=O)[O-]] | Educt: 20b 60 min at 170° C. (microwave irradiation) | 441 | R_t: 1.49 min Method A | 6a |
| 127b | 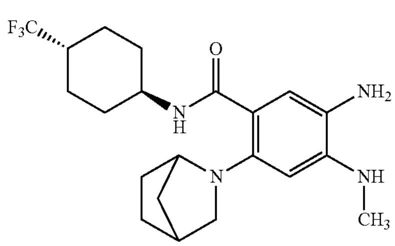 [SMILES: CNc1cc(N2CC3CCC2C3)c(C(=O)N[C@H]2CC[C@H](C(F)(F)F)CC2)cc1N] | | 411 | R_t: 1.28 min Method A | 6b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 129a | 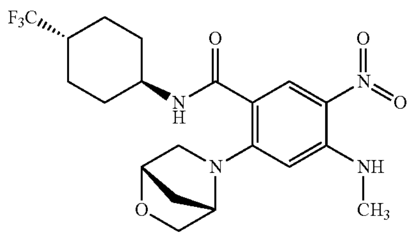 [SMILES: CNc1cc(N2C[C@@H]3C[C@H]2CO3)c(C(=O)N[C@H]2CC[C@H](C(F)(F)F)CC2)cc1[N+](=O)[O-]] | Educt: 20b and (1S,4S)-2-Oxa-5-azabicyclo[2.2.1]heptane; 45 min at 160° C. (microwave irradiation) | 443 | R$_t$: 1.34 min Method A | 6a |
| 129b | 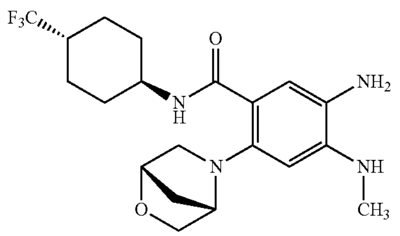 [SMILES: CNc1cc(N2C[C@@H]3C[C@H]2CO3)c(C(=O)N[C@H]2CC[C@H](C(F)(F)F)CC2)cc1N] | | 413 | R$_t$: 1.18 min Method A | 6b |
| 130a | 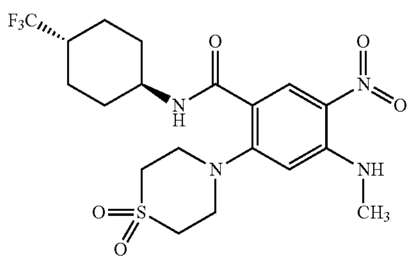 [SMILES: CNc1cc(N2CCS(=O)(=O)CC2)c(C(=O)N[C@H]2CC[C@H](C(F)(F)F)CC2)cc1[N+](=O)[O-]] | Educt: 20b 45 min at 160° C. (microwave irradiation) | 479 | R$_t$: 1.31 min Method A | 6a |
| 130b | 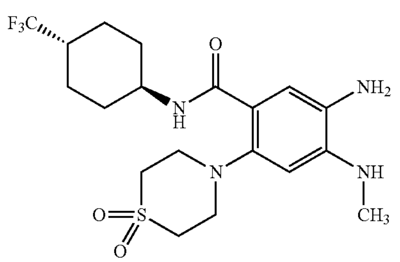 [SMILES: CNc1cc(N2CCS(=O)(=O)CC2)c(C(=O)N[C@H]2CC[C@H](C(F)(F)F)CC2)cc1N] | | 449 | R$_t$: 1.30 min Method A | 6b |
| 131a | 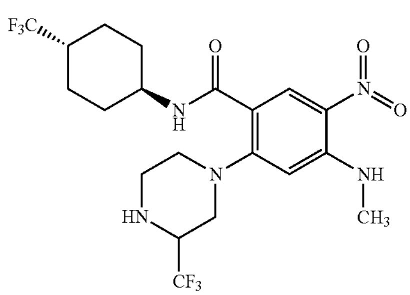 [SMILES: CNc1cc(N2CCNC(C(F)(F)F)C2)c(C(=O)N[C@H]2CC[C@H](C(F)(F)F)CC2)cc1[N+](=O)[O-]] | Educt: WO2010/100249 See example 4a; 45 min at 160° C. (microwave irradiation) | 498 | R$_t$: 1.33 min Method A | 6a |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 131b | 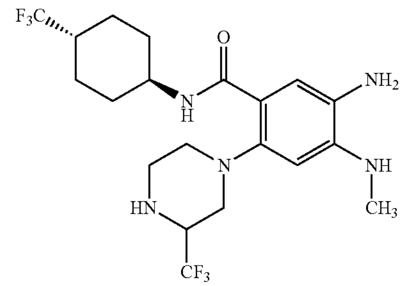 [SMILES: CNc1cc(N2CCNC(C(F)(F)F)C2)c(C(=O)N[C@H]2CC[C@H](C(F)(F)F)CC2)cc1N] | | 468 | R$_t$: 1.50 min Method A | 6b |
| 132a | 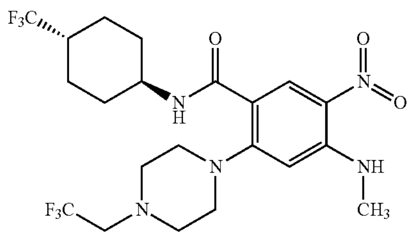 [SMILES: CNc1cc(N2CCN(CC(F)(F)F)CC2)c(C(=O)N[C@H]2CC[C@H](C(F)(F)F)CC2)cc1[N+](=O)[O-]] | Educt: 20b 45 min at 160° C. (microwave irradiation) | | | 6a |
| 132b | 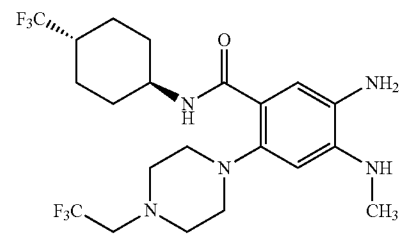 [SMILES: CNc1cc(N2CCN(CC(F)(F)F)CC2)c(C(=O)N[C@H]2CC[C@H](C(F)(F)F)CC2)cc1N] | | 482 | R$_t$: 1.39 min Method A | 6b |
| 133a | 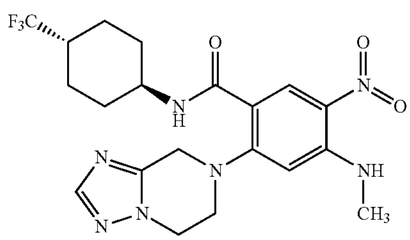 [SMILES: CNc1cc(N2CCn3ncnc3C2)c(C(=O)N[C@H]2CC[C@H](C(F)(F)F)CC2)cc1[N+](=O)[O-]] | Educt: 20b 45 min at 160° C. (microwave irradiation) | 468 | R$_t$: 1.33 min Method A | 6a |
| 133b | 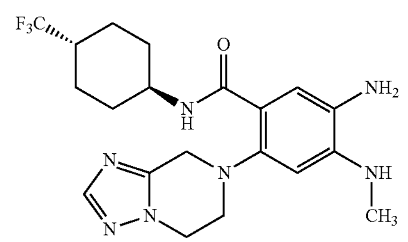 [SMILES: CNc1cc(N2CCn3ncnc3C2)c(C(=O)N[C@H]2CC[C@H](C(F)(F)F)CC2)cc1N] | | 438 | R$_t$: 1.13 min Method A | 6b |
| 134a | 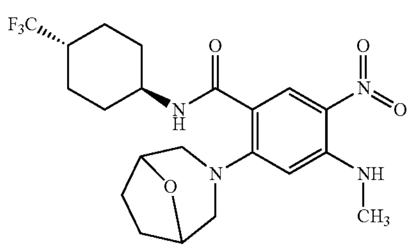 [SMILES: CNc1cc(N2CC3CCC(C2)O3)c(C(=O)N[C@H]2CC[C@H](C(F)(F)F)CC2)cc1[N+](=O)[O-]] | Educt: 20b 45 min at 160° C. (microwave irradiation) | 457 | R$_t$: 1.41 min Method A | 6a |

TABLE I-continued

Intermediates (prepared in analogy to the indicated procedure)

| Ex. | Structure | remarks | MS* m/z [M + H]⁺ | $R_f$(TLC, silica gel) or $R_t$ [min] (HPLC- method) | Prepared in analogy to example |
|---|---|---|---|---|---|
| 134b | 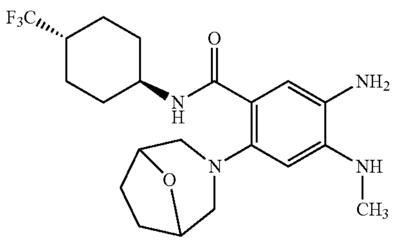 [SMILES: CNc1cc(N2CC3CCC(C2)O3)c(C(=O)N[C@H]2CC[C@H](C(F)(F)F)CC2)cc1N] | The compound is directly used in the next step. | | | 6b |
| 135a | 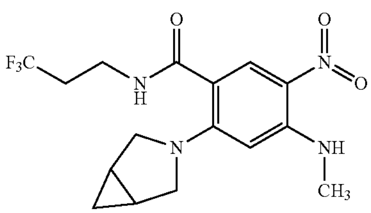 [SMILES: CNc1cc(N2CC3CC3C2)c(C(=O)NCCC(F)(F)F)cc1[N+](=O)[O-]] | Educt: 81a | 373 | $R_t$: 1.28 min Method A | 6a |
| 135b | 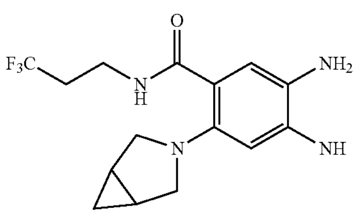 [SMILES: Nc1cc(C(=O)NCCC(F)(F)F)c(N2CC3CC3C2)cc1N] | | 343 | $R_t$: 1.07 min Method A | 6b |
| 136a | 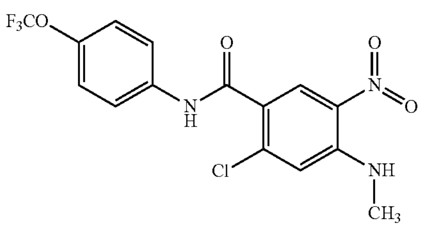 [SMILES: CNc1cc(Cl)c(C(=O)Nc2ccc(OC(F)(F)F)cc2)cc1[N+](=O)[O-]] | Educt: 20a | 390 | $R_t$: 1.51 min Method A | 77b |
| 136b | 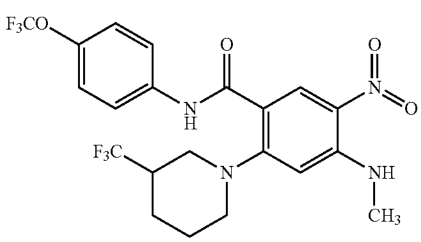 [SMILES: CNc1cc(N2CCCC(C(F)(F)F)C2)c(C(=O)Nc2ccc(OC(F)(F)F)cc2)cc1[N+](=O)[O-]] | Dioxane as solvent | 507 | $R_t$: 1.64 min Method A | 6a |
| 136c | 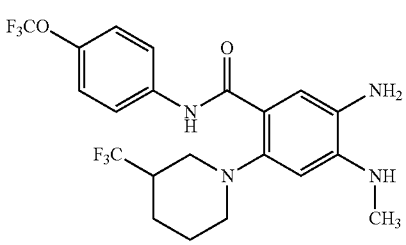 [SMILES: CNc1cc(N2CCCC(C(F)(F)F)C2)c(C(=O)Nc2ccc(OC(F)(F)F)cc2)cc1N] | | 477 | $R_t$: 1.54 min Method A | 6b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 137a | 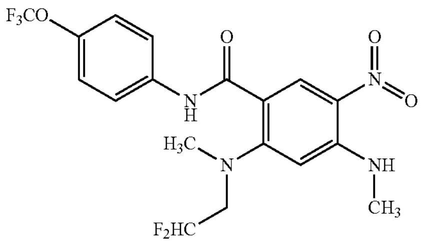 [SMILES: CNc1cc(N(C)CC(F)F)c(C(=O)Nc2ccc(OC(F)(F)F)cc2)cc1[N+](=O)[O-]] | Educt: 136a 165 min at 180° C. (microwave irradiation) | 449 | R$_t$: 1.54 min Method A | 6a |
| 137b | 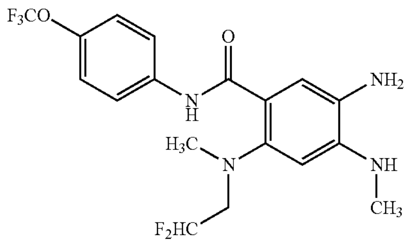 [SMILES: CNc1cc(N(C)CC(F)F)c(C(=O)Nc2ccc(OC(F)(F)F)cc2)cc1N] | | 419 | R$_t$: 1.44 min Method A | 6b |
| 138a | 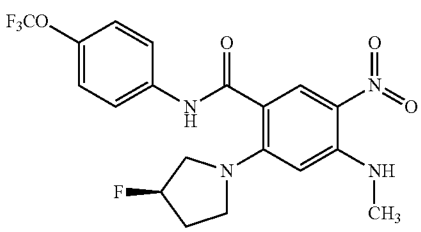 [SMILES: CNc1cc(N2CC[C@@H](F)C2)c(C(=O)Nc2ccc(OC(F)(F)F)cc2)cc1[N+](=O)[O-]] | Educt: 136a | 443 | R$_t$: 1.54 min Method I | 6a |
| 138b | 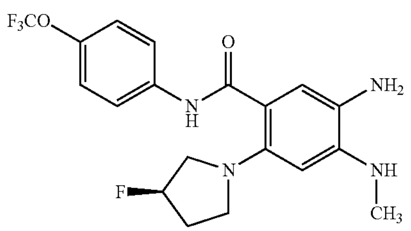 [SMILES: CNc1cc(N2CC[C@@H](F)C2)c(C(=O)Nc2ccc(OC(F)(F)F)cc2)cc1N] | The compound is directly used in the next step. | | | 6b |
| 139a | 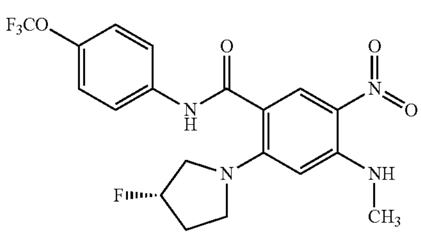 [SMILES: CNc1cc(N2CC[C@H](F)C2)c(C(=O)Nc2ccc(OC(F)(F)F)cc2)cc1[N+](=O)[O-]] | Educt: 136a | 443 | R$_t$: 1.49 min Method A | 6a |
| 139b | 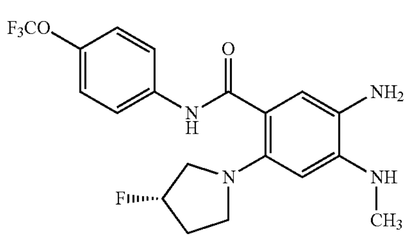 [SMILES: CNc1cc(N2CC[C@H](F)C2)c(C(=O)Nc2ccc(OC(F)(F)F)cc2)cc1N] | | 413 | R$_t$: 1.38 min Method A | 6b |

TABLE I-continued

Intermediates (prepared in analogy to the indicated procedure)

| Ex. | Structure | remarks | MS* m/z [M + H]⁺ | R$_f$ (TLC, silica gel) or R$_t$ [min] (HPLC-method) | Prepared in analogy to example |
|---|---|---|---|---|---|
| 140a | 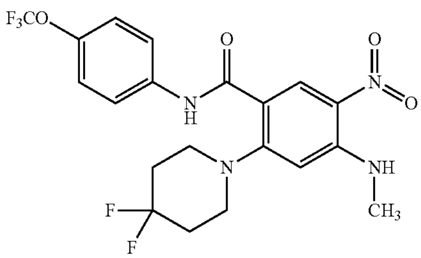 [SMILES: CNc1cc(N2CCC(F)(F)CC2)c(C(=O)Nc2ccc(OC(F)(F)F)cc2)cc1[N+](=O)[O-]] | Educt: 136a Dioxane as solvent | 475 | R$_t$: 1.59 min Method A | 6a |
| 140b | 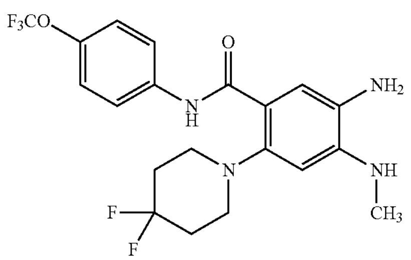 [SMILES: CNc1cc(N2CCC(F)(F)CC2)c(C(=O)Nc2ccc(OC(F)(F)F)cc2)cc1N] | | 445 | R$_t$: 1.47 min Method A | 6b |
| 141a | 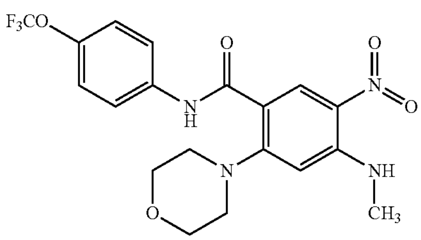 [SMILES: CNc1cc(N2CCOCC2)c(C(=O)Nc2ccc(OC(F)(F)F)cc2)cc1[N+](=O)[O-]] | Educt: 136a DCM as solvent; Morpholine as base | 441 | R$_t$: 1.50 min Method A | 6a |
| 141b | 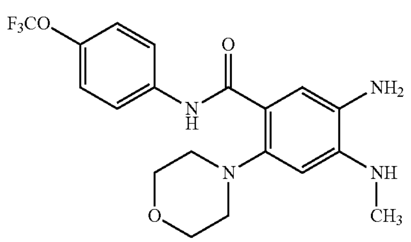 [SMILES: CNc1cc(N2CCOCC2)c(C(=O)Nc2ccc(OC(F)(F)F)cc2)cc1N] | | 411 | R$_t$: 1.33 min Method A | 6b |
| 143a | 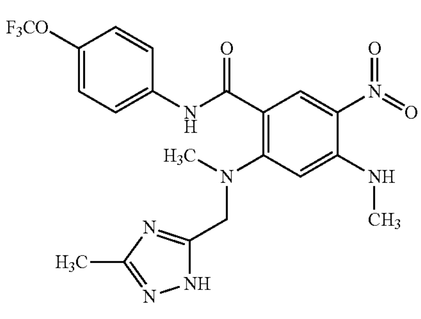 [SMILES: CNc1cc(N(C)Cc2nc(C)n[nH]2)c(C(=O)Nc2ccc(OC(F)(F)F)cc2)cc1[N+](=O)[O-]] | Educt: 136a 45 min at 150° C. (microwave irradiation) | 479 | R$_t$: 1.54 min Method H | 6a |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-(method) | Prepared in analogy to example |
|---|---|---|---|---|---|
| 143b | 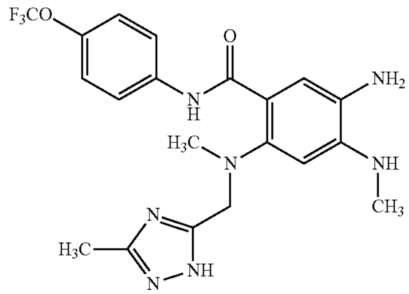 [SMILES: CNc1cc(N(C)Cc2nc(C)n[nH]2)c(C(=O)Nc2ccc(OC(F)(F)F)cc2)cc1N] | | 449 | R$_t$: 1.26 min Method H | 6b |
| 146a | 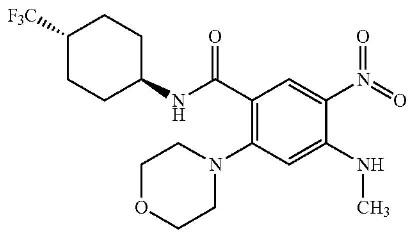 [SMILES: CNc1cc(N2CCOCC2)c(C(=O)N[C@H]2CC[C@H](C(F)(F)F)CC2)cc1[N+](=O)[O-]] | Educt: 20b and 45 min at 150° C. (microwave irradiation) | 431 | R$_t$: 1.34 min Method H | 6a |
| 146b | 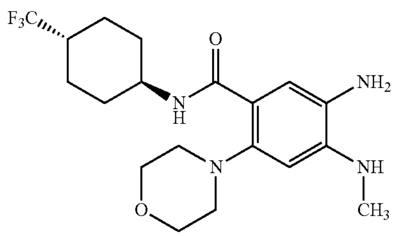 [SMILES: CNc1cc(N2CCOCC2)c(C(=O)N[C@H]2CC[C@H](C(F)(F)F)CC2)cc1N] | The compound is directly used in the next step. | 401 | | 6b |
| 147a | 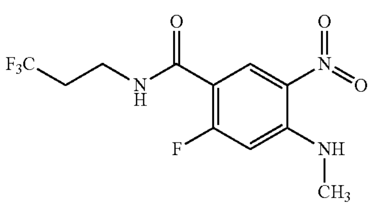 [SMILES: CNc1cc(F)c(C(=O)NCCC(F)(F)F)cc1[N+](=O)[O-]] | Educt: 1a | 310 | R$_t$: 1.21 min Method A | 81a |
| 147b | 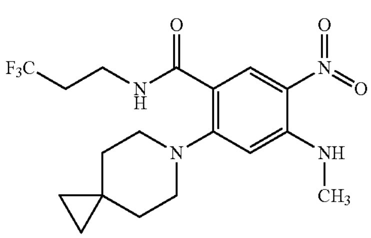 [SMILES: CNc1cc(N2CCC3(CC2)CC3)c(C(=O)NCCC(F)(F)F)cc1[N+](=O)[O-]] | | 401 | R$_t$: 1.49 min Method A | 6a |
| 147c | 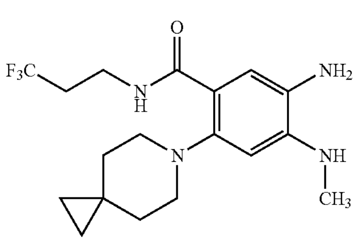 [SMILES: CNc1cc(N2CCC3(CC2)CC3)c(C(=O)NCCC(F)(F)F)cc1N] | | 371 | R$_t$: 1.19 min Method A | 6b |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-(method) | Prepared in analogy to example |
|---|---|---|---|---|---|
| 148a | 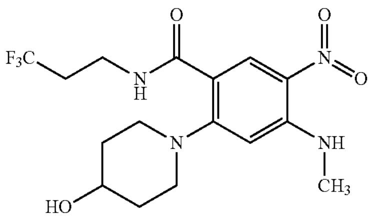 [SMILES: CNc1cc(N2CCC(O)CC2)c(C(=O)NCCC(F)(F)F)cc1[N+](=O)[O-]] | Educt: 147a K$_2$CO$_3$ as base in DMF | 391 | R$_t$: 1.16 min Method A | 6a |
| 148b | 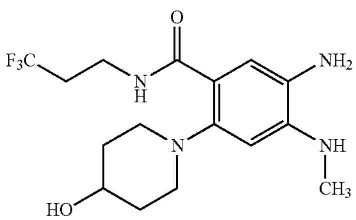 [SMILES: CNc1cc(N2CCC(O)CC2)c(C(=O)NCCC(F)(F)F)cc1N] | | 360 | R$_t$: 0.91 min Method A | 6b |
| 149a | 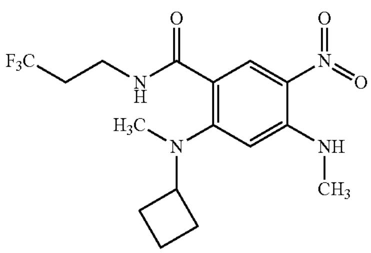 [SMILES: CNc1cc(N(C)C2CCC2)c(C(=O)NCCC(F)(F)F)cc1[N+](=O)[O-]] | Educt: 147a Dioxane as solvent | 375 | R$_t$: 1.38 min Method A | 6a |
| 149b | 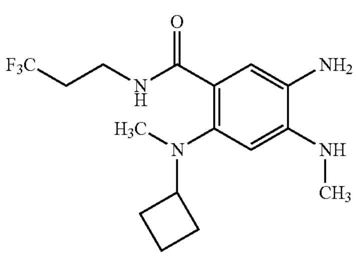 [SMILES: CNc1cc(N(C)C2CCC2)c(C(=O)NCCC(F)(F)F)cc1N] | | 345 | R$_t$: 1.08 min Method A | 6b |
| 150a | 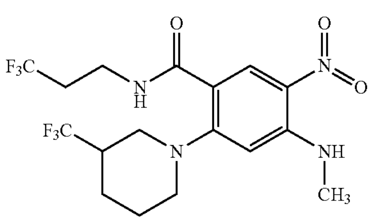 | Educt: 147a Dioxane as solvent | | | 6a |
| 150b | 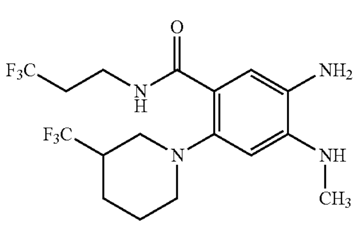 [SMILES: CNc1cc(N2CCCC(C(F)(F)F)C2)c(C(=O)NCCC(F)(F)F)cc1N] | | 413 | R$_t$: 1.27 min Method A | 6b |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC-method) | Prepared in analogy to example |
|---|---|---|---|---|---|
| 151a | 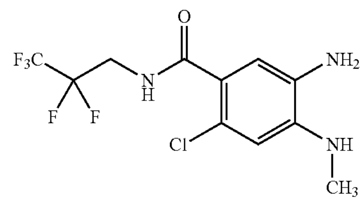 [SMILES: CNc1cc(Cl)c(C(=O)NCC(F)(F)C(F)(F)F)cc1N] | Educt 20a. | 362 | R$_t$: 1.41 min Method H | 5c |
| 151b | 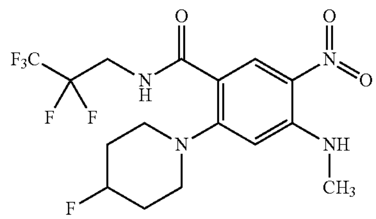 [SMILES: CNc1cc(N2CCC(F)CC2)c(C(=O)NCC(F)(F)C(F)(F)F)cc1[N+](=O)[O-]] | 45 min at 165° C. (microwave irradiation) | 429 | R$_t$: 1.52 min Method H | 6a |
| 151c | 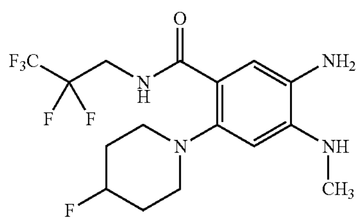 [SMILES: CNc1cc(N2CCC(F)CC2)c(C(=O)NCC(F)(F)C(F)(F)F)cc1N] | The compound is directly used in the next step. | | | 6b |
| 152a | 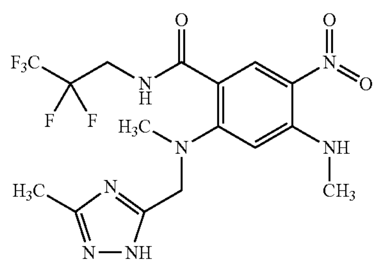 [SMILES: CNc1cc(N(C)Cc2nc(C)n[nH]2)c(C(=O)NCC(F)(F)C(F)(F)F)cc1[N+](=O)[O-]] | Educt 151a. 45 min at 150° C. (microwave irradiation) | 451 | R$_t$: 1.36 min Method H | 6a |
| 152b | 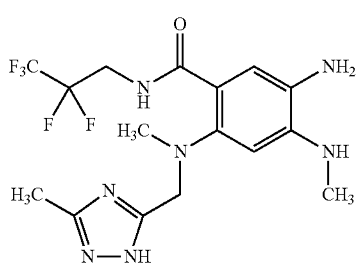 [SMILES: CNc1cc(N(C)Cc2nc(C)n[nH]2)c(C(=O)NCC(F)(F)C(F)(F)F)cc1N] | The compound is directly used in the next step. | | | 6b |
| 153a | 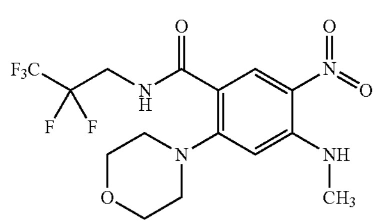 [SMILES: CNc1cc(N2CCOCC2)c(C(=O)NCC(F)(F)C(F)(F)F)cc1[N+](=O)[O-]] | Educt 151a; 45 min at 150° C. (microwave irradiation) | 412 | R$_t$: 1.42 min Method H | 6a |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-(method) | Prepared in analogy to example |
|---|---|---|---|---|---|
| 153b | 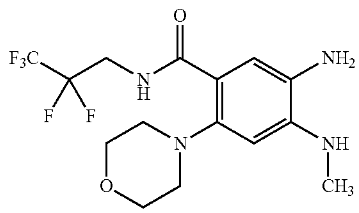 [SMILES: CNc1cc(N2CCOCC2)c(C(=O)NCC(F)(F)C(F)(F)F)cc1N] | | 382 | R$_t$: 1.11 min Method H | 6b |
| 154a | 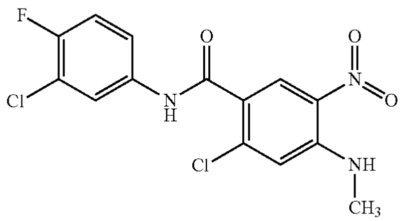 [SMILES: CNc1cc(Cl)c(C(=O)Nc2ccc(F)c(Cl)c2)cc1[N+](=O)[O-]] | Educt: 20a | 443 | R$_t$: 1.47 min Method A | 1b |
| 154b | 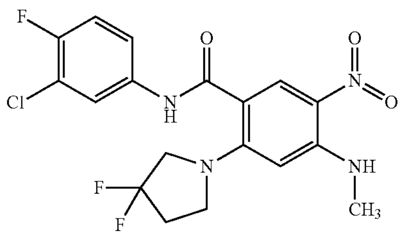 [SMILES: CNc1cc(N2CCC(F)(F)C2)c(C(=O)Nc2ccc(F)c(Cl)c2)cc1[N+](=O)[O-]] | DCM as solvent. | 429 | R$_t$: 1.51 min Method A | 6a |
| 154c | 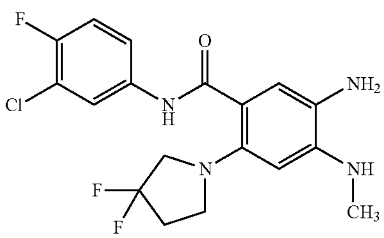 [SMILES: CNc1cc(N2CCC(F)(F)C2)c(C(=O)Nc2ccc(F)c(Cl)c2)cc1N] | | 399 | R$_t$: 1.41 min Method A | 6b |
| 155a | 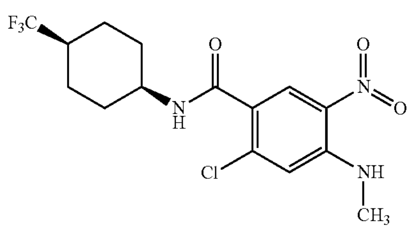 [SMILES: CNc1cc(Cl)c(C(=O)N[C@H]2CC[C@@H](C(F)(F)F)CC2)cc1[N+](=O)[O-]] | Educt: 20a; | 380 | R$_t$: 1.42 min Method A | 20b |
| 155b | 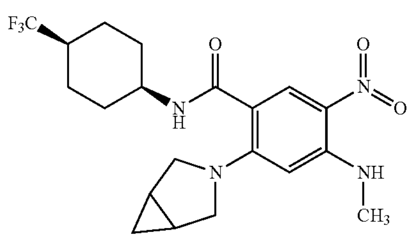 [SMILES: CNc1cc(N2CC3CC3C2)c(C(=O)N[C@H]2CC[C@@H](C(F)(F)F)CC2)cc1[N+](=O)[O-]] | 150 min at 150° C. (microwave irradiation) | 427 | R$_t$: 1.45 min Method A | 6a |

TABLE I-continued

Intermediates (prepared in analogy to the indicated procedure)

| Ex. | Structure | remarks | MS* m/z [M + H]+ | R_f (TLC, silica gel) or R_t [min] (HPLC- (method) | Prepared in analogy to example |
|---|---|---|---|---|---|
| 155c | 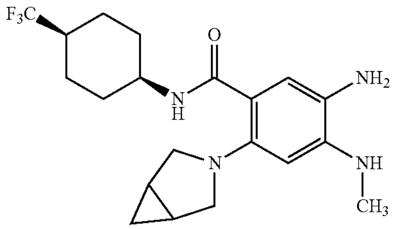 [SMILES: CNc1cc(N2CC3CC3C2)c(C(=O)N[C@H]2CC[C@@H](C(F)(F)F)CC2)cc1N] | | 397 | R_t: 1.28 min Method A | 6b |
| 163a | 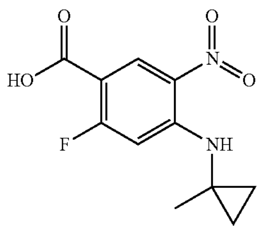 [SMILES: CC1(Nc2cc(F)c(C(=O)O)cc2[N+](=O)[O-])CC1] | | 255 | R_t: 1.33 min Method A | 77a |
| 163b | 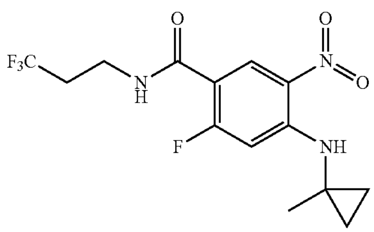 [SMILES: CC1(Nc2cc(F)c(C(=O)NCCC(F)(F)F)cc2[N+](=O)[O-])CC1] | | 350 | R_f = 0.25 DCM/EtOH 95:5 | 5c |
| 163c | | | 425 | R_t: 1.46 min Method A | 2a |
| 163e | | | 395 | R_t: 1.30 min Method A | 6b |
| 164a | 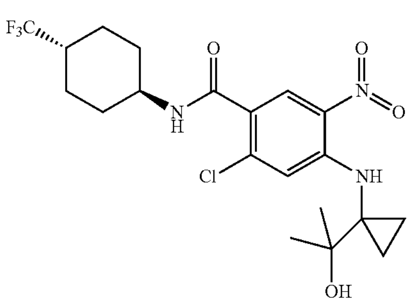 [SMILES: CC(C)(O)C1(Nc2cc(Cl)c(C(=O)N[C@H]3CC[C@H](C(F)(F)F)CC3)cc2[N+](=O)[O-])CC1] | | 464 | R_t: 1.56 min Method A | 5c |

TABLE I-continued

Intermediates (prepared in analogy to the indicated procedure)

| Ex. | Structure | remarks | MS* m/z [M + H]+ | R_f (TLC, silica gel) or R_t [min] (HPLC-(method) | Prepared in analogy to example |
|---|---|---|---|---|---|
| 164b | 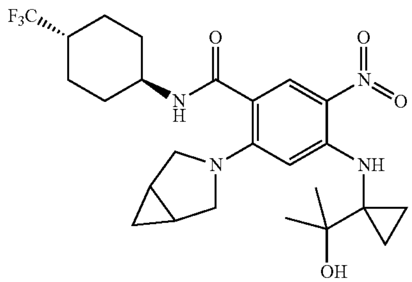 [SMILES: CC(C)(O)C1(Nc2cc(N3CC4CC4C3)c(C(=O)N[C@H]3CC[C@H](C(F)(F)F)CC3)cc2[N+](=O)[O-])CC1] | | 511 | R_t: 1.59 min Method H | 6a |
| 164c | 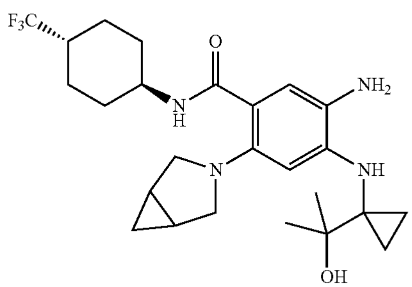 [SMILES: CC(C)(O)C1(Nc2cc(N3CC4CC4C3)c(C(=O)N[C@H]3CC[C@H](C(F)(F)F)CC3)cc2N)CC1] | | 481 | R_t: 1.39 min Method A | 6b |
| 165a | 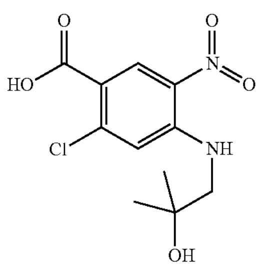 [SMILES: CC(C)(O)CNc1cc(Cl)c(C(=O)O)cc1[N+](=O)[O-]] | Cs_2CO_3 as base, DMF as solvent | 289 | R_t: 1.26 min Method H | 77a |
| 165b | 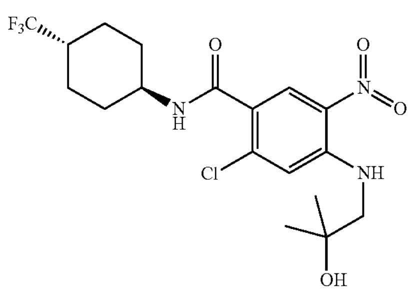 [SMILES: CC(C)(O)CNc1cc(Cl)c(C(=O)N[C@H]2CC[C@H](C(F)(F)F)CC2)cc1[N+](=O)[O-]] | | 437 | R_t: 1.51 min Method H | 5c |
| 165c | 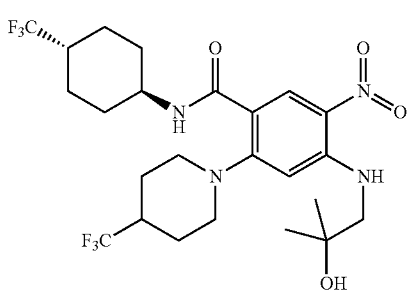 [SMILES: CC(C)(O)CNc1cc(N2CCC(C(F)(F)F)CC2)c(C(=O)N[C@H]2CC[C@H](C(F)(F)F)CC2)cc1[N+](=O)[O-]] | 45 min at 150° C. (microwave irradiation) | 555 | R_t: 1.65 min Method H | 6a |

TABLE I-continued

Intermediates (prepared in analogy to the indicated procedure)

| Ex. | Structure | remarks | MS* m/z [M + H]+ | R$_f$ (TLC, silica gel) or R$_t$ [min] (HPLC- (method) | Prepared in analogy to example |
|---|---|---|---|---|---|
| 165d | 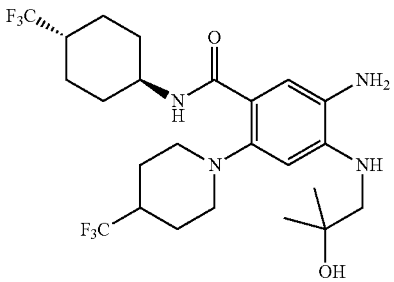 [SMILES: CC(C)(O)CNc1cc(N2CCC(C(F)(F)F)CC2)c(C(=O)N[C@H]2CC[C@H](C(F)(F)F)CC2)cc1N] | | 525 | R$_t$: 1.44 min Method H | 6b |
| 167a | 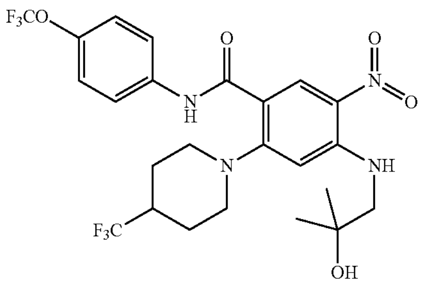 [SMILES: CC(C)(O)CNc1cc(N2CCC(C(F)(F)F)CC2)c(C(=O)Nc2ccc(OC(F)(F)F)cc2)cc1[N+](=O)[O-]] | Educt: 166b; | 565 | R$_t$: 1.70 min Method H | 166c |
| 167b | 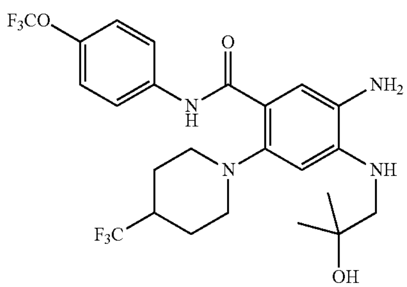 [SMILES: CC(C)(O)CNc1cc(N2CCC(C(F)(F)F)CC2)c(C(=O)Nc2ccc(OC(F)(F)F)cc2)cc1N] | | 535 | R$_t$: 1.53 min Method H | 167d |
| 168a | 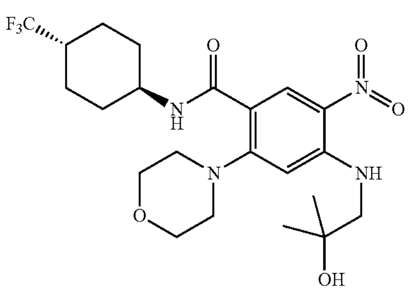 [SMILES: CC(C)(O)CNc1cc(N2CCOCC2)c(C(=O)N[C@H]2CC[C@H](C(F)(F)F)CC2)cc1[N+](=O)[O-]] | Educt: 165b; | 489 | R$_t$: 1.50 min Method H | 166c |
| 168b | 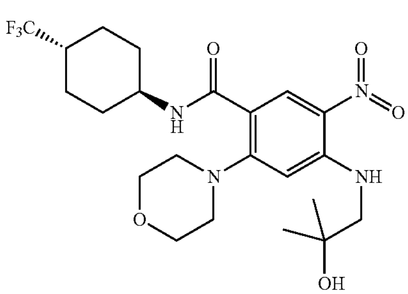 [SMILES: CC(C)(O)CNc1cc(N2CCOCC2)c(C(=O)N[C@H]2CC[C@H](C(F)(F)F)CC2)cc1[N+](=O)[O-]] | | 459 | R$_t$: 1.23 min Method H | 167d |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-method) | Prepared in analogy to example |
|---|---|---|---|---|---|
| 169a | 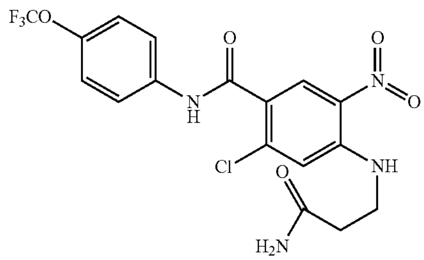 [SMILES: NC(=O)CCNc1cc(Cl)c(C(=O)Nc2ccc(OC(F)(F)F)cc2)cc1[N+](=O)[O-]] | Educt 166a TEA is used as base | 447 | R$_t$: 1.54 min Method H | 166b |
| 169b | 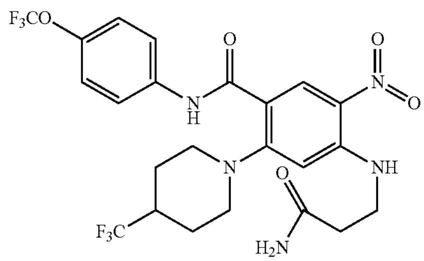 [SMILES: NC(=O)CCNc1cc(N2CCC(C(F)(F)F)CC2)c(C(=O)Nc2ccc(OC(F)(F)F)cc2)cc1[N+](=O)[O-]] | 45 min at 150° C. (microwave irradiation) | 563 | R$_t$: 1.67 min Method H | 6a |
| 169c | 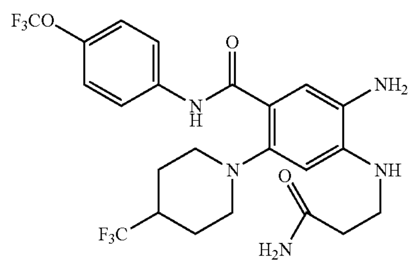 [SMILES: NC(=O)CCNc1cc(N2CCC(C(F)(F)F)CC2)c(C(=O)Nc2ccc(OC(F)(F)F)cc2)cc1N] | | 533 | R$_t$: 1.49 min Method H | 6b |
| 170a | 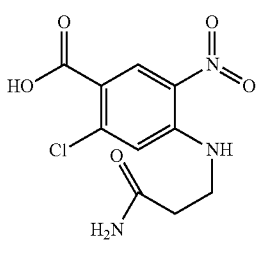 [SMILES: NC(=O)CCNc1cc(Cl)c(C(=O)O)cc1[N+](=O)[O-]] | Cs$_2$CO$_3$ as base, DMF as solvent | 288 | R$_t$: 0.98 min Method H | 77a |
| 170b | 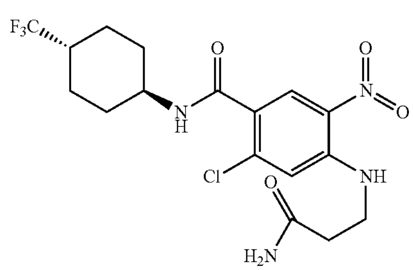 [SMILES: NC(=O)CCNc1cc(Cl)c(C(=O)N[C@H]2CC[C@H](C(F)(F)F)CC2)cc1[N+](=O)[O-]] | | 437 | R$_t$: 1.43 min Method H | 5c |

TABLE I-continued

Intermediates (prepared in analogy to the indicated procedure)

| Ex. | Structure | remarks | MS* m/z [M + H]⁺ | R$_f$ (TLC, silica gel) or R$_t$ [min] (HPLC-method) | Prepared in analogy to example |
|---|---|---|---|---|---|
| 170c | 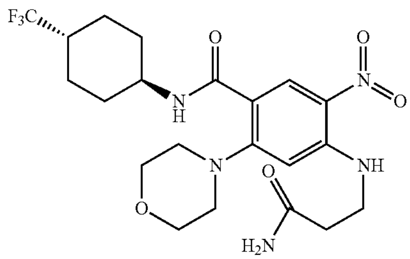 [SMILES: NC(=O)CCNc1cc(N2CCOCC2)c(C(=O)N[C@H]2CC[C@H](C(F)(F)F)CC2)cc1[N+](=O)[O-]] | 45 min at 120° C. (microwave irradiation) | 488 | R$_t$: 1.42 min Method H | 6a |
| 170d | 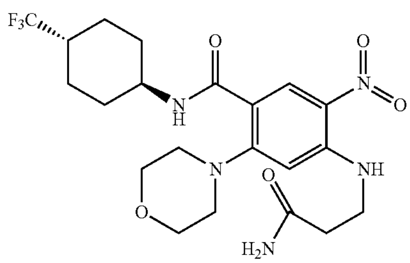 [SMILES: NC(=O)CCNc1cc(N2CCOCC2)c(C(=O)N[C@H]2CC[C@H](C(F)(F)F)CC2)cc1[N+](=O)[O-]] | | 458 | R$_t$: 1.14 min Method H | 6b |
| 171a | 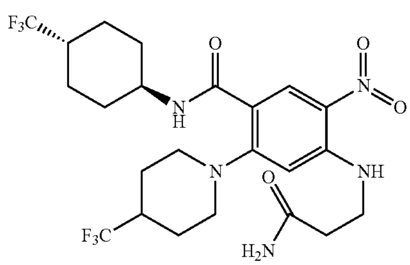 [SMILES: NC(=O)CCNc1cc(N2CCC(C(F)(F)F)CC2)c(C(=O)N[C@H]2CC[C@H](C(F)(F)F)CC2)cc1[N+](=O)[O-]] | Educt 170b; 45 min at 120° C. (microwave irradiation) | 554 | R$_t$: 1.62 min Method H | 6a |
| 171b | 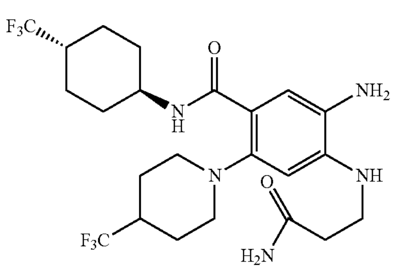 [SMILES: NC(=O)CCNc1cc(N2CCC(C(F)(F)F)CC2)c(C(=O)N[C@H]2CC[C@H](C(F)(F)F)CC2)cc1N] | | 524 | R$_t$: 1.37 min Method H | 6b |
| 262a | 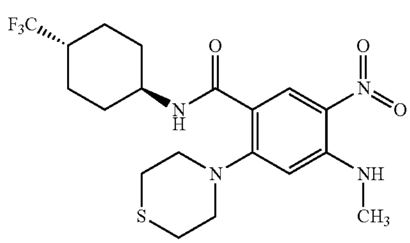 [SMILES: CNc1cc(N2CCSCC2)c(C(=O)N[C@H]2CC[C@H](C(F)(F)F)CC2)cc1[N+](=O)[O-]] | Educt 20b and 45 min at 165° C. (microwave irradiation) | 446 | R$_t$: 1.43 min Method H | 103a |

TABLE I-continued

Intermediates (prepared in analogy to the indicated procedure)

| Ex. | Structure | remarks | MS* m/z [M + H]+ | R$_f$(TLC, silica gel) or R$_t$ [min] (HPLC-(method) | Prepared in analogy to example |
|---|---|---|---|---|---|
| 262b | 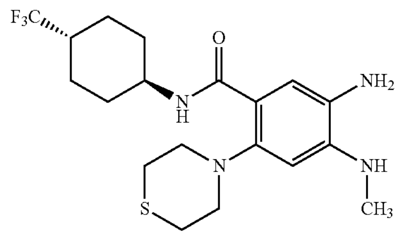 | | 416 | R$_t$: 1.28 min Method H | 6b |
| 263a | 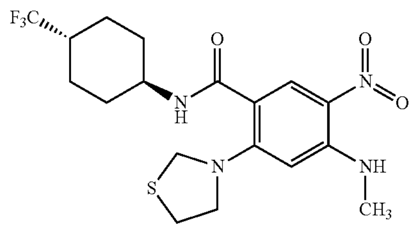 [SMILES: CNc1cc(N2CCSC2)c(C(=O)N[C@H]2CC[C@H](C(F)(F)F)CC2)cc1[N+](=O)[O-]] | Educt 20b and 45 min at 165° C. (microwave irradiation) | 432 | R$_t$: 1.55 min Method H | 103a |
| 263b | 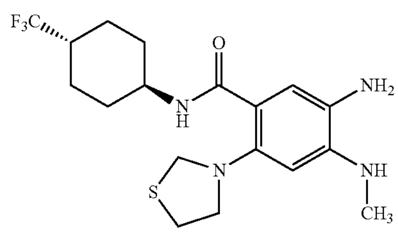 [SMILES: CNc1cc(N2CCSC2)c(C(=O)N[C@H]2CC[C@H](C(F)(F)F)CC2)cc1N] | | 402 | R$_t$: 1.35 min Method H | 6b |
| 264a | 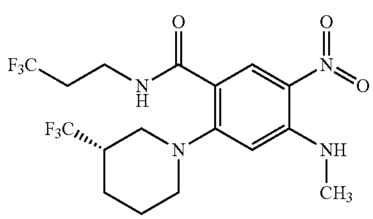 [SMILES: CNc1cc(N2CCC[C@H](C(F)(F)F)C2)c(C(=O)NCCC(F)(F)F)cc1[N+](=O)[O-]] | Educt: 81a | 443 | R$_t$: 1.48 min Method A | 81b |
| 264b | 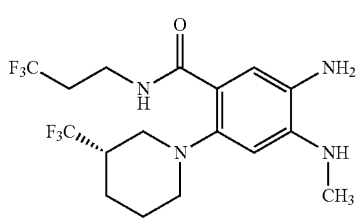 [SMILES: CNc1cc(N2CCC[C@H](C(F)(F)F)C2)c(C(=O)NCCC(F)(F)F)cc1N] | | 413 | R$_t$: 1.28 min Method H | 81c |
| 265a | 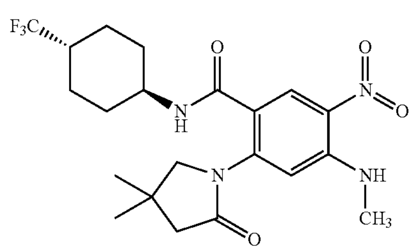 [SMILES: CNc1cc(N2CC(C)(C)CC2=O)c(C(=O)N[C@H]2CC[C@H](C(F)(F)F)CC2)cc1[N+](=O)[O-]] | Educt: 20b | 456 | R$_t$: 1.54 min Method H | 29a |

TABLE I-continued

Intermediates (prepared in analogy to the indicated procedure)

| Ex. | Structure | remarks | MS* m/z [M + H]⁺ | $R_f$(TLC, silica gel) or $R_t$ [min] (HPLC-(method) | Prepared in analogy to example |
|---|---|---|---|---|---|
| 265b | 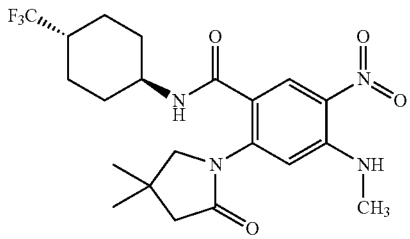 [SMILES: CNc1cc(N2CC(C)(C)CC2=O)c(C(=O)N[C@H]2CC[C@H](C(F)(F)F)CC2)cc1[N+](=O)[O-]] | | 426 | $R_t$: 1.33 min Method H | 6b |
| 267a | 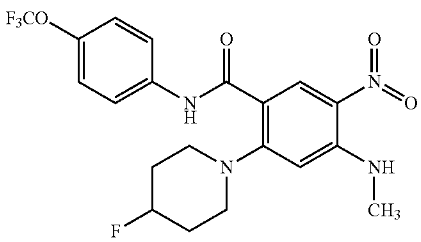 [SMILES: CNc1cc(N2CCC(F)CC2)c(C(=O)Nc2ccc(OC(F)(F)F)cc2)cc1[N+](=O)[O-]] | Educt: 136a | 457 | $R_t$: 1.66 min Method H | 6a |
| 267b | 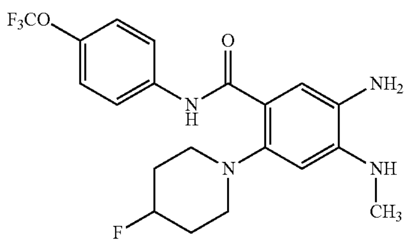 [SMILES: CNc1cc(N2CCC(F)CC2)c(C(=O)Nc2ccc(OC(F)(F)F)cc2)cc1N] | | 427 | $R_t$: 1.33 min Method H | 6b |
| 268a | 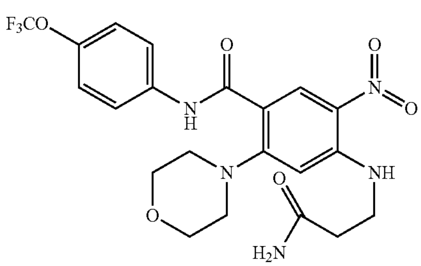 [SMILES: NC(=O)CCNc1cc(N2CCOCC2)c(C(=O)Nc2ccc(OC(F)(F)F)cc2)cc1[N+](=O)[O-]] | Educt: 169a 45 min at 150° C. (microwave irradiation) | 497 | $R_t$: 1.52 min Method H | 6a |
| 268b | 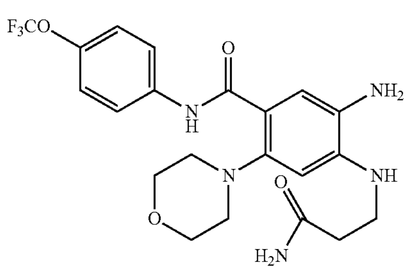 [SMILES: NC(=O)CCNc1cc(N2CCOCC2)c(C(=O)Nc2ccc(OC(F)(F)F)cc2)cc1N] | | 467 | $R_t$: 1.28 min Method H | 6b |

TABLE I-continued

Intermediates (prepared in analogy to the indicated procedure)

| Ex. | Structure | remarks | MS* m/z [M + H]⁺ | $R_f$(TLC, silica gel) or $R_t$ [min] (HPLC-(method) | Prepared in analogy to example |
|---|---|---|---|---|---|
| 269a | 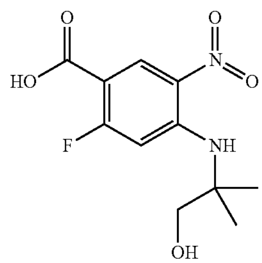 [SMILES: CC(C)(CO)Nc1cc(F)c(C(=O)O)cc1[N+](=O)[O-]] | | 272 | $R_t$: 1.14 min Method A | 77a |
| 269b | 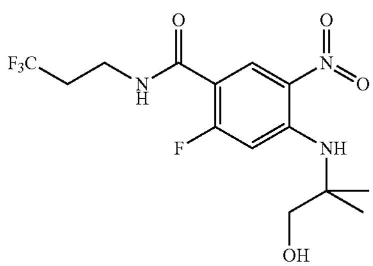 [SMILES: CC(C)(CO)Nc1cc(F)c(C(=O)NCCC(F)(F)F)cc1[N+](=O)[O-]] | | 368 | $R_f$ = 0.31 PE/EtOAc 1:1 | 81a |
| 269c | 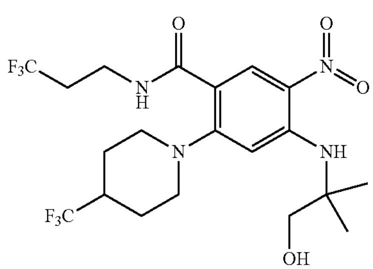 [SMILES: CC(C)(CO)Nc1cc(N2CCC(C(F)(F)F)CC2)c(C(=O)NCCC(F)(F)F)cc1[N+](=O)[O-]] | | 501 | $R_t$: 1.50 min Method A | 6a |
| 269d | 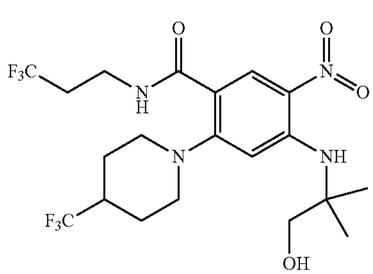 [SMILES: CC(C)(CO)Nc1cc(N2CCC(C(F)(F)F)CC2)c(C(=O)NCCC(F)(F)F)cc1[N+](=O)[O-]] | | 471 | $R_t$: 1.30 min Method A | 6b |

The following examples in Table II are prepared in analogy to the methods described above. Table II examples

| Ex. | Structure | Formula/ Mw. | MS* m/z [M + H]+ | $R_f$ (TLC, silica gel) or $R_t$ [min] (HPLC-method) | Prepared in analogy to example |
|---|---|---|---|---|---|
| 10 | 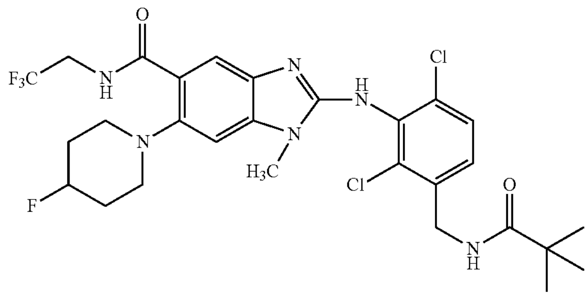 [SMILES: Cn1c(Nc2c(Cl)ccc(CNC(=O)C(C)(C)C)c2Cl)nc2cc(C(=O)NCC(F)(F)F)c(N3CCC(F)CC3)cc21] | $C_{28}H_{32}Cl_2F_4N_6O_2$ 631.49 | 631 | $R_f$ = 0.22 DCM:EtOH 19:1 | 1e |
| 11 | 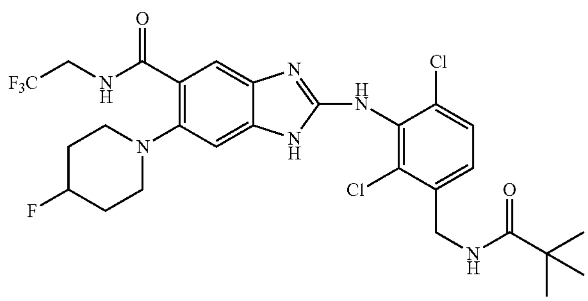 [SMILES: CC(C)(C)C(=O)NCc1ccc(Cl)c(Nc2nc3cc(C(=O)NCC(F)(F)F)c(N4CCC(F)CC4)cc3[nH]2)c1Cl] | $C_{27}H_{30}Cl_2F_4N_6O_2$ 617.47 | 617 | $R_f$ = 0.13 DCM:EtOH 19:1 | 1e |
| 12 | 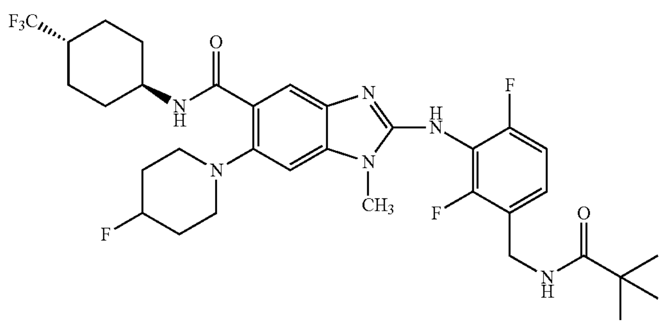 [SMILES: Cn1c(Nc2c(F)ccc(CNC(=O)C(C)(C)C)c2F)nc2cc(C(=O)N[C@H]3CC[C@H](C(F)(F)F)CC3)c(N3CCC(F)CC3)cc21] | $C_{33}H_{40}F_6N_6O_2$ 666.70 | 667 | $R_t$: 1.39 min Method B | 5e |
| 14 | 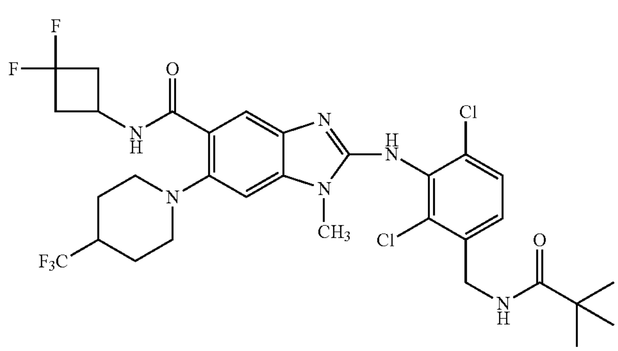 [SMILES: Cn1c(Nc2c(Cl)ccc(CNC(=O)C(C)(C)C)c2Cl)nc2cc(C(=O)NC3CC(F)(F)C3)c(N3CCC(C(F)(F)F)CC3)cc21] | $C_{31}H_{35}Cl_2F_5N_6O_2$ 689.55 | 689 | $R_f$ = 0.28 DCM:EtOH 19:1 | 1e |

-continued
| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 15 | 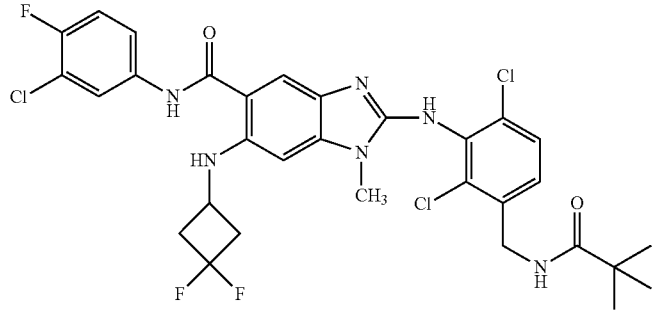 [SMILES: Cn1c(Nc2c(Cl)ccc(CNC(=O)C(C)(C)C)c2Cl)nc2cc(C(=O)Nc3ccc(F)c(Cl)c3)c(NC3CC(F)(F)C3)cc21] | $C_{31}H_{30}Cl_3F_3N_6O_2$ 681.952 | 681 | $R_f$ = 0.29 DCM: EtOH 19:1 | 1e |
| 16 | 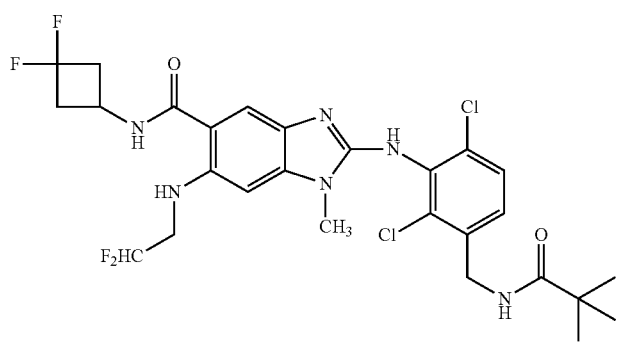 [SMILES: Cn1c(Nc2c(Cl)ccc(CNC(=O)C(C)(C)C)c2Cl)nc2cc(C(=O)NC3CC(F)(F)C3)c(NCC(F)F)cc21] | $C_{27}H_{30}Cl_2F_4N_6O_2$ 617.465 | 617 | $R_f$ = 0.22 DCM: EtOH 19:1 | 1e |
| 17 | 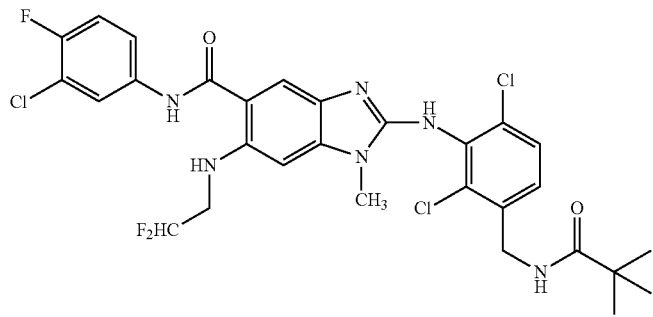 [SMILES: Cn1c(Nc2c(Cl)ccc(CNC(=O)C(C)(C)C)c2Cl)nc2cc(C(=O)Nc3ccc(F)c(Cl)c3)c(NCC(F)F)cc21] | $C_{29}H_{28}Cl_3F_3N_6O_2$ 655.935 | 655 | $R_f$ = 0.38 DCM: EtOH 19:1 | 1e |
| 18 | 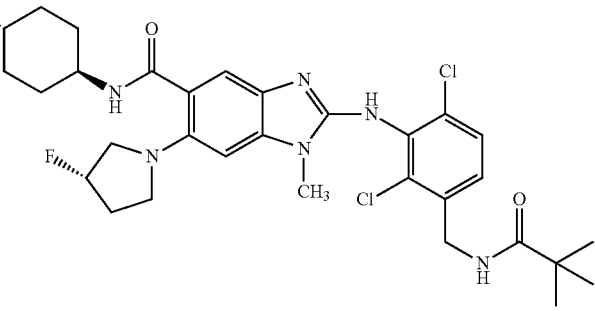 | $C_{32}H_{38}Cl_2F_4N_6O_2$ 685.582 | 685 | $R_t$: 1.49 min Method A | 6c |

-continued
| Ex. | Structure | Formula/ Mw. | MS* m/z [M + H]+ | $R_f$ (TLC, silica gel) or $R_t$ [min] (HPLC-method) | Prepared in analogy to example |
|---|---|---|---|---|---|
| 19 | 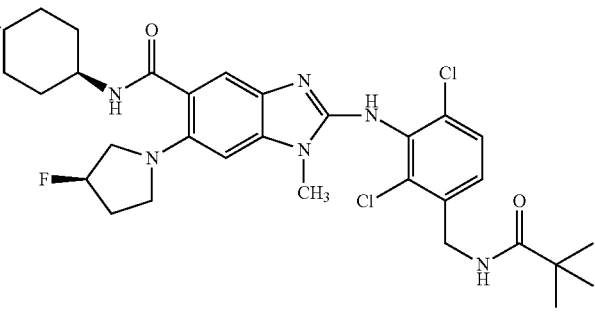 | $C_{32}H_{38}Cl_2F_4N_6O_2$ 685.582 | 685 | $R_t$: 1.49 min Method A | 6c |
| 21 | 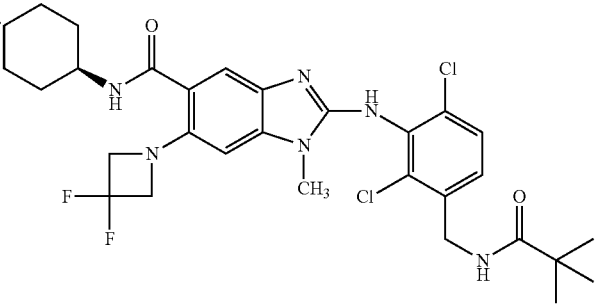 | $C_{31}H_{35}Cl_2F_5N_6O_2$ 689.546 | 690 | $R_t$: 1.47 min Method A | 6c |
| 22 | 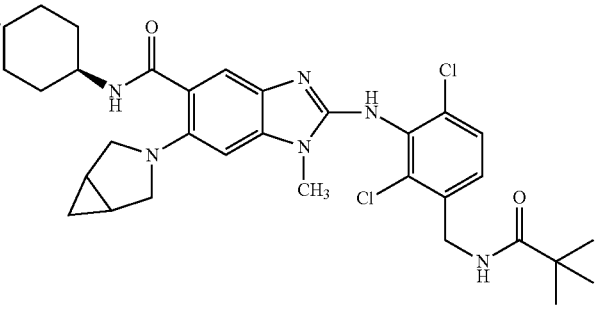 | $C_{33}H_{39}Cl_2F_3N_6O_2$ 679.603 | 680 | $R_t$: 1.51 min Method A | 6c |
| 23 | 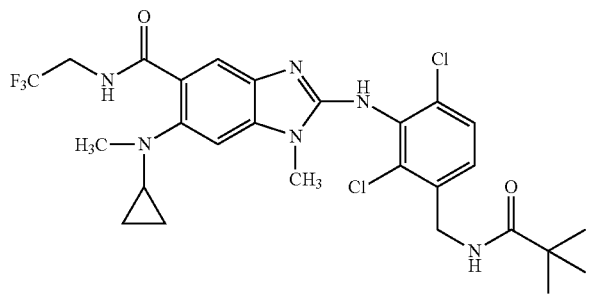 [SMILES: CN(c1cc2c(cc1C(=O)NCC(F)(F)F)nc(Nc1c(Cl)ccc(CNC(=O)C(C)(C)C)c1Cl)n2C)C1CC1] | $C_{27}H_{31}Cl_2F_3N_6O_2$ 599.475 | 599 | $R_t$: 1.43 min Method A | 6c |

-continued

| Ex. | Structure | Formula/Mw. | MS* m/z [M + H]+ | R$_f$(TLC, silica gel) or R$_t$ [min] (HPLC-method) | Prepared in analogy to example |
|---|---|---|---|---|---|
| 24 | 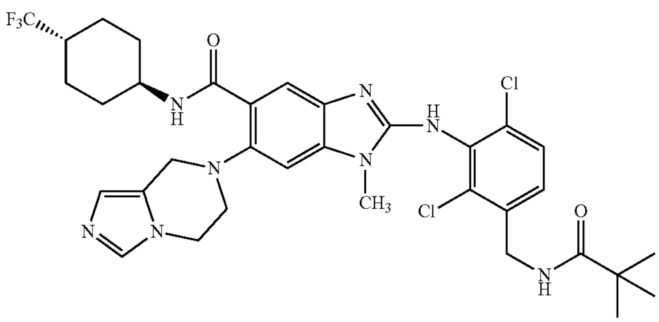 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCn4cncc4C3)cc21] | C$_{34}$H$_{39}$Cl$_2$F$_3$N$_8$O$_2$ 719.627 | 719 | R$_t$: 1.29 min Method A | 6c |
| 25 | 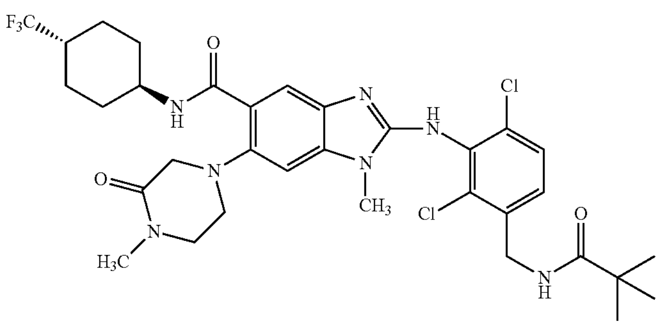 [SMILES: CN1CCN(c2cc3c(cc2C(=O)N[C@H]2CC[C@H](C(F)(F)F)CC2)nc(Nc2c(Cl)ccc(CNC(=O)C(C)(C)C)c2Cl)n3C)CC1=O] | C$_{33}$H$_{40}$Cl$_2$F$_3$N$_7$O$_3$ 710.617 | 711 | R$_t$: 1.40 min Method A | 6c |
| 27 | 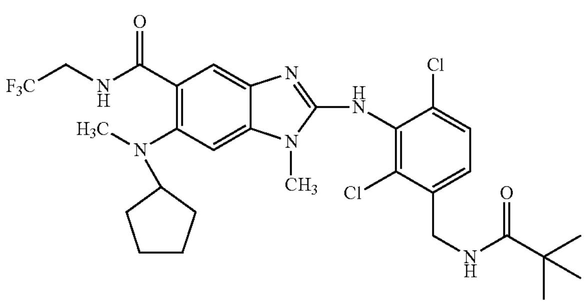 [SMILES: CN(c1cc2c(cc1C(=O)NCC(F)(F)F)nc(Nc1c(Cl)ccc(CNC(=O)C(C)(C)C)c1Cl)n2C)C1CCCC1] | C$_{29}$H$_{35}$Cl$_2$F$_3$N$_6$O$_2$ 627.528 | 627 | R$_t$: 1.44 min Method A | 6c |
| 28 | 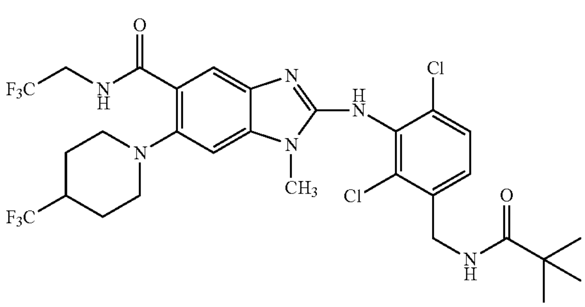 [SMILES: Cn1c(Nc2c(Cl)ccc(CNC(=O)C(C)(C)C)c2Cl)nc2cc(C(=O)NCC(F)(F)F)c(N3CCC(C(F)(F)F)CC3)cc21] | C$_{29}$H$_{32}$Cl$_2$F$_6$N$_6$O$_2$ 681.199 | 681 | R$_t$: 1.48 min Method A | 6c |

-continued

| Ex. | Structure | Formula/ Mw. | MS* m/z [M + H]+ | R<sub>f</sub> (TLC, silica gel) or R<sub>t</sub> [min] (HPLC-method) | Prepared in analogy to example |
|---|---|---|---|---|---|
| 30 | 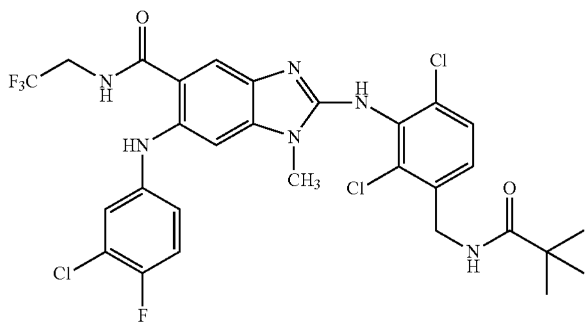 [SMILES: Cn1c(Nc2c(Cl)ccc(CNC(=O)C(C)(C)C)c2Cl)nc2cc(C(=O)NCC(F)(F)F)c(Nc3ccc(F)c(Cl)c3)cc21] | C₂₉H₂₉Cl₃F₄N₆O₂ 673.916 | 673 | R<sub>t</sub>: 1.52 min Method A | 6c |
| 31 | 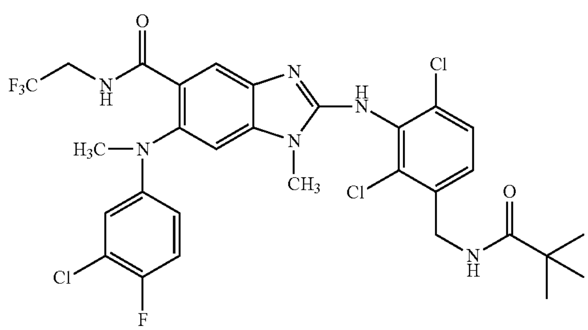 [SMILES: CN(c1ccc(F)c(Cl)c1)c1cc2c(cc1C(=O)NCC(F)(F)F)nc(Nc1c(Cl)ccc(CNC(=O)C(C)(C)C)c1Cl)n2C] | C₃₀H₂₉Cl₃F₄N₆O₂ 687.942 | 687 | R<sub>t</sub>: 1.46 min Method A | 6c |
| 32 | 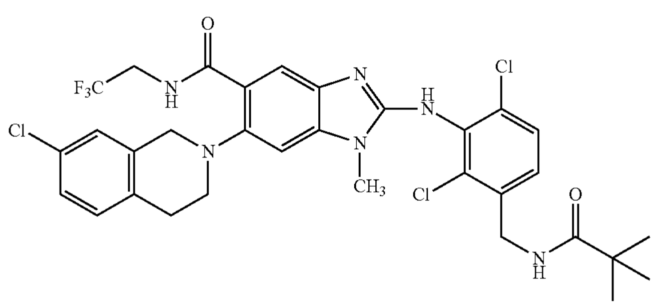 [SMILES: Cn1c(Nc2c(Cl)ccc(CNC(=O)C(C)(C)C)c2Cl)nc2cc(C(=O)NCC(F)(F)F)c(N3CCc4ccc(Cl)cc4C3)cc21] | C₃₃H₃₂Cl₃F₃N₆O₂ 695.989 | 695 | R<sub>t</sub>: 1.63 min Method A | 6c |
| 33 | 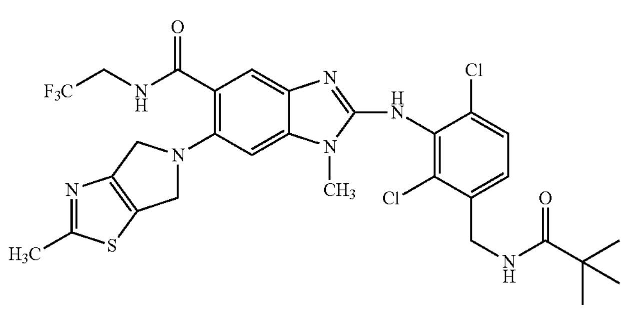 [SMILES: Cc1nc2c(s1)CN(c1cc3c(cc1C(=O)NCC(F)(F)F)nc(Nc1c(Cl)ccc(CNC(=O)C(C)(C)C)c1Cl)n3C)C2] | C₂₉H₃₀Cl₂F₃N₇O₂S 668.561 | 668 | R<sub>t</sub>: 1.34 min Method A | 6c |

-continued

| Ex. | Structure | Formula/Mw. | MS* m/z [M+H]+ | $R_f$(TLC, silica gel) or $R_t$ [min] (HPLC-method) | Prepared in analogy to example |
|---|---|---|---|---|---|
| 34 | 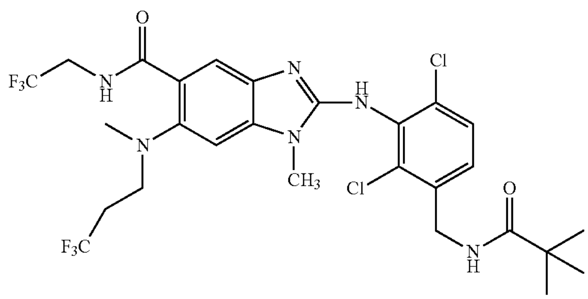 [SMILES: CN(CCC(F)(F)F)c1cc2c(cc1C(=O)NCC(F)(F)F)nc(Nc1c(Cl)ccc(CNC(=O)C(C)(C)C)c1Cl)n2C] | $C_{27}H_{30}Cl_2F_6N_6O_2$ 655.462 | 655 | $R_t$: 1.45 min Method A | 6c |
| 36 | 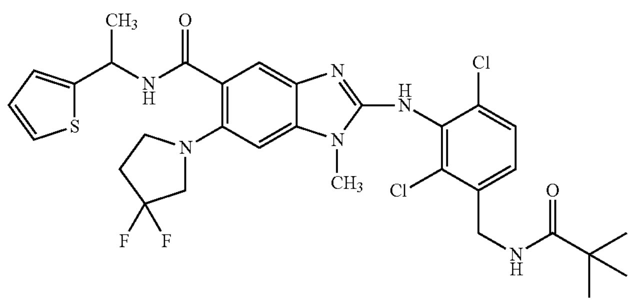 [SMILES: CC(NC(=O)c1cc2nc(Nc3c(Cl)ccc(CNC(=O)C(C)(C)C)c3Cl)n(C)c2cc1N1CCC(F)(F)C1)c1cccs1] | $C_{31}H_{34}Cl_2F_2N_6O_2S$ 663.618 | 663 | $R_t$: 0.57 min Method F | 35 |
| 37 | 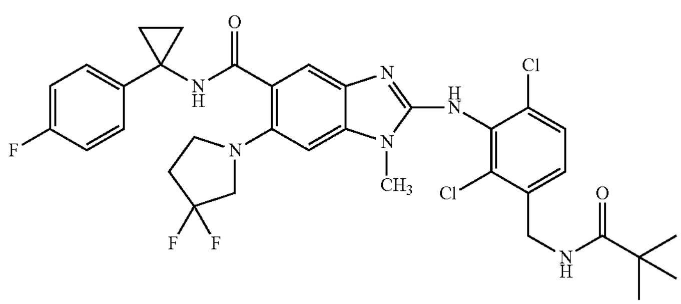 [SMILES: Cn1c(Nc2c(Cl)ccc(CNC(=O)C(C)(C)C)c2Cl)nc2cc(C(=O)NC3(c4ccc(F)cc4)CC3)c(N3CCC(F)(F)C3)cc21] | $C_{34}H_{35}Cl_2F_3N_6O_2$ 687.591 | 687 | $R_t$: 0.58 min Method F | 35 |
| 38 | 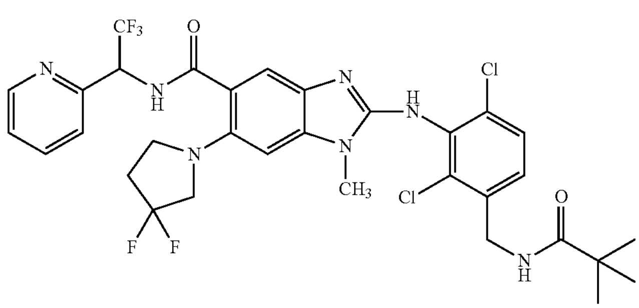 [SMILES: Cn1c(Nc2c(Cl)ccc(CNC(=O)C(C)(C)C)c2Cl)nc2cc(C(=O)NC(c3ccccn3)C(F)(F)F)c(N3CCC(F)(F)C3)cc21] | $C_{32}H_{32}Cl_2F_5N_7O_2$ 712.548 | 712 | $R_t$: 0.58 min Method F | 35 |

-continued
| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 39 | 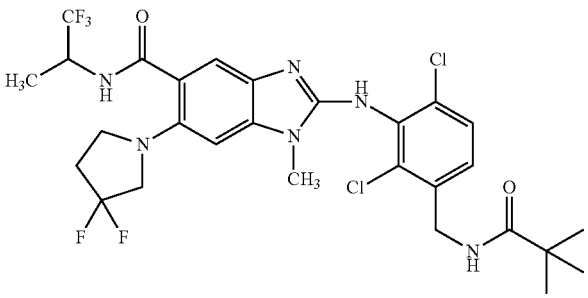 [SMILES: CC(NC(=O)c1cc2nc(Nc3c(Cl)ccc(CNC(=O)C(C)(C)C)c3Cl)n(C)c2cc1N1CCC(F)(F)C1)C(F)(F)F] | C28H31Cl2F5N6O2 649.489 | 649 | R_t: 0.57 min Method F | 35 |
| 40 | 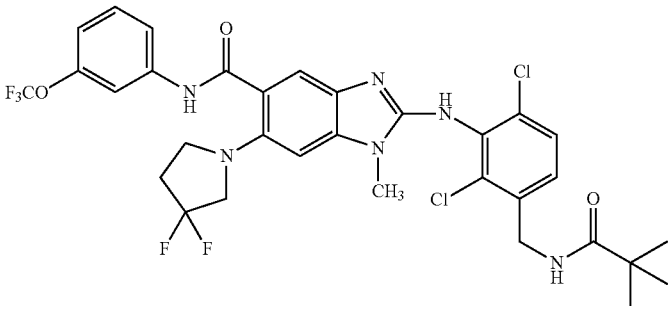 [SMILES: Cn1c(Nc2c(Cl)ccc(CNC(=O)C(C)(C)C)c2Cl)nc2cc(C(=O)Nc3cccc(OC(F)(F)F)c3)c(N3CCC(F)(F)C3)cc21] | C32H31Cl2F5N6O3 713.532 | 713 | R_t: 0.61 min Method F | 35 |
| 41 | 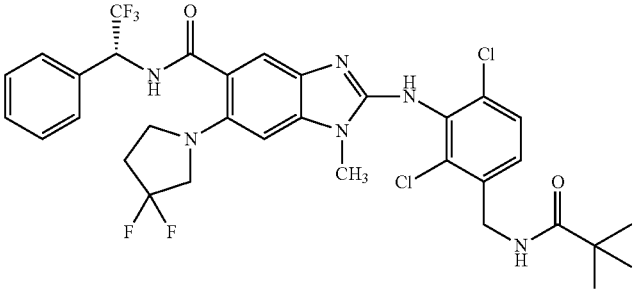 [SMILES: Cn1c(Nc2c(Cl)ccc(CNC(=O)C(C)(C)C)c2Cl)nc2cc(C(=O)N[C@H](c3ccccc3)C(F)(F)F)c(N3CCC(F)(F)C3)cc21] | C33H33Cl2F5N6O2 711.56 | 711 | R_t: 0.59 min Method F | 35 |
| 42 | 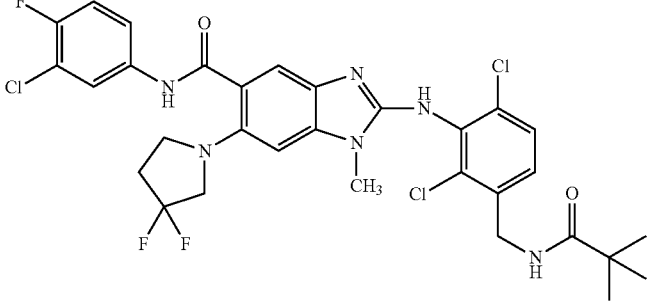 | C31H30Cl3F3N6O2 681.971 | 681 | R_t: 0.60 min Method F | 35 |

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 43 | 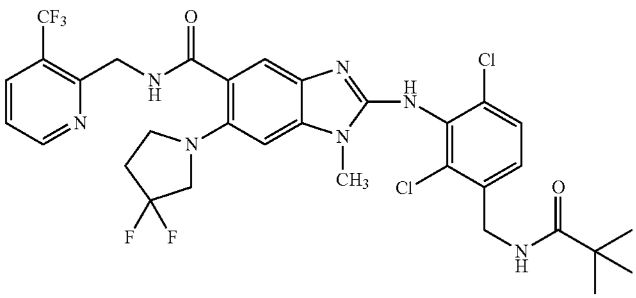 [SMILES: Cn1c(Nc2c(Cl)ccc(CNC(=O)C(C)(C)C)c2Cl)nc2cc(C(=O)NCc3ncccc3C(F)(F)F)c(N3CCC(F)(F)C3)cc21] | C₃₂H₃₂Cl₂F₅N₇O₂ 712.548 | 712 | R_t: 0.57 min Method F | 35 |
| 44 | 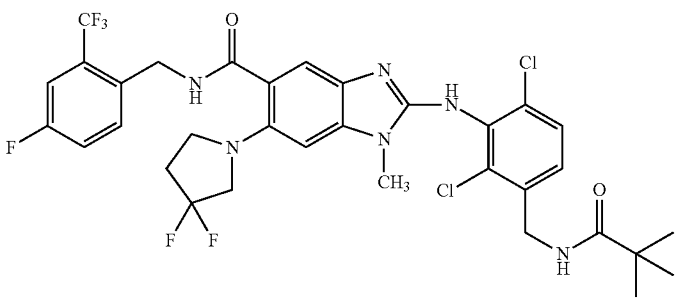 [SMILES: Cn1c(Nc2c(Cl)ccc(CNC(=O)C(C)(C)C)c2Cl)nc2cc(C(=O)NCc3ccc(F)cc3C(F)(F)F)c(N3CCC(F)(F)C3)cc21] | C₃₃H₃₂Cl₂F₆N₆O₂ 729.55 | 729 | R_t: 0.59 min Method F | 35 |
| 45 | 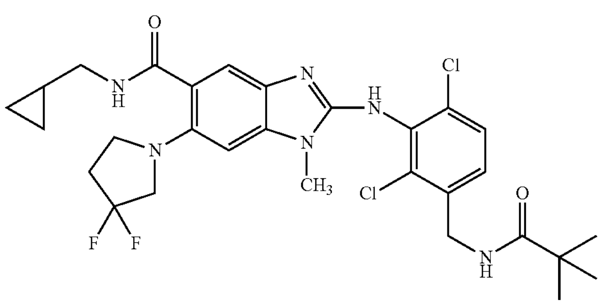 [SMILES: Cn1c(Nc2c(Cl)ccc(CNC(=O)C(C)(C)C)c2Cl)nc2cc(C(=O)NCC3CC3)c(N3CCC(F)(F)C3)cc21] | C₂₉H₃₄Cl₂F₂N₆O₂ 607.53 | 607 | R_t: 0.56 min Method F | 35 |
| 46 | 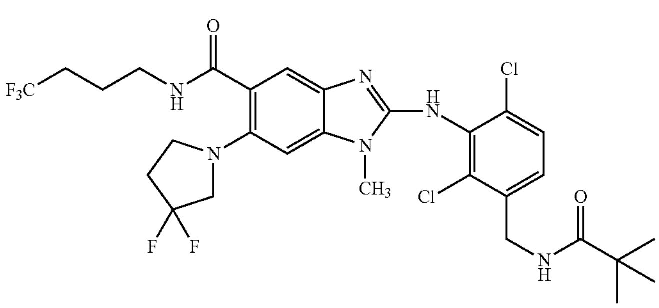 [SMILES: Cn1c(Nc2c(Cl)ccc(CNC(=O)C(C)(C)C)c2Cl)nc2cc(C(=O)NCCCC(F)(F)F)c(N3CCC(F)(F)C3)cc21] | C₂₉H₃₃Cl₂F₅N₆O₂ 663.516 | 663 | R_t: 0.56 min Method F | 35 |

-continued
| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 47 | 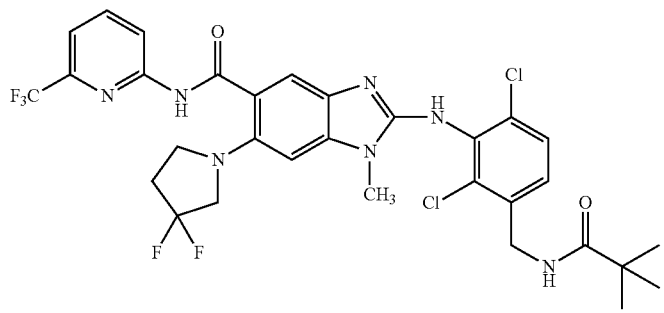 [SMILES: Cn1c(Nc2c(Cl)ccc(CNC(=O)C(C)(C)C)c2Cl)nc2cc(C(=O)Nc3cccc(C(F)(F)F)n3)c(N3CCC(F)(F)C3)cc21] | C_{31}H_{30}Cl_2F_5N_7O_2 698.521 | 698 | R_t: 0.6 min Method F | 35 |
| 48 | 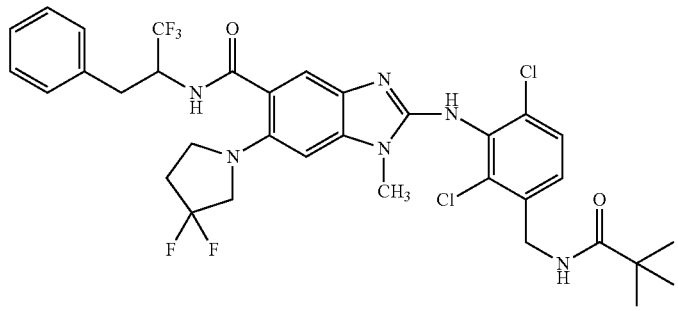 [SMILES: Cn1c(Nc2c(Cl)ccc(CNC(=O)C(C)(C)C)c2Cl)nc2cc(C(=O)NC(Cc3ccccc3)C(F)(F)F)c(N3CCC(F)(F)C3)cc21] | C_{34}H_{35}Cl_2F_5N_6O_2 725.587 | 725 | R_t: 0.60 min Method F | 35 |
| 49 | 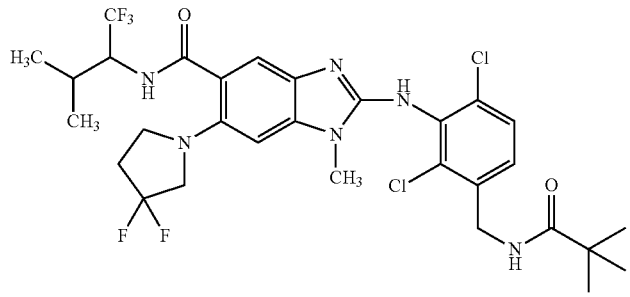 [SMILES: CC(C)C(NC(=O)c1cc2nc(Nc3c(Cl)ccc(CNC(=O)C(C)(C)C)c3Cl)n(C)c2cc1N1CCC(F)(F)C1)C(F)(F)F] | C_{30}H_{35}Cl_2F_5N_6O_2 677.543 | 677 | R_t: 0.59 min Method F | 35 |
| 50 | 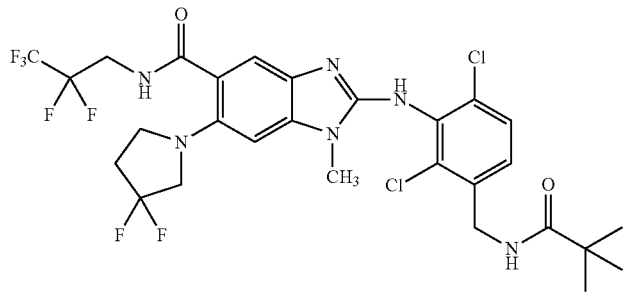 [SMILES: Cn1c(Nc2c(Cl)ccc(CNC(=O)C(C)(C)C)c2Cl)nc2cc(C(=O)NCC(F)(F)C(F)(F)F)c(N3CCC(F)(F)C3)cc21] | C_{28}H_{29}Cl_2F_7N_6O_2 685.469 | 685 | R_t: 0.57 min Method F | 35 |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 51 | 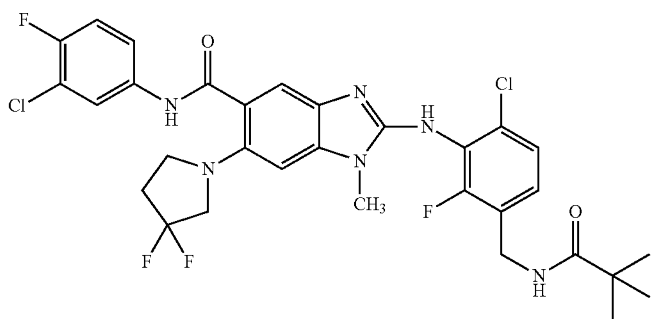 [SMILES: Cn1c(Nc2c(Cl)ccc(CNC(=O)C(C)(C)C)c2F)nc2cc(C(=O)Nc3ccc(F)c(Cl)c3)c(N3CCC(F)(F)C3)cc21] | C31H30Cl2F4N6O2 665.508 | 665 | R_t: 1.53 min Method A | 1e |
| 53 | 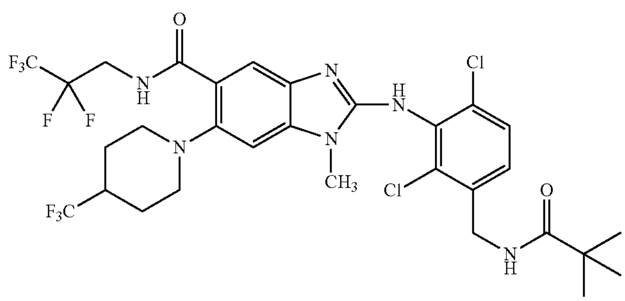 | C30H32Cl2F8N6O2 731.513 | 731 | R_f = 0.50 PE/EtOAc 1:1 | 52e |
| 55 | 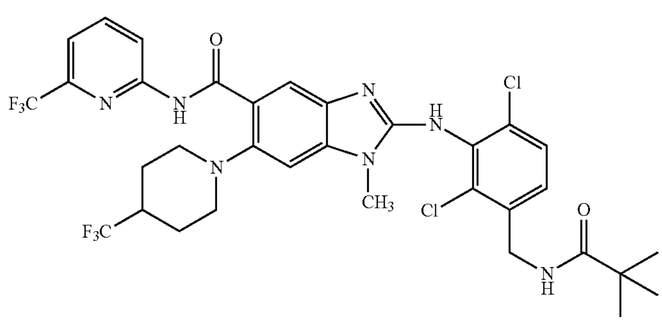 [SMILES: Cn1c(Nc2c(Cl)ccc(CNC(=O)C(C)(C)C)c2Cl)nc2cc(C(=O)Nc3cccc(C(F)(F)F)n3)c(N3CCC(C(F)(F)F)CC3)cc21] | C33H33Cl2F6N7O2 744.565 | 744 | R_t: 1.82 min Method G | 54 |
| 56 | 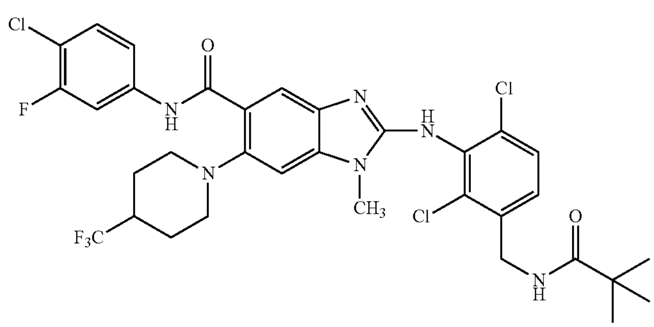 [SMILES: Cn1c(Nc2c(Cl)ccc(CNC(=O)C(C)(C)C)c2Cl)nc2cc(C(=O)Nc3ccc(Cl)c(F)c3)c(N3CCC(C(F)(F)F)CC3)cc21] | C33H33Cl3F4N6O2 728.015 | 727 | R_t: 1.85 min Method G | 54 |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 57 | 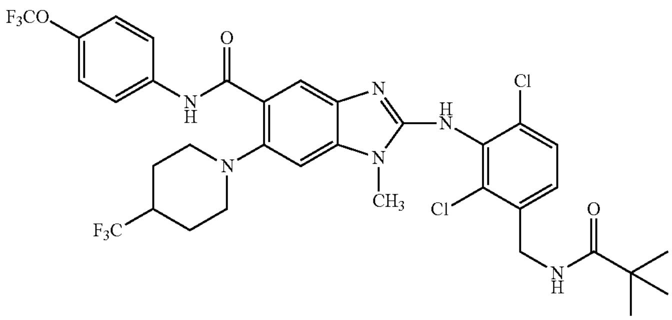 [SMILES: Cn1c(Nc2c(Cl)ccc(CNC(=O)C(C)(C)C)c2Cl)nc2cc(C(=O)Nc3ccc(OC(F)(F)F)cc3)c(N3CCC(C(F)(F)F)CC3)cc21] | $C_{34}H_{34}Cl_2F_6N_6O_3$ 759.576 | 759 | $R_t$: 1.83 min Method G | 54 |
| 58 | 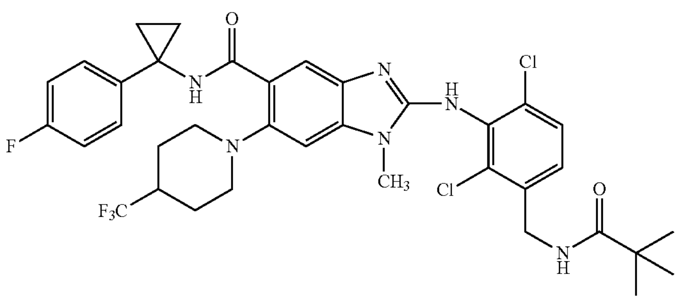 [SMILES: Cn1c(Nc2c(Cl)ccc(CNC(=O)C(C)(C)C)c2Cl)nc2cc(C(=O)NC3(c4ccc(F)cc4)CC3)c(N3CCC(C(F)(F)F)CC3)cc21] | $C_{36}H_{38}Cl_2F_4N_6O_2$ 733.634 | 733 | $R_t$: 1.72 min Method G | 54 |
| 59 | 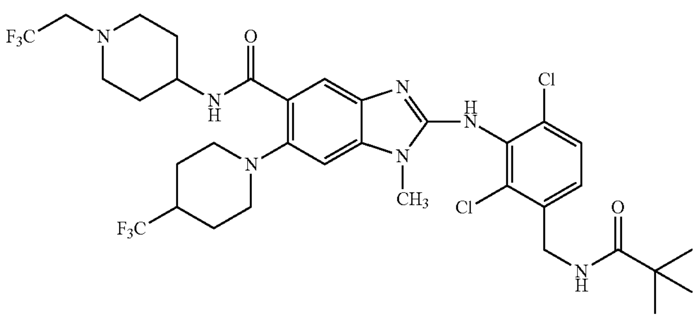 [SMILES: Cn1c(Nc2c(Cl)ccc(CNC(=O)C(C)(C)C)c2Cl)nc2cc(C(=O)NC3CCN(CC(F)(F)F)CC3)c(N3CCC(C(F)(F)F)CC3)cc21] | $C_{34}H_{41}Cl_2F_6N_7O_2$ 764.639 | 764 | $R_t$: 1.63 min Method G | 54 |
| 60 | 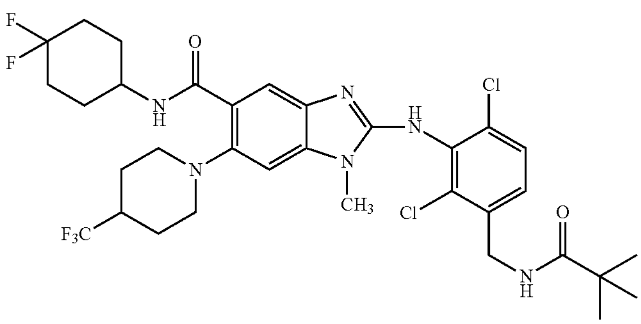 [SMILES: Cn1c(Nc2c(Cl)ccc(CNC(=O)C(C)(C)C)c2Cl)nc2cc(C(=O)NC3CCC(F)(F)CC3)c(N3CCC(C(F)(F)F)CC3)cc21] | $C_{33}H_{39}Cl_2F_5N_6O_2$ 717.607 | 717 | $R_t$: 1.67 min Method G | 54 |

-continued

| Ex. | Structure | Formula/Mw. | MS* m/z [M + H]+ | $R_f$(TLC, silica gel) or $R_t$ [min] (HPLC-method) | Prepared in analogy to example |
|---|---|---|---|---|---|
| 61 | 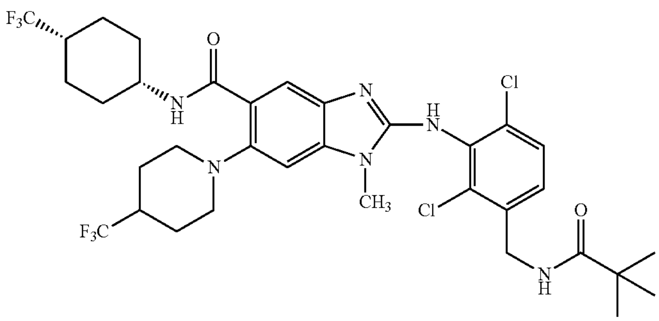 [SMILES: Cn1c(Nc2c(Cl)ccc(CNC(=O)C(C)(C)C)c2Cl)nc2cc(C(=O)N[C@H]3CC[C@@H](C(F)(F)F)CC3)c(N3CCC(C(F)(F)F)CC3)cc21] | $C_{34}H_{40}Cl_2F_6N_6O_2$ 749.624 | 749 | $R_t$: 1.73 min Method G | 54 |
| 62 | 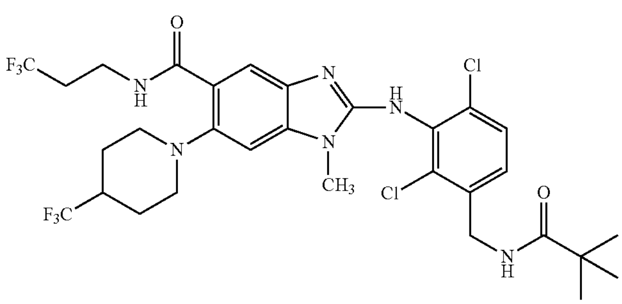 [SMILES: Cn1c(Nc2c(Cl)ccc(CNC(=O)C(C)(C)C)c2Cl)nc2cc(C(=O)NCCC(F)(F)F)c(N3CCC(C(F)(F)F)CC3)cc21] | $C_{30}H_{34}Cl_2F_6N_6O_2$ 695.533 | 695 | $R_t$: 1.64 min Method G | 54 |
| 63 | 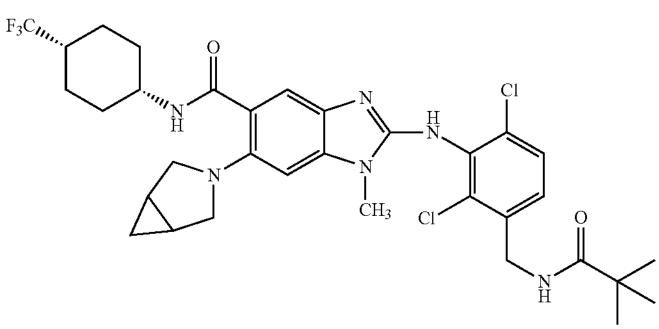 [SMILES: Cn1c(Nc2c(Cl)ccc(CNC(=O)C(C)(C)C)c2Cl)nc2cc(C(=O)N[C@H]3CC[C@@H](C(F)(F)F)CC3)c(N3CC4CC4C3)cc21] | $C_{33}H_{39}Cl_2F_3N_6O_2$ 679.611 | 679 | $R_t$: 1.62 min Method G | 54 |
| 64 | 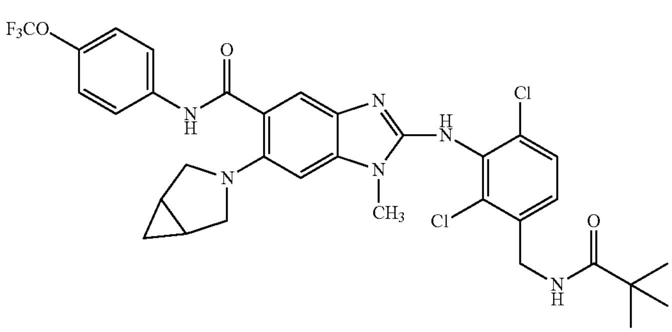 [SMILES: Cn1c(Nc2c(Cl)ccc(CNC(=O)C(C)(C)C)c2Cl)nc2cc(C(=O)Nc3ccc(OC(F)(F)F)cc3)c(N3CC4CC4C3)cc21] | $C_{33}H_{33}Cl_2F_3N_6O_3$ 689.563 | 689 | $R_t$: 1.62 min Method G | 54 |

-continued

| Ex. | Structure | Formula/ Mw. | MS* m/z [M + H]⁺ | R_f (TLC, silica gel) or R_t [min] (HPLC-method) | Prepared in analogy to example |
|---|---|---|---|---|---|
| 65 | 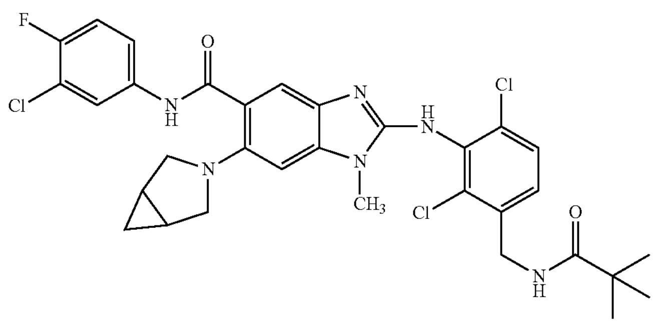 [SMILES: Cn1c(Nc2c(Cl)ccc(CNC(=O)C(C)(C)C)c2Cl)nc2cc(C(=O)Nc3ccc(F)c(Cl)c3)c(N3CC4CC4C3)cc21] | $C_{32}H_{32}Cl_3FN_6O_2$ 658.002 | 657 | R_t: 1.67 min Method G | 54 |
| 66 | 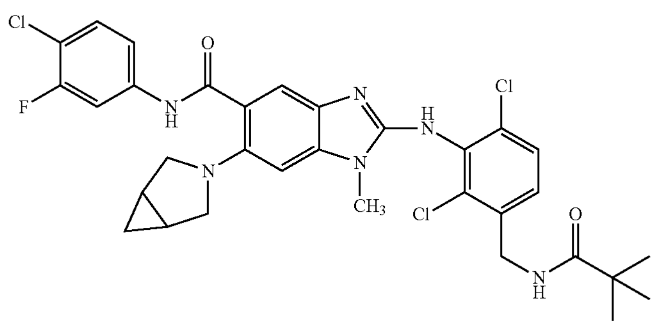 [SMILES: Cn1c(Nc2c(Cl)ccc(CNC(=O)C(C)(C)C)c2Cl)nc2cc(C(=O)Nc3ccc(Cl)c(F)c3)c(N3CC4CC4C3)cc21] | $C_{32}H_{32}Cl_3FN_6O_2$ 658.002 | 657 | R_t: 1.67 min Method G | 52e |
| 67 | 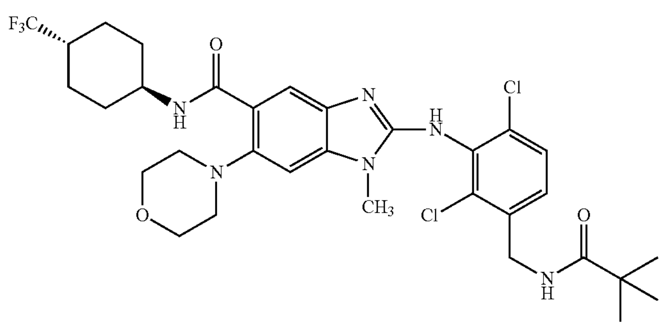 | $C_{32}H_{39}Cl_2F_3N_6O_3$ 683.599 | 683 | R_f = 0.19 PE/EtOAc 1:1 | 52e |
| 68 | 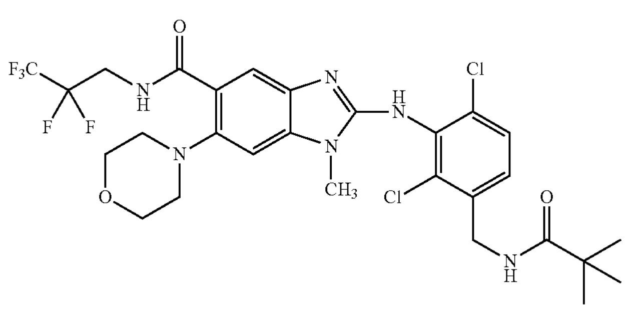 [SMILES: Cn1c(Nc2c(Cl)ccc(CNC(=O)C(C)(C)C)c2Cl)nc2cc(C(=O)NCC(F)(F)C(F)(F)F)c(N3CCOCC3)cc21] | $C_{28}H_{31}Cl_2F_5N_6O_3$ 665.488 | 665 | R_f = 0.22 PE/EtOAc 1:1 | 52e |

| Ex. | Structure | Formula/Mw. | MS* m/z [M + H]+ | R_f (TLC, silica gel) or R_t [min] (HPLC-method) | Prepared in analogy to example |
|---|---|---|---|---|---|
| 69 | 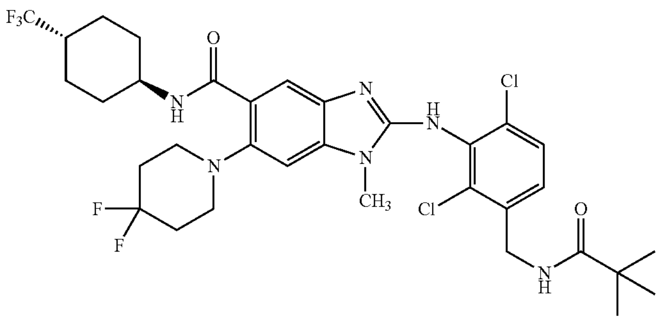 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(F)(F)CC3)cc21] | C₃₃H₃₉Cl₂F₅N₆O₂ 717.607 | 717 | R_f = 0.44 PE/EtOAc 1:1 | 52e |
| 70 | 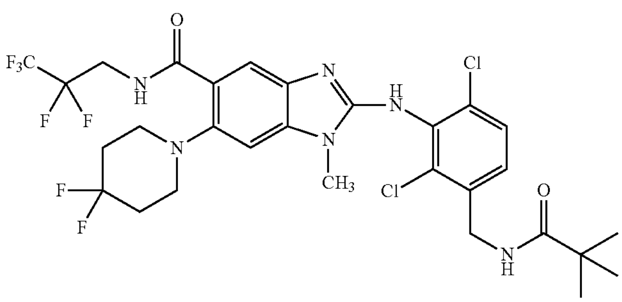 [SMILES: Cn1c(Nc2c(Cl)ccc(CNC(=O)C(C)(C)C)c2Cl)nc2cc(C(=O)NCC(F)(F)C(F)(F)F)c(N3CCC(F)(F)CC3)cc21] | C₂₉H₃₁Cl₂F₇N₆O₂ 699.496 | 699 | R_f = 0.63 PE/EtOAc 1:1 | 52e |
| 72 | 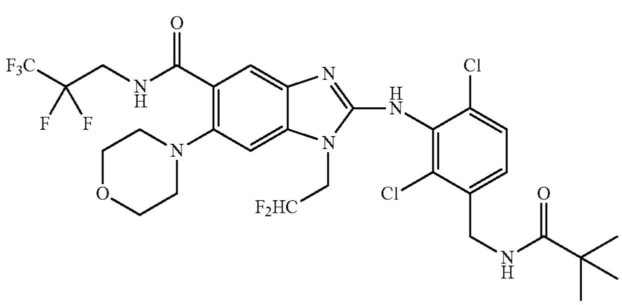 [SMILES: CC(C)(C)C(=O)NCc1ccc(Cl)c(Nc2nc3cc(C(=O)NCC(F)(F)C(F)(F)F)c(N4CCOCC4)cc3n2CC(F)F)c1Cl] | C₂₉H₃₁Cl₂F₇N₆O₃ 715.50 | 716 | R_f = 0.32 PE/EtOAc 1:1 | 71f |
| 73 | 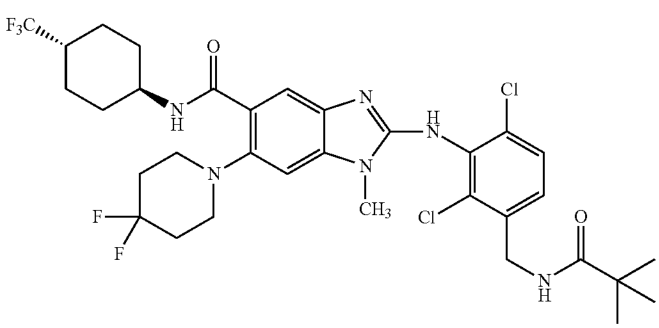 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(F)(F)CC3)cc21] | C₃₄H₃₉Cl₂F₇N₆O₂ 767.62 | 767 | R_f = 0.13 PE/EtOAc 1:1 | 71f |

-continued
| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 74 | 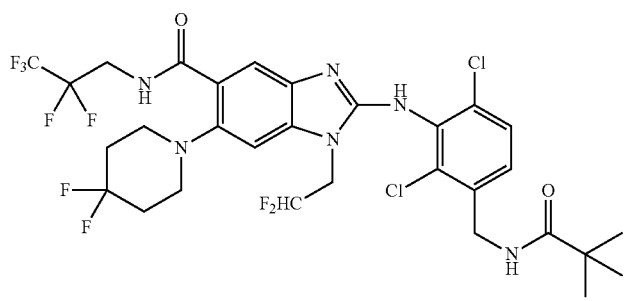 [SMILES: CC(C)(C)C(=O)NCc1ccc(Cl)c(Nc2nc3cc(C(=O)NCC(F)(F)C(F)(F)F)c(N4CCC(F)(F)CC4)cc3n2CC(F)F)c1Cl] | $C_{30}H_{31}Cl_2F_9N_6O_2$ 749.51 | 749 | $R_f$ = 0.30 PE/EtOAc 1:1 | 71f |
| 75 | 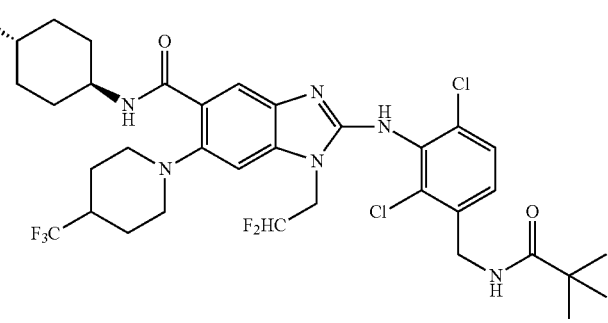 | $C_{35}H_{40}Cl_2F_8N_6O_2$ 799.63 | 799 | | 71f |
| 76 | 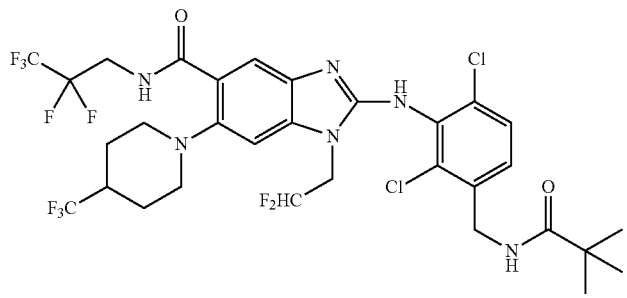 [SMILES: CC(C)(C)C(=O)NCc1ccc(Cl)c(Nc2nc3cc(C(=O)NCC(F)(F)C(F)(F)F)c(N4CCC(C(F)(F)F)CC4)cc3n2CC(F)F)c1Cl] | $C_{31}H_{32}Cl_2F_{10}N_6O_2$ 781.52 | 781 | $R_f$ = 0.28 PE/EtOAc 1:1 | 71f |
| 78 | 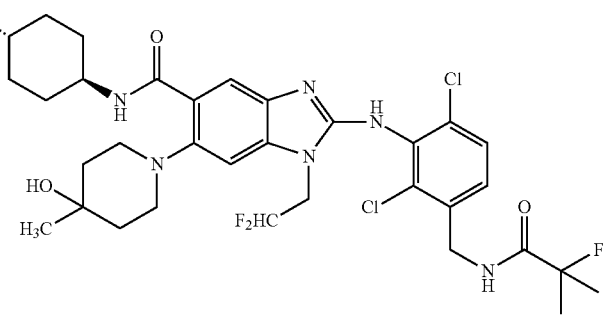 | $C_{34}H_{40}Cl_2F_6N_6O_3$ 765.62 | 765 | $R_t$: 1.66 min Method I | 77e |

| Ex. | Structure | Formula/Mw. | MS* m/z [M + H]+ | R_f (TLC, silica gel) or R_t [min] (HPLC-method) | Prepared in analogy to example |
|---|---|---|---|---|---|
| 79 | 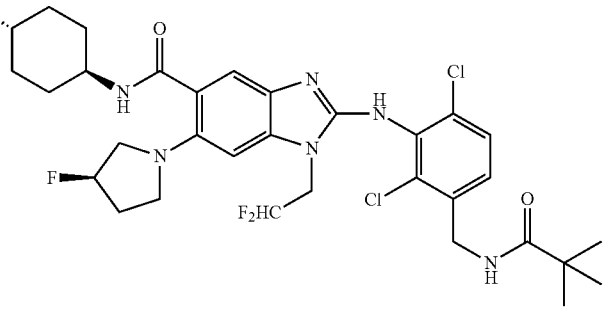 | C₃₃H₃₈Cl₂F₆N₆O₂ 735.59 | 736 | R_t: 1.52 min Method A | 77e |
| 80 | 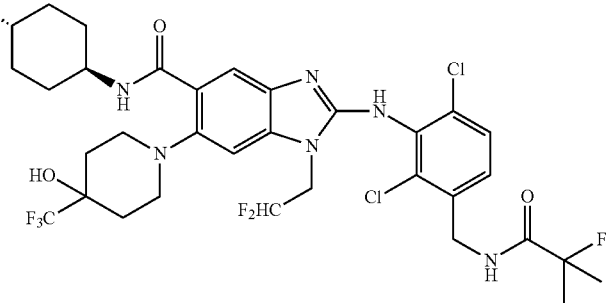 | C₃₄H₃₇Cl₂F₉N₆O₃ 819.59 | 819 | R_t: 1.69 min Method I | 77e |
| 82 | 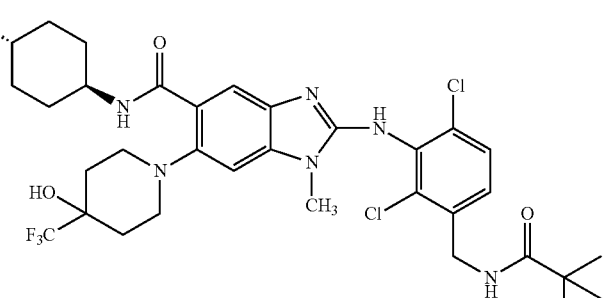 | C₃₄H₄₀Cl₂F₆N₆O₃ 765.62 | 765 | R_f = 0.29 DCM/ EtOH 95:5 | 1e |
| 83 | 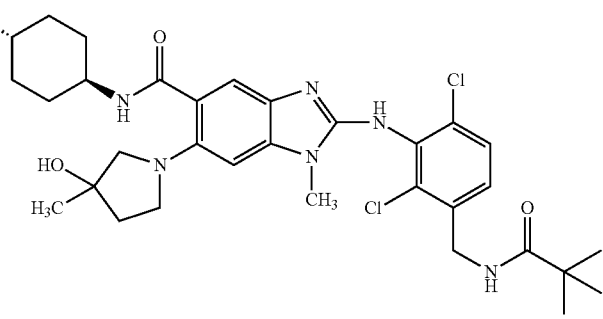 | C₃₃H₄₁Cl₂F₃N₆O₃ 697.62 | 697 | R_f = 0.22 DCM/ EtOH 95:5 | 1e |

| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 84 | 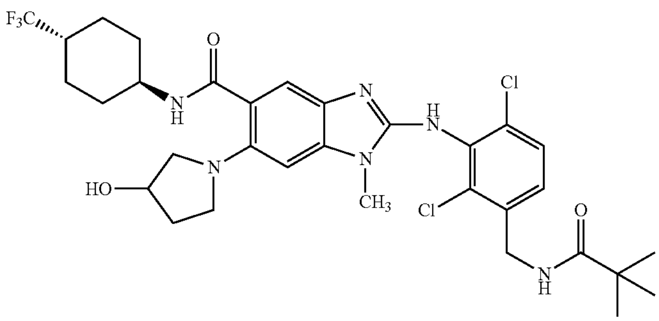 | $C_{32}H_{39}Cl_2F_3N_6O_3$ 683.59 | 683 | $R_t$: 1.43 min Method A | 6c |
| 85 | 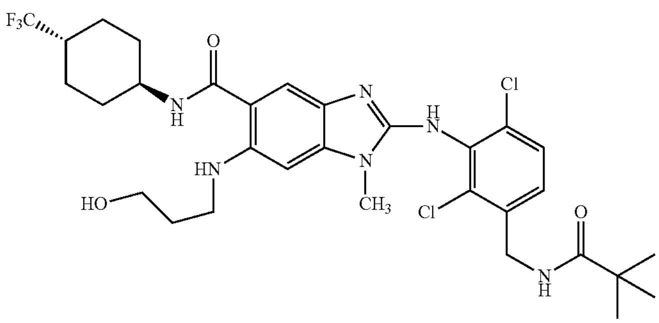 [SMILES: Cn1c(Nc2c(Cl)ccc(CNC(=O)C(C)(C)C)c2Cl)nc2cc(C(=O)N[C@H]3CC[C@H](C(F)(F)F)CC3)c(NCCCO)cc21] | $C_{31}H_{39}Cl_2F_3N_6O_3$ 671.58 | 671 | $R_t$: 1.43 min Method A | 6c |
| 86 | 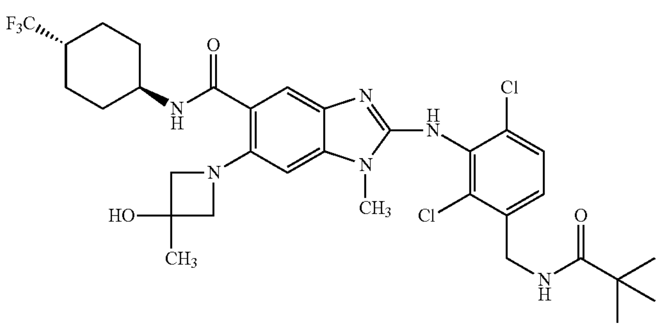 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(C)(O)C3)cc21] | $C_{32}H_{39}Cl_2F_3N_6O_3$ 683.59 | 683 | $R_t$: 1.40 min Method A | 6c |
| 87 | 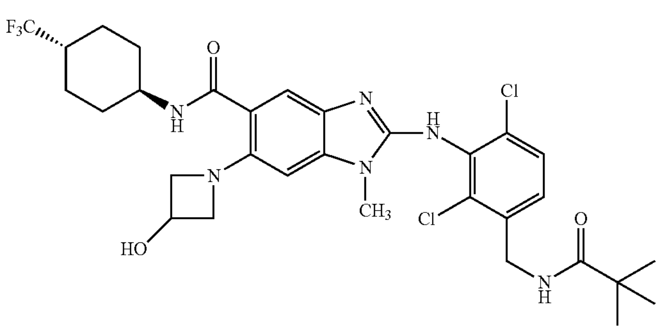 | $C_{31}H_{37}Cl_2F_3N_6O_3$ 669.57 | 669 | $R_t$: 1.55 min Method A | 1e |

| Ex. | Structure | Formula/ Mw. | MS* m/z [M + H]⁺ | R_f(TLC, silica gel) or R_t [min] (HPLC-method) | Prepared in analogy to example |
|---|---|---|---|---|---|
| 88 | 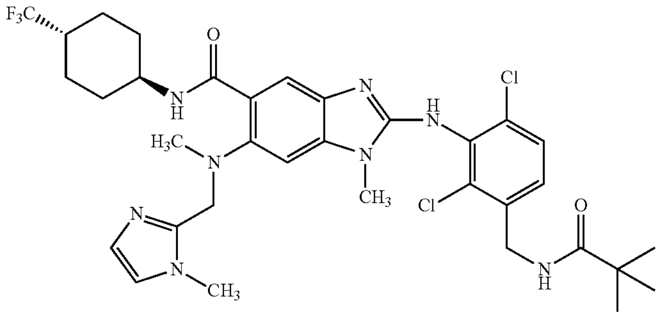 [SMILES: CN(Cc1nccn1C)c1cc2c(cc1C(=O)N[C@H]1CC[C@H](C(F)(F)F)CC1)nc(Nc1c(Cl)ccc(CNC(=O)C(C)(C)C)c1Cl)n2C] | C₃₄H₄₁Cl₂F₃N₈O₂ 721.64 | 721 | R_f = 0.06 DCM/ EtOH 95:5 | 1e |
| 89 | 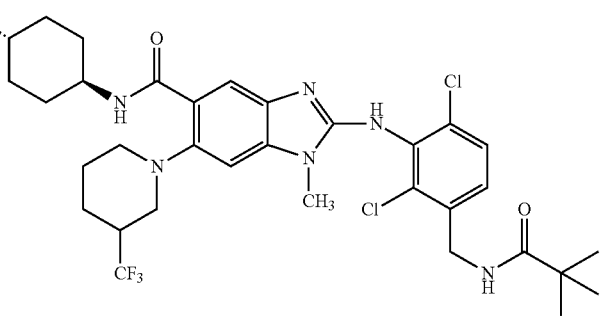 | C₃₄H₄₀Cl₂F₆N₆O₂ 749.62 | 749 | R_t: 1.59 min Method A | 6c |
| 90 | 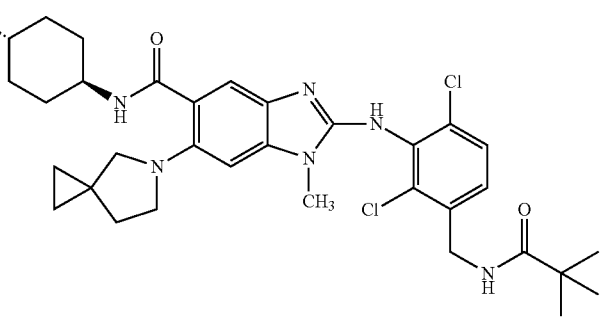 | C₃₄H₄₁Cl₂F₃N₆O₂ 693.63 | 693 | R_t: 1.52 min Method A | 6c |
| 91 | 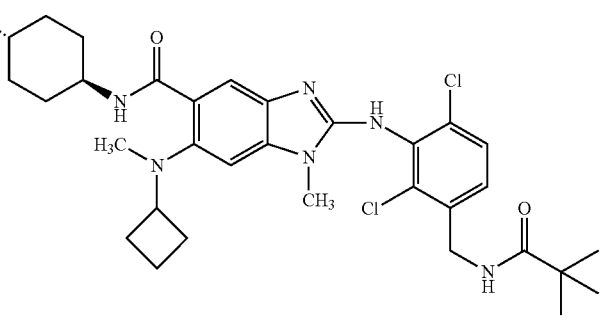 | C₃₃H₄₁Cl₂F₃N₆O₂ 681.62 | 681 | R_t: 1.52 min Method A | 6c |

| Ex. | Structure | Formula/ Mw. | MS* m/z [M + H]+ | R$_f$ (TLC, silica gel) or R$_t$ [min] (HPLC-method) | Prepared in analogy to example |
|---|---|---|---|---|---|
| 92 | 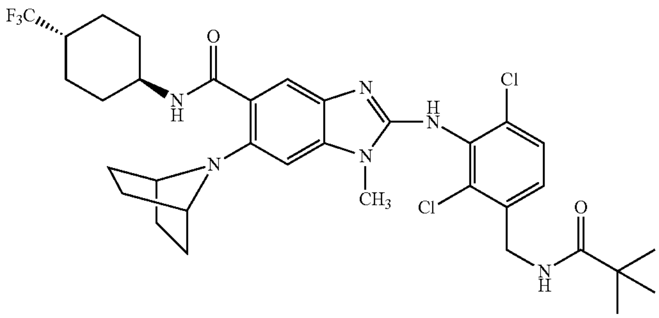 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3C4CCC3CC4)cc21] | C$_{34}$H$_{41}$Cl$_2$F$_3$N$_6$O$_2$ 693.63 | 693 | R$_t$: 1.51 min Method A | 6c |
| 93 | 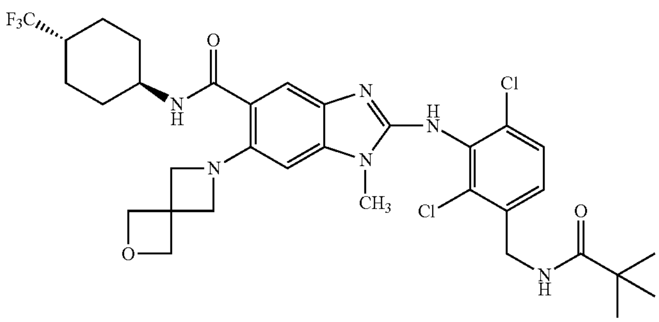 | C$_{33}$H$_{39}$Cl$_2$F$_3$N$_6$O$_3$ 695.60 | 695 | R$_t$: 1.39 min Method A | 6c |
| 94 | 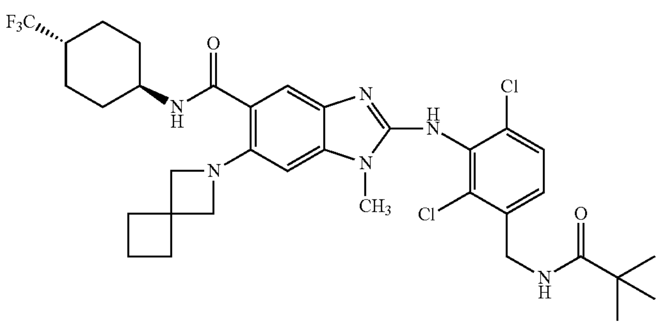 | C$_{34}$H$_{41}$Cl$_2$F$_3$N$_6$O$_2$ 693.63 | 693 | R$_t$: 1.52 min Method A | 6c |
| 95 | 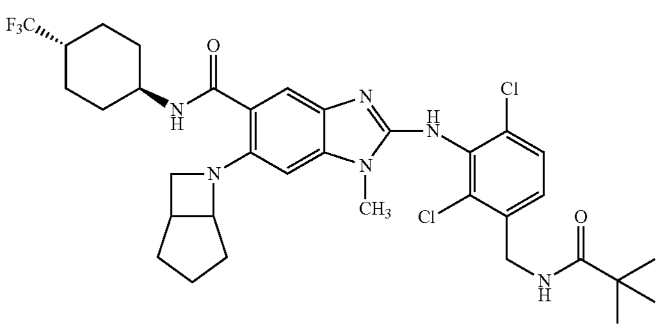 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCCC43)cc21] | C$_{34}$H$_{41}$Cl$_2$F$_3$N$_6$O$_2$ 693.63 | 693 | R$_t$: 1.51 min Method A | 1e |

| Ex. | Structure | Formula/Mw. | MS* m/z [M+H]+ | R_f (TLC, silica gel) or R_t [min] (HPLC-method) | Prepared in analogy to example |
|---|---|---|---|---|---|
| 96 | 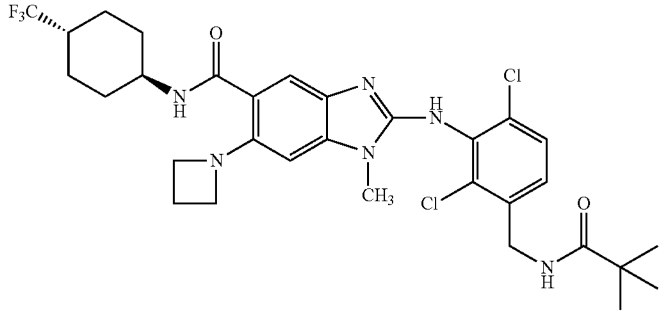 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC3)cc21] | C31H37Cl2F3N6O2 653.57 | 653 | R_t: 1.63 min Method I | 1e |
| 97 | 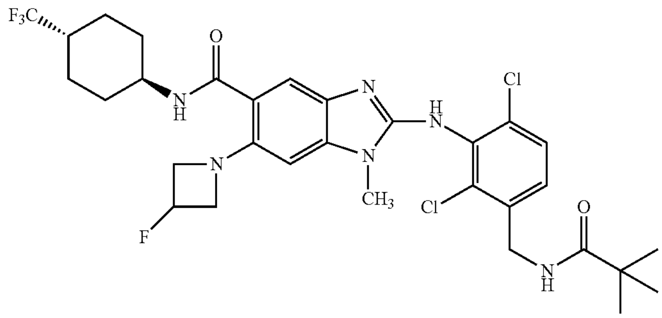 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(F)C3)cc21] | C31H36Cl2F4N6O2 671.56 | 671 | R_t: 1.42 min Method A | 6c |
| 98 | 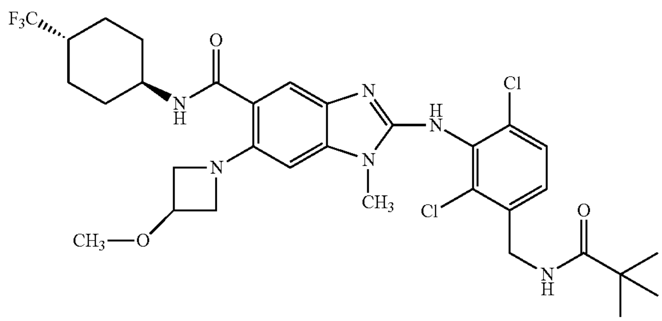 | C32H39Cl2F3N6O3 683.59 | 683 | R_t: 1.42 min Method A | 6c |
| 99 | 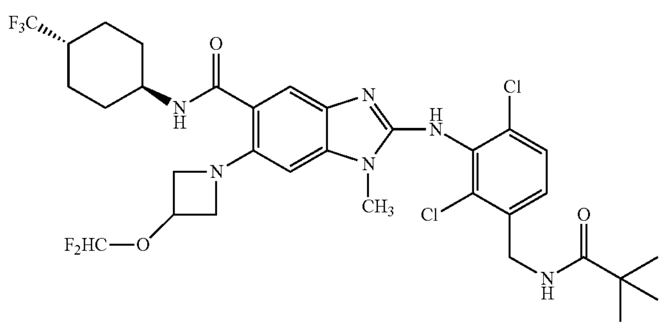 | C32H37Cl2F5N6O3 719.57 | 719 | R_t: 1.42 min Method H | 6c |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 100 | 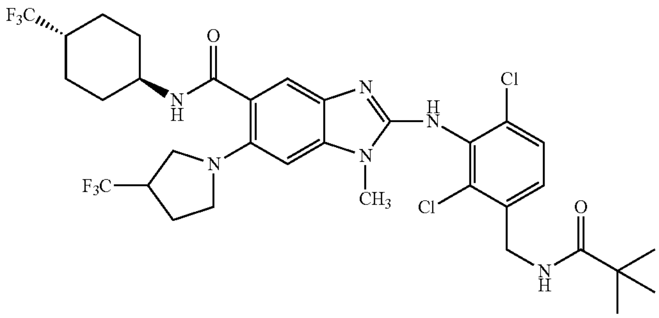 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(C(F)(F)F)C3)cc21] | C33H38Cl2F6N6O2 735.59 | 735 | R_t: 1.18 min Method I | 6c |
| 101 | 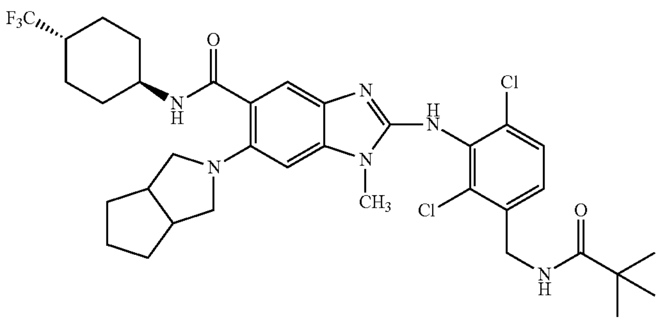 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCCC4C3)cc21] | C35H43Cl2F3N6O2 707.66 | 707 | R_t: 1.58 min Method A | 1e |
| 102 | 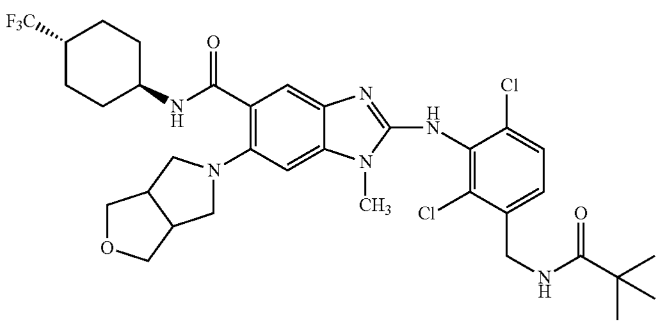 | C35H41Cl2F3N6O3 709.63 | 709 | R_t: 1.41 min Method H | 26e |
| 104 | 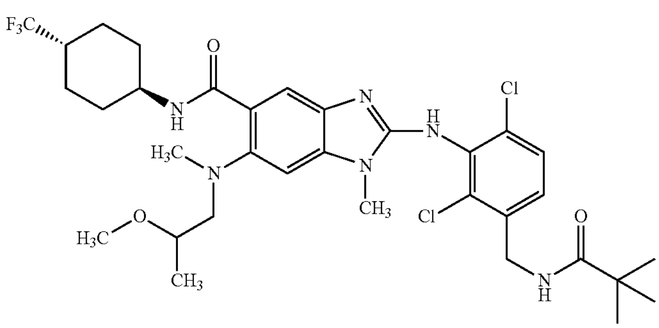 [SMILES: COC(C)CN(C)c1cc2c(cc1C(=O)N[C@H]1CC[C@H](C(F)(F)F)CC1)nc(Nc1c(Cl)ccc(CNC(=O)C(C)(C)C)c1Cl)n2C] | C33H43Cl2F3N6O3 699.63 | 699 | R_t: 1.49 min Method A | 1e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 105 | 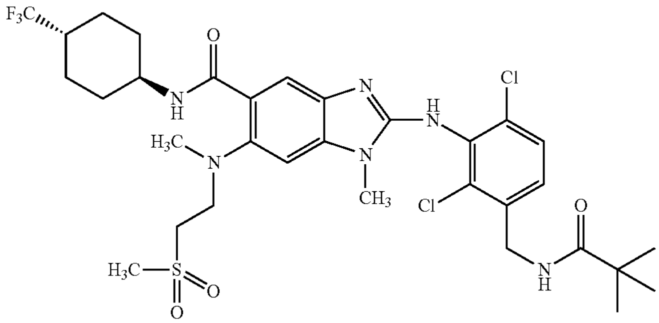 [SMILES: CN(CCS(C)(=O)=O)c1cc2c(cc1C(=O)N[C@H]1CC[C@H](C(F)(F)F)CC1)nc(Nc1c(Cl)ccc(CNC(=O)C(C)(C)C)c1Cl)n2C] | C₃₂H₄₁Cl₂F₃N₆O₄S 733.67 | 733 | R_t: 1.58 min Method I | 6c |
| 106 | 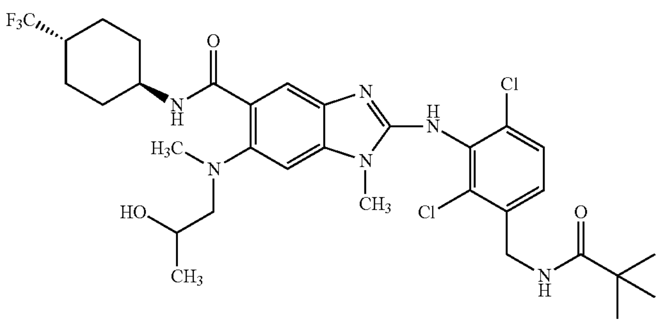 [SMILES: CC(O)CN(C)c1cc2c(cc1C(=O)N[C@H]1CC[C@H](C(F)(F)F)CC1)nc(Nc1c(Cl)ccc(CNC(=O)C(C)(C)C)c1Cl)n2C] | C₃₂H₄₁Cl₂F₃N₆O₃ 685.61 | 685 | R_t: 1.42 min Method A | 1e |
| 107 | 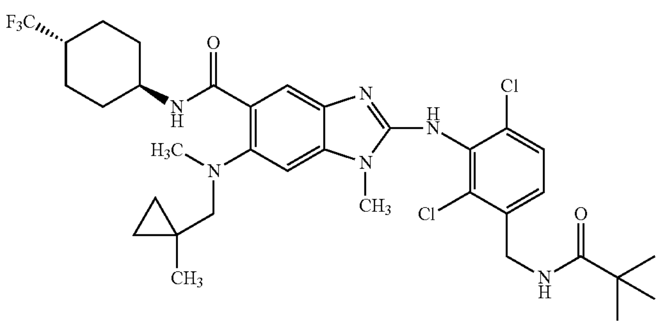 [SMILES: CN(CC1(C)CC1)c1cc2c(cc1C(=O)N[C@H]1CC[C@H](C(F)(F)F)CC1)nc(Nc1c(Cl)ccc(CNC(=O)C(C)(C)C)c1Cl)n2C] | C₃₄H₄₃Cl₂F₃N₆O₂ 695.65 | 695 | R_t: 1.52 min Method A | 1e |
| 108 | 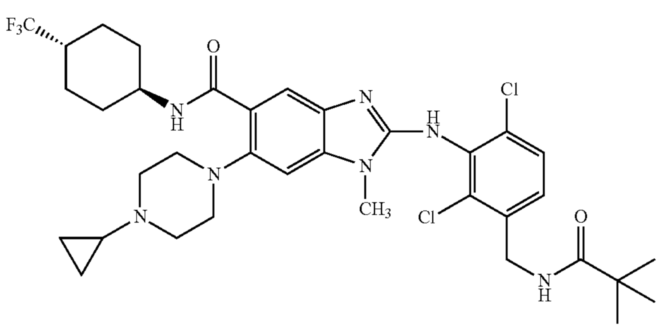 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCN(C4CC4)CC3)cc21] | C₃₅H₄₄Cl₂F₃N₇O₂ 722.67 | 722 | R_t: 1.33 min Method A | 1e |

| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 109 | 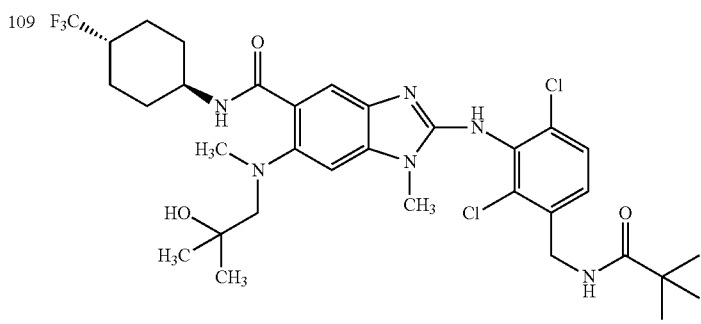 | $C_{33}H_{43}Cl_2F_3N_6O_3$ 699.63 | 699 | $R_t$: 1.39 min Method H | 1e |
| 111 | 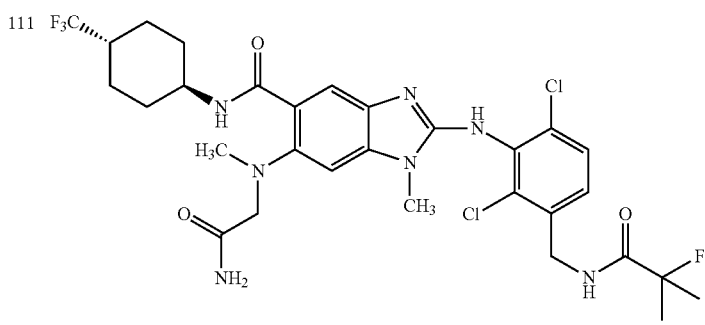 | $C_{30}H_{35}Cl_2F_4N_7O_3$ 688.54 | 688 | $R_t$: 1.54 min Method I | 1e |
| 113 | 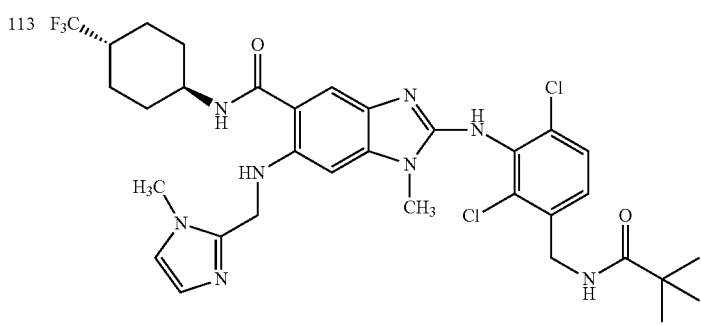 | $C_{33}H_{39}Cl_2F_3N_8O_2$ 707.62 | 707 | $R_t$: 1.22 min Method H | 6c |
| 114 | 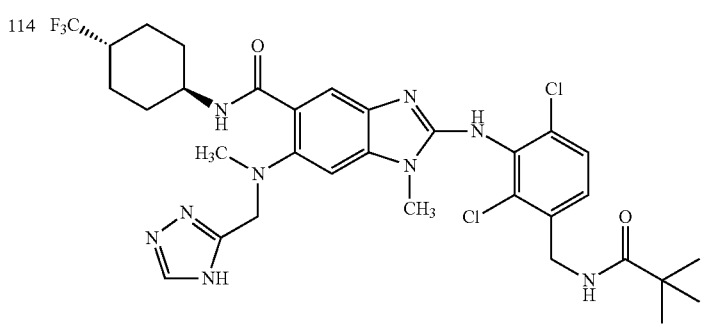 | $C_{32}H_{38}Cl_2F_3N_9O_2$ 708.60 | 708 | $R_t$: 1.57 min Method I | 6c |

-continued

| Ex. | Structure | Formula/Mw. | MS* m/z [M+H]+ | R_f (TLC, silica gel) or R_t [min] (HPLC-method) | Prepared in analogy to example |
|---|---|---|---|---|---|
| 115 | 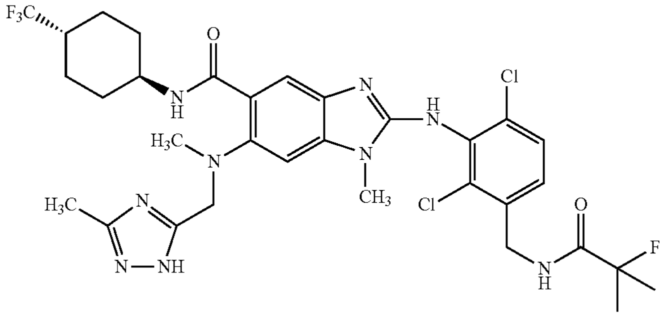 [SMILES: Cc1n[nH]c(CN(C)c2cc3c(cc2C(=O)N[C@H]2CC[C@H](C(F)(F)F)CC2)nc(Nc2c(Cl)ccc(CNC(=O)C(C)(C)F)c2Cl)n3C)n1] | C₃₂H₃₇Cl₂F₄N₉O₂ 726.60 | 726 | R_t: 1.58 min Method I | 6c |
| 116 | 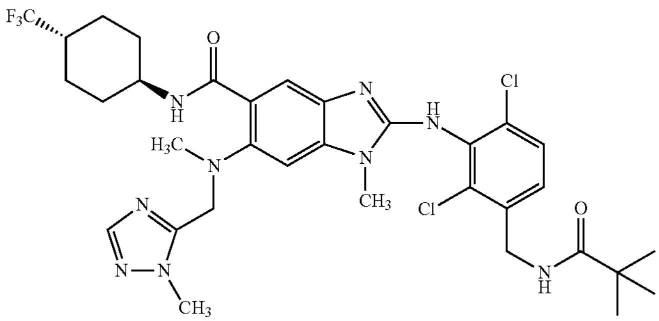 | C₃₃H₄₀Cl₂F₃N₉O₂ 722.63 | 722 | R_t: 1.34 min Method H | 6c |
| 117 | 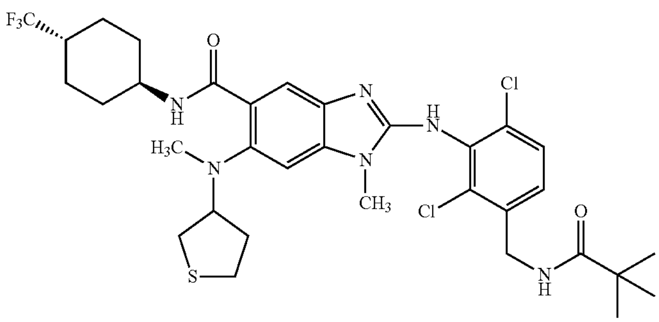 [SMILES: CN(c1cc2c(cc1C(=O)N[C@H]1CC[C@H](C(F)(F)F)CC1)nc(Nc1c(Cl)ccc(CNC(=O)C(C)(C)C)c1Cl)n2C)C1CCSC1] | C₃₃H₄₁Cl₂F₃N₆O₂S 713.68 | 713 | R_t: 1.55 min Method A | 6c |
| 120 | 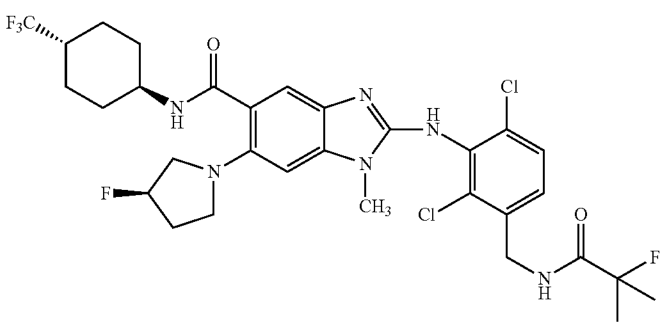 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CC[C@@H](F)C3)cc21] | C₃₁H₃₅Cl₂F₅N₆O₂ 689.55 | 690 | R_t: 1.44 min Method A | 1e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 121 | 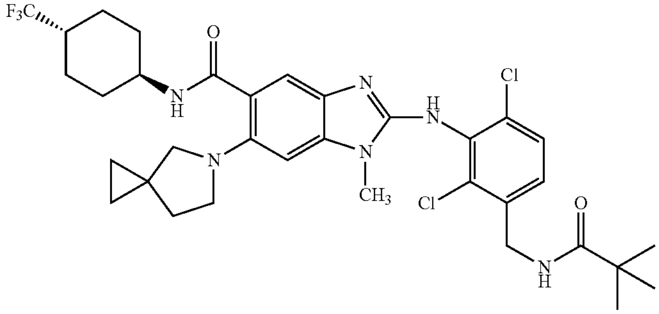 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC4(CC4)C3)cc21] | C34H41Cl2F3N6O2 693.63 | 693 | R_t: 1.52 min Method A | 6c |
| 122 | 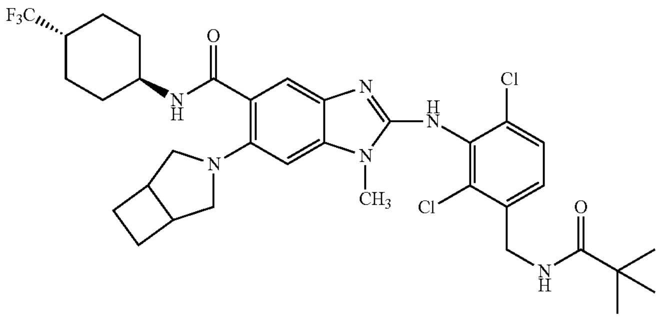 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCC4C3)cc21] | C34H41Cl2F3N6O2 693.63 | 693 | R_t: 1.52 min Method A | 1e |
| 123 | 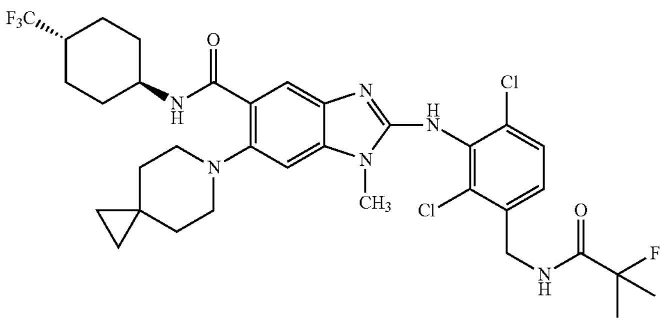 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC4(CC3)CC4)cc21] | C34H40Cl2F4N6O2 711.62 | 711 | R_t: 1.53 min Method A | 1e |
| 124 | 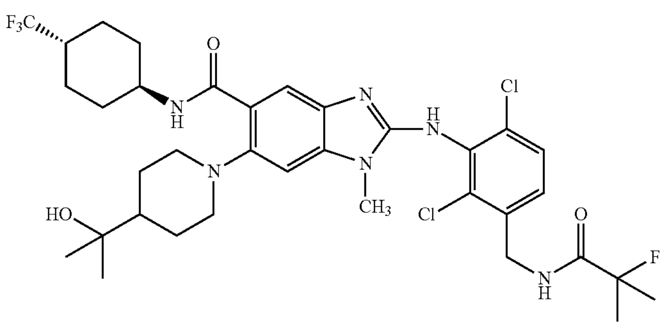 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC(C(C)(C)O)CC3)cc21] | C35H44Cl2F4N6O2 743.66 | 744 | R_t: 1.46 min Method A | 1e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 125 | 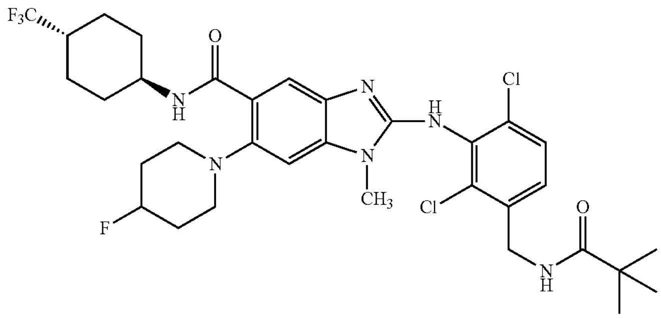 | C₃₃H₄₀Cl₂F₄N₆O₂ 699.61 | 699 | R_t: 1.46 min Method H | 6c |
| 126 | 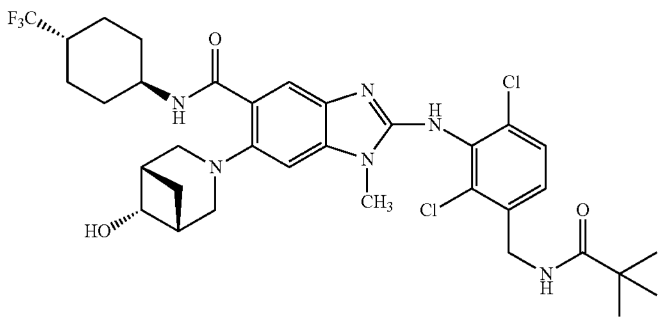 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3C[C@H]4C[C@@H](C3)[C@H]4O)cc21] | C₃₄H₄₁Cl₂F₃N₆O₃ 709.63 | 709 | R_t: 1.49 min Method A | 1e |
| 127 | 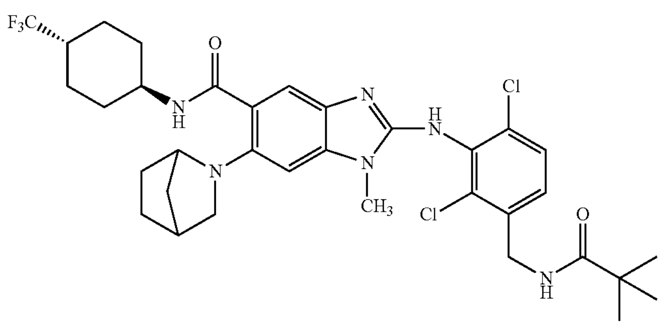 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCC3C4)cc21] | C₃₄H₄₁Cl₂F₃N₆O₂ 693.63 | 693 | R_t: 1.48 min Method A | 6c |
| 128 | 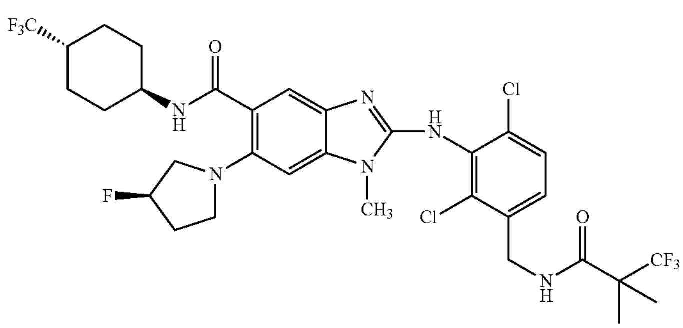 [SMILES: Cn1c(Nc2c(Cl)ccc(CNC(=O)C(C)(C)C(F)(F)F)c2Cl)nc2cc(C(=O)N[C@H]3CC[C@H](C(F)(F)F)CC3)c(N3CC[C@@H](F)C3)cc21] | C₃₂H₃₅Cl₂F₇N₆O₂ 739.55 | 739 | R_t: 1.50 min Method A | 6c with edukt 120b |

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 129 | 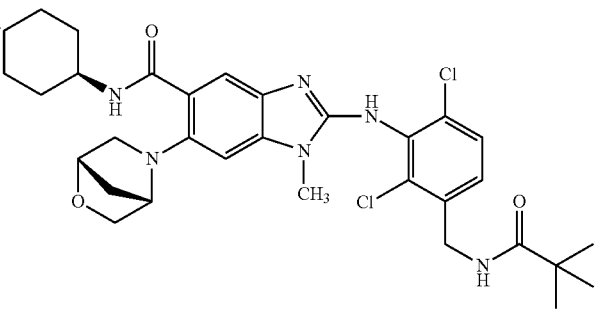 | C$_{33}$H$_{39}$Cl$_2$F$_3$N$_6$O$_3$ 695.60 | 695 | R$_f$: 0.87 Method K | 1e |
| 130 | 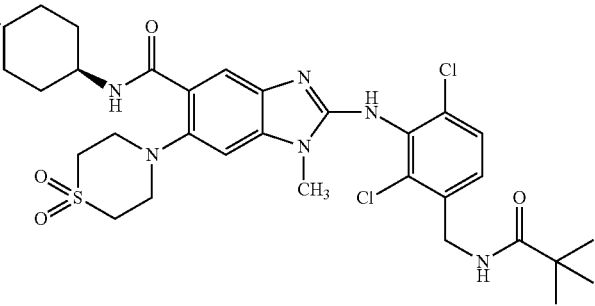 | C$_{32}$H$_{39}$Cl$_2$F$_3$N$_6$O$_4$S 731.66 | 731 | R$_t$: 1.36 min Method A | 1e |
| 131 | 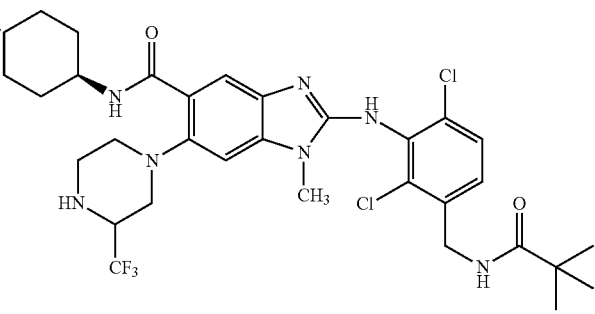 | C$_{33}$H$_{39}$Cl$_2$F$_6$N$_7$O$_2$ 750.61 | 750 | R$_t$: 1.40 min Method A | 1e |
| 132 | 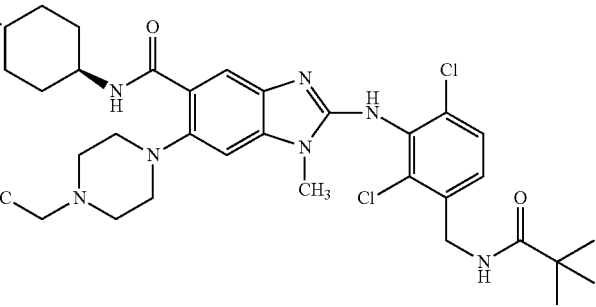 | C$_{34}$H$_{41}$Cl$_2$F$_6$N$_7$O$_2$ 764.63 | 764 | R$_t$: 1.54 min Method A | 1e |

-continued

| Ex. | Structure | Formula/Mw. | MS* m/z [M + H]+ | R_f (TLC, silica gel) or R_t [min] (HPLC-method) | Prepared in analogy to example |
|---|---|---|---|---|---|
| 133 | 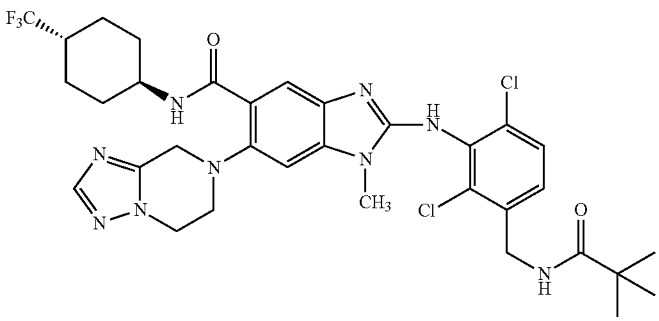 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCn4ncnc4C3)cc21] | C33H38Cl2F3N9O2 720.62 | 720 | R_t: 0.97 min Method K | 1e |
| 134 | 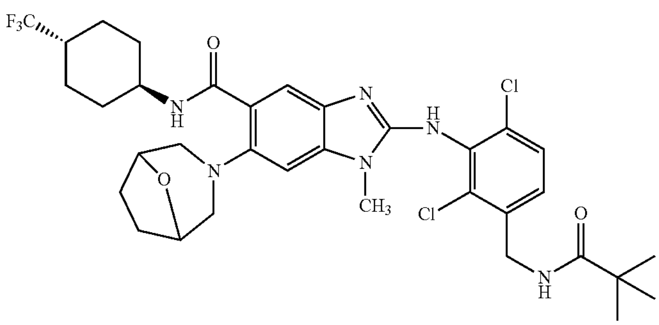 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCC(C3)O4)cc21] | C34H41Cl2F3N6O3 709.64 | 709 | R_t: 1.46 min Method I | 1e |
| 135 | 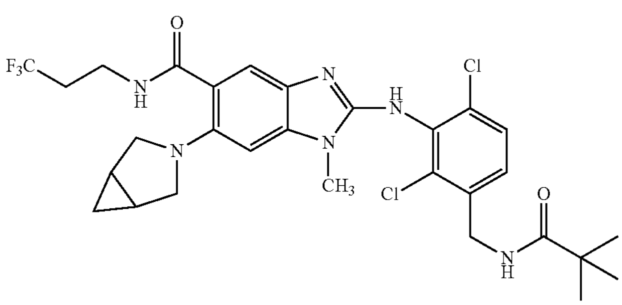 [SMILES: Cn1c(Nc2c(Cl)ccc(CNC(=O)C(C)(C)C)c2Cl)nc2cc(C(=O)NCCC(F)(F)F)c(N3CC4CC4C3)cc21] | C29H33Cl2F3N6O2 625.51 | 625 | R_t: 1.38 min Method A | 6c |
| 136 | 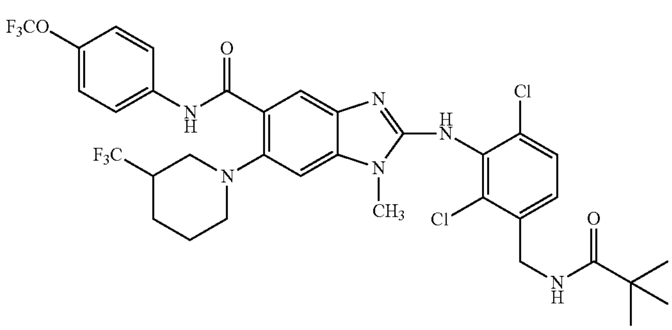 [SMILES: Cn1c(Nc2c(Cl)ccc(CNC(=O)C(C)(C)C)c2Cl)nc2cc(C(=O)Nc3ccc(OC(F)(F)F)cc3)c(N3CCCC(C(F)(F)F)C3)cc21] | C34H34Cl2F6N6O3 759.57 | 759 | R_t: 1.61 min Method A | 6c |

| Ex. | Structure | Formula/ Mw. | MS* m/z [M+H]+ | R$_f$(TLC, silica gel) or R$_t$ [min] (HPLC-method) | Prepared in analogy to example |
|---|---|---|---|---|---|
| 137 | 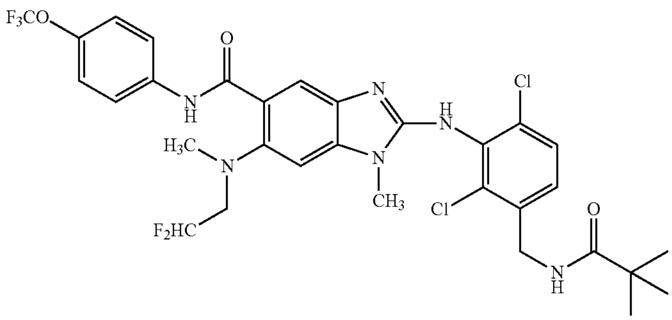 [SMILES: CN(CC(F)F)c1cc2c(cc1C(=O)Nc1ccc(OC(F)(F)F)cc1)nc(Nc1c(Cl)ccc(CNC(=O)C(C)(C)C)c1Cl)n2C] | C$_{31}$H$_{31}$Cl$_2$F$_5$N$_6$O$_3$ 701.51 | 701 | R$_t$: 1.56 min Method A | 6c |
| 138 | 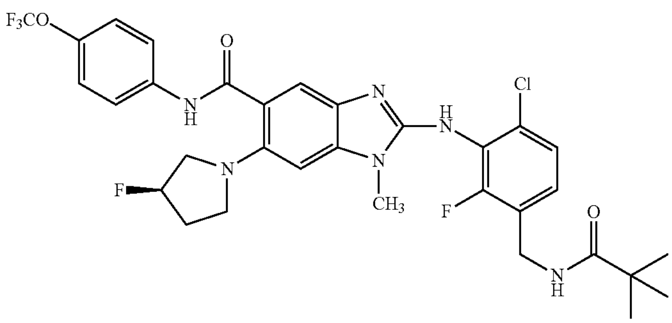 [SMILES: Cn1c(Nc2c(Cl)ccc(CNC(=O)C(C)(C)C)c2F)nc2cc(C(=O)Nc3ccc(OC(F)(F)F)cc3)c(N3CC[C@@H](F)C3)cc21] | C$_{32}$H$_{32}$ClF$_5$N$_6$O$_3$ 679.08 | 679 | R$_t$: 1.14 min Method I | 6c |
| 139 | 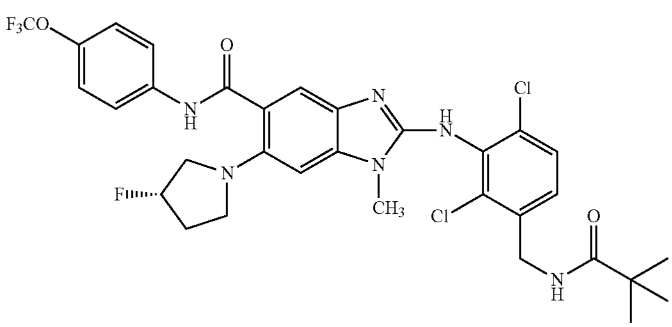 [SMILES: Cn1c(Nc2c(Cl)ccc(CNC(=O)C(C)(C)C)c2Cl)nc2cc(C(=O)Nc3ccc(OC(F)(F)F)cc3)c(N3CC[C@H](F)C3)cc21] | C$_{32}$H$_{32}$Cl$_2$F$_4$N$_6$O$_3$ 695.53 | 695 | R$_t$: 1.54 min Method A | 6c |
| 140 | 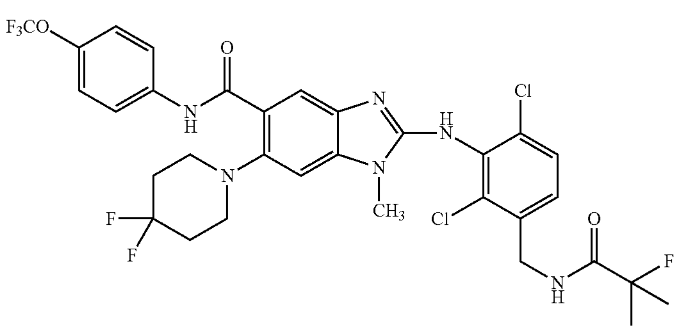 [SMILES: Cn1c(Nc2c(Cl)ccc(CNC(=O)C(C)(C)F)c2Cl)nc2cc(C(=O)Nc3ccc(OC(F)(F)F)cc3)c(N3CCC(F)(F)CC3)cc21] | C$_{34}$H$_{30}$Cl$_2$F$_6$N$_6$O$_3$ 731.52 | 731 | R$_t$: 1.54 min Method A | 1e |

-continued

| Ex. | Structure | Formula/ Mw. | MS* m/z [M+H]+ | R_f (TLC, silica gel) or R_t [min] (HPLC-method) | Prepared in analogy to example |
|---|---|---|---|---|---|
| 141 | 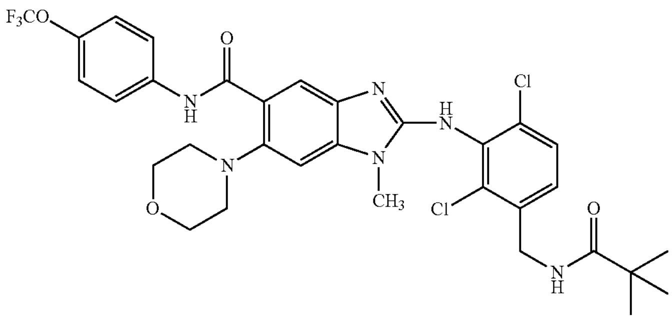 [SMILES: Cn1c(Nc2c(Cl)ccc(CNC(=O)C(C)(C)C)c2Cl)nc2cc(C(=O)Nc3ccc(OC(F)(F)F)cc3)c(N3CCOCC3)cc21] | $C_{32}H_{33}Cl_2F_3N_6O_4$ 693.54 | 693 | R_t: 1.51 min Method A | 1e |
| 142 | 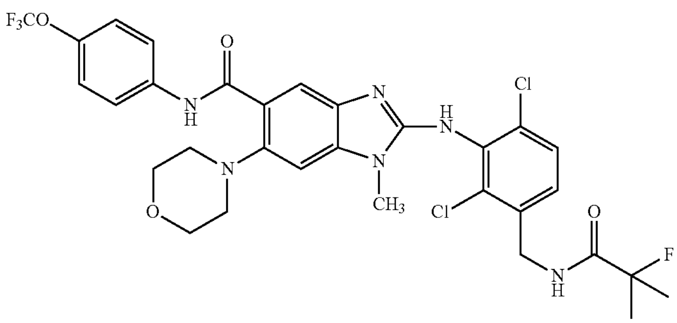 [SMILES: Cn1c(Nc2c(Cl)ccc(CNC(=O)C(C)(C)F)c2Cl)nc2cc(C(=O)Nc3ccc(OC(F)(F)F)cc3)c(N3CCOCC3)cc21] | $C_{31}H_{30}Cl_2F_4N_6O_4$ 697.51 | 697 | R_t: 1.65 min Method I | 6c |
| 143 | 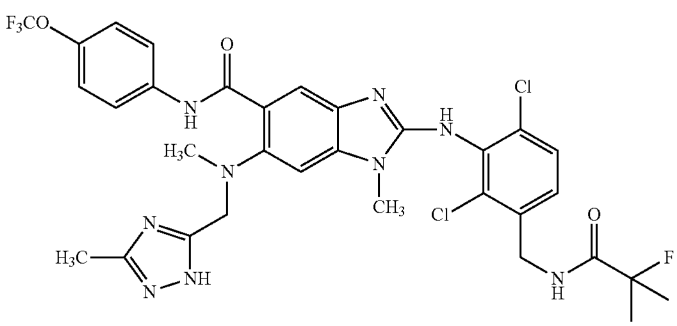 [SMILES: Cc1n[nH]c(CN(C)c2cc3c(cc2C(=O)Nc2ccc(OC(F)(F)F)cc2)nc(Nc2c(Cl)ccc(CNC(=O)C(C)(C)F)c2Cl)n3C)n1] | $C_{32}H_{31}Cl_2F_4N_9O_3$ 736.55 | 736 | R_t: 1.44 min Method H | 1e |
| 146 | 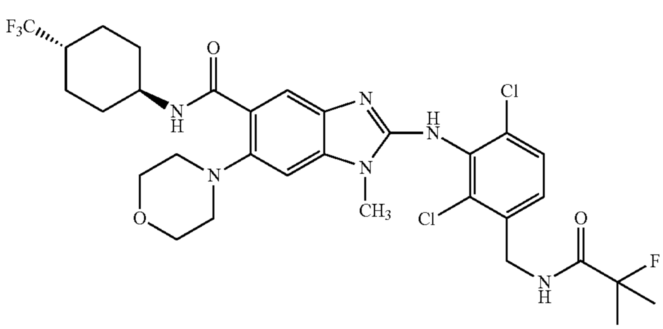 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCOCC3)cc21] | $C_{31}H_{36}Cl_2F_4N_6O_3$ 687.56 | 687 | R_t: 1.39 min Method H | 6c |

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 147 | 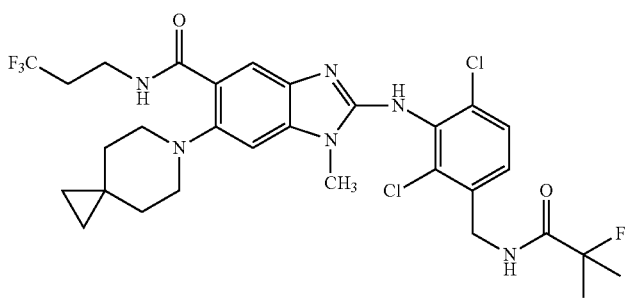 [SMILES: Cn1c(Nc2c(Cl)ccc(CNC(=O)C(C)(C)F)c2Cl)nc2cc(C(=O)NCCC(F)(F)F)c(N3CCC4(CC3)CC4)cc21] | C30H34Cl2F4N6O2 657.53 | 657 | R_t: 1.40 min Method A | 1e |
| 148 | 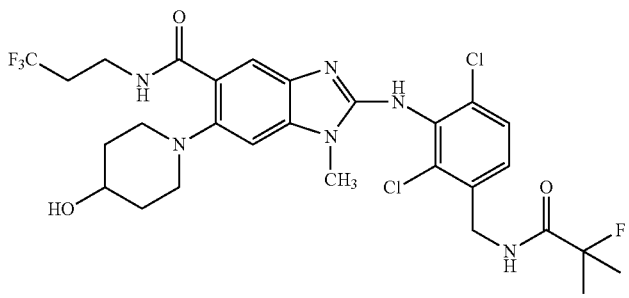 [SMILES: Cn1c(Nc2c(Cl)ccc(CNC(=O)C(C)(C)F)c2Cl)nc2cc(C(=O)NCCC(F)(F)F)c(N3CCC(O)CC3)cc21] | C28H32Cl2F4N6O3 647.49 | 647 | R_t: 1.24 min Method A | 1e |
| 149 | 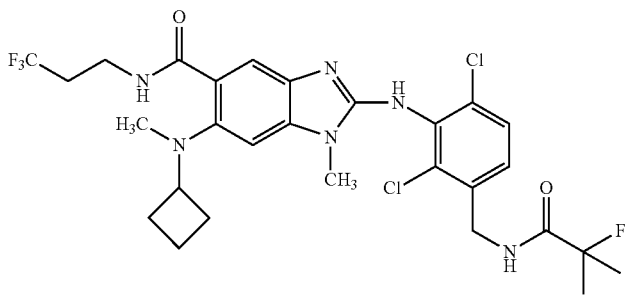 [SMILES: CN(c1cc2c(cc1C(=O)NCCC(F)(F)F)nc(Nc1c(Cl)ccc(CNC(=O)C(C)(C)F)c1Cl)n2C)C1CCC1] | C28H32Cl2F4N6O2 631.49 | 631 | R_t: 1.35 min Method A | 1e |
| 150 | 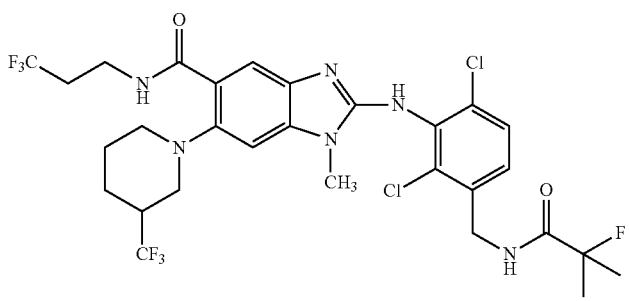 [SMILES: Cn1c(Nc2c(Cl)ccc(CNC(=O)C(C)(C)F)c2Cl)nc2cc(C(=O)NCCC(F)(F)F)c(N3CCCC(C(F)(F)F)C3)cc21] | C29H31Cl2F7N6O2 699.49 | 699 | R_t: 1.45 min Method A | 1e |

| Ex. | Structure | Formula/Mw. | MS* m/z [M + H]+ | $R_f$ (TLC, silica gel) or $R_t$ [min] (HPLC-method) | Prepared in analogy to example |
|---|---|---|---|---|---|
| 151 | 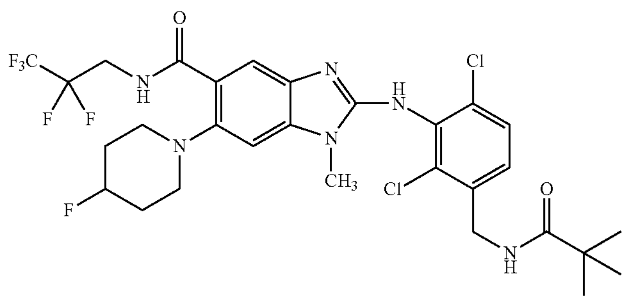 [SMILES: Cn1c(Nc2c(Cl)ccc(CNC(=O)C(C)(C)C)c2Cl)nc2cc(C(=O)NCC(F)(F)C(F)(F)F)c(N3CCC(F)CC3)cc21] | $C_{29}H_{32}Cl_2F_6N_6O_2$ 681.50 | 681 | $R_t$: 1.44 min Method H | 6c |
| 152 | 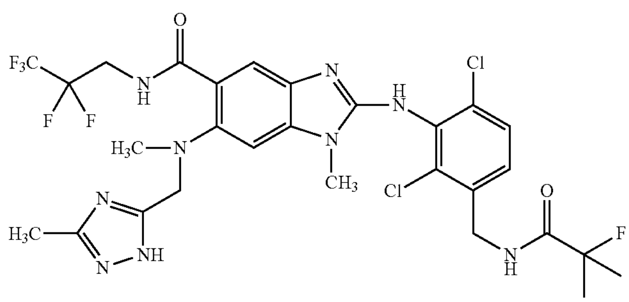 [SMILES: Cc1n[nH]c(CN(C)c2cc3c(cc2C(=O)NCC(F)(F)C(F)(F)F)nc(Nc2c(Cl)ccc(CNC(=O)C(C)(C)F)c2Cl)n3C)n1] | $C_{28}H_{29}Cl_2F_6N_9O_2$ 708.49 | 708 | $R_t$: 1.55 min Method I | 6c |
| 153 | 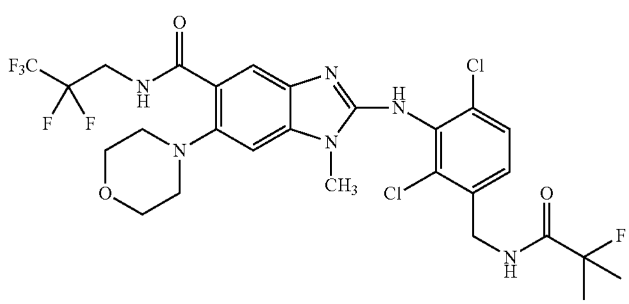 [SMILES: Cn1c(Nc2c(Cl)ccc(CNC(=O)C(C)(C)F)c2Cl)nc2cc(C(=O)NCC(F)(F)C(F)(F)F)c(N3CCOCC3)cc21] | $C_{27}H_{28}Cl_2F_6N_6O_3$ 669.45 | 669 | $R_t$: 1.59 min Method I | 6c |
| 154 | 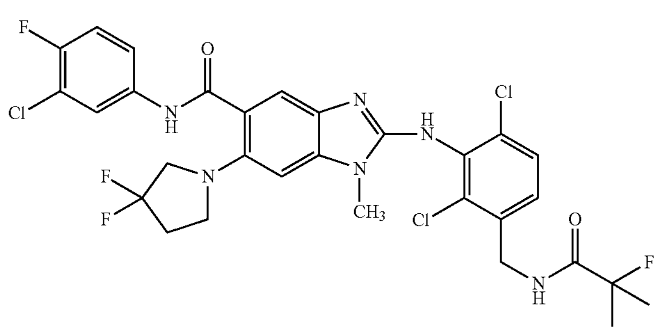 [SMILES: Cn1c(Nc2c(Cl)ccc(CNC(=O)C(C)(C)F)c2Cl)nc2cc(C(=O)Nc3ccc(F)c(Cl)c3)c(N3CCC(F)(F)C3)cc21] | $C_{30}H_{27}Cl_3F_4N_6O_2$ 685.93 | 685 | $R_t$: 1.49 min Method A | 1e |

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 155 | 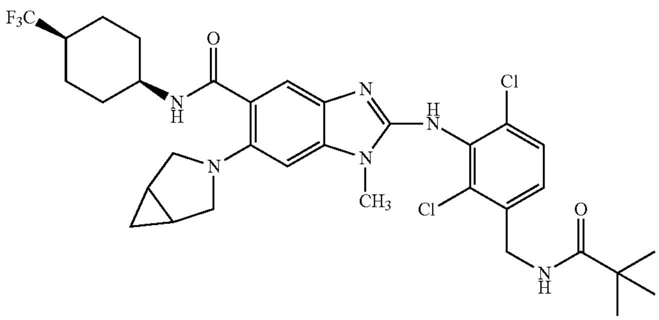 [SMILES: Cn1c(Nc2c(Cl)ccc(CNC(=O)C(C)(C)C)c2Cl)nc2cc(C(=O)N[C@H]3CC[C@@H](C(F)(F)F)CC3)c(N3CC4CC4C3)cc21] | C_{33}H_{39}Cl_2F_3N_6O_2 679.60 | 679 | R_t: 1.42 min Method H | 1e |
| 156 | 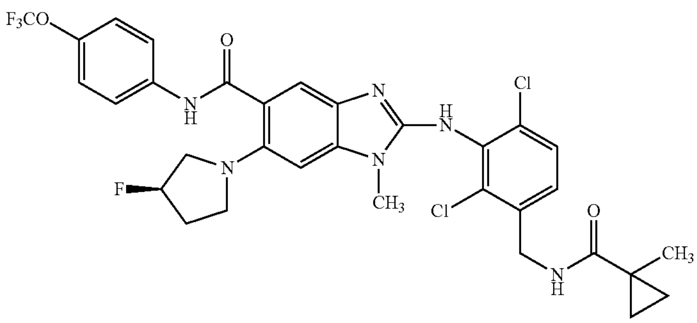 [SMILES: Cn1c(Nc2c(Cl)ccc(CNC(=O)C3(C)CC3)c2Cl)nc2cc(C(=O)Nc3ccc(OC(F)(F)F)cc3)c(N3CC[C@@H](F)C3)cc21] | C_{32}H_{30}Cl_2F_4N_6O_3 693.52 | 693 | R_f = 0.4 DCM/ EtOH 95:5 | 1e Educt: 138b |
| 158 | 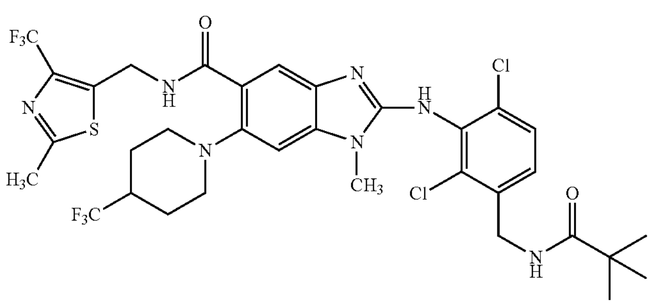 [SMILES: Cc1nc(C(F)(F)F)c(CNC(=O)c2cc3nc(Nc4c(Cl)ccc(CNC(=O)C(C)(C)C)c4Cl)n(C)c3cc2N2CCC(C(F)(F)F)CC2)s1] | C_{33}H_{35}Cl_2F_6N_7O_2S 778.64 | 778 | R_f = 0.29 DCM/ EtOH 95:5 | 157f |
| 159 | 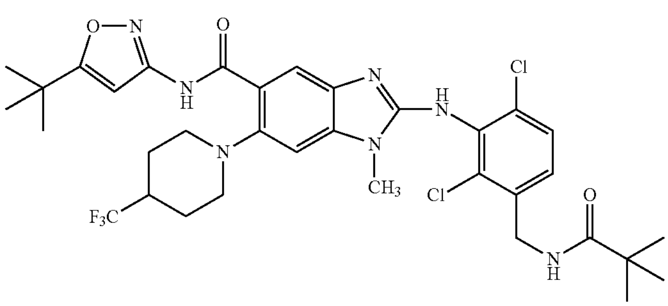 [SMILES: Cn1c(Nc2c(Cl)ccc(CNC(=O)C(C)(C)C)c2Cl)nc2cc(C(=O)Nc3cc(C(C)(C)C)on3)c(N3CCC(C(F)(F)F)CC3)cc21] | C_{34}H_{40}Cl_2F_3N_7O_3 722.63 | 722 | R_t: 1.69 min Method A | 157f |

| Ex. | Structure | Formula/Mw. | MS* m/z [M+H]+ | R$_f$(TLC, silica gel) or R$_t$ [min] (HPLC-method) | Prepared in analogy to example |
|---|---|---|---|---|---|
| 160 | 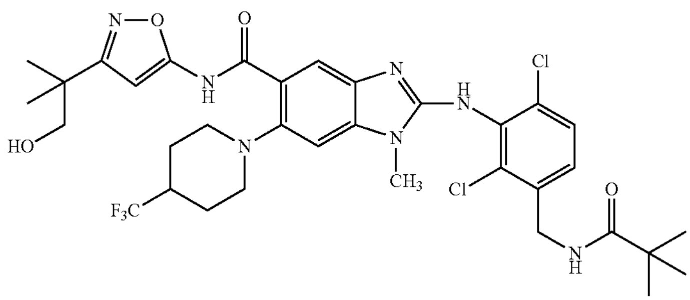 [SMILES: Cn1c(Nc2c(Cl)ccc(CNC(=O)C(C)(C)C)c2Cl)nc2cc(C(=O)Nc3cc(C(C)(C)CO)no3)c(N3CCC(C(F)(F)F)CC3)cc21] | C$_{34}$H$_{40}$Cl$_2$F$_3$N$_7$O$_4$ 738.63 | 738 | R$_t$: 1.62 min Method A | 157f |
| 161 | 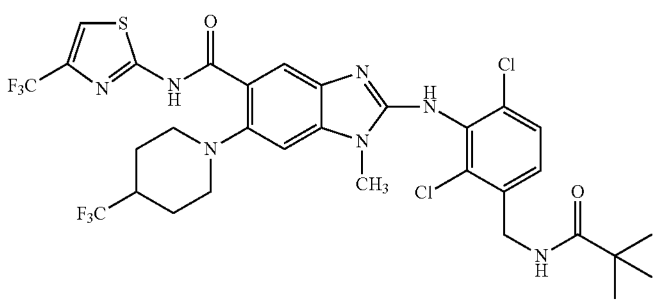 [SMILES: Cn1c(Nc2c(Cl)ccc(CNC(=O)C(C)(C)C)c2Cl)nc2cc(C(=O)Nc3nc(C(F)(F)F)cs3)c(N3CCC(C(F)(F)F)CC3)cc21] | C$_{31}$H$_{31}$Cl$_2$F$_6$N$_7$O$_2$S 750.59 | 750 | R$_t$: 1.60 min Method A | 157f |
| 162 | 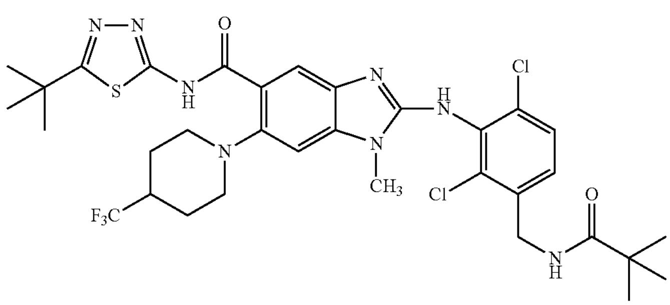 [SMILES: Cn1c(Nc2c(Cl)ccc(CNC(=O)C(C)(C)C)c2Cl)nc2cc(C(=O)Nc3nnc(C(C)(C)C)s3)c(N3CCC(C(F)(F)F)CC3)cc21] | C$_{33}$H$_{39}$Cl$_2$F$_3$N$_8$O$_2$S 739.68 | 739 | R$_t$: 1.58 min Method A | 157f |
| 163 | 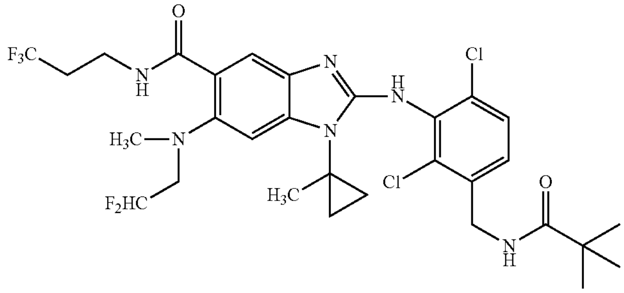 [SMILES: CN(CC(F)F)c1cc2c(cc1C(=O)NCCC(F)(F)F)nc(Nc1c(Cl)ccc(CNC(=O)C(C)(C)C)c1Cl)n2C1(C)CC1] | C$_{29}$H$_{32}$Cl$_2$F$_6$N$_6$O$_2$ 681.50 | 681 | R$_f$= 0.31 DCM/EtOH 95:5 | 1e |

| Ex. | Structure | Formula/Mw. | MS* m/z [M + H]⁺ | $R_f$ (TLC, silica gel) or $R_t$ [min] (HPLC-method) | Prepared in analogy to example |
|---|---|---|---|---|---|
| 164 | 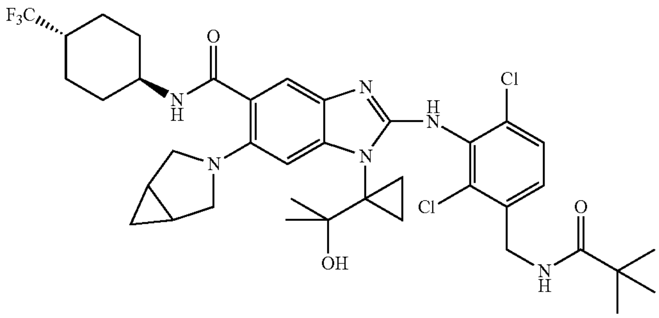 [SMILES: CC(C)(C)C(=O)NCc1ccc(Cl)c(Nc2nc3cc(C(=O)N[C@H]4CC[C@H](C(F)(F)F)CC4)c(N4CC5CC5C4)cc3n2C2(C(C)(C)O)CC2)c1Cl] | $C_{38}H_{47}Cl_2F_3N_6O_3$ 763.72 | 763 | $R_t$: 1.49 min Method H | 6c |
| 165 | 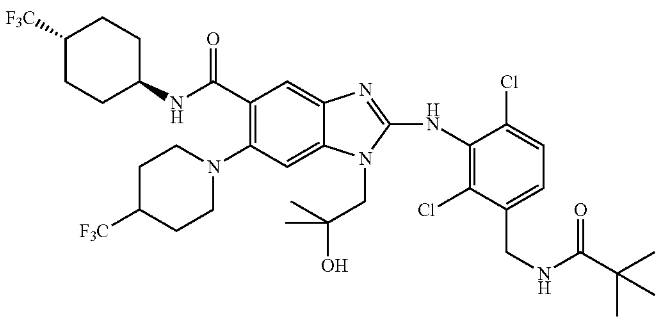 [SMILES: CC(C)(O)Cn1c(Nc2c(Cl)ccc(CNC(=O)C(C)(C)C)c2Cl)nc2cc(C(=O)N[C@H]3CC[C@H](C(F)(F)F)CC3)c(N3CCC(C(F)(F)F)CC3)cc21] | $C_{37}H_{46}Cl_2F_6N_6O_3$ 807 | 807 | $R_t$: 1.58 min Method H | 6c |
| 167 | 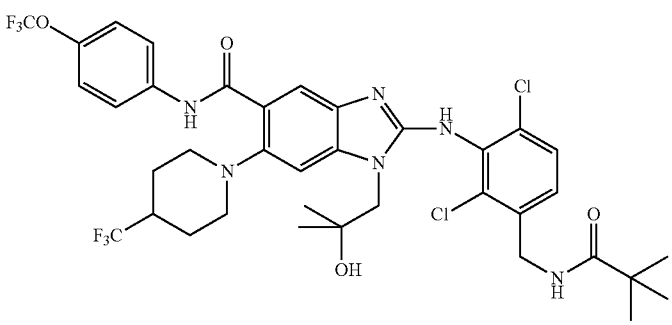 [SMILES: CC(C)(O)Cn1c(Nc2c(Cl)ccc(CNC(=O)C(C)(C)C)c2Cl)nc2cc(C(=O)Nc3ccc(OC(F)(F)F)cc3)c(N3CCC(C(F)(F)F)CC3)cc21] | $C_{37}H_{40}Cl_2F_6N_6O_4$ 817.65 | 817 | $R_t$: 1.64 min Method H | 6c |
| 168 | 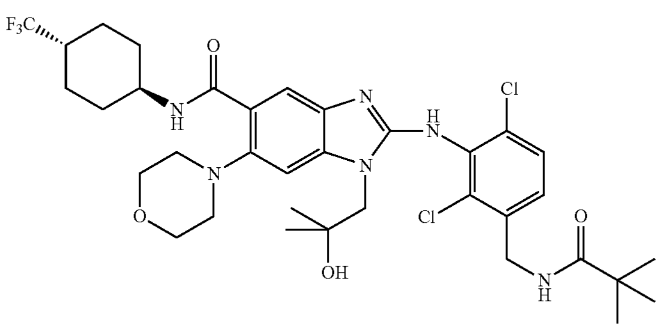 [SMILES: CC(C)(O)Cn1c(Nc2c(Cl)ccc(CNC(=O)C(C)(C)C)c2Cl)nc2cc(C(=O)N[C@H]3CC[C@H](C(F)(F)F)CC3)c(N3CCOCC3)cc21] | $C_{35}H_{45}Cl_2F_3N_6O_4$ 741.67 | 741 | $R_t$: 1.45 min Method H | 6c |

-continued
| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 169 | 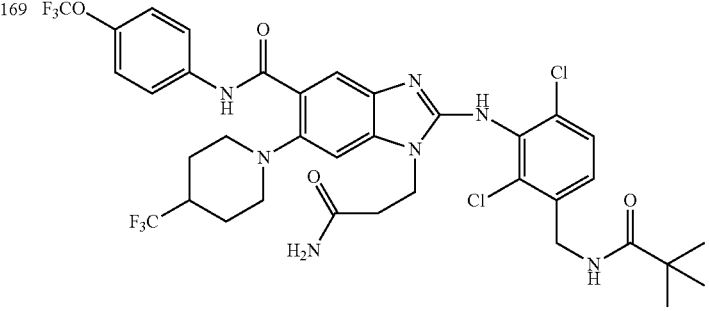 | $C_{36}H_{37}Cl_2F_6N_7O_4$ 816.62 | 816 | R_t: 1.61 min Method H | 6c |
| 170 | 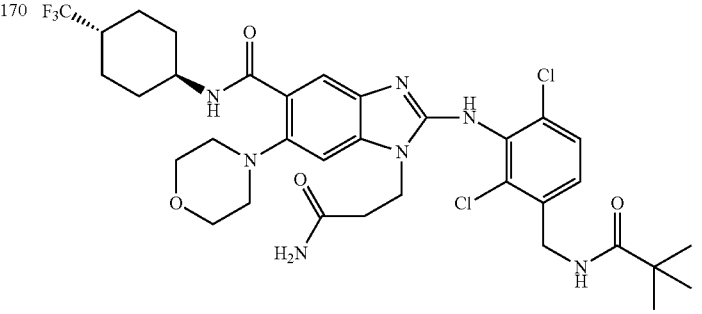 | $C_{34}H_{42}Cl_2F_3N_7O_4$ 740.64 | 740 | R_t: 1.60 min Method I | 6c |
| 171 | 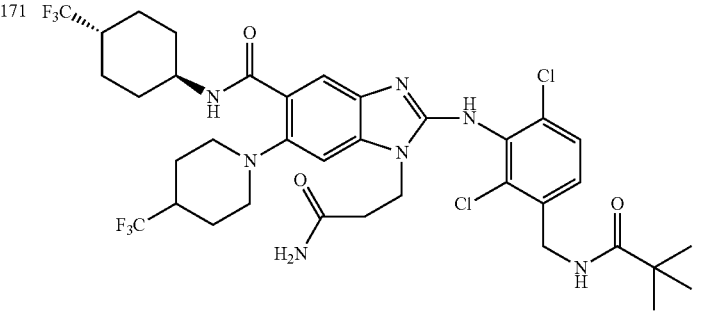 | $C_{36}H_{43}Cl_2F_6N_7O_3$ 806.67 | 806 | R_t: 1.54 min Method H | 6c |
| 175 | 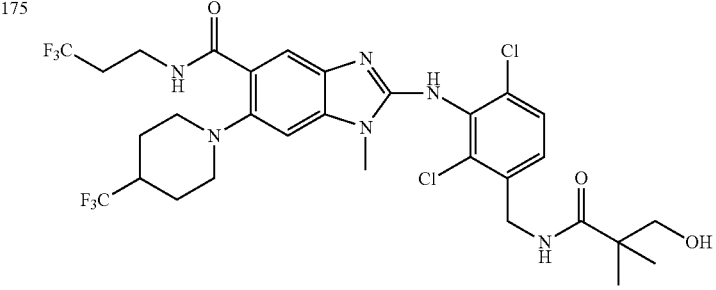 | $C_{30}H_{34}Cl_2F_6N_6O_3$ 711.53 | 711 | R_f = 0.16 DCM/ EtOH 95:5 | 173b |

-continued

| Ex. | Structure | Formula/ Mw. | MS* m/z [M + H]+ | R_f(TLC, silica gel) or R_t [min] (HPLC-method) | Prepared in analogy to example |
|---|---|---|---|---|---|
| 176 | 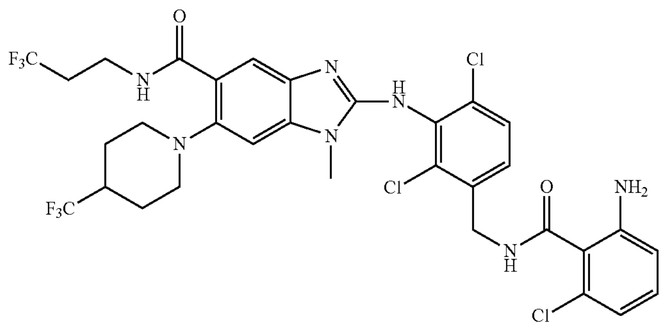 [SMILES: Cn1c(Nc2c(Cl)ccc(CNC(=O)c3c(N)cccc3Cl)c2Cl)nc2cc(C(=O)NCCC(F)(F)F)c(N3CCC(C(F)(F)F)CC3)cc21] | $C_{32}H_{30}Cl_3F_6N_7O_2$ 764.98 | 764 | $R_f = 0.27$ DCM/ EtOH 95:5 | 173b |
| 177 | 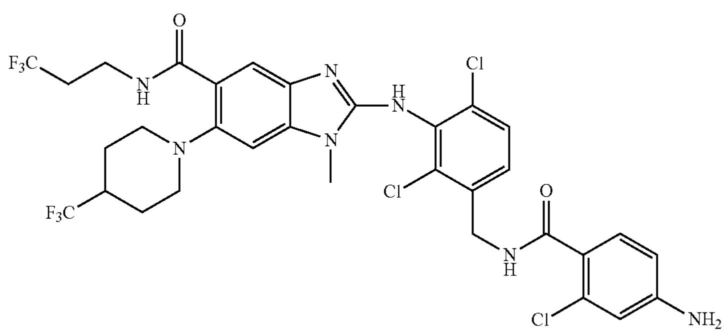 [SMILES: Cn1c(Nc2c(Cl)ccc(CNC(=O)c3ccc(N)cc3Cl)c2Cl)nc2cc(C(=O)NCCC(F)(F)F)c(N3CCC(C(F)(F)F)CC3)cc21] | $C_{32}H_{30}Cl_3F_6N_7O_2$ 764.98 | 764 | $R_f = 0.20$ DCM/ EtOH 95:5 | 173b |
| 178 | 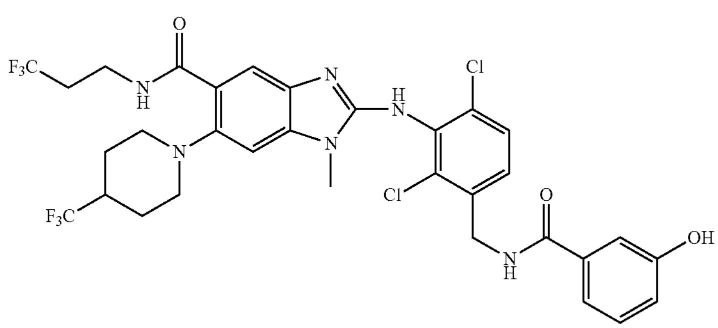 [SMILES: Cn1c(Nc2c(Cl)ccc(CNC(=O)c3cccc(O)c3)c2Cl)nc2cc(C(=O)NCCC(F)(F)F)c(N3CCC(C(F)(F)F)CC3)cc21] | $C_{32}H_{30}Cl_2F_6N_6O_3$ 731.52 | 731 | $R_f = 0.24$ DCM/ EtOH 95:5 | 173b |
| 179 | 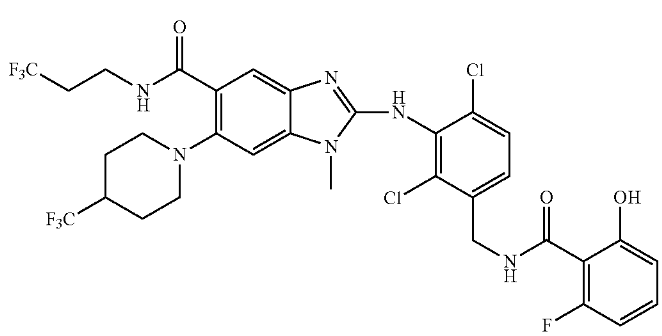 [SMILES: Cn1c(Nc2c(Cl)ccc(CNC(=O)c3c(O)cccc3F)c2Cl)nc2cc(C(=O)NCCC(F)(F)F)c(N3CCC(C(F)(F)F)CC3)cc21] | $C_{32}H_{29}Cl_2F_7N_6O_3$ 749.51 | 749 | $R_f = 0.28$ DCM/ EtOH 95:5 | 173b |

-continued

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 180 | 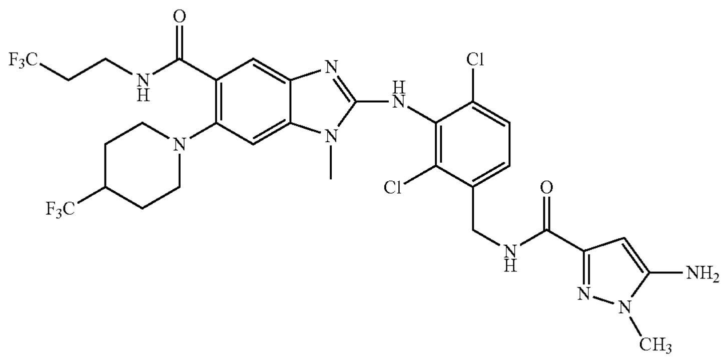 [SMILES: Cn1nc(C(=O)NCc2ccc(Cl)c(Nc3nc4cc(C(=O)NCCC(F)(F)F)c(N5CCC(C(F)(F)F)CC5)cc4n3C)c2Cl)cc1N] | C$_{30}$H$_{31}$Cl$_2$F$_6$N$_9$O$_2$ 734.52 | 734 | R$_t$: 1.39 min Method A | 173b |
| 181 | 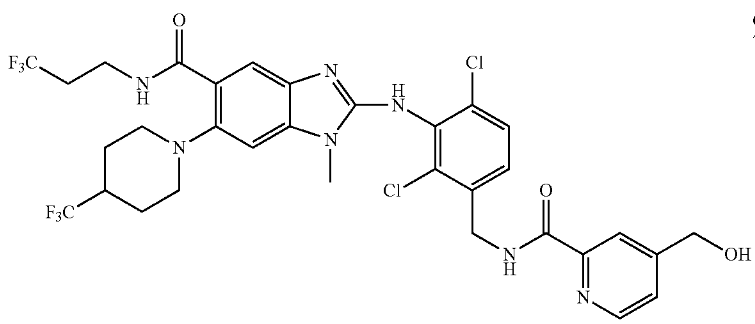 | C$_{32}$H$_{31}$Cl$_2$F$_6$N$_7$O$_3$ 746.53 | 746 | R$_t$: 1.41 min Method A | 173b |
| 182 | 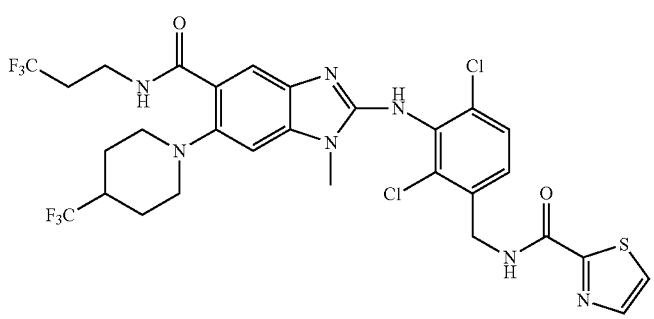 [SMILES: Cn1c(Nc2c(Cl)ccc(CNC(=O)c3nccs3)c2Cl)nc2cc(C(=O)NCCC(F)(F)F)c(N3CCC(C(F)(F)F)CC3)cc21] | C$_{29}$H$_{27}$Cl$_2$F$_6$N$_7$O$_3$S 722.53 | 722 | R$_f$ = 0.29 DCM/ EtOH 95:5 | 173b |
| 183 | 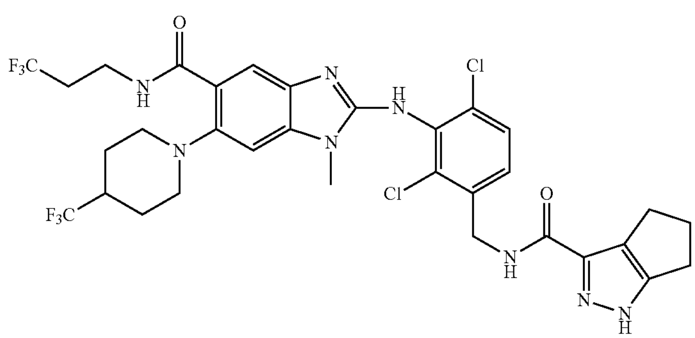 [SMILES: Cn1c(Nc2c(Cl)ccc(CNC(=O)c3n[nH]c4c3CCC4)c2Cl)nc2cc(C(=O)NCCC(F)(F)F)c(N3CCC(C(F)(F)F)CC3)cc21] | C$_{32}$H$_{32}$Cl$_2$F$_6$N$_8$O$_3$ 745.55 | 745 | R$_t$: 1.46 min Method A | 174 |

| Ex. | Structure | Formula/ Mw. | MS* m/z [M + H]+ | $R_f$ (TLC, silica gel) or $R_t$ [min] (HPLC-method) | Prepared in analogy to example |
|---|---|---|---|---|---|
| 184 | 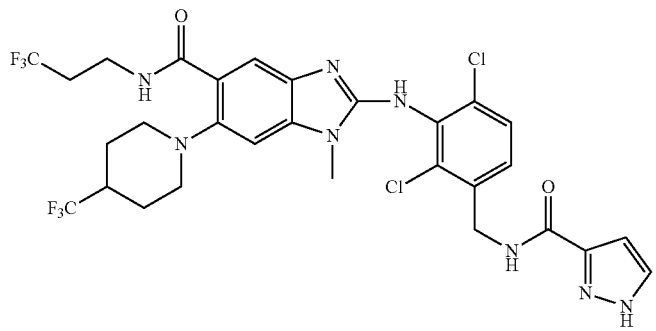 [SMILES: Cn1c(Nc2c(Cl)ccc(CNC(=O)c3cc[nH]n3)c2Cl)nc2cc(C(=O)NCCC(F)(F)F)c(N3CCC(C(F)(F)F)CC3)cc21] | C29H28Cl2F6N8O2 705.48 | 705 | $R_t$: 1.41 min Method A | 174 |
| 187 | 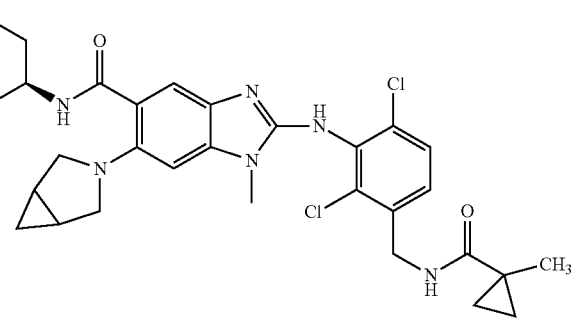 | C33H37Cl2F3N6O2 677.59 | 677 | $R_t$: 0.268 min Method L | 186 |
| 188 | 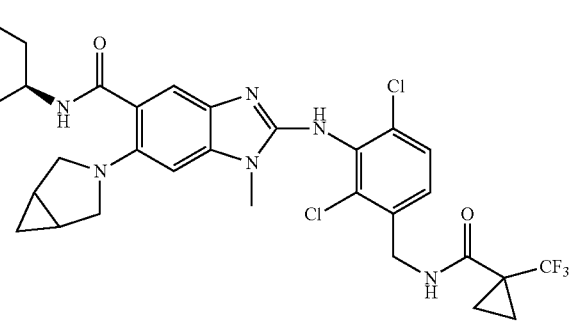 | C33H34Cl2F6N6O2 731.56 | 731 | $R_t$: 0.281 min Method L | 186 |
| 189 | 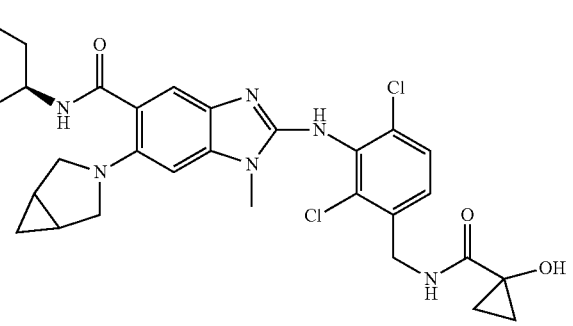 | C32H35Cl2F3N6O3 679.57 | 679 | $R_t$: 0.249 min Method L | 186 |

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 190 | 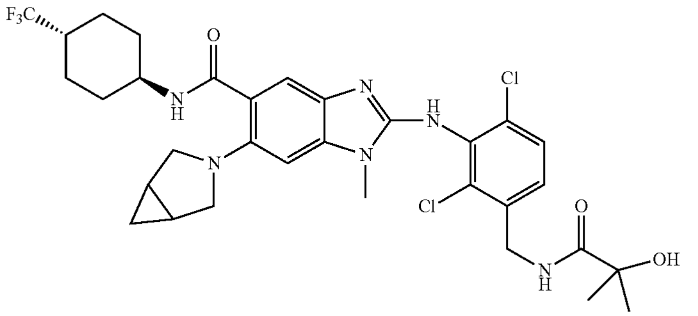 [SMILES: Cn1c(Nc2c(Cl)ccc(CNC(=O)C(C)(C)O)c2Cl)nc2cc(C(=O)N[C@H]3CC[C@H](C(F)(F)F)CC3)c(N3CC4CC4C3)cc21] | C$_{32}$H$_{37}$Cl$_2$F$_3$N$_6$O$_3$ 681.58 | 681 | R$_t$: 0.250 min Method L | 186 |
| 191 | 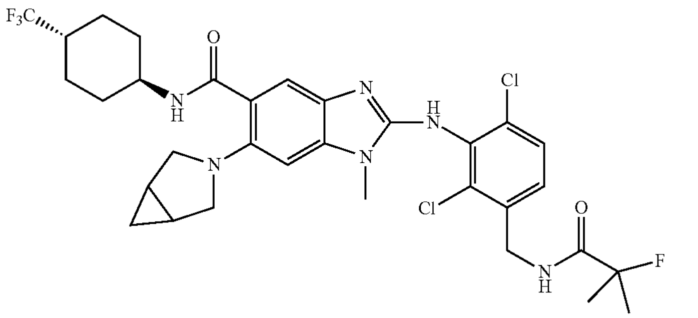 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CC4CC4C3)cc21] | C$_{32}$H$_{36}$Cl$_2$F$_4$N$_6$O$_2$ 683.57 | 683 | R$_t$: 0.267 min Method L | 186 |
| 192 | 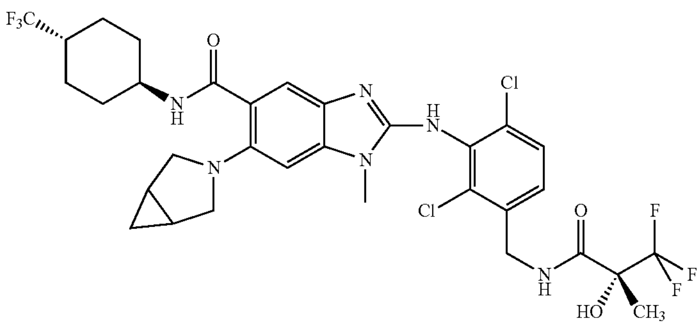 [SMILES: Cn1c(Nc2c(Cl)ccc(CNC(=O)[C@@](C)(O)C(F)(F)F)c2Cl)nc2cc(C(=O)N[C@H]3CC[C@H](C(F)(F)F)CC3)c(N3CC4CC4C3)cc21] | C$_{32}$H$_{34}$Cl$_2$F$_6$N$_6$O$_3$ 735.55 | 735 | R$_t$: 0.267 min Method L | 186 |
| 193 | 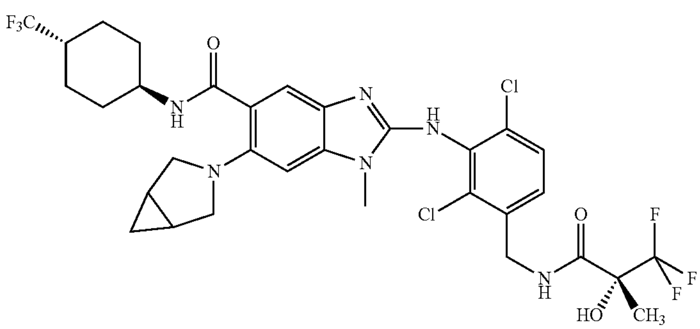 [SMILES: Cn1c(Nc2c(Cl)ccc(CNC(=O)[C@@](C)(O)C(F)(F)F)c2Cl)nc2cc(C(=O)N[C@H]3CC[C@H](C(F)(F)F)CC3)c(N3CC4CC4C3)cc21] | C$_{32}$H$_{34}$Cl$_2$F$_6$N$_6$O$_3$ 735.55 | 735 | R$_t$: 0.267 min Method L | 186 |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 194 | 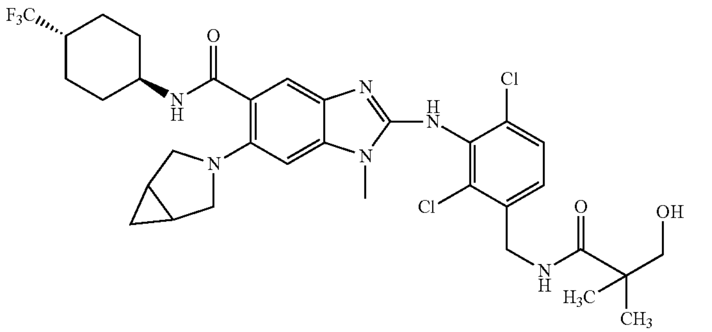 [SMILES: Cn1c(Nc2c(Cl)ccc(CNC(=O)C(C)(C)CO)c2Cl)nc2cc(C(=O)N[C@H]3CC[C@H](C(F)(F)F)CC3)c(N3CC4CC4C3)cc21] | C33H39Cl2F3N6O3 695.61 | 695 | R_f: 0.253 Method L | 186 |
| 195 | 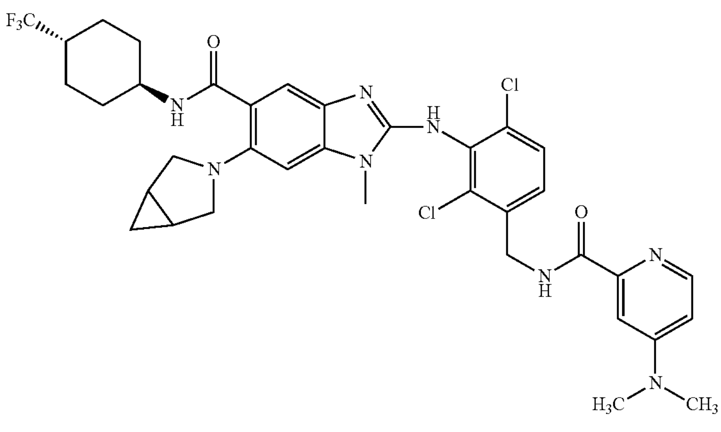 [SMILES: CN(C)c1ccnc(C(=O)NCc2ccc(Cl)c(Nc3nc4cc(C(=O)N[C@H]5CC[C@H](C(F)(F)F)CC5)c(N5CC6CC6C5)cc4n3C)c2Cl)c1] | C36H39Cl2F3N8O2 743.65 | 743 | R_f: 0.232 Method L | 186 |
| 196 | 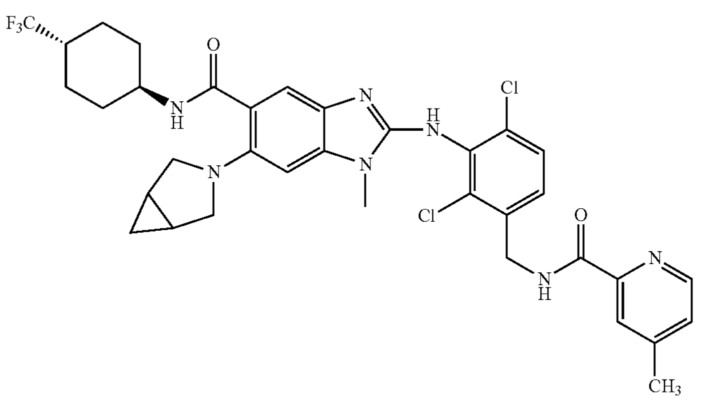 [SMILES: Cc1ccnc(C(=O)NCc2ccc(Cl)c(Nc3nc4cc(C(=O)N[C@H]5CC[C@H](C(F)(F)F)CC5)c(N5CC6CC6C5)cc4n3C)c2Cl)c1] | C35H36Cl2F3N7O2 714.62 | 714 | R_f: 0.274 Method L | 186 |

-continued
| Ex. | Structure | Formula/ Mw. | MS* m/z [M + H]+ | R$_f$ (TLC, silica gel) or R$_t$ [min] (HPLC-method) | Prepared in analogy to example |
|---|---|---|---|---|---|
| 197 | 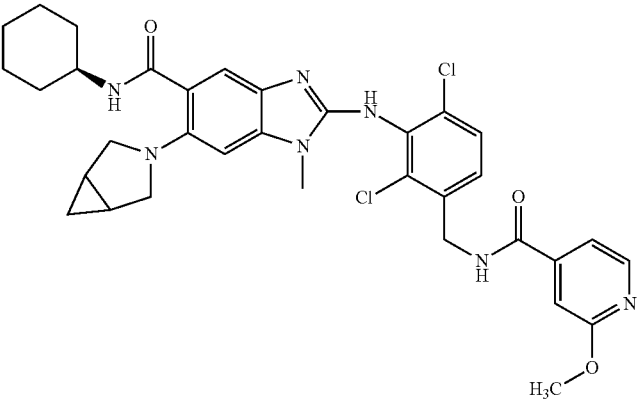 | C$_{35}$H$_{36}$Cl$_2$F$_3$N$_7$O$_3$ 730.62 | 730 | R$_f$: 0.268 Method L | 186 |
| 198 | 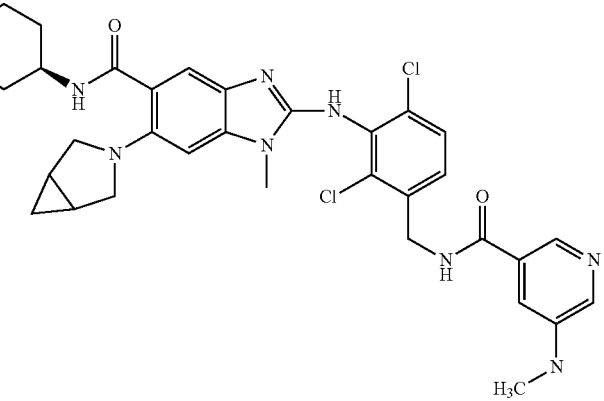 | C$_{35}$H$_{37}$Cl$_2$F$_3$N$_8$O$_2$ 729.63 | 729 | R$_f$: 0.231 min Method L | 186 |
| 199 | 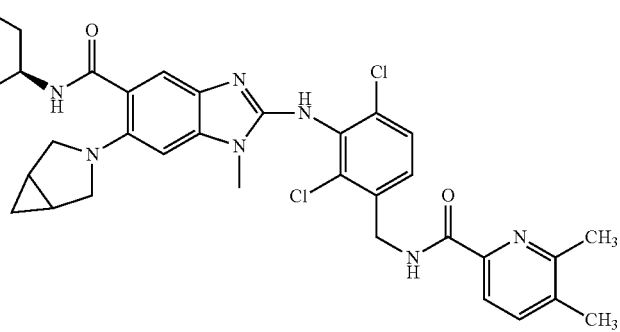 | C$_{36}$H$_{38}$Cl$_2$F$_3$N$_7$O$_2$ 728.64 | 728 | R$_f$: 0.282 min Method L | 186 |

-continued
| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 200 | 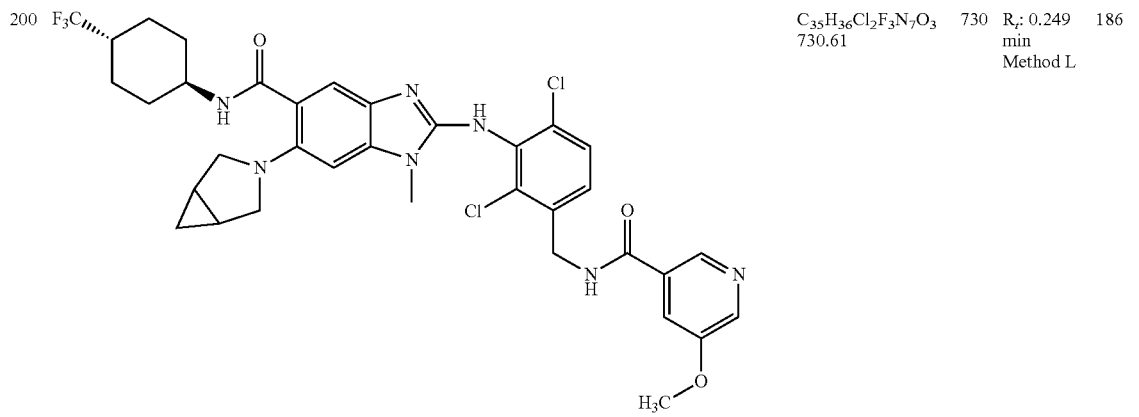 | C$_{35}$H$_{36}$Cl$_2$F$_3$N$_7$O$_3$ 730.61 | 730 | R$_t$: 0.249 min Method L | 186 |
| 201 | 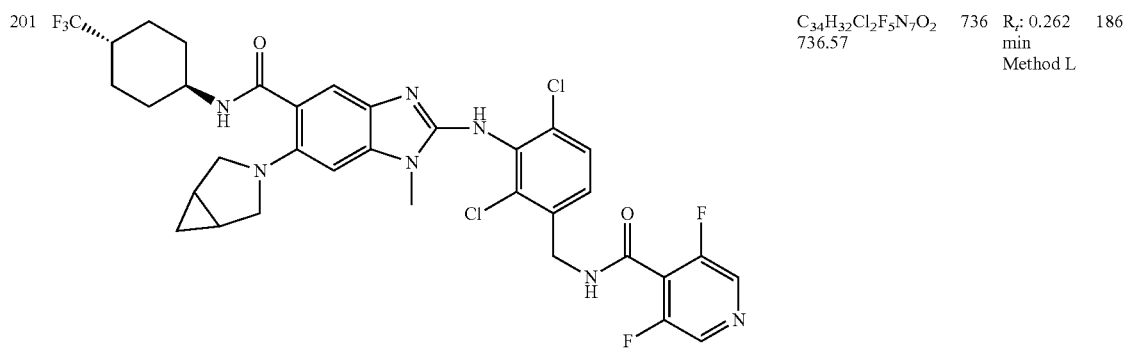 | C$_{34}$H$_{32}$Cl$_2$F$_5$N$_7$O$_2$ 736.57 | 736 | R$_t$: 0.262 min Method L | 186 |
| 202 | 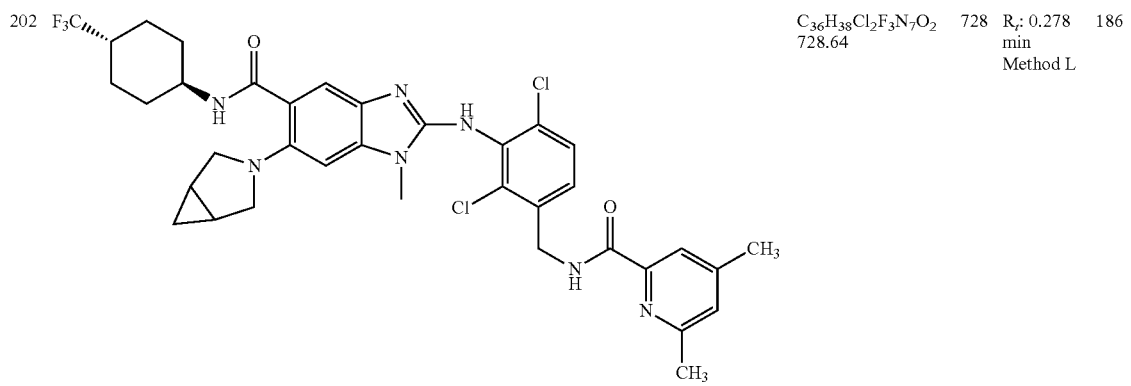 | C$_{36}$H$_{38}$Cl$_2$F$_3$N$_7$O$_2$ 728.64 | 728 | R$_t$: 0.278 min Method L | 186 |

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 203 | 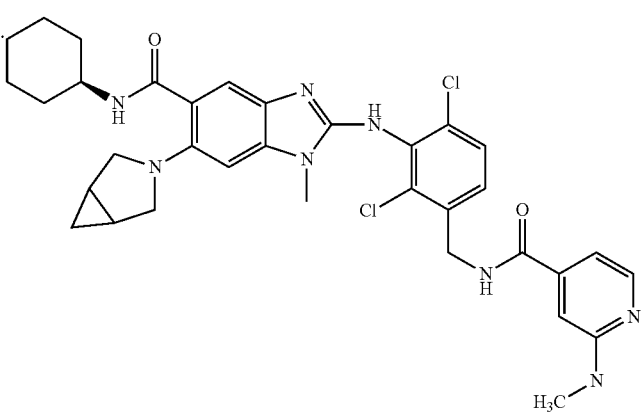 | C35H37Cl2F3N8O2 729.63 | 729 | R_f: 0.229 Method L | 186 |
| 204 | 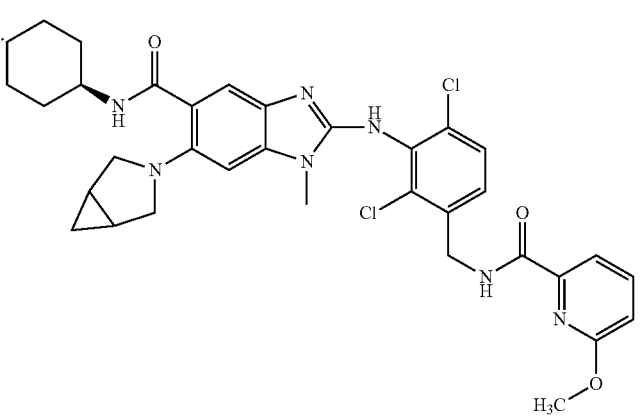 | C35H36Cl2F3N7O3 730.61 | 730 | R_f: 0.283 min Method L | 186 |
| 205 | 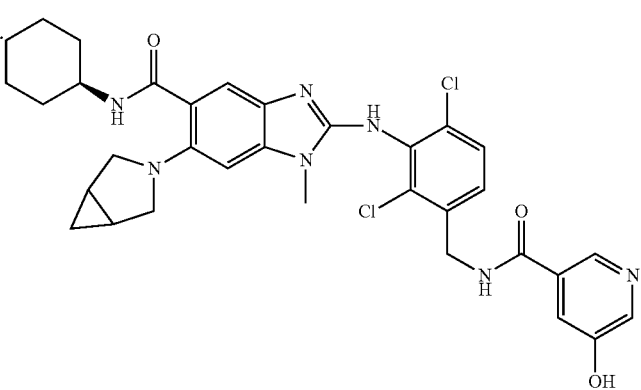 | C34H34Cl2F3N7O3 716.58 | 716 | R_f: 0.235 min Method L | 186 |

-continued
| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 206 | 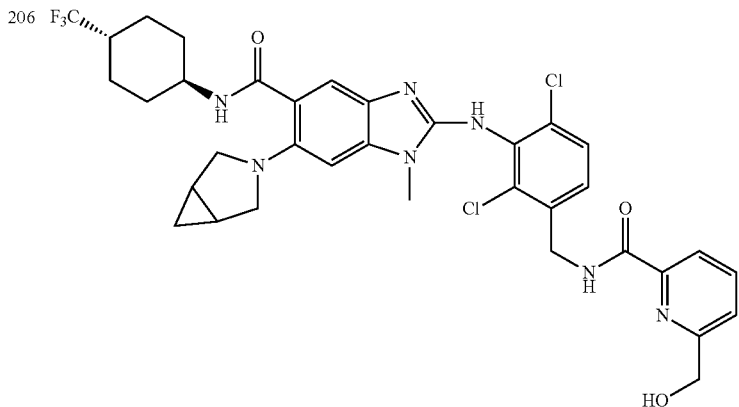 | C$_{35}$H$_{36}$Cl$_2$F$_3$N$_7$O$_3$ 730.61 | 730 | R$_t$: 0.256 min Method L | 186 |
| 207 | 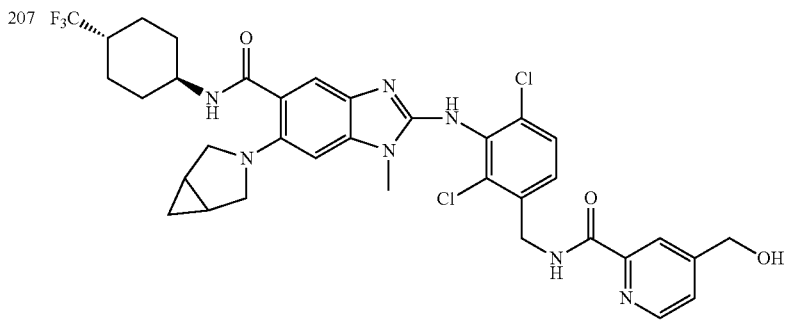 | C$_{35}$H$_{36}$Cl$_2$F$_3$N$_7$O$_3$ 730.61 | 730 | R$_t$: 0.253 min Method L | 186 |
| 208 | 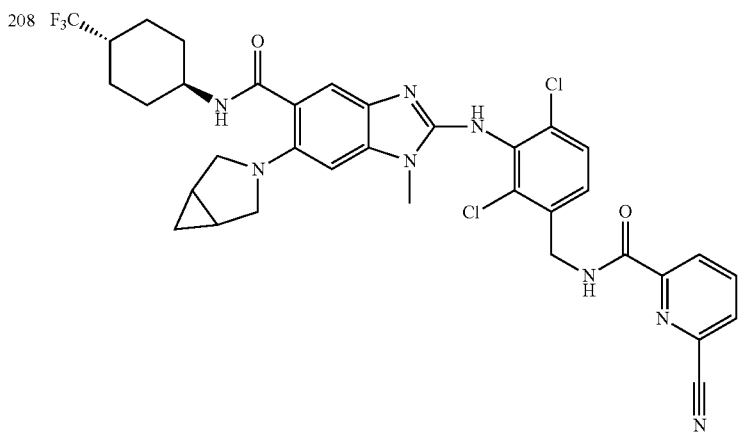 | C$_{35}$H$_{33}$Cl$_2$F$_3$N$_8$O$_2$ 725.60 | 725 | R$_t$: 0.273 min Method L | 186 |

| Ex. | Structure | Formula/ Mw. | MS* m/z [M + H]+ | $R_f$ (TLC, silica gel) or $R_t$ [min] (HPLC-method) | Prepared in analogy to example |
|---|---|---|---|---|---|
| 209 | 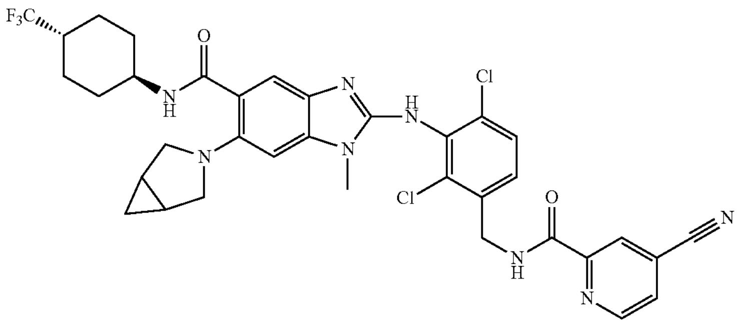 [SMILES: Cn1c(Nc2c(Cl)ccc(CNC(=O)c3cc(C#N)ccn3)c2Cl)nc2cc(C(=O)N[C@H]3CC[C@H](C(F)(F)F)CC3)c(N3CC4CC4C3)cc21] | $C_{35}H_{33}Cl_2F_3N_8O_2$ 725.60 | 725 | $R_f$: 0.271 Method L | 186 |
| 210 | 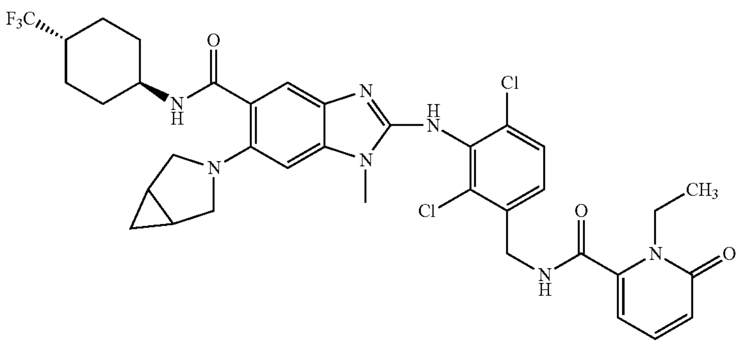 [SMILES: CCn1c(C(=O)NCc2ccc(Cl)c(Nc3nc4cc(C(=O)N[C@H]5CC[C@H](C(F)(F)F)CC5)c(N5CC6CC6C5)cc4n3C)c2Cl)cccc1=O] | $C_{33}H_{38}Cl_2F_3N_7O_3$ 744.64 | 744 | $R_f$: 0.251 min Method L | 186 |
| 211 | 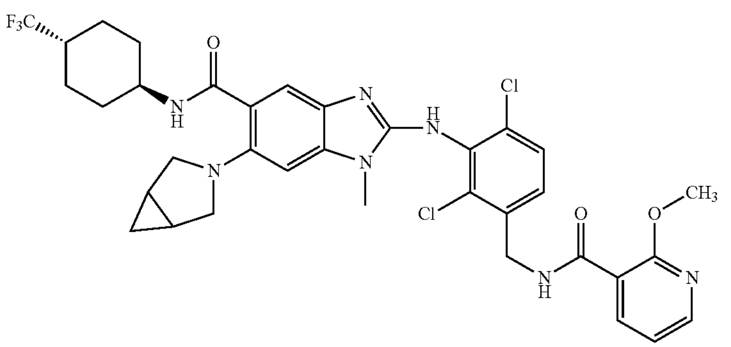 [SMILES: COc1ncccc1C(=O)NCc1ccc(Cl)c(Nc2nc3cc(C(=O)N[C@H]4CC[C@H](C(F)(F)F)CC4)c(N4CC5CC5C4)cc3n2C)c1Cl] | $C_{35}H_{36}Cl_2F_3N_7O_3$ 730.62 | 730 | $R_f$: 0.275 min Method L | 186 |
| 212 | 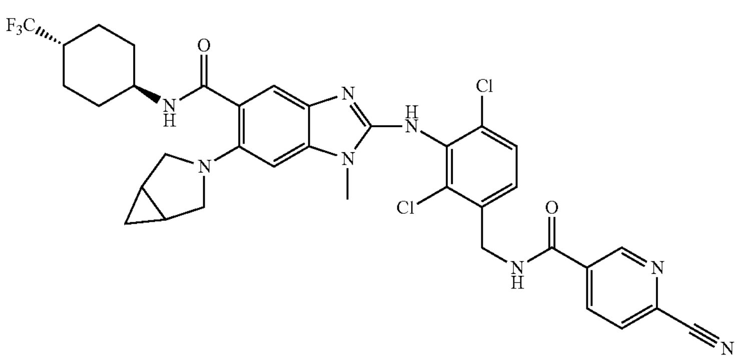 [SMILES: Cn1c(Nc2c(Cl)ccc(CNC(=O)c3ccc(C#N)nc3)c2Cl)nc2cc(C(=O)N[C@H]3CC[C@H](C(F)(F)F)CC3)c(N3CC4CC4C3)cc21] | $C_{35}H_{33}Cl_2F_3N_8O_2$ 725.60 | 725 | $R_f$: 0.265 min Method L | 186 |

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 213 | 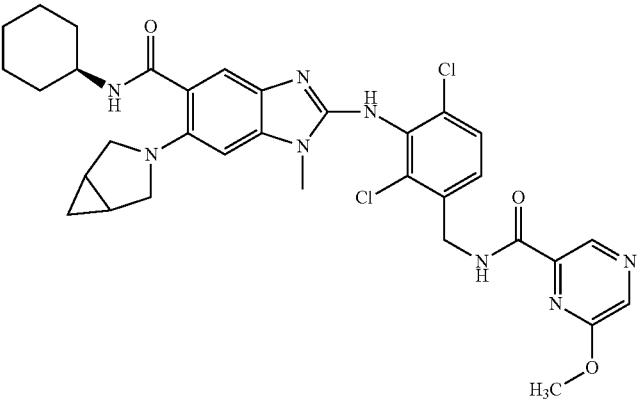 | C_34H_35Cl_2F_3N_8O_3 731.60 | 731 | R_t: 0.269 min Method L | 186 |
| 214 | 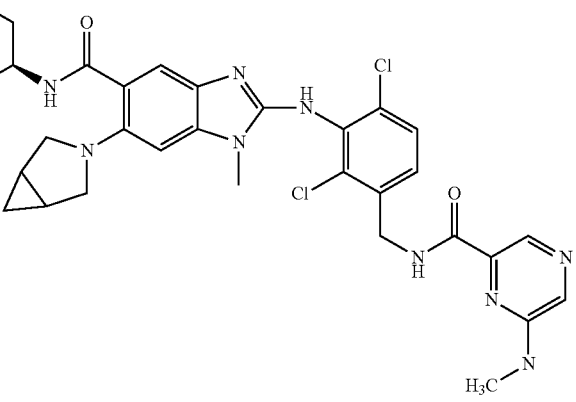 | C_34H_36Cl_2F_3N_9O_2 730.61 | 730 | R_t: 0.257 min Method L | 186 |
| 215 | 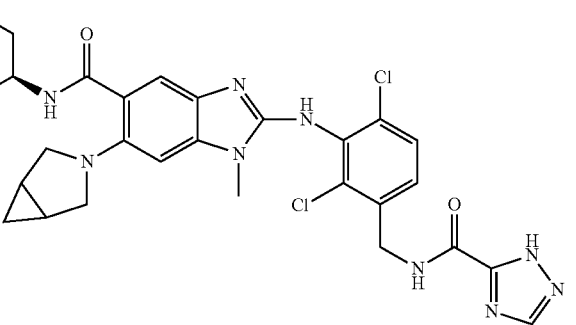 | C_31H_32Cl_2F_3N_9O_2 690.55 | 690 | R_t: 0.241 min Method L | 186 |

| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 216 | 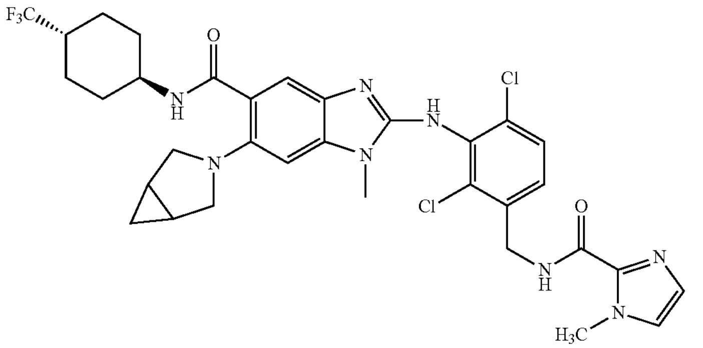 [SMILES: Cn1ccnc1C(=O)NCc1ccc(Cl)c(Nc2nc3cc(C(=O)N[C@H]4CC[C@H](C(F)(F)F)CC4)c(N4CC5CC5C4)cc3n2C)c1Cl] | $C_{33}H_{35}Cl_2F_3N_8O_2$ 703.59 | 703 | $R_f$: 0.247 Method L | 186 |
| 217 | 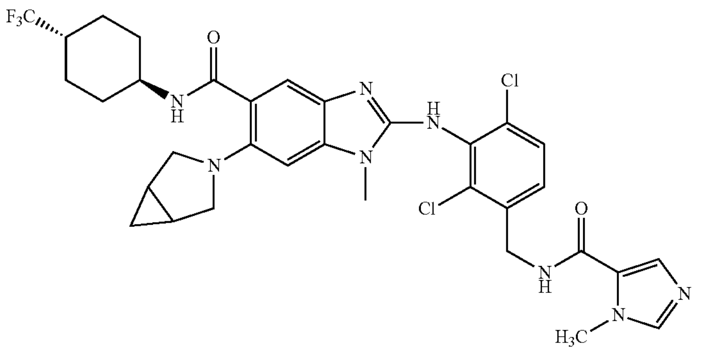 [SMILES: Cn1cncc1C(=O)NCc1ccc(Cl)c(Nc2nc3cc(C(=O)N[C@H]4CC[C@H](C(F)(F)F)CC4)c(N4CC5CC5C4)cc3n2C)c1Cl] | $C_{33}H_{35}Cl_2F_3N_8O_2$ 703.59 | 703 | $R_f$: 0.228 min Method L | 186 |
| 218 | 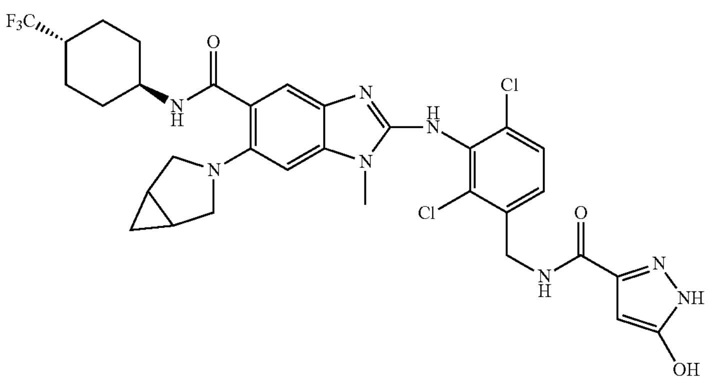 [SMILES: Cn1c(Nc2c(Cl)ccc(CNC(=O)c3cc(O)[nH]n3)c2Cl)nc2cc(C(=O)N[C@H]3CC[C@H](C(F)(F)F)CC3)c(N3CC4CC4C3)cc21] | $C_{32}H_{33}Cl_2F_3N_8O_3$ 705.56 | 705 | $R_f$: 0.243 min Method L | 186 |
| 219 | 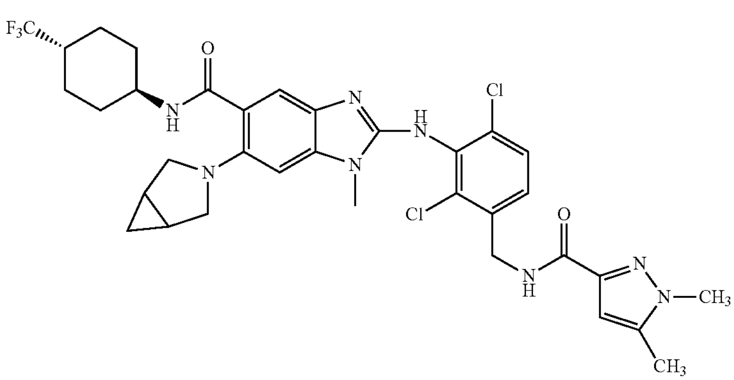 [SMILES: Cc1cc(C(=O)NCc2ccc(Cl)c(Nc3nc4cc(C(=O)N[C@H]5CC[C@H](C(F)(F)F)CC5)c(N5CC6CC6C5)cc4n3C)c2Cl)nn1C] | $C_{34}H_{37}Cl_2F_3N_8O_2$ 717.62 | 717 | $R_f$: 0.262 min Method L | 186 |

-continued

| Ex. | Structure | Formula/ Mw. | MS* m/z [M + H]⁺ | $R_f$ (TLC, silica gel) or $R_t$ [min] (HPLC-method) | Prepared in analogy to example |
|---|---|---|---|---|---|
| 220 | 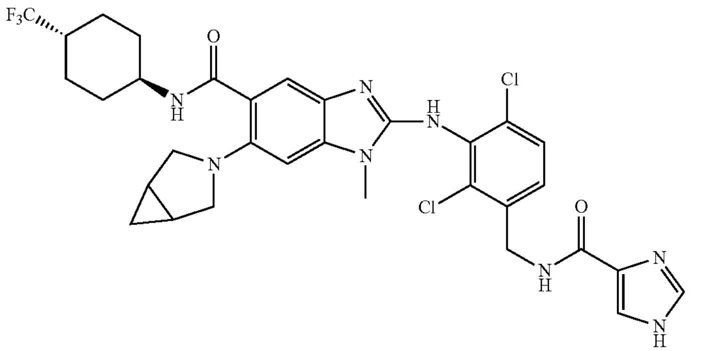 [SMILES: Cn1c(Nc2c(Cl)ccc(CNC(=O)c3c[nH]cn3)c2Cl)nc2cc(C(=O)N[C@H]3CC[C@H](C(F)(F)F)CC3)c(N3CC4CC4C3)cc21] | $C_{32}H_{33}Cl_2F_3N_8O_2$ 689.56 | 689 | $R_t$: 0.229 min Method L | 186 |
| 221 | 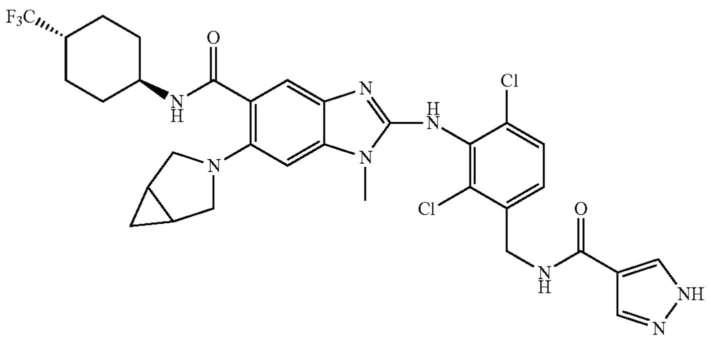 [SMILES: Cn1c(Nc2c(Cl)ccc(CNC(=O)c3cn[nH]c3)c2Cl)nc2cc(C(=O)N[C@H]3CC[C@H](C(F)(F)F)CC3)c(N3CC4CC4C3)cc21] | $C_{32}H_{33}Cl_2F_3N_8O_2$ 689.56 | 689 | $R_t$: 0.243 min Method L | 186 |
| 222 | 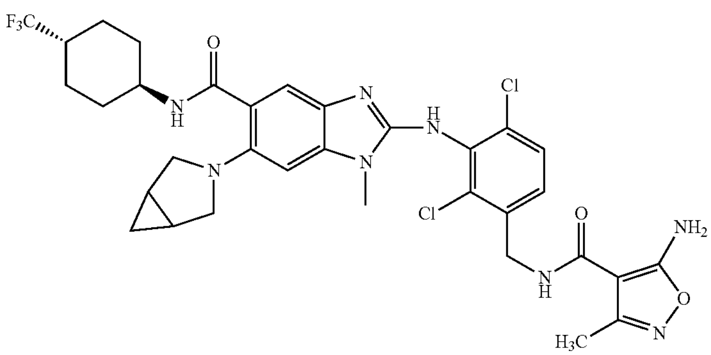 [SMILES: Cc1noc(N)c1C(=O)NCc1ccc(Cl)c(Nc2nc3cc(C(=O)N[C@H]4CC[C@H](C(F)(F)F)CC4)c(N4CC5CC5C4)cc3n2C)c1Cl] | $C_{33}H_{35}Cl_2F_3N_8O_3$ 719.59 | 719 | $R_t$: 0.256 min Method L | 186 |
| 223 | 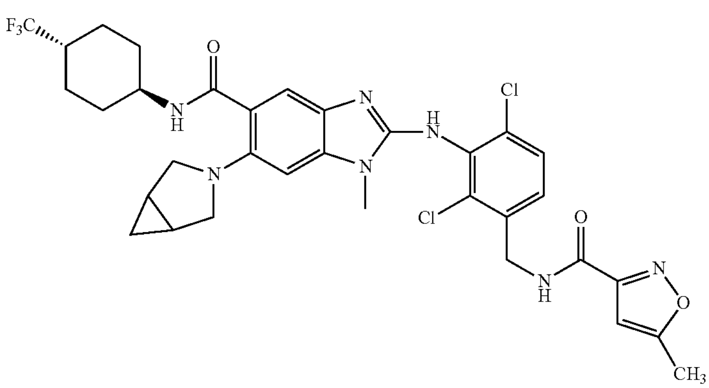 | $C_{33}H_{34}Cl_2F_3N_7O_3$ 704.57 | 704 | $R_t$: 0.267 min Method L | 186 |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 224 | 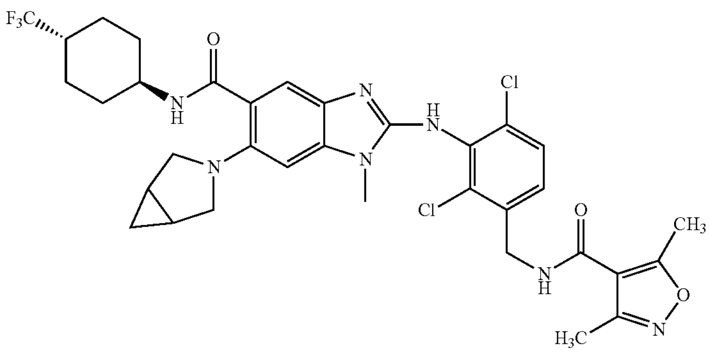 | $C_{34}H_{36}Cl_2F_3N_7O_3$ 718.60 | 718 | R_t: 0.264 min Method L | 186 |
| 225 | 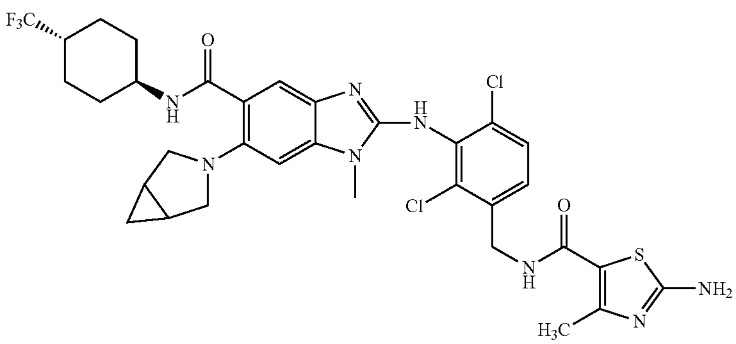 [SMILES: Cc1nc(N)sc1C(=O)NCc1ccc(Cl)c(Nc2nc3cc(C(=O)N[C@H]4CC[C@H](C(F)(F)F)CC4)c(N4CC5CC5C4)cc3n2C)c1Cl] | $C_{33}H_{35}Cl_2F_3N_8O_2S$ 735.65 | 735 | R_t: 0.233 min Method L | 186 |
| 226 | 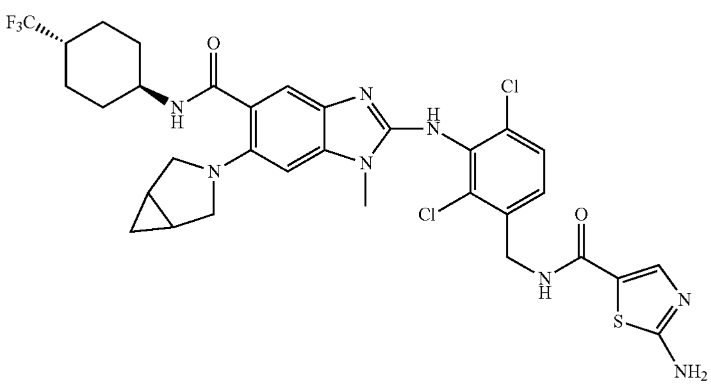 [SMILES: Cn1c(Nc2c(Cl)ccc(CNC(=O)c3cnc(N)s3)c2Cl)nc2cc(C(=O)N[C@H]3CC[C@H](C(F)(F)F)CC3)c(N3CC4CC4C3)cc21] | $C_{32}H_{33}Cl_2F_3N_8O_2S$ 721.63 | 721 | R_t: 0.234 min Method L | 186 |
| 227 | 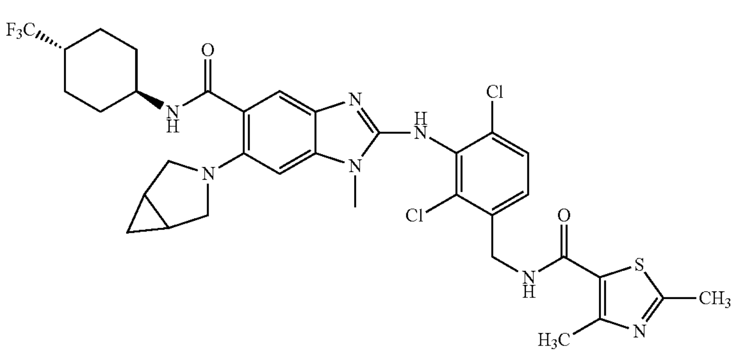 | $C_{34}H_{36}Cl_2F_3N_7O_2S$ 734.67 | 734 | R_t: 0.261 min Method L | 186 |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 228 | 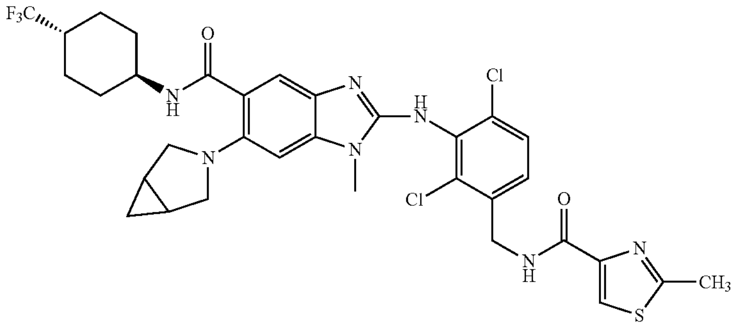 | $C_{33}H_{34}Cl_2F_3N_7O_2S$ 720.64 | 720 | R_f: 0.269 Method L | 186 |
| 229 | 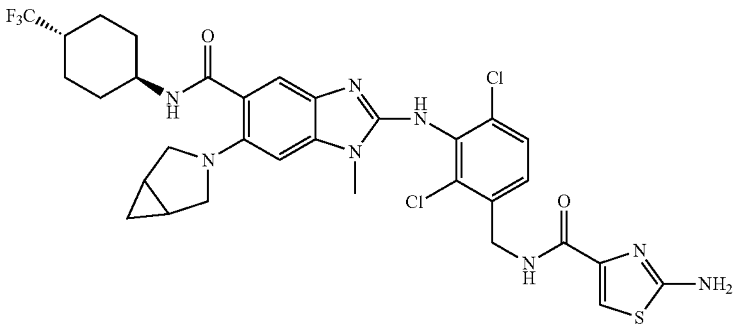 | $C_{32}H_{33}Cl_2F_3N_8O_2S$ 721.63 | 721 | R_f: 0.246 Method L | 186 |
| 230 | 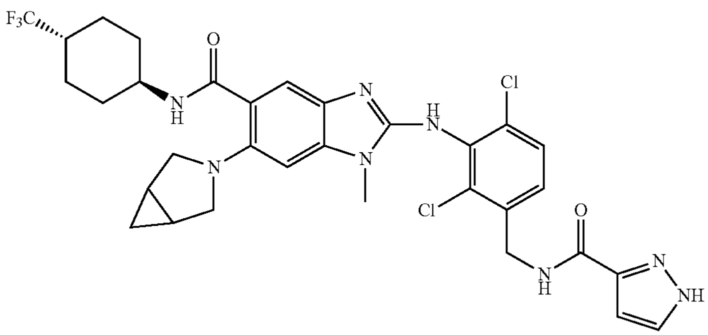 [SMILES: Cn1c(Nc2c(Cl)ccc(CNC(=O)c3cc[nH]n3)c2Cl)nc2cc(C(=O)N[C@H]3CC[C@H](C(F)(F)F)CC3)c(N3CC4CC4C3)cc21] | $C_{32}H_{33}Cl_2F_3N_8O_2$ 689.56 | 689 | R_f: 0.249 Method L | 186 |
| 232 | 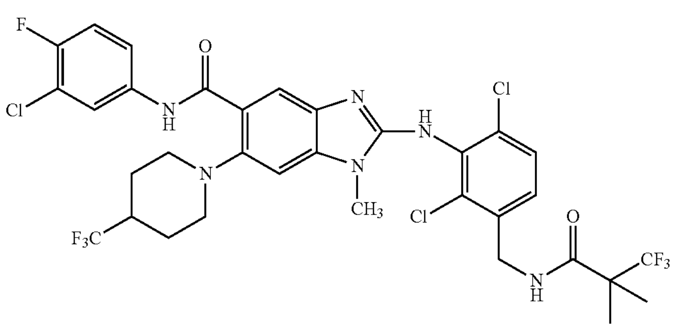 [SMILES: Cn1c(Nc2c(Cl)ccc(CNC(=O)C(C)(C)C(F)(F)F)c2Cl)nc2cc(C(=O)Nc3ccc(F)c(Cl)c3)c(N3CCC(C(F)(F)F)CC3)cc21] | $C_{33}H_{30}Cl_3F_7N_6O_2$ 781.98 | 781 | R_t: 0.631 min Method F | 231e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 233 | 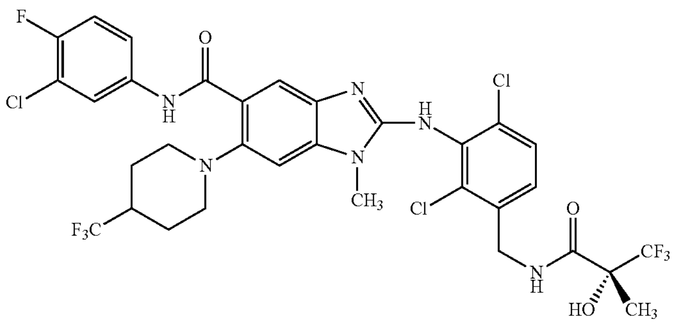 [SMILES: Cn1c(Nc2c(Cl)ccc(CNC(=O)[C@@](C)(O)C(F)(F)F)c2Cl)nc2cc(C(=O)Nc3ccc(F)c(Cl)c3)c(N3CCC(C(F)(F)F)CC3)cc21] | $C_{32}H_{28}Cl_3F_7N_6O_3$ 783.96 | 783 | $R_t$: 0.600 min Method F | 231e |
| 234 | 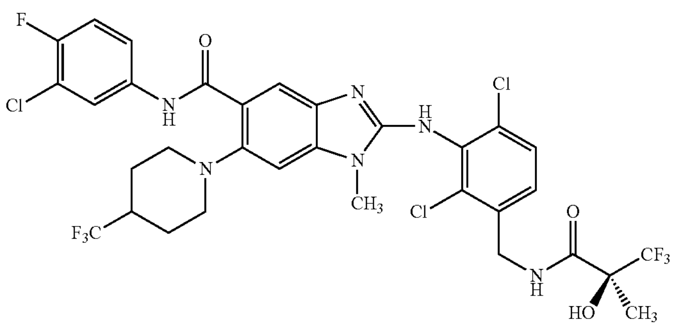 [SMILES: Cn1c(Nc2c(Cl)ccc(CNC(=O)[C@](C)(O)C(F)(F)F)c2Cl)nc2cc(C(=O)Nc3ccc(F)c(Cl)c3)c(N3CCC(C(F)(F)F)CC3)cc21] | $C_{32}H_{28}Cl_3F_7N_6O_3$ 783.96 | 783 | $R_t$: 0.610 min Method F | 231e |
| 235 | 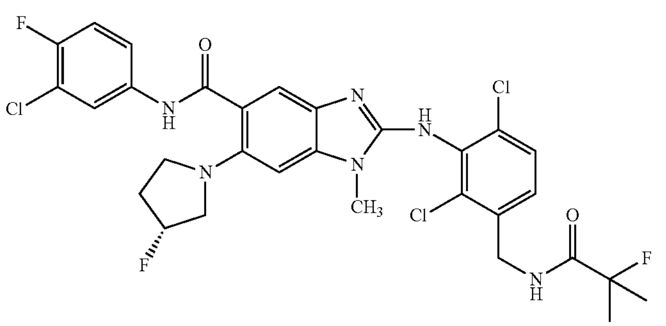 [SMILES: Cn1c(Nc2c(Cl)ccc(CNC(=O)C(C)(C)F)c2Cl)nc2cc(C(=O)Nc3ccc(F)c(Cl)c3)c(N3CC[C@@H](F)C3)cc21] | $C_{30}H_{28}Cl_3F_3N_6O_2$ 667.94 | 667 | $R_t$: 0.557 min Method F | 231e |
| 236 | 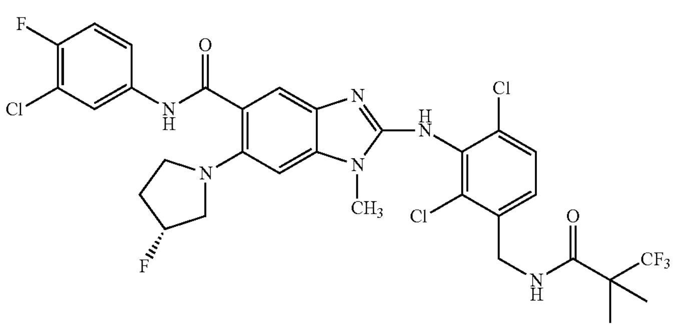 [SMILES: Cn1c(Nc2c(Cl)ccc(CNC(=O)C(C)(C)C(F)(F)F)c2Cl)nc2cc(C(=O)Nc3ccc(F)c(Cl)c3)c(N3CC[C@@H](F)C3)cc21] | $C_{31}H_{28}Cl_3F_3N_6O_2$ 717.95 | 717 | $R_t$: 0.590 min Method F | 231e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 237 | 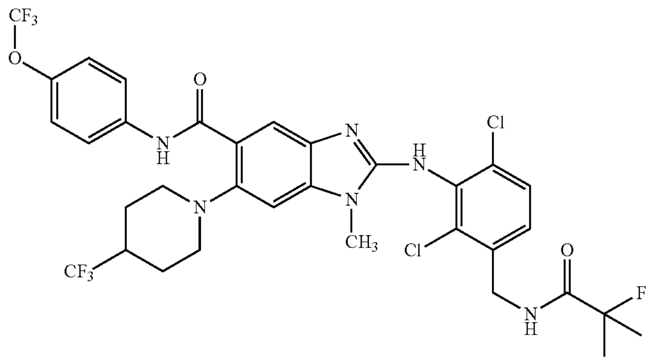 [SMILES: Cn1c(Nc2c(Cl)ccc(CNC(=O)C(C)(C)F)c2Cl)nc2cc(C(=O)Nc3ccc(OC(F)(F)F)cc3)c(N3CCC(C(F)(F)F)CC3)cc21] | $C_{33}H_{31}Cl_2F_7N_6O_3$ 763.54 | 763 | $R_t$: 0.630 min Method F | 231e |
| 238 | 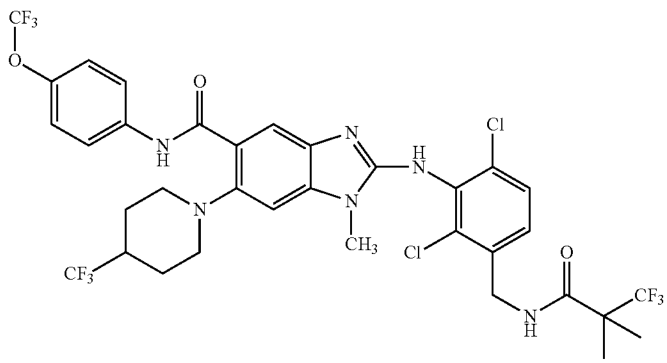 [SMILES: Cn1c(Nc2c(Cl)ccc(CNC(=O)C(C)(C)C(F)(F)F)c2Cl)nc2cc(C(=O)Nc3ccc(OC(F)(F)F)cc3)c(N3CCC(C(F)(F)F)CC3)cc21] | $C_{34}H_{31}Cl_2F_9N_6O_3$ 813.55 | 813 | $R_t$: 0.650 min Method F | 231e |
| 239 | 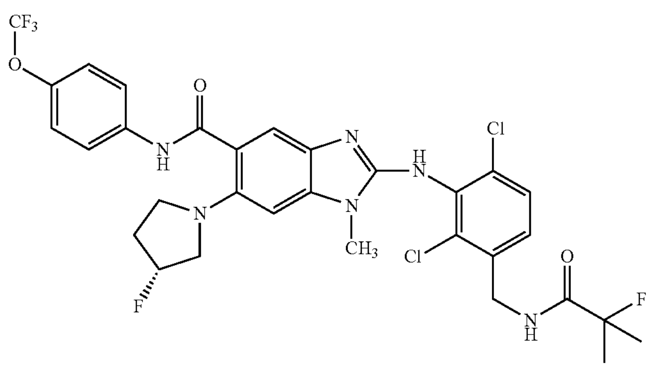 [SMILES: Cn1c(Nc2c(Cl)ccc(CNC(=O)C(C)(C)F)c2Cl)nc2cc(C(=O)Nc3ccc(OC(F)(F)F)cc3)c(N3CC[C@@H](F)C3)cc21] | $C_{31}H_{29}Cl_2F_5N_6O_3$ 699.51 | 699 | $R_t$: 0.580 min Method F | 231e |
| 240 | 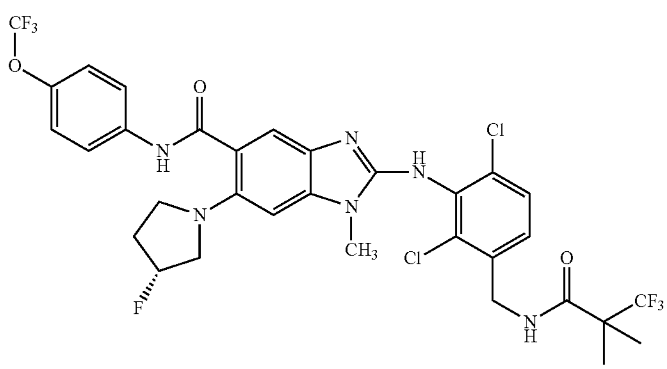 [SMILES: Cn1c(Nc2c(Cl)ccc(CNC(=O)C(C)(C)C(F)(F)F)c2Cl)nc2cc(C(=O)Nc3ccc(OC(F)(F)F)cc3)c(N3CC[C@@H](F)C3)cc21] | $C_{32}H_{29}Cl_2F_7N_6O_3$ 749.51 | 749 | $R_t$: 0.610 min Method F | 231e |

-continued
| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 241 | 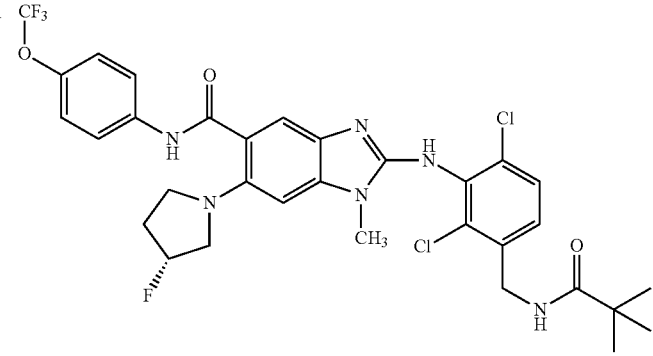 | $C_{32}H_{32}Cl_2F_4N_6O_3$ 695.54 | 695 | $R_t$: 0.620 min Method F | 231e |
| 242 | 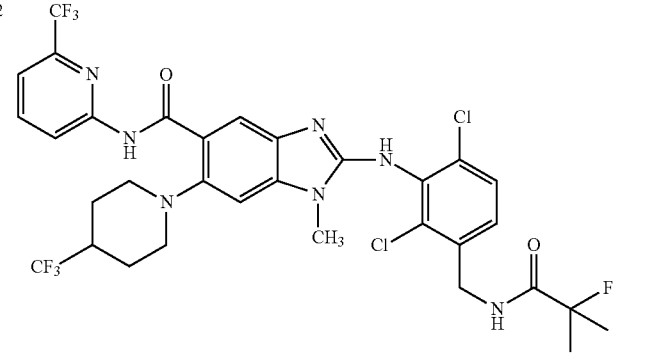 | $C_{32}H_{30}Cl_2F_7N_7O_2$ 748.53 | 748 | $R_t$: 0.637 min Method F | 231e |
| 243 | 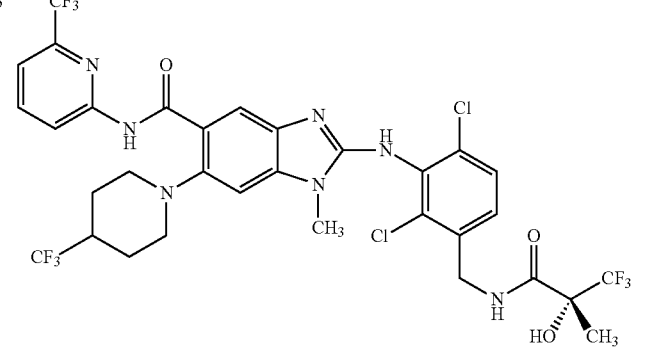 | $C_{32}H_{28}Cl_2F_9N_7O_3$ 800.51 | 800 | $R_t$: 0.640 min Method F | 231e |
| 244 | 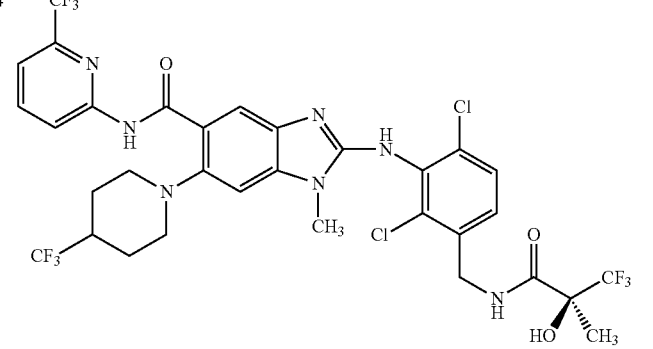 | $C_{32}H_{28}Cl_2F_9N_7O_3$ 800.51 | 800 | $R_t$: 0.640 min Method F | 231e |

-continued

| Ex. | Structure | Formula/ Mw. | MS* m/z [M + H]+ | R<sub>f</sub>(TLC, silica gel) or R<sub>t</sub> [min] (HPLC-method) | Prepared in analogy to example |
|---|---|---|---|---|---|
| 245 | 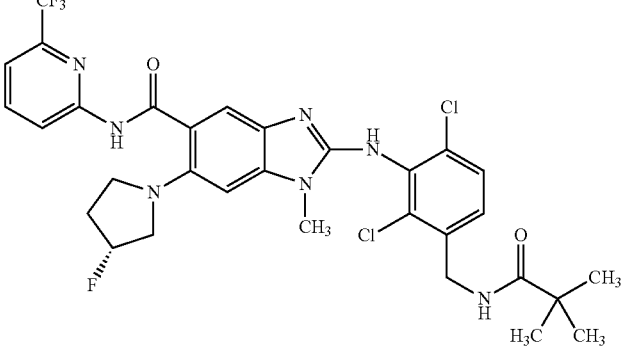 | C<sub>31</sub>H<sub>31</sub>Cl<sub>2</sub>F<sub>4</sub>N<sub>7</sub>O<sub>2</sub> 680.53 | 680 | R<sub>t</sub>: 0.610 min Method F | 231e |
| 246 | 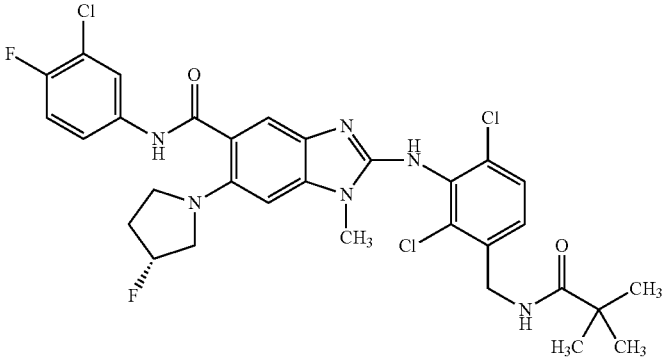 [SMILES: Cn1c(Nc2c(Cl)ccc(CNC(=O)C(C)(C)C)c2Cl)nc2cc(C(=O)Nc3ccc(F)c(Cl)c3)c(N3CC[C@@H](F)C3)cc21] | C<sub>31</sub>H<sub>31</sub>Cl<sub>3</sub>F<sub>2</sub>N<sub>6</sub>O<sub>2</sub> 663.98 | 663 | R<sub>t</sub>: 0.602 min Method F | 231e |
| 247 | 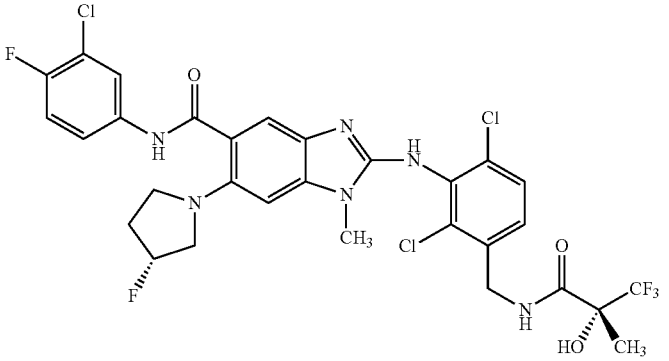 [SMILES: Cn1c(Nc2c(Cl)ccc(CNC(=O)[C@@](C)(O)C(F)(F)F)c2Cl)nc2cc(C(=O)Nc3ccc(F)c(Cl)c3)c(N3CC[C@@H](F)C3)cc21] | C<sub>30</sub>H<sub>26</sub>Cl<sub>3</sub>F<sub>5</sub>N<sub>6</sub>O<sub>3</sub> 719.92 | 719 | R<sub>t</sub>: 0.589 min Method F | 231e |
| 248 | 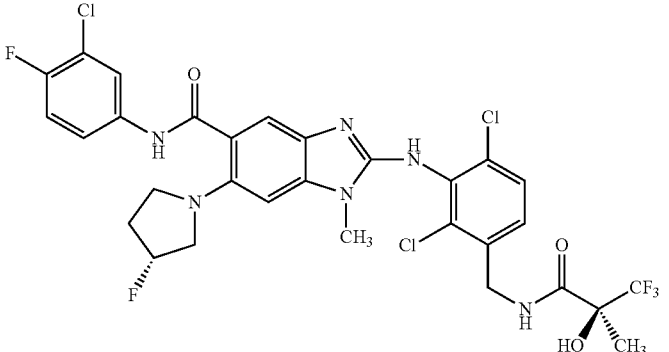 | C<sub>30</sub>H<sub>26</sub>Cl<sub>3</sub>F<sub>5</sub>N<sub>6</sub>O<sub>3</sub> 719.92 | 719 | R<sub>t</sub>: 0.590 min Method F | 231e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 249 | 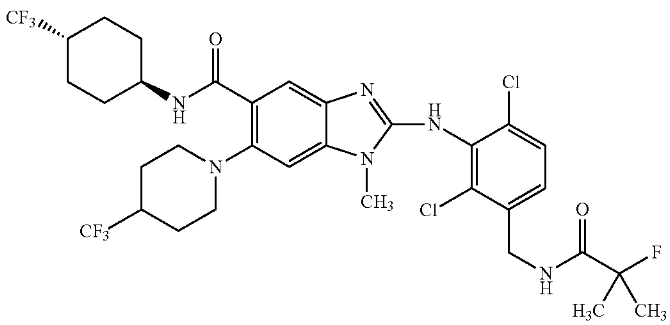 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC(C(F)(F)F)CC3)cc21] | $C_{33}H_{37}Cl_2F_7N_6O_2$ 753.59 | 753 | R_t: 0.626 min Method F | 231e |
| 250 | 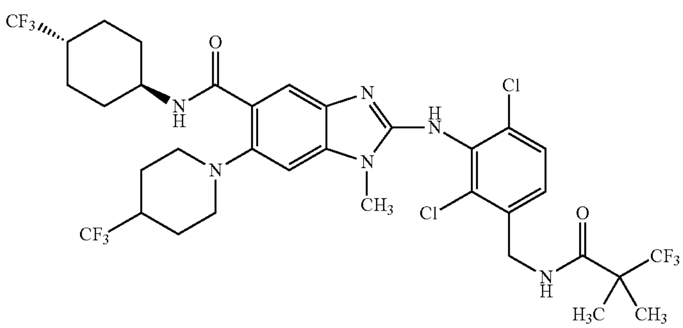 [SMILES: Cn1c(Nc2c(Cl)ccc(CNC(=O)C(C)(C)C(F)(F)F)c2Cl)nc2cc(C(=O)N[C@H]3CC[C@H](C(F)(F)F)CC3)c(N3CCC(C(F)(F)F)CC3)cc21] | $C_{34}H_{37}Cl_2F_9N_6O_2$ 803.59 | 803 | R_t: 0.645 min Method F | 231e |
| 251 | 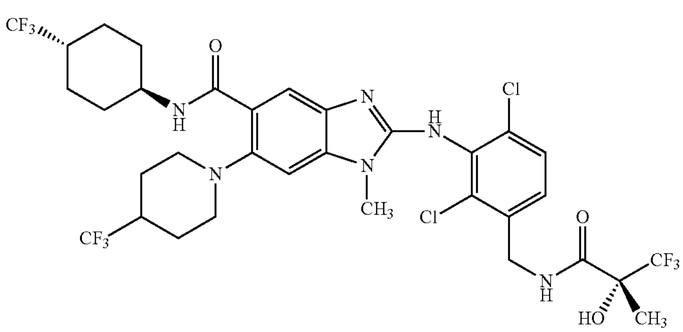 [SMILES: Cn1c(Nc2c(Cl)ccc(CNC(=O)[C@@](C)(O)C(F)(F)F)c2Cl)nc2cc(C(=O)N[C@H]3CC[C@H](C(F)(F)F)CC3)c(N3CCC(C(F)(F)F)CC3)cc21] | $C_{33}H_{35}Cl_2F_9N_6O_3$ 805.57 | 805 | R_t: 0.626 min Method F | 231e |
| 252 | 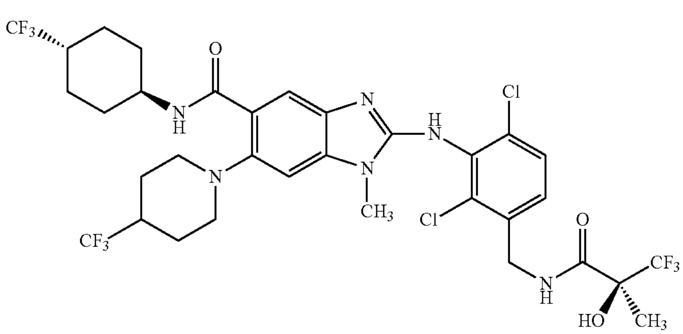 [SMILES: Cn1c(Nc2c(Cl)ccc(CNC(=O)[C@](C)(O)C(F)(F)F)c2Cl)nc2cc(C(=O)N[C@H]3CC[C@H](C(F)(F)F)CC3)c(N3CCC(C(F)(F)F)CC3)cc21] | $C_{33}H_{35}Cl_2F_9N_6O_3$ 805.57 | 805 | R_t: 0.625 min Method F | 231e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 253 | 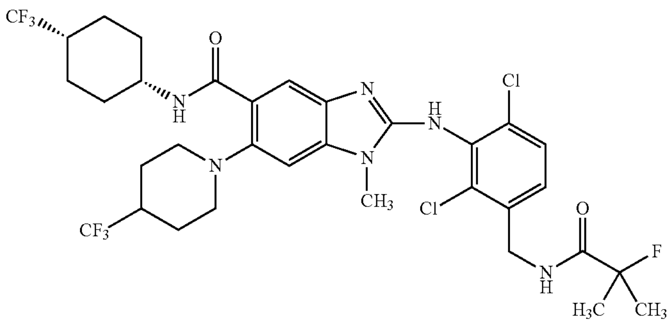 [SMILES: Cn1c(Nc2c(Cl)ccc(CNC(=O)C(C)(C)F)c2Cl)nc2cc(C(=O)N[C@H]3CC[C@@H](C(F)(F)F)CC3)c(N3CCC(C(F)(F)F)CC3)cc21] | C₃₃H₃₇Cl₂F₇N₆O₂ 753.59 | 753 | R_f: 0.635 Method F | 231e |
| 254 | 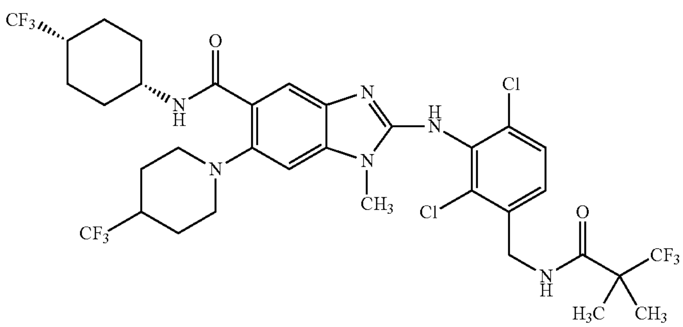 [SMILES: Cn1c(Nc2c(Cl)ccc(CNC(=O)C(C)(C)C(F)(F)F)c2Cl)nc2cc(C(=O)N[C@H]3CC[C@@H](C(F)(F)F)CC3)c(N3CCC(C(F)(F)F)CC3)cc21] | C₃₄H₃₇Cl₂F₉N₆O₂ 803.59 | 803 | R_f: 0.656 Method F | 231e |
| 255 | 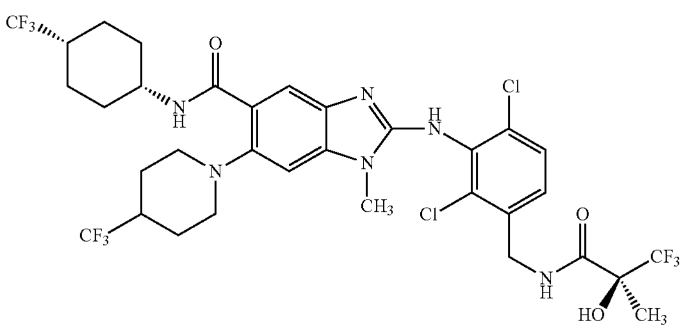 [SMILES: Cn1c(Nc2c(Cl)ccc(CNC(=O)[C@](C)(O)C(F)(F)F)c2Cl)nc2cc(C(=O)N[C@H]3CC[C@@H](C(F)(F)F)CC3)c(N3CCC(C(F)(F)F)CC3)cc21] | C₃₃H₃₅Cl₂F₉N₆O₃ 805.57 | 805 | R_f: 0.635 Method F | 231e |
| 256 | 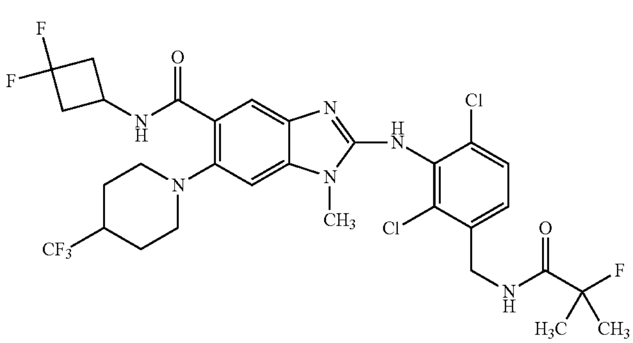 [SMILES: Cn1c(Nc2c(Cl)ccc(CNC(=O)C(C)(C)F)c2Cl)nc2cc(C(=O)NC3CC(F)(F)C3)c(N3CCC(C(F)(F)F)CC3)cc21] | C₃₀H₃₂Cl₂F₆N₆O₂ 693.52 | 693 | R_f: 0.586 Method F | 231e |

-continued

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 257 | 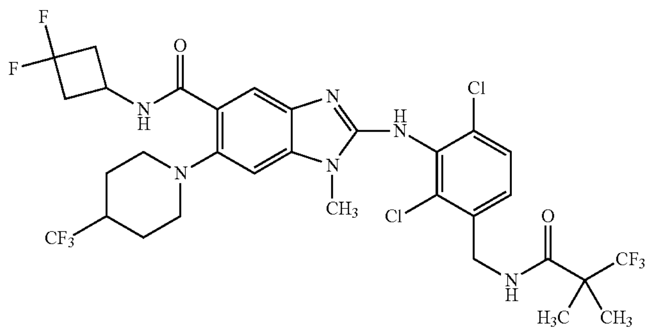 [SMILES: Cn1c(Nc2c(Cl)ccc(CNC(=O)C(C)(C)C(F)(F)F)c2Cl)nc2cc(C(=O)NC3CC(F)(F)C3)c(N3CCC(C(F)(F)F)CC3)cc21] | C$_{31}$H$_{32}$Cl$_2$F$_8$N$_6$O$_2$ 743.52 | 743 | R$_t$: 0.617 min Method F | 231e |
| 258 | 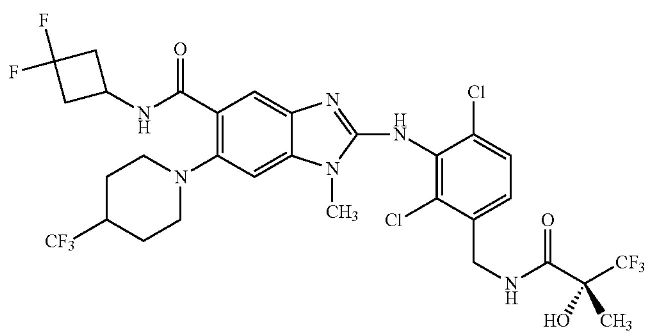 [SMILES: Cn1c(Nc2c(Cl)ccc(CNC(=O)[C@@](C)(O)C(F)(F)F)c2Cl)nc2cc(C(=O)NC3CC(F)(F)C3)c(N3CCC(C(F)(F)F)CC3)cc21] | C$_{30}$H$_{30}$Cl$_2$F$_8$N$_6$O$_3$ 745.50 | 745 | R$_t$: 0.590 min Method F | 231e |
| 259 | 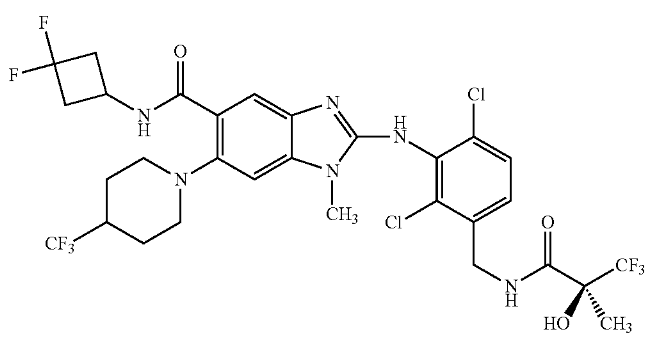 [SMILES: Cn1c(Nc2c(Cl)ccc(CNC(=O)[C@](C)(O)C(F)(F)F)c2Cl)nc2cc(C(=O)NC3CC(F)(F)C3)c(N3CCC(C(F)(F)F)CC3)cc21] | C$_{30}$H$_{30}$Cl$_2$F$_8$N$_6$O$_3$ 745.50 | 745 | R$_t$: 0.594 min Method F | 231e |
| 260 | 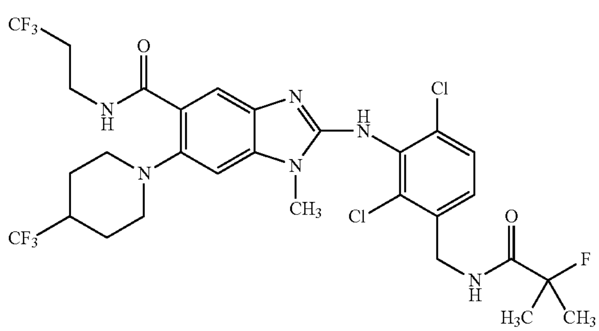 [SMILES: Cn1c(Nc2c(Cl)ccc(CNC(=O)C(C)(C)F)c2Cl)nc2cc(C(=O)NCCC(F)(F)F)c(N3CCC(C(F)(F)F)CC3)cc21] | C$_{29}$H$_{31}$Cl$_2$F$_7$N$_6$O$_2$ 699.50 | 699 | R$_t$: 0.550 min Method F | 231e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 261 | 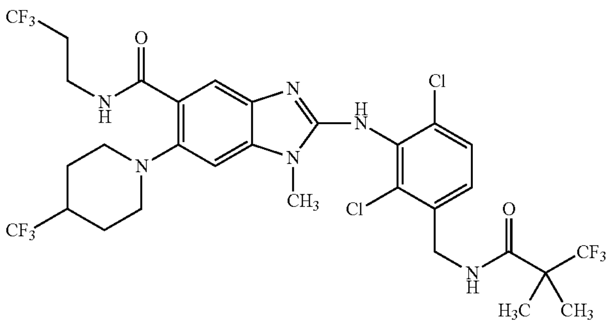 [SMILES: Cn1c(Nc2c(Cl)ccc(CNC(=O)C(C)(C)C(F)(F)F)c2Cl)nc2cc(C(=O)NCCC(F)(F)F)c(N3CCC(C(F)(F)F)CC3)cc21] | $C_{30}H_{31}Cl_2F_9N_6O_2$ 749.50 | 749 | $R_f$: 0.574 Method F | 231e |
| 262 | 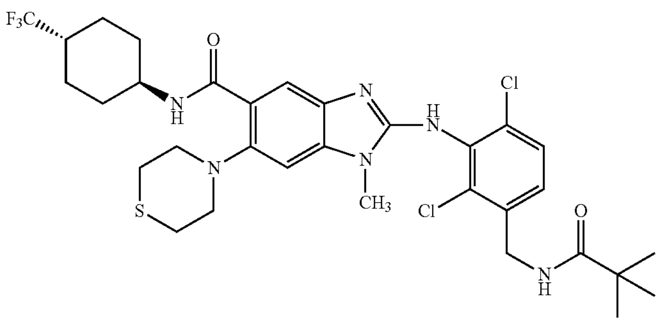 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCSCC3)cc21] | $C_{32}H_{39}Cl_2F_3N_6O_2S$ 699.66 | 699 | $R_t$: 1.70 min Method I | 6c |
| 263 | 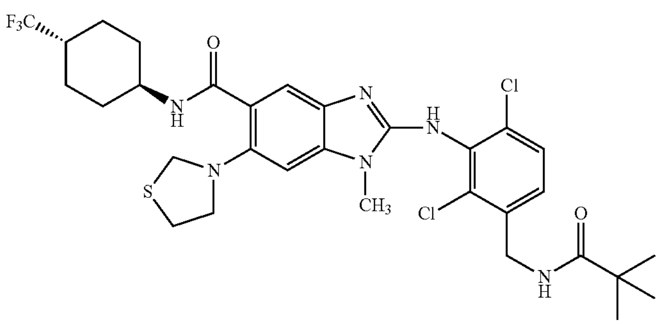 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCSC3)cc21] | $C_{31}H_{37}Cl_2F_3N_6O_2S$ 685.63 | 685 | $R_t$: 1.45 min Method H | 6c |
| 264 | 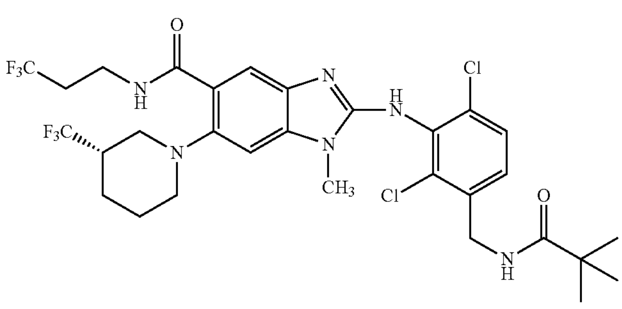 | $C_{30}H_{34}Cl_2F_6N_6O_2$ 695.53 | 695 | $R_t$: 1.48 min Method A | 1e |

-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 265 | 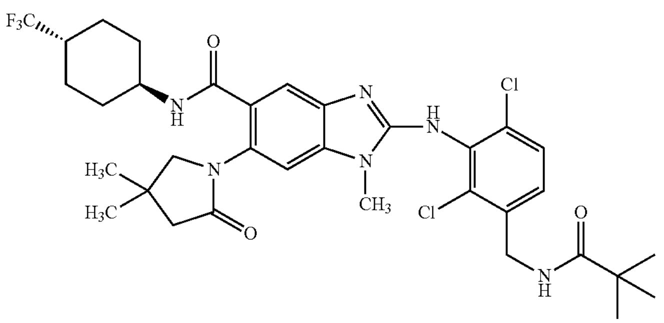 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(C)(C)CC3=O)cc21] | $C_{34}H_{41}Cl_2F_3N_6O_3$ 709.63 | 709 | $R_t$: 1.43 min Method H | 6c |
| 266 | 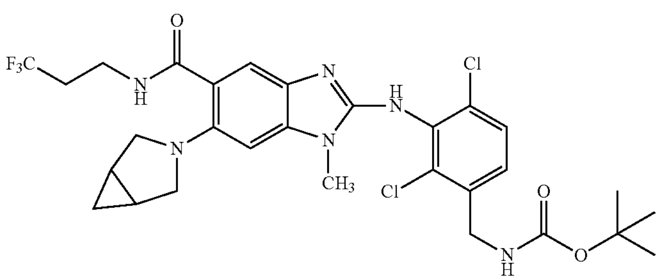 [SMILES: Cn1c(Nc2c(Cl)ccc(CNC(=O)OC(C)(C)C)c2Cl)nc2cc(C(=O)NCCC(F)(F)F)c(N3CC4CC4C3)cc21] | $C_{29}H_{33}Cl_2F_3N_6O_3$ 641.51 | 641 | $R_f$ = 0.33 DCM/ EtOH 95:5 | 172e |
| 267 | 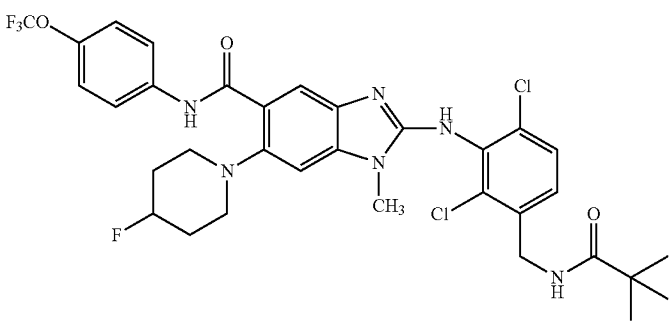 [SMILES: Cn1c(Nc2c(Cl)ccc(CNC(=O)C(C)(C)C)c2Cl)nc2cc(C(=O)Nc3ccc(OC(F)(F)F)cc3)c(N3CCC(F)CC3)cc21] | $C_{33}H_{34}Cl_2F_4N_6O_3$ 709.56 | 709 | $R_t$: 1.53 min Method H | 6c |
| 268 | 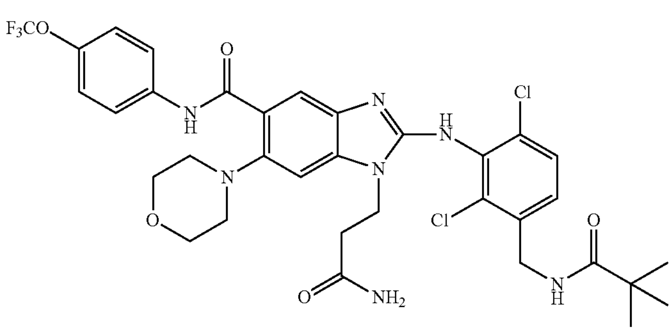 [SMILES: CC(C)(C)C(=O)NCc1ccc(Cl)c(Nc2nc3cc(C(=O)Nc4ccc(OC(F)(F)F)cc4)c(N4CCOCC4)cc3n2CCC(N)=O)c1Cl] | $C_{34}H_{36}Cl_2F_3N_7O_5$ 750.59 | 750 | $R_t$: 1.48 min Method H | 6c |

| Ex. | Structure | Formula/ Mw. | MS* m/z [M+H]+ | $R_f$ (TLC, silica gel) or $R_t$ [min] (HPLC-method) | Prepared in analogy to example |
|---|---|---|---|---|---|
| 269 | 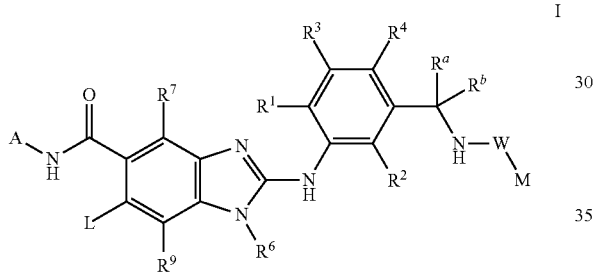 | $C_{32}H_{37}Cl_2F_7N_6O_3$ 757.57 | 757 | $R_f$= 0.36 DCM/ EtOH 95:5 | 1e |

The invention claimed is:

1. A compound of formula I $$I$$

in which
- $R^1$ represents halo, OH, —CN, $C_{1-3}$ alkyl, $C_{2-6}$ alkynyl, or $OC_{1-3}$ alkyl which latter three groups are optionally substituted by one or more substituents selected from fluoro, —CN, =O, OH, —OCH$_3$, or —OCF$_3$;
- $R^2$ represents halo, —CN, $C_{1-3}$ alkyl, or $OC_{1-3}$ alkyl which latter two groups are optionally substituted by one or more substituents selected from fluoro, —CN, =O, OH, —OCH$_3$, or —OCF$_3$;
- $R^3$ and $R^4$ independently represent hydrogen, halo, —CN, $C_{1-3}$ alkyl, or $OC_{1-3}$ alkyl which latter two groups are optionally substituted by one or more substituents selected from fluoro, —CN, =O, OH, —OCH$_3$, or —OCF$_3$;
- $R^a$, $R^b$ independently represent hydrogen, or $C_{1-3}$ alkyl optionally substituted by one or more fluoro atoms,
  or both together with the carbon atom which they are bound to, form a $C_{3-7}$ cycloalkylene ring, or a 4-6 membered heterocycloalkylene ring which latter two rings are optionally substituted by one or more fluorine atoms;
- W represents —C(O)—, —S(O)—, —S(O)$_2$—, —C(O)O—, or —C(O)NR$^d$— which groups are bound to the nitrogen of the —NH-moiety via carbon or sulfur atom;
- $R^d$ represents hydrogen, or $C_{1-3}$ alkyl;
- M represents $C_{1-8}$ alkyl, $C_{2-8}$ alkynyl, $C_{3-8}$ cycloalkyl-$C_{0-4}$ alkyl, or 4-10 membered heterocycloalkyl-$C_{0-4}$ alkyl- which latter four groups are optionally substituted by one or more groups selected from fluoro, —OH, =O, —CN, —NH$_2$, $C_{1-3}$ alkyl, —NH(C$_{1-3}$ alkyl), —N(C$_{1-3}$ alkyl)$_2$, azetidinyl, pyrrolidinyl, piperidinyl, or —OC$_{1-3}$ alkyl [which latter seven alkyl groups can be substituted by one or more substituents selected from fluoro, OH, —CN, or OC$_{1-2}$ alkyl (which latter alkyl group is optionally substituted by one or more fluorine atoms)],
  aryl, or heteroaryl [which latter two groups are optionally substituted by one or more substituents selected from halo, OH, —CN, $C_{1-3}$ alkyl, or OC$_{1-3}$alkyl (which latter two alkyl groups are optionally substituted by one or more fluorine atoms)], or
  aryl, or heteroaryl which latter two groups are optionally substituted by one or more substituents selected from halo, —OH, —CN, —NH$_2$, aryl, or heteroaryl [which latter two groups are optionally substituted by one or more substituents selected from halo, OH, —CN, $C_{1-3}$ alkyl, or —OC$_{1-3}$ alkyl (which latter two alkyl groups are optionally substituted by one or more fluorine atoms)],
  $C_{1-7}$ alkyl, $C_{2-7}$ alkynyl, $C_{3-7}$ cycloalkyl, 4-7 membered heterocycloalkyl, —NH(C$_{1-3}$ alkyl), —N(C$_{1-3}$ alkyl)$_2$,
  —OC$_{1-3}$ alkyl, —O—C$_{0-2}$alkyl-aryl, or —SC$_{1-3}$ alkyl, (which latter alkyl, alkynyl, heterocycloalkyl or cycloalkyl groups are optionally substituted by one or more substituents selected from fluoro, —CN, =O, —NH$_2$, —NH(C$_{1-3}$ alkyl), —N(C$_{1-3}$ alkyl)$_2$, —OH, or —OC$_{1-3}$alkyl, and which latter aryl group is optionally substituted by one or more substituents selected from fluoro, —CN, —NH$_2$, —NH(C$_{1-3}$ alkyl), —N(C$_{1-3}$ alkyl)$_2$, —OH, or —OC$_{1-3}$alkyl)];
- $R^6$ represents hydrogen, $C_{1-5}$ alkyl, $C_{3-6}$ alkynyl, 4-7 membered hetero-cycloalkyl-$C_{0-2}$ alkyl or $C_{3-7}$cycloalkyl-$C_{0-2}$ alkyl [which latter four groups are optionally substituted by one or more substituents selected from fluoro, —CN, =O, —C(O)—NH$_2$, —C(O)—NH(C$_{1-3}$ alkyl), —C(O)—N(C$_{1-3}$ alkyl)$_2$, $C_{1-3}$ alkyl optionally substituted by OH or fluoro, —OH, —NH$_2$, —OC$_{1-3}$ alkyl, —NH(C$_{1-3}$ alkyl), or —N(C$_{1-3}$ alkyl)$_2$];
- $R^7$ and $R^9$ independently represent hydrogen, halo, —CN, $C_{1-5}$ alkyl, $C_{3-5}$ cycloalkyl-$C_{0-2}$ alkyl-, $C_{1-5}$ alkyl-O—, or $C_{3-5}$cycloalkyl-$C_{0-2}$ alkyl-O— (in which latter four groups, the alkyl and cycloalkyl fragments are optionally substituted by one or more substituents selected from fluoro, —CN, =O, OH, or —OC$_{1-3}$ alkyl or by one or more C$_{1-3}$ alkyl groups which are optionally substituted by one or more fluorine atoms);

L represents —NH$_2$, —NHR$^{10}$, —NR$^{10}$R$^{11}$, or a 4-10-membered heterocyclo-alkyl group which is bound to the benzimidazole through a nitrogen atom and which can optionally be annulated to a phenyl or a 5- or 6-membered heteroaryl ring and which is optionally substituted by one or more substituents R$^{12}$;

R$^{10}$ and R$^{11}$ independently represent C$_{1-7}$ alkyl, C$_{3-6}$ alkynyl,
C$_{3-7}$ cycloalkyl-C$_{0-4}$ alkyl- or C$_{4-7}$ heterocycloalkyl-C$_{0-4}$ alkyl- [which latter four groups are optionally substituted by one or more groups selected from fluoro, —OH, NH$_2$, —C(O)NH$_2$, —CN, =O, C$_{1-3}$ alkyl, —NH(C$_{1-3}$ alkyl),
—N(C$_{1-3}$ alkyl)$_2$, —OC$_{1-5}$ alkyl, —OC$_{3-6}$ cycloalkyl, —OC$_{4-6}$ heterocycloalkyl,
—SC$_{1-3}$ alkyl, —S(O)C$_{1-3}$ alkyl, or —S(O)$_2$C$_{1-3}$ alkyl (which latter nine groups are optionally substituted by one or more substituents selected from fluoro, —CF$_3$, —CHF$_2$, —CH$_2$F, or —CH$_3$)],
or
aryl-C$_{0-4}$ alkyl-, or heteroaryl-C$_{0-4}$ alkyl- [which latter two groups are optionally substituted by one or more substituents selected from halo, —OH, —NH$_2$, —CN, C$_{1-3}$ alkyl, C$_{3-5}$ cycloalkyl, C$_{1-3}$ alkyl-O—, or C$_{3-5}$ cycloalkyl-O— (which latter four groups are optionally substituted by one or more fluorine atoms)];

each R$^{12}$ independently represents halo, —OH, —NH$_2$, =O, —CN, —C(=O)—NH$_2$, C$_{1-4}$ alkyl, C$_{3-5}$ cycloalkyl-C$_{0-2}$ alkyl-, C$_{4-5}$ heterocycloalkyl-C$_{0-2}$ alkyl-, C$_{1-4}$ alkyl-O—, C$_{1-3}$ alkyl-C(=O)—, —C(=O)—NH(C$_{1-3}$ alkyl), or —C(=O)—N(C$_{1-3}$ alkyl)$_2$ [which latter seven groups are optionally substituted by one or more groups selected from: fluoro, —OH, oxo, —NH$_2$, —CN, C$_{1-3}$ alkyl, —NH(C$_{1-3}$ alkyl), —N(C$_{1-3}$ alkyl)$_2$, —OC$_{1-3}$ alkyl, or —OC$_{3-5}$ cycloalkyl [which latter five groups are optionally substituted by one or more substituents selected from fluoro, —CF$_3$, —CHF$_2$, or —CH$_2$F],
or
aryl-C$_{0-4}$ alkyl-, or heteroaryl-C$_{0-4}$ alkyl- [which latter two groups are optionally substituted by one or more substituents selected from halo, —OH, —CN, C$_{1-3}$ alkyl, C$_{3-5}$ cycloalkyl, C$_{1-3}$ alkyl-O—, or C$_{3-5}$ cycloalkyl-O—
(which latter four groups are optionally substituted by one or more fluorine atoms)];

A represents C$_{1-8}$ alkyl, C$_{3-8}$ alkynyl, aryl-C$_{0-3}$alkyl-,
C$_{3-8}$ cycloalkyl-C$_{0-3}$ alkyl-, 4-7 membered heterocycloalkyl-C$_{0-3}$ alkyl-, or heteroaryl-C$_{0-3}$alkyl- in which latter six groups, the alkyl-, alkynyl-, cycloalkyl- and heterocycloalkyl-fragments are optionally substituted by one or more substituents selected from R$^{14}$ and the aryl and heteroaryl fragments are optionally substituted by one or more substituents selected from R$^{15}$;

each R$^{14}$ independently represents fluoro, —OH, —CN, =O, —NH$_2$, —NH(C$_{1-3}$ alkyl), —N(C$_{1-3}$ alkyl)$_2$, —OC$_{1-6}$ alkyl, or C$_{1-6}$alkyl [in which latter four groups the alkyl fragments are optionally substituted by one or more substituents selected from fluoro, —CN, =O, —NH$_2$, —NH(C$_{1-3}$ alkyl), N(C$_{1-3}$ alkyl)$_2$, —OH, or —OC$_{1-3}$ alkyl] or aryl, or heteroaryl [which latter two groups are optionally substituted by one or more substituents selected from halo, OH, —CN, C$_{1-3}$ alkyl, or OC$_{1-3}$ alkyl (which latter two alkyl groups are optionally substituted by one or more fluorine atoms)];

each R$^{15}$ independently represents halo, —OH, —CN, —NH$_2$, —NH(C$_{1-3}$ alkyl), —N(C$_{1-3}$ alkyl)$_2$, or —OC$_{1-3}$ alkyl [in which latter three groups the alkyl fragments are optionally substituted by one or more substituents selected from fluoro, —CN, =O, —NH$_2$, —NH(C$_{1-3}$ alkyl), N(C$_{1-3}$ alkyl)$_2$, —OH, or —OC$_{1-3}$ alkyl] or aryl, or heteroaryl [which latter two groups are optionally substituted by one or more substituents selected from halo, OH, —CN, C$_{1-3}$ alkyl, or OC$_{1-3}$ alkyl (which latter two alkyl groups are optionally substituted by one or more fluorine atoms)] or C$_{1-7}$ alkyl, C$_{2-7}$ alkynyl, C$_{3-7}$ cycloalkyl, or 4-7 membered heterocycloalkyl [which latter alkyl, alkynyl, heterocycloalkyl or cycloalkyl groups are optionally substituted by one or more substituents selected from fluoro, —CN, =O,
—NH$_2$, —NH(C$_{1-3}$ alkyl), N(C$_{1-3}$ alkyl)$_2$, —OH, or OC$_{1-3}$alkyl];

or a salt thereof.

2. A compound according to claim 1, wherein
R$^1$ represents halo, C$_{1-3}$ alkyl, or —OC$_{1-3}$ alkyl which latter two groups are optionally substituted by one or more fluorine atoms;
or a pharmaceutically acceptable salt thereof.

3. A compound according to claim 1, wherein
R$^2$ represents halo, or C$_{1-3}$ alkyl optionally substituted by one or more fluorine atoms;
or a pharmaceutically acceptable salt thereof.

4. A compound according to claim 1, wherein
R$^3$, R$^4$, R$^7$ and R$^9$ independently represent hydrogen, fluoro, chloro, or methyl;
or a pharmaceutically acceptable salt thereof.

5. A compound according to claim 1, wherein
M represents C$_{1-6}$ alkyl, or C$_{3-8}$ cycloalkyl-C$_{0-1}$ alkyl- [which latter two groups are optionally substituted by one or more groups selected from fluoro,
—OH, or C$_{1-3}$ alkyl optionally substituted by —OH or one or more fluorine atoms];
or phenyl, pyrazolyl, imidazolyl, 1,2,3-triazolyl,1,2,4-triazolyl, oxazolyl, isoxazolyl, thiazolyl, pyridinyl, pyridazinyl, pyrazinyl or

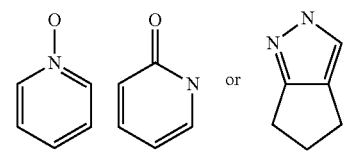

all of which groups are optionally substituted by one or more substituents selected from fluoro, —OH, —CN, —NH$_2$, C$_{1-3}$ alkyl, —NH(C$_{1-3}$ alkyl), —N(C$_{1-3}$ alkyl)$_2$, or —OC$_{1-3}$ alkyl (which latter alkyl groups are optionally substituted by one or more substituents selected from fluoro or —OH);
or a pharmaceutically acceptable salt thereof.

6. A compound according to claim 1, wherein
L represents —NH$_2$, —NHR$^{10}$, —NR$^{10}$R$^{11}$, or
azetidinyl-, pyrrolidinyl-, thiazolidinyl-, piperidinyl-, morpholinyl-, thiomorpholinyl-, piperazinyl- or

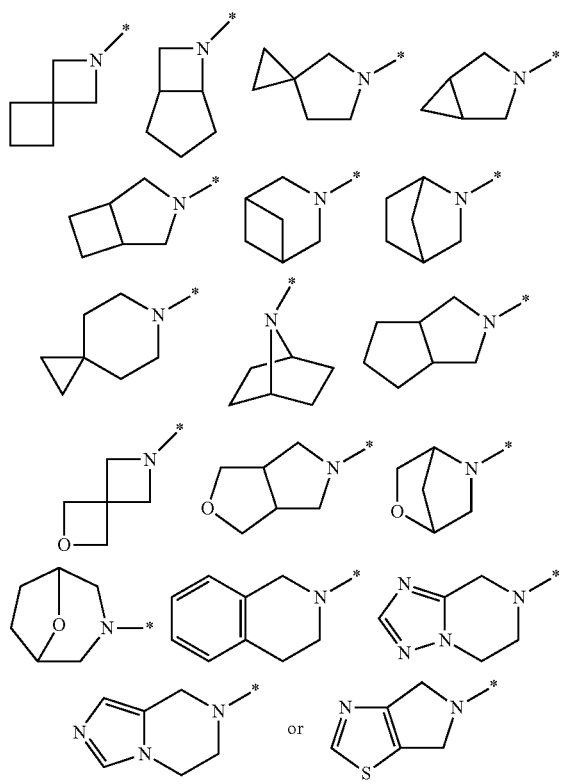

all of which heterocyclic groups are optionally substituted by one or more substituents $R^{12}$, while the above mentioned groups are bonded to the benzimidazole core through a nitrogen atom;

$R^{10}$ and $R^{11}$ independently represent $C_{1-5}$ alkyl, $C_{3-5}$ alkynyl, $C_{3-6}$ cycloalkyl-$C_{0-1}$ alkyl- or $C_{4-6}$ heterocycloalkyl-$C_{0-1}$ alkyl- [which latter four groups are optionally substituted by one or more groups selected from fluoro, —OH, —CN, =O, $C_{1-3}$ alkyl, —OC$_{1-3}$ alkyl, —C(O)—NH$_2$, —SC$_{1-3}$ alkyl, —S(O)C$_{1-3}$ alkyl, or —S(O)$_2$C$_{1-3}$ alkyl (which latter five alkyl groups are optionally substituted by one or more fluorine atoms)], or phenyl-$C_{0-1}$ alkyl-, imidazolyl-$C_{0-1}$ alkyl-, or triazolyl-$C_{0-1}$ alkyl- [which latter three groups are optionally substituted by one or more substituents selected from fluoro, chloro, CH$_3$, CH$_2$F, CHF$_2$, CF$_3$, —OCH$_3$, —OCH$_2$F, —OCHF$_2$, or —OCF$_3$];

each $R^{12}$ independently represents fluoro, —OH, =O, —C(=O)NH$_2$, $C_{1-4}$ alkyl, $C_{3-5}$ cycloalkyl, or $C_{1-4}$ alkyl-O— [which latter three groups are optionally substituted by one or more groups selected from fluoro or —OH], or phenyl optionally substituted by one or more substituents selected from halo, $C_{1-3}$ alkyl which is optionally substituted by one or more fluorine atoms;

or a pharmaceutically acceptable salt thereof.

7. A compound according to claim 1, namely a compound of formula Ia

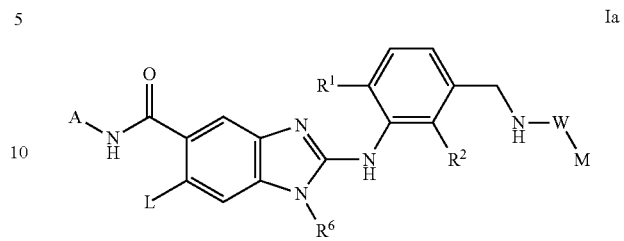

in which $R^1$ represents halo, $C_{1-3}$ alkyl, or —OC$_{1-3}$ alkyl which latter two groups are optionally substituted by one or more fluorine atoms;

$R^2$ represents halo, or $C_{1-3}$ alkyl optionally substituted by one or more fluorine atoms;

$R^6$ represents hydrogen, $C_{1-5}$ alkyl or $C_{3-7}$cycloalkyl-$C_{0-2}$ alkyl [which latter two groups are optionally substituted by one or more substituents selected from fluoro, —OH, $C_{1-3}$ alkyl optionally substituted by OH, —OC$_{1-3}$ alkyl or —C(O)—NH$_2$,];

W represents —C(O)—, —S(O)$_2$—, or —C(O)O— which groups are bound to the nitrogen of the —NH— moiety via carbon or sulfur atom;

M represents $C_{1-6}$ alkyl, or $C_{3-8}$ cycloalkyl-$C_{0-1}$ alkyl- [which latter two groups are optionally substituted by one or more groups selected from fluoro, —OH, or $C_{1-3}$ alkyl optionally substituted by —OH or one or more fluorine atoms];

or phenyl, pyrazolyl, imidazolyl, 1,2,3-triazolyl,1,2,4-triazolyl, oxazolyl, isoxazolyl, thiazolyl, pyridinyl, pyridazinyl, pyrazinyl or all of which groups are optionally substituted by one or more substituents selected from fluoro, —OH, —CN, —NH$_2$, $C_{1-3}$ alkyl, —NH($C_{1-3}$ alkyl), —N($C_{1-3}$ alkyl)$_2$, or —OC$_{1-3}$ alkyl (which latter alkyl groups are optionally substituted by one or more substituents selected from fluoro or —OH);

A represents $C_{1-6}$ alkyl, aryl-$C_{0-3}$alkyl-, $C_{3-8}$cycloalkyl-$C_{0-3}$alkyl-, 4-7 membered heterocycloalkyl-$C_{0-3}$ alkyl-, or heteroaryl-$C_{0-3}$alkyl- in which latter groups, the alkyl-, cycloalkyl- and heterocycloalkyl-fragments are optionally substituted by one or more substituents selected from $R^{14}$ and the aryl and heteroaryl fragments are optionally substituted by one or more substituents selected from $R^{15}$;

each $R^{14}$ independently represents fluoro, or $C_{1-3}$alkyl optionally substituted by one or more fluorine atoms, or phenyl optionally substituted by one or more halogen atoms;

each $R^{15}$ represents independently halo, —OC$_{1-3}$ alkyl, or $C_{1-5}$ alkyl [which latter two groups are optionally substituted by one or more —OH or one or more fluorine atoms];

L represents —NH$_2$, —NHR$^{10}$, —NR$^{10}$R$^{11}$, or azetidinyl-, pyrrolidinyl-, thiazolidinyl-, piperidinyl-, morpholinyl-, thiomorpholinyl-, piperazinyl-

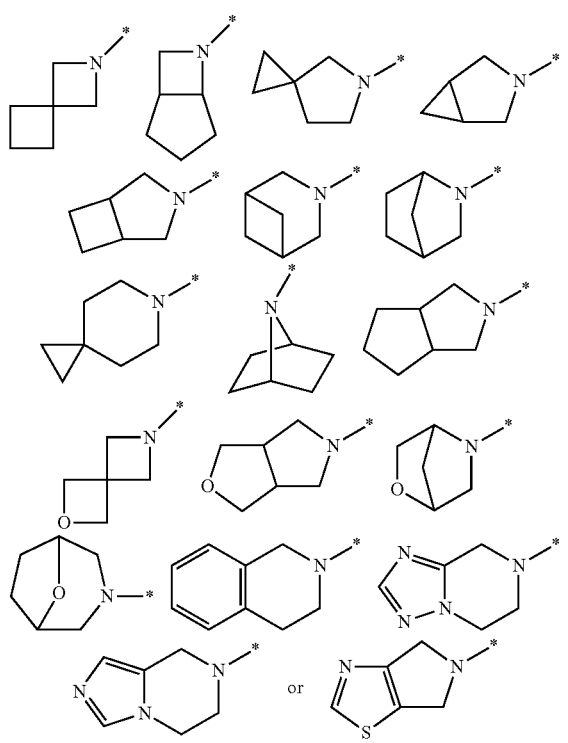

or
all of which heterocyclic groups are optionally substituted by one or more substituents $R^{12}$, while the above mentioned groups are bonded to the benzimidazole core through a nitrogen atom;

$R^{10}$ and $R^{11}$ independently represent $C_{1-5}$ alkyl, $C_{3-5}$ alkynyl, $C_{3-6}$ cycloalkyl-$C_{0-1}$ alkyl- or $C_{4-6}$ heterocycloalkyl-$C_{0-1}$ alkyl- [which latter four groups are optionally substituted by one or more groups selected from fluoro, —OH, —CN, =O, $C_{1-3}$ alkyl, —$OC_{1-3}$ alkyl, —C(O)—NH$_2$, —$SC_{1-3}$ alkyl, —S(O)$C_{1-3}$ alkyl, or —S(O)$_2C_{1-3}$ alkyl (which latter five alkyl groups are optionally substituted by one or more fluorine atoms)], or phenyl-$C_{0-1}$ alkyl-, imidazolyl-$C_{0-1}$ alkyl-, or triazolyl-$C_{0-1}$ alkyl- [which latter three groups are optionally substituted by one or more substituents selected from fluoro, chloro, CH$_3$, CH$_2$F, CHF$_2$, CF$_3$, —OCH$_3$, —OCH$_2$F, —OCHF$_2$, or —OCF$_3$];

each $R^{12}$ independently represents fluoro, —OH, =O, —C(=O)NH$_2$, $C_{1-4}$ alkyl, $C_{3-5}$ cycloalkyl, or $C_{1-4}$ alkyl-O— [which latter three groups are optionally substituted by one or more groups selected from fluoro or —OH], or phenyl optionally substituted by one or more substituents selected from halo, $C_{1-3}$ alkyl which is optionally substituted by one or more fluorine atoms;

or a pharmaceutically acceptable salt thereof.

8. A compound according to claim 1, wherein

A represents phenyl-$C_{0-2}$ alkyl-, pyridyl- $C_{0-1}$ alkyl-, pyrimidinyl-$C_{0-1}$ alkyl-, thienyl-$C_{0-1}$ alkyl-, thiazolyl-$C_{0-1}$ alkyl-, thiadiazolyl-$C_{0-1}$ alkyl-, isoxazolyl-$C_{0-1}$ alkyl-, $C_{1-6}$ alkyl, $C_{3-6}$cycloalkyl-$C_{0-1}$ alkyl-, or piperidin-4-yl [in which groups the alkyl- or cycloalkyl- and piperidin-4-yl fragments are optionally substituted by one or more substituents selected from $R^{14}$ and the phenyl or heteroaryl fragments are optionally substituted by one or more substituents selected from $R^{15}$;

each $R^{14}$ independently represents fluoro, CH$_3$, CH$_2$F, CHF$_2$, CF$_3$, ethyl optionally substituted by one or more fluorine atoms, or phenyl optionally substituted by one or more fluorine or chlorine atoms each $R^{15}$ represents independently fluoro, chloro, CH$_3$, CH$_2$F, CHF$_2$, CF$_3$, $C_{2-4}$ alkyl optionally substituted by —OH or one or more fluorine atoms, —OCH$_3$, —OCH$_2$F, —OCHF$_2$, or —OCF$_3$;

or a pharmaceutically acceptable salt thereof.

9. A compound according to claim 1, wherein

M represents a group selected from

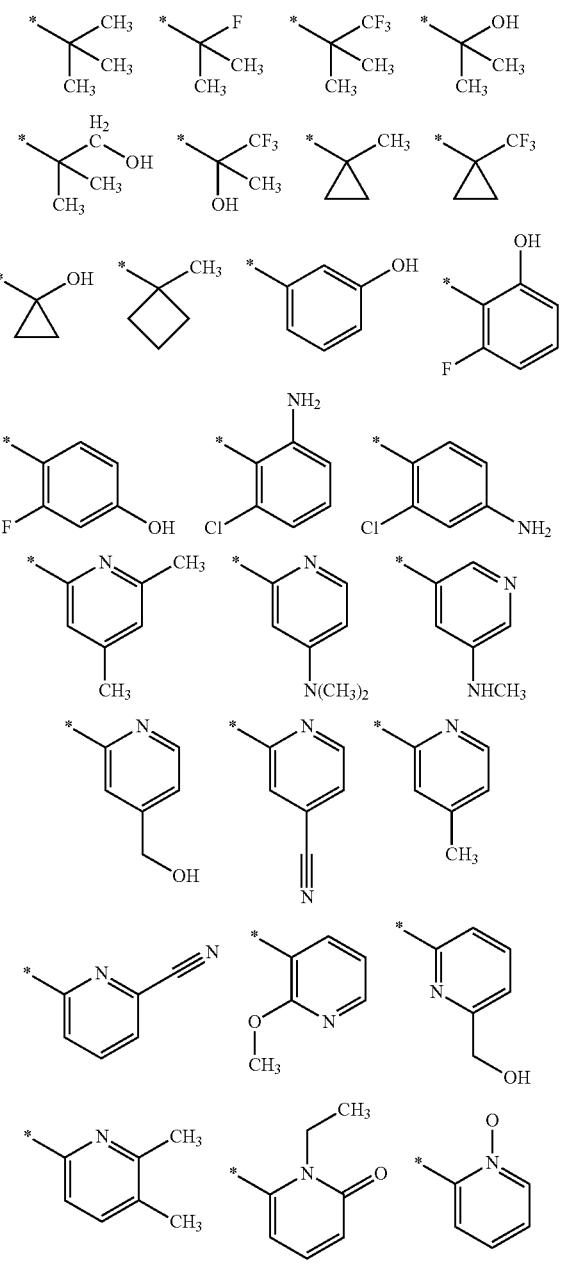

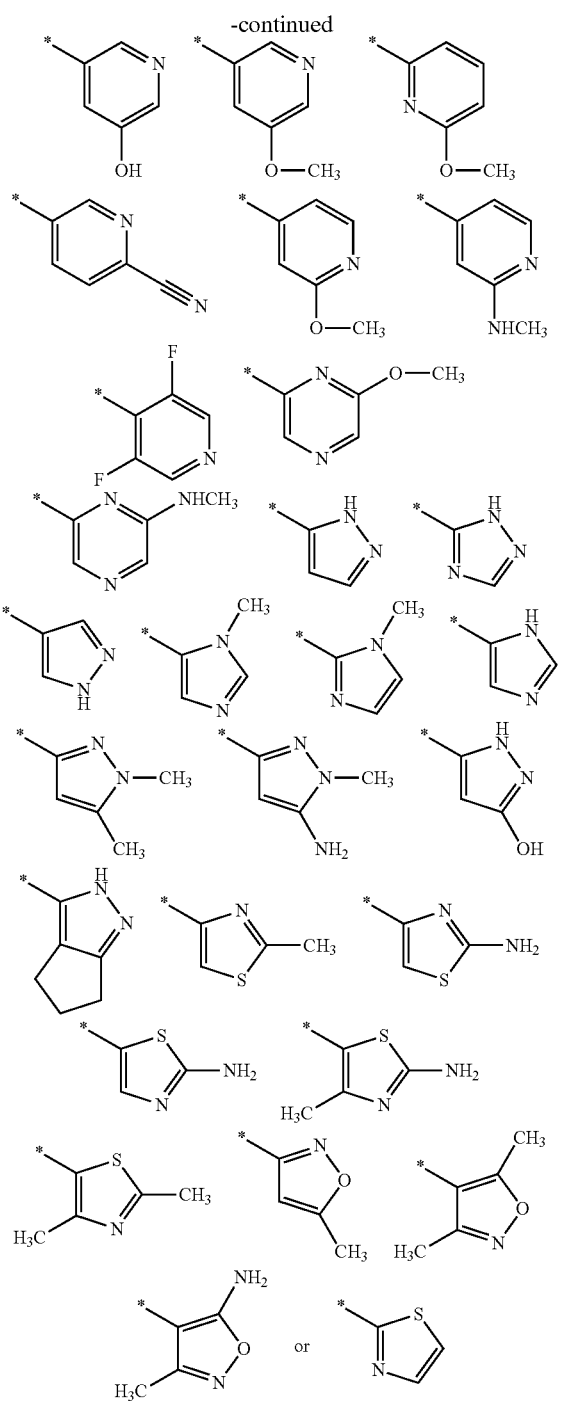
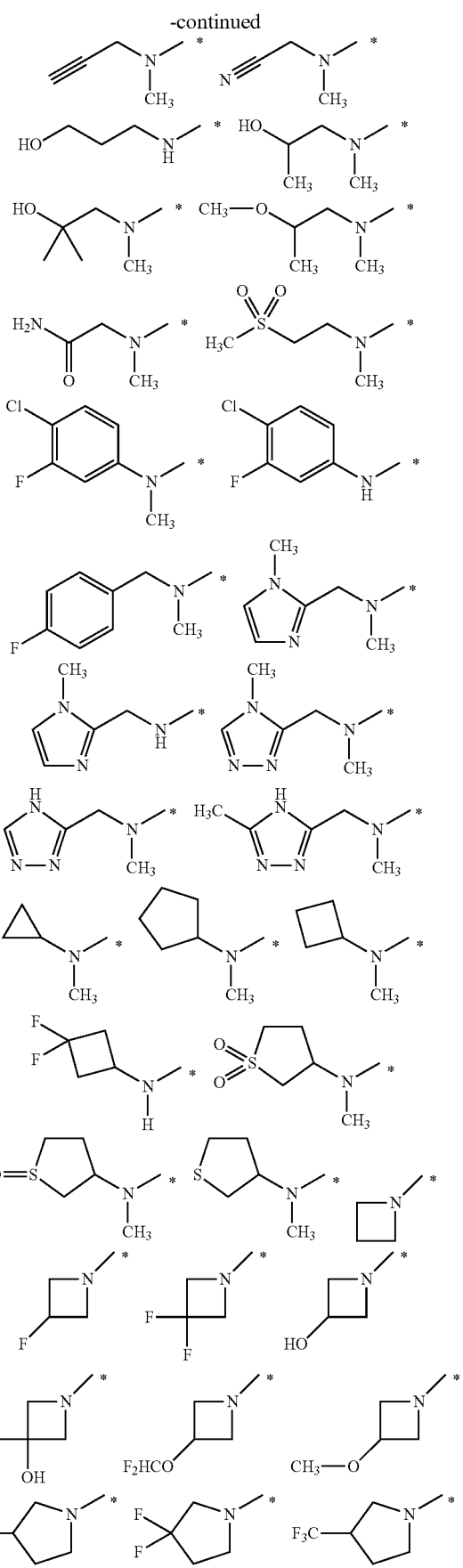
or a pharmaceutically acceptable salt thereof.
10. A compound according to claim 1, wherein L represents a group selected from
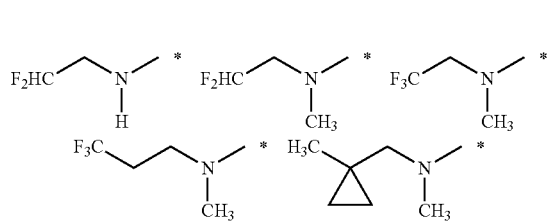

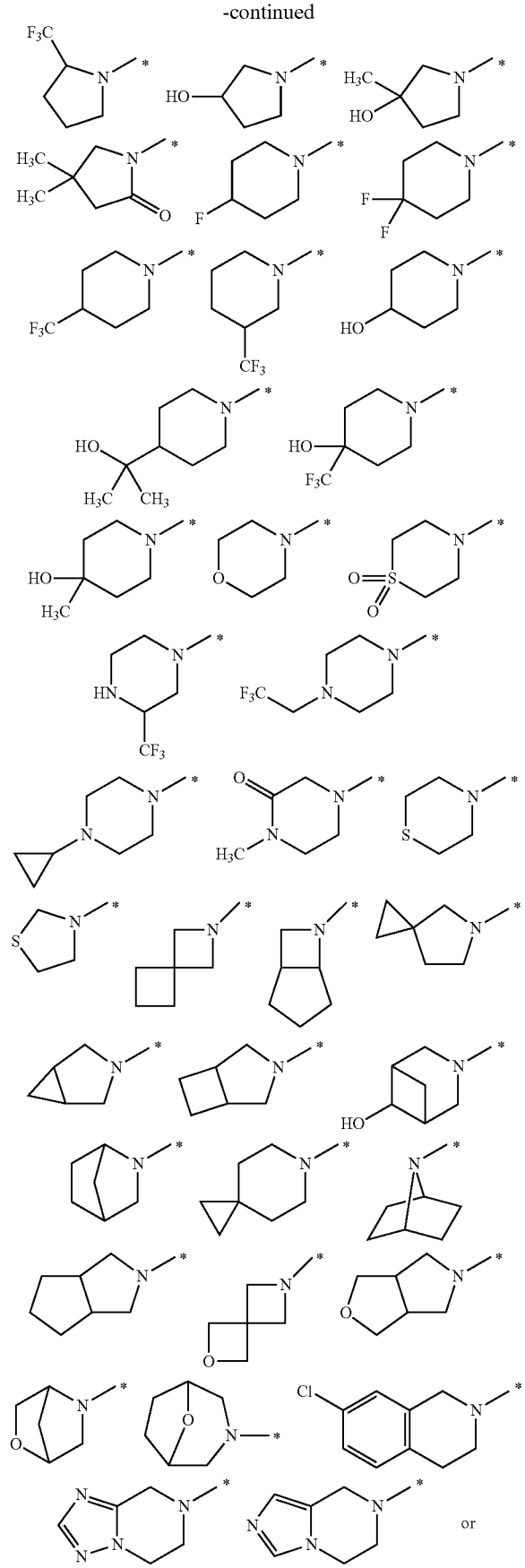
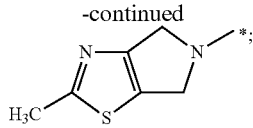
or a pharmaceutically acceptable salt thereof.
11. A compound according to claim 1, namely a compound of formula Ib
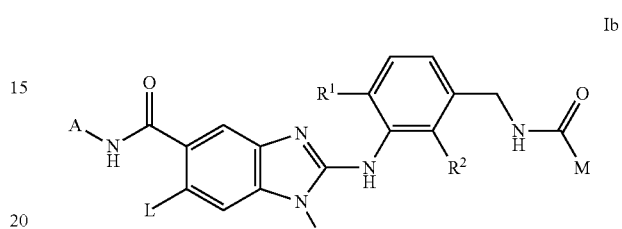
in which
R¹ represents fluoro, or chloro;
R² represents fluoro, or chloro;
R⁶ represents hydrogen, $CH_3$, —$CH_2CH_2F$, —$CH_2CHF_2$, —$CH_2CF_3$, tert.-butyl,
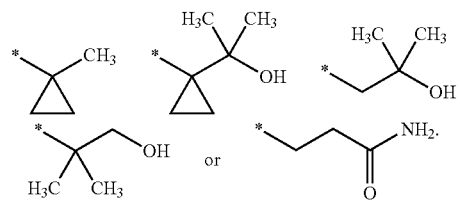
M represents a group selected from
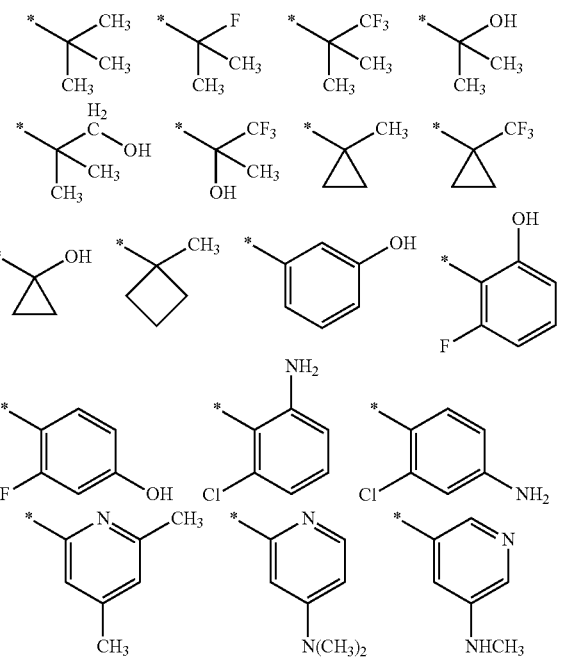

351
-continued
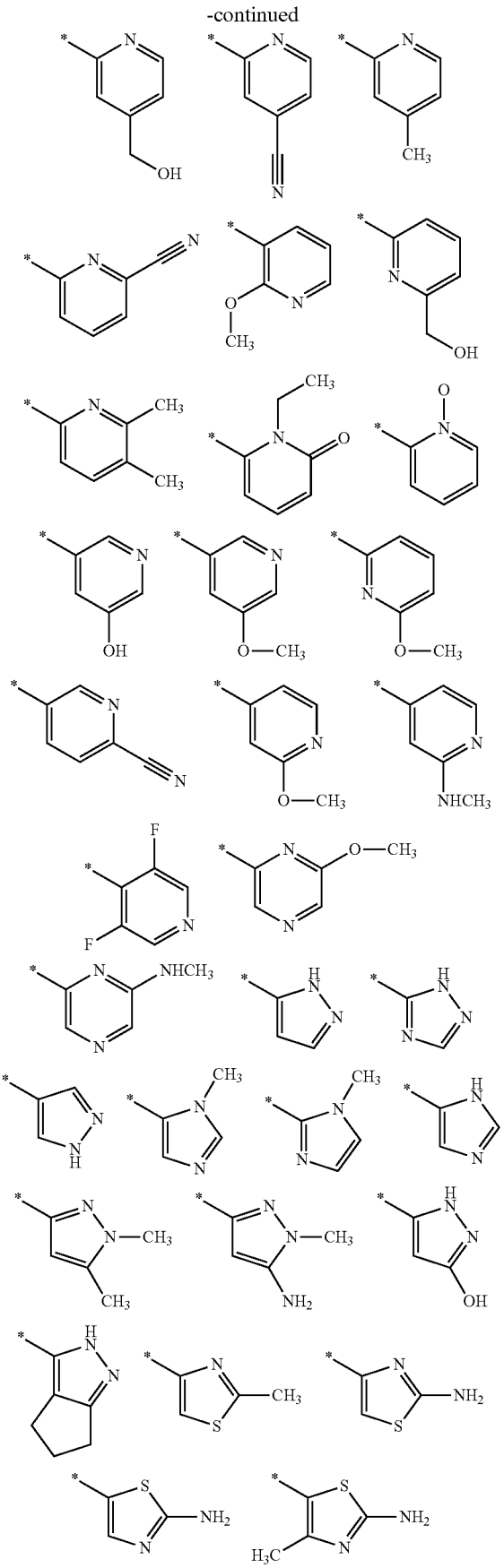
352
-continued
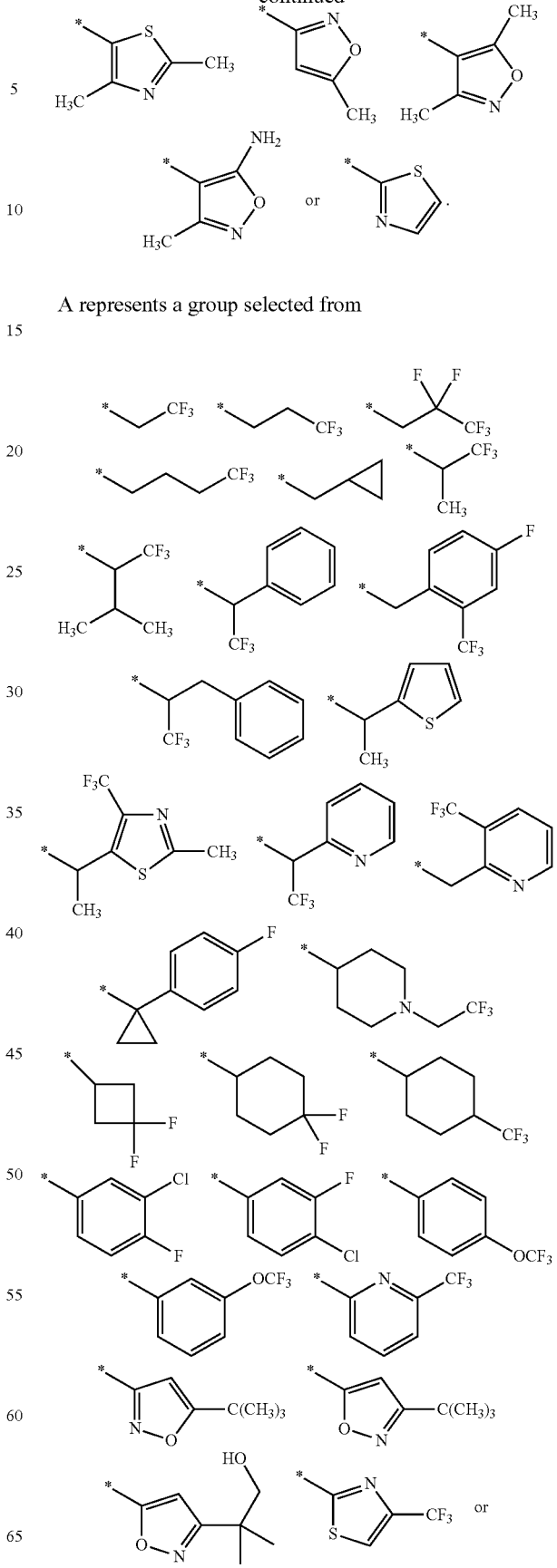
A represents a group selected from
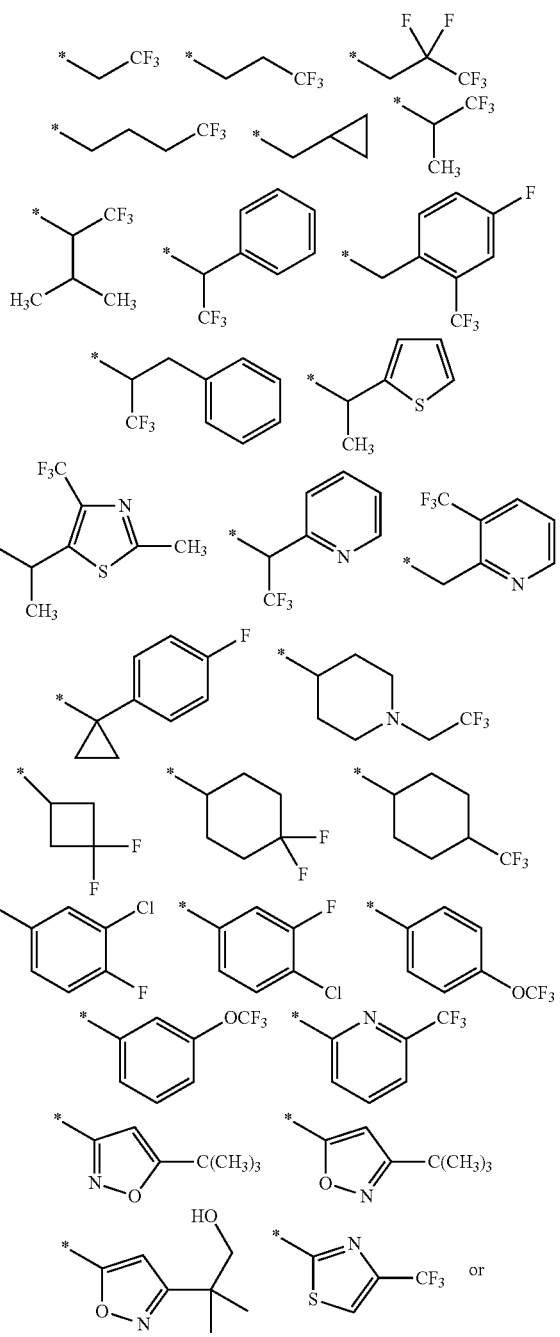

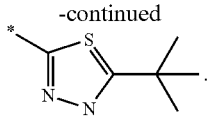
L represents a group selected from
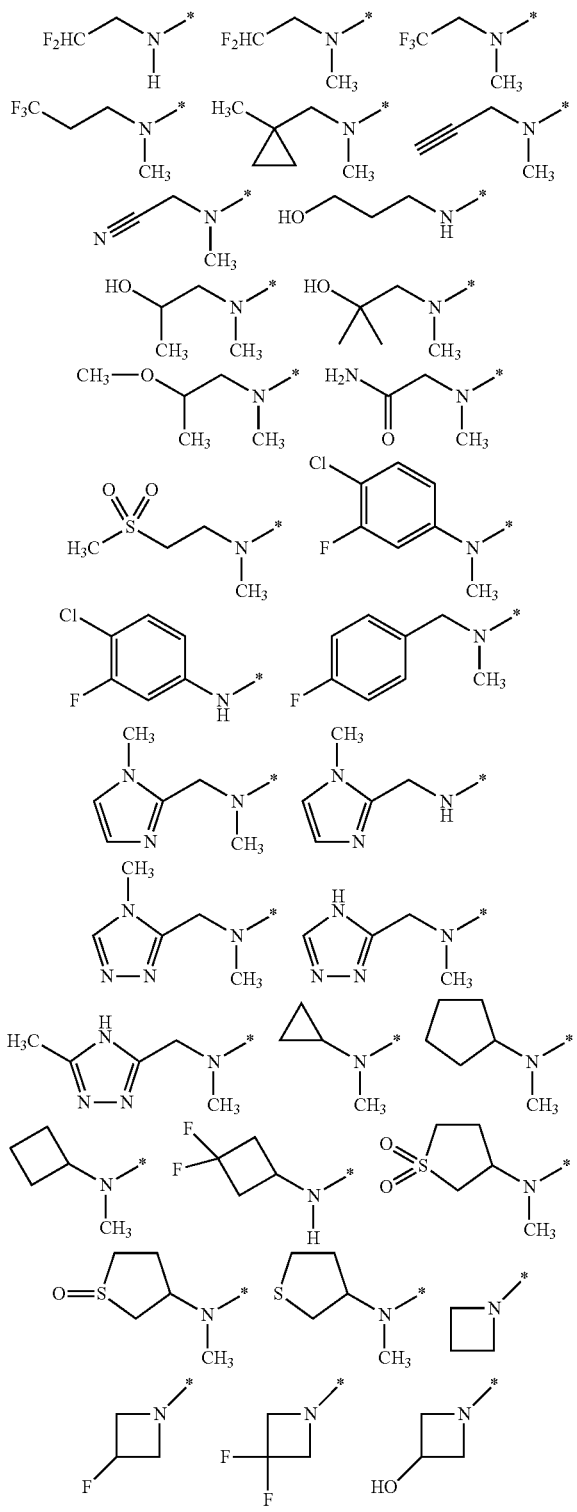
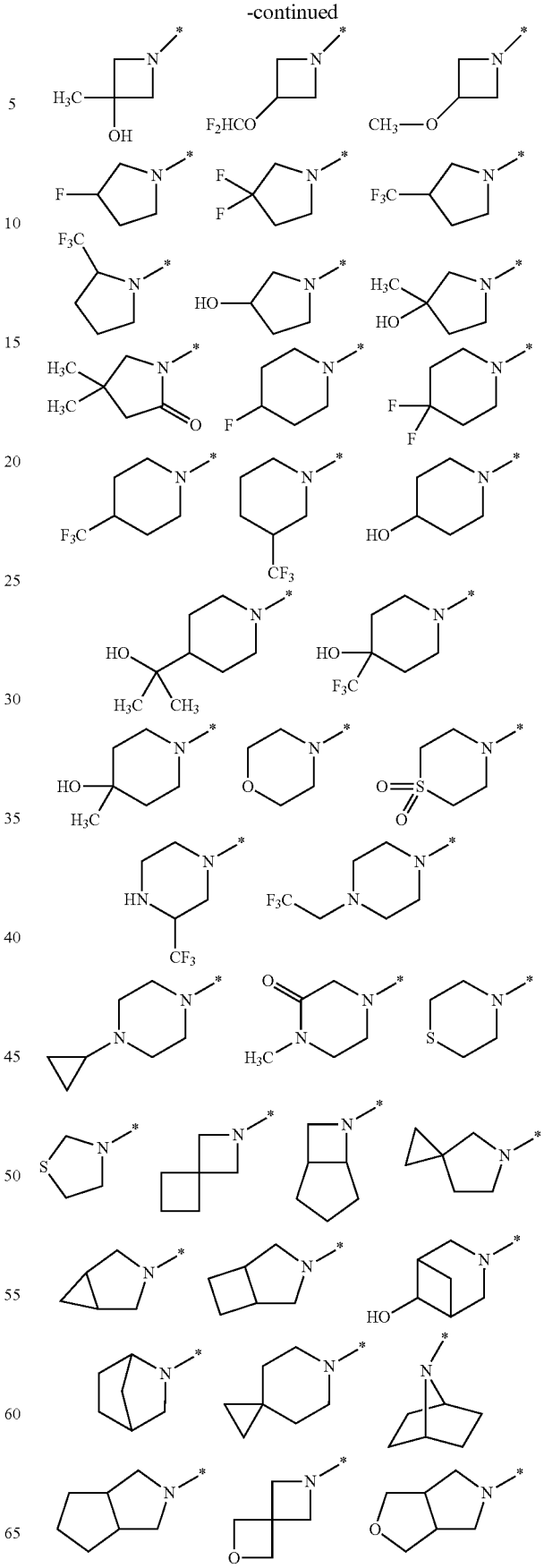

-continued
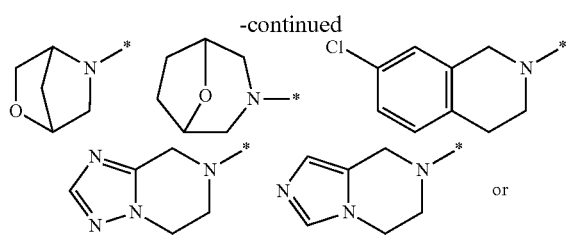
-continued
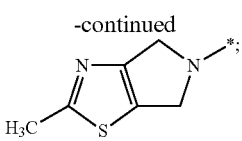
or a pharmaceutically acceptable salt thereof.
12. A compound according to claim 1 selected from the compounds in the following table:

-continued
| | Structure |
|---|---|
| 6 | 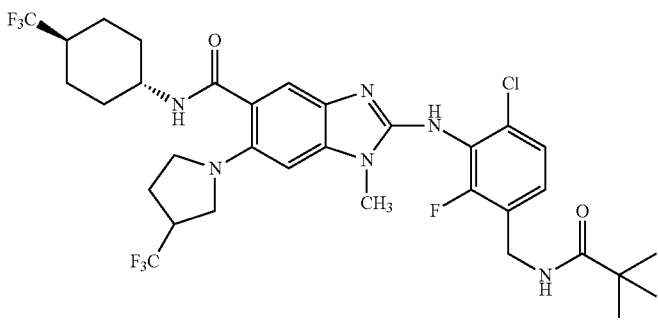 [SMILES: Cn1c(Nc2c(Cl)ccc(CNC(=O)C(C)(C)C)c2F)nc2cc(C(=O)N[C@H]3CC[C@H](C(F)(F)F)CC3)c(N3CCC(C(F)(F)F)C3)cc21] |
| 10 | 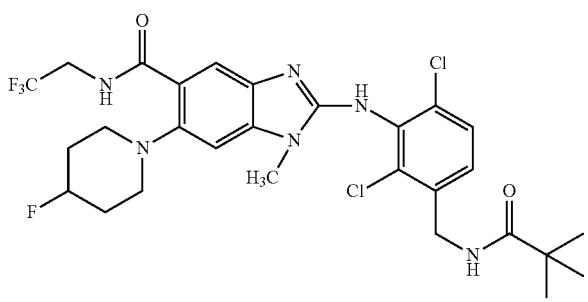 [SMILES: Cn1c(Nc2c(Cl)ccc(CNC(=O)C(C)(C)C)c2Cl)nc2cc(C(=O)NCC(F)(F)F)c(N3CCC(F)CC3)cc21] |
| 11 | 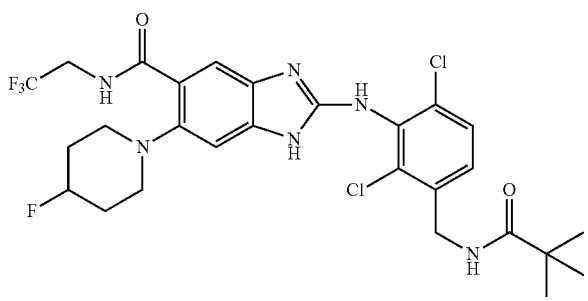 [SMILES: CC(C)(C)C(=O)NCc1ccc(Cl)c(Nc2nc3cc(C(=O)NCC(F)(F)F)c(N4CCC(F)CC4)cc3[nH]2)c1Cl] |
| 12 | 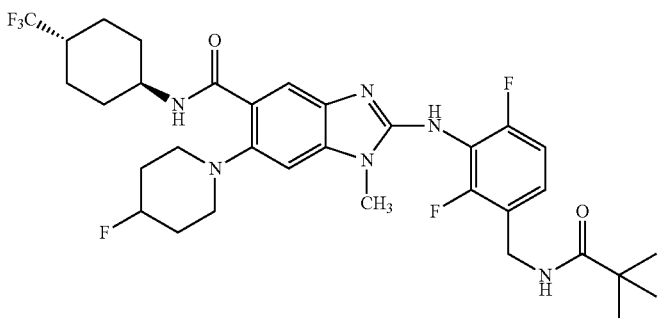 [SMILES: Cn1c(Nc2c(F)ccc(CNC(=O)C(C)(C)C)c2F)nc2cc(C(=O)N[C@H]3CC[C@H](C(F)(F)F)CC3)c(N3CCC(F)CC3)cc21] |
| 14 | 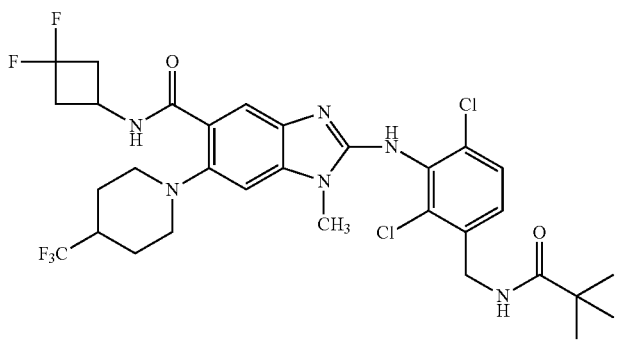 [SMILES: Cn1c(Nc2c(Cl)ccc(CNC(=O)C(C)(C)C)c2Cl)nc2cc(C(=O)NC3CC(F)(F)C3)c(N3CCC(C(F)(F)F)CC3)cc21] |

| | Structure |
|---|---|
| 15 | 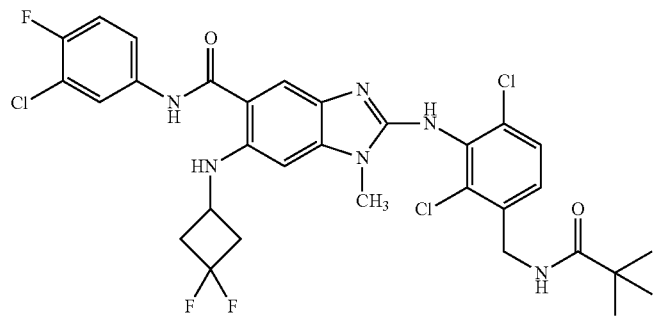 [SMILES: Cn1c(Nc2c(Cl)ccc(CNC(=O)C(C)(C)C)c2Cl)nc2cc(C(=O)Nc3ccc(F)c(Cl)c3)c(NC3CC(F)(F)C3)cc21] |
| 16 | 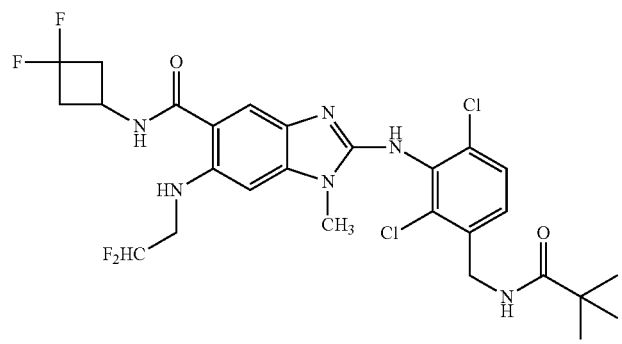 [SMILES: Cn1c(Nc2c(Cl)ccc(CNC(=O)C(C)(C)C)c2Cl)nc2cc(C(=O)NC3CC(F)(F)C3)c(NCC(F)F)cc21] |
| 17 | 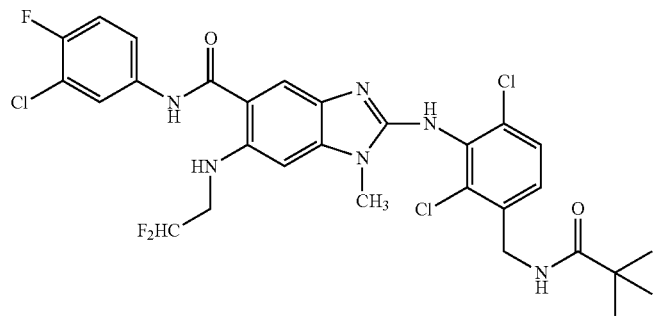 [SMILES: Cn1c(Nc2c(Cl)ccc(CNC(=O)C(C)(C)C)c2Cl)nc2cc(C(=O)Nc3ccc(F)c(Cl)c3)c(NCC(F)F)cc21] |
| 18 | 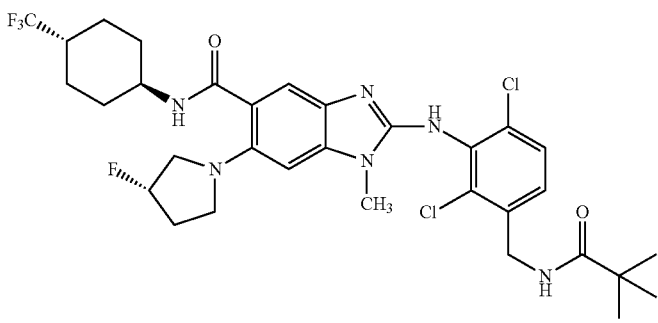 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC[C@H](F)C3)cc21] |

| | Structure |
|---|---|
| 19 | 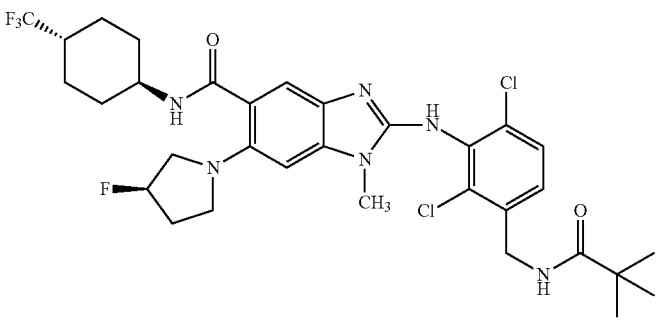 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC[C@@H](F)C3)cc21] |
| 20 | 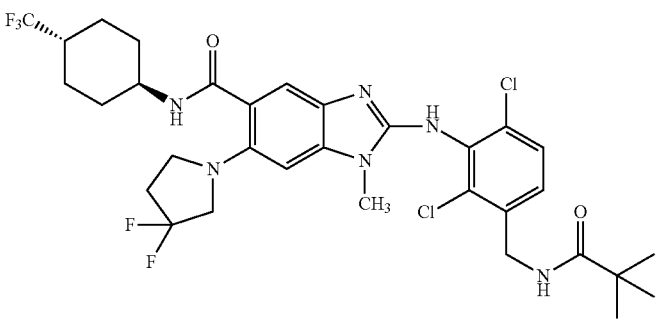 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(F)(F)C3)cc21] |
| 21 | 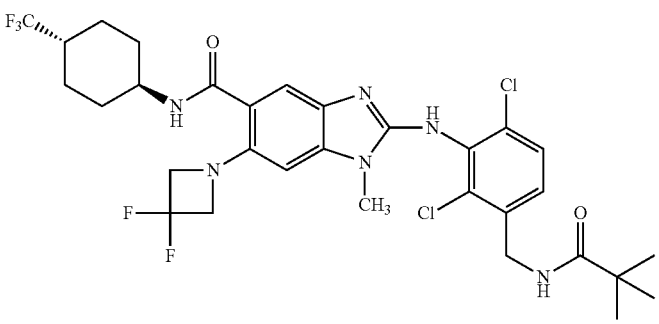 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(F)(F)C3)cc21] |
| 22 | 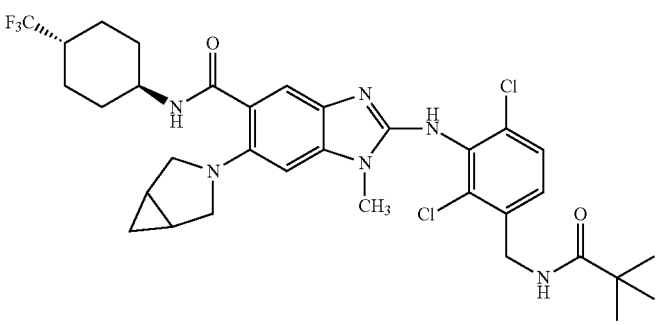 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CC4C3)cc21] |
| 23 | 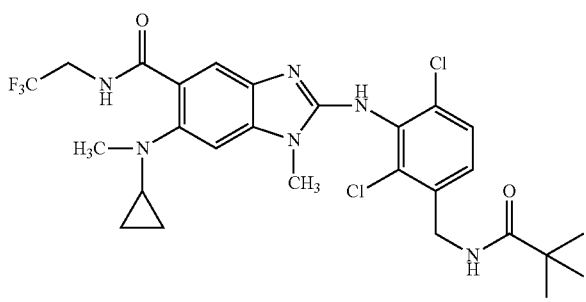 [SMILES: CN(c1cc2c(cc1C(=O)NCC(F)(F)F)nc(Nc1c(Cl)ccc(CNC(=O)C(C)(C)C)c1Cl)n2C)C1CC1] |

| | Structure |
|---|---|
| 24 | 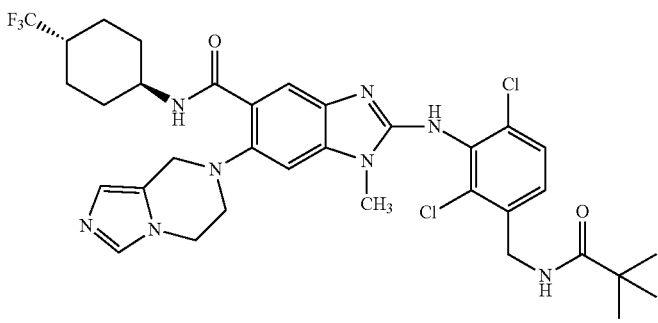 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCn4cncc4C3)cc21] |
| 25 | 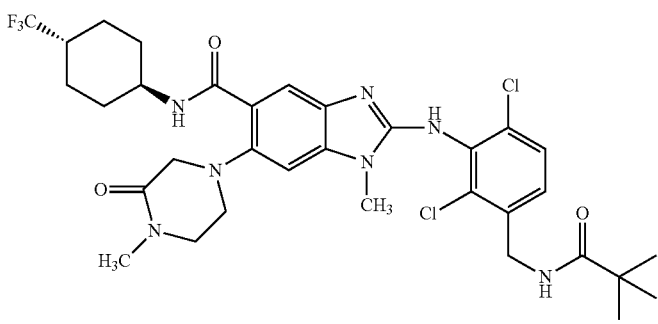 [SMILES: CN1CCN(c2cc3c(cc2C(=O)N[C@H]2CC[C@H](C(F)(F)F)CC2)nc(Nc2c(Cl)ccc(CNC(=O)C(C)(C)C)c2Cl)n3C)CC1=O] |
| 26 | 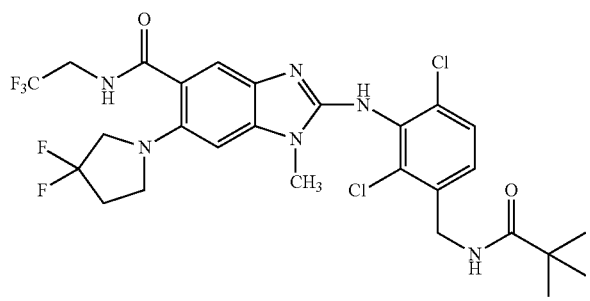 [SMILES: Cn1c(Nc2c(Cl)ccc(CNC(=O)C(C)(C)C)c2Cl)nc2cc(C(=O)NCC(F)(F)F)c(N3CCC(F)(F)C3)cc21] |
| 27 | 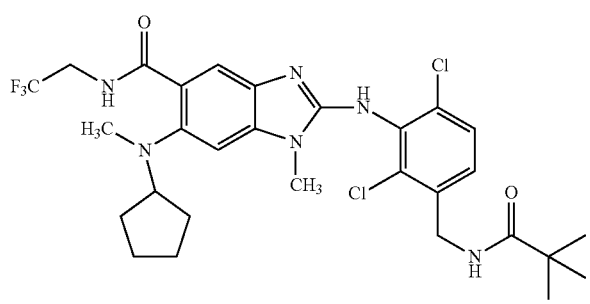 [SMILES: CN(c1cc2c(cc1C(=O)NCC(F)(F)F)nc(Nc1c(Cl)ccc(CNC(=O)C(C)(C)C)c1Cl)n2C)C1CCCC1] |
| 28 | 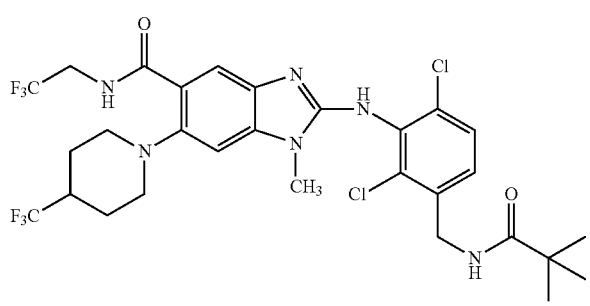 [SMILES: Cn1c(Nc2c(Cl)ccc(CNC(=O)C(C)(C)C)c2Cl)nc2cc(C(=O)NCC(F)(F)F)c(N3CCC(C(F)(F)F)CC3)cc21] |

| | Structure |
|---|---|
| 29 | 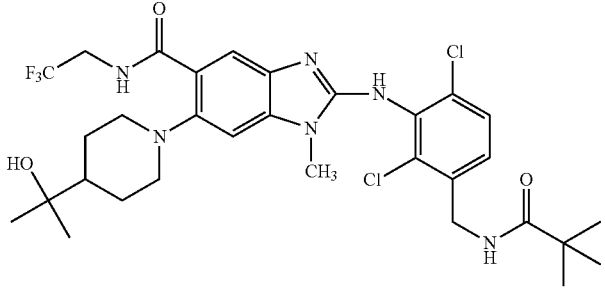 [SMILES: Cn1c(Nc2c(Cl)ccc(CNC(=O)C(C)(C)C)c2Cl)nc2cc(C(=O)NCC(F)(F)F)c(N3CCC(C(C)(C)O)CC3)cc21] |
| 30 | 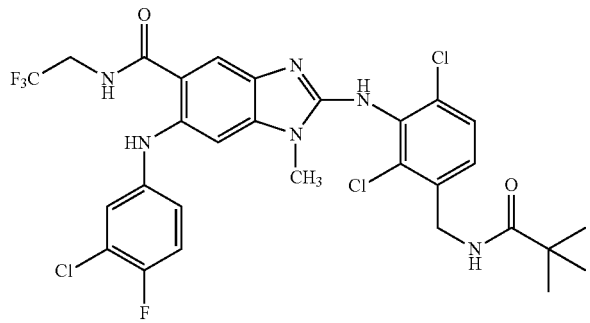 [SMILES: Cn1c(Nc2c(Cl)ccc(CNC(=O)C(C)(C)C)c2Cl)nc2cc(C(=O)NCC(F)(F)F)c(Nc3ccc(F)c(Cl)c3)cc21] |
| 31 | 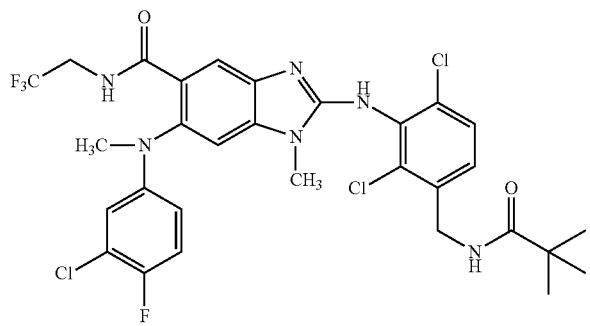 [SMILES: CN(c1ccc(F)c(Cl)c1)c1cc2c(cc1C(=O)NCC(F)(F)F)nc(Nc1c(Cl)ccc(CNC(=O)C(C)(C)C)c1Cl)n2C] |
| 32 | 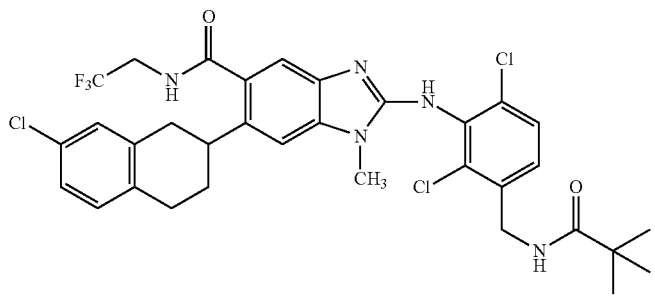 |
| 33 | 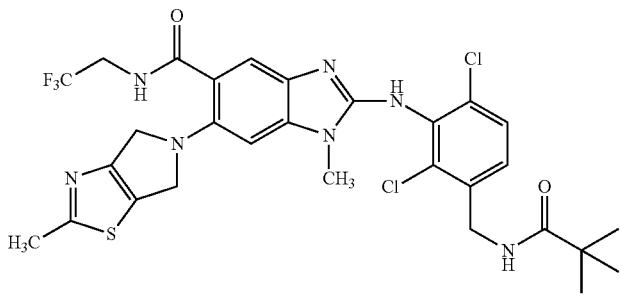 [SMILES: Cc1nc2c(s1)CN(c1cc3c(cc1C(=O)NCC(F)(F)F)nc(Nc1c(Cl)ccc(CNC(=O)C(C)(C)C)c1Cl)n3C)C2] |

-continued
| | Structure |
|---|---|
| 34 | 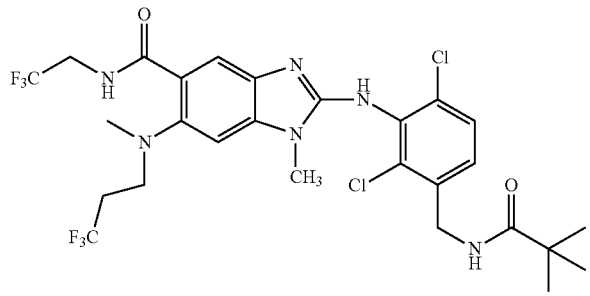 [SMILES: CN(CCC(F)(F)F)c1cc2c(cc1C(=O)NCC(F)(F)F)nc(Nc1c(Cl)ccc(CNC(=O)C(C)(C)C)c1Cl)n2C] |
| 35 | 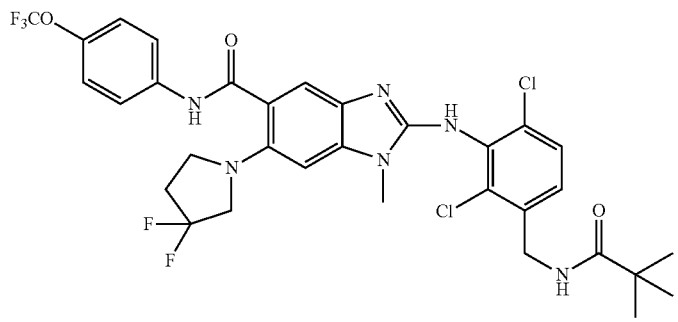 [SMILES: Cn1c(Nc2c(Cl)ccc(CNC(=O)C(C)(C)C)c2Cl)nc2cc(C(=O)Nc3ccc(OC(F)(F)F)cc3)c(N3CCC(F)(F)C3)cc21] |
| 36 | 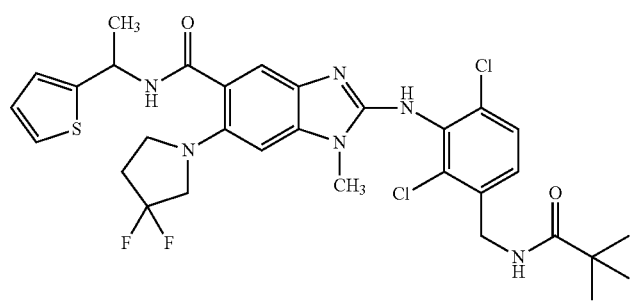 [SMILES: CC(NC(=O)c1cc2nc(Nc3c(Cl)ccc(CNC(=O)C(C)(C)C)c3Cl)n(C)c2cc1N1CCC(F)(F)C1)c1cccs1] |
| 37 | 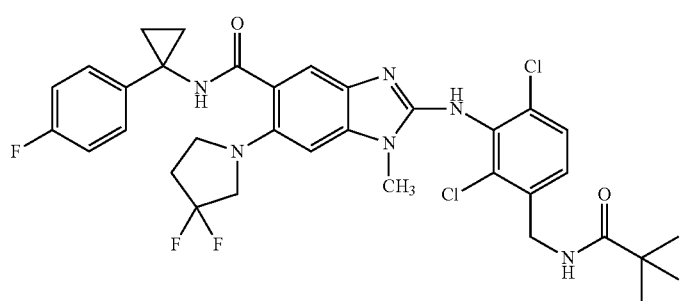 [SMILES: Cn1c(Nc2c(Cl)ccc(CNC(=O)C(C)(C)C)c2Cl)nc2cc(C(=O)NC3(c4ccc(F)cc4)CC3)c(N3CCC(F)(F)C3)cc21] |
| 38 | 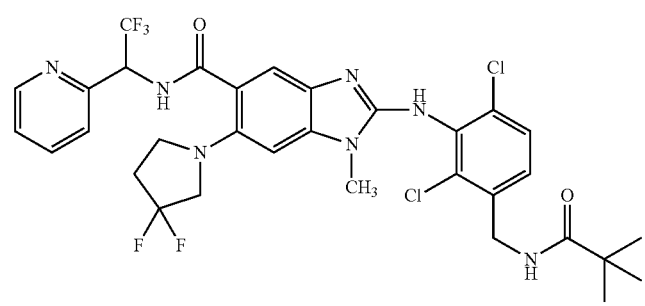 [SMILES: Cn1c(Nc2c(Cl)ccc(CNC(=O)C(C)(C)C)c2Cl)nc2cc(C(=O)NC(c3ccccn3)C(F)(F)F)c(N3CCC(F)(F)C3)cc21] |

| | Structure |
|---|---|
| 39 | 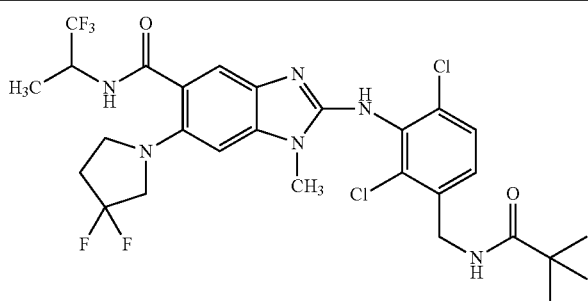 |
| 40 | 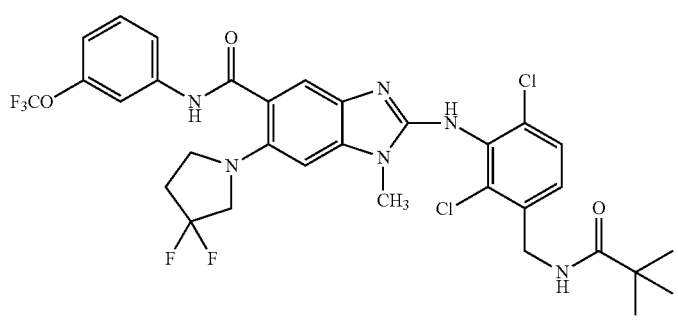 [SMILES: Cn1c(Nc2c(Cl)ccc(CNC(=O)C(C)(C)C)c2Cl)nc2cc(C(=O)Nc3cccc(OC(F)(F)F)c3)c(N3CCC(F)(F)C3)cc21] |
| 41 | 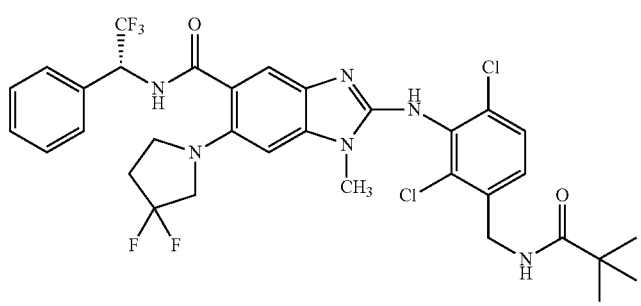 [SMILES: Cn1c(Nc2c(Cl)ccc(CNC(=O)C(C)(C)C)c2Cl)nc2cc(C(=O)N[C@H](c3ccccc3)C(F)(F)F)c(N3CCC(F)(F)C3)cc21] |
| 42 | 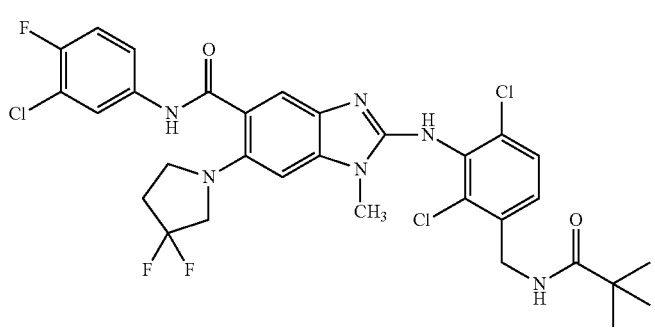 |
| 43 | 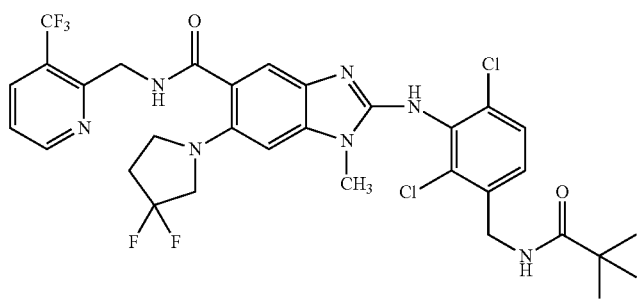 [SMILES: Cn1c(Nc2c(Cl)ccc(CNC(=O)C(C)(C)C)c2Cl)nc2cc(C(=O)NCc3ncccc3C(F)(F)F)c(N3CCC(F)(F)C3)cc21] |

| Structure |
|---|
| 44 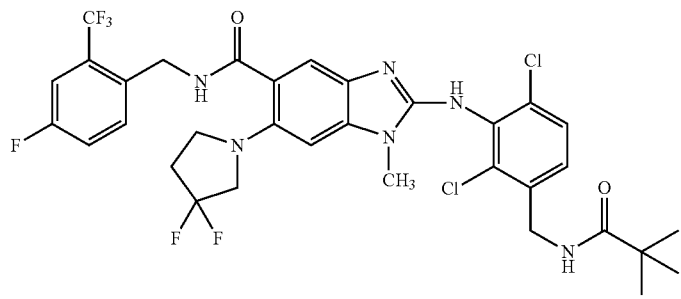 [SMILES: Cn1c(Nc2c(Cl)ccc(CNC(=O)C(C)(C)C)c2Cl)nc2cc(C(=O)NCc3ccc(F)cc3C(F)(F)F)c(N3CCC(F)(F)C3)cc21] |
| 45 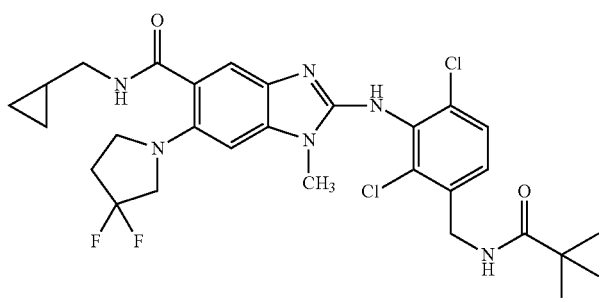 [SMILES: Cn1c(Nc2c(Cl)ccc(CNC(=O)C(C)(C)C)c2Cl)nc2cc(C(=O)NCC3CC3)c(N3CCC(F)(F)C3)cc21] |
| 46 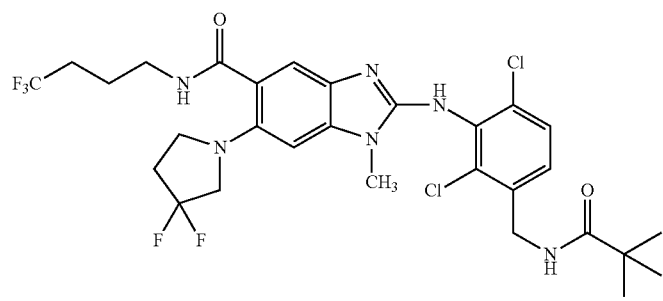 [SMILES: Cn1c(Nc2c(Cl)ccc(CNC(=O)C(C)(C)C)c2Cl)nc2cc(C(=O)NCCCC(F)(F)F)c(N3CCC(F)(F)C3)cc21] |
| 47 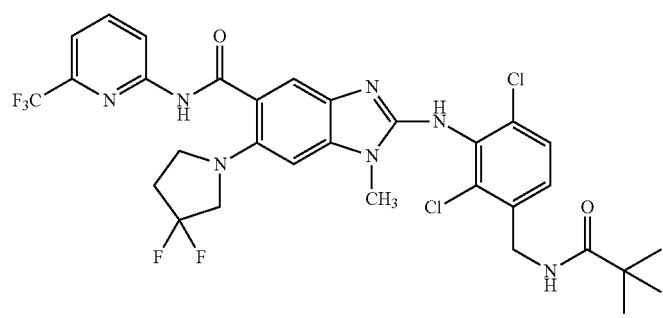 [SMILES: Cn1c(Nc2c(Cl)ccc(CNC(=O)C(C)(C)C)c2Cl)nc2cc(C(=O)Nc3cccc(C(F)(F)F)n3)c(N3CCC(F)(F)C3)cc21] |
| 48 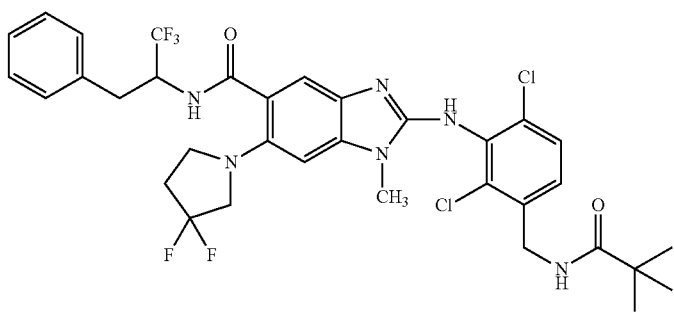 [SMILES: Cn1c(Nc2c(Cl)ccc(CNC(=O)C(C)(C)C)c2Cl)nc2cc(C(=O)NC(Cc3ccccc3)C(F)(F)F)c(N3CCC(F)(F)C3)cc21] |

-continued
| | Structure |
|---|---|
| 49 | 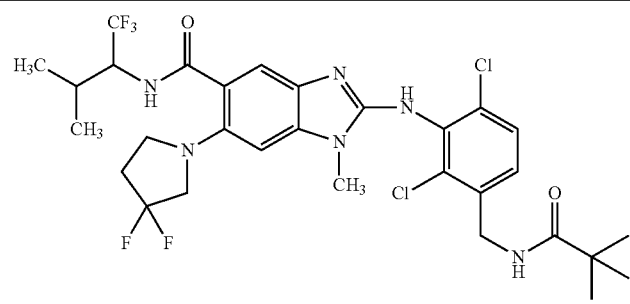 |
| 50 | 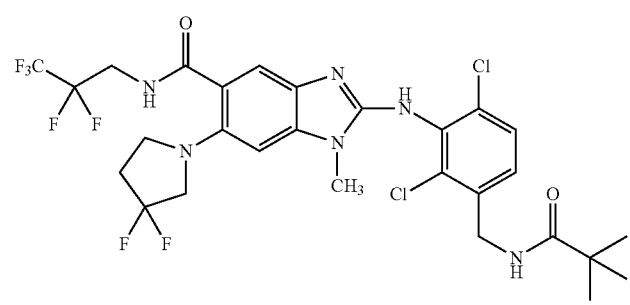 [SMILES: Cn1c(Nc2c(Cl)ccc(CNC(=O)C(C)(C)C)c2Cl)nc2cc(C(=O)NCC(F)(F)C(F)(F)F)c(N3CCC(F)(F)C3)cc21] |
| 51 | 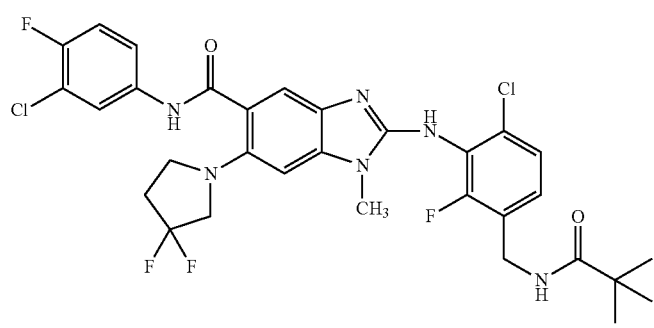 |
| 52 | 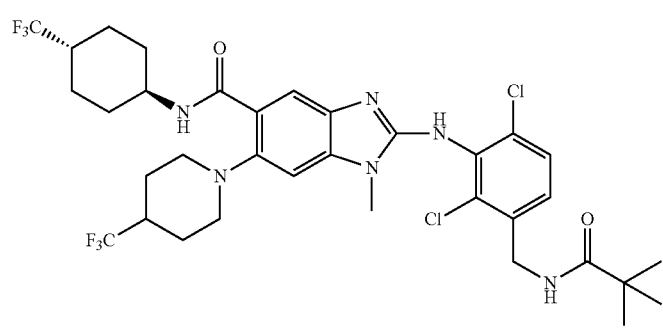 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(C(F)(F)F)CC3)cc21] |
| 53 | 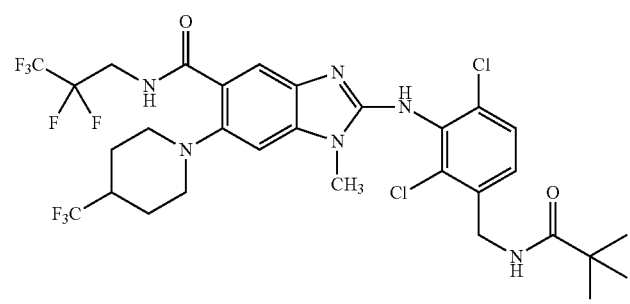 |

| | Structure |
|---|---|
| 54 | 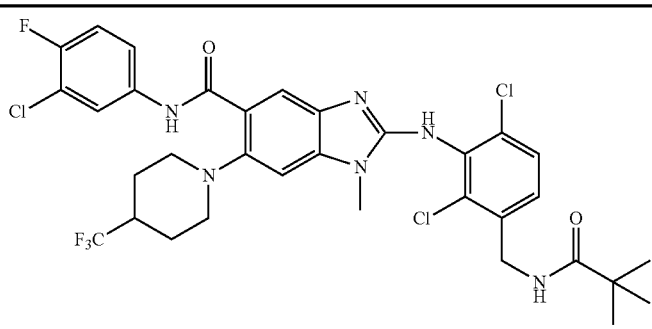 |
| 55 | 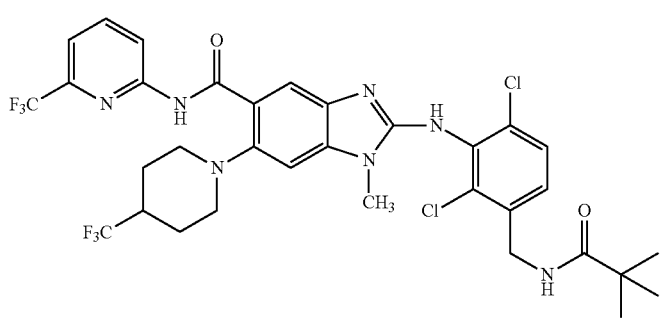 [SMILES: Cn1c(Nc2c(Cl)ccc(CNC(=O)C(C)(C)C)c2Cl)nc2cc(C(=O)Nc3cccc(C(F)(F)F)n3)c(N3CCC(C(F)(F)F)CC3)cc21] |
| 56 | 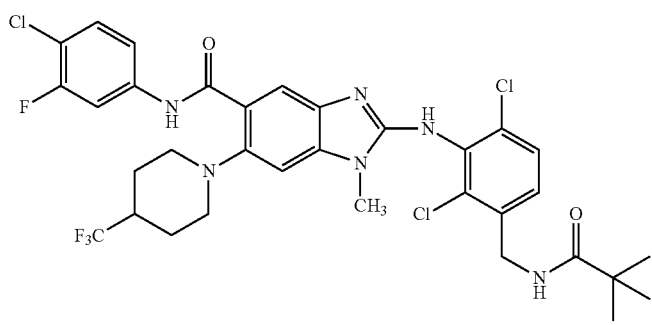 [SMILES: Cn1c(Nc2c(Cl)ccc(CNC(=O)C(C)(C)C)c2Cl)nc2cc(C(=O)Nc3ccc(Cl)c(F)c3)c(N3CCC(C(F)(F)F)CC3)cc21] |
| 57 | 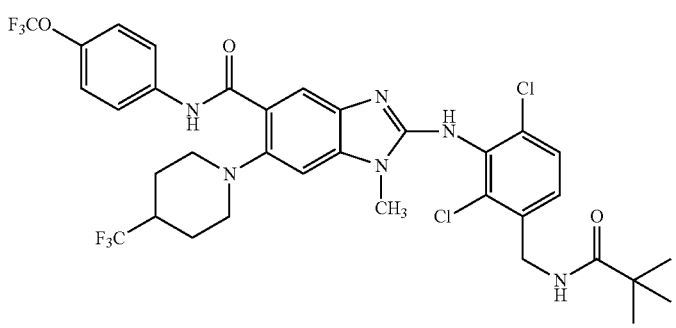 [SMILES: Cn1c(Nc2c(Cl)ccc(CNC(=O)C(C)(C)C)c2Cl)nc2cc(C(=O)Nc3ccc(OC(F)(F)F)cc3)c(N3CCC(C(F)(F)F)CC3)cc21] |
| 58 | 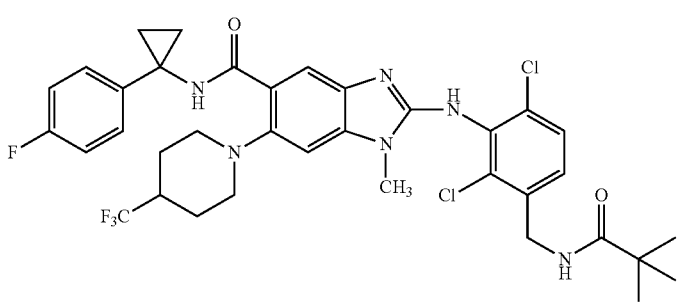 [SMILES: Cn1c(Nc2c(Cl)ccc(CNC(=O)C(C)(C)C)c2Cl)nc2cc(C(=O)NC3(c4ccc(F)cc4)CC3)c(N3CCC(C(F)(F)F)CC3)cc21] |

| | Structure |
|---|---|
| 59 | 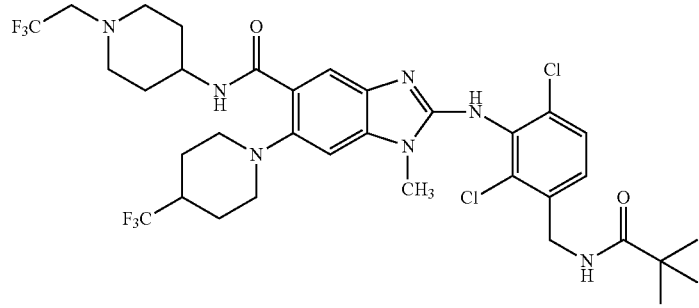 [SMILES: Cn1c(Nc2c(Cl)ccc(CNC(=O)C(C)(C)C)c2Cl)nc2cc(C(=O)NC3CCN(CC(F)(F)F)CC3)c(N3CCC(C(F)(F)F)CC3)cc21] |
| 60 | 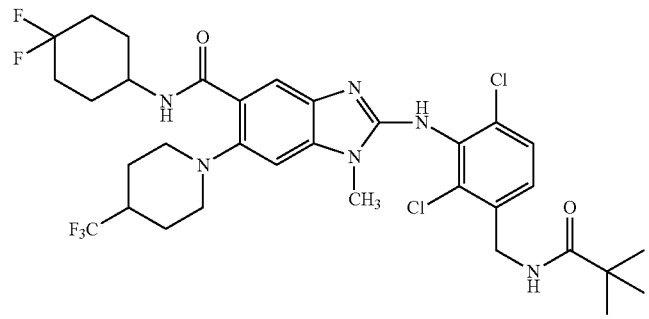 [SMILES: Cn1c(Nc2c(Cl)ccc(CNC(=O)C(C)(C)C)c2Cl)nc2cc(C(=O)NC3CCC(F)(F)CC3)c(N3CCC(C(F)(F)F)CC3)cc21] |
| 61 | 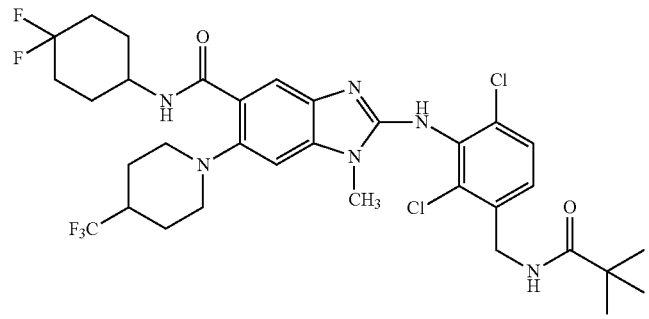 [SMILES: Cn1c(Nc2c(Cl)ccc(CNC(=O)C(C)(C)C)c2Cl)nc2cc(C(=O)NC3CCC(F)(F)CC3)c(N3CCC(C(F)(F)F)CC3)cc21] |
| 62 | 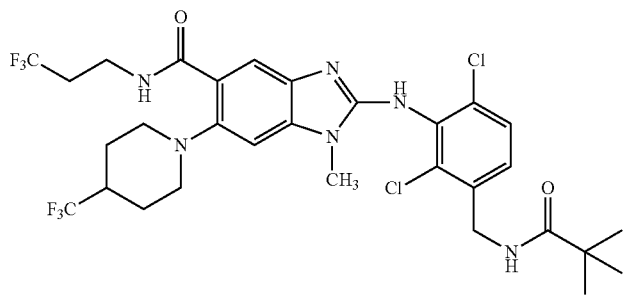 [SMILES: Cn1c(Nc2c(Cl)ccc(CNC(=O)C(C)(C)C)c2Cl)nc2cc(C(=O)NCCC(F)(F)F)c(N3CCC(C(F)(F)F)CC3)cc21] |
| 63 | 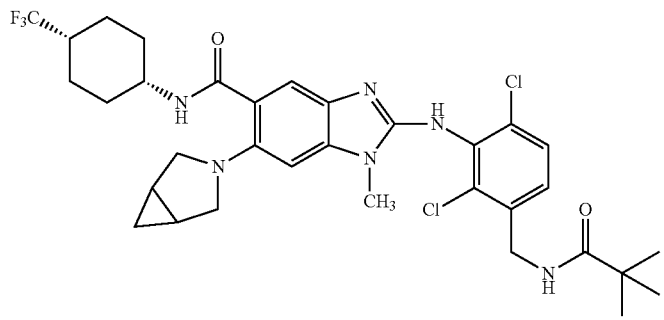 [SMILES: Cn1c(Nc2c(Cl)ccc(CNC(=O)C(C)(C)C)c2Cl)nc2cc(C(=O)N[C@H]3CC[C@@H](C(F)(F)F)CC3)c(N3CC4CC4C3)cc21] |

-continued
| | Structure |
|---|---|
| 64 | 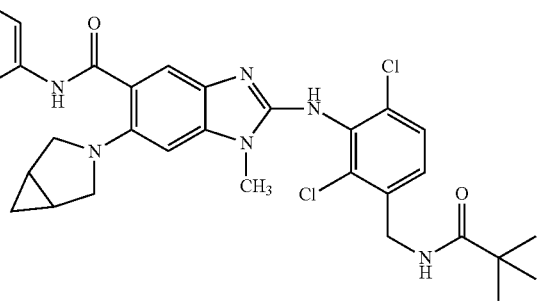 |
| 65 | 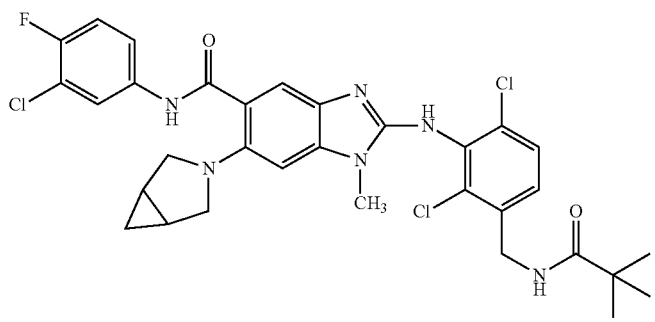 |
| 66 | 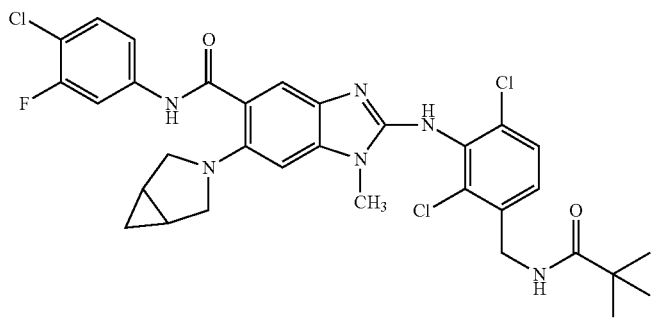 |
| 67 | 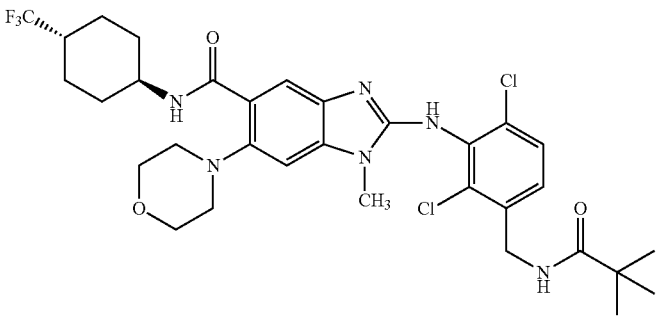 |
| 68 | 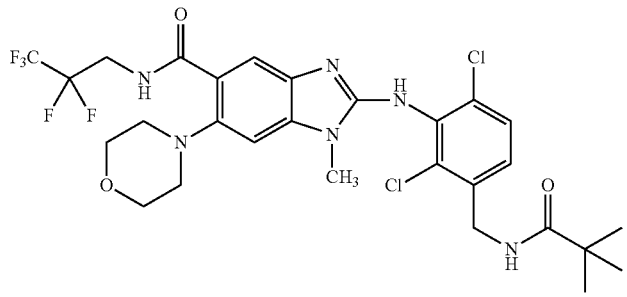 [SMILES: Cn1c(Nc2c(Cl)ccc(CNC(=O)C(C)(C)C)c2Cl)nc2cc(C(=O)NCC(F)(F)C(F)(F)F)c(N3CCOCC3)cc21] |

| | Structure |
|---|---|
| 69 | 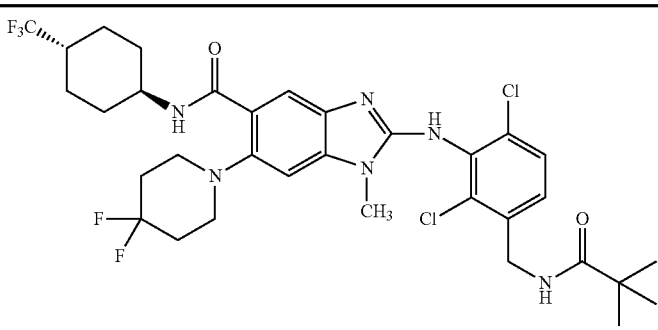 |
| 70 | 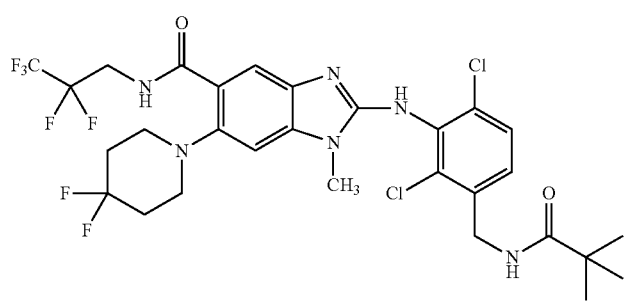 |
| 71 | 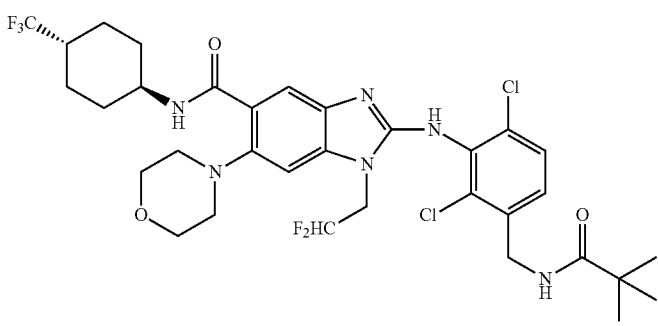 [SMILES: CC(C)(C)C(=O)NCc1ccc(Cl)c(Nc2nc3cc(C(=O)N[C@H]4CC[C@H](C(F)(F)F)CC4)c(N4CCOCC4)cc3n2CC(F)F)c1Cl] |
| 72 | 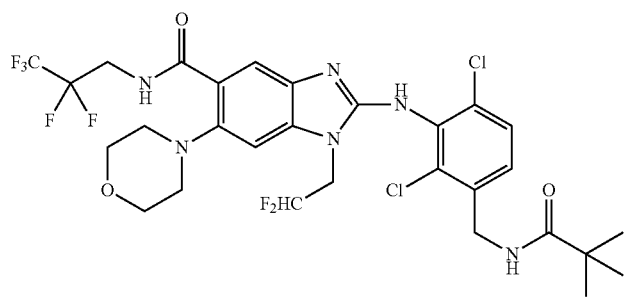 [SMILES: CC(C)(C)C(=O)NCc1ccc(Cl)c(Nc2nc3cc(C(=O)NCC(F)(F)C(F)(F)F)c(N4CCOCC4)cc3n2CC(F)F)c1Cl] |
| 73 | 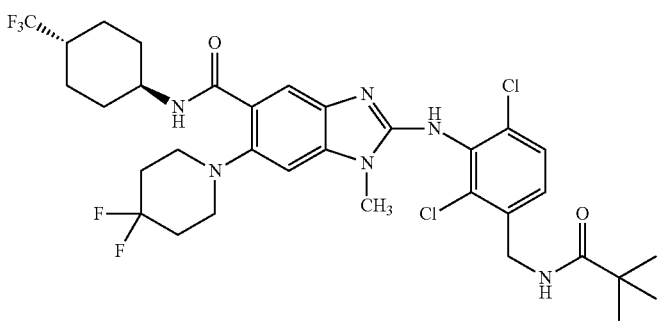 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(F)(F)CC3)cc21] |

| | Structure |
|---|---|
| 74 | 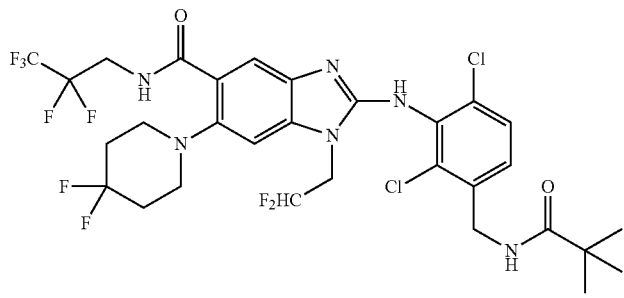 [SMILES: CC(C)(C)C(=O)NCc1ccc(Cl)c(Nc2nc3cc(C(=O)NCC(F)(F)C(F)(F)F)c(N4CCC(F)(F)CC4)cc3n2CC(F)F)c1Cl] |
| 75 | 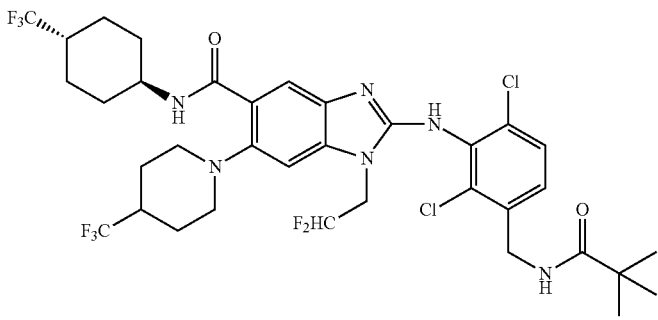 [SMILES: CC(C)(C)C(=O)NCc1ccc(Cl)c(Nc2nc3cc(C(=O)N[C@H]4CC[C@H](C(F)(F)F)CC4)c(N4CCC(C(F)(F)F)CC4)cc3n2CC(F)F)c1Cl] |
| 76 | 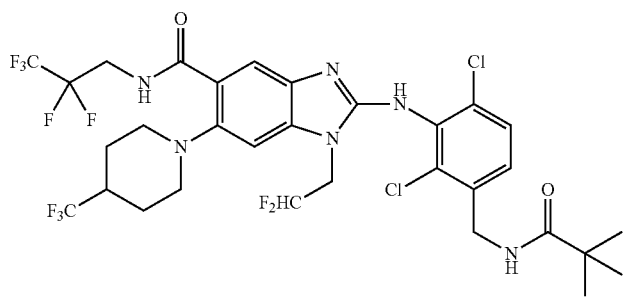 [SMILES: CC(C)(C)C(=O)NCc1ccc(Cl)c(Nc2nc3cc(C(=O)NCC(F)(F)C(F)(F)F)c(N4CCC(C(F)(F)F)CC4)cc3n2CC(F)F)c1Cl] |
| 77 | 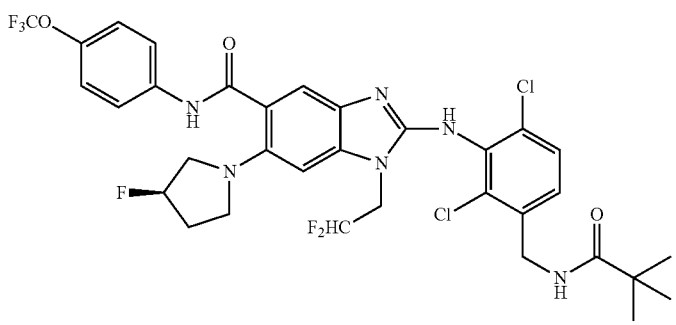 [SMILES: CC(C)(C)C(=O)NCc1ccc(Cl)c(Nc2nc3cc(C(=O)Nc4ccc(OC(F)(F)F)cc4)c(N4CC[C@@H](F)C4)cc3n2CC(F)F)c1Cl] |
| 78 | 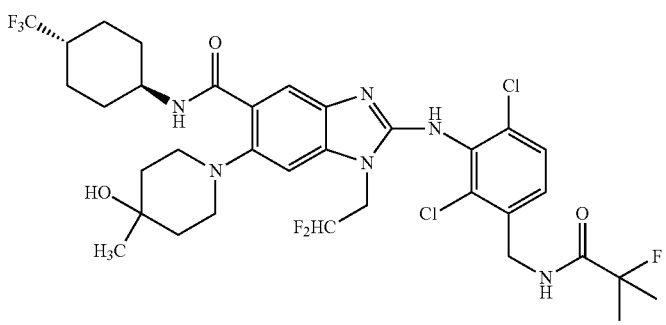 [SMILES: CC1(O)CCN(c2cc3c(cc2C(=O)N[C@H]2CC[C@H](C(F)(F)F)CC2)nc(Nc2c(Cl)ccc(CNC(=O)C(C)(C)F)c2Cl)n3CC(F)F)CC1] |

-continued
| | Structure |
|---|---|
| 79 | 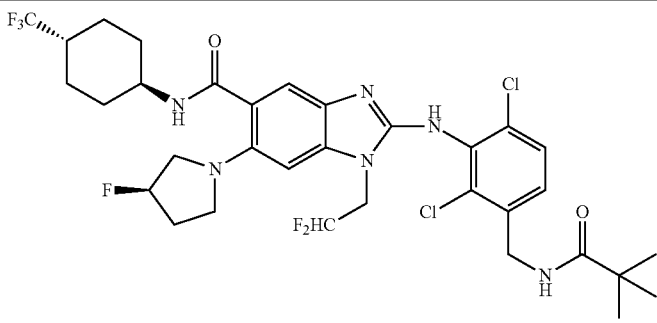 |
| 80 | 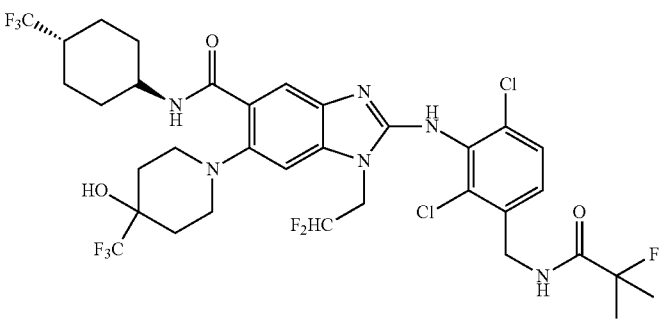 |
| 81 | 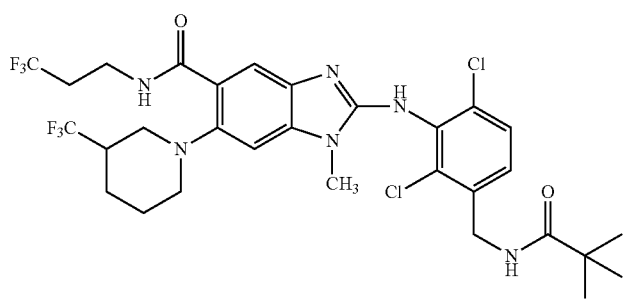 |
| 82 | 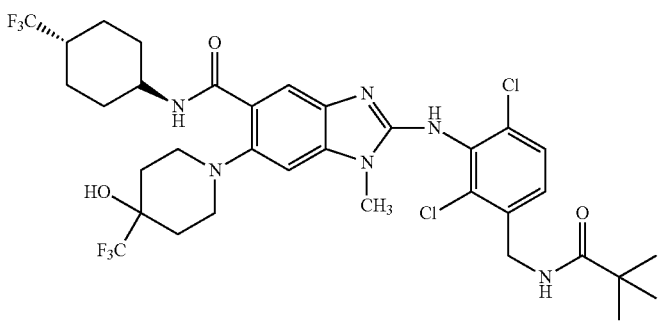 |
| 83 | 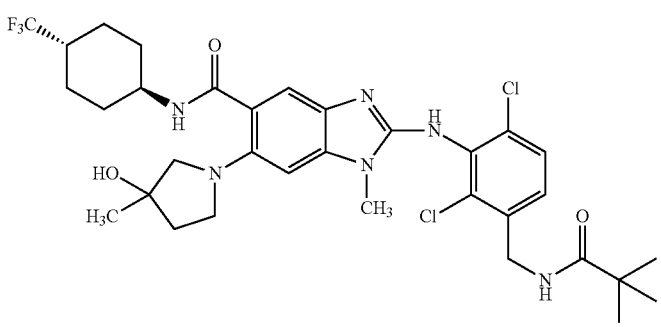 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(C)(O)C3)cc21] |

-continued
| | Structure |
|---|---|
| 84 | 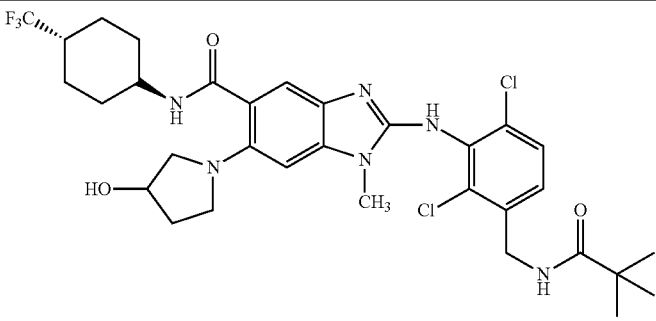 |
| 85 | 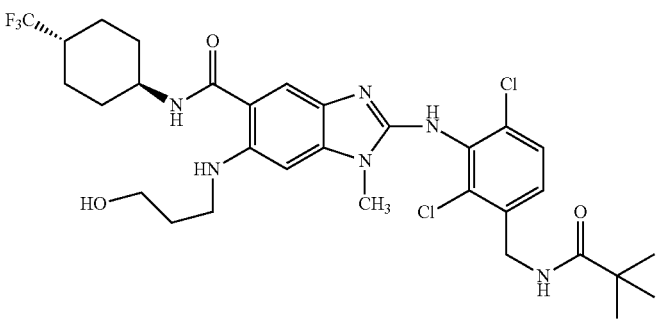 [SMILES: Cn1c(Nc2c(Cl)ccc(CNC(=O)C(C)(C)C)c2Cl)nc2cc(C(=O)N[C@H]3CC[C@H](C(F)(F)F)CC3)c(NCCCO)cc21] |
| 86 | 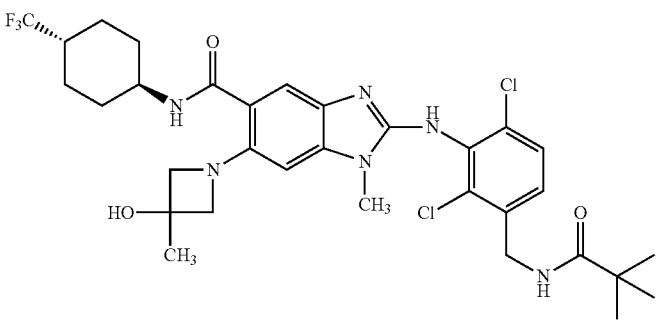 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(C)(O)C3)cc21] |
| 87 | 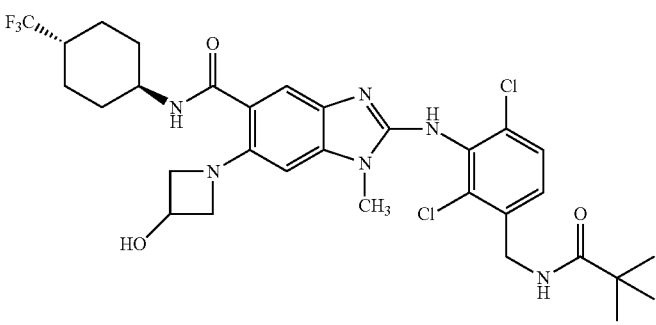 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(O)C3)cc21] |
| 88 | 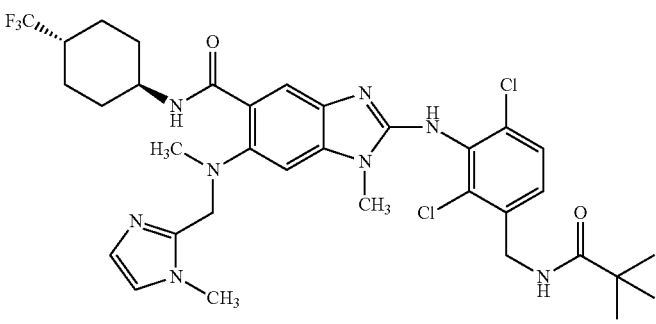 [SMILES: CN(Cc1nccn1C)c1cc2c(cc1C(=O)N[C@H]1CC[C@H](C(F)(F)F)CC1)nc(Nc1c(Cl)ccc(CNC(=O)C(C)(C)C)c1Cl)n2C] |

| | Structure |
|---|---|
| 89 | 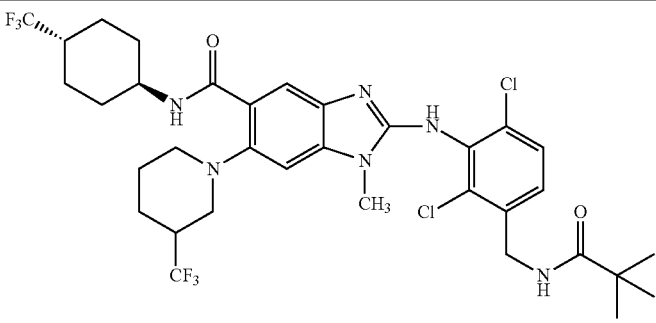 |
| 90 | 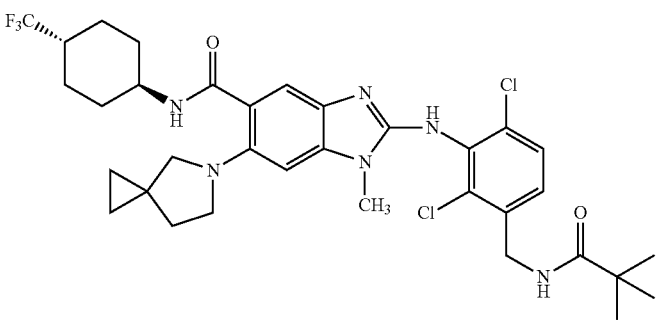 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC4(CC4)C3)cc21] |
| 91 | 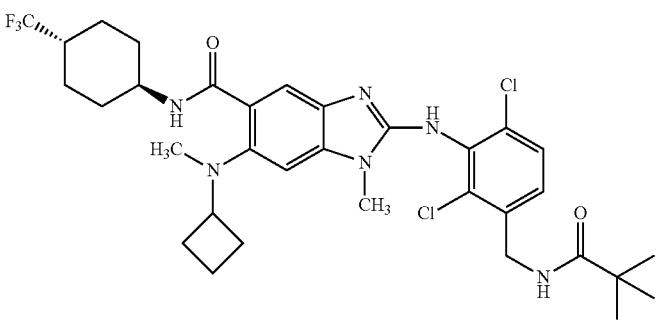 [SMILES: CN(c1cc2c(cc1C(=O)N[C@H]1CC[C@H](C(F)(F)F)CC1)nc(Nc1c(Cl)ccc(CNC(=O)C(C)(C)C)c1Cl)n2C)C1CCC1] |
| 92 | 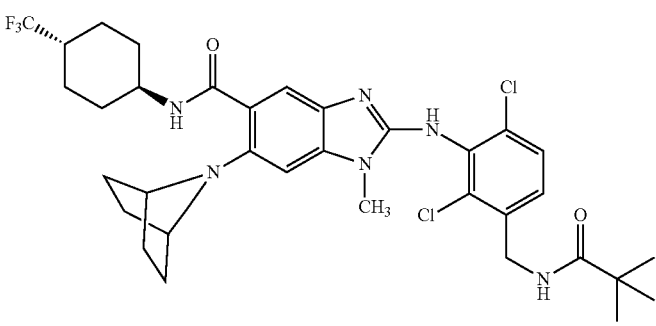 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCC3CC4)cc21] |
| 93 | 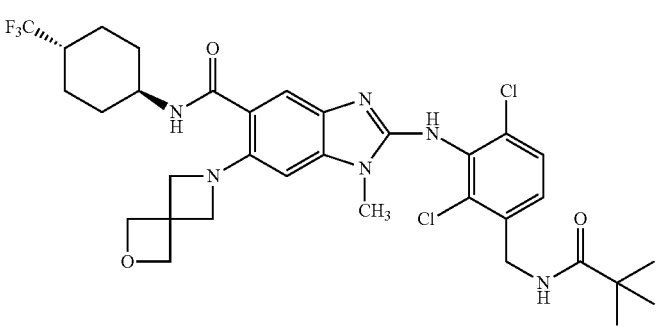 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4(COC4)C3)cc21] |

-continued
| | Structure |
|---|---|
| 94 | 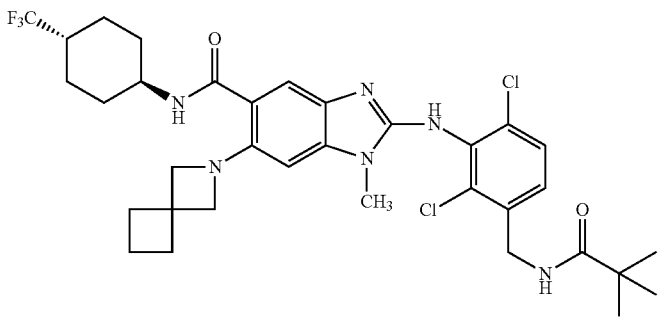 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4(CCC4)C3)cc21] |
| 95 | 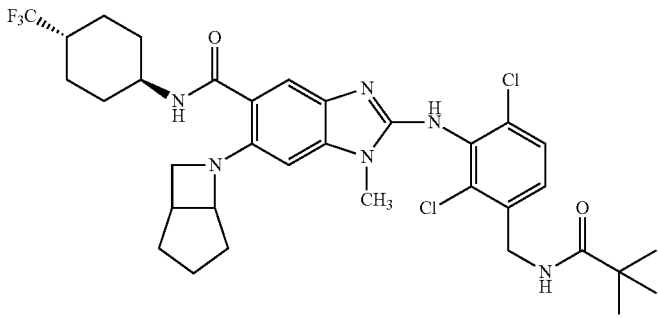 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCCC43)cc21] |
| 96 | 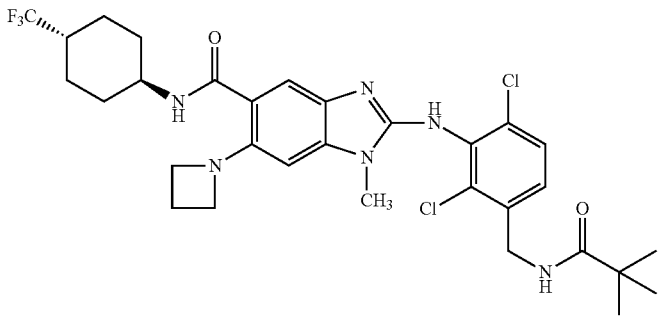 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC3)cc21] |
| 97 | 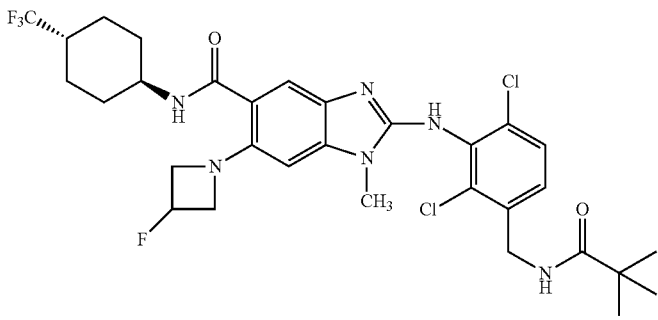 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(F)C3)cc21] |

|     | Structure |
| --- | --- |
| 98  | 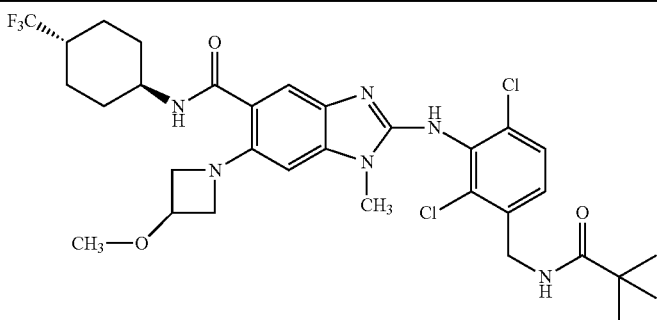 |
| 99  | 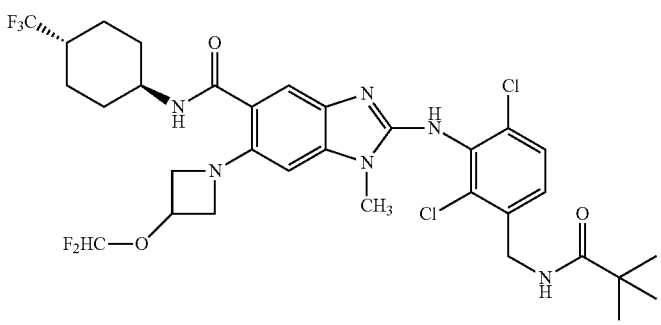 [SMILES: COC1CN(c2cc3c(cc2C(=O)N[C@H]2CC[C@H](C(F)(F)F)CC2)nc(Nc2c(Cl)ccc(CNC(=O)C(C)(C)C)c2Cl)n3C)C1] |
| 100 | 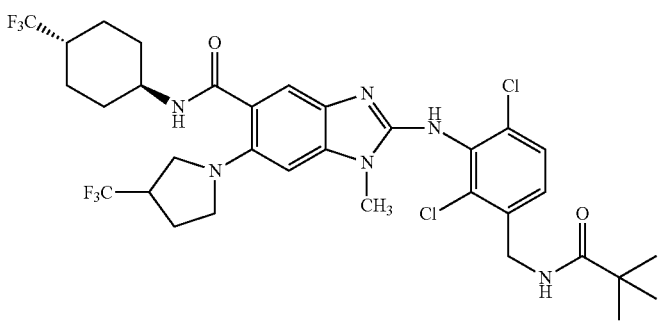 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC(C(F)(F)F)C3)cc21] |
| 101 | 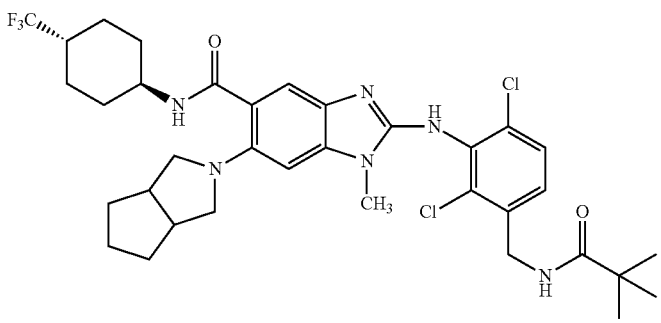 |
| 102 | 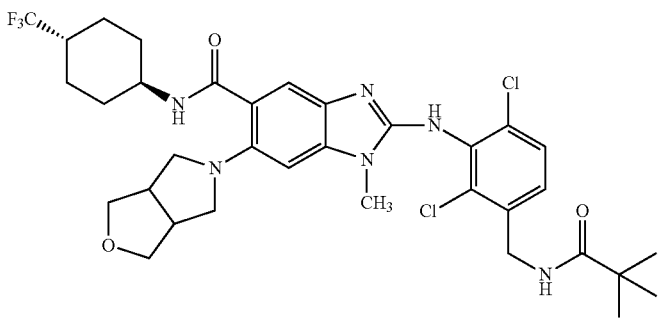 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4COCC4C3)cc21] |

| Structure |
|---|
| 103 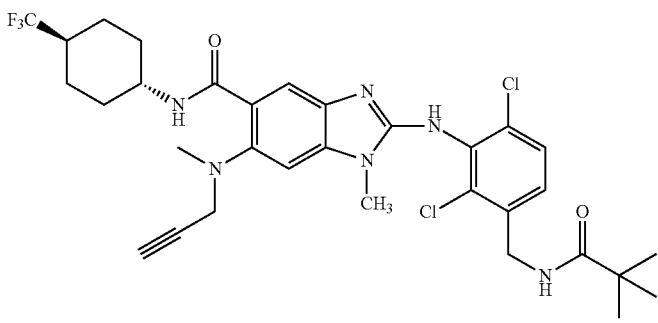 [SMILES: C#CCN(C)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 104 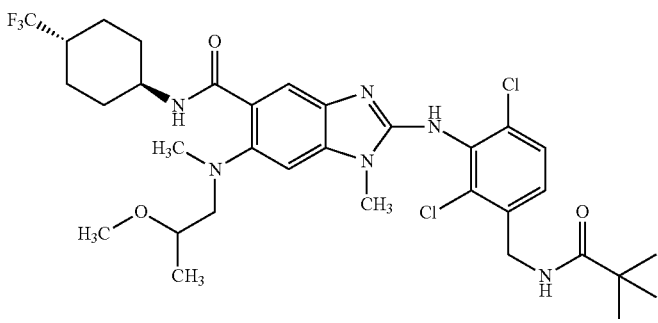 [SMILES: COC(C)CN(C)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 105 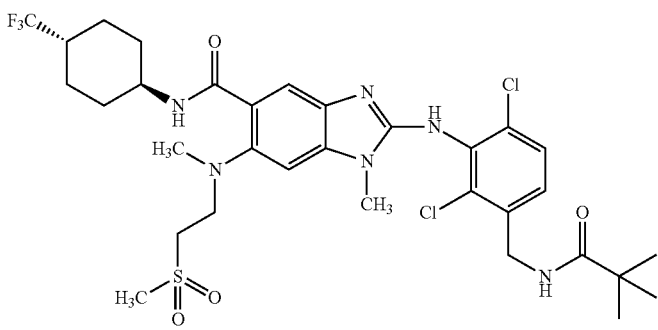 [SMILES: CN(CCS(C)(=O)=O)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 106 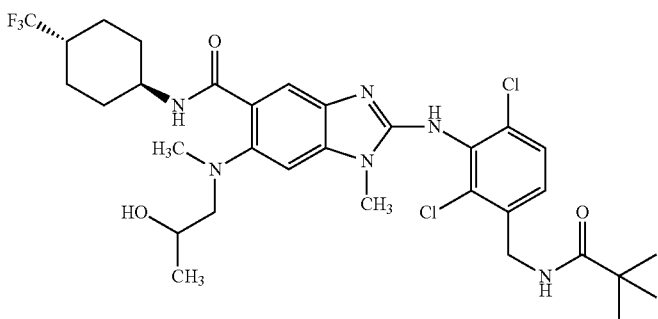 [SMILES: CC(O)CN(C)c1cc2c(cc1C(=O)N[C@H]1CC[C@H](C(F)(F)F)CC1)nc(Nc1c(Cl)ccc(CNC(=O)C(C)(C)C)c1Cl)n2C] |

-continued
| | Structure |
|---|---|
| 107 | 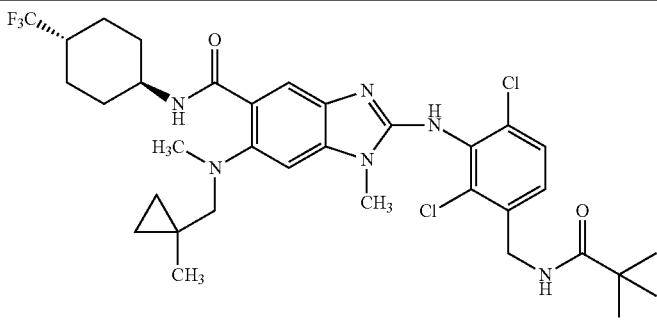 |
| 108 | 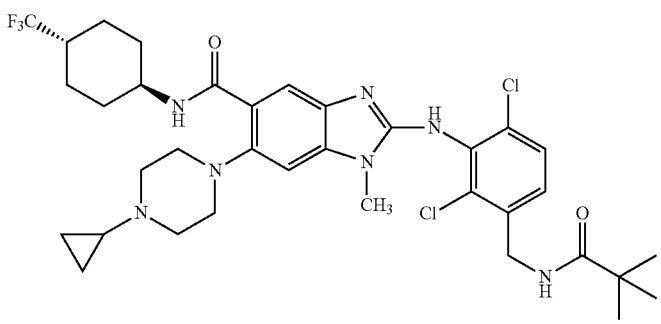 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCN(C4CC4)CC3)cc21] |
| 109 | 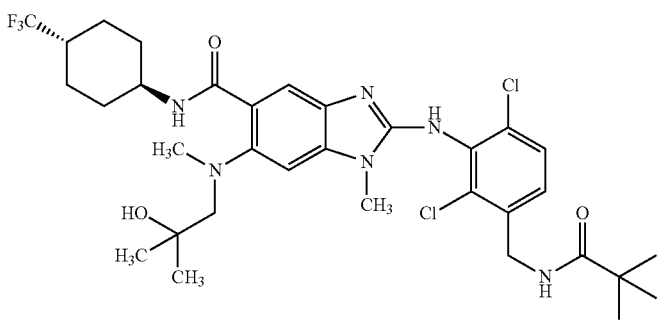 [SMILES: CN(CC(C)(C)O)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 110 | 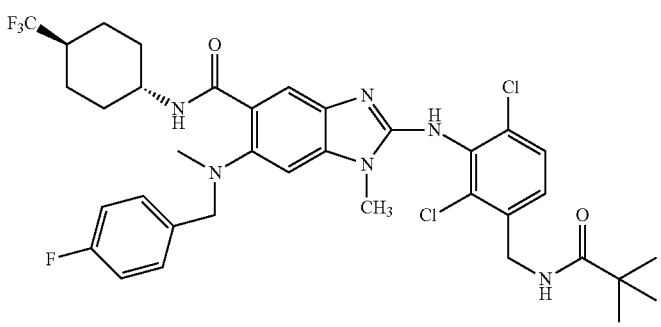 [SMILES: CN(Cc1ccc(F)cc1)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 111 | 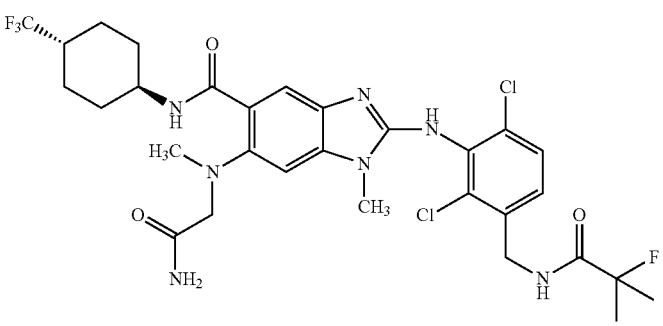 [SMILES: CN(CC(N)=O)c1cc2c(cc1C(=O)N[C@H]1CC[C@H](C(F)(F)F)CC1)nc(Nc1c(Cl)ccc(CNC(=O)C(C)(C)F)c1Cl)n2C] |

-continued
| | Structure |
|---|---|
| 112 | 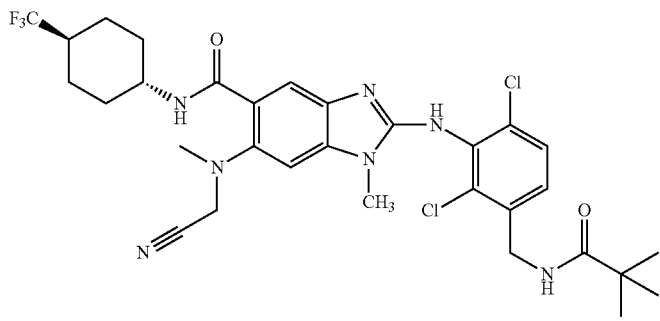 [SMILES: CN(CC#N)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 113 | 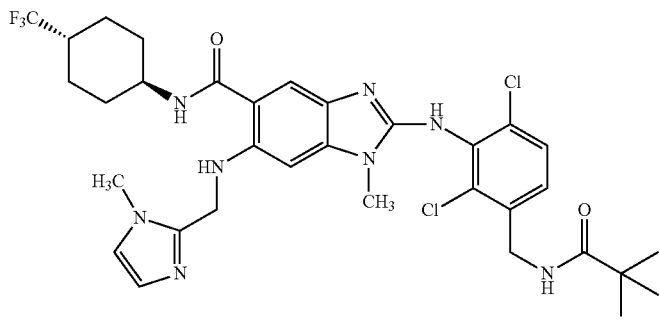 [SMILES: Cn1ccnc1CNc1cc2c(cc1C(=O)N[C@H]1CC[C@H](C(F)(F)F)CC1)nc(Nc1c(Cl)ccc(CNC(=O)C(C)(C)C)c1Cl)n2C] |
| 114 | 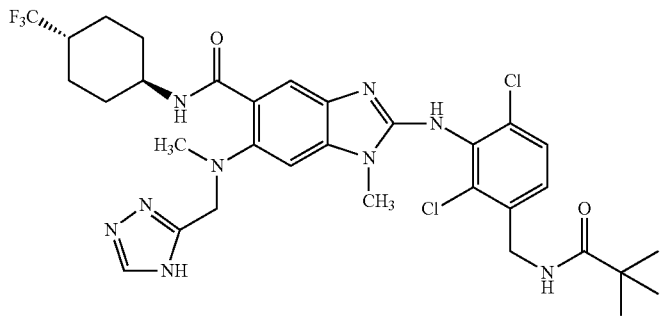 [SMILES: CN(Cc1nnc[nH]1)c1cc2c(cc1C(=O)N[C@H]1CC[C@H](C(F)(F)F)CC1)nc(Nc1c(Cl)ccc(CNC(=O)C(C)(C)C)c1Cl)n2C] |
| 115 | 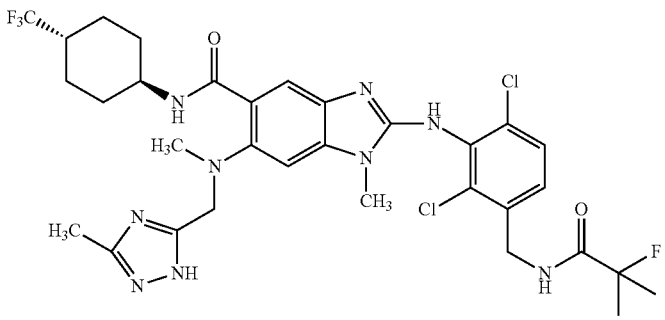 [SMILES: Cc1n[nH]c(CN(C)c2cc3c(cc2C(=O)N[C@H]2CC[C@H](C(F)(F)F)CC2)nc(Nc2c(Cl)ccc(CNC(=O)C(C)(C)F)c2Cl)n3C)n1] |

|   | Structure |
|---|---|
| 116 | 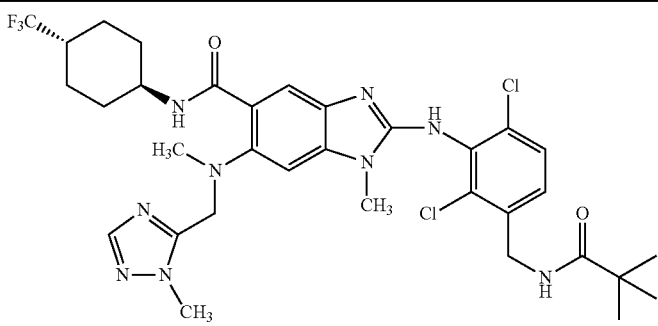 |
| 117 | 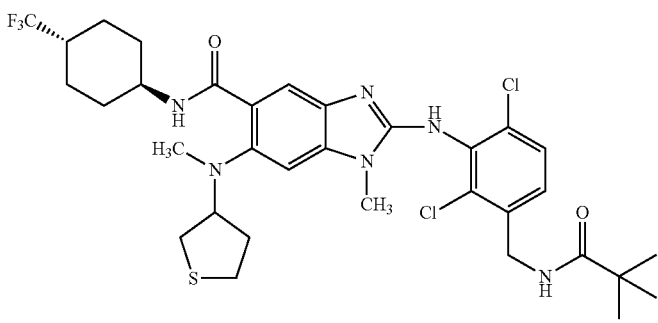 [SMILES: CN(c1cc2c(cc1C(=O)N[C@H]1CC[C@H](C(F)(F)F)CC1)nc(Nc1c(Cl)ccc(CNC(=O)C(C)(C)C)c1Cl)n2C)C1CCSC1] |
| 118 | 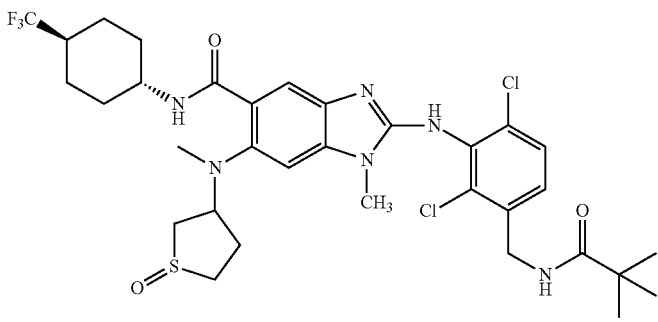 [SMILES: CN(c1cc2c(cc1C(=O)N[C@H]1CC[C@H](C(F)(F)F)CC1)nc(Nc1c(Cl)ccc(CNC(=O)C(C)(C)C)c1Cl)n2C)C1CCS(=O)C1] |
| 119 | 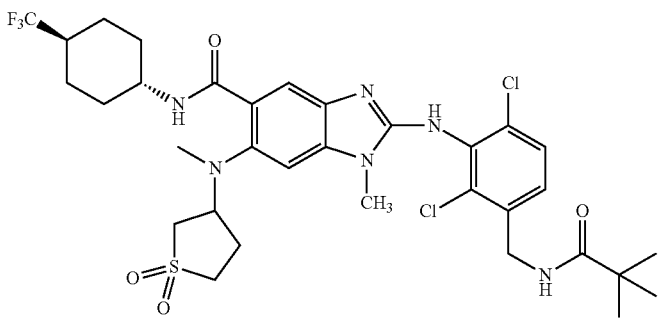 [SMILES: CN(c1cc2c(cc1C(=O)N[C@H]1CC[C@H](C(F)(F)F)CC1)nc(Nc1c(Cl)ccc(CNC(=O)C(C)(C)C)c1Cl)n2C)C1CCS(=O)(=O)C1] |
| 120 | 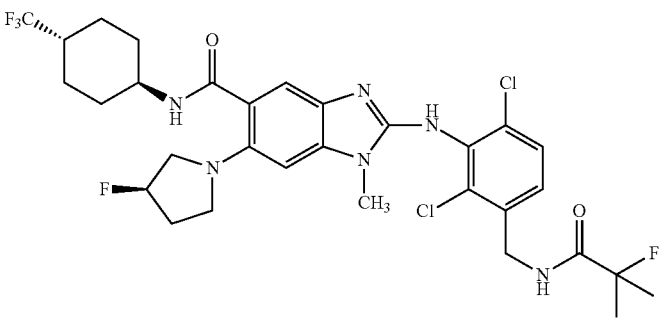 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CC[C@@H](F)C3)cc21] |

| | Structure |
|---|---|
| 121 | 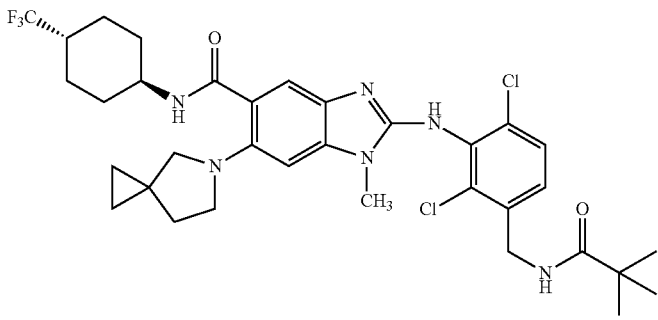 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCC4(CC4)C3)cc21] |
| 122 | 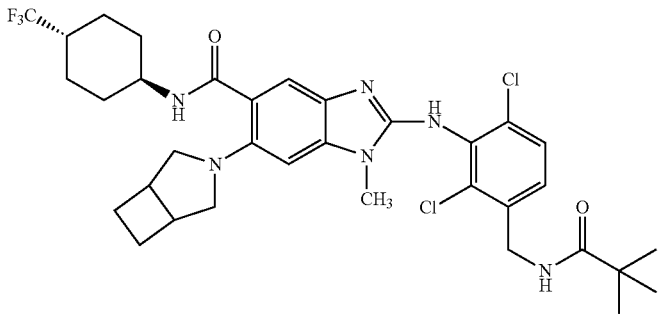 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCC4C3)cc21] |
| 123 | 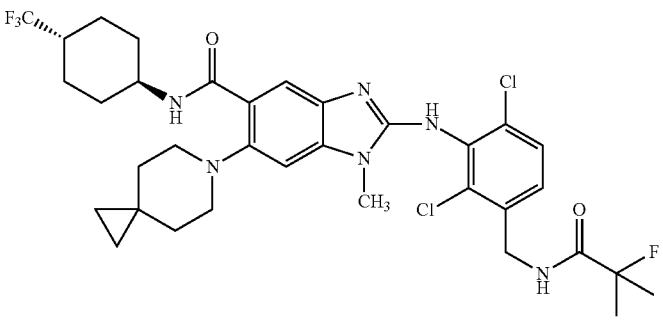 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC4(CC3)CC4)cc21] |
| 124 | 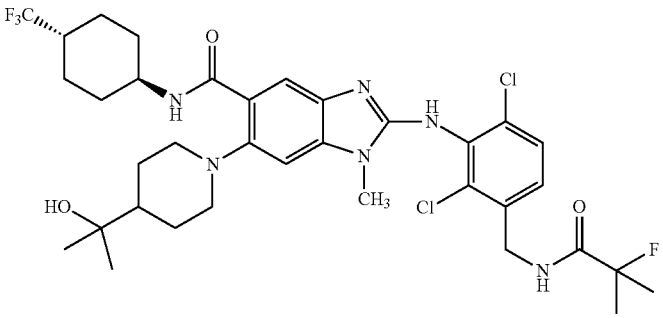 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC(C(C)(C)O)CC3)cc21] |

-continued
| | Structure |
|---|---|
| 125 | 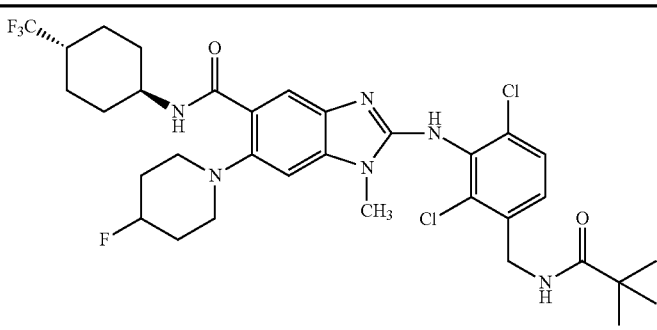 |
| 126 | 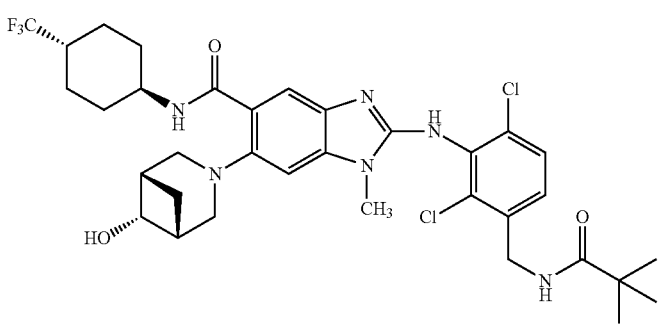 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3C[C@H]4C[C@@H](C3)[C@H]4O)cc21] |
| 127 | 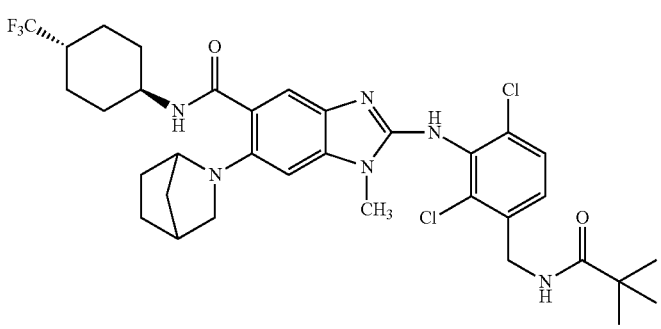 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC4CCC3C4)cc21] |
| 128 | 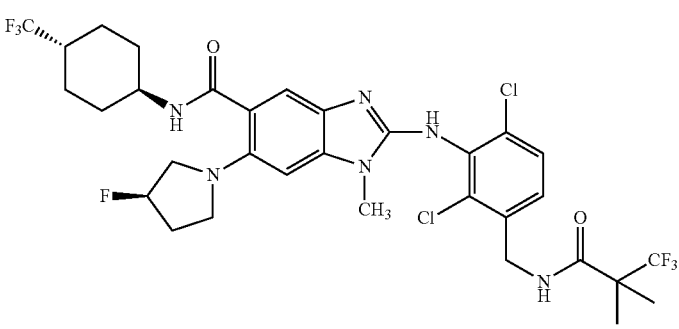 [SMILES: Cn1c(Nc2c(Cl)ccc(CNC(=O)C(C)(C)C(F)(F)F)c2Cl)nc2cc(C(=O)N[C@H]3CC[C@H](C(F)(F)F)CC3)c(N3CC[C@@H](F)C3)cc21] |
| 129 | 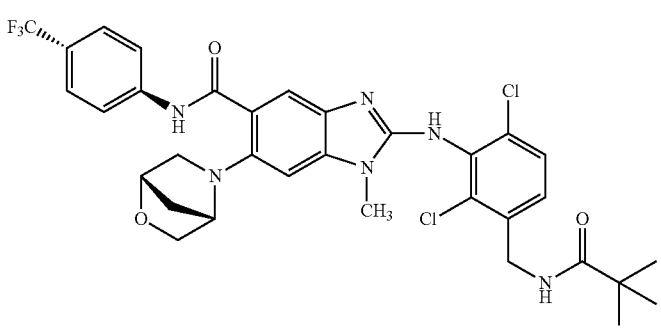 |

| | Structure |
|---|---|
| 130 | 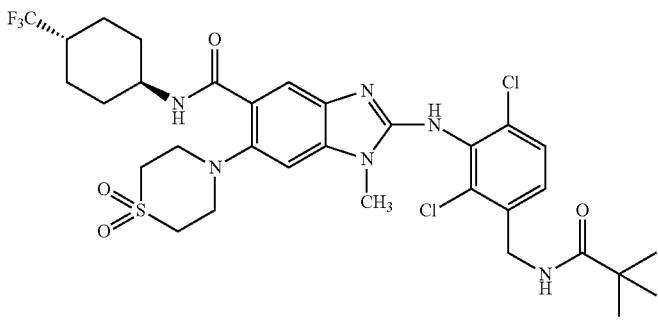 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCS(=O)(=O)CC3)cc21] |
| 131 | 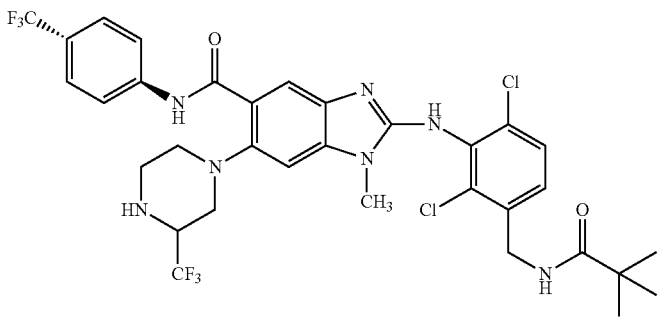 |
| 132 | 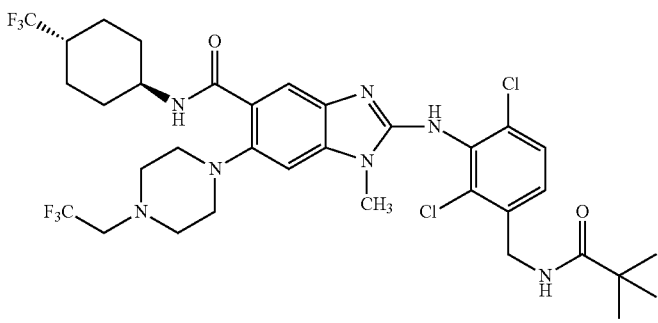 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCN(CC(F)(F)F)CC3)cc21] |
| 133 | 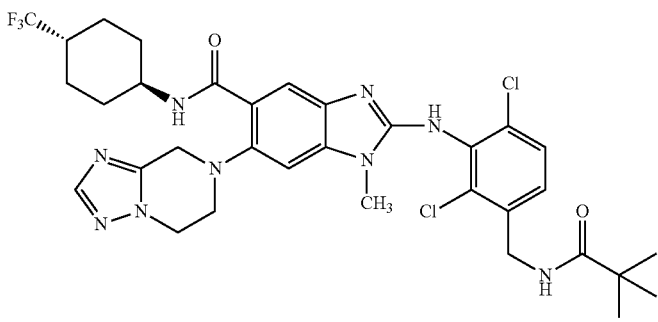 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCn4ncnc4C3)cc21] |

| | Structure |
|---|---|
| 134 | 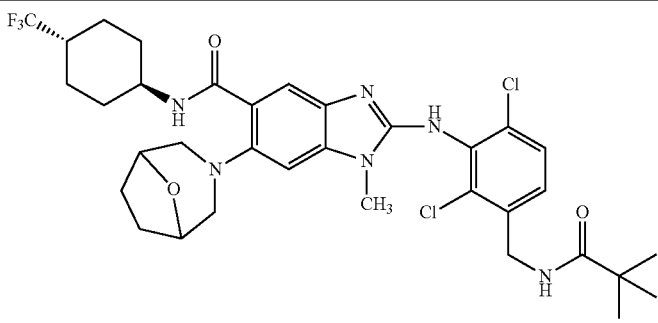 |
| 135 | 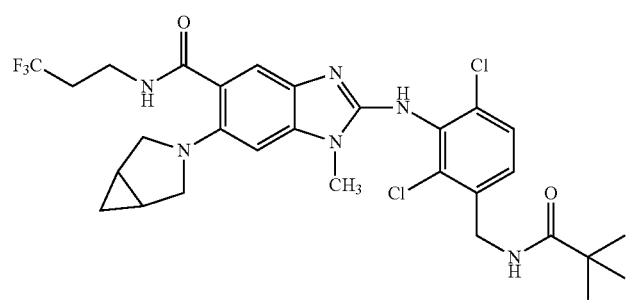 [SMILES: Cn1c(Nc2c(Cl)ccc(CNC(=O)C(C)(C)C)c2Cl)nc2cc(C(=O)NCCC(F)(F)F)c(N3CC4CC4C3)cc21] |
| 136 | 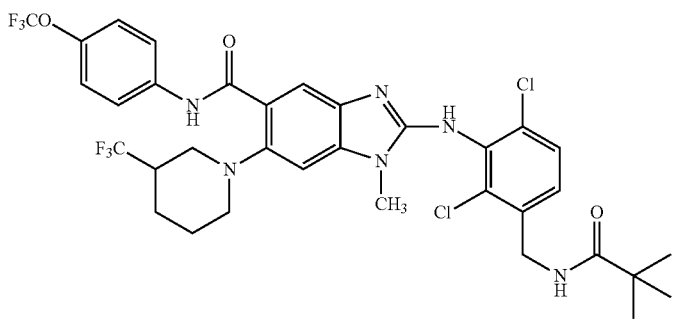 |
| 137 | 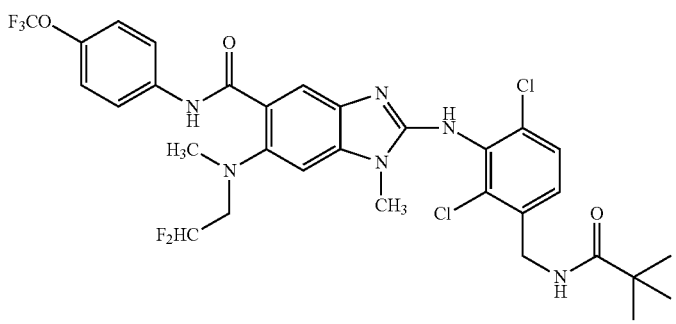 [SMILES: CN(CC(F)F)c1cc2c(cc1C(=O)Nc1ccc(OC(F)(F)F)cc1)nc(Nc1c(Cl)ccc(CNC(=O)C(C)(C)C)c1Cl)n2C] |
| 138 | 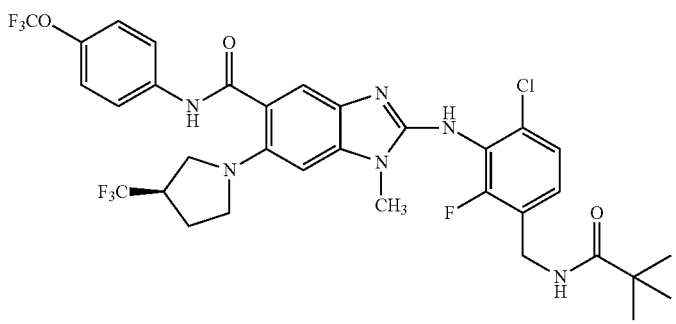 |

| | Structure |
|---|---|
| 139 | 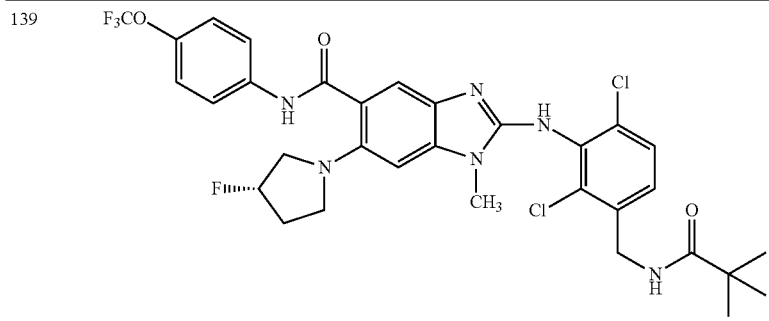 |
| 140 | 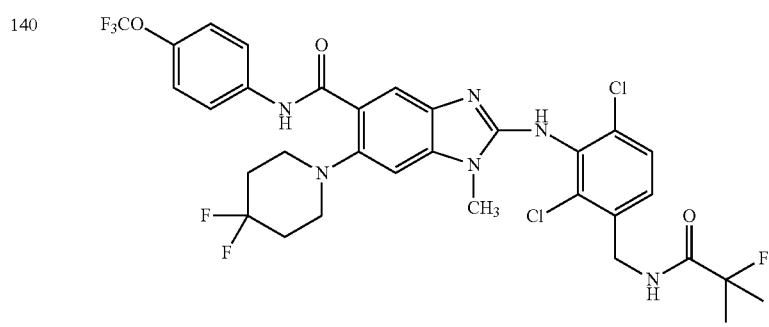 |
| 141 | 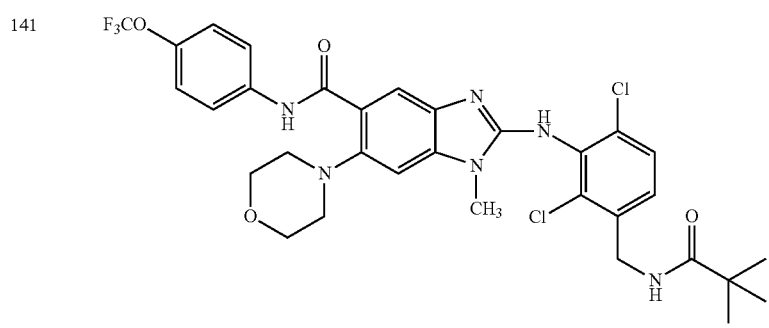 |
| 142 | 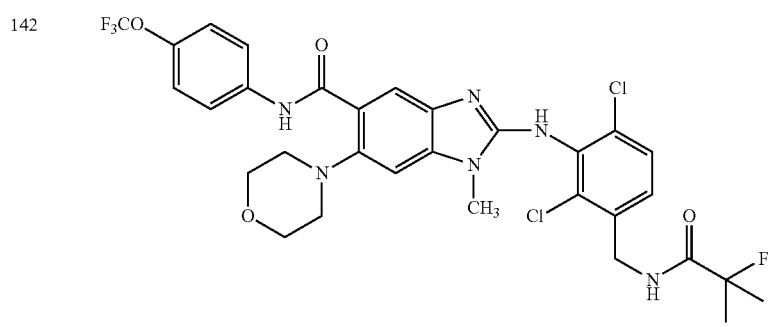 |
| 143 | 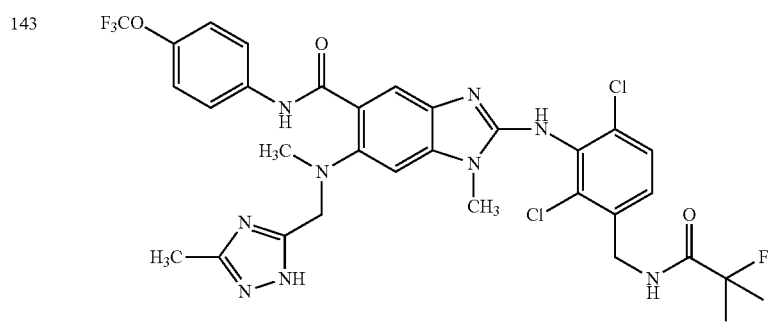 |

-continued
| | Structure |
|---|---|
| 144 | 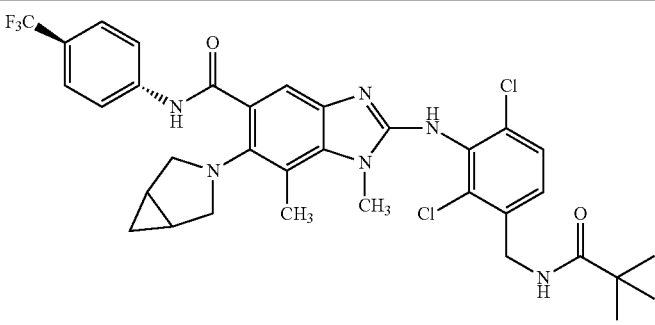 |
| 145 | 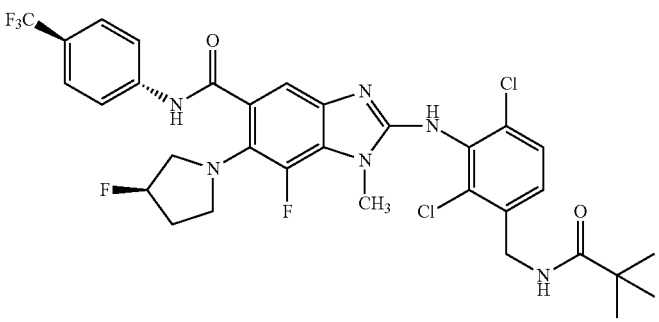 |
| 146 | 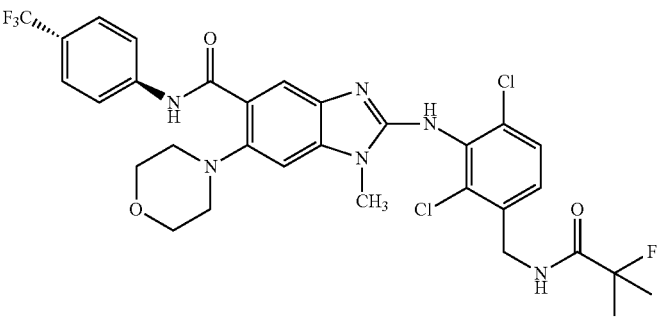 |
| 147 | 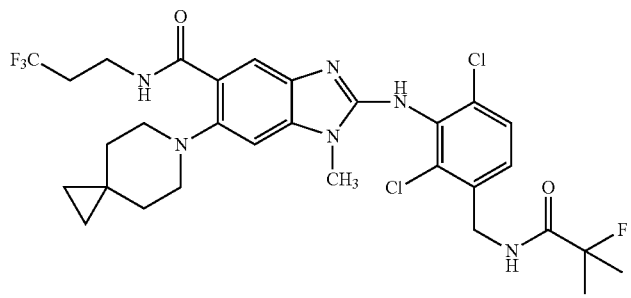 [SMILES: Cn1c(Nc2c(Cl)ccc(CNC(=O)C(C)(C)F)c2Cl)nc2cc(C(=O)NCCC(F)(F)F)c(N3CCC4(CC3)CC4)cc21] |
| 148 | 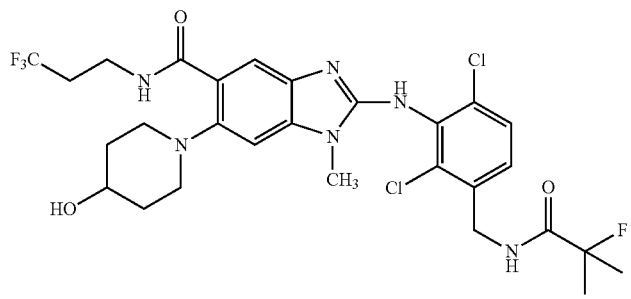 |

| Structure |
|---|
| 149 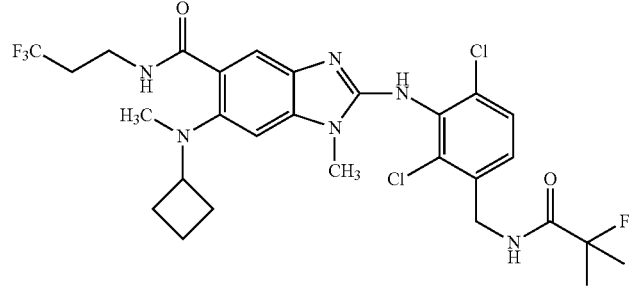 [SMILES: CN(c1cc2c(cc1C(=O)NCCC(F)(F)F)nc(Nc1c(Cl)ccc(CNC(=O)C(C)(C)F)c1Cl)n2C)C1CCC1] |
| 150 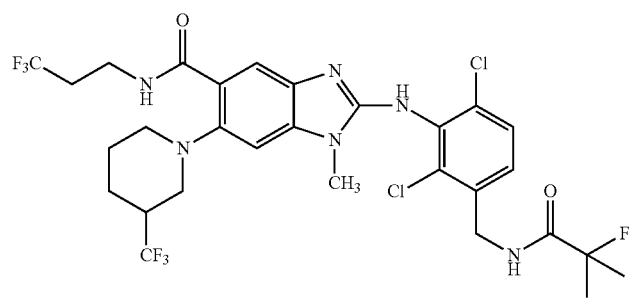 [SMILES: Cn1c(Nc2c(Cl)ccc(CNC(=O)C(C)(C)F)c2Cl)nc2cc(C(=O)NCCC(F)(F)F)c(N3CCCC(C(F)(F)F)C3)cc21] |
| 151 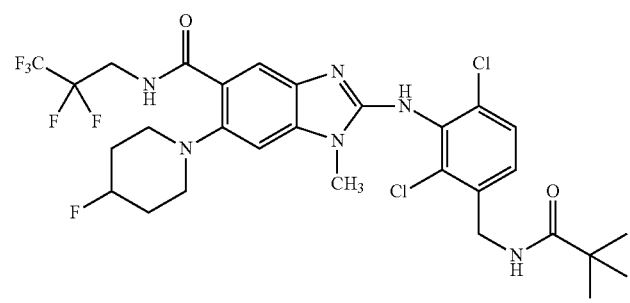 [SMILES: Cn1c(Nc2c(Cl)ccc(CNC(=O)C(C)(C)C)c2Cl)nc2cc(C(=O)NCC(F)(F)C(F)(F)F)c(N3CCC(F)CC3)cc21] |
| 152 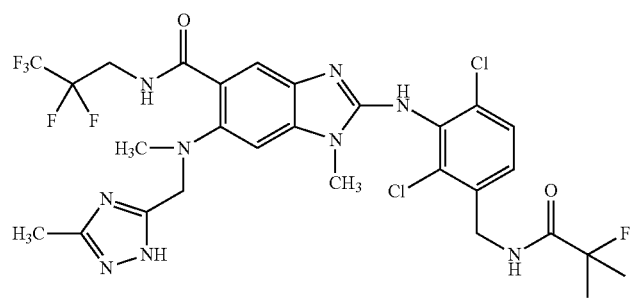 [SMILES: Cc1n[nH]c(CN(C)c2cc3c(cc2C(=O)NCC(F)(F)C(F)(F)F)nc(Nc2c(Cl)ccc(CNC(=O)C(C)(C)F)c2Cl)n3C)n1] |
| 153 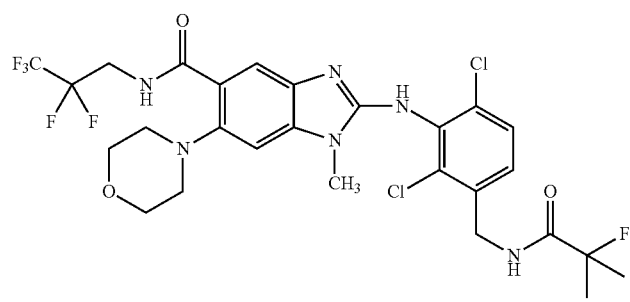 [SMILES: Cn1c(Nc2c(Cl)ccc(CNC(=O)C(C)(C)F)c2Cl)nc2cc(C(=O)NCC(F)(F)C(F)(F)F)c(N3CCOCC3)cc21] |

| | Structure |
|---|---|
| 154 | 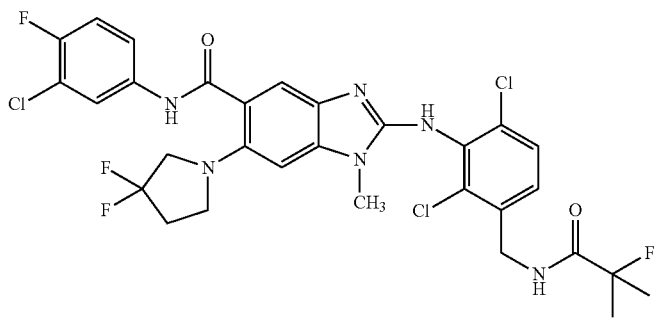 [SMILES: Cn1c(Nc2c(Cl)ccc(CNC(=O)C(C)(C)F)c2Cl)nc2cc(C(=O)Nc3ccc(F)c(Cl)c3)c(N3CCC(F)(F)C3)cc21] |
| 155 | 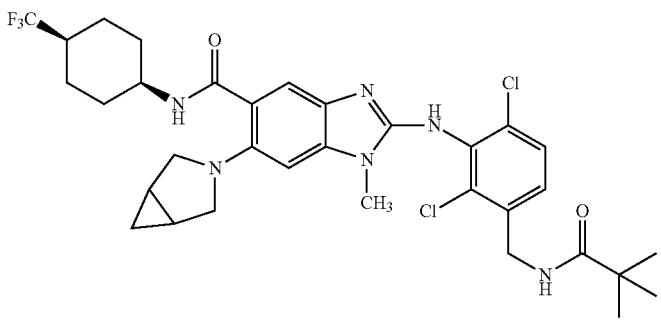 [SMILES: Cn1c(Nc2c(Cl)ccc(CNC(=O)C(C)(C)C)c2Cl)nc2cc(C(=O)N[C@H]3CC[C@@H](C(F)(F)F)CC3)c(N3CC4CC4C3)cc21] |
| 156 | 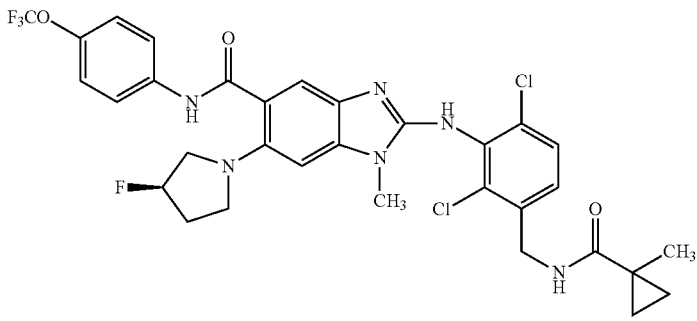 [SMILES: Cn1c(Nc2c(Cl)ccc(CNC(=O)C3(C)CC3)c2Cl)nc2cc(C(=O)Nc3ccc(OC(F)(F)F)cc3)c(N3CC[C@@H](F)C3)cc21] |
| 157 | 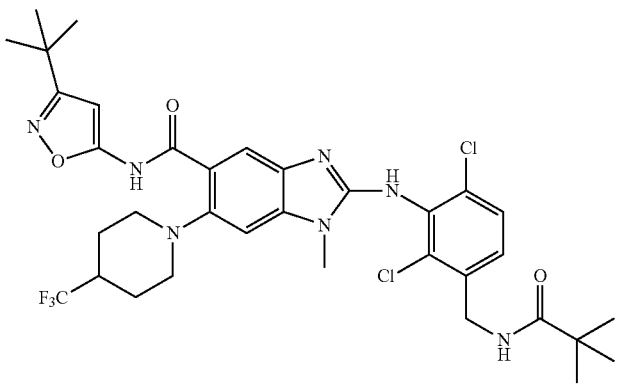 [SMILES: Cn1c(Nc2c(Cl)ccc(CNC(=O)C(C)(C)C)c2Cl)nc2cc(C(=O)Nc3cc(C(C)(C)C)no3)c(N3CCC(C(F)(F)F)CC3)cc21] |

| | Structure |
|---|---|
| 158 | 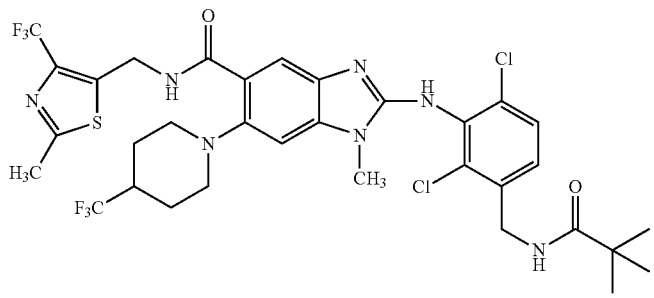 [SMILES: Cc1nc(C(F)(F)F)c(CNC(=O)c2cc3nc(Nc4c(Cl)ccc(CNC(=O)C(C)(C)C)c4Cl)n(C)c3cc2N2CCC(C(F)(F)F)CC2)s1] |
| 159 | 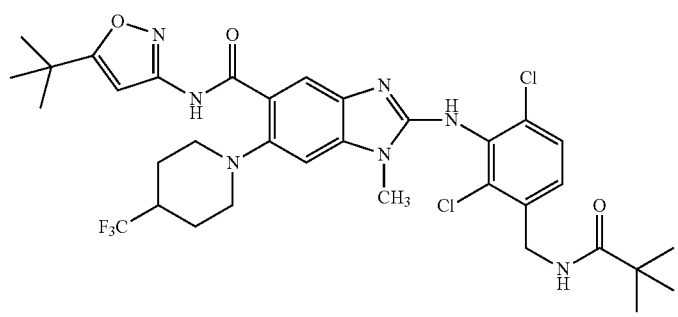 [SMILES: Cn1c(Nc2c(Cl)ccc(CNC(=O)C(C)(C)C)c2Cl)nc2cc(C(=O)Nc3cc(C(C)(C)C)on3)c(N3CCC(C(F)(F)F)CC3)cc21] |
| 160 | 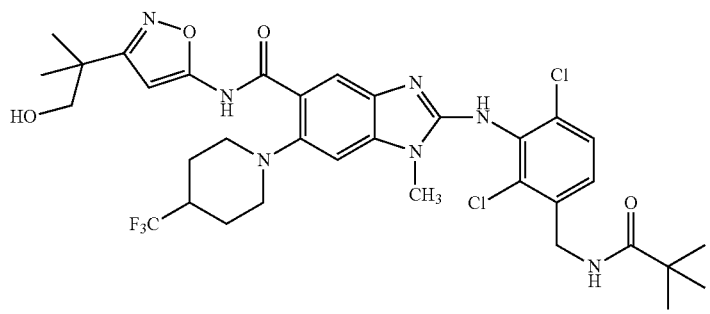 [SMILES: Cn1c(Nc2c(Cl)ccc(CNC(=O)C(C)(C)C)c2Cl)nc2cc(C(=O)Nc3cc(C(C)(C)CO)no3)c(N3CCC(C(F)(F)F)CC3)cc21] |
| 161 | 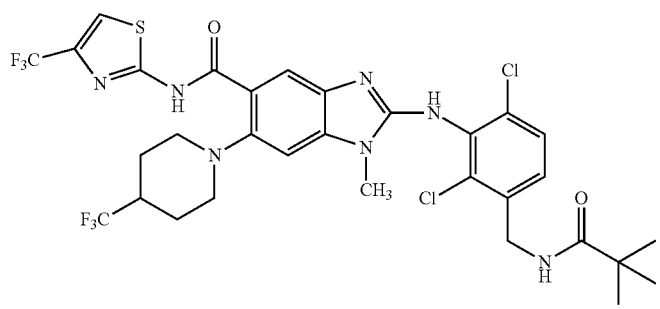 [SMILES: Cn1c(Nc2c(Cl)ccc(CNC(=O)C(C)(C)C)c2Cl)nc2cc(C(=O)Nc3nc(C(F)(F)F)cs3)c(N3CCC(C(F)(F)F)CC3)cc21] |
| 162 | 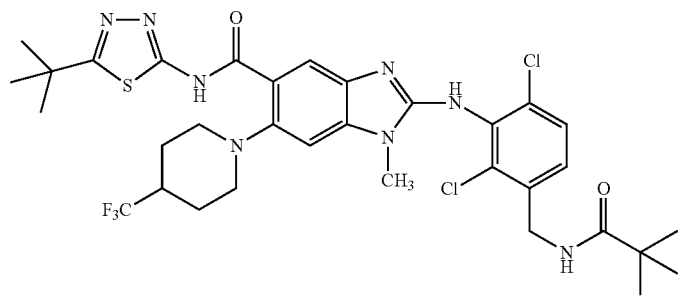 [SMILES: Cn1c(Nc2c(Cl)ccc(CNC(=O)C(C)(C)C)c2Cl)nc2cc(C(=O)Nc3nnc(C(C)(C)C)s3)c(N3CCC(C(F)(F)F)CC3)cc21] |

-continued
| | Structure |
|---|---|
| 163 | 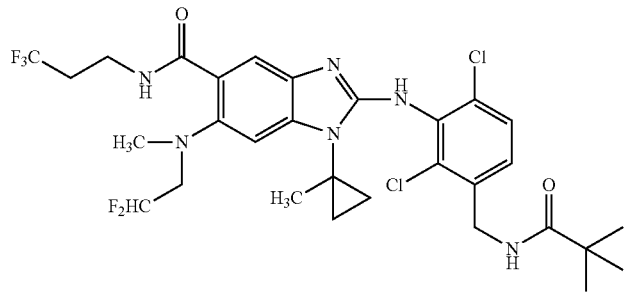 [SMILES: CN(CC(F)F)c1cc2c(cc1C(=O)NCCC(F)(F)F)nc(Nc1c(Cl)ccc(CNC(=O)C(C)(C)C)c1Cl)n2C1(C)CC1] |
| 164 | 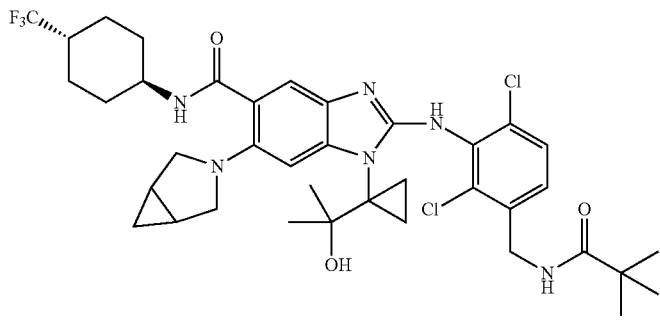 [SMILES: CC(C)(C)C(=O)NCc1ccc(Cl)c(Nc2nc3cc(C(=O)N[C@H]4CC[C@H](C(F)(F)F)CC4)c(N4CC5CC5C4)cc3n2C2(C(C)(C)O)CC2)c1Cl] |
| 165 | 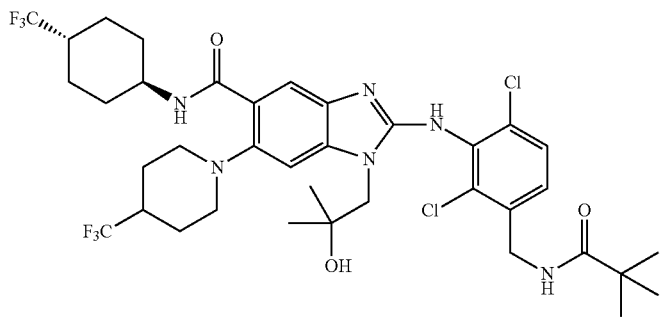 [SMILES: CC(C)(O)Cn1c(Nc2c(Cl)ccc(CNC(=O)C(C)(C)C)c2Cl)nc2cc(C(=O)N[C@H]3CC[C@H](C(F)(F)F)CC3)c(N3CCC(C(F)(F)F)CC3)cc21] |
| 166 | 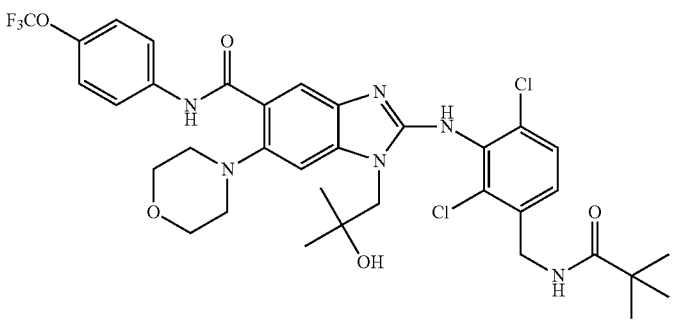 [SMILES: CC(C)(O)Cn1c(Nc2c(Cl)ccc(CNC(=O)C(C)(C)C)c2Cl)nc2cc(C(=O)Nc3ccc(OC(F)(F)F)cc3)c(N3CCOCC3)cc21] |
| 167 | 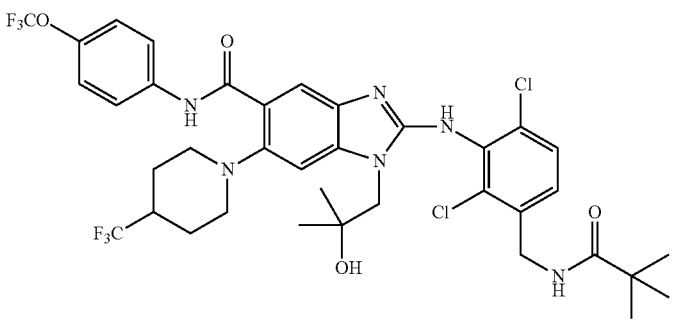 [SMILES: CC(C)(O)Cn1c(Nc2c(Cl)ccc(CNC(=O)C(C)(C)C)c2Cl)nc2cc(C(=O)Nc3ccc(OC(F)(F)F)cc3)c(N3CCC(C(F)(F)F)CC3)cc21] |

|   | Structure |
|---|---|
| 168 | 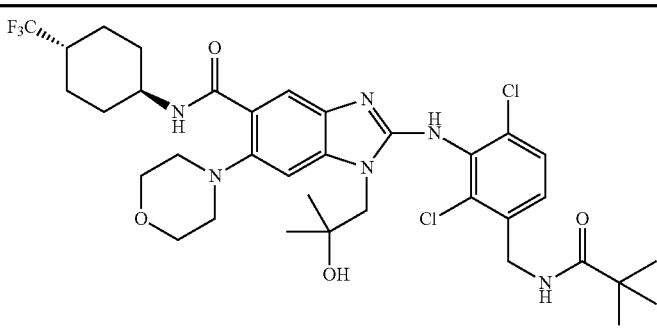 |
| 169 | 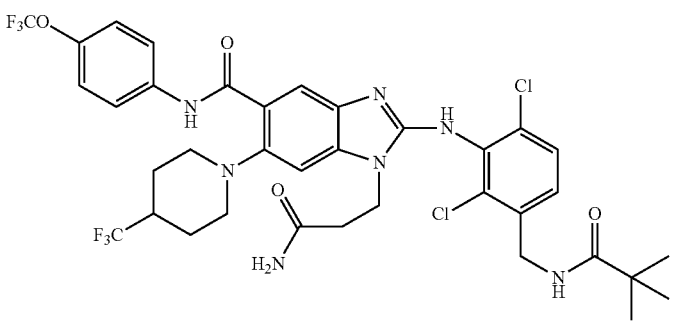 [SMILES: CC(C)(C)C(=O)NCc1ccc(Cl)c(Nc2nc3cc(C(=O)Nc4ccc(OC(F)(F)F)cc4)c(N4CCC(C(F)(F)F)CC4)cc3n2CCC(N)=O)c1Cl] |
| 170 | 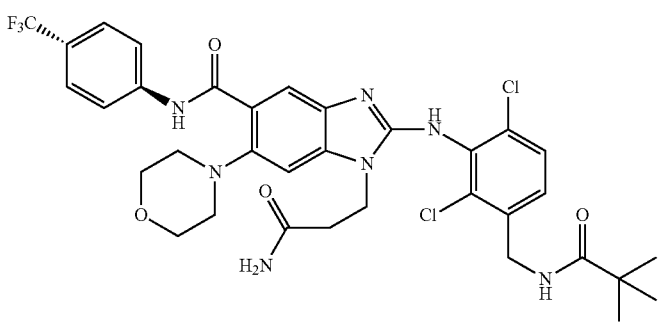 |
| 171 | 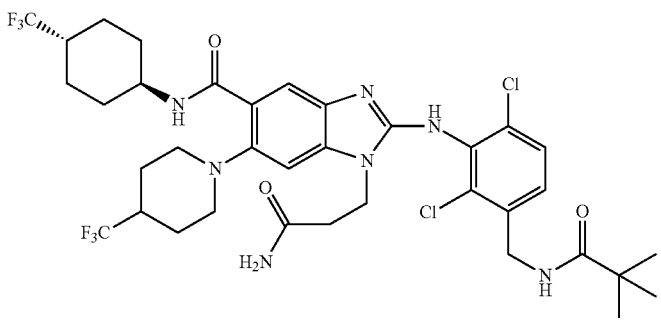 [SMILES: CC(C)(C)C(=O)NCc1ccc(Cl)c(Nc2nc3cc(C(=O)N[C@H]4CC[C@H](C(F)(F)F)CC4)c(N4CCC(C(F)(F)F)CC4)cc3n2CCC(N)=O)c1Cl] |
| 172 | 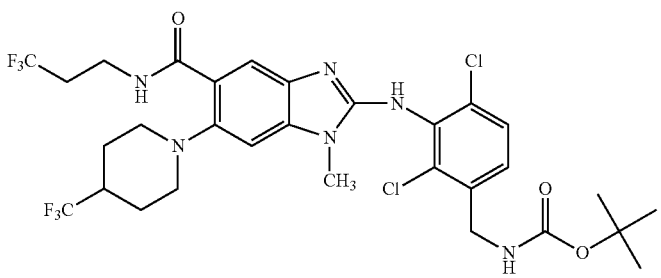 [SMILES: Cn1c(Nc2c(Cl)ccc(CNC(=O)OC(C)(C)C)c2Cl)nc2cc(C(=O)NCCC(F)(F)F)c(N3CCC(C(F)(F)F)CC3)cc21] |

-continued
| | Structure |
|---|---|
| 173 | 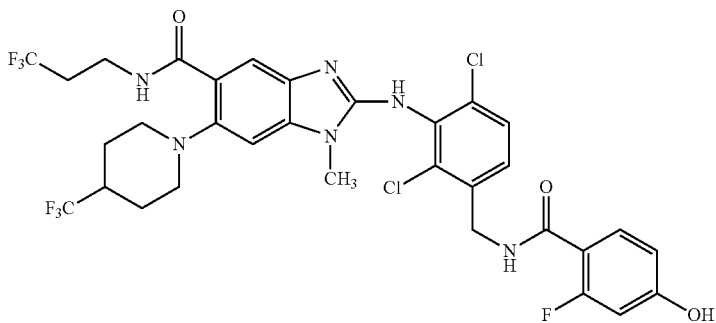 [SMILES: Cn1c(Nc2c(Cl)ccc(CNC(=O)c3ccc(O)cc3F)c2Cl)nc2cc(C(=O)NCCC(F)(F)F)c(N3CCC(C(F)(F)F)CC3)cc21] |
| 174 | 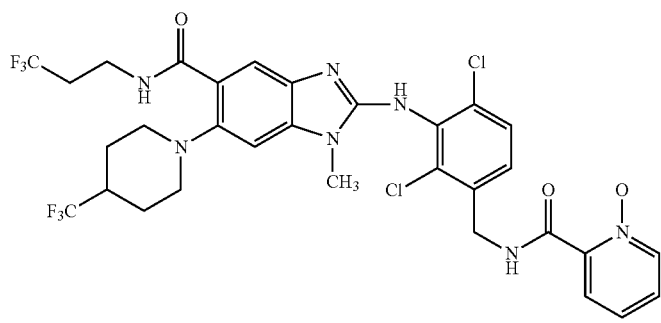 |
| 175 | 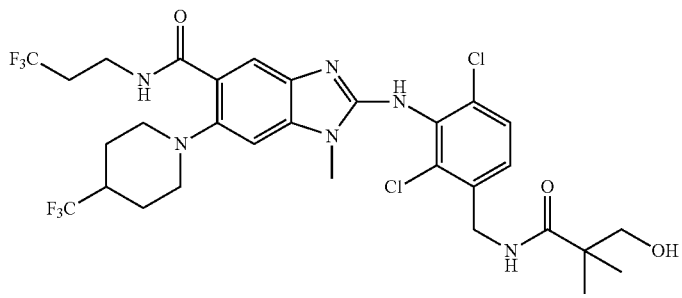 [SMILES: Cn1c(Nc2c(Cl)ccc(CNC(=O)C(C)(C)CO)c2Cl)nc2cc(C(=O)NCCC(F)(F)F)c(N3CCC(C(F)(F)F)CC3)cc21] |
| 176 | 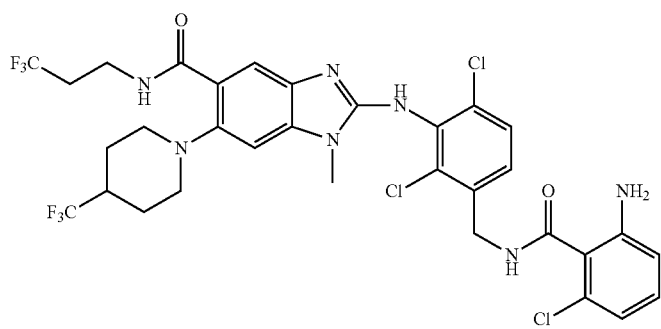 [SMILES: Cn1c(Nc2c(Cl)ccc(CNC(=O)c3c(N)cccc3Cl)c2Cl)nc2cc(C(=O)NCCC(F)(F)F)c(N3CCC(C(F)(F)F)CC3)cc21] |
| 177 | 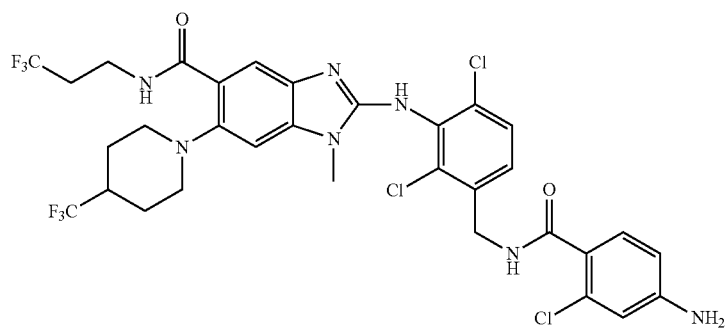 [SMILES: Cn1c(Nc2c(Cl)ccc(CNC(=O)c3ccc(N)cc3Cl)c2Cl)nc2cc(C(=O)NCCC(F)(F)F)c(N3CCC(C(F)(F)F)CC3)cc21] |

| Structure |
|---|
| 178 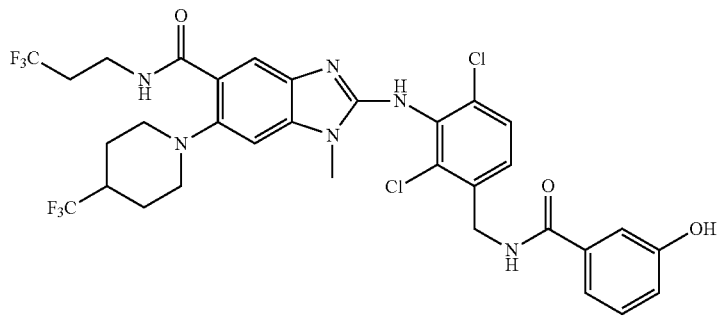 [SMILES: Cn1c(Nc2c(Cl)ccc(CNC(=O)c3cccc(O)c3)c2Cl)nc2cc(C(=O)NCCC(F)(F)F)c(N3CCC(C(F)(F)F)CC3)cc21] |
| 179 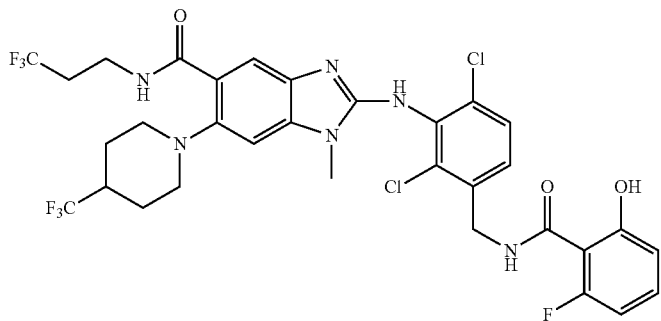 [SMILES: Cn1c(Nc2c(Cl)ccc(CNC(=O)c3c(O)cccc3F)c2Cl)nc2cc(C(=O)NCCC(F)(F)F)c(N3CCC(C(F)(F)F)CC3)cc21] |
| 180 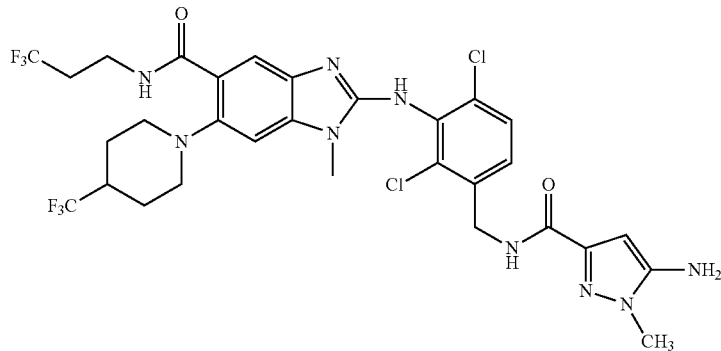 [SMILES: Cn1nc(C(=O)NCc2ccc(Cl)c(Nc3nc4cc(C(=O)NCCC(F)(F)F)c(N5CCC(C(F)(F)F)CC5)cc4n3C)c2Cl)cc1N] |
| 181 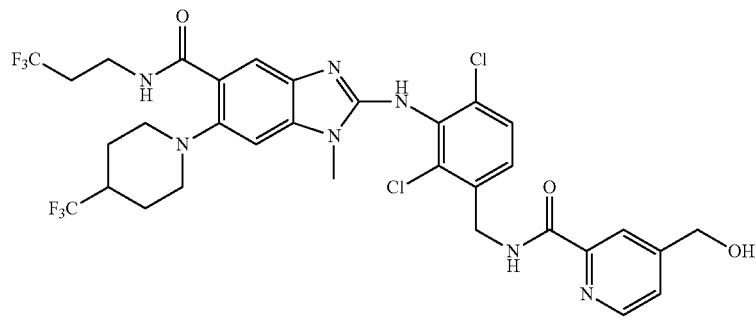 [SMILES: Cn1c(Nc2c(Cl)ccc(CNC(=O)c3cc(CO)ccn3)c2Cl)nc2cc(C(=O)NCCC(F)(F)F)c(N3CCC(C(F)(F)F)CC3)cc21] |

| | Structure |
|---|---|
| 182 | 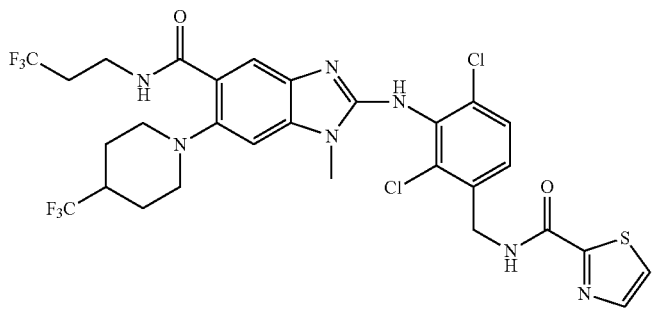 [SMILES: Cn1c(Nc2c(Cl)ccc(CNC(=O)c3nccs3)c2Cl)nc2cc(C(=O)NCCC(F)(F)F)c(N3CCC(C(F)(F)F)CC3)cc21] |
| 183 | 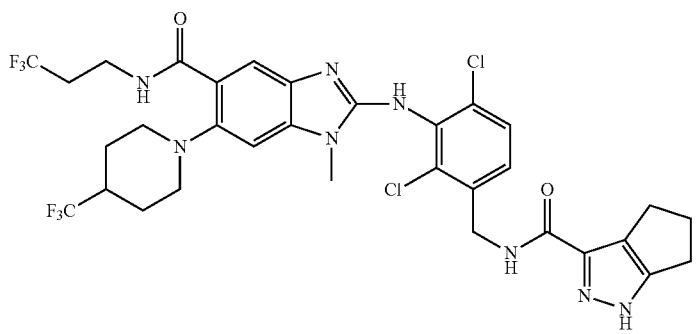 [SMILES: Cn1c(Nc2c(Cl)ccc(CNC(=O)c3n[nH]c4c3CCC4)c2Cl)nc2cc(C(=O)NCCC(F)(F)F)c(N3CCC(C(F)(F)F)CC3)cc21] |
| 184 | 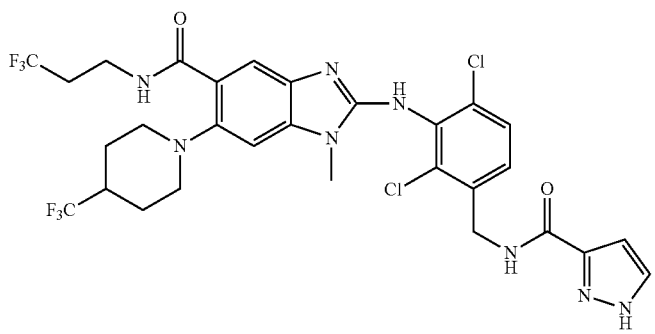 [SMILES: Cn1c(Nc2c(Cl)ccc(CNC(=O)c3cc[nH]n3)c2Cl)nc2cc(C(=O)NCCC(F)(F)F)c(N3CCC(C(F)(F)F)CC3)cc21] |
| 185 | 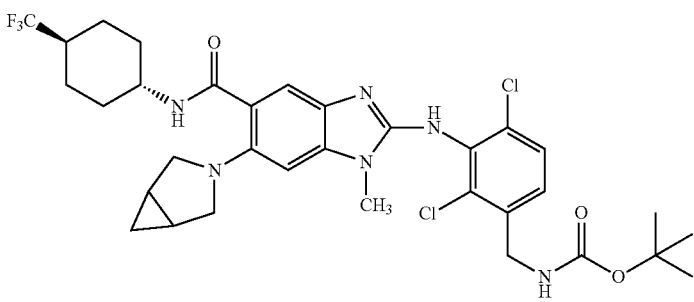 [SMILES: Cn1c(Nc2c(Cl)ccc(CNC(=O)OC(C)(C)C)c2Cl)nc2cc(C(=O)N[C@H]3CC[C@H](C(F)(F)F)CC3)c(N3CC4CC4C3)cc21] |
| 186 | 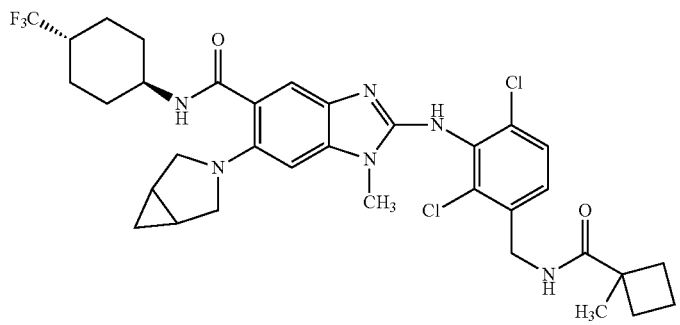 [SMILES: Cn1c(Nc2c(Cl)ccc(CNC(=O)C3(C)CCC3)c2Cl)nc2cc(C(=O)N[C@H]3CC[C@H](C(F)(F)F)CC3)c(N3CC4CC4C3)cc21] |

|     | Structure |
|-----|-----------|
| 187 | 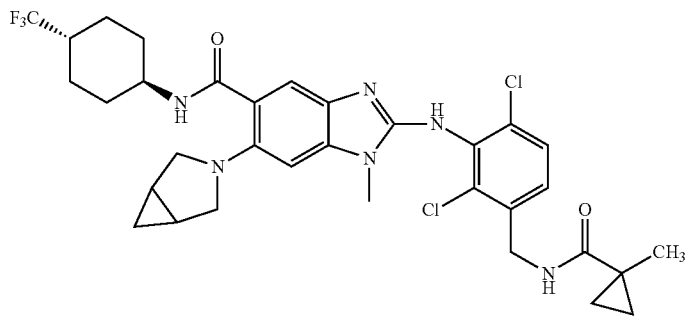 [SMILES: Cn1c(Nc2c(Cl)ccc(CNC(=O)C3(C)CC3)c2Cl)nc2cc(C(=O)N[C@H]3CC[C@H](C(F)(F)F)CC3)c(N3CC4CC4C3)cc21] |
| 188 | 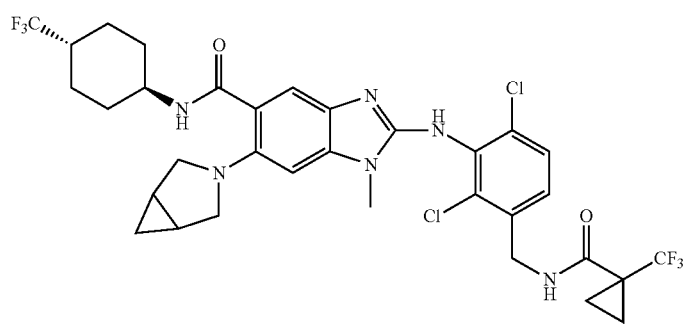 [SMILES: Cn1c(Nc2c(Cl)ccc(CNC(=O)C3(C(F)(F)F)CC3)c2Cl)nc2cc(C(=O)N[C@H]3CC[C@H](C(F)(F)F)CC3)c(N3CC4CC4C3)cc21] |
| 189 | 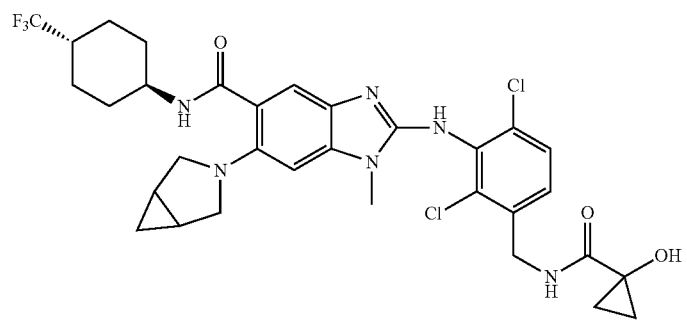 [SMILES: Cn1c(Nc2c(Cl)ccc(CNC(=O)C3(O)CC3)c2Cl)nc2cc(C(=O)N[C@H]3CC[C@H](C(F)(F)F)CC3)c(N3CC4CC4C3)cc21] |
| 190 | 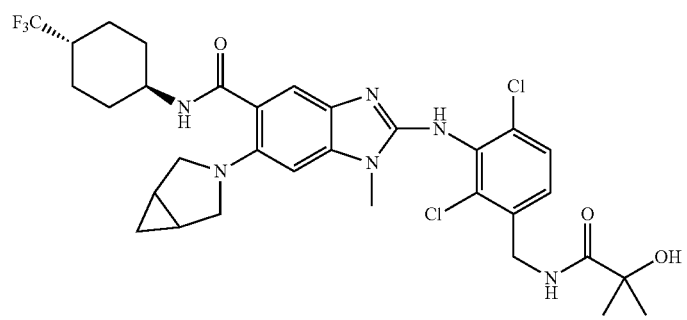 [SMILES: Cn1c(Nc2c(Cl)ccc(CNC(=O)C(C)(C)O)c2Cl)nc2cc(C(=O)N[C@H]3CC[C@H](C(F)(F)F)CC3)c(N3CC4CC4C3)cc21] |
| 191 | 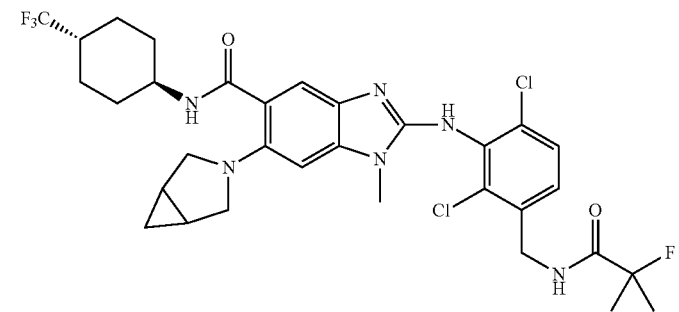 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CC4CC4C3)cc21] |

| | Structure |
|---|---|
| 192 | 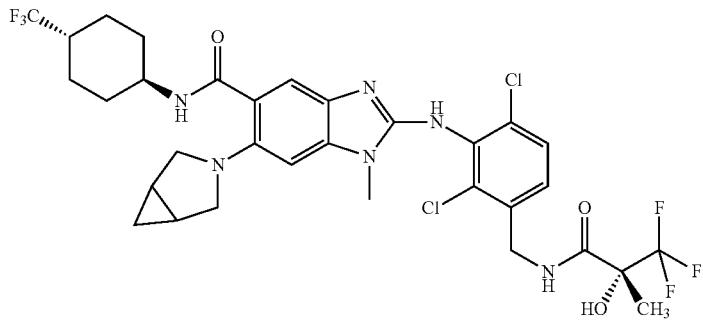 [SMILES: Cn1c(Nc2c(Cl)ccc(CNC(=O)[C@@](C)(O)C(F)(F)F)c2Cl)nc2cc(C(=O)N[C@H]3CC[C@H](C(F)(F)F)CC3)c(N3CC4CC4C3)cc21] |
| 193 | 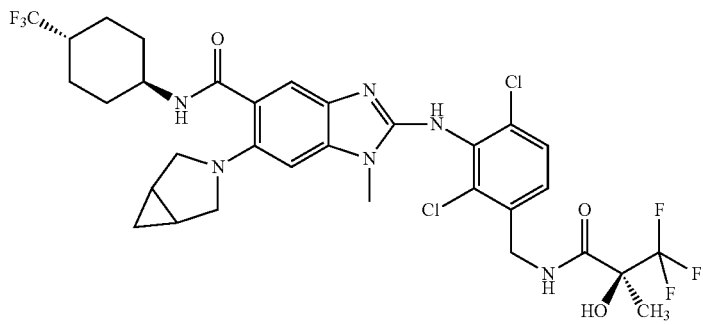 [SMILES: Cn1c(Nc2c(Cl)ccc(CNC(=O)[C@](C)(O)C(F)(F)F)c2Cl)nc2cc(C(=O)N[C@H]3CC[C@H](C(F)(F)F)CC3)c(N3CC4CC4C3)cc21] |
| 194 | 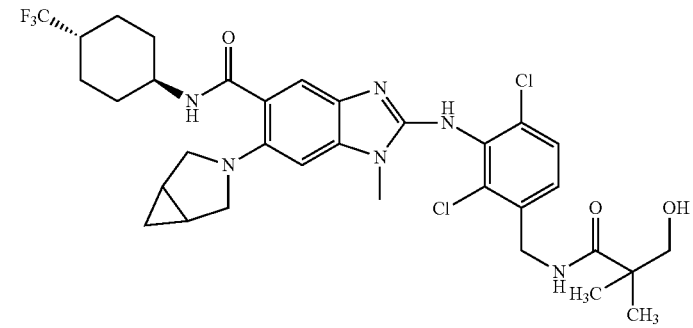 [SMILES: Cn1c(Nc2c(Cl)ccc(CNC(=O)C(C)(C)CO)c2Cl)nc2cc(C(=O)N[C@H]3CC[C@H](C(F)(F)F)CC3)c(N3CC4CC4C3)cc21] |
| 195 | 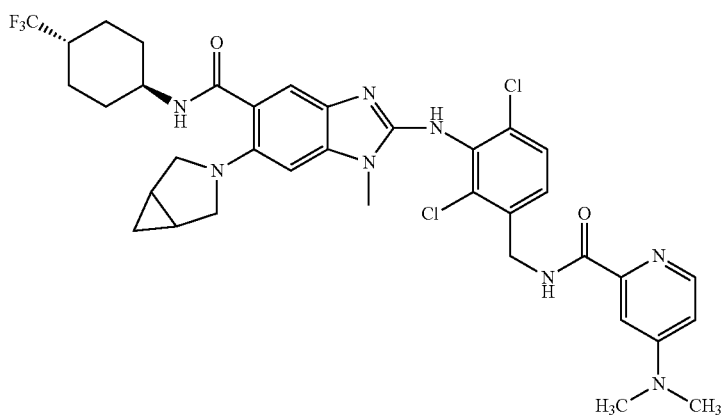 [SMILES: CN(C)c1ccnc(C(=O)NCc2ccc(Cl)c(Nc3nc4cc(C(=O)N[C@H]5CC[C@H](C(F)(F)F)CC5)c(N5CC6CC6C5)cc4n3C)c2Cl)c1] |

-continued
| | Structure |
|---|---|
| 196 | 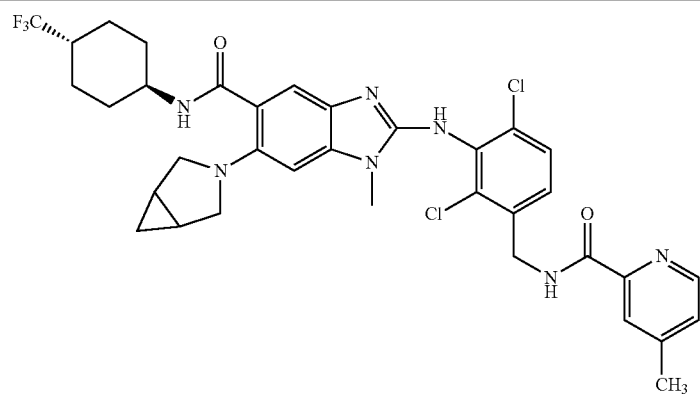 [SMILES: Cc1ccnc(C(=O)NCc2ccc(Cl)c(Nc3nc4cc(C(=O)N[C@H]5CC[C@H](C(F)(F)F)CC5)c(N5CC6CC6C5)cc4n3C)c2Cl)c1] |
| 197 | 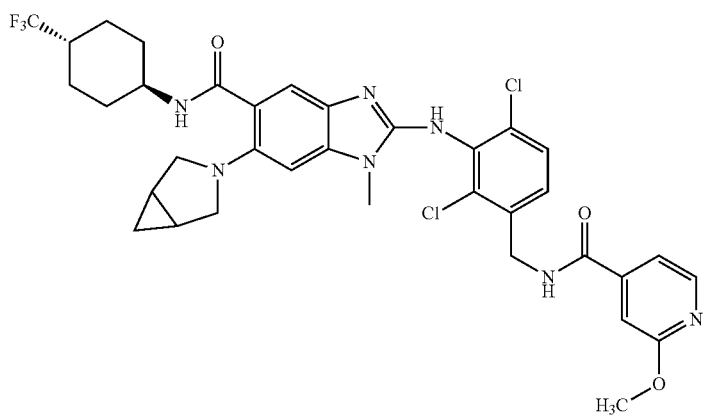 [SMILES: COc1cc(C(=O)NCc2ccc(Cl)c(Nc3nc4cc(C(=O)N[C@H]5CC[C@H](C(F)(F)F)CC5)c(N5CC6CC6C5)cc4n3C)c2Cl)ccn1] |
| 198 | 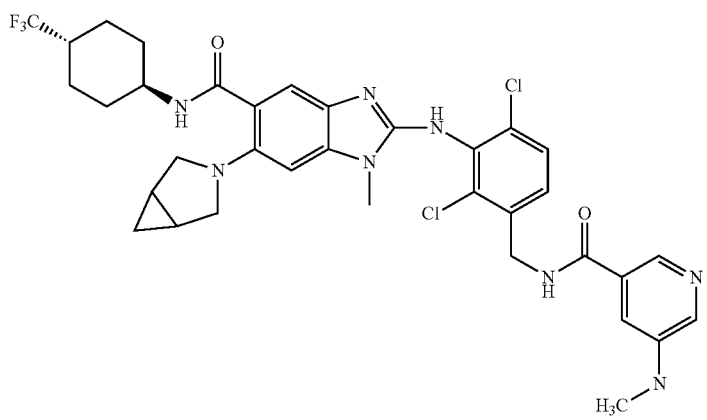 |
| 199 | 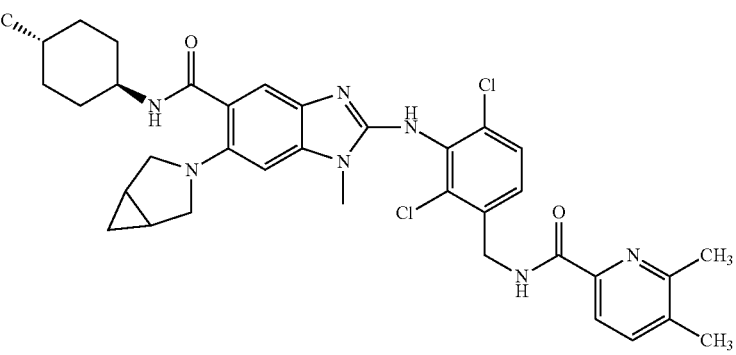 |

| | |
|---|---|
| | -continued |
| | Structure |
| 200 | 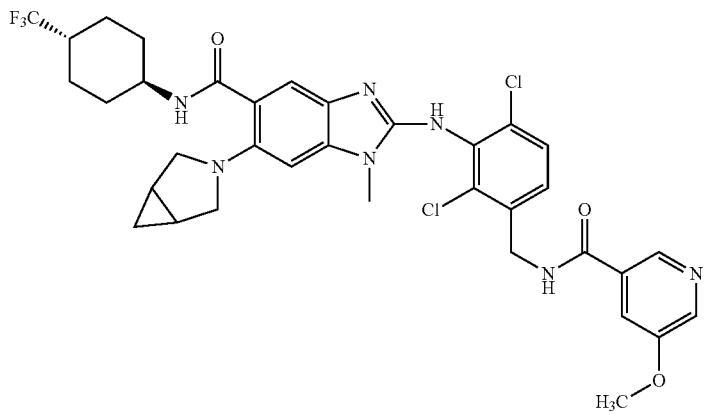 |
| 201 | 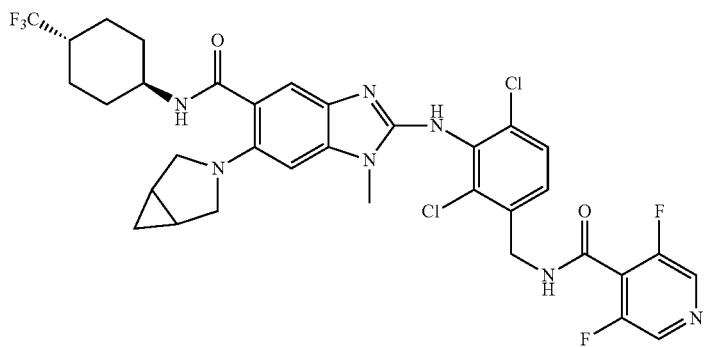 [SMILES: Cn1c(Nc2c(Cl)ccc(CNC(=O)c3c(F)cncc3F)c2Cl)nc2cc(C(=O)N[C@H]3CC[C@H](C(F)(F)F)CC3)c(N3CC4CC4C3)cc21] |
| 202 | 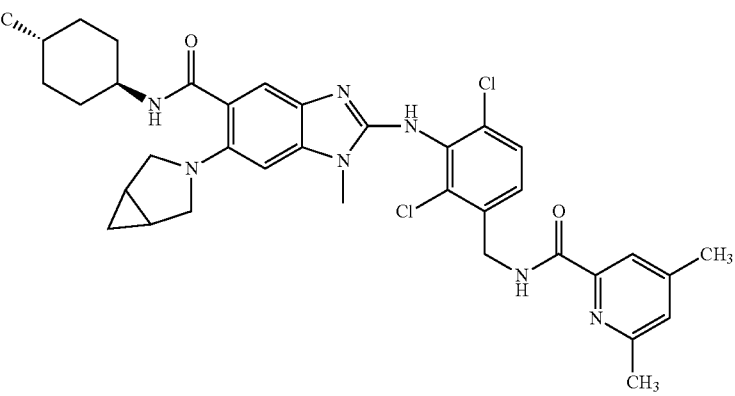 |
| 203 | 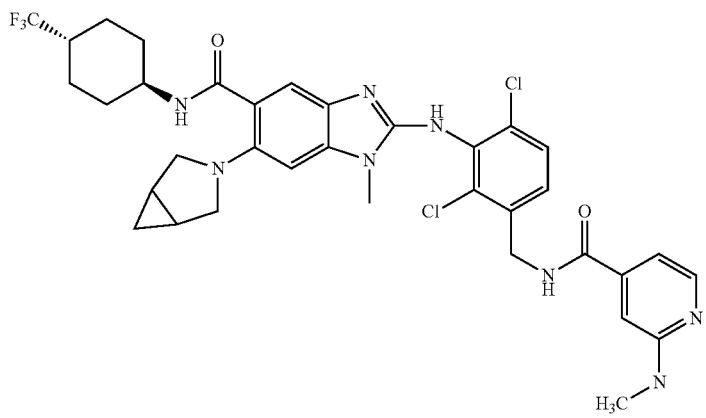 [SMILES: CNc1cc(C(=O)NCc2ccc(Cl)c(Nc3nc4cc(C(=O)N[C@H]5CC[C@H](C(F)(F)F)CC5)c(N5CC6CC6C5)cc4n3C)c2Cl)ccn1] |

| Structure |
|---|
| 204 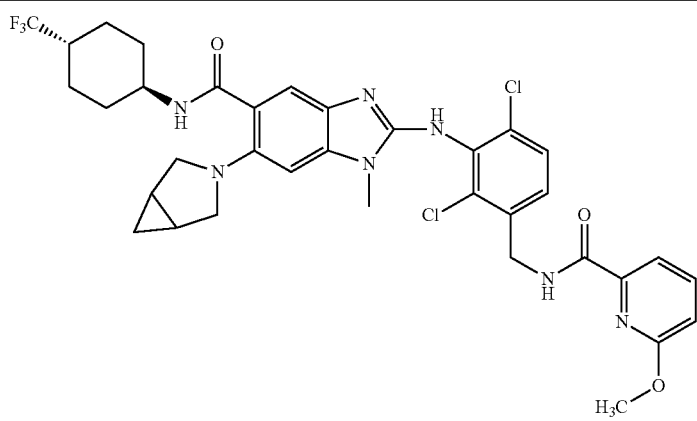 |
| 205 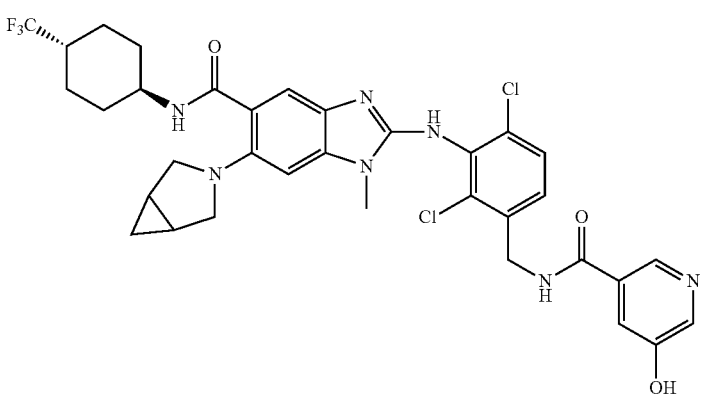 [SMILES: Cn1c(Nc2c(Cl)ccc(CNC(=O)c3cncc(O)c3)c2Cl)nc2cc(C(=O)N[C@H]3CC[C@H](C(F)(F)F)CC3)c(N3CC4CC4C3)cc21] |
| 206 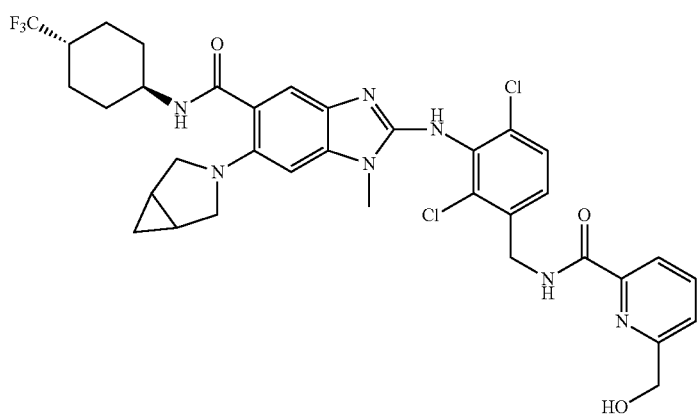 [SMILES: Cn1c(Nc2c(Cl)ccc(CNC(=O)c3cccc(CO)n3)c2Cl)nc2cc(C(=O)N[C@H]3CC[C@H](C(F)(F)F)CC3)c(N3CC4CC4C3)cc21] |
| 207 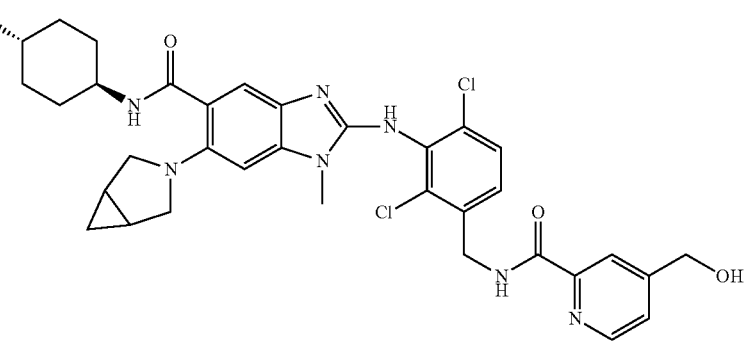 |

| | Structure |
|---|---|
| 208 | 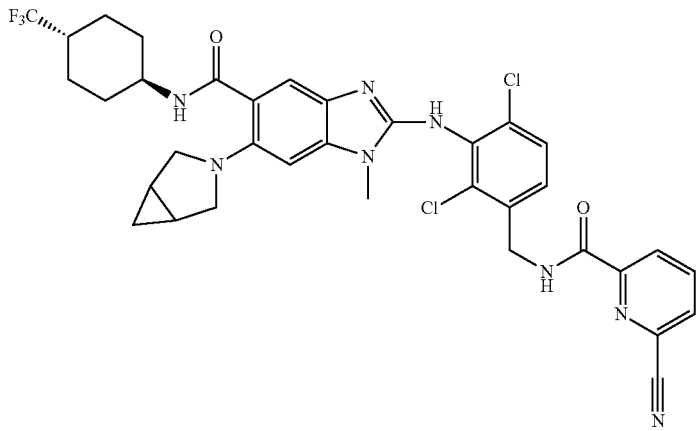 [SMILES: Cn1c(Nc2c(Cl)ccc(CNC(=O)c3cccc(C#N)n3)c2Cl)nc2cc(C(=O)N[C@H]3CC[C@H](C(F)(F)F)CC3)c(N3CC4CC4C3)cc21] |
| 209 | 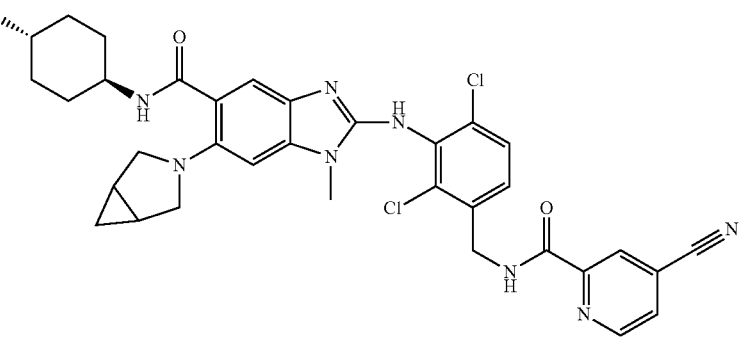 |
| 210 | 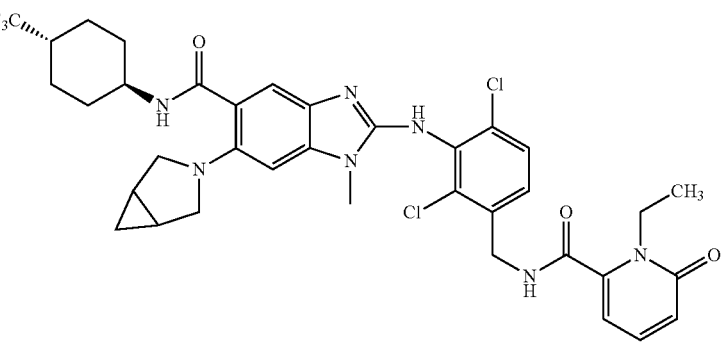 |
| 211 | 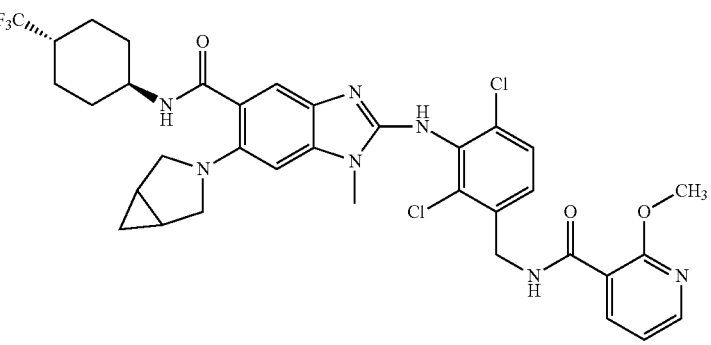 |

| | Structure |
|---|---|
| 212 | 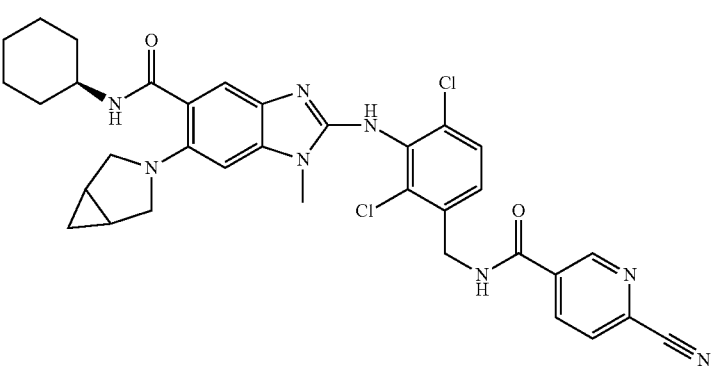 |
| 213 | 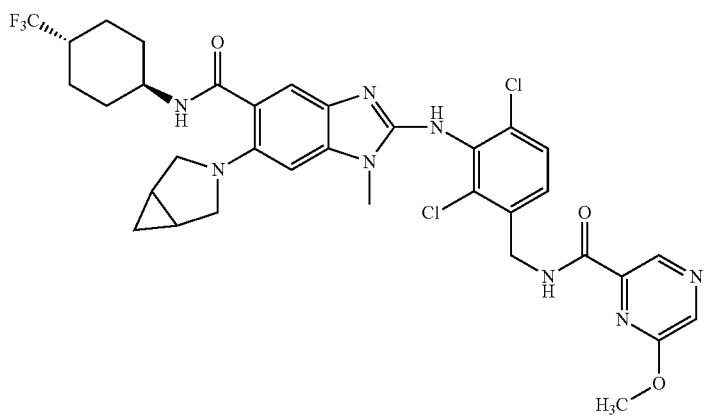 [SMILES: COc1cncc(C(=O)NCc2ccc(Cl)c(Nc3nc4cc(C(=O)N[C@H]5CC[C@H](C(F)(F)F)CC5)c(N5CC6CC6C5)cc4n3C)c2Cl)n1] |
| 214 | 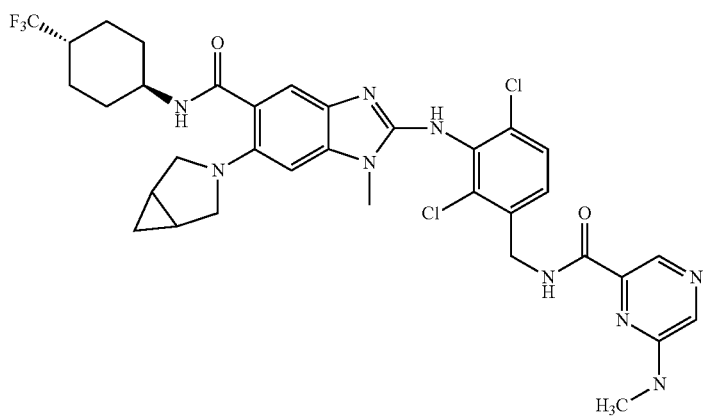 [SMILES: CNc1cncc(C(=O)NCc2ccc(Cl)c(Nc3nc4cc(C(=O)N[C@H]5CC[C@H](C(F)(F)F)CC5)c(N5CC6CC6C5)cc4n3C)c2Cl)n1] |
| 215 | 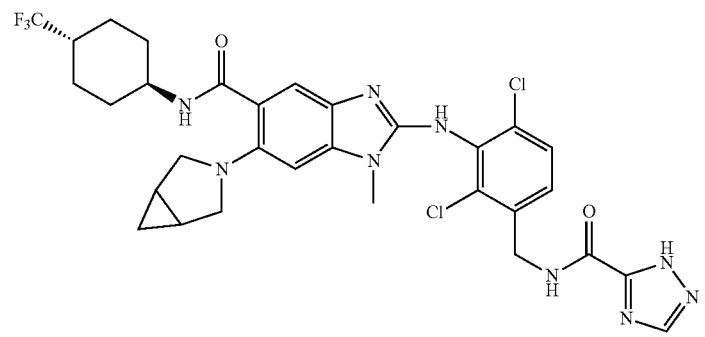 [SMILES: Cn1c(Nc2c(Cl)ccc(CNC(=O)c3ncn[nH]3)c2Cl)nc2cc(C(=O)N[C@H]3CC[C@H](C(F)(F)F)CC3)c(N3CC4CC4C3)cc21] |

-continued
| | Structure |
|---|---|
| 216 | 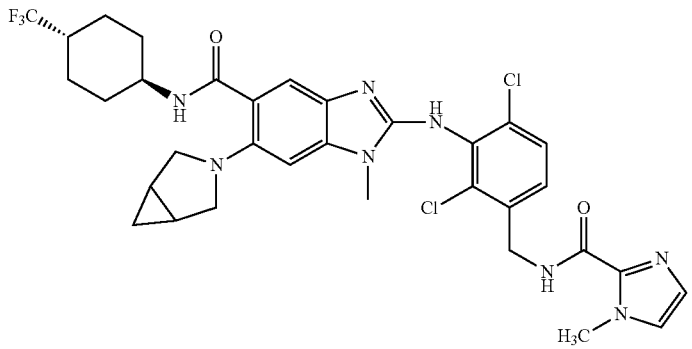 [SMILES: Cn1ccnc1C(=O)NCc1ccc(Cl)c(Nc2nc3cc(C(=O)N[C@H]4CC[C@H](C(F)(F)F)CC4)c(N4CC5CC5C4)cc3n2C)c1Cl] |
| 217 | 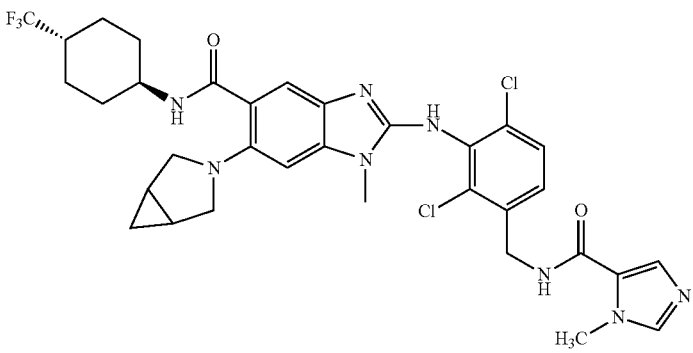 [SMILES: Cn1cncc1C(=O)NCc1ccc(Cl)c(Nc2nc3cc(C(=O)N[C@H]4CC[C@H](C(F)(F)F)CC4)c(N4CC5CC5C4)cc3n2C)c1Cl] |
| 218 | 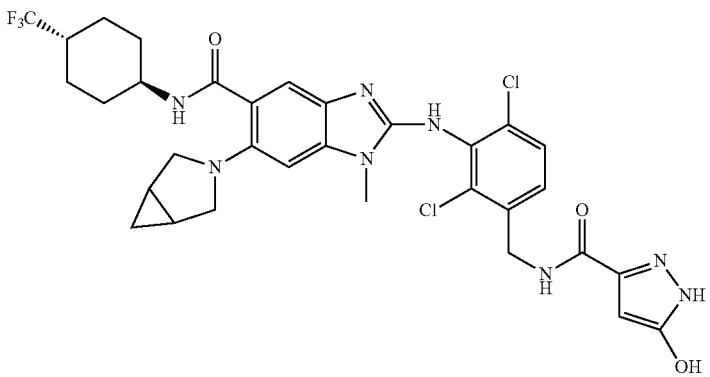 [SMILES: Cn1c(Nc2c(Cl)ccc(CNC(=O)c3cc(O)[nH]n3)c2Cl)nc2cc(C(=O)N[C@H]3CC[C@H](C(F)(F)F)CC3)c(N3CC4CC4C3)cc21] |
| 219 | 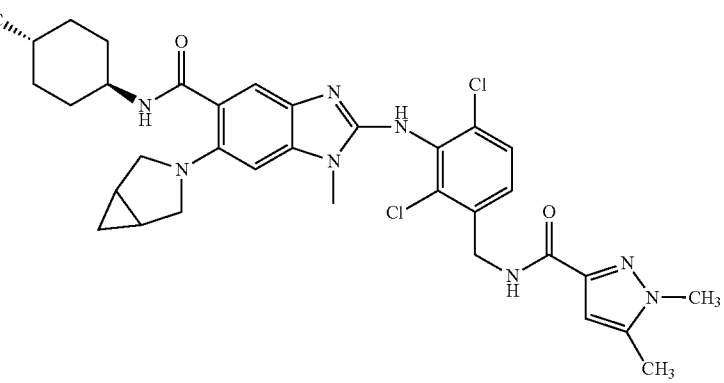 |

-continued
| | Structure |
|---|---|
| 220 | 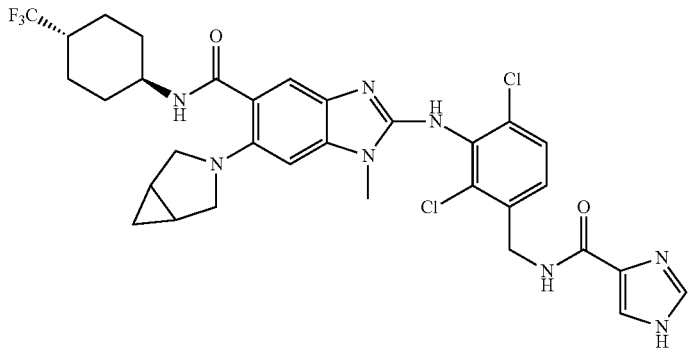 [SMILES: Cn1c(Nc2c(Cl)ccc(CNC(=O)c3c[nH]cn3)c2Cl)nc2cc(C(=O)N[C@H]3CC[C@H](C(F)(F)F)CC3)c(N3CC4CC4C3)cc21] |
| 221 | 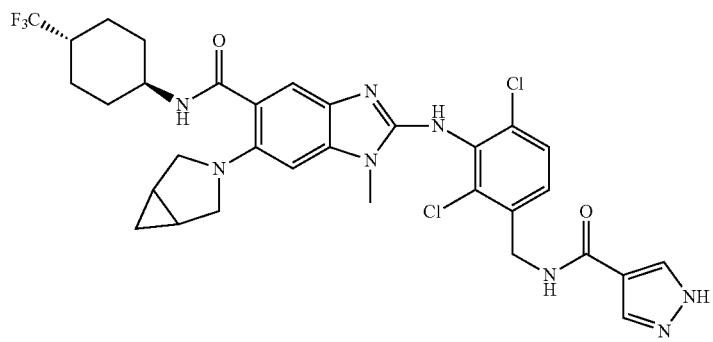 [SMILES: Cn1c(Nc2c(Cl)ccc(CNC(=O)c3cn[nH]c3)c2Cl)nc2cc(C(=O)N[C@H]3CC[C@H](C(F)(F)F)CC3)c(N3CC4CC4C3)cc21] |
| 222 | 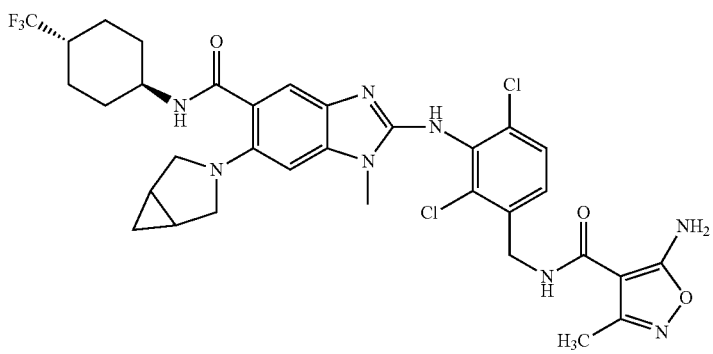 [SMILES: Cc1noc(N)c1C(=O)NCc1ccc(Cl)c(Nc2nc3cc(C(=O)N[C@H]4CC[C@H](C(F)(F)F)CC4)c(N4CC5CC5C4)cc3n2C)c1Cl] |
| 223 | 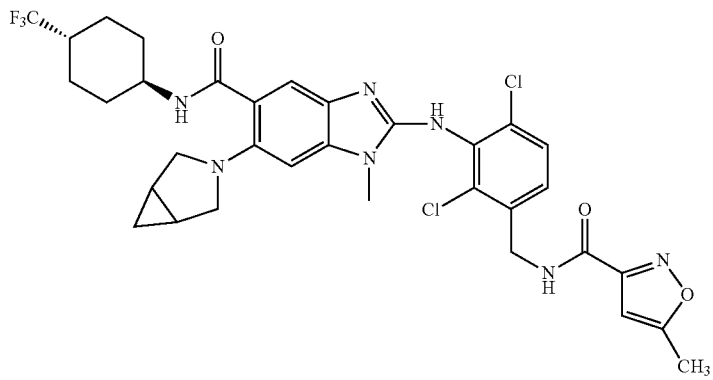 [SMILES: Cc1cc(C(=O)NCc2ccc(Cl)c(Nc3nc4cc(C(=O)N[C@H]5CC[C@H](C(F)(F)F)CC5)c(N5CC6CC6C5)cc4n3C)c2Cl)no1] |

| | Structure |
|---|---|
| 224 | 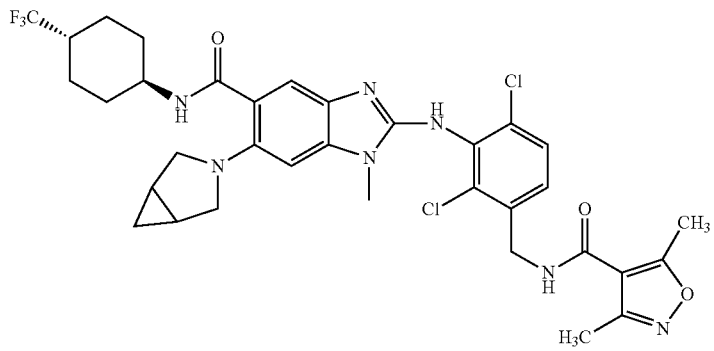 |
| 225 | 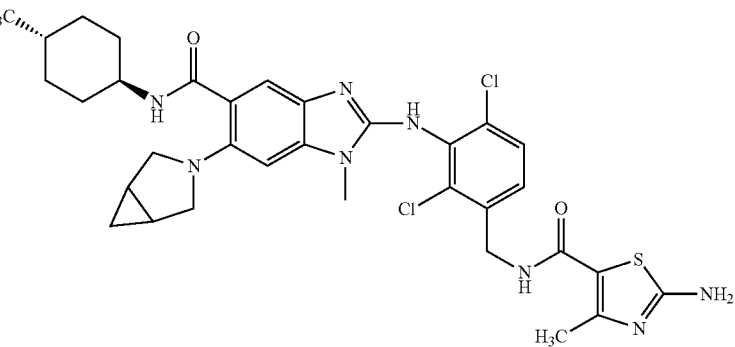 |
| 226 | 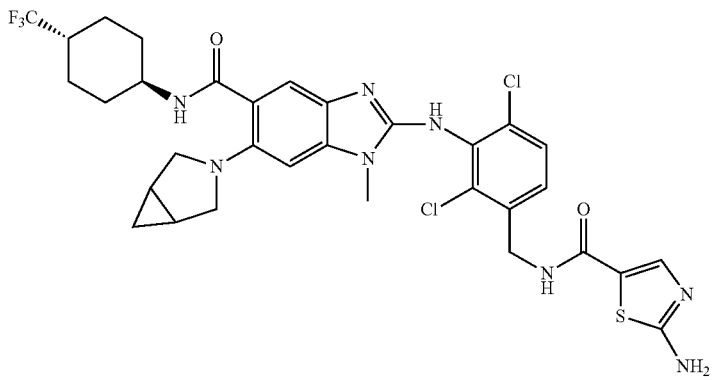 [SMILES: Cn1c(Nc2c(Cl)ccc(CNC(=O)c3cnc(N)s3)c2Cl)nc2cc(C(=O)N[C@H]3CC[C@H](C(F)(F)F)CC3)c(N3CC4CC4C3)cc21] |
| 227 | 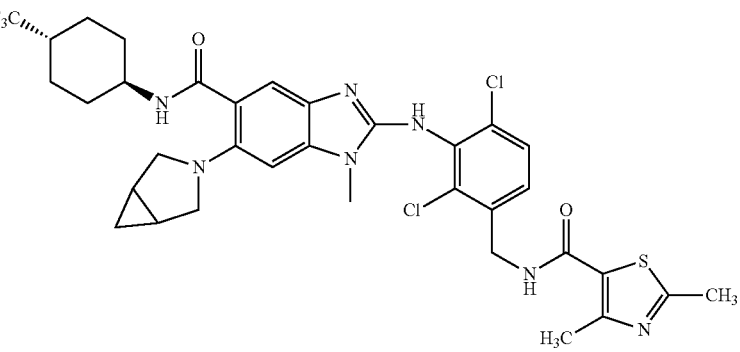 |

| | Structure |
|---|---|
| 228 | 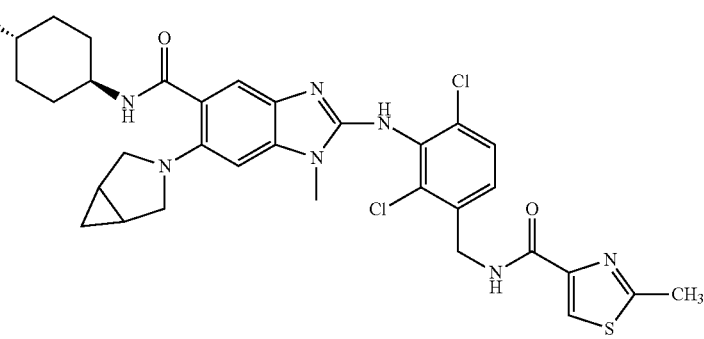 |
| 229 | 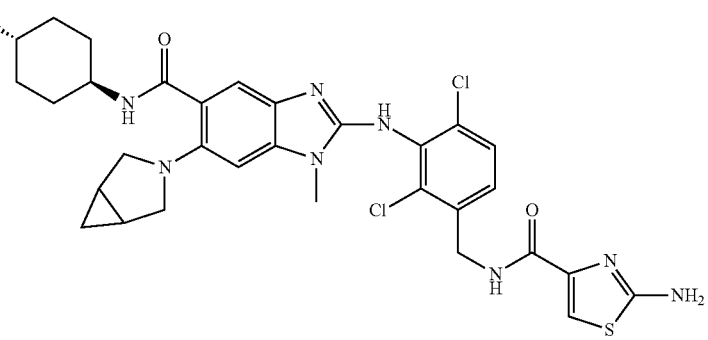 |
| 230 | 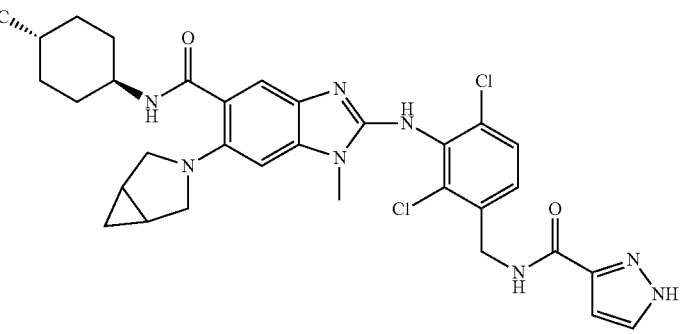 |
| 231 | 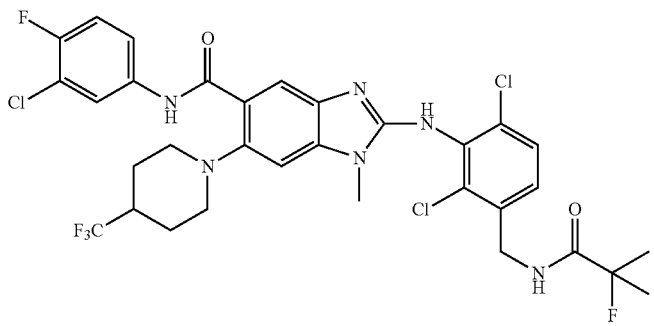 [SMILES: Cn1c(Nc2c(Cl)ccc(CNC(=O)C(C)(C)F)c2Cl)nc2cc(C(=O)Nc3ccc(F)c(Cl)c3)c(N3CCC(C(F)(F)F)CC3)cc21] |

-continued
| | Structure |
|---|---|
| 232 | 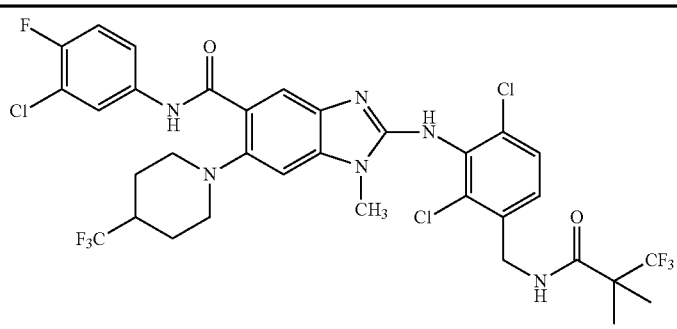 |
| 233 | 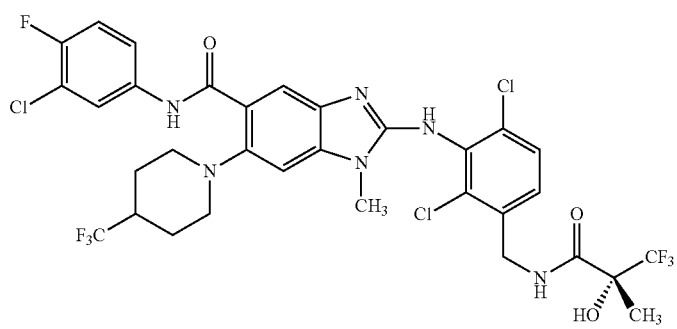 [SMILES: Cn1c(Nc2c(Cl)ccc(CNC(=O)[C@@](C)(O)C(F)(F)F)c2Cl)nc2cc(C(=O)Nc3ccc(F)c(Cl)c3)c(N3CCC(C(F)(F)F)CC3)cc21] |
| 234 | 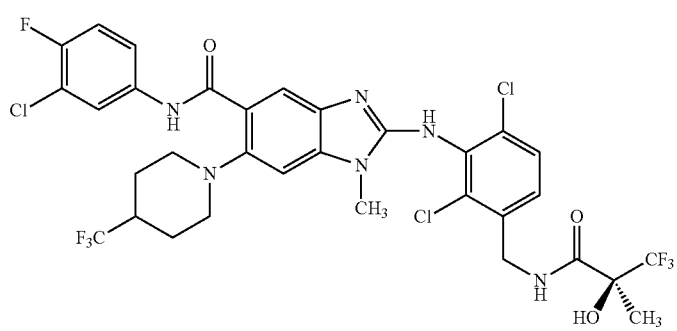 [SMILES: Cn1c(Nc2c(Cl)ccc(CNC(=O)[C@](C)(O)C(F)(F)F)c2Cl)nc2cc(C(=O)Nc3ccc(F)c(Cl)c3)c(N3CCC(C(F)(F)F)CC3)cc21] |
| 235 | 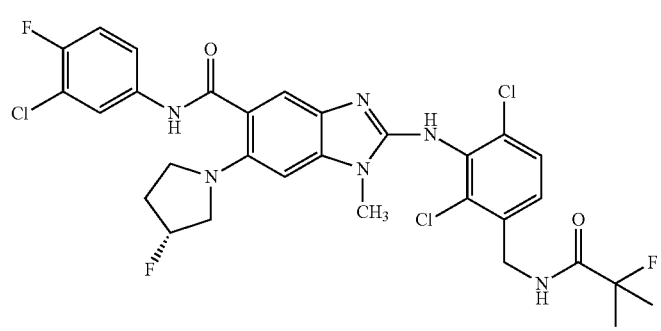 [SMILES: Cn1c(Nc2c(Cl)ccc(CNC(=O)C(C)(C)F)c2Cl)nc2cc(C(=O)Nc3ccc(F)c(Cl)c3)c(N3CC[C@@H](F)C3)cc21] |
| 236 | 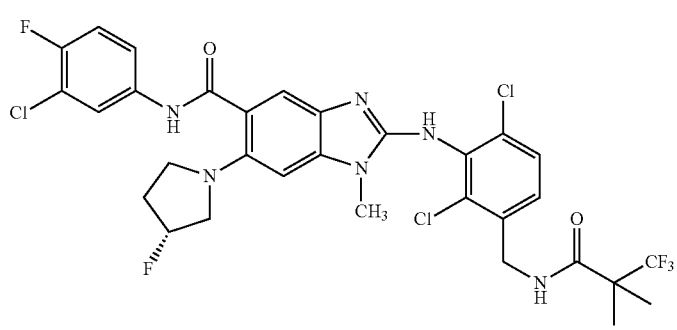 [SMILES: Cn1c(Nc2c(Cl)ccc(CNC(=O)C(C)(C)C(F)(F)F)c2Cl)nc2cc(C(=O)Nc3ccc(F)c(Cl)c3)c(N3CC[C@@H](F)C3)cc21] |

-continued
| | Structure |
|---|---|
| 237 | 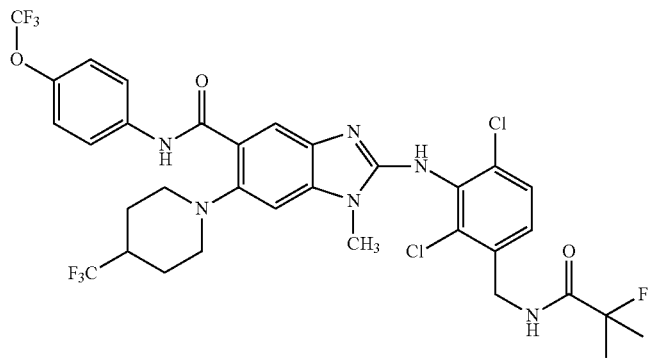 [SMILES: Cn1c(Nc2c(Cl)ccc(CNC(=O)C(C)(C)F)c2Cl)nc2cc(C(=O)Nc3ccc(OC(F)(F)F)cc3)c(N3CCC(C(F)(F)F)CC3)cc21] |
| 238 | 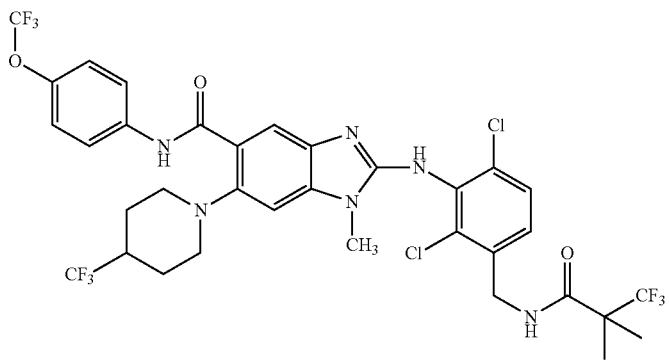 [SMILES: Cn1c(Nc2c(Cl)ccc(CNC(=O)C(C)(C)C(F)(F)F)c2Cl)nc2cc(C(=O)Nc3ccc(OC(F)(F)F)cc3)c(N3CCC(C(F)(F)F)CC3)cc21] |
| 239 | 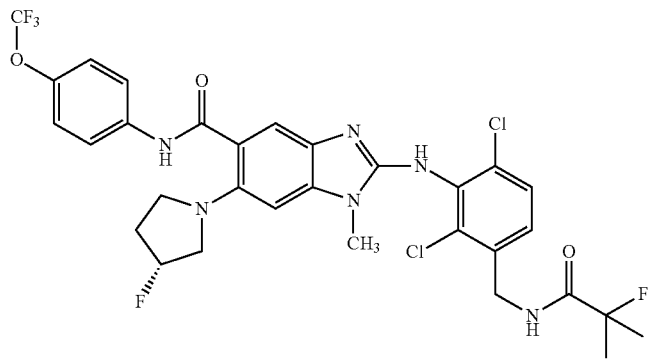 [SMILES: Cn1c(Nc2c(Cl)ccc(CNC(=O)C(C)(C)F)c2Cl)nc2cc(C(=O)Nc3ccc(OC(F)(F)F)cc3)c(N3CC[C@@H](F)C3)cc21] |
| 240 | 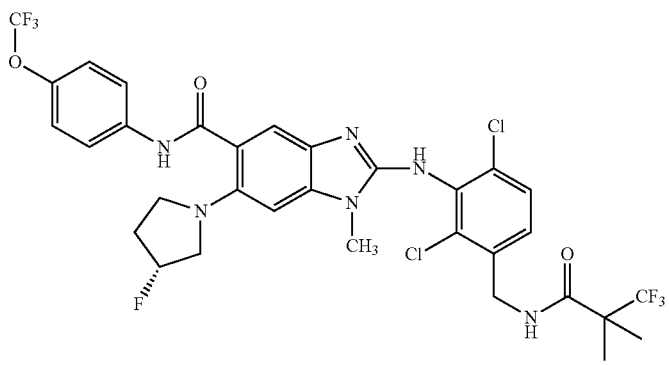 [SMILES: Cn1c(Nc2c(Cl)ccc(CNC(=O)C(C)(C)C(F)(F)F)c2Cl)nc2cc(C(=O)Nc3ccc(OC(F)(F)F)cc3)c(N3CC[C@@H](F)C3)cc21] |

| Structure |
|---|
| 241 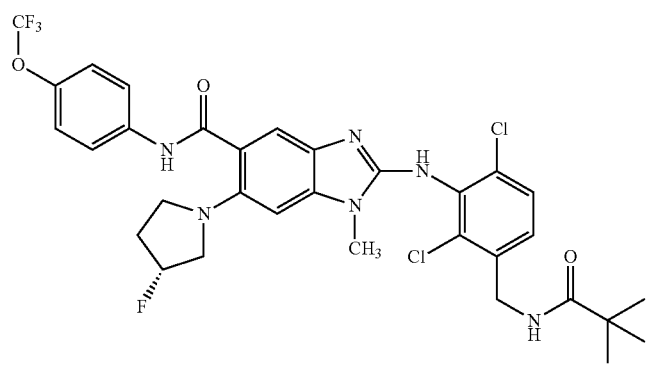 [SMILES: Cn1c(Nc2c(Cl)ccc(CNC(=O)C(C)(C)C)c2Cl)nc2cc(C(=O)Nc3ccc(OC(F)(F)F)cc3)c(N3CC[C@@H](F)C3)cc21] |
| 242 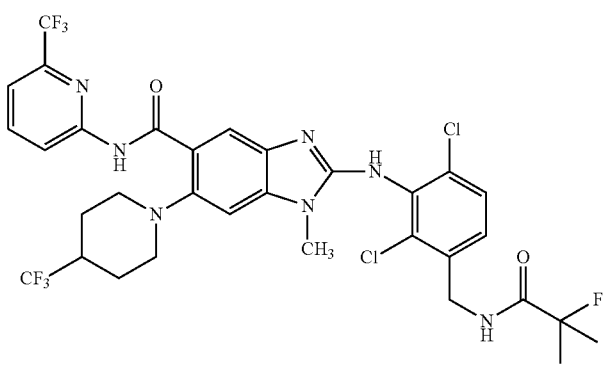 [SMILES: Cn1c(Nc2c(Cl)ccc(CNC(=O)C(C)(C)F)c2Cl)nc2cc(C(=O)Nc3cccc(C(F)(F)F)n3)c(N3CCC(C(F)(F)F)CC3)cc21] |
| 243 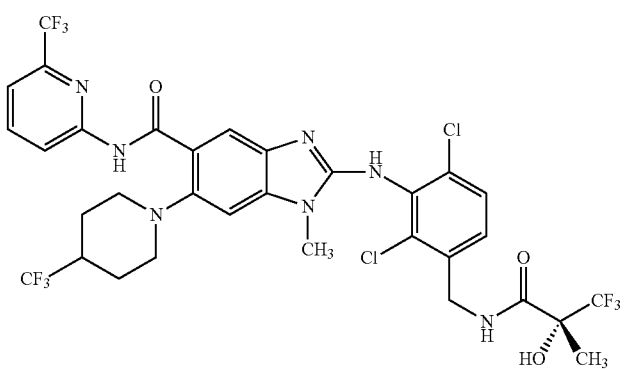 [SMILES: Cn1c(Nc2c(Cl)ccc(CNC(=O)[C@@](C)(O)C(F)(F)F)c2Cl)nc2cc(C(=O)Nc3cccc(C(F)(F)F)n3)c(N3CCC(C(F)(F)F)CC3)cc21] |
| 244 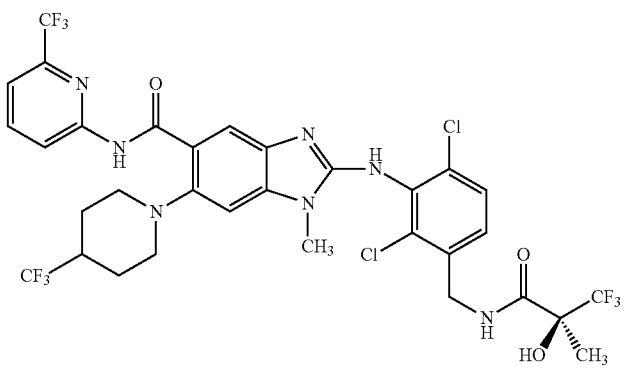 [SMILES: Cn1c(Nc2c(Cl)ccc(CNC(=O)[C@](C)(O)C(F)(F)F)c2Cl)nc2cc(C(=O)Nc3cccc(C(F)(F)F)n3)c(N3CCC(C(F)(F)F)CC3)cc21] |

| | Structure |
|---|---|
| 245 | 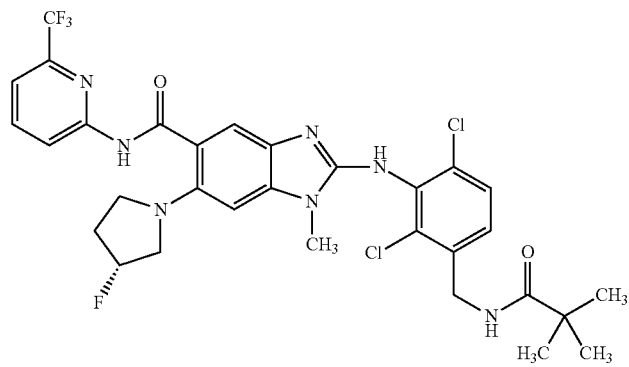 [SMILES: Cn1c(Nc2c(Cl)ccc(CNC(=O)C(C)(C)C)c2Cl)nc2cc(C(=O)Nc3cccc(C(F)(F)F)n3)c(N3CC[C@@H](F)C3)cc21] |
| 246 | 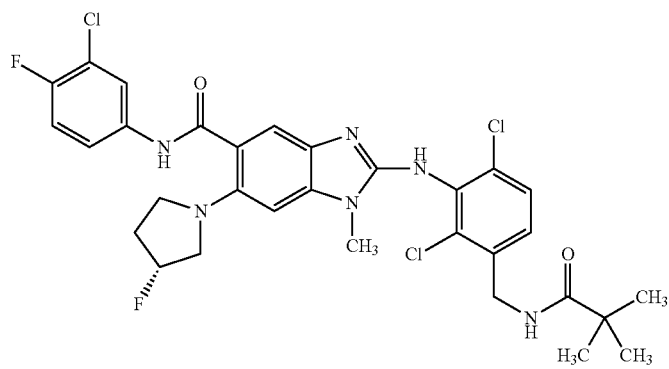 [SMILES: Cn1c(Nc2c(Cl)ccc(CNC(=O)C(C)(C)C)c2Cl)nc2cc(C(=O)Nc3ccc(F)c(Cl)c3)c(N3CC[C@@H](F)C3)cc21] |
| 247 | 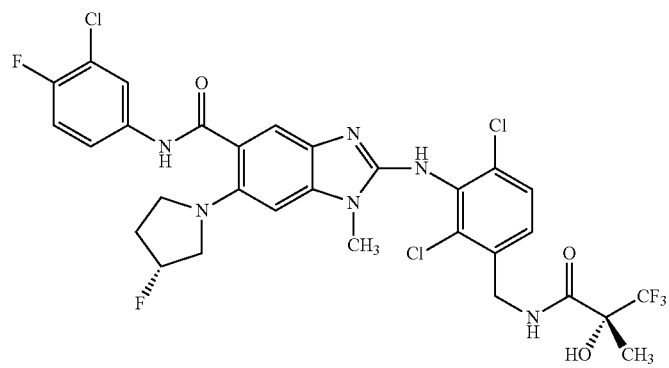 [SMILES: Cn1c(Nc2c(Cl)ccc(CNC(=O)[C@@](C)(O)C(F)(F)F)c2Cl)nc2cc(C(=O)Nc3ccc(F)c(Cl)c3)c(N3CC[C@@H](F)C3)cc21] |
| 248 | 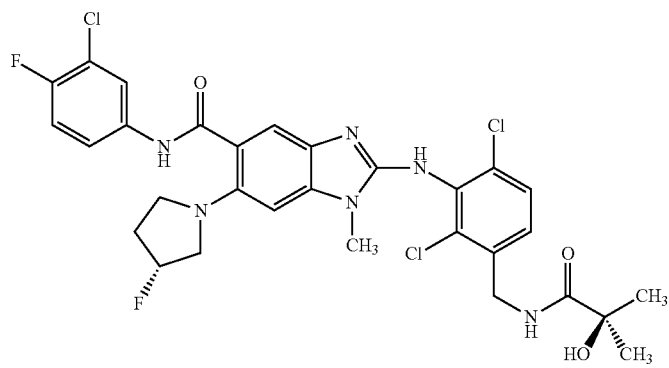 |

| Structure |
|---|
| 249 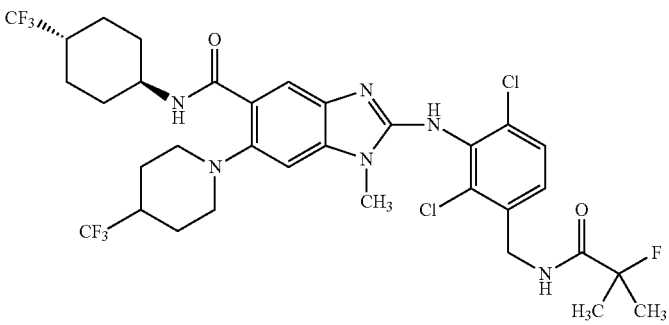 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC(C(F)(F)F)CC3)cc21] |
| 250 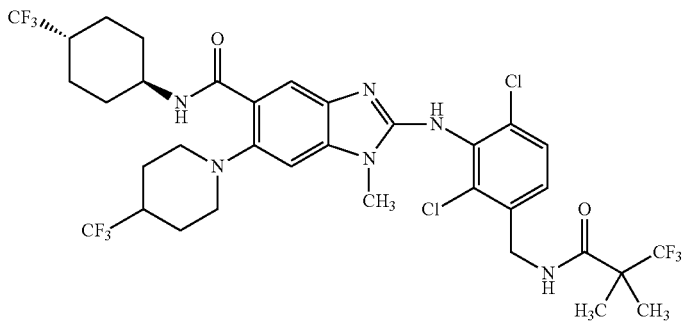 [SMILES: Cn1c(Nc2c(Cl)ccc(CNC(=O)C(C)(C)C(F)(F)F)c2Cl)nc2cc(C(=O)N[C@H]3CC[C@H](C(F)(F)F)CC3)c(N3CCC(C(F)(F)F)CC3)cc21] |
| 251 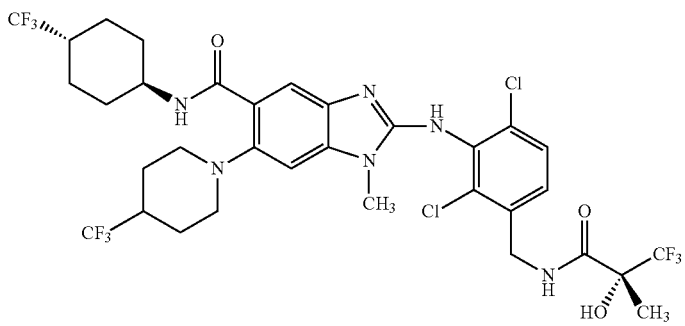 [SMILES: Cn1c(Nc2c(Cl)ccc(CNC(=O)[C@@](C)(O)C(F)(F)F)c2Cl)nc2cc(C(=O)N[C@H]3CC[C@H](C(F)(F)F)CC3)c(N3CCC(C(F)(F)F)CC3)cc21] |
| 252 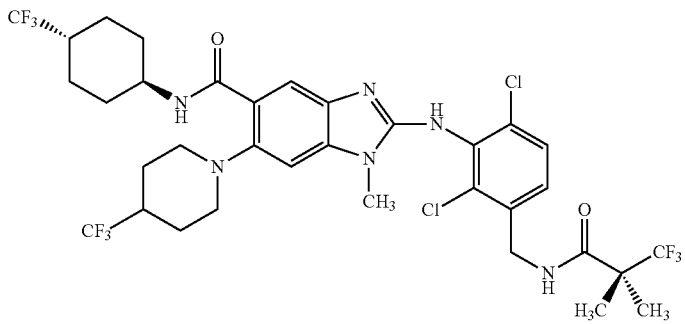 |

| Structure |
|---|
| 253 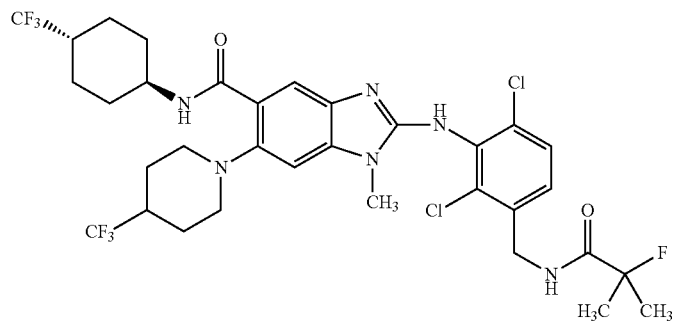 [SMILES: Cn1c(Nc2c(Cl)ccc(CNC(=O)C(C)(C)F)c2Cl)nc2cc(C(=O)N[C@H]3CC[C@H](C(F)(F)F)CC3)c(N3CCC(C(F)(F)F)CC3)cc21] |
| 254 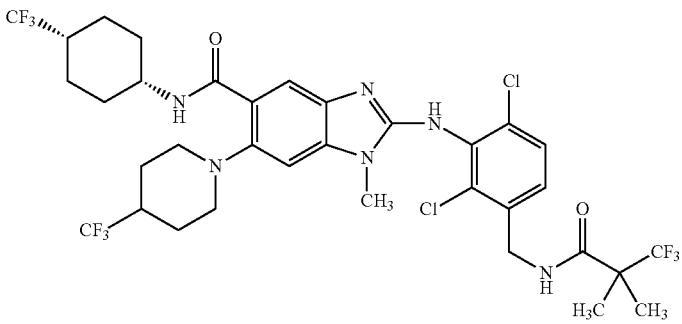 |
| 255 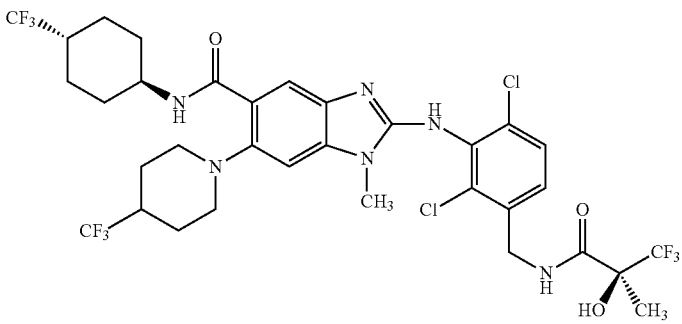 |
| 256 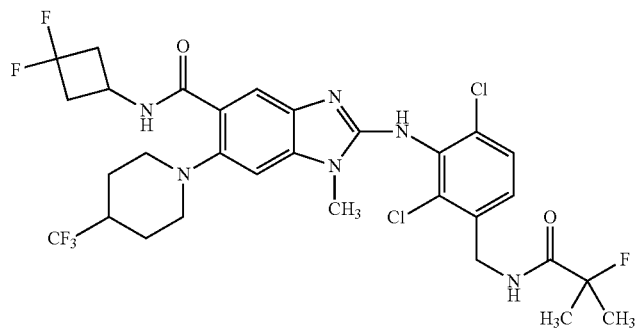 [SMILES: Cn1c(Nc2c(Cl)ccc(CNC(=O)C(C)(C)F)c2Cl)nc2cc(C(=O)NC3CC(F)(F)C3)c(N3CCC(C(F)(F)F)CC3)cc21] |

-continued
| | Structure |
|---|---|
| 257 | 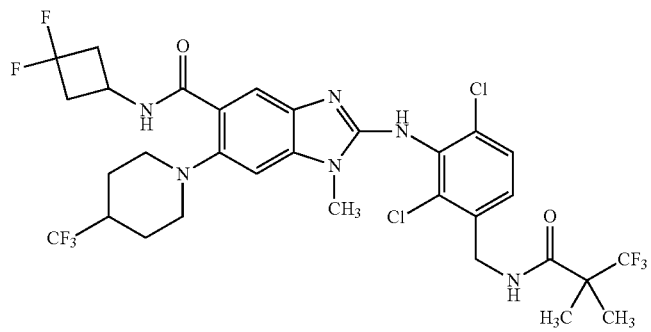 [SMILES: Cn1c(Nc2c(Cl)ccc(CNC(=O)C(C)(C)C(F)(F)F)c2Cl)nc2cc(C(=O)NC3CC(F)(F)C3)c(N3CCC(C(F)(F)F)CC3)cc21] |
| 258 | 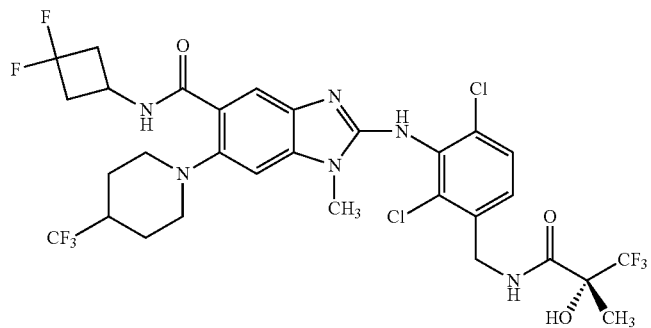 |
| 259 | 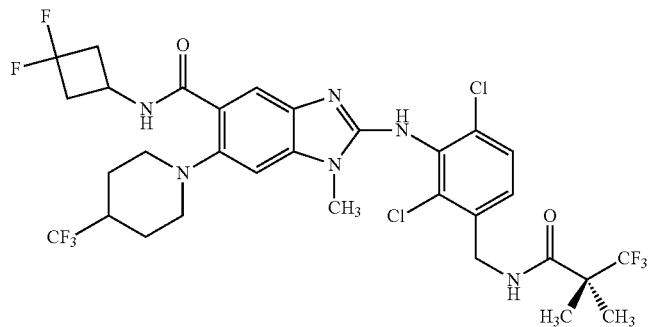 |
| 260 | 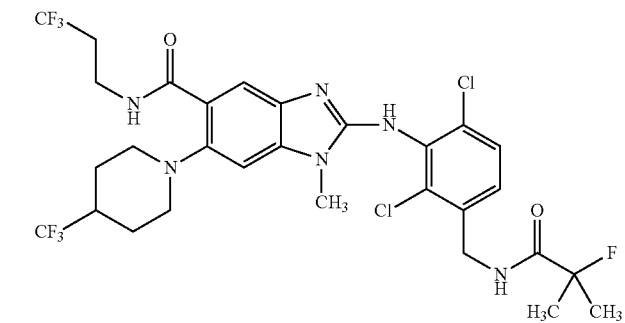 [SMILES: Cn1c(Nc2c(Cl)ccc(CNC(=O)C(C)(C)F)c2Cl)nc2cc(C(=O)NCCC(F)(F)F)c(N3CCC(C(F)(F)F)CC3)cc21] |

-continued
| | Structure |
|---|---|
| 261 | 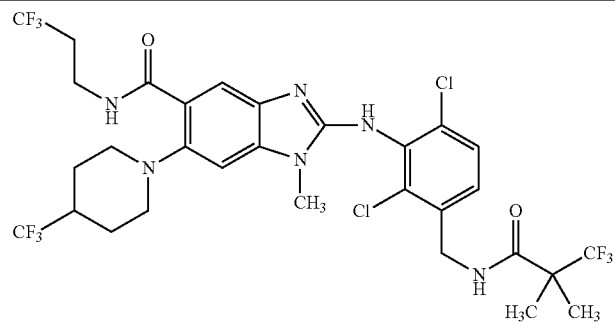 |
| 262 | 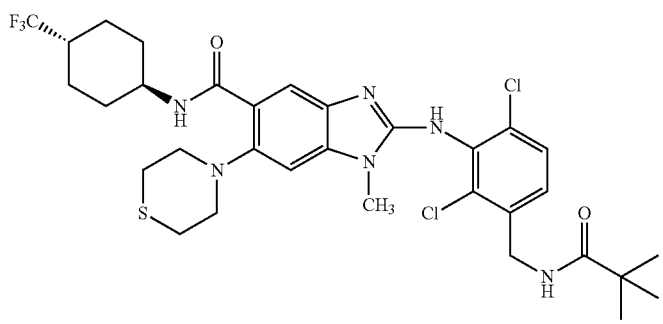 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCSCC3)cc21] |
| 263 | 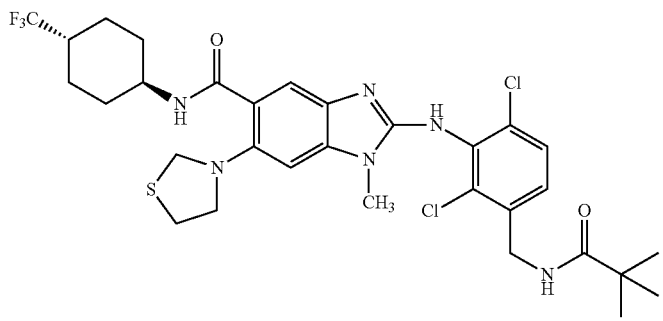 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CCSC3)cc21] |
| 264 | 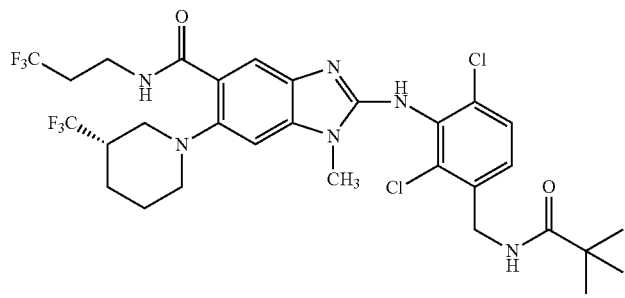 |
| 265 | 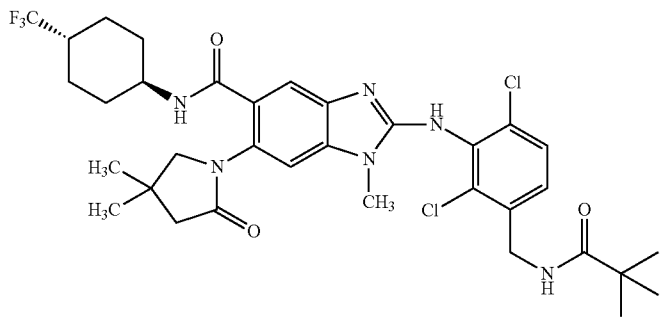 [SMILES: Cn1c(Nc2c(Cl)ccc(CNC(=O)C(C)(C)C)c2Cl)nc2cc(C(=O)N[C@H]3CC[C@H](C(F)(F)F)CC3)c(N3CC(C)(C)CC3=O)cc21] |

-continued
| | Structure |
|---|---|
| 266 | 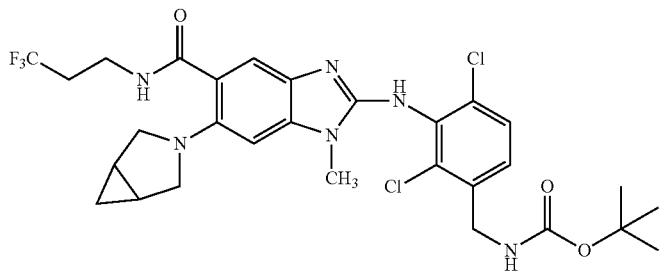 [SMILES: Cn1c(Nc2c(Cl)ccc(CNC(=O)OC(C)(C)C)c2Cl)nc2cc(C(=O)NCCC(F)(F)F)c(N3CC4CC4C3)cc21] |
| 267 | 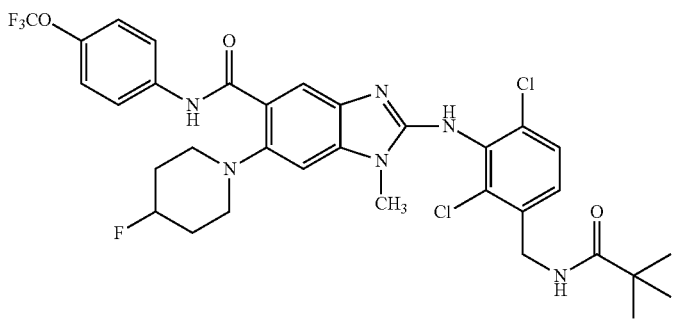 [SMILES: Cn1c(Nc2c(Cl)ccc(CNC(=O)C(C)(C)C)c2Cl)nc2cc(C(=O)Nc3ccc(OC(F)(F)F)cc3)c(N3CCC(F)CC3)cc21] |
| 268 | 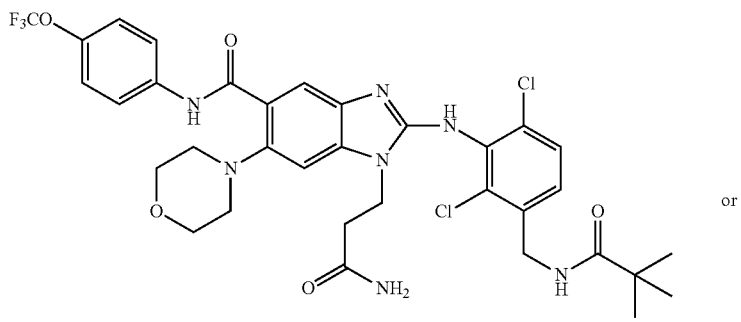 [SMILES: CC(C)(C)C(=O)NCc1ccc(Cl)c(Nc2nc3cc(C(=O)Nc4ccc(OC(F)(F)F)cc4)c(N4CCOCC4)cc3n2CCC(N)=O)c1Cl] or |
| 269 | 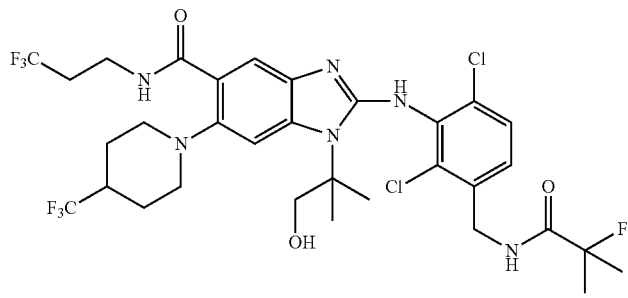 [SMILES: CC(C)(F)C(=O)NCc1ccc(Cl)c(Nc2nc3cc(C(=O)NCCC(F)(F)F)c(N4CCC(C(F)(F)F)CC4)cc3n2C(C)(C)CO)c1Cl] |
and pharmaceutically acceptable salts thereof.
13. A pharmaceutical composition comprising at least one compound according to claim 1, or a pharmaceutically acceptable salt thereof, in admixture with a pharmaceutically acceptable adjuvant, diluent and/or carrier.
* * * * *